United States Patent
Manzanares et al.

(10) Patent No.: US 7,410,969 B2
(45) Date of Patent: Aug. 12, 2008

(54) ANTITUMORAL ANALOGS OF ET-743

(75) Inventors: Ignacio Manzanares, Madrid (ES); María Jesús Martin, Salamanca (ES); Alberto Rodriguez, Madrid (ES); Simon Munt, Madrid (ES); Carmen Cuevas, Madrid (ES); Marta Perez, Madrid (ES)

(73) Assignee: Pharma Mar, S.A., Madrid (ES)

( * ) Notice: Subject to any disclaimer, the term of this patent is extended or adjusted under 35 U.S.C. 154(b) by 81 days.

(21) Appl. No.: 11/045,595

(22) Filed: Jan. 26, 2005

(65) Prior Publication Data

US 2006/0019960 A1 Jan. 26, 2006

Related U.S. Application Data

(63) Continuation of application No. 10/257,857, filed as application No. PCT/GB01/02110 on May 15, 2001.

(30) Foreign Application Priority Data

May 15, 2000 (GB) ..................... PCT/GB00/01852

(51) Int. Cl.
C07D 471/22 (2006.01)
C07D 487/22 (2006.01)
A61K 31/496 (2006.01)
A61P 35/00 (2006.01)

(52) U.S. Cl. .................. 514/250; 540/453; 540/466; 540/454

(58) Field of Classification Search ................ 544/453, 544/454, 466; 514/250
See application file for complete search history.

(56) References Cited

U.S. PATENT DOCUMENTS

| | | | |
|---|---|---|---|
| 5,089,273 | A | 2/1992 | Rinehart et al. |
| 5,149,804 | A | 9/1992 | Rinehart et al. |
| 5,256,663 | A | 10/1993 | Rinehart et al. |
| 5,478,932 | A | 12/1995 | Rinehart et al. |
| 5,654,426 | A | 8/1997 | Rinehart et al. |
| 5,721,362 | A | 2/1998 | Corey et al. |
| 5,985,876 | A | 11/1999 | Rinehart et al. |
| 6,124,292 | A | 9/2000 | Corey |
| 6,124,293 | A | 9/2000 | Rinehart et al. |
| 6,316,214 | B1 | 11/2001 | Rinehart et al. |
| 6,348,467 | B1 | 2/2002 | Corey |
| 6,686,470 | B2 | 2/2004 | Danishefsky et al. |
| 6,867,334 | B2 | 3/2005 | Rinehart et al. |
| 2003/0216397 | A1 | 11/2003 | Flores et al. |
| 2004/0002602 | A1 | 1/2004 | Francesch et al. |

FOREIGN PATENT DOCUMENTS

| | | |
|---|---|---|
| EP | 0 309 477 B1 | 11/1991 |
| JP | 59-225189 | 12/1984 |
| JP | 60-84288 | 5/1985 |
| WO | WO 87/07610 | 12/1987 |
| WO | WO 92/09607 | 6/1992 |
| WO | WO 98/12198 | 3/1998 |
| WO | WO 98/46080 | 10/1998 |
| WO | WO 99/51238 | 10/1999 |
| WO | WO 99/58125 | 11/1999 |
| WO | WO 00/18233 | 4/2000 |
| WO | WO 00/69862 | 11/2000 |
| WO | WO 01/77115 | 10/2001 |
| WO | WO 01/87895 | 11/2001 |

OTHER PUBLICATIONS

Cecil Textbook of Medicine, edited by Bennet, J.C., and Plum, F., 20th edition, vol. 1, 1004-1010, 1996.*
Valoti et al. Clin. Cancer Res. 4(8): 1977-83, 1998.*
Kania, R.S. "The First Enantioselective Total Synthesis of Dolabellatrienone and Ecteinascidin 743", Ph.D. Thesis, Harvard University, Sep. 1997, pp. 1-225.
Kubo et al., "Stereoselective Total Synthesis of (±) Saframycin B", J. Org. Chem., vol. 53, No. 18, 1988, pp. 4295-4310.
Moore et al., "NMR-Based Model of an Ecteinascidin 743-DNA Adduct", J/ Am. Chem. Soc., vol. 119, 1997, pp. 5475-5476.
Sparidans, R.S., et al., "Search for metabolites of ecteinascidin 743, a novel marine-derived, anti-cancer agent in man." Anti-Cancer Drugs 2001, 12, 653-666.
Calabresi et al., "Chemotherapy of Neoplastic Diseases", Goodman & Gilman's The Pharmacological Basis of Therapeutics, 9th ed. New York: McGraw-Hill, 1996, pp. 1225-1229.
Cecil Textbook of Medicine (Bennet, J.C. and Plum, F., eds.) 20th Edition, vol. 1, pp. 1004-1010 (1996).
Valoti et al. Clin. Cancer Res. 4(8): 1977-83 (1998).
Fukuyama, Tohru et al., "Total Synthesis of (±)-Saframycin A", *Journal of American Chemical Society*, vol. 112, pp. 3712-3713 (1990).

(Continued)

*Primary Examiner*—Venkataraman Balasubramanian
(74) *Attorney, Agent, or Firm*—Fish & Richardson P.C.

(57) ABSTRACT

Antitumor compounds have the five membered fused ring ecteinascidin structure of the formula (XIV). The present compounds lack a 1,4-bridging group as found in the ecteinascidins. They have at the C-1 position a substituent selected from an optionally protected or derivatised aminomethylene group or an optionally protected or derivatised hydroxymethylene group

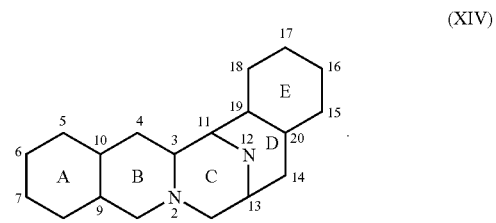

66 Claims, No Drawings

OTHER PUBLICATIONS

Garcia-Rocha, M. et al., "Characterisation of antimitotic products from marine organisms that disorganize the microtubule network: ecteinascidin 743, isohomohalichondrin-B and LL-15", *British Journal of Cancer*, vol. 73, pp. 875-883 (1996).

Goldwasser, F, et al. "Characterization of ecteinascidin 743-induced DNA damages in cells", *Proceedings of the American Association for Cancer Research*, vol. 39, #4066, pp. 598 (1998).

Guan, Yue et al., "Molecular and Crystal Structures of Ecteinascidins: Potent Antitumor Compounds from the Caribbean Tunicate Ecteinascidia Turbinata", *Journal of Biomolecular Structure & Dynamics*, vol. 10, No. 5, pp. 793-818 (1993).

Gulavita, Nanda K., et al., "Antimicrobial Constituents of a Sponge-Nudibranch Pair from Sri Lanka", *Bioactive Compounds from Marine Organisms*, Oxford & IBH Publishing Co. Pvt. Ltd., pp. 229-233 (1991).

He, Hai-yin et al., "Renieramycins E and F from the Sponge Reniera sp.: Reassignment of the Stereochemistry of the Renieramycins", *The Journal of Organic Chemistry*, vol. 54, No. 24, pp. 5822-5824 (1989).

Hendriks, H.R. et al., "High antitumor activity of ET743 in human tumor xenograft models", *Proceedings of the American Association for Cancer Research*, vol. 37, #2653, pp. 389 (1996).

Ikeda, Yoshifumi et al., "Safracins, New Antitumor Antibiotics I. Producing Organism, Fermentation and Isolation", *The Journal of Antibiotics*, vol. XXXVI, No. 10, pp. 1279-1283 (1983).

Ikeda, Yoshifumi et al., "Safracins, New Antitumor Antibiotics I. Producing Organism, Fermentation and Isolation", *The Journal of Antibiotics*, vol. XXXVI, No. 10, pp. 1284-1289 (1983).

Ito, Yoichiro, "High-Speed Countercurrent Chromatography", *Critical Reviews in Analytical Chemistry*, vol. 17, No. 1, pp. 65-143 (1986).

Koenig, Karl E., "The Applicability of Asymmetric Homogeneous Catalytic Hodrogenation", *Asymmetric Synthesis*, Ed. Morrison, Academic Press, Inc., Orlando, FL, vol. 5, pp. 71 (1985)

Kofron, William G. et al., "A Convenient Method for Estimation of Alkyllithium Concentrations", *The Journal of Organic Chemistry*, vol. 41, No. 10, pp. 1879-1880 (1976).

Kubo, Akinori et al., "Structure of Saframycin D, A New Dimeric Isoquinolinequinone Antibiotic", *Chem. Pharm. Bull.*, vol. 35, No. 1, pp. 440-442 (1987).

Kuffel, M.J. et al., "Cytochrome P450 catalyzed metabolism of Ecteinascidin 743 by rat and human liver microsomes", *Proceedings of the American Association for Cancer Research*, vol. 38, #4003, pp. 596 (1997).

Lichter, W. et al., "Biological Activities Exerted by Extracts of Ecteinascidia Turbinata", *Food and Drugs from the Sea Proceedings*, pp. 117-127 (1972).

Lown, J. William et al., "Molecular Mechanisms of Binding and Single-Strand Scission of Doexyribonucleic Acid by the Antitumor Antibiotics Saframycins A and C", *Biochemistry*, vol. 21, No. 3, pp. 419-428 (1982).

Lown, J. William et al., "Structure and Confirmation of Saframycin R Determined by High Field $^1$H and $^{13}$C NMR and its Interactions with DNA in Soloution", *The Journal of Antibiotics*, vol. XXXVI, No. 9, pp. 1184-1194 (1983).

Rinehart, Kenneth L., "Antitumor Compounds from Tunicates", *Medicinal Research Reviews*, vol. 20, No. 1, pp. 1-27 (2000).

Saito, Naoki et al., "Synthesis of Saframycins. 3. Preparation of a Key Tricyclic Lactam Intermediate to Saframycin A", *The Journal of Organic Chemistry*, vol. 54, No. 22, pp. 5391-5395 (1989).

Sakai, Ryuichi et al., "Additional antitumor ecteinascidins from a Caribbean tunicate: Crystal structures and activities in vivo", *Proceedings of the National Academy of Sciences*, vol. 89, No. 23, pp. 11456-11460 (1992).

Sakai, Ryuichi et al., "Ecteinascidins: Putative Biosynthetic Precursors and Absolute Stereochemistry", *Journal of the American Chemical Society*, vol. 118, No. 38, pp. 9017-9023 (1996).

Shamma, Maurice et al., *Carbon-13 NMR Shift Assignments of Amines and Alkaloids*, pp. 206 (1979).

Still, W. Clark et al., "Rapid Chromatographic Technique for Preparative Separations with Moderate Resolution", *Journal of Organic Chemistry*, vol. 43, No. 14, pp. 2923-2925 (1978).

Takahashi, Katsuhiro et al., "Microbial Conversion of Saframycin A to 25-Dihydrosaframycin A and 21-Decyano-25-Dihydrosaframycin A (25-Dihydrosaframycin B) and Their Biological Activities", *The Journal of Antibiotics*, vol. XXXV, No. 2, pp. 196-202 (1982).

Takahashi, Katsuhiro, "New Antibiotics, Saframycins A, B, C, D and E", *The Journal of Antibiotics*, vol. XXX, No. 11, pp. 1015-1018 (1977).

Trowitzsch-Kienast, Wolfram et al., "Isolierung und Strukturaufklarung der Saframycine Mx 1 und Mx 2, neue antitumoraktive Antibiotika aus *Myxococcus xanthus*", *Liebigs Ann. Chem.*, vol. XXXV, pp. 475-481 (1988).

Witten, Jane L. et al., "Structures of Two Cockroach Neuropeptides Assigned by Fast Atom bombardment Mass Spectrometry", *Biochemical and Biophysical Research Communications*, vol. 124, No. 2, pp. 350-358 (1984).

Wright, Amy E. et al., "Antitumor Tetrahydroisoquinoline Alkaloids from the Colonial Ascidian Ecteinascidia Turbinata", *The Journal of Organic Chemistry*, vol. 55, No. 15, pp. 4508-4512 (1990).

Yazawa, Katsukiyo et al., "Bioconversions of Saframycin A Specific to some Genera of Actinomycetes", *The Journal of Antibiotics*, vol. XXXV, No. 7, pp. 915-917 (1982).

Yazawa, Katsukiyo et al., "Isolation and Structural Elucidation of New Saframycins Y3, Yd-1, Yd-2, Ad-1, Y2b and Y2b-d", *The Journal of Antibiotics*, vol. XXXIX, No. 12, pp. 1639-1650 (1986).

Zmijewski, Milton J., Jr. et al., "The in vitro Interaction of Naphthyridinomycin with Deoxyribonucleic Acids", *Chemico-Biological Interactions*, vol. 52, No. 3, pp. 361-375 (1985).

Martinez et al., "A New, More Efficient and Effective Process for the Synthesis of a Key Pentacyclic Intermediate for Production of Ecteinascidin and Phthalascidin Antitumor Agents", *Organic Letters*, 2(7):993-996 (2000).

Martinez et al., "Enantioselective Synthesis of Saframycin A and Evaluation of Antitumor Activity Relative to Ecteinascidin/Saframycin Hybirds", *Organic Letters*, 1(7):75-77 (1999).

Martinez, Eduardo J. et al., "Phthalascidin, a synthetic antitumor agent with potency and mode of action comparable to ecteinascidin 743", *Proc. Natl. Acad. Sci. USA*, vol. 96, pp. 3496-3501 (1999).

Mikami, Yuzuru et al., "Structural Studies on Minor Components of Saframycin Group Antibiotics Saframycins F, G and H", *The Journal of Antibiotics*, vol. XLI, No. 6, pp. 734-740 (1988).

Mirsalis, J.C. et al., "Toxicity of Ecteinascidin 743 in female Fischer-344 rats administered i.v. in a multiple-dose regimen", *Proceedings of the American Association for Cancer Research*, vol. 38, #2073, pp. 309 (1997).

Moore, B.M. et al., "The NMR model of an ecteinascidin 743-DNA adduct", *Proceedings of the American Association for Cancer Research*, vol. 38, #2105, pp. 314 (1997).

Myers et al., "A Concise, Stereocontrolled Syntheis of (-)-Saframycin A by the Directed Condensation of α-Amino Aldehyde Precursors", *J. Am. Chem. Soc.*, 121:10828-10829 (1999).

Nakagawa, Masako et al., "Total Synthesis of (-)-Eudistomin L and (-)-Debromoeudistomin L", *Journal of the American Chemical Society*, vol. 111, No. 7, pp. 2721-2722 (1989).

Parulekar, A.H. et al., "Bioactivity and Chemical Ecology of Some Interdial Animals", *Bioactivity and Chemical Ecology*, pp. 29-35, 1991.

Pommier, Yves et al., "DNA Sequence- and Strcture-Selective Alkylation of Guanine N2 in the DNA Minor Groove by Ecteinascidin 743, a Potent Antitumor Compound from the Caribbean Tunicate Ecteinascidia Turbinata", *Biochemistry*, vol. 35, pp. 13303-13309 (1996).

Pretsch et al., *Tables of Spectral Data for Structure Determination of Organic Compounds*, pp. H125 (1983).

Reid, Joel M. et al., "Preclinical pharmacology of ecteinascidin 729, a marine natural product with potent antitumor activity", *Cancer Chemotherapy and Pharmacology*, vol. 38, No. 4, pp. 329-334 (1996).

Remers, William A., "Saframycins, Renieramycins, and Safracins", *The Chemistry of Antitumor Antibiotics*, vol. 2, pp. 93-119 (1988).

Rinehart et al., "Novel Bioactive Natural Products from Marine Organisms", *Topics in Pharmaceutical Sciences 1989*, pp. 613-626, D.D. Breimer, D.J.A. Cromwelin, K.K. Midha, Eds., Amsterdam Medical Press B.V. Noordwijk, The Netherlands (1989).

Rinehart, Kenneth L. et al., "Applications of High-Resolution Tandem FAB Mass Spectrometry", *Biological Mass Spectrometry*, eds. Burlingame et al., Elsevier Amsterdam, pp. 233-258 (1990).

Rinehart, Kenneth L. et al., "Bioactive Compounds from Aquatic and Terrestrial Sources", *Journal of Natural Products*, vol. 53, No. 4, pp. 771-792 (1990).

Rinehart, Kenneth L. et al., "Biologically active natural products", *Pure and Applied Chemistry*, vol. 62, No. 7, pp. 1277-1280 (1990).

Rinehart, Kenneth L. et al., "Ecteinascidins 729, 743, 759A, 759B, and 770: Potent Antitumor Agents from the Caribbean Tunicate Exteinascidia Turbinata", *The Journal of Organic Chemistry*, vol. 55, no. 15, pp. 4512-4515 (1990).

Arai, T. et al., "The Structure of a Novel Antitumor Antibiotic, Saframycin A", *Experientia*, vol. 36, pp. 1025-1027 (1980).

Arai, Tadashi et al., "Directed Biosynthesis of New Saframycin Derivatives with Resting Cells of *Streptomyces lavendulae*", *Antimicrobial Agents and Chemotherapy*, vol. 28, No. 1, pp. 5-11 (1985).

Arai, Tadashi et al., "Increased Production of Saframycin A and Isolation of Saframycin S", *The Journal of Antibiotics*, vol. XXXIII, No. 9, pp. 951-960 (1980).

Arai, Tadashi et al., "Increased Production of Saframycin A and Isolation of Saframycin S", *The Journal of Antibiotics*, vol. XXXIII, No. 9, pp. 951-960 (1980).

Arai, Tadashi et al., "Isoquinolineinones from Actinomycetes and Sponges", *The Alkaloids Chemistry and Pharmacology*, vol. XXI, pp. 56-100 (1983).

Arai, Tadashi et al., "New Antibiotics, Safraycins A, B, C, D and E", *The Journal of Antibiotics*, vol. XXX, No. 11, pp. 1015-1018 (1977).

Asaoka, Takemitsu et al., "A New Saframycin, Saframycin R", *The Journal of Antibiotics*, vol. XXXV, No. 12, pp. 1708-1710 (1982).

Barton, Derek H.R. et al, "Synthesis and Properties of a Series of Sterically Hindered Guanidine Bases[1]", *Journal of the Chemical Society Perkin Transactions I*, No. 9, pp. 2085-2090 (1982).

Brown, J.M., "NCI's Anticancer Drug Screening Program May Not Be Selecting for Clinically Active Compounds," Oncol. Res. 9(5):213-215 (1997).

Cable, Karl M. et al., "The Biosynthesis of Tuberin from Tyrosine and Glycine; Observations on the Stereochemistry Associated with the Conversion of Glycine through Methylenetetrahydrofolate into Methenyltetrahydrofolate", *Journal of the Chemical Society Perkins Transactions I*, No. 7, pp. 1593-1598 (1987).

Cooper, Raymond et al., "Structure of the Quinone Antibiotic EM5519 and the Behavior of Quinones in Fast Atom Bombardment Mass Spectrometry", *The Journal of Antibiotics*, vol. XXXVIII, No. 1, pp. 24-30 (1985).

Corey, E.J. et al., "Enantioselective Total Synthesis of Ecteinascidin 743", *Journal of the American Chemical Society*, vol. 118, No. 38, pp. 9202-9203 (1996).

Cuevas, Carmen et al., "Synthesis of Ecteinascidin ET-743 and Phthalascidin Pt-650 from Cyanosafracin B", *Organic Letters*, vol. 2, No. 16, pp. 2545-2549 (2000).

Draetta, G. and Pagano, M., "Annual Reports in Medicinal Chemistry, vol. 31," Academic Press, San Diego, pp. 241-246 (1996).

Eckhardt, S.G. et al., "Activity of ecteinascidin, a novel marine cytotoxic, against primary human tumor colony-forming units", *Proceedings of the American Association for Cancer Research*, vol. 37, #2791, pp. 409 (1996).

Faircloth, G. et al., "Ecteinascidin-743 (ET743): in vitro (IVT) and in vivo (INV) Results in Tumor Models", *The European Journal of Cancer*, vol. 32A, Supp. 1, #24 O, pp. S5 (1996).

Flam, Faye, "Chemical Prospectors Scour the Seas for Promising Drugs", *Science*, vol. 266, pp. 1324-1325 (1994).

Frincke, James M. et al., "Antimicrobial Metabolites of the Sponge *Reniera* sp.", *Journal of the American Chemical Society*, vol. 104, pp. 265-269 (1982).

Fukuyama, Tohru et al., "Stereocontrolled Total Synthesis of (±)-Saframycin B", *Journal of the American Chemical Society*, vol. 104, pp. 4957-4958 (1982).

\* cited by examiner

ANTITUMORAL ANALOGS OF ET-743

This application is a continuation of U.S. application Ser. No. 10/257,857, filed Mar. 31, 2003, which is the National Stage of International Application No. PCT/GB01/02110, filed on May 15, 2001, which claims the benefit of International Application No. PCT/GB00/01852, filed on May 15, 2000. The contents of each of these prior applications are incorporated herein by reference in their entireties.

The present invention relates to antitumoral compounds, and in particular to antitumoral analogs of ecteinascidin 743, ET-743.

BACKGROUND OF THE INVENTION

European Patent 309,477 relates to ecteinascidins 729, 743, 745, 759A, 759B and 770. The ecteinascidin compounds are disclosed to have antibacterial and other useful properties. Ecteinascidin 743 is now undergoing clinical trials as an antitumour agent.

Ecteinascidin 743 has a complex tris(tetrahydroisoquinolinephenol) structure of the following formula (I):

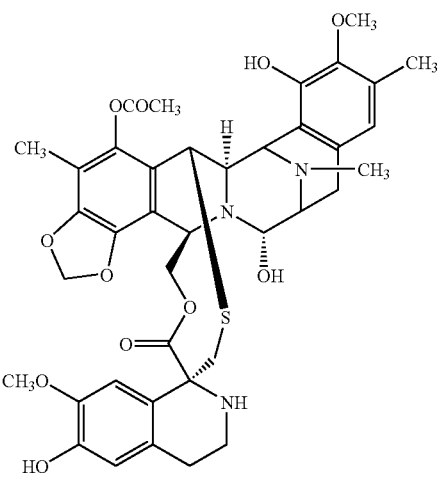

In ecteinascidin 743, the 1,4 bridge has the structure of formula (IV):

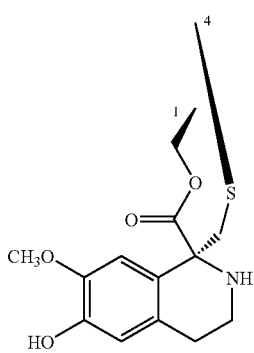

Other known ecteinascidins include compounds with a different bridged cyclic ring system, such as occurs in ecteinascidin 722 and 736, where the bridge has the structure of formula (V):

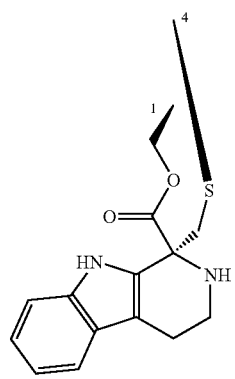

ecteinascidins 583 and 597, where the bridge has the structure of formula (VI):

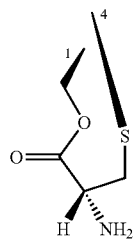

and ecteinascidin 594 and 596, where the bridge has the structure of formula (VII):

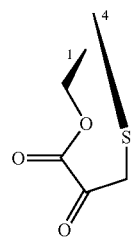

The complete structure for these and related compounds is given in J. Am. Chem. Soc. (1996) 118, 9017-9023. This article is incorporated by reference.

The ecteinascidins are currently prepared by isolation from extracts of the marine tunicate *Ecteinascidin turbinata*. The yield is low, and alternative preparative processes have been sought.

A synthetic process for producing ecteinascidin compounds is described in U.S. Pat. No. 5,721,362, see also WO 9812198. The claimed method is long and complicated. By way of illustration, there are 38 Examples each describing one or more steps in the synthetic sequence to arrive at ecteinascidin 743.

Claim 25 of U.S. Pat. No. 5,721,362 is directed at an intermediate phenol compound of a given formula (11), which we refer to also as Intermediate 11 or Int-11. It has the following bis(tetrahydroisoquinolinephenol) structure (II):

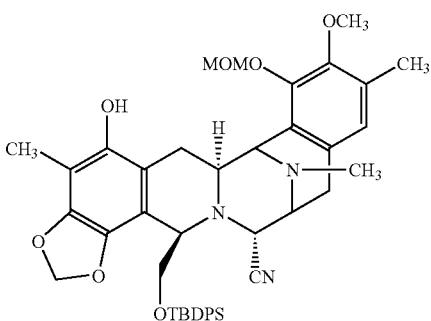

where MOM is a methoxymethyl substituent and TBDPS is a tert-butyldiphenylsilyl substituent.

From Intermediate 11 it is possible to synthesise another interesting antitumour agent, phthalascidin, see Proc. Natl. Acad. Sci. USA, 96, 3496-3501, 1999. Phthalascidin is a bis(tetrahydroisoquinolinephenol) derivative of formula (III):

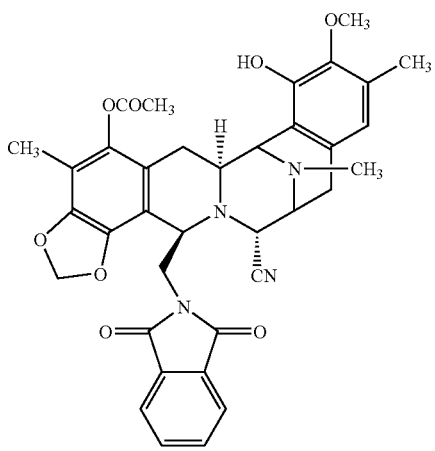

More generally, phthalascidin and related compounds are described in WO 0018233. Claim 1 is directed at compounds of formula:

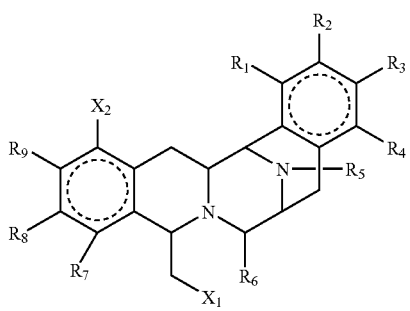

wherein the substituent groups defined by $R_1$, $R_2$, $R_3$, $R_4$, $R_5$, $R_6$, $R_7$, $R_8$ and $R_9$ are each independently selected from the group consisting of H, OH, OR', SH, SR', SOR', $SO_2R'$, $NO_2$, $NH_2$, NHR', $N(R')_2$, NHC(O)R', CN, halogen, =O, C(=O)H, C(=O)R', $CO_2H$, $CO_2R'$, $C_1$-$C_{12}$ alkyl, $C_2$-$C_{12}$ alkenyl, $C_2$-$C_{12}$ alkynyl, substituted or unsubstituted aryl, substituted or unsubstituted aralkyl, and substituted or unsubstituted heteroaromatic;

wherein each of the R' groups is independently selected from the group consisting of H, OH, $NO_2$, $NH_2$, SH, CN, halogen, =O, C(=O)H, C(=O)$CH_3$, $CO_2H$, $CO_2CH_3$, $C_1$-$C_{12}$ alkyl, $C_2$-$C_{12}$ alkenyl, $C_2$-$C_{12}$ alkynyl, aryl, aralkyl, and heteroaromatic;

wherein each dotted circle represents one, two or three optional double bonds;

wherein $R_7$ and $R_8$ may be joined into a carbocyclic or heterocyclic ring system;

and wherein $X_1$ and $X_2$ are each independently defined as above for $R_1$-$R_8$ and further include various permitted definitions.

Further naturally occuring compounds are known which lack a bridged cyclic ring system. They include the bis(tetrahydroisoquinolinequinone) antitumor-antimicrobial antibiotics safracins and saframycins, and the marine natural products renieramicins and xestomycin isolated from cultured microbes or sponges. They all have a common dimeric tetrahydroisoquinoline carbon framework. These compounds can be classified into four types, types I to IV, with respect to the oxidation pattern of the aromatic rings.

Type I, dimeric isoquinolinequinones, is a system of formula (VIII) most commonly occurring in this class of compounds, see the following table I.

TABLE I

Structure of Type I Saframycin Antibiotics.

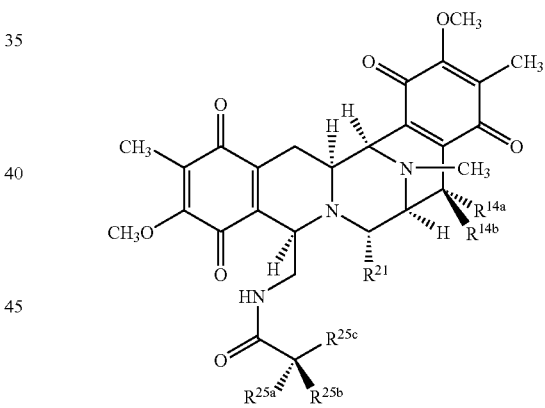

| Compound | $R^{14a}$ | $R^{14b}$ | $R^{21}$ | $R^{25a}$ | $R^{25b}$ | $R^{25c}$ |
|---|---|---|---|---|---|---|
| saframycin A | H | H | CN | O | O | $CH_3$ |
| saframycin B | H | H | H | O | O | $CH_3$ |
| saframycin C | H | $OCH_3$ | H | O | O | $CH_3$ |
| saframycin G | H | OH | CN | O | O | $CH_3$ |
| saframycin H | H | H | CN | OH | $CH_2COCH_3$ | $CH_3$ |
| saframycin S | H | H | OH | O | O | $CH_3$ |
| saframycin $Y_3$ | H | H | CN | $NH_2$ | H | $CH_3$ |
| saframycin $Yd_1$ | H | H | CN | $NH_2$ | H | $C_2H_5$ |
| saframycin $Ad_1$ | H | H | CN | O | O | $C_2H_5$ |
| saframycin $Yd_2$ | H | H | CN | $NH_2$ | H | H |
| saframycin $Y_{2b}$ | H | $Q^b$ | CN | $NH_2$ | H | $CH_3$ |
| saframycin $Y_{2b-d}$ | H | $Q^b$ | CN | $NH_2$ | H | $C_2H_5$ |
| saframycin $AH_2$ | H | H | CN | $H^a$ | $OH^a$ | $CH_3$ |
| saframycin $AH_2Ac$ | H | H | CN | H | OAc | $CH_3$ |
| saframycin $AH_1$ | H | H | CN | $OH^a$ | HO | $CH_3$ |
| saframycin $AH_1Ac$ | H | H | CN | OAc | H | $CH_3$ |
| saframycin $AR_3$ | H | H | H | H | OH | $CH_3$ |

TABLE I-continued

Structure of Type I Saframycin Antibiotics.

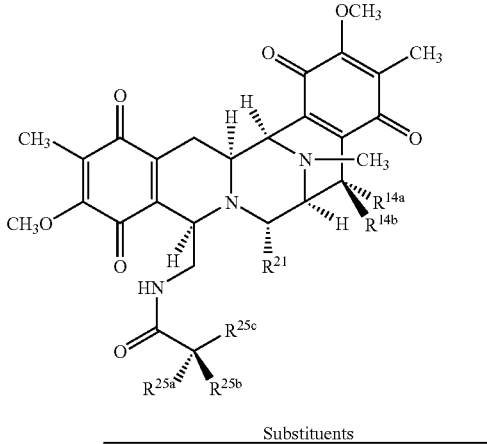

| Compound | $R^{14a}$ | $R^{14b}$ | $R^{21}$ | $R^{25a}$ | $R^{25b}$ | $R^{25c}$ |
|---|---|---|---|---|---|---|

[a] assignments are interchangeable.
[b] where the group Q is of formula (IX):

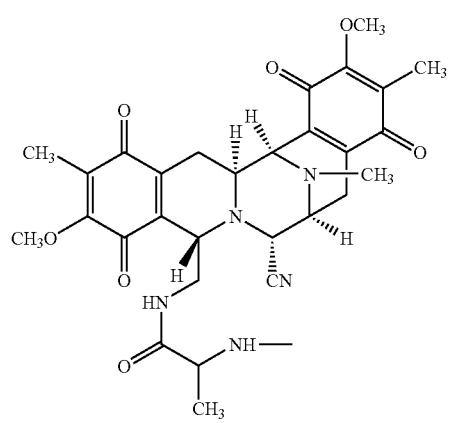

Type I aromatic rings are seen in saframycins A, B and C; G and H; and S isolated from *Streptomyces lavendulae* as minor components. A cyano derivative of saframycin A, called cyanoquinonamine, is known from Japanese Kokai JP-A2 59/225189 and 60/084,288. Saframycins $Y_3$, $Yd_1$, $Ad_1$, and $Yd_2$ were produced by *S. lavendulae* by directed biosynthesis, with appropriate supplementation of the culture medium. Saframycins $Y_{2b}$ and $Y_{2b-d}$ dimers formed by linking the nitrogen on the C-25 of one unit to the C-14 of the other, have also been produced in supplemented culture media of *S. lavendulae*. Saframycins $AR_1$ (=$AH_2$,), a microbial reduction product of saframycin A at C-25 produced by *Rhodococcus amidophilus*, is also prepared by nonstereoselective chemical reduction of saframycin A by sodium borohydride as a 1:1 mixture of epimers followed by chromatographic separation [the other isomer $AH_1$ is less polar]. The further reduction product saframycin $AR_3$. 21-decyano-25-dihydro-saframycin A. (=25-dihydrosaframycin B) was produced by the same microbial conversion. Another type of microbial conversion of saframycin A using a *Nocardia* species produced saframycin B and further reduction by a *Mycobacterium* species produced saframycin $AH^1Ac$. The 25-O-acetates of saframycin $AH_1$ and $AH_1$ have also been prepared chemically for biological studies.

Type I compounds of formula (X) have also been isolated from marines sponges, see Table II.

TABLE II

Structures of Type I Compounds from Marine Sponges.

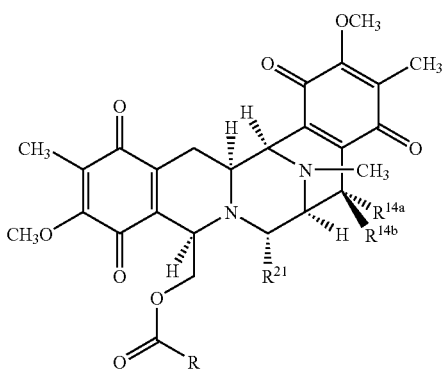

| | Substituents | | | |
|---|---|---|---|---|
| | $R^{14a}$ | $R^{14b}$ | $R^{21}$ | R |
| renieramycin A | OH | H | H | —C(CH$_3$)=CH—CH$_3$ |
| renieramycin B | OC$_2$H$_5$ | H | H | —C(CH$_3$)=CH—CH$_3$ |
| renieramycin C | OH | O | O | —C(CH$_3$)=CH—CH$_3$ |
| renieramycin D | OC$_2$H$_5$ | O | O | —C(CH$_3$)=CH—CH$_3$ |
| renieramycin E | H | H | OH | —C(CH$_3$)=CH—CH$_3$ |
| renieramycin F | OCH$_3$ | H | OH | —C(CH$_3$)=CH—CH$_3$ |
| xestomycin | OCH$_3$ | H | H | —CH$_3$ |

Renieramycins A-D were isolated from the antimicrobial extract of a sponge, a *Reniera* species collected in Mexico, along with the biogenetically related monomeric isoquinolines renierone and related compounds. The structure of renieramycin A was initially assigned with inverted stereochemistry at C-3, C-11, and C-13. However, careful examination of the $^1$H NMR data for new, related compounds renieramycins E and F, isolated from the same sponge collected in Palau, revealed that the ring junction of renieramycins was identical to that of saframycins. This result led to the conclusion that the formerly assigned stereochemistry of renieramycins A to D must be the same as that of saframycins.

Xestomycin was found in a sponge, a *Xestospongia* species collected from Sri Lancan waters.

Type II compounds of formula (XI) with a reduced hydroquinone ring include saframycins D and F, isolated from *S. lavendulae*, and saframycins Mx-1 and Mx-2, isolated from *Myxococcus xanthus*. See table III.

TABLE III

Type II Compounds

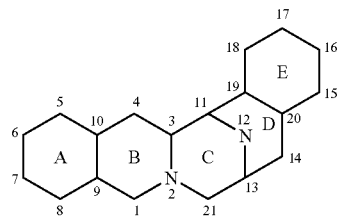

| Compound | Substituents | | | | | |
|---|---|---|---|---|---|---|
| | $R^{14a}$ | $R^{14b}$ | $R^{21}$ | $R^{25a}$ | $R^{25b}$ | $R^{25c}$ |
| saframycin D | O | O | H | O | O | $CH_3$ |
| saframycin F | O | O | CN | O | O | $CH_3$ |
| saframycin Mx-1 | H | $OCH_3$ | OH | H | $CH_3$ | $NH_2$ |
| saframycin Mx-2 | H | $OCH_3$ | H | H | $CH_3$ | $NH_2$ |

The type III skeleton is found in the antibiotics safracins A and B, isolated from cultured *Pseudomonas fluorescens*. These antibiotics of formula (XII) consist of a tetrahydroisoquinoline-quinone subunit and a tetrahydroisoquninolinephenol subunit.

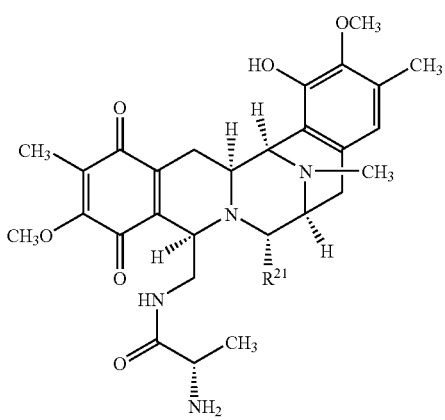

where $R^{21}$ is —H in safracin A and is —OH in safracin B.

Saframycin R, the only compound classified as the Type IV skeleton, was also isolated from *S. lavendulae*. This compound of formula (XIII), consisting of a hydroquinone ring with a glycolic ester sidechain on one of the phenolic oxygens, is conceivably a pro-drug of saframycin A because of its moderate toxicity.

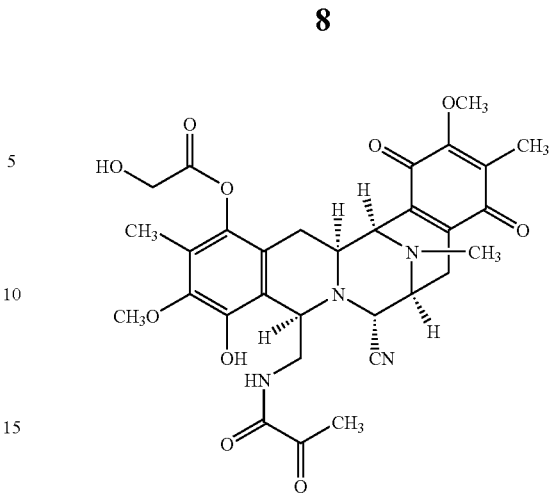

All these known compounds have a fused system of five rings (A) to (E) as shown in the following structure of formula (XIV):

The rings A and E are phenolic in the ecteinascidins and some other compounds, while in other compounds, notably the saframycins, the rings A and E are quinolic. In the known compounds, the rings B and D are tetrahydro, while ring C is perhydro.

SUMMARY OF THE INVENTION

The present invention provides new compounds with the fused system of five rings (A) to (E). In particular, it provides new compounds which can be made from intermediates described in WO 9812198 or by a new process which is part of this invention. In this latter respect, we refer to our WO 0069862 published 23 Nov. 2000, and which relates to hemi-synthetic methods and new compounds. The present application claims priority from that PCT filing, and we incorporate that text by reference to the extent that there is disclosure therein which is not in the present specification.

In WO 0069862, various routes are described for the preparation of ecteinascidin compounds, including ecteinascidin 743, as well as ecteinascidin analogs including phthaliscidin. The present invention is founded partly on the use of intermediates of WO 0069862 to prepare further analogs of the ecteinasacidins.

PREFERRED EMBODIMENTS

We have found that compounds of the invention have exceptional activity in the treatment of cancers, such as leukaemias, lung cancer, colon cancer, kidney cancer and melanoma.

Thus, the present invention provides a method of treating any mammal, notably a human, affected by cancer which comprises administering to the affected individual a therapeutically effective amount of a compound of the invention, or a pharmaceutical composition thereof.

The present invention also relates to pharmaceutical preparations, which contain as active ingredient a compound or compounds of the invention, as well as the processes for their preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the compounds or compositions of the present invention may be by any suitable method, such as intravenous infusion, oral preparations, intraperitoneal and intravenous administration. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);

b) antimetabolite drugs such as 5-fluorouracil, cytarabine, gemcitabine, purine analogues such as pentostatin, methotrexate);

c) alkylating agents such as nitrogen mustards (such as cyclophosphamide or ifosphamide);

d) drugs which target DNA such as the antracycline drugs adriamycin, doxorubicin, pharmorubicin or epirubicin;

e) drugs which target topoisomerases such as etoposide;

f) hormones and hormone agonists or antagonists such as estrogens, antiestrogens (tamoxifen and related compounds) and androgens, flutamide, leuprorelin, goserelin, cyprotrone or octreotide;

g) drugs which target signal transduction in tumour cells including antibody derivatives such as herceptin;

h) alkylating drugs such as platinum drugs (cis-platin, carbonplatin, oxaliplatin, paraplatin) or nitrosoureas;

i) drugs potentially affecting metastasis of tumours such as matrix metalloproteinase inhibitors;

j) gene therapy and antisense agents;

k) antibody therapeutics;

l) other bioactive compounds of marine origin, notably the didemnins such as aplidine;

m) steroid analogues, in particular dexamethasone;

n) anti-inflammatory drugs, in particular dexamethasone;

o) anti-emetic drugs, in particular dexamethasone;

p) skeletal muscle protectors, such as L-carnitine or precursor amino acids.

The present invention also extends to the compounds of the invention for use in a method of treatment, and to the use of the compounds in the preparation of a composition for treatment of cancer.

In one aspect of the invention, we make no claim to the compounds 2, 3, 5, 8-OH-2, and 14 to 21 described in one or more of the GB priority patent applications for our PCT application published as 0069862. In a related aspect, the present invention extends to compounds which differ in respect of one or more of the substituents present at C-1, C-5, C-7, C-8, or C-18 in the compounds of these GB priority patent applications.

The compounds of this invention include compounds which do not have a hydroxy group at the C-18 position. Furthermore, the compounds of this invention include compounds which do not have a dicarboximidomethyl substituent, such as phthalimidomethyl, at the C-1 position. In particular, we provide active compounds where the subsituent $X_1$ is not as shown in the penultimate line at page 19 of WO0018233.

In one aspect, the analogs of this invention are typically of the formula (XVIIa):

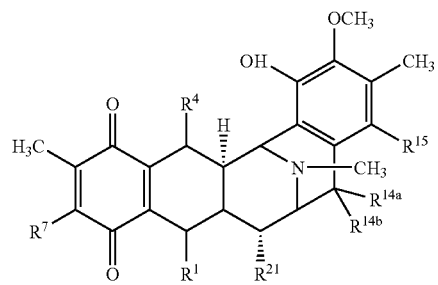

or formula (XVIIb):

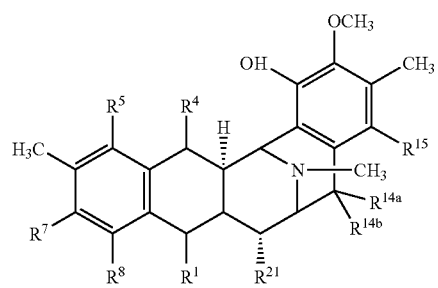

where $R^1$ is an optionally protected or derivatised aminomethylene group, an optionally protected or derivatised hydroxymethylene group;

$R^4$ is —H;

$R^5$ is —H or —OH;

$R^7$ is —OCH$_3$ and $R^8$ is —OH or $R^7$ and $R^8$ together form a group —O—CH$_2$—O—;

$R^{14a}$ and $R^{14b}$ are both —H or one is —H and the other is —OH, —OCH$_3$ or —OCH$_2$CH$_3$—, or $R^{14a}$ and $R^{14b}$ together form a keto group; and $R^{15}$ is —H or —OH;

$R^{21}$ is —H, —OH or —CN;

and derivatives including acyl derivatives thereof especially where $R^5$ is acetyloxy or other acyloxy group of up to 4 carbon atoms.

In the present invention, a key class of products includes phthalascidin and has the general formula (XX):

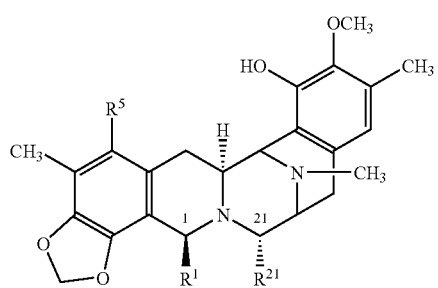

where $R^1$ is an amidomethylene group; $R^5$ is a small oxysidechain; and $R^{21}$ is a cyano group or a hydroxy group. For phthalascidin, $R^1$ is a phthalimidomethylene group; $R^5$ an acetoxy group; and $R^{21}$ is a cyano group. Other groups for $R^1$ include mono- and di-N-substituted amidomethylenes as well as other cyclic amidomethylenes, and other groups for $R^5$ include further C$_1$-C$_4$ acyl groups, as well as C$_1$-C$_4$ alkyl groups.

In the present invention, a key class of intermediates and analogs includes Intermediate 11 and has the general formula (XXI):

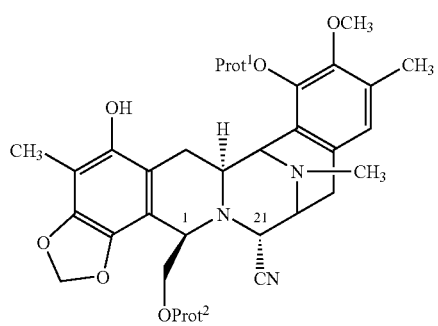

where Prot$^1$ and Prot$^2$ are hydroxy protecting groups, preferably different. For Intermediate 11 itself, the group Prot$^1$ is a methoxymethyl group, and Prot$^2$ is a t-butyldiphenylsilyl group.

In the light of the preceding explanations, it can be seen that the present invention provides novel analogs and novel intermediate compounds. Depending on ring A, the compounds include those of formula (XXIIa):

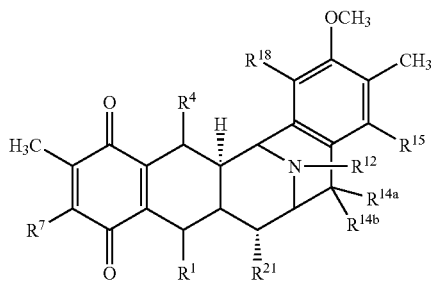

or of formula (XXIIb):

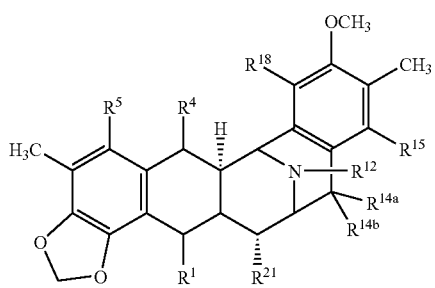

where:

$R^1$ is —CH$_2$NH$_2$ or —CH$_2$OH, or a protected or derivatised version of such a group and $R^4$ is —H;

$R^5$ is —OH or a protected or derivatised version of such a group;

$R^{14a}$ and $R^{14b}$ are both —H or one is —H and the other is —OH or a protected or derivatised version of such a group, —OCH$_3$ or —OCH$_2$CH$_3$, or $R^{14a}$ and $R^{14b}$ together form a keto group;

$R^{12}$ is —H—, —CH$_3$— or —CH$_2$CH$_3$—;

$R^{15}$ is —H, —OH or a protected or derivatised version of such a group; and $R^{18}$ is —OH or a protected or derivatised version of such a group.

In one embodiment, preferably at least of $R^1$, $R^5$, $R^{14a}$, $R^{14b}$, $R^{15}$ or $R^{18}$ is a protected or derivatised group.

In one variation of this invention, the group $R^1$ is not a tert-butyldiphenylsilyl substituent and/or the group $R^{18}$ is not a methoxymethyloxy group.

Preferably $R^1$ is —CH$_2$NH$_2$ or —CH$_2$OH, or a protected or derivatised version of such a group and $R^4$ is —H.

Preferably $R^{14a}$ and $R^{14b}$ are both —H.

Preferably $R^{12}$ is CH$_3$.

One preferred class of intermediates includes the compound which we identify as compound 25, of formula:

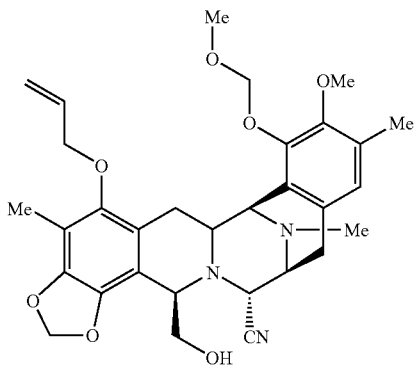

The preferred class is thus of the general formula where the group MOM is replaced by any other protecting group, and/or the allyl is replaced by any other protecting group.

Other preferred intermediates includes the compounds which we identify as compounds 17, 43 and 45.

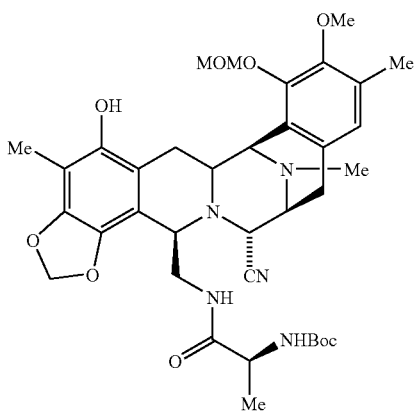

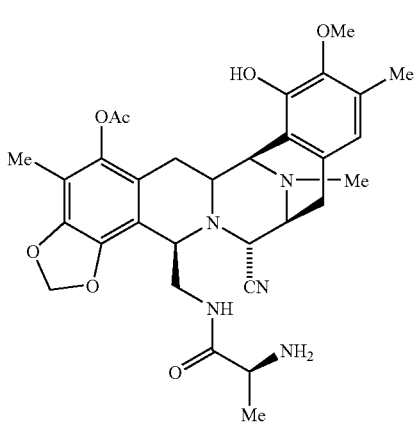

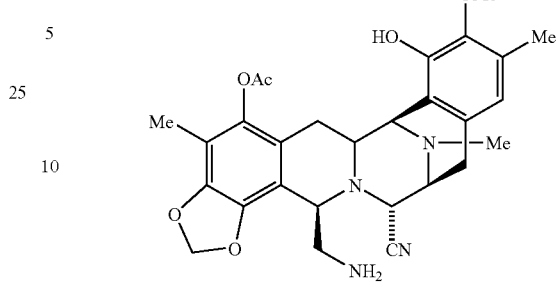

Other N-acyl derivatives may readily be made from compound 45 and are an important part of this invention. Suitable acyl groups include those previously mentioned. The corresponding 21-hydroxy compounds are also useful and are among the active compounds which we have found.

From the activity data and other considerations, it can be seen that the active compounds of this invention include a preferred class of compounds of the general formula (XXIII):

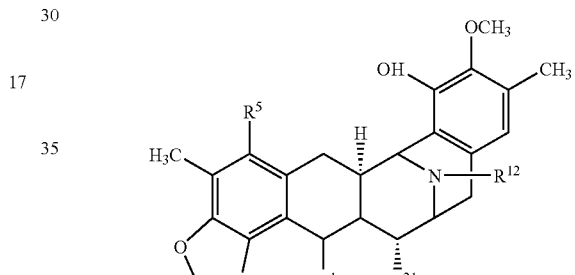

where $R^1$ is as previously defined for formula (XVIIb) and is preferably a derivatised aminomethylene group of moderate bulk;

$R^5$ is as previously defined for formula (XVIIb) and is preferably a derivatised hydroxy group of low bulk;

$R^{12}$ is as previously defined and is preferably —$CH_3$—; and $R^{21}$ is a hydroxy or cyano group.

$R^1$ is suitably a hydrophobic group and which thus lacks free amino, hydroxy or other hydrophilic function. Typically $R^1$ is a group —$CH_2$—$NH_2$—CO—$R^a$, where $R^a$ is as defined but preferably has a linear chain length of less than 20 atoms, more preferably less than 15 or 10 atoms, where a 1,4-phenyl is counted as a chain length of four atoms and similar considerations apply to other cyclic groups (for example, 1,2-cyclohexyl is chain length of two), and the linear chain of less than 10, 15 or 20 atoms can itself be substituted. In particular, the data suggests there is a balance to be achieved between having no such group $R^a$—CO— and having a large, bulky group.

In one variation, we prefer that $R^1$ is free from cyclic groups, especially aromatic groups. In a related variation, the present invention does not prepare the compounds which are described in the article Proc. Natl. Acad. Sci. USA, 96, 3496-3501, 1999, incorporated by reference. Our preferred groups for $R^1$ exclude the corresponding substituents $CH_2R_2$ shown in Table 1 of that article, specifically the groups A, B, C and D for $R_2$.

$R^5$ is preferably an acetyl group.

In particularly preferred compounds, the group $R^1$ is acylated on an —$NH_2$ group, and for example N-acyl derivatives can be formed from groups —$CH_2NH_2$ and —$CH_2$—NH-aa. The acyl derivatives can be N-acyl or N-thioacyl derivatives thereof. The acyl groups can be of formula —CO—$R^a$, where $R^a$ is as defined and is chosen to meet the indicated criteria. Suitable acyl groups include alanyl, arginyl, aspartyl, asparagyl, cystyl, glutamyl, glutaminyl, glycyl, histidyl, hydroxyprolyl, isoleucyl, leucyl, lysyl, methionyl, phenylalanyl, prolyl, seryl, threonyl, thyronyl, tryptophyl, tyrosyl, valyl, as well as other amino acid acyl groups, which may be L- or D-. Such amino acid acyl groups are preferred derivatised on the amino group to give hydrophobicity.

In a variation, the group $R^1$ is a derivatised hydroxymethylene group. Similar considerations apply as with the derivatised aminomethylene group.

The invention extends to compounds where the various substituents around the ring are as defined in the WO 0018233, which we incorporate by reference. Thus, as appropriate, substituents in the present compounds can be chosen, among other possibilites from H, OH, OR', SH, SR', SOR', $SO_2R'$, $NO_2$, $NH_2$, NHR', $N(R')_2$, NHC(O)R', CN, halogen, =O, $C_1$-$C_6$ alkyl, substituted or unsubstituted aryl, substituted or unsubstituted aralkyl, and substituted or unsubstituted heteroaromatic;

wherein each of the R' groups is independently selected from the group consisting of H, OH, $NO_2$, $NH_2$, SH, CN, halogen, =O, C(=O)H, C(=O)$CH_3$, $CO_2H$, $CO_2CH_3$, $C_1$-$C_6$ alkyl, phenyl, benzyl and heteroaromatic.

Suitable halogen substituents in the compounds of the present invention include F, Cl, Br and I.

Alkyl groups preferably have from 1 to about 12 carbon atoms, more preferably 1 to about 8 carbon atoms, still more preferably 1 to about 6 carbon atoms, and most prefereably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms, more preferably 2 to about 8 carbon atoms, still more prefereably 2 to about 6 carbon atoms, even more prefereably 1, 2, 3 or 4 carbon atoms. The terms alkenyl and alkynyl as used herein refere to both cyclic and noncyclic groups, although straight or branched noncyclic groups are generally more preferred.

Preferred alkoxy groups in the compounds of the present invention include groups having one or more oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more thioether linkages and from 1 to about 12 carbon atoms, more prefereably from 1 to about 8 carbon atoms, and still more preferably 1 to about 6 carbon atoms. Alkylthio groups having 1, 2, 3 or 4 carbon atoms are particularly preferred.

Preferred alkylsulfinyl groups in the compounds of the present invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred.

Preferred alkylsulfonyl groups in the compounds of the present invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, finyl, pyrrolyl, thienyl, thiazolyl, oxazolyl, imidazolyl, indolyl, benzofuranyl and benzothiazol. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolindinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic arykl groups include phenyl including substituted phenyl, such as 2-substituted phenyl, 3-substituted phenyl, 2,3-substituted phenyl, 2,5-substituted phenyl, 2,3,5-substituted and 2,4,5-substituted phenyl, including where one or more of the phenyl substituents is an electron-withdrawing group such as halogen, cyano, nitro, alkanoyl, sulfinyl, sulfonyl and the like; naphthyl including 1-naphthyl and 2-naphthyl; biphenyl; phenanthryl; and anthracyl.

Any references herein to substituted groups in the compounds of the present invention refer to the specified moiety that may be substituted at one or more available positions by one or more suitable groups, e.g., halogen such as fluoro, chloro, bromo and iodide; cyano; hydroxyl; nitro; azido; alkanoyl such as a C1-6 alkanoyl group such as acyl and the like; carboxamido; alkyl groups including those groups having 1 to about °2 carbon atoms or from 1 to about 6 carbon atoms and more preferably 1-3 carbon atoms; alkenyl and alkynyl groups including groups having one or more unsaturated link-ages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbo atoms; alkylsulfinyl groups including those moieties having one or more sulfinyl linkages and from 1 to about 12 carbon atoms or from 1 to about 6 carbon atoms; alkylsulfinyl groups including those moieties having one or more sulfonyl link-ages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocyclic aryl having 6 or more carbons, particularly phenyl (e.g., R being a substituted or unsubstituted biphenyl moiety); and aralkyl such as benzyl.

Without being exhaustive, in terms of the formula:

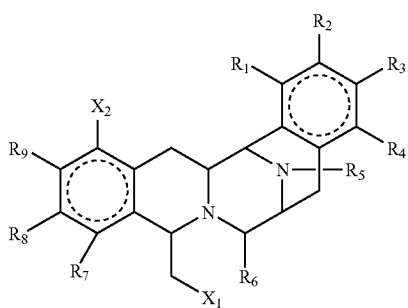

preferred compounds of this invention have one or more of the following definitions:

$R_1$ is —OR, where R is H, acyl, especially acetyl, alkyl-CO— (alkyl being up to about 20 carbon atoms, more preferably from 1 to about 12 carbon atoms, and especially an odd number of carbon atoms such as 3, 5, 7 and 9), cycloalkyl-alkyl-CO— and especially alkyl groupings with a terminal cyclohexyl group and up to six additional carbon atoms in the sidechain, or a protecting group, especially methoxymethyl, and $R_1$ is more especially OH.

$R_2$ is methoxy.

$R_3$ is methyl.

$R_4$ is hydrogen.

$R_5$ is methyl or hydrogen, especially methyl.

$R_6$ is —CN or —OH.

$X_1$ is —NHR', —NH-aa-R' or —OR' where aa is an optionally protected amino acid acyl group, especially alanine, phenylalanine, cysteine, proline, valine, arginine, tryptophan or other amino acid. Other possibilities for $X_1$ include —N(R')$_2$, —N(R')-aa-R', and —N-(aa-R')$_2$. In the case of any group -aa-R', the R' is usually on the amino group of the amino acid, and there may be two such substituents. R' is preferably H; alkyl-CO— (alkyl being up to 25 carbon atoms, such as up to 17, 19 or 21 carbon atoms and preferably an odd number of carbon atoms corresponding to a fatty acid carboxylic acid of even number of carbon atoms or else a low number of carbon atoms such as 1 to 6), especially $CH_3$—$(CH_2)_n$—CO— where n is for example 1, 2, 4, 12 or 16; alkenyl, especially allyl; haloalkyl-CO—, especially $CF_3$—CO—; cycloalkyl-alkyl-CO—, preferably alkyl groupings with a terminal cyclohexyl group and up to six additional carbon atoms in the sidechain, especially cyclohexyl-($CH_2$), —CO— where n is for example 1 or 2; haloalkyl-O—CO—, especially trichloroethoxycarbonyl; arylalkyl-CO— or arylalkenyl-CO— especially phenyl-methyl/ethyl/vinyl-CO—, where aryl may be substituted as in trifluoromethylcinnamoyl; optionally substituted heteroaryl-CO—, where the substituents and heterocyclic group are as elsewhere discussed, as in 2-chloronicotinoyl; alkenyl-CO— especially crotonyl; optionally substituted aminoalkyl-CO—, particularly amino acid acyl, especially alanine, phenylalanine, cysteine, proline, valine, arginine, tryptophan or other amino acid, or a derivative thereof, as in Boc-phenylalanine, valine, proline, arginine or tryptophan, or as in phenethylalanine, trifluoroethylacetylalanine, trifluorodiacetylalanine and isomers thereof, or diacetyl- or dipropionyl-trifluoroacetyl, or as in or as in Cbz-Val- or a group notionally derived from cysteine and being of general formula Prot$^{SH}$-S—$CH_2$—C(=NOProt$^{OH}$)-CO— or Prot$^{SH}$-S—CH=C(—OProt$^{OH}$)-CO—, where Prot$^{SH}$ and Prot$^{OH}$ are protecting groups for thiol and for hydroxy, especially where Prot$^{SH}$ is Fm and Prot$^{OH}$ is methoxy for the first formula or MOM for the second formula; or other possibilities such as a protecting group as in an alkoxycarbonyl such as Boc, or PhNR'CS. The various groups may be susbtituted as indicated elsewhere in this specification.

$R_7$ and $R_8$ are —O—$CH_2$—O— or $R_7$ is =O and $R_8$ is OMe, especially $R_7$ and $R_8$ are —O—$CH_2$—O—

$R_9$ is methyl.

$X_2$ is —OR", where R" is preferably H; alkyl-CO—, especially acetyl; alkenyl especially allyl; alkenyl-O—CO—, especially allyl-O—CO—; haloalkyl-CO—, especially trifluoromethylcarbonyl or chloromethylcarbonyl or 2-chloroethylcarbonyl or perfluoropropylcarbonyl.

Of special interest are compounds wherein:

$R_1$ is —OR, where R is H or acetyl, alkyl-CO—, especially n-propyl-CO—, and $R_1$ is more especially OH.

$R_2$ is methoxy.

$R_3$ is methyl.

$R_4$ is hydrogen.

$R_5$ is methyl.

$R_6$ is —CN or —OH.

$X_1$ is —NHR', where R' is preferably alkenyl, especially allyl, alkyl-CO— (alkyl being 1 to 6 carbon atoms, especially $CH_3$—$(CH_2)_n$—CO— where n is for example 1 to 6, and more especially 1 to 4); cycloalkyl-alkyl-CO—, especially cyclohexyl-($CH_2$), —CO where n is 1 or 2; arylalkyl-CO— or arylalkenyl-CO— especially phenethylcarbonyl, phenylvinylcarbonyl or benzylcarbonyl, alkenyl-CO— especially $CH_3$—CH=CH—CO—; amino acid acyl, especially Cbz-Val-; optionally substituted heteroaryl-CO—, especially 2-chloropyridinylcarbonyl;

or $X_1$ is —NH-aa-R' where aa is alanine, phenylalanine, tryptophan or valine; R' is an amino subsituent and is arylalkyl-CO— especially phenethylcarbonyl or benzylcarbonyl; alkyl-CO— (alkyl being 1 to 6 carbon atoms, especially $CH_3$—$(CH_2)$n-CO— where n is for example 1 to 6 and more especially 1, 2 or 4; alkenyl-CO— especially $CH_3$—CH=CH—CO—; or protecting group especially alkyloxy-CO as in Boc;

or $X_1$ is —OR' where R' is preferably alkyl-CO— (alkyl being 1 to 6 carbon atoms, especially $CH_3$—$(CH_2)$n-CO— where n is for example 1 to 6, and more especially 2; arylalkyl-CO— or arylalkenyl-CO— especially phenethylcarbonyl, phenylvinylcarbonyl or trifluoromethylcinnamoyl.

$R_7$ and $R_8$ are —O—$CH_2$—O—.

$R_9$ is methyl.

$X_2$ is —OR", where R" is H; acetyl, allyloxycarbonyl, chloromethylcarbonyl or perfluoropropylcarbonyl; and R" is more especially H; acetyl or allyloxycarbonyl.

Especially preferred embodiments of the present invention are the novel ecteinascidin-like compounds with the following general structures I, II and III that have been prepared from compounds 17, 25, 43 and 45 derived from cyanosafracin B. Compound 25 corresponds to the synthetic intermediate 3 described in U.S. Pat. No. 6,124,292.

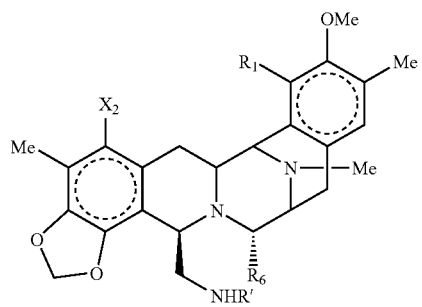
(I)

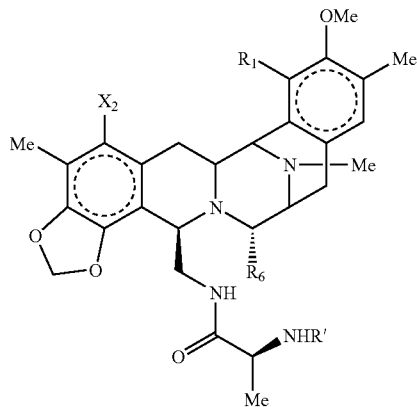
(II)

-continued

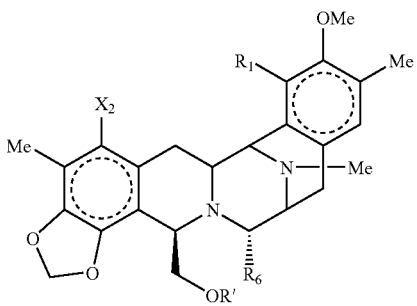
(III)

Wherein R', $X_2$, $R_1$ and $R_6$ are each independently selected from the groups defined below:

| R' | $X_2$ | $R_1$ | $R_6$ |
|---|---|---|---|
| H | OH | OH | CN |
| $CH_2CH=CH_2$ | OAc | OAc | OH |
| $COCH_2CH_3$ | $OCH_2CH=CH_2$ | OMOM | |
| $COCH_2CH_2CH_3$ | $OCOOCH_2CH=CH_2$ | $OCOCH_2C_6H_{11}$ | |
| $CO(CH_2)_4CH_3$ | $OCOCF_3$ | $OCOCH_2CH_2C_6H_{11}$ | |
| $CO(CH_2)_{12}CH_3$ | $OCOCH_2Cl$ | $OCOCH_2CH_2CH_3$ | |
| $CO(CH_2)_{16}CH_3$ | $OCOCH_2CH_2Cl$ | $OCO(CH_2)_4CH_3$ | |
| $COCH_2C_6H_{11}$ | $OCOCF_2CF_2CF_3$ | $OCO(CH_2)_8CH_3$ | |
| $COCH_2CH_2C_6H_{11}$ | | $OCO(CH_2)_{16}CH_3$ | |
| $COOCH_2CCl_3$ | | | |
| $COCH_2Ph$ | | | |
| $COCH_2CH_2Ph$ | | | |
| $COCH=CHCH_3$ | | | |
| $COCH=CHPh$ | | | |
| $COCH=CHArCF_3$ | | | |
| $COCH(CH_3)NHCOCH_2CH_2Ph$ | | | |
| CO—(S)—$CH(CH_3)NHCOCF_3$ | | | |
| CO—(R)—$CH(CH_3)NHCOCF_3$ | | | |
| CO—(S)—$CH(NHCbz)CH(CH_3)_2$ | | | |
| Boc | | | |
| CSNHPh | | | |

-continued

| R' | X₂ | R₁ | R₆ |
|---|---|---|---|

[Structure: acetyl group with NHBoc and benzyl (Ph) substituent]

[Structure: acetyl group with NHBoc and isopropyl substituent]

[Structure: acetyl-pyrrolidine with N-Boc]

[Structure: acetyl group with NHBoc and side chain –(CH₂)₃–NH–C(=NH)–NH₂ (arginine-like)]

[Structure: acetyl group with NHBoc and indolylmethyl (tryptophan-like) substituent]

[Structure: acetyl-(2-chloro-3-pyridyl)]

In the formulae (XVIIa) or (XVIIb), $R^1$ is typically aminomethylene, amidomethylene or $R^1$ with $R^4$ forms a group (IV) or (V). Suitable amidomethylene groups include those of formula —$CH_2$—NH—CO—$CHCH_3$—$NH_2$ derived from alanine, and similar groups derived from other amino acids, notably, both D and L, glycine, valine, leucine, isoleucine, phenylalanine, tyrosine, tryptophan, methionine, cysteine, aspartate, asparagine, glutamatic acid, glutamine, lysine, arginine, proline, serine, threonine, histidine and hydroxyproline. A general formula for the group $R^1$ is then —$CH_2$—NH-aa, where aa indicates an acyl amino acid group.

The group $R^1$ can be acylated on an —$NH_2$ group, and for example N-acyl derivatives can be formed from groups —$CH_2NH_2$ and —CH, —NH-aa. The acyl derivatives can be N-acyl or N-thioacyl derivatives thereof, as well as cyclic amides. The acyl groups can illustratively be alkanoyl, haloalkanoyl, arylalkanoyl, alkenoyl, heterocyclylacyl, aroyl, arylaroyl, haloaroyl, nitroaroyl, or other acyl groups. The acyl groups can be of formula —CO—$R^a$, where $R^a$ can be various groups such as alkyl, alkoxy, alkylene, arylalkyl, arylalkylene, amino acid acyl, or heterocyclyl, each optionally substituted with halo, cyano, nitro, carboxyalkyl, alkoxy, aryl, aryloxy, heterocyclyl, heterocyclyloxy, alkyl, amino or substituted amino. Other acylating agents include isothiocyanates, such as aryl isothiocyanates, notably phenyl isocyanate. The alkyl, alkoxy or alkylene groups of $R^a$ suitably have 1 to 6 or 12 carbon atoms, and can be linear, branched or cyclic. Aryl groups are typically phenyl, biphenyl or naphthyl. Heterocyclyl groups can be aromatic or partially or completely unsaturated and suitably have 4 to 8 ring atoms, more preferably 5 or 6 ring atoms, with one or more heteroatoms selected from nitrogen, sulphur and oxygen.

Without being exhaustive, typical $R^a$ groups include alkyl, haloalkyl, alkoxyalkyl, haloalkoxyalkyl, arylalkylene, haloalkylarylakylene, acyl, haloacyl, arlyalkyl, alkenyl and amino acid. For example, $R^a$—CO— can be acetyl, trifluoroacetyl, 2,2,2-trichloroethoxycarbonyl, isovalerylcarbonyl, trans-3-(trifluoromethyl)cinnamoylcarbonyl, heptafluorobutyrylcarbonyl, decanoylcarbonyl, trans-cinnamoylcarbonyl, butyrylcarbonyl, 3-chloropropyonylcarbonyl, cinnamoylcarbonyl, 4-methylcinnamoylcarbonyl, hydrocinnamoylcarbonyl, or trans-hexenoylcarbonyl, or alanyl, arginyl, aspartyl, asparagyl, cystyl, glutamyl, glutaminyl, glycyl, histidyl, hydroxyprolyl, isoleucyl, leucyl, lysyl, methionyl, phenylalanyl, prolyl, seryl, threonyl, thyronyl, tryptophyl, tyrosyl, valyl, as well as other less common amino acid acyl groups, as well as phthalimido and other cyclic amides. Other examples may be found among the listed protecting groups.

Compounds wherein —CO—$R^a$ is derived from an amino acid and include an amino group can themselves form acyl derivatives. Suitable N-acyl commands include dipeptides which in turn can form N-acyl derivatives.

In an important aspect of this invetnion, there are provided preferred compounds of the formula:

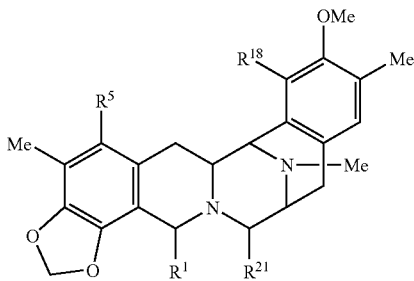

wherein:

$R^1$ is —$CH_2$—$N(R^a)_2$ or —$CH_2$—$OR^a$, where $R^a$ is H; alkyl-CO—; haloalkyl-CO—; cycloalkylalkyl-CO—; haloalkyl-O—CO—; arylalkyl-CO—; arylalkenyl-CO—; heteroaryl-CO—; alkenyl-CO—; alkenyl; amino acid acyl; or a protecting group;

$R^5$ is —OR", where R" is H; alkyl-CO—; cycloalkyl-CO—; haloalkyl-CO— or a protecting group;

$R^{18}$ is —OR, where R is H, alkyl-CO—; cycloalkylalkyl-CO—; or a protecting group;

$R^{21}$ is —CN or —H.

Typically such a compound is of the formula:

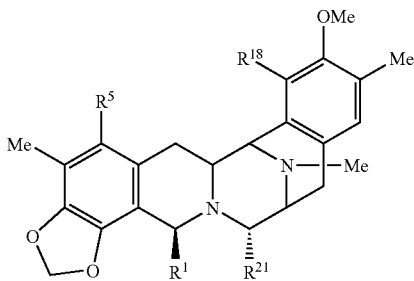

wherein $R^1$, $R^5$, $R^{18}$, and $R^{21}$ are as defined.

In such preferred compounds of this invention, $R^1$ can be —$CH_2$—$NHR^a$.

$R^a$ can be -aa-$R^b$ where aa is amino acid acyl and $R^b$ is as defined for $R^a$. The amino acid acyl is optionally further substituted with one or more $R^a$ groups.

In further preferred comopunds, $R^1$ is —$CH_2$—NH-aa-$R^b$ where aa is an amino acid and $R^b$ is hydrogen; protecting group; arylalkenyl-CO—; haloalkyl-CO—; alkyl-CO—; arylalkyl-CO—; or amino acid acyl. Such comopunds include those wherein $R^1$ is CH, —NH-aa-$R^b$ where aa is alanine and $R^b$ is hydrogen, Boc, PhNHCS—, $CF_3CO$—, PhNAcCS—, trifluorocinnamoyl, cinnamoyl, $C_3F_7CO$—, butyryl, 3-chloroproprionoyl, hydrocinnamoyl, hexanoyl, phenylacetyl, Cbz-val or acetyl; —$CH_2$-aa-$R^b$ where aa is valine and $R^b$ is Cbz or Boc; —$CH_2$-aa-$R^b$ where aa is phenylalanine and $R^b$ is Boc; —$CH_2$-aa-$R^b$ where aa is proline and $R^b$ is Boc; —$CH^2$-aa-$R^b$ where aa is arginine and $R^b$ is Boc; or $CH^2$-aa-$R^b$ where aa is tryptophan and $R^b$ is Boc.

$R^1$ can be —$CH_2$—$NR^a$-aa-$R^b$ where aa is an amino acid, $R^a$ is alkyl-CO— and $R^b$ is haloalkyl-CO—. Such compounds include those wherein $R^1$ is —$CH_2$—$NR^a$-aa-$R^b$ where aa is acetylalanine, $R^a$ is acetyl or butyryl, and $R^b$ is $CF_3$—CO—.

$R^1$ can be —$CH_2$—$NHR^a$ where $R^a$ is hydrogen, protecting group, alkyl-CO—, alkenyl-CO—; arylalkenyl-CO—; arylalkyl-CO—; heteroaryl-CO—; cycloalkylalkyl-CO—; or alkenyl. Such compounds include those wherein $R^1$ is —$CH^2$—$NHR^a$ where $R^a$ is hydrogen. Troc, acetyl; isovaleroyl, decanoyl, cinnamoyl, hydrocinnamoyl, phenylacetyl, propionyl, myristoyl, stearoyl, hexanoyl, crotonyl, chloronicotinoyl, cyclohexylacetyl, cyclohexylpropionyl or allyl.

$R^1$ can be —$CH_2$—$OR^a$ where $R^a$ is hydrogen; a protected cysteine; a cysteine derivative of the formula $Prot^{SH}$-S—$CH_2$—C(NH$Prot^{NH}$)-CO—, where $Prot^{SH}$ and $Prot^{NH}$ are protecting groups for thiol and for amino; a protecting group; alkyl-CO—; arylalkyl-CO—; arylalkenyl-CO—;

a cysteine derivative of the formula $Prot^{SH}$-S—$CH_2$—C(=NO$Prot^{OH}$)-CO— where $Prot^{SH}$ and $Prot^{OH}$ are protecting groups for thiol and for hydroxy; or a cysteine derivative of formula $Prot^{SH}$-S—CH=C(—O$Prot^{OH}$)-CO—, where $Prot^{SH}$ and $Prot^{OH}$ are protecting groups for thiol and for hydroxy. Such compounds include those wherein $R^1$ is —$CH^2$—$OR^a$ where $R^a$ is hydrogen; S—Fm—O-TBDMS-cysteine; a cysteine derivative of the formula $Prot^{SH}$-S—$CH_2$—C(NH$Prot^{NH}$)-CO—, where $Prot^{SH}$ is Fm and $Prot^{OH}$ is Troc; TBDPS; butyryl; trfiluormethylcinnamoyl; cinnamoyl; hydrocinnamoyl; a cysteine derivative of the formula $Prot^{SH}$-S—$CH_2$—C(=NO$Prot^{OH}$)-CO— where $Prot^{SH}$ is Fm and $Prot^{OH}$ is methoxy; or a cysteine derivative of formula $Prot^{SH}$-S—CH=C(—O$Prot^{OH}$)-CO—, where $Prot^{SH}$ is Fm and $Prot^{OH}$ is MOM.

In these preferred compounds, $R^5$ is suitably —OR", where R" is H; alkyl-CO where the alkyl has an odd number of carbon atoms. ω-cyclohexylalkyl-CO—; or a protecting group.

In these preferred compounds, $R^{18}$ is suitably —OR, where R is H, alkyl-CO—; or a protecting group;

In one variation which relates to intermediate products, the ring A is modified to incorporate the substructure shown as formula (XX) or (XXI), discussed later.

In another variation relating to intermediates, the group $R^1$ can be —$CH_2O$—CO—CFu-$CH_2$—S-$Prot^3$, derived from a compound of formula (XIX), where $Prot^3$ and Fu have the indicated meanings. In such a case, $R^7$ and $R^8$ from the oxymethyleneoxy group. The group $R^{18}$ is usually protected. Usually $R^{21}$ is cyano.

Preferably $R^{14a}$ and $R^{14b}$ are hydrogen. Preferably $R^{15}$ is hydrogen. The O-acyl derivatives are suitably aliphatic O-acyl derivatives, especially acyl derivatives of 1 to 4 carbon atoms, and typically an O-acetyl group, notably at the 5-position.

Suitable protecting groups for phenols and hydroxy groups include ethers and esters, such as alkyl, alkoxyalkyl, aryloxyalkyl, alkoxyalkoxyalkyl, alkylsilylalkoxyalkyl, alkyltrioalkyl, arylthioalkyl, azidoalkyl, cyanoalkyl, chloroalkyl, heterocyclic, arylacyl, haloarylacyl, cycloalkylalkyl, alkenyl, cycloalkyl, alyklarylalkyl, alkoxyarylalkyl, nitroarylalkyl, haloarylalkyl, alkylaminocarbonylarylalkyl, alkylsulfinylarylalky, alkylsilyl and other ethers, and arylacyl, aryl alkyl carbonate, aliphatic carbonate, alkylsulfinylarlyalkyl carbonate, alkyl carbonate, aryl haloalkyl carbonate, aryl alkenyl carbonate, aryl carbamate, alkyl phosphinyl, alkylphosphinothioyl, aryl phosphinothioyl, aryl alkyl sulphonate and other esters. Such groups may optionally be substituted with the previously mentioned groups in $R^1$.

Suitable protecting groups for amines include carbamates, amides, and other protecting groups, such as alkyl, arylalkyl, sulpho- or halo-arylalkyl, haloalkyl, alkylsilylalkyl, aryalkyl, cycloalkylalkyl, alkylarylalkyl, heterocyclylalkyl, nitroainlalkyl, acylaminoalkyl, nitroaryldithioarylalkyl, dicycloalkylcarboxamidoalkyl, cycloalkyl, alkenyl, arylalkenyl, nitroarylalkenyl, heterocyclylalkenyl, heterocyclyl, hydroxyheterocyclyl, alkyldithio, alkoxy- or halo- or alkylsulphinyl arylalkyl, hetercyclylacyl, and other carbamates, and alkanoyl, haloalkanoyl, arylalkanoyl, alkenoyl, heterocyclylacyl, aroyl, arylaroyl, haloaroyl, nitroaroyl, and other amides, as well as alkyl, alkenyl, alkylsilylalkoxyalkyl, alkoxyalkyl, cyanoalkyl, heterocyclyl, alkoxyarylalkyl, cycloalkyl, nitroaryl, arylalkyl, alkoxy- or hydroxy-arylalkyl, and many other groups. Such groups may optionally be substituted with the previously mentioned groups in $R^1$.

Examples of such protecting groups are given in the following tables.

| protection for —OH group | |
|---|---|
| ethers | abbreviation |
| methyl | |
| methoxymethyl | MOM |
| benzyloxymethyl | BOM |
| methoxyethoxymethyl | MEM |
| 2-(trimethylsilyl)ethoxymethyl | SEM |
| methylthiomethyl | MTM |
| phenylthiomethyl | PTM |
| azidomethyl | |
| cyanomethyl | |
| 2,2-dichloro-1,1-difluoroethyl | |
| 2-chloroethyl | |
| 2-bromoethyl | |
| tetrahydropyranyl | THP |
| 1-ethoxyethyl | EE |
| phenacyl | |
| 4-bromophenacyl | |
| cyclopropylmethyl | |
| allyl | |
| propargyl | |
| isopropyl | |
| cyclohexyl | |
| t-butyl | |
| benzyl | |
| 2,6-dimethylbenzyl | |
| 4-methoxybenzyl | MPM or PMB |
| o-nitrobenzyl | |
| 2,6-dichlorobenzyl | |
| 3,4-dichlorobenzyl | |
| 4-(dimethylamino)carbonylbenzyl | |
| 4-methylsuflinylbenzyl | Msib |
| 9-anthrylmethyl | |
| 4-picolyl | |
| heptafluoro-p-tolyl | |
| tetrafluoro-4-pyridyl | |
| trimethylsilyl | TMS |
| t-butyldimethylsilyl | TBDMS |
| t-butyldiphenylsilyl | TBDPS |
| triisopropylsilyl | TIPS |
| esters | |
| aryl formate | |
| aryl acetate | |
| aryl levulinate | |

-continued

| | |
|---|---|
| aryl pivaloate | ArOPv |
| aryl benzoate | |
| aryl 9-fluorocarboxylate | |
| aryl methyl carbonate | |
| 1-adamantyl carbonate | |
| t-butyl carbonate | BOC-OAr |
| 4-methylsulfinylbenzyl carbonate | Msz-Oar |
| 2,4-dimethylpent-3-yl carbonate | Doc-Oar |
| aryl 2,2,2-trichloroethyl carbonate | |
| aryl vinyl carbonate | |
| aryl benzyl carbonate | |
| aryl carbamate | |
| dimethylphosphinyl | Dmp-OAr |
| dimethylphosphinothioyl | Mpt-OAr |
| diphenylphosphinothioyl | Dpt-Oar |
| aryl methanesulfonate | |
| aryl toluenesulfonate | |
| aryl 2-formylbenzenesulfonate | |

| protection for the —NH$_2$ group | |
|---|---|
| carbamates | abbreviation |
| methyl | |
| ethyl | |
| 9-fluorenylmethyl | Fmoc |
| 9-(2-sulfo)fluoroenylmethyl | |
| 9-(2,7-dibromo)fluorenylmethyl | |
| 17-tetrabenzo[a,c,g,i]fluorenylmethyl | Tbfmoc |
| 2-chloro-3-indenylmethyl | Climoc |
| benz[f]inden-3-ylmethyl | Bimoc |
| 2,7-di-t-butyl[9-(10,10-dioxo-10,10,10-tetrahydrothioxanthyl)]methyl | DBD-Tmoc |
| 2,2,2-trichloroethyl | Troc |
| 2-trimethylsilylethyl | Teoc |
| 2-phenylethyl | hZ |
| 1-(1-adamantyl)-1-methylethyl | Adpoc |
| 2-chlooethyl | |
| 1,1-dimethyl-2-chloroethyl | |
| 1,1-dimethyl-2-bromoethyl | |
| 1,1-dimethyl-2,2-dibromoethyl | DB-t-BOC |
| 1,1-dimethyl-2,2,2-trichloroethyl | TCBOC |
| 1-methyl-1-(4-biphenyl)ethyl | Bpoc |
| 1-(3,5-di-t-butylphenyl)-1-1-methylethyl | t-Burmeoc |
| 2-(2'-and 4'-pyridyl)ethyl | Pyoc |
| 2,2-bis(4'-nitropbenyl)ethyl | Bnpeoc |
| n-(2-pivaloylamino)-1,1-dimethylethyl | |
| 2-[(2-nitrophenyl)dithio]-1-phenylethyl | NpSSPeoc |
| 2-(n,n-dicyclohexylcarboxamido)ethyl | |
| t-butyl | BOC |
| 1-adamantyl | 1-Adoc |
| 2-adamantyl | 2-Adoc |
| vinyl | Voc |
| allyl | Aloc or Alloc |
| 1-isopropylallyl | Ipaoc |
| cinnamyl | Coc |
| 4-nitrocinnamyl | Noc |
| 3-(3'-pyridyl)prop-2-enyl | Paloc |
| 8-quinolyl | |
| n-hydroxypiperidinyl | |
| alkyldithio | |
| benzyl | Cbz or Z |
| p-methoxybenzyl | Moz |
| p-nitrobenzyl | PNZ |
| p-bromobenzyl | |
| p-chlorobenzyl | |
| 2,4-dichlorobenzyl | |
| 4-methylsulfinylbenzyl | Msz |
| 9-anthrylmethyl | |
| diphenylmethyl | |
| phenothiazinyl-(10)-carbonyl | |
| n'-p-toluenesulfonylaminocarbonyl | |
| n'-phenylaminothiocarbonyl | |

-continued

| amides | |
|---|---|
| formamide | |
| acetamide | |
| chloroacetamide | |
| trifluoroacetamide | TFA |
| phenylacetamide | |
| 3-phenylpropanamide | |
| pent-4-enamide | |
| picolinamide | |
| 3-pyridylcarboxamide | |
| benzamide | |
| p-phenylbenzamide | |
| n-phthalimide | |
| n-tetrachlorophthalimide | TCP |
| 4-nitro-n-phthalimide | |
| n-dithiasuccinimide | Dts |
| n-2,3-diphenylmaleimide | |
| n-2,5-dimethylpyrrole | |
| n-2,5-bis(triisopropylsiloxyl)pyrrole | BIPSOP |
| n-1,1,4,4-tetramethyldisiliazacyclopentante adduct | STABASE |
| 1,1,3,3-tetramethyl-1,3-disilaisoindoline | BSB |

| special-NH protective groups | |
|---|---|
| n-methylamine | |
| n-t-butylamine | |
| n-allylamine | |
| n-[2-trimethylsilyl)ethoxy]methylamine | SEM |
| n-3-acetoxypropylamine | |
| n-cyanomethylamine | |
| n-(1-isopropyl-4-nitro-2-oxo-3-pyrrolin-3-yl)amine | |
| n-2,4-dimethoxybenzylamine | Dmb |
| 2-azanorbornenes | |
| n-2,4-dinitrophenylamine | |
| n-benzylamine | Bn |
| n-4-methoxybenzylamine | MPM |
| n-2,4-dimethoxybenzylamine | DMPM |
| n-2-hydroxybenzylamine | Hbn |
| n-(diphenylmethyl)amino | DPM |
| n-bis(4-methoxyphenyl)methylamine | |
| n-5-dibenzosuberylamine | DBS |
| n-triphenylmethylamine | Tr |
| n-[(4-methoxyphenyl)diphenylmethyl]amino | MMTr |
| n-9-phenylflurenylamine | Pf |
| n-ferrocenylmethylamine | Fcm |
| n-2-picolylamine n'-oxide | |
| n-1,1-dimethylthiomethyleneamine | |
| n-benzylideneamine | |
| n-p-methoxybenzylideneamine | |
| n-diphenylmethyleneamine | |
| n-(5,5-dimethyl-3-oxo-1-cyclohexenyl)amine | |
| n-nitroamine | |
| n-nitrosoamine | |
| diphenylphosphinamide | Dpp |
| dimethylthiophosphinamide | Mpt |
| diphenylthiophosphinamide | Ppt |
| dibenzyl phosphoramidate | |
| 2-nitrobenzenesulfenamide | Nps |
| n-1-(2,2,2-trifluoro-1,1-diphenyl)ethylsufenamide | TDE |
| 3-nitro-2-pyridinesulfenamide | Npys |
| p-toluenesulfonamide | Ts |
| benzenesulfonamide | |

Examples of preferred methods of this invention will firstly be considered with reference to starting compunds 45, 43 and 25. It will be appreicated that the particular substituents, notably at positions C-5 and C-18, can be varied in the light of the present disclosure.

The preferred methods of producing the compounds of formula I, II and III are described below in the following reaction schemes with examples of typical substituent groups.

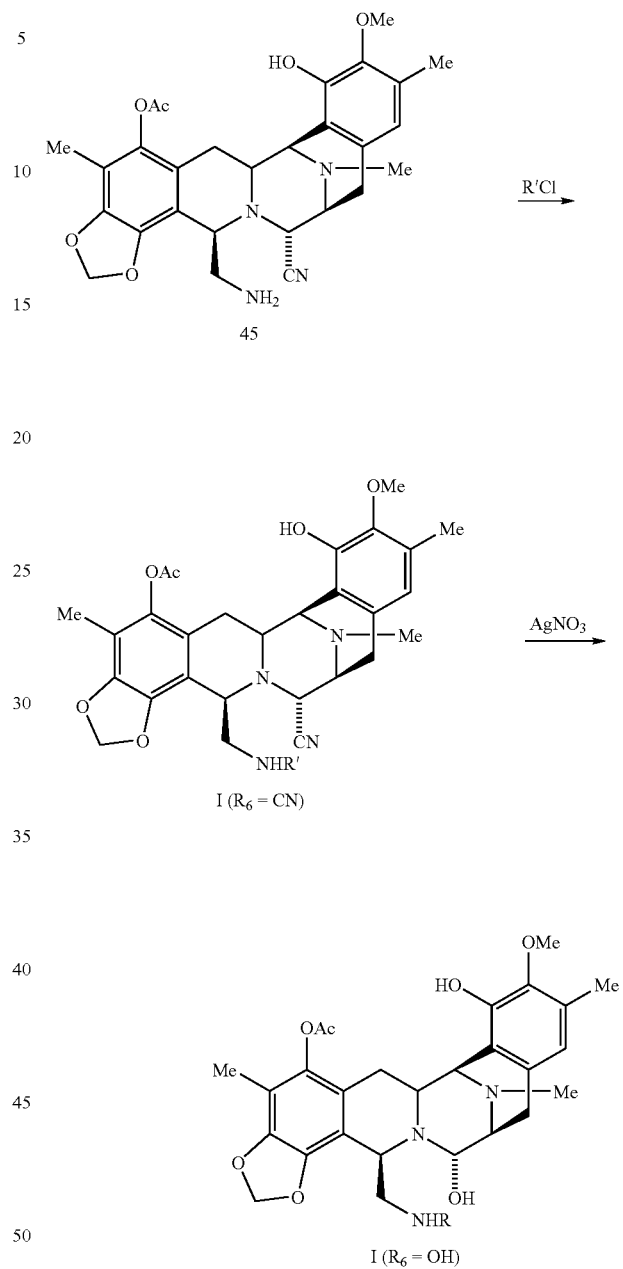

Scheme 1

As illustrated in Scheme 1 the first step for producing the preferred compounds (I) (where $R_1$=OH, $X_2$=OAc and $R_6$=CN or OH) of the present invention from compound 45 is the high yielding conversion of the amino group to the amide group.

After acylation of the amino group the second step is the transformation of the CN group into an OH group by reaction with silver nitrate in $AcCN/H_2O$.

The preparation of other compounds of the general formula I of the present invention starting from compound 17 is described below (Scheme 4).

Scheme 2

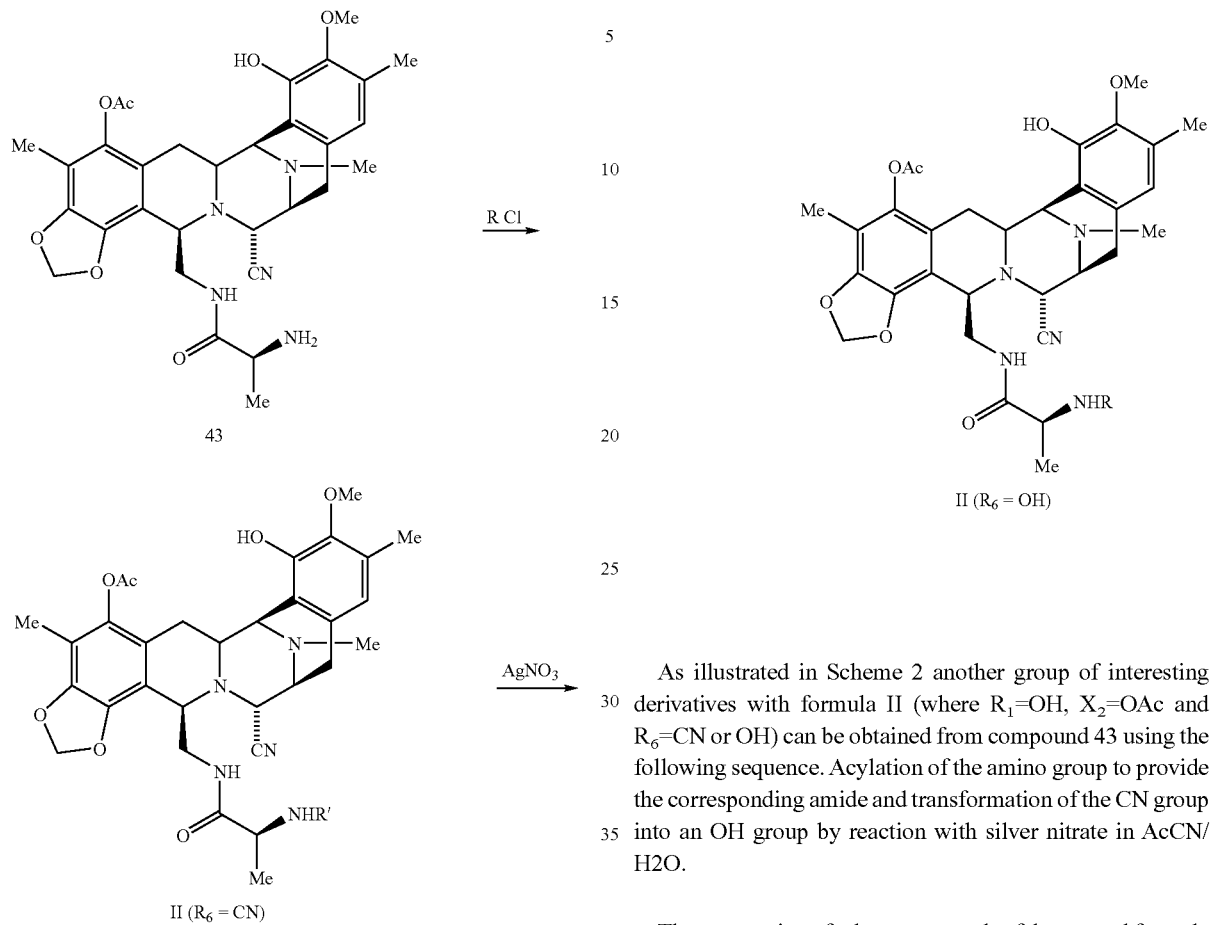

As illustrated in Scheme 2 another group of interesting derivatives with formula II (where $R_1$=OH, $X_2$=OAc and $R_6$=CN or OH) can be obtained from compound 43 using the following sequence. Acylation of the amino group to provide the corresponding amide and transformation of the CN group into an OH group by reaction with silver nitrate in AcCN/H2O.

The preparation of other compounds of the general formula II of the present invention starting from compound 17 is described below (Scheme 4).

Scheme 3

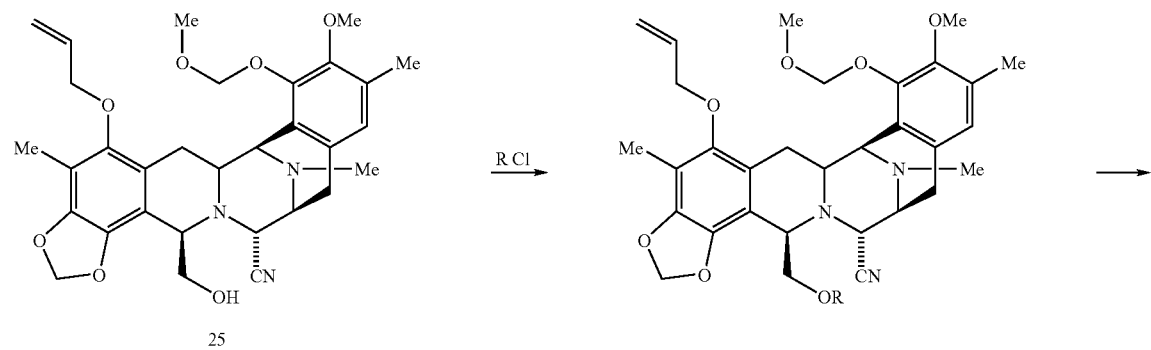

-continued

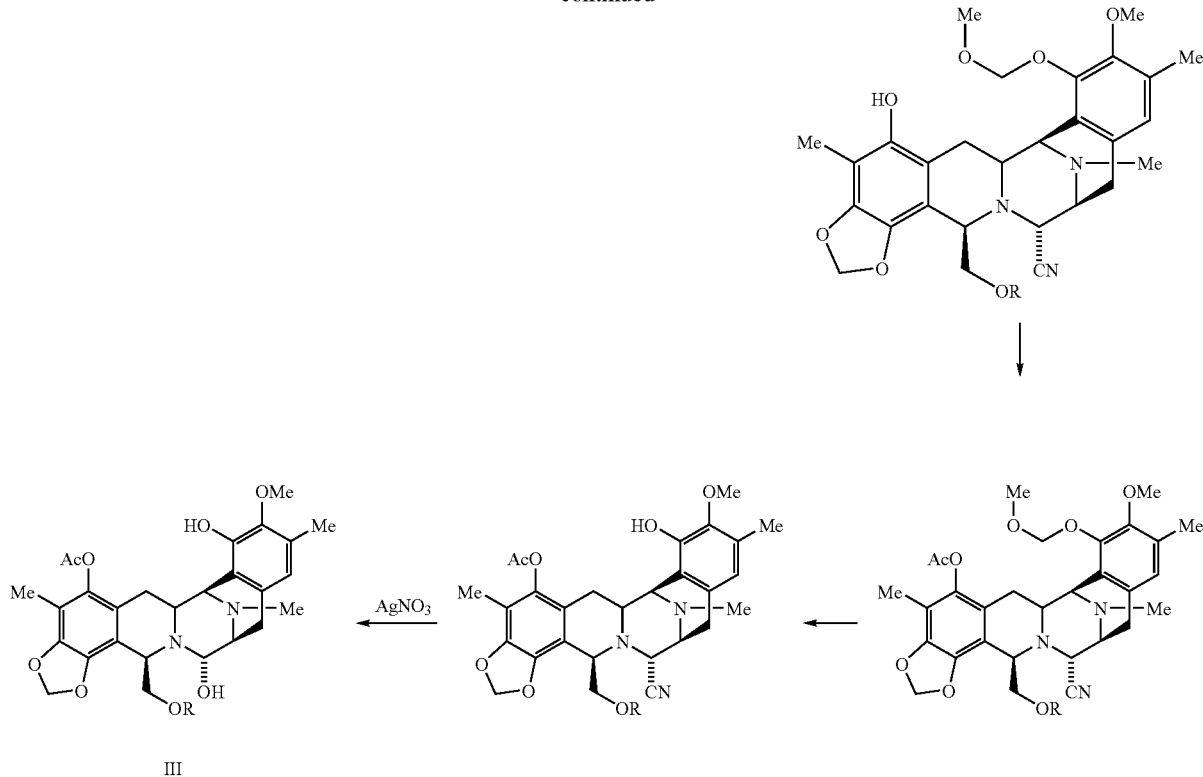

The preferred procedure for producing compounds of formula III is the transformation of compound 25 into the corresponding ester derivatives by acylation of the OH group, deprotection of the phenol group followed by acetylation and deprotection of the MOM group to provide the corresponding ester followed by transformation of the CN group to the OH group by reaction with silver nitrate in AcCN/H$_2$O to give the compound of formula III (where R$_1$=OH, X$_2$=OAc and R$_6$=CN or OH).

Other compounds of the general formulae I and II of the present invention can be prepared from compound 17 via the amine intermediate 120 as described in Scheme 4.

Scheme 4

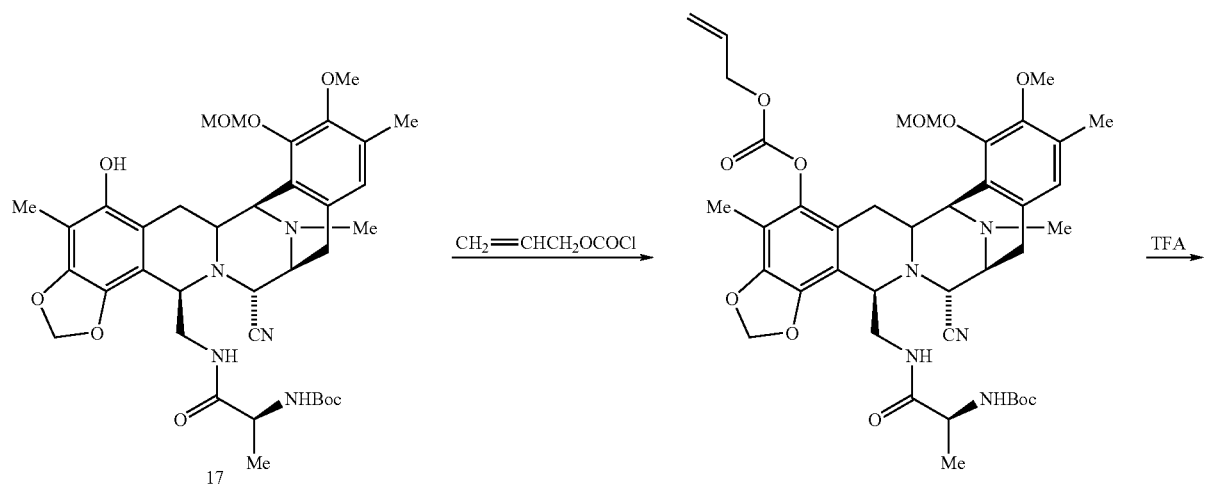

-continued
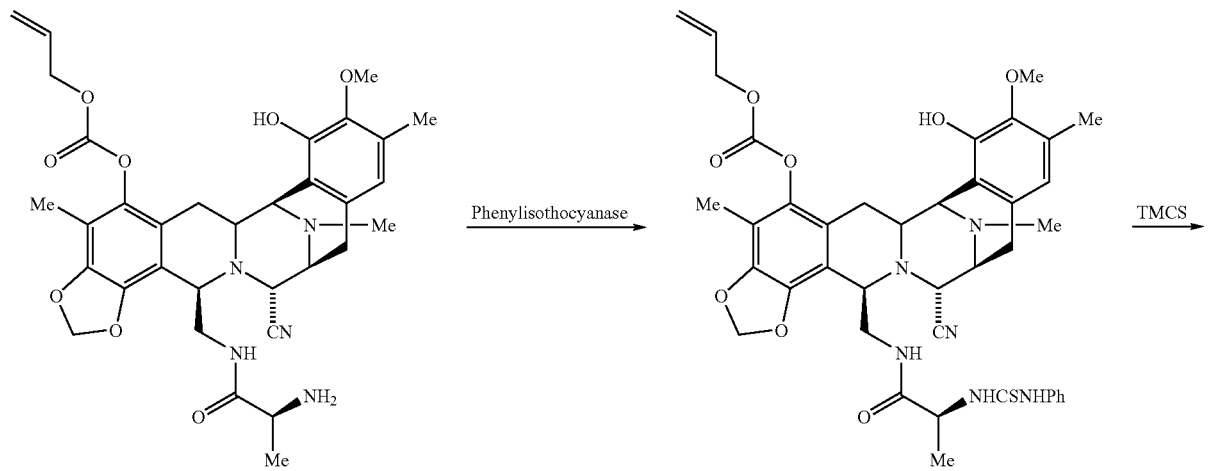
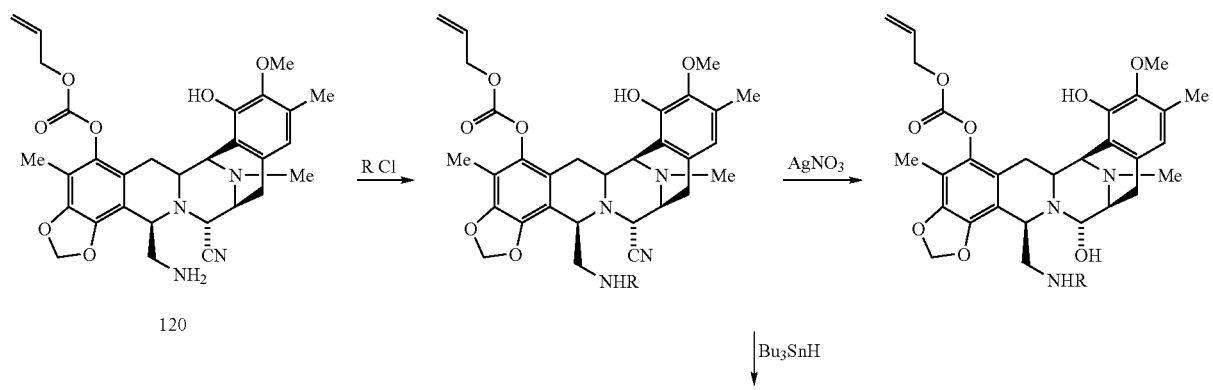
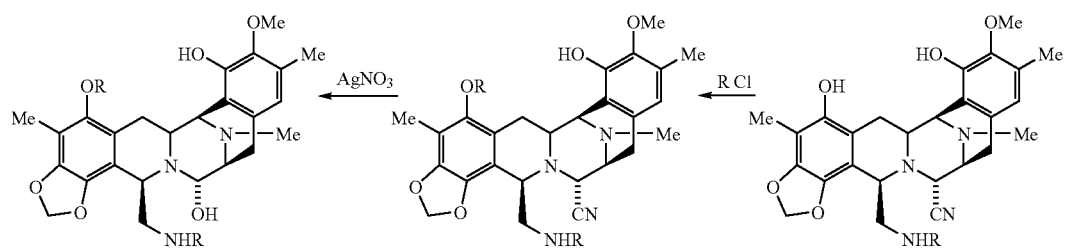

The following additional compounds of the present invention (including for example 140 and 141) have been prepared starting from cyanosafracin B (2) as described in detail in the examples (Scheme 5).

Scheme 5

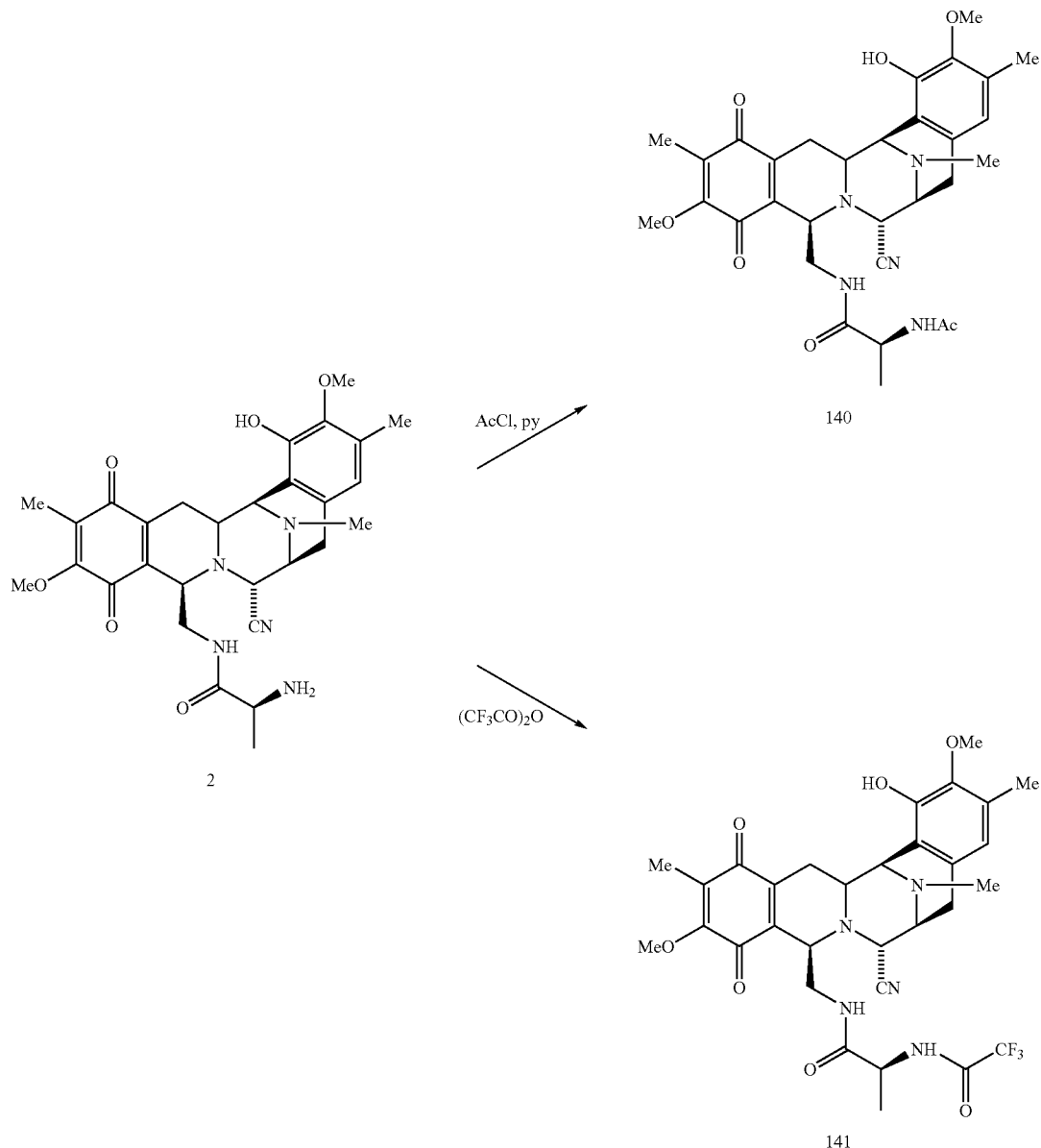

As the skilled artisan will readily appreciate, the reaction schemes described herein may be modified and/or combined in various ways, and the compounds generated therefore are to be considered as being part of this invention. In particular the starting material and/or reagents and reactions can be varied to suit other combinations of the substituent groups in the formulae I, II and III.

In a related aspect, the present invention is directed at the use of a known compound, safracin B, also referred to as quinonamine, in hemisynthetic synthesis.

More generally, the invention relates to a hemisynthetic process for the formation of intermediates, derivatives and related structures of ecteinascidin or other tetrahydroisoquinolinephenol compounds starting from natural bis(tetrahydroisoquinoline) alkaloids. Suitable starting materials for the hemi-synthetic process include the classes of saframycin and safracin antibiotics available from different culture broths, and also the classes of reineramicin and xestomycin compounds available from marine sponges.

A general formula (XV) for the starting compounds is as follows:

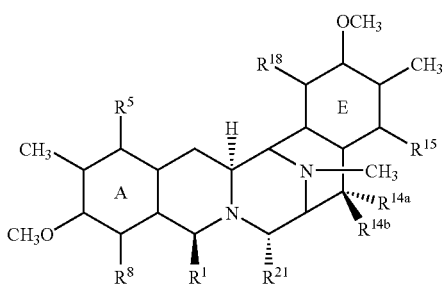

where:

$R^1$ is an amidomethylene group such as —$CH_2$—NH—CO—$CR^{25a}R^{25b}R^{25c}$ where $R^{25a}$ and $R^{25b}$ form a keto group or one is —OH, —$NH_2$ or —$OCOCH_3$ and the other is —$CH_2COCH_3$, —H, —OH or —$OCOCH_3$, provided that when $R^{25a}$ is —OH or —$NH_2$ then $R^{25b}$ is not —OH, and $R^{25c}$ is —H, —$CH_3$ or —$CH_2CH_3$, or $R^1$ is an acyloxymethylene group such as —$CH_2$—O—CO—R, where R is —C($CH_3$)=CH—$CH_3$ or —$CH_3$;

$R^5$ and $R^8$ are independently chosen from —H, —OH or —$OCOCH_2OH$, or $R^5$ and $R^8$ are both keto and the ring A is a p-benzoquinone ring;

$R^{14a}$ and $R^{14b}$ are both —H or one is —H and the other is —OH, —$OCH_3$ or —$OCH_2CH_3$, or $R^{14a}$ $R^{15}$ and $R^{18}$ are independently chosen from —H or —OH, or $R^5$ and $R^8$ are both keto and the ring A is a p-benzoquinone ring; and $R^{21}$ is —OH or —CN.

A more general formula for these class of compounds is provided below:

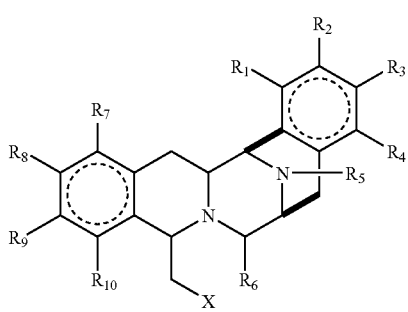

wherein the substituent groups defined by $R_1$, $R_2$, $R_3$, $R_4$, $R_5$, $R_6$, $R_7$, $R_8$, $R_9$, $R_{10}$ are each independently selected from the group consisting of H, OH, $OCH_3$, CN, =O, $CH_3$;

wherein X are the different amide or ester functionalities contained in the mentioned natural products;

wherein each dotted circle represents one, two or three optional double bonds.

Thus, according to the present invention, we now provide hemisynthetic routes for the production of intermediates including Intermediate 11 and thus for the production of the ecteinascidin compounds as well as phthalascidin and additional compounds. The hemisynthetic routes of the invention each comprise a number of transformation steps to arrive at the desired product. Each step in itself is a process in accordance with this invention. The invention is not limited to the routes that are exemplified, and alternative routes may be provided by, for example, changing the order of the transformation steps, as appropriate.

In particular, this invention involves the provision of a 21-cyano starting material of general formula (XVI):

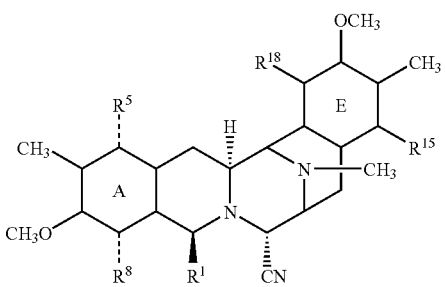

where $R^1$, $R^5$, $R^8$, $R^{14a}$, $R^{14b}$, $R^{15}$ and $R^{18}$ are as defined.

Other compounds of formula (XVI) with different substituents at the 21-position may also represent possible starting materials. In general, any derivative capable of production by nucleophilic displacement of the 21-hydroxy group of compounds of formula (XV) wherein $R^{21}$ is a hydroxy group cis a candidate. Examples of suitable 21-substituents include but are not limited to:

a mercapto group;

an alkylthio group (the alkyl group having from 1 to 6 carbon atoms);

an arylthio group (the aryl group having from 6 to 10 carbon atoms and being unsubstituted or substituted by from 1 to 5 substituents selected from, for example, alkyl group having from 1 to 6 carbon atoms, alkoxy groups having from 1 to 6 carbon atoms, halogen atoms, mercapto groups and nitro groups);

an amino group;

a mono- or dialkylamino (the or each alkyl group having from 1 to 6 carbon atoms);

a mono- or diarylamino group (the or each aryl group being as defined above in relation to arylthio groups);

an α-carbonylalkyl group of formula —C($R^a$)($R^b$)—C(=O)$R^c$, where $R^a$ and $R^b$ are selected from hydrogen atoms, alkyl groups having from 1 to 20 carbon atoms, aryl groups (as defined above in relation to arylthio groups) and aralkyl groups (in which an alkyl group having from 1 to 4 carbon atoms is substituted by an aryl group a defined above in relation to arylthio groups), with the proviso that one of $R^a$ and $R^b$ is a hydrogen atom;

$R^c$ is selected from a hydrogen atom, an alkyl group having from 1 to 20 carbon atoms, aryl groups (as defined above in relation to arylthio groups), an aralkyl group (in which an alkyl group having from 1 to 4 carbon atoms is substituted by an aryl group a defined above in relation to arylthio groups), an alkoxy group having from 1 to 6 carbon atoms, an amino group or a mono- or dialkylamino group as defined above.

Thus, in a more general aspect, the present invention relates to processes where the first step is to form a 21-deriviative using a nucleophilic reagent. We refer to such compounds as 21-Nuc compounds.

The presence of the 21-cyano group is required for some of the end-products, notably ecteinascidin 770 and phthalascidin, while for other end-products it acts as a protecting group which can readily be converted to another substituent, such as the 21-hydroxy group of ecteinascidin 743 or of 21-hydroxyphthalascidin. The adoption of the 21-cyano compound as the starting material effectively stabilises the molecule during the ensuing synthetic steps, until it is optionally removed. Other 21-Nuc compounds can offer this and other advantages.

In one important aspect, the present invention consists in the use of a 21-cyano compound of the general formula (XVI) in the preparation of a bis- or tris(tetrahydroisoquinolinephenol) compounds. Products which may be prepared include intermediates such as Intermediate 11, and the ecteinascidins and phthalascidin, as well as new and known compounds of related structure.

Preferred starting materials include those compounds of formula (XV) or (XVI) where $R^{14a}$ and $R^{14b}$ are both hydrogen. Preferred starting materials also include compounds of formula (XV) or (XVI) where $R^{15}$ is hydrogen. Furthermore, the preferred starting materials include compounds of formula (XV) or (XVI) where ring E is a phenolic ring. Preferred starting materials further include compounds of formula (XV) or (XVI) where at least one, better at least two or three of $R^5$, $R^8$, $R^{15}$ and $R^{18}$ is not hydrogen.

Examples of suitable starting materials for this invention include saframycin A, saframycin B, saframycin C, saframycin G, saframycin H, saframycin S, saframycin $Y_3$, saframycin $Yd_1$, saframycin $Ad_1$, saframycin $Yd_2$, saframycin $AH_2$, saframycin $AH_2Ac$, saframycin $AH_1$, saframycin $AH_1Ac$ saframycin $AR_3$, renieramycin A, renieramycin B, renieramycin C, renieramycin D, renieramycin E, renieramycin F, xestomycin, saframycin D, saframycin F, saframycin Mx-1, saframycin Mx-2, safracin A, safracin B and saframycin R. Preferred starting materials have a cyano group in position 21, for the group $R^{21}$.

In a particularly preferred aspect, the invention involves a hemisynthetic process wherein the transformation steps are applied to safracin B:

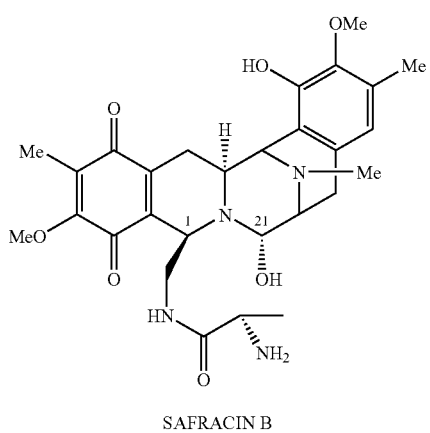

SAFRACIN B

Safracin B presents a ring system closely related to the ecteinascidins. This compound has the same pentacycle structure and the same substitution pattern in the right-hand aromatic ring, ring E. Also, safracin B presents very close similarities to some of the synthetic intermediates in the total synthesis of ET-743, particularly to the intermediate 11. Such intermediate can be transformed into Et-743 using a well established method. Synthetic conversion of safracin B into intermediate 11 will therefore provide an hemi-synthetic method to obtain ET-743.

Thus, we provide Intermediate 11 made from this compound safracin B, and compounds derived from Intermediate 11, particularly ecteinascidin compounds. We further provide phthalascidin made from safracin B. The invention also relates to use of safracin B in the production of Intermediate 11, phthalascidin, ecteinascidin compounds and the other intermediates of the invention. The invention also relates to compounds described herein derived from the other suggested starting materials and use of those compounds in the production of such compounds.

The more preferred starting materials of this invention have a 21-cyano group. The currently most preferred compound of the present invention is the compound of Formula 2. This compound is obtained directly from safracin B and is considered a key intermediate in the hemisynthetic process.

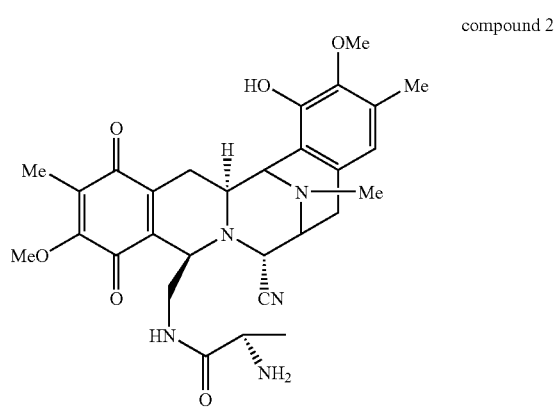

compound 2

In a related aspect, we provide cyanosafracin B by fermentation of a safracin B-producing strain of *Pseudomonas fluorescens*, and working up the cultured broth using cyanide ion. The preferred strain of *Pseudomonas fluorescens* is strain A2-2, FERM BP-14, which is employed in the procedure of EP 055,299. A suitable source of cyanide ion is potassium cyanide. In a typical work-up, the broth is filtered and excess cyanide ion is added. After an appropriate interval of agitation, such as 1 hour, the pH is rendered alkaline, say pH 9.5, and an organic extraction gives a crude extract which can be further purified to give the cyanosafracin B.

Safracin B includes an alanyl sidechain. In one aspect of the invention, we have found that protection of the free amino group with a Boc group can give strong advantages.

In general, the conversion of the 21-cyano starting compound to an ecteinascidin analog of this invention can be carried out in accordance with our copending PCT patent application, attorney reference wpp83894, which also claims priority from the PCT filing published as WO 0069862 published 23 Nov. 2000, and which relates to hemisynthetic methods and new compounds. We incorporate the text of the copending PCT application, attorney reference wpp83894, by reference to the extent that there is disclosure therein which is not in the present specification.

Typically the hemisynthesis of an analog of this invention involves:

a) conversion if necessary of a quinone system for the ring E into the phenol system b) conversion if necessary of a quinone system for the ring A into the phenol system;

c) conversion of the phenol system for the ring A into the methylenedioxyphenol ring; and d) derivatisation as appropriate, such as acylation.

Step (a), conversion if necessary of a quinone system for the ring E into the phenol system, can be effected by conventional reduction procedures. A suitable reagent system is hydrogen with a palladium-carbon catalyst, though other reducing systems can be employed.

Step (b), conversion if necessary of a quinone system for the ring A into the phenol system is analogous to step (a), and more detail is not needed.

Step (c), conversion of the phenol system for the ring A into the methylenedioxyphenol ring, can be effected in several ways, possibly along with step (b). For example, a quinone ring A can be demethylated in the methoxy substituent at the 7-position and reduced to a dihydroquinone and trapped with a suitable electrophilic reagent such as $CH_2Br_2$, $BrCH_2Cl$, or a similar divalent reagent directly yielding the methylenedioxy ring system, or with a divalent reagent such as thiocarbonyldiimidazol which yields a substituted methylenedioxy ring system which can be converted to the desired ring.

Derivatisation in step (d) can include acylation, for instance with a group $R^a$—CO— as well as conversion of the 12-$NCH_3$ group to 12-NH or 12-$NCH_2CH_3$. Such conversion can be effected before or after the other steps, using available methods.

By way of illustration, it is now feasible to transform cyanosafracin B in a shorter and more straightforward way to make new analogs. Cyanosafracin B can be transformed into Intermediate 25;

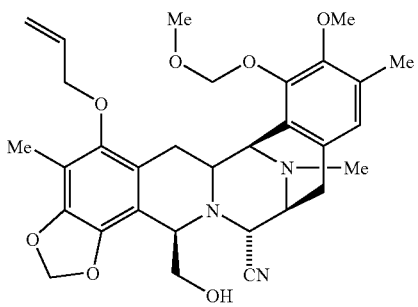

INT-25 and from this derivative it is possible to introduce further analogs of this invention.

One method of this invention transforms cyanosafracin B into intermediate 25 through a sequence of reactions that involves essentially (1) removal of methoxy group placed in ring A, (2) reduction of ring A and formation of methylenedioxy group in one pot, (3) hydrolysis of amide function placed over carbon 1, (4) transformation of the resulting amine group into hydroxyl group.

The conversion of the 2-cyano compound into Intermediate 25 usually involves the following steps (see scheme II):

formation of the protected compound of Formula 14 by reacting 2 with tert-butoxycarbonyl anhydride;

converting of 14 into the di-protected compound of Formula 15 by reacting with bromomethylmethyl ether and diisopropylethylamine in acetonitrile;

selectively elimination of the methoxy group of the quinone system in 15 to obtain the compound of Formula 16 by reacting with a methanolic solution of sodium hydroxide;

transforming of 16 into the methylene-dioxy compound of Formula 18 by employing the next preferred sequence: (1) quinone group of compound 16 is reduced with 10% Pd/C under hydrogen atmosphere; (2) the hydroquinone intermediate is converted into the methylenedioxy compound of Formula 17 by reacting with bromochloromethane and caesium carbonate under hydrogen atmosphere; (3) 17 is transformed into the compound of Formula 18 by protecting the free hydroxyl group as a $OCH_2R$ group. This reaction is carried out with $BrCH_2R$ and caesium carbonate, where R can be aryl. $CH=CH_2$, OR' etc.

elimination of the tert-butoxycarbonyl and the methyloxymethyl protecting groups of 18 to afford the compound of Formula 19 by reacting with a solution of HCl in dioxane. Also this reaction is achieved by mixing 18 with a solution of trifluoroacetic acid in dichloromethane;

formation of the thiourea compound of Formula 20 by reacting 19 with phenylisothiocyanate;

converting compound of Formula 20 into the amine compound of Formula 21 by reacting with a solution of hydrogen chloride in dioxane;

transforming compound of Formula 21 into the N-Troc derivative 22 by reacting with trichloroethyl chloroformate and pyridine;

formation of the protected hydroxy compound of Formula 23 by reacting 22 with bromomethylmethyl ether and diisopropylethylamine;

transforming compound of Formula 23 into the N—H derivative 24 by reacting with acetic acid and zinc;

conversion of compound of Formula 24 into the hydroxy compound of Formula 25 by reaction with sodium nitrite in acetic acid. Alternatively, it can be used nitrogen tetroxide in a mixture of acetic acid and acetonitrile followed by treatment with sodium hydroxide. Also, it can be used sodium nitrite in a mixture of acetic anhydride-acetic acid, followed by treatment with sodium hydroxide.

Scheme II

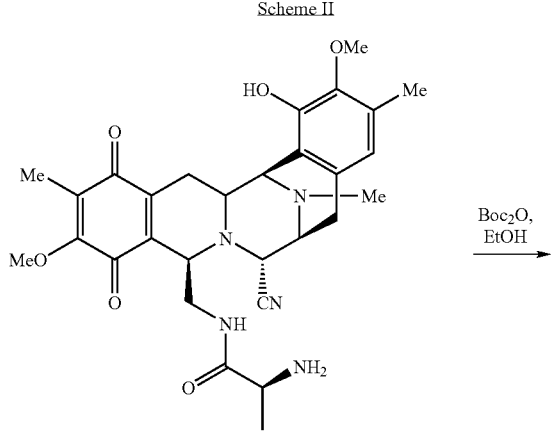

2

-continued
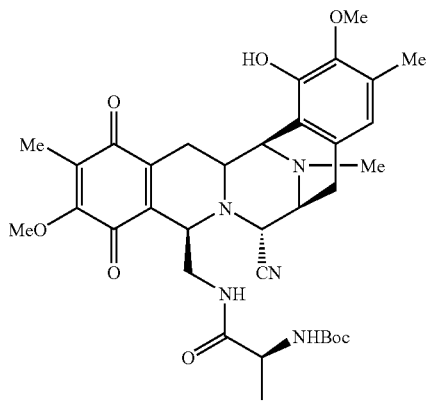
14
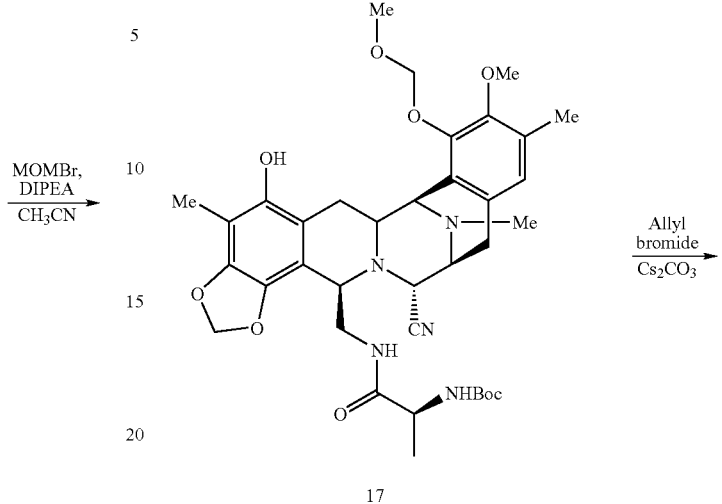
17
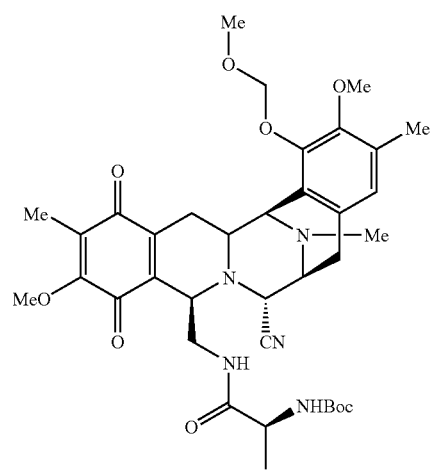
15
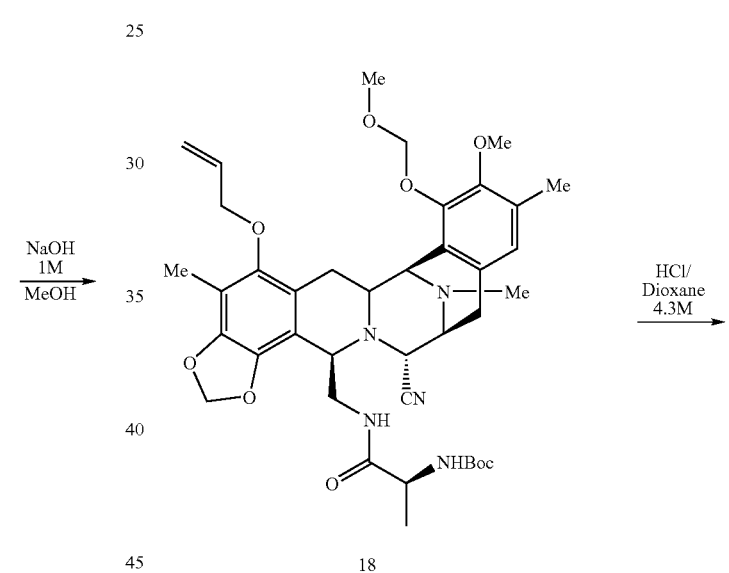
18
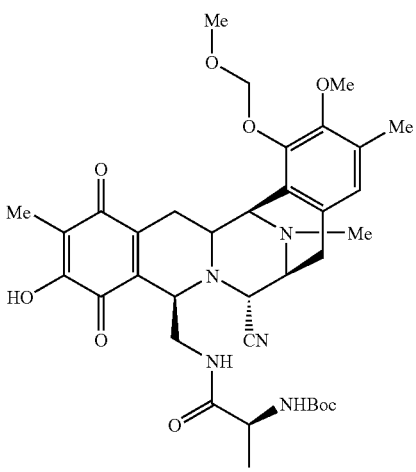
16
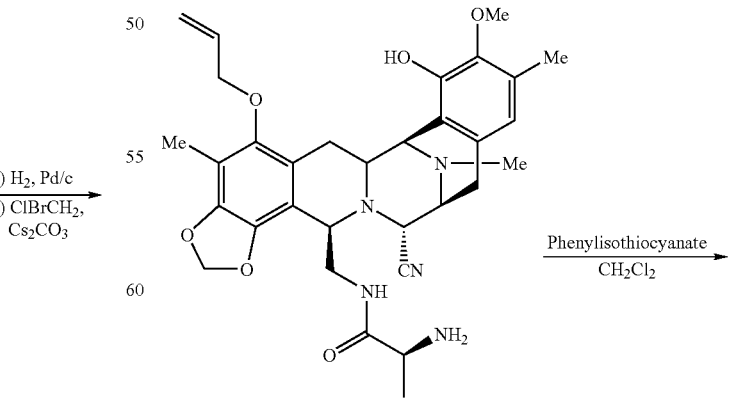
19

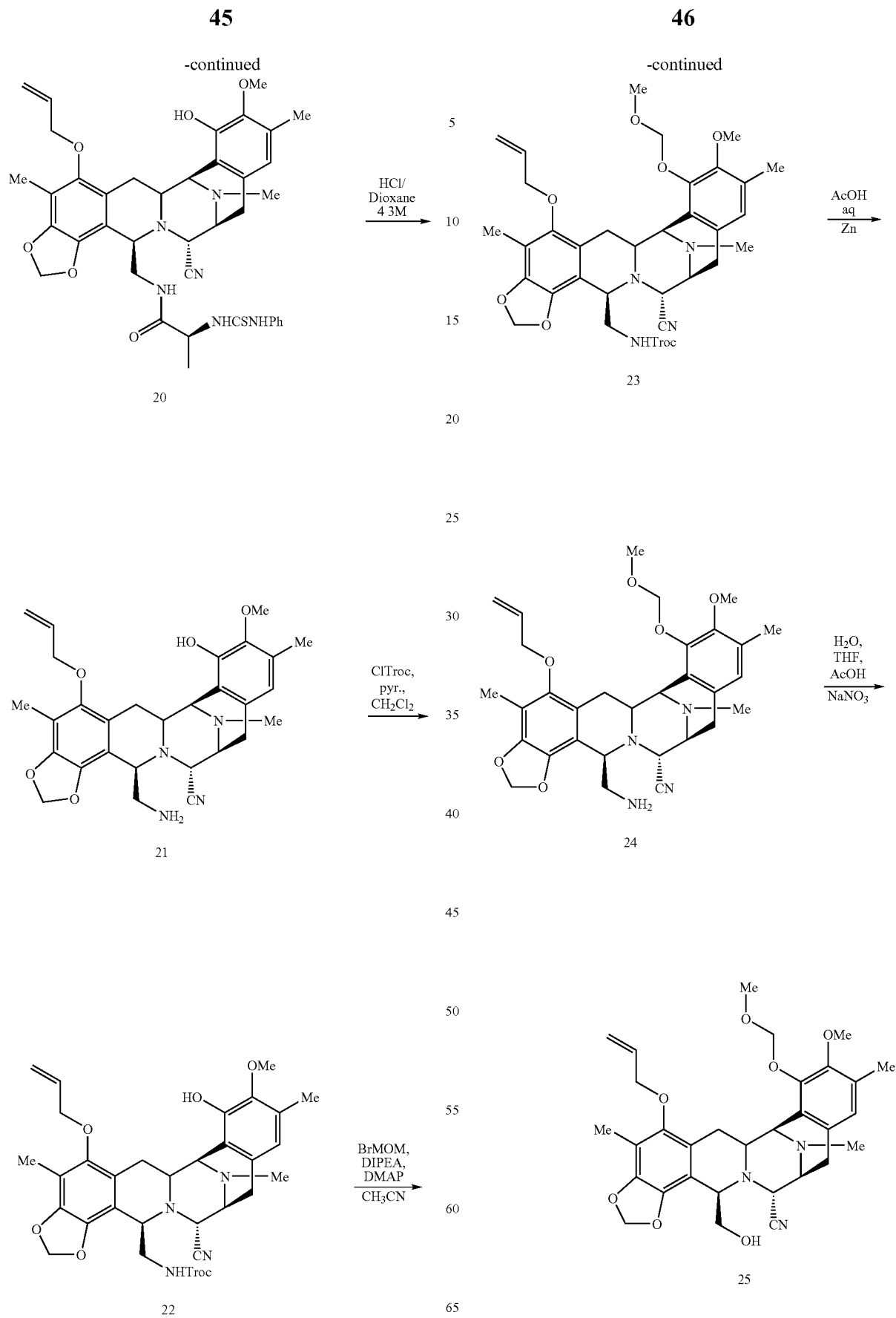

The conversion of the Intermediate 25 compound into other analogs of this invention is then readily achieved, as illustrated for example in Scheme III, which usually involves the following steps:

transforming compound of formula 24 into the derivative 30 by protecting the primary hydroxyl function with (S)-N-2,2, 2-tricloroethoxycarbonyl-S-(9H-fluoren-9-ylmethyl)cysteine 29;

converting the protected compound of formula 30 into the phenol derivative 31 by cleavage of the allyl group with tributyltin hydride and dichloropalladium-bis (triphenylphosphine), transforming the phenol compound of Formula 31 into compound of formula 32 by oxidation with benzeneseleninic anhydride at low temperature;

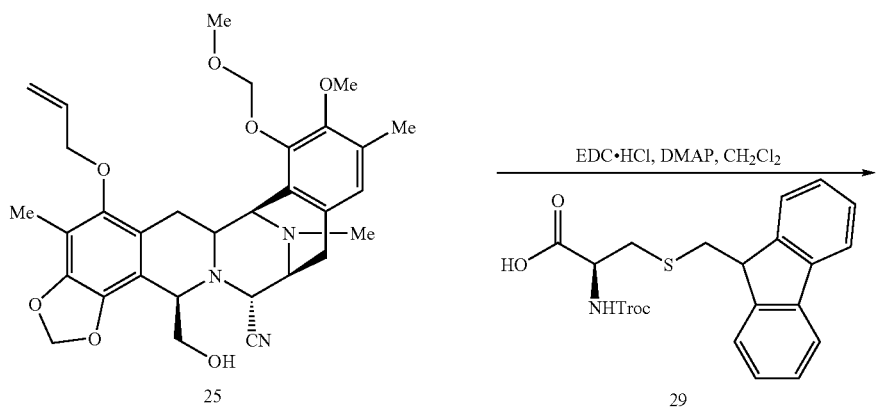

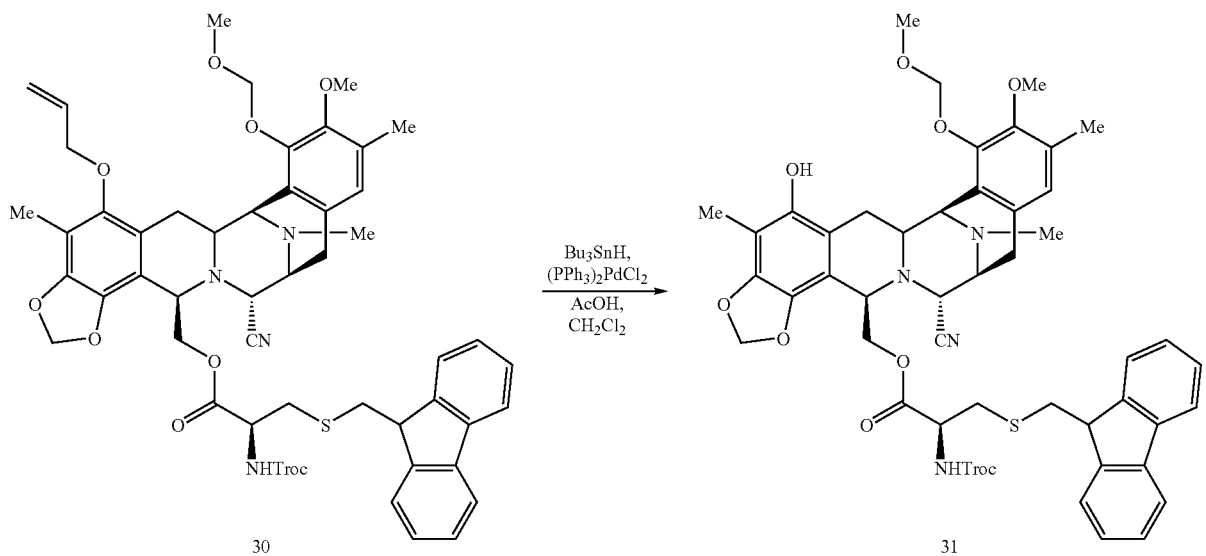

The route described above to transform Intermediate 25 can be conveniently modified to form other derivatives.

In more detail, the conversion of the starting 21-cyano compound to a related product of this invention, such as one of formula (XX), usually involves the following steps:

a) conversion if necessary of a quinone system for the ring E into the phenol system b) formation of the —$R^5$ group at the 5-position in ring A;

c) formation of the $R^1$ group at the 1-position in ring B; and d) conversion if necessary of a quinone system for the ring A into the phenol system;

e) conversion of the phenol system for the ring A into the methylenedioxyphenol ring.

These steps have many similarities with the steps given previously. Step (c) typically involves forming a group —$CH_2NH_2$ at the 1-position and acylating it.

Phthlascidin can be made using Intermediates described in the conversion of cyanosafracin B into Intermediate 25. For example, Intermediates 21 and 17 are suitable starting materials to make Phthlascidin and other analogs of this invention.

As shown in scheme V, the process for the synthetic formation of phthlascidin starting from Intermediate 21 comprises the sequential steps of:

transforming of 21 into the compound of Formula 27 by reaction with phthalic anhydride in dichloromethane and carbonyldiimidazole.

converting of 27 into phthlascidin by reacting with tributyltin hydride and dichloro palladium-bis(triphenylphosphine) or basic media, followed by reaction with acetyl chloride.

Scheme V

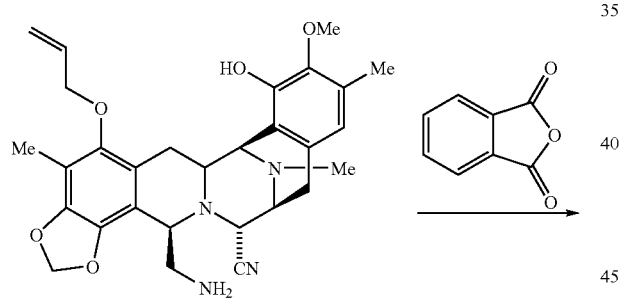

21

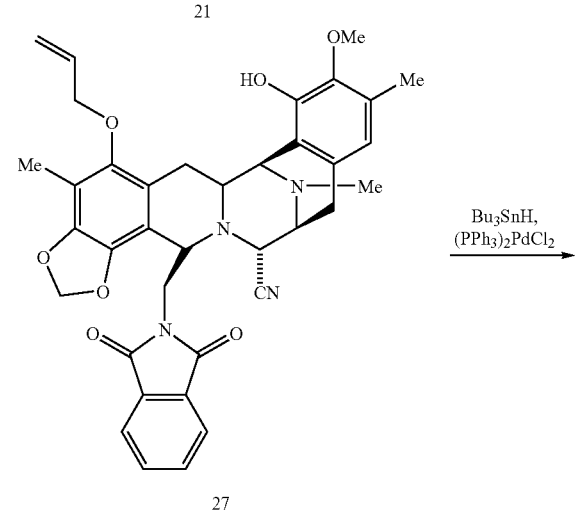

27

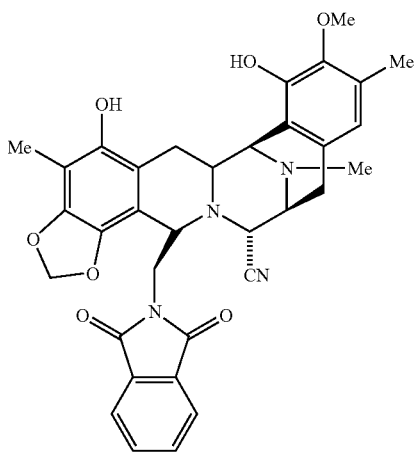

28

↓ AcCl,

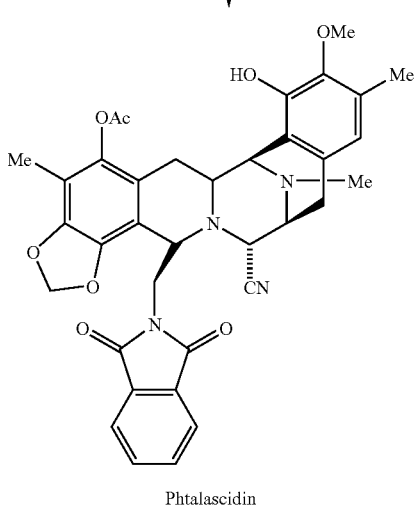

Phtalascidin

As shown in scheme VI, the process for the synthetic formation of phthlascidin starting from Intermediate 17 comprises the sequential steps of:

acetylation of the hydroxyl group of compound of formula 17 with acetyl chloride and pyridine to give the acetylated intermediate compound of formula 42;

removal of the tert-butoxycarbonyl and the methyloxymethyl protecting groups of 42 to afford the compound of Formula 43 by reacting with a solution of HCl in dioxane. Also this reaction is achieved by mixing 42 with a solution of trifluoroacetic acid in dichloromethane;

formation of the thiourea compound of Formula 44 by reacting 43 with phenylisothiocyanate;

converting compound of Formula 44 into the amine compound of Formula 45 by reacting with a solution of hydrogen chloride in dioxane;

transforming of 45 into phthascidin by reaction with phthalic an hydride in dichloromethane and carbonyldiimidazole.

Other analogs can be made for example from 43 or 45 by a similar manner.
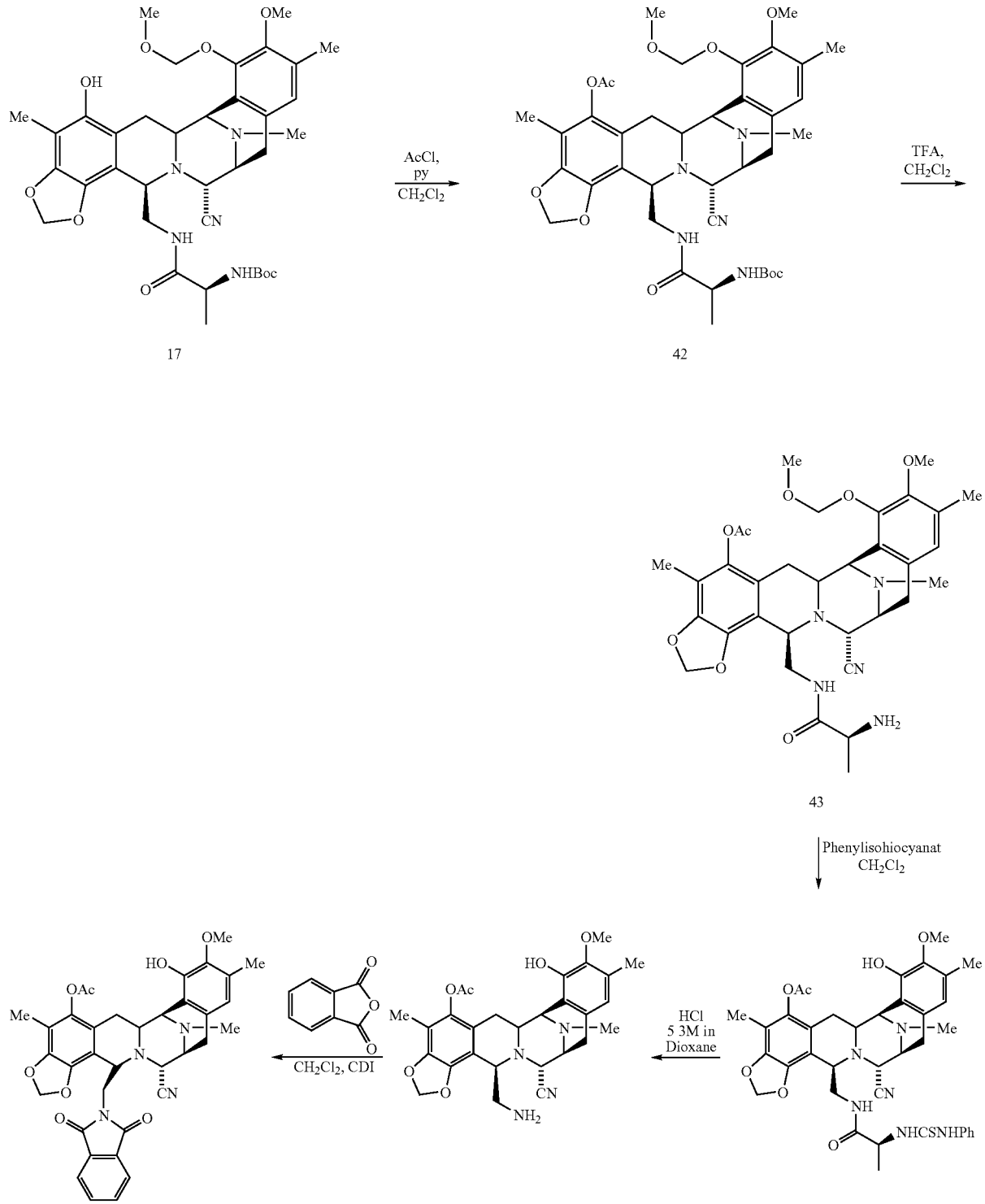
Scheme VI The conversion of the 21-cyano compound to Intermediate 11 or a related intermediate of formula (XXI) usually involves the following steps:

a) conversion if necessary of a quinone system for the ring E into the phenol system b) formation of the —OProt$^1$ group at the 18-position, in ring E;

c) formation of the —CH$_2$—OProt$^2$ group at the 1-position, in ring B; and d) conversion if necessary of a quinone system for the ring A into the phenol system;

e) conversion of the phenol system for the ring A into the methylenedioxyphenol ring.

Step (b), formation of the —OProt$^1$ group at the 18-position in ring E, is a typical protection reaction for a phenol group, and no special comments need to be made. Appropriate conditions are chosen depending on the nature of the protecting group. The other steps are similar to the other reactions.

Step (b), formation of the —CH$_2$—OProt$^2$ group at the 1-position in ring B, is normally carried out by forming a group —CH$_2$NH$_2$ at the 1-position and then converting the amine function to a hydroxy function and protecting. Thus, where the starting material has a group R$^1$ which is —CH$^2$—NH—CO—CR$^{25a}$R$^{25b}$R$^{25c}$ then it is matter of removing the N-acyl group. Where the starting material has a group R$^1$ which is —CH$_2$—O—CO—R then no change may be needed for an ecteinascidin product where the substituent R$^1$ is the same. For other products, it is matter of removing the O-acyl group. Various procedures are available for such de-acylations. In one variation, the deacylation and conversion to a hydroxy function are performed in one step. Thereafter, the hydroxy group can be acylated or otherwise converted to give the appropriate R$^1$ group.

U.S. Pat. No. 5,721,362 describe synthetic methods to make ET-743 through a long multistep synthesis. One of the Intermediates of this synthesis is Intermediate 11. Using cyanosafracin B as starting material it is possible to reach Intermediate 11 providing a much shorter way to make such Intermediate and therefor improving the method to make ET-743

Cyanosafracin B can be converted into Intermediate 25 by the methods described above. From Intermediate 25 is possible to reach Intermediate 11 using the following steps, see scheme VII.

formation of the protected hydroxy compound of Formula 26 by reacting 25 with tert-butyldiphenylsilyl chloride in the presence of a base;

final cleavage of the allyl group with tributyltin hydride and dichloropalladium-bis (triphenylphosphine) in 26 that leads to the formation of the intermediate 11.

Scheme VII

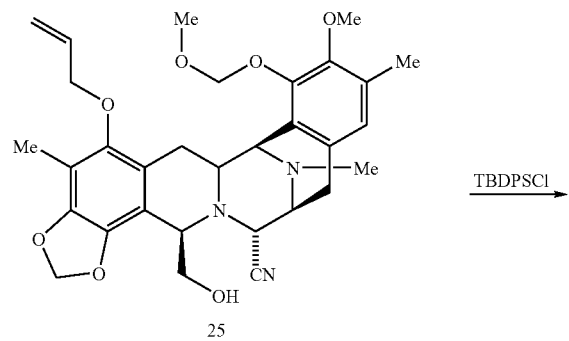

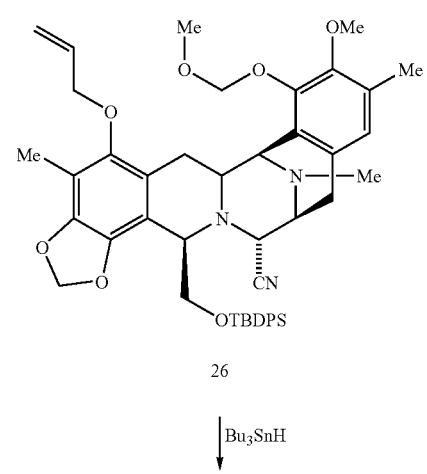

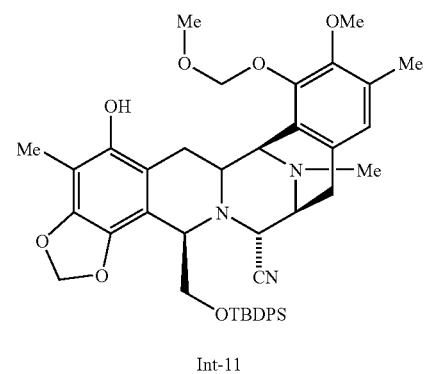

One embodiment of the synthetic process of the present invention to transform safracin B into intermediate 11 is a modification and extension of Scheme VIII and comprises the sequential steps of:

stereospecifically converting the compound Safracin B to the compound of Formula 2 by selective replacement of OH by CN by reacting with KCN in acid media;

forming the thiourea compound of Formula 3 by reacting compound of Formula 2 with phenyl isothiocyanate;

converting the thiourea compound of Formula 3 into the acetamide of Formula 5 by an hydrolysis in acid media followed by addition of acetic anhydride; The intermediate amine compound of Formula 4 can be isolated by quenching the hydrolysis in acid media with sodium bicarbonate, but this intermediate is highly unstable, and is transformed quickly into a five member cyclic imine, named compound 6;

forming the protected compound of Formula 7 by reacting with bromomethylmethyl ether and diisopropylethylamine in dichloromethane;

selectively de-methylating the methoxy group of the quinone system of compound of Formula 7 into the compound of Formula 8 by reacting with methanolic solution of sodium hydroxide;

transforming the compound of Formula 8 into methylene-dioxy-compound of Formula 9 by the preferred following sequence: (1) quinone group of compound 8 is reduced with 10% Pd/C under hydrogen atmosphere; (2) the hydroquinone intermediate is converted into the methylene-dioxy compound of Formula 9 by reacting with bromochloromethane and cesium carbonate under hydrogen atmosphere; (3) compound of Formula 9 is transformed into compound of Formula 10 by protecting the free hydroxyl group as a $OCH_2R$ group, by reacting with $BrCH_2R$ and cesium carbonate, where R can be aryl, $CH=CH_2$, OR' etc.;

converting the acetamide group of compound of Formula 10 into the corresponding hydroxyl group of Formula 11 by reaction with nitrogen tetroxide in a mixture of acetic acid and acetic acetate followed by treatment with sodium hydroxide; alternatively can be used sodium nitrite in a mixture of acetic anhydride acetic acid, followed by treatment with sodium hydroxide; alternatively the acetamide group of compound of Formula 10 can be converted into the primary amine group by reacting with hydrazine or with $Boc_2O$, DMAP followed by hydrazine; such primary amine can be converted into the corresponding hydroxyl group (compound of Formula 11) by an oxidative conversion of the primary amine into the corresponding aldehyde with 4-formyl-1-methylpyridinium benzenesulphonate or other pyridinium ion, followed by DBU or other base treatment and further hydrolization, and followed by the reduction of the aldehyde to the corresponding hydroxyl group with lithium aluminium hydride or other reducing agent;

forming the protected compound of Formula 26 by reacting with t-butyldiphenylsilyl chloride and dimethylaminopyridine in dichloromethane;

transforming the silylated compound of Formula 26 into the intermediate 11 by deprotection of the $OCH_2R$ protecting group, by reacting under reductive conditions or acid conditions.

Typical procedures are with palladium black under hydrogen atmosphere, or aqueous TFA, or tributyltin hydride and dichlorobis (triphenylphosphine palladium).

In yet another preferred modification, the cyano compound of Formula 2 can be transformed into Intermediate 11 using an extension of the scheme II, involving the further steps of.

formation of the protected hydroxy compound of Formula 26 by reacting 25 with tert-butyldiphenylsilyl chloride in the presence of a base;

final cleavage of the allyl group with tributyltin hydride and dichloropalladium-bis (triphenylphosphine) in 26 that leads to the formation of the intermediate 11.

Thus, it is possible to transform cyanosafracin B into a number of intermediates and derivatives with potential anti-tumor therapeutic activity. These intermediates can be made starting from already described compounds, or using alternative routes.

Intermediates described herein comprise compound 47, and a numbers of amide derivatives made using compounds 45 or 43.

In Scheme VIII is described formation of compound 47 using the following sequence:

forming the thiourea compound of Formula 3 by reacting compound of Formula 2 with phenyl isothiocyanate;

converting the thiourea compound of Formula 3 into the acetamide of Formula 5 by an hydrolysis in acid media followed by addition of acetic anhydride, The intermediate amine compound of Formula 4 can be isolated by quenching the hydrolysis in acid media with sodium bicarbonate, but this intermediate is highly unstable, and is transformed quickly into a five member cyclic imine, named compound 6;

forming the protected compound of Formula 7 by reacting with bromomethylmethyl ether and diisopropylethylamine in dichloromethane;

selectively de-methylating the methoxy group of the quinone system of compound of Formula 7 into the compound of Formula 8 by reacting with methanolic solution of sodium hydroxide;

transforming the compound of Formula 8 into methylene-dioxy-compound of Formula 10 by the preferred following sequence: (1) quinone group of compound 8 is reduced with 10% Pd/C under hydrogen atmosphere; (2) the hydroquinone intermediate is converted into the methylene-dioxy compound of Formula 9 by reacting with bromochloromethane and cesium carbonate under hydrogen atmosphere; (3) compound of Formula 9 is transformed into compound of Formula 10 by protecting the free hydroxyl group as a allyloxy group, by reacting with allyl-bromide and cesium carbonate;

transforming the compound of formula 9 into acetyl-derivative 46 by reaction with acetyl chloride in pyridine;

transforming compound of formula 46 into de-protected compound 47 by reaction with hydrochloric acid in dioxane.

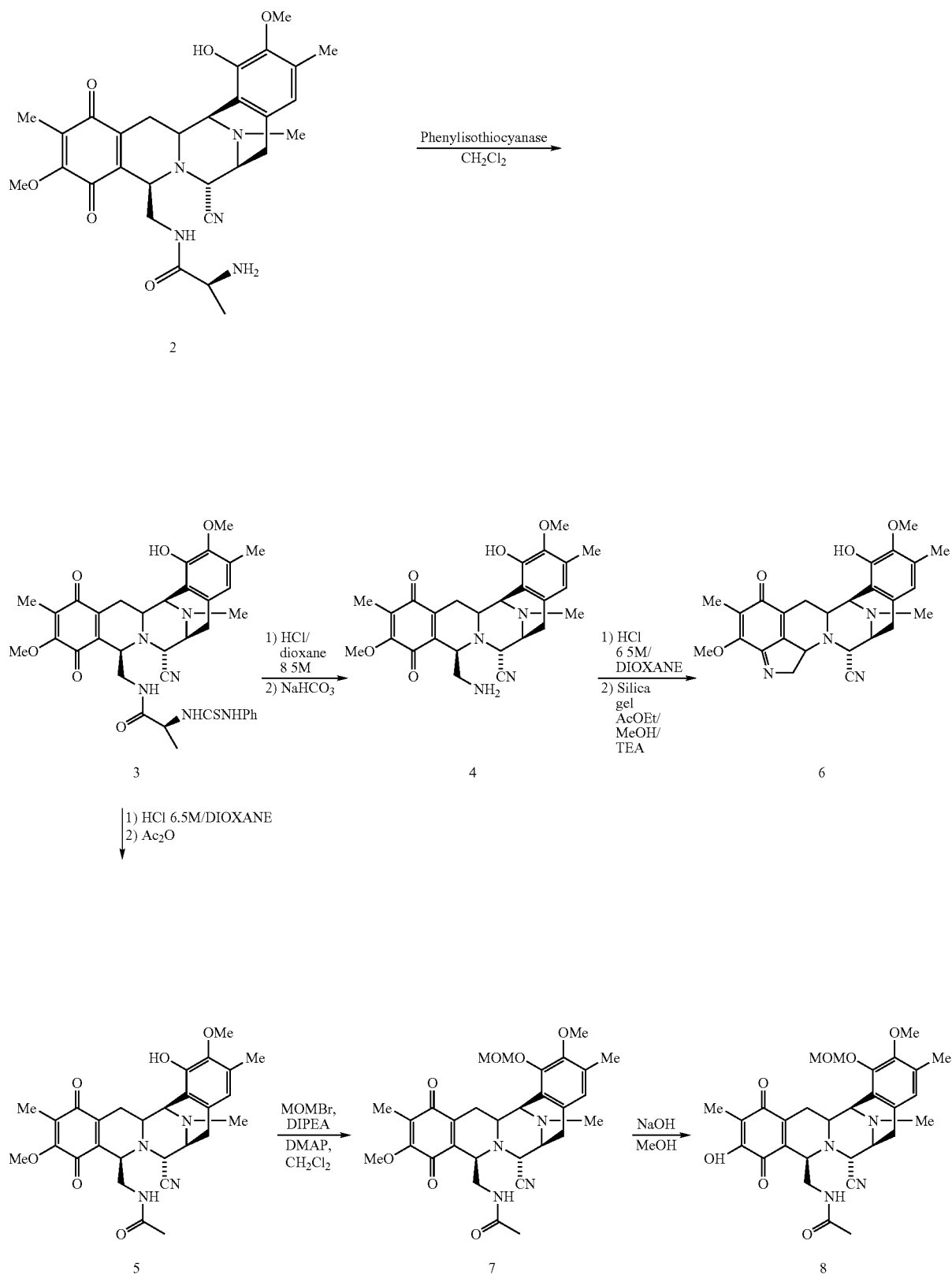

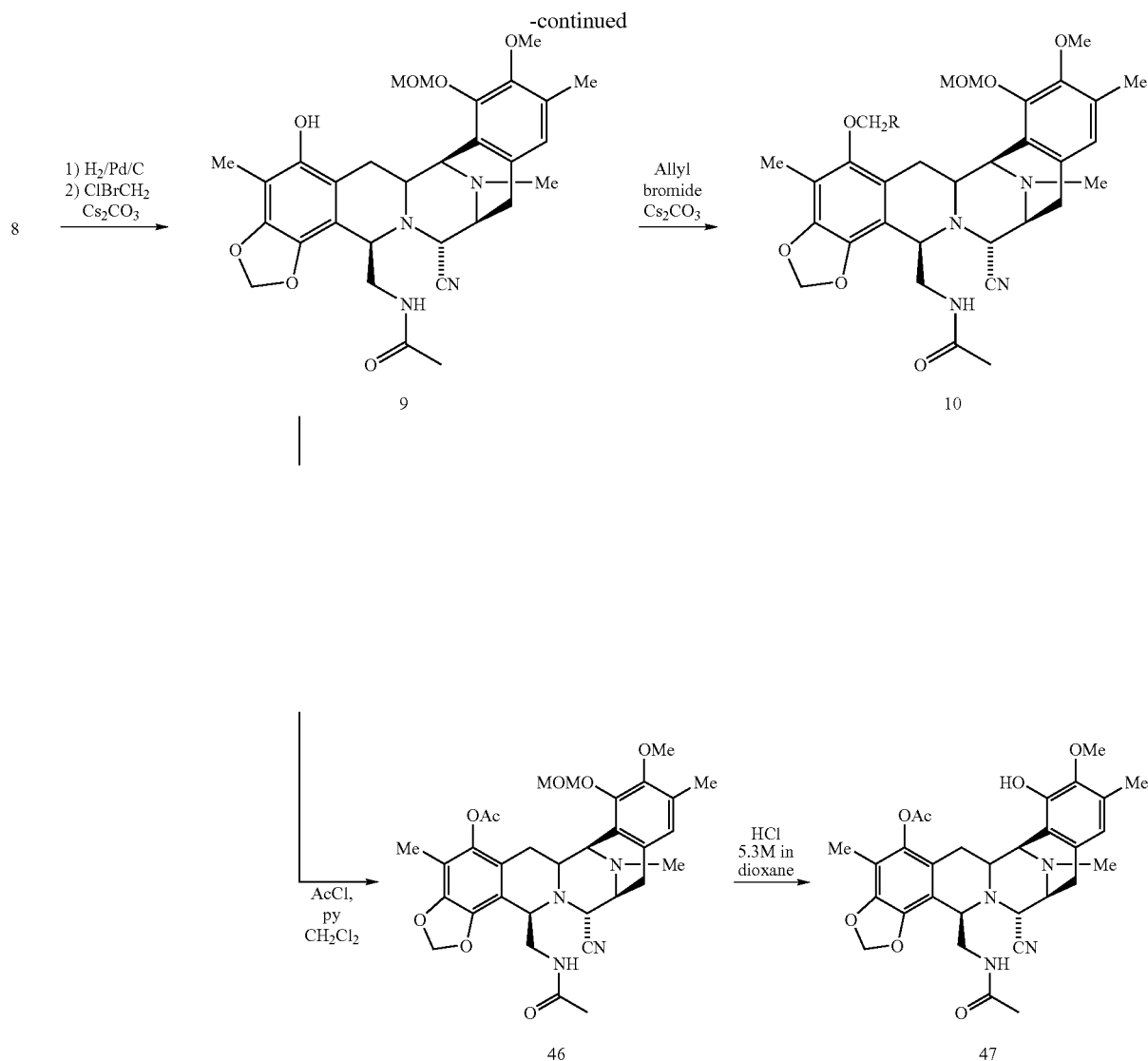
Other useful amide intermediate derivatives are made starting from already described intermediate 45 using the next scheme:
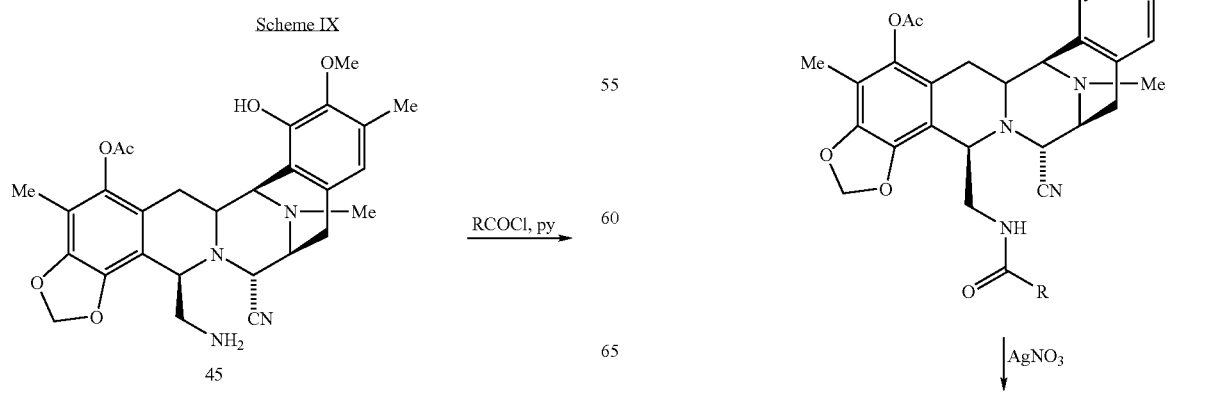

-continued

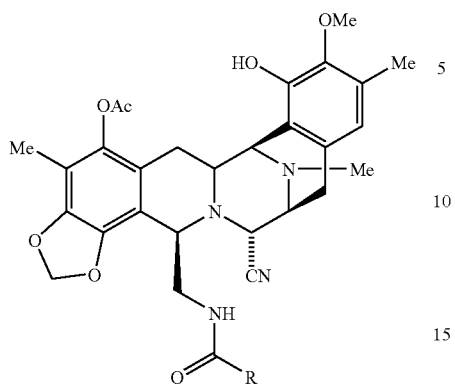

5

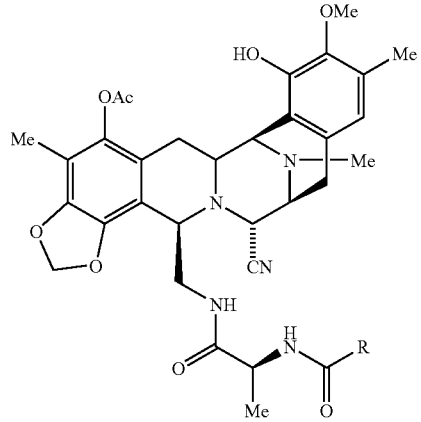

The second step is optional. This process is an important part of the invention, particularly where the group R is a group $R^a$ as previously defined. Furthermore, the Scheme VIII can be readily broadened to enable preparation of compounds of formula (XXIII), by inclusion in the starting material of a different group at the 5-position, either a group directly intended for the product or a group which can be removed or otherwise modified to give the desired group.

From compound 45 can be made a group of analogs through the following sequence:

acylation in the amino group of compound of Formula 45 by a wide range of acyl derivatives to provide the corresponding amides, where preferred acyl groups are acetyl, cinnamoyl chloride, p-trifluorocinnamoyl chloride, isovaleryl chloride phenylisothiocyanate or aminoacids, or the other examples previously given of groups $R^aCO$—.

transforming the CN group into an OH group by reaction with silver nitrate in a mixture AcN/H$_2$O.

Other useful amide intermediate derivatives are made starting from already described intermediate 43 using the next scheme:

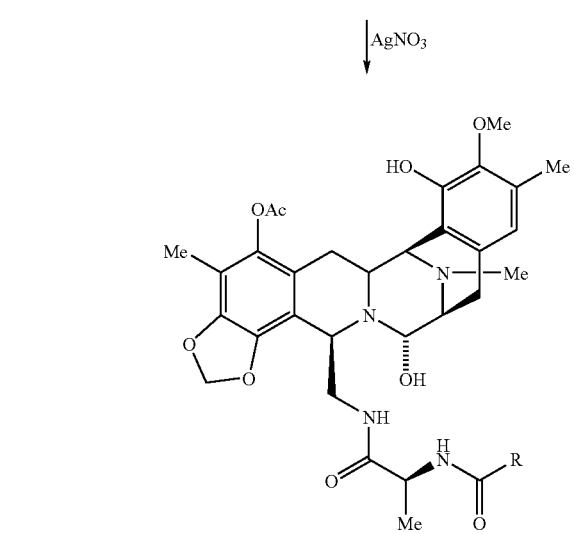

From Compound 43 can be obtained another group of interesting derivatives using the following sequence:

(a) acylation in the amino group of compound of Formula 43 by a wide range of acyl derivatives to provide the corresponding amides, where preferred acyl groups are acetyl, cinnamoyl chloride, p-trifluorocinnamoyl chloride, isovaleryl chloride or aminoacids, or the other examples previously given of groups $R^aCO$—.

(b) transforming the CN group into an OH group by reaction with silver nitrate in a mixture AcN/H$_2$O Reflecting the active compounds, an important process in accordance with this invention is as follows:

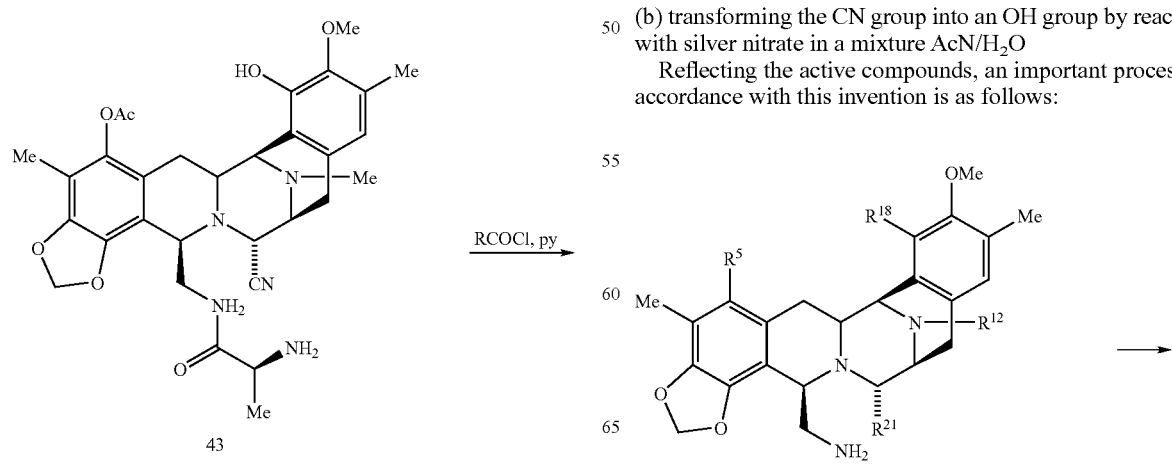

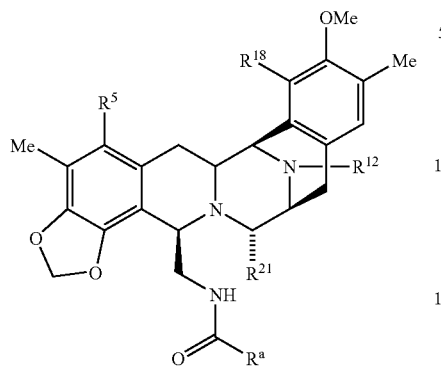

where $R^5$ for the end product is as defined for the compound (XXII) and may be different in the starting material and converted thereto as part of the process, $R^{18}$ is a hydroxy group in the end product but may be a protected hydroxy group in the starting material and converted thereto as part of the process, $R^{12}$ for the end product may be the same as in the starting material or may be converted thereto as part of the process, $R^{21}$ for the end product is as defined and if a hydroxy group may be formed from a cyano group as part of the process, $R^a$ is as defined, and may be further acylated as part of the process to give an end product with an acylated $R^a$ group as discussed.

$R^5$ is preferably oxyacetyl or other small oxyacyl group in the starting material and is not changed in the reaction. $R^{18}$ is preferably a hydroxy group in the starting material and is not changed in the reaction. $R^{12}$ is preferably —NCH$_3$— in the starting material and is not changed in the reaction. $R^{21}$ the end product is as defined and if a hydroxy group may be formed from a cyano group as part of the process. $R^a$ is in the final product is preferably as defined in relation to the compound of formula (XXIII).

Another important method of this invention includes the reaction:

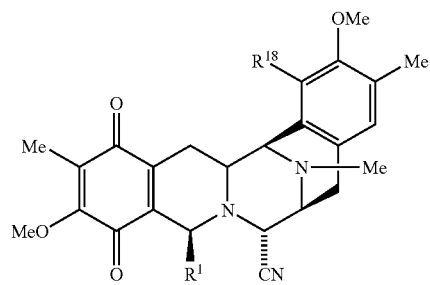

Another important method of this invention includes the reaction:

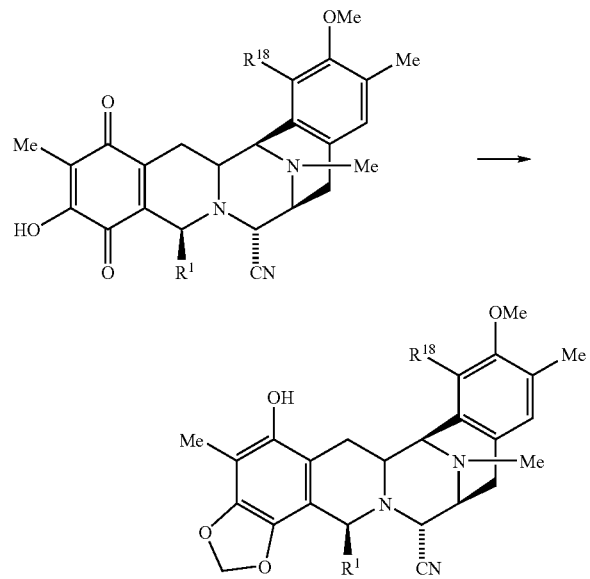

Another important method of this invention includes the reaction includes the reaction where a group $R^1$ is aminomethylene is converted to a hydroxymethylene group.

Another important method of this invention includes the reaction for preparing a 21-cyano compound of formula (XVI) which comprises reacting a compound of formula (XV):

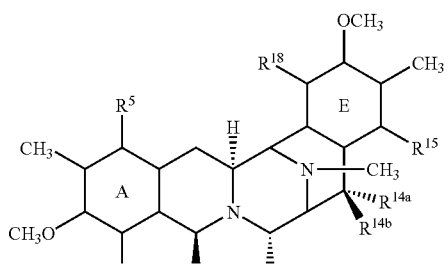

where $R^1$, $R^5$, $R^8$, $R^{14a}$, $R^{14b}$, $R^{15}$ and $R^{18}$ are as defined and $R^{21}$ is a hydroxy group, with a source of cyanide ion, to give the desired 21-cyano compound.

In addition, processes using other nucleophile-containing compounds, to produce similar compounds of formula (XVI)

wherein the 21-position is protected by another nucleophilic group, a 21-Nuc group, are also envisaged. For example, a 21-Nuc compound of formula (XVI) with an alkylamino substituent at the 21-position can be produced by reacting the compound of formula (XV) wherein $R^{21}$ is a hydroxy group with a suitable alkylamine. A 21-Nuc compound of formula (XVI) with an alkylthio substituent at the 21-position can also be produced by reacting the compound of formula (XV) wherein $R^{21}$ is a hydroxy group with a suitable alkanethiol. Alternatively, a 21-Nuc compound of formula (XVI) with an α-carbonylalkyl substituent at the 21-position can be produced by reacting the compound of formula (XV) wherein $R^{21}$ is a hydroxy group with a suitable carbonyl compound, typically in the presence of a base. Other synthetic routes are available for other 21-Nuc compounds.

Another important reaction of this invention involves treatment of a 21-cyano product of this invention to form a 21-hydroxy compound. Such compounds have interesting in vivo properties.

For the avoidance of doubt, the stereochemistries indicated in this patent specification are based on our understanding of the correct stereochemistry of the natural products. To the extent that an error is discovered in the assigned stereochemistry, then the appropriate correction needs to be made in the formulae given throughout in this patent specification. Furthermore, to the extent that the syntheses are capable of modification, this invention extends to stereoisomers.

Cytotoxic Activity

| Compound | $IC_{50}$ (μM) | | | | | |
|---|---|---|---|---|---|---|
| | P-388 | A-549 | HT-29 | MEL-28 | CV-1 | DU-145 |
| | 0.009 | 0.018 | 0.018 | 0.018 | 0.023 | |

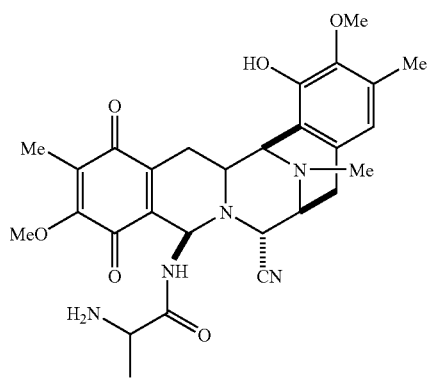

2

| | 0.15 | >0.15 | 0.15 | >0.15 | | |
|---|---|---|---|---|---|---|

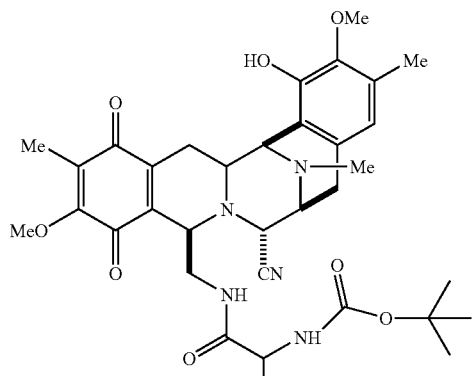

14

-continued
| Compound | IC$_{50}$ (μM) | | | | | |
|---|---|---|---|---|---|---|
| | P-388 | A-549 | HT-29 | MEL-28 | CV-1 | DU-145 |
| 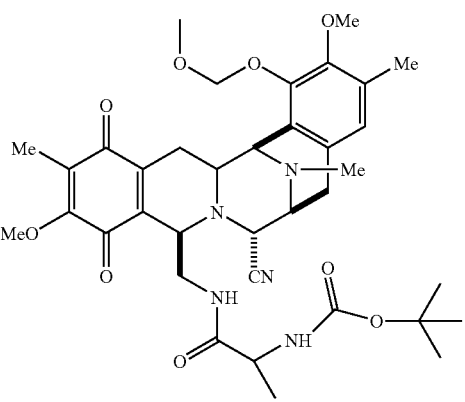<br>15 | 1.44 | 1.44 | 1.44 | 1.44 | | |
| 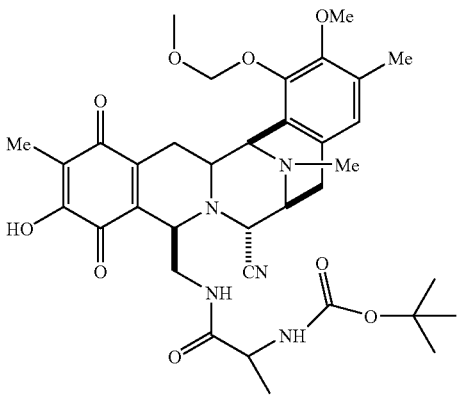<br>16 | >1.5 | >1.5 | >1.5 | >1.5 | | |
| 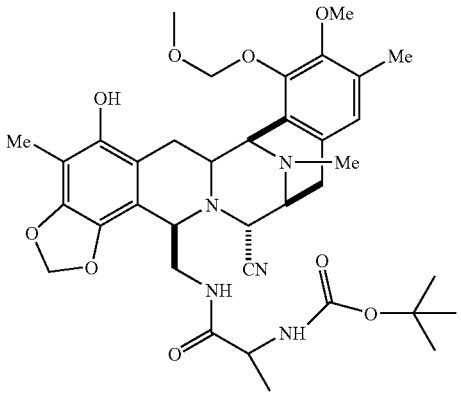<br>17 | 1.4 | 1.4 | 1.4 | 1.4 | | |

-continued
| Compound | IC$_{50}$ (μM) | | | | | |
|---|---|---|---|---|---|---|
| | P-388 | A-549 | HT-29 | MEL-28 | CV-1 | DU-145 |
| 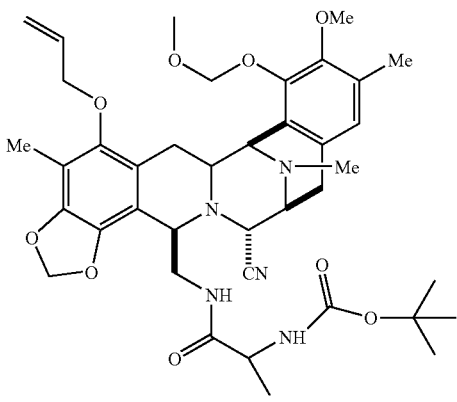<br>18 | 0.01 | 0.01 | 0.01 | 0.01 | | |
| 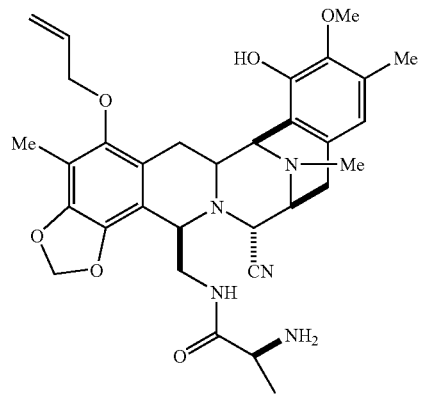<br>19 | 0.08 | 0.16 | 0.01 | 0.16 | | |
| 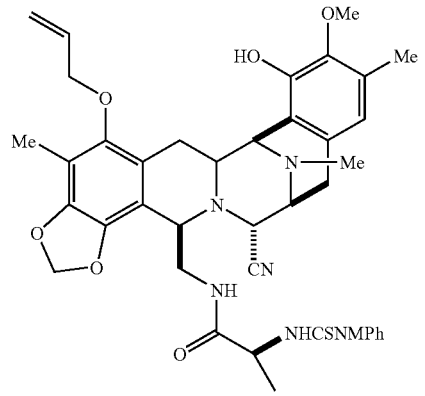<br>20 | 0.01 | 0.01 | 0.01 | 0.01 | | |

-continued
| Compound | IC$_{50}$ (μM) | | | | | |
|---|---|---|---|---|---|---|
| | P-388 | A-549 | HT-29 | MEL-28 | CV-1 | DU-145 |
| 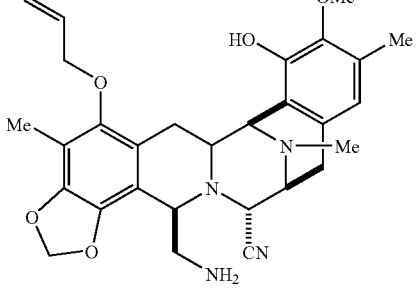<br>21 | 0.019 | 0.019 | 0.019 | 0.019 | | |
| 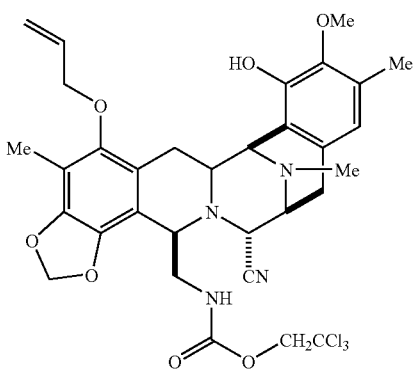<br>22 | 0.014 | 0.014 | 0.014 | 0.014 | 0.014 | 0.014 |
| 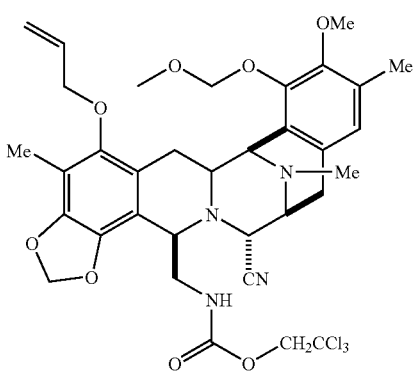<br>23 | 0.13 | 0.13 | 0.13 | 0.13 | 0.13 | 0.13 |
| 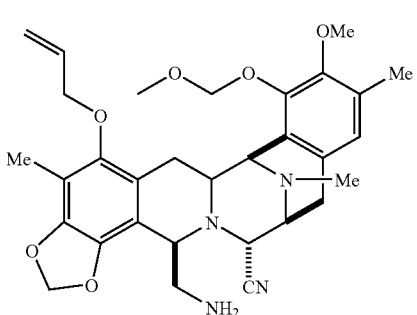<br>24 | 0.18 | 1.8 | 1.8 | 1.8 | 1.8 | 1.8 |

-continued
| Compound | IC$_{50}$ (μM) | | | | | |
|---|---|---|---|---|---|---|
| | P-388 | A-549 | HT-29 | MEL-28 | CV-1 | DU-145 |
| 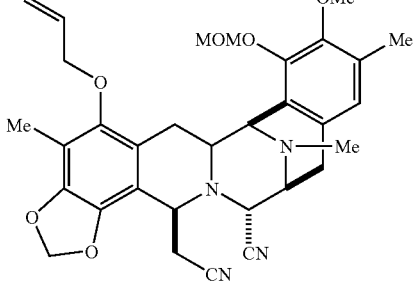<br>25 | 0.2 | 0.2 | 0.2 | 0.2 | | 0.2 |
| 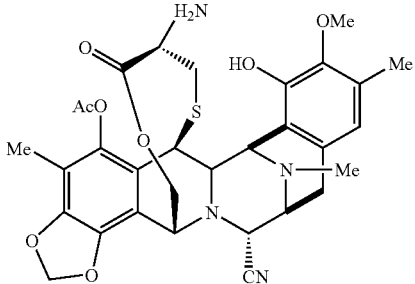<br>35 | 0.008 | 0.008 | 0.008 | 0.008 | | |
| 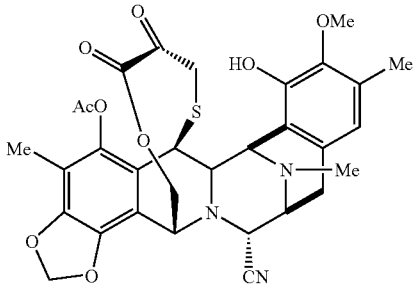<br>36 | 0.01 | 0.01 | 0.01 | 0.01 | | |
| 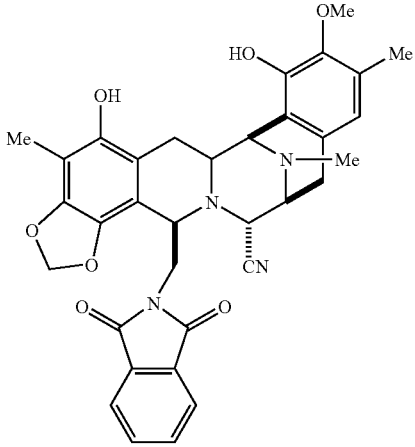<br>28 | 0.001 | 0.001 | 0.001 | 0.001 | 0.001 | 0.001 |

-continued

| Compound | IC$_{50}$ (μM) | | | | | |
|---|---|---|---|---|---|---|
| | P-388 | A-549 | HT-29 | MEL-28 | CV-1 | DU-145 |
| 42 | 0.13 | 0.13 | 0.13 | 0.13 | | 0.13 |
| 43 | 0.008 | 0.016 | 0.008 | 0.008 | | 0.016 |
| 44 | 0.001 | 0.001 | 0.001 | 0.001 | | 0.001 |

-continued
| Compound | IC₅₀ (μM) | | | | | |
|---|---|---|---|---|---|---|
| | P-388 | A-549 | HT-29 | MEL-28 | CV-1 | DU-145 |
| 45 | 0.01 | 0.01 | 0.01 | 0.01 | | 0.01 |
| 3 | 0.015 | 0.015 | 0.015 | 0.015 | 0.018 | |
| 6 | 2.171 | 2.171 | 2.171 | 2.171 | 2.171 | |
| 5 | 0.005 | 0.005 | 0.005 | 0.005 | | |
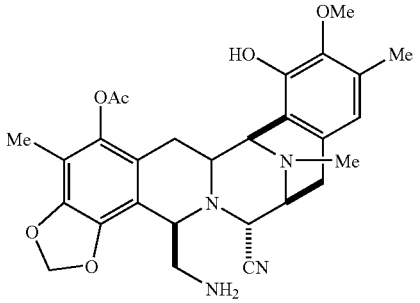
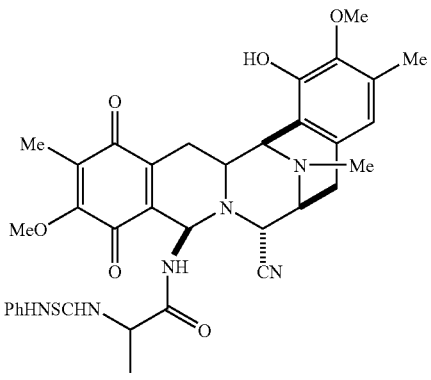
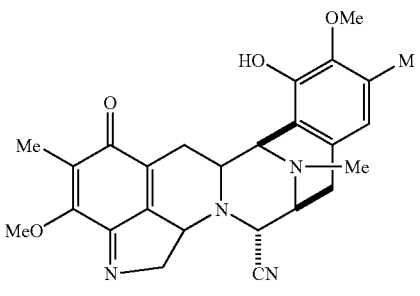
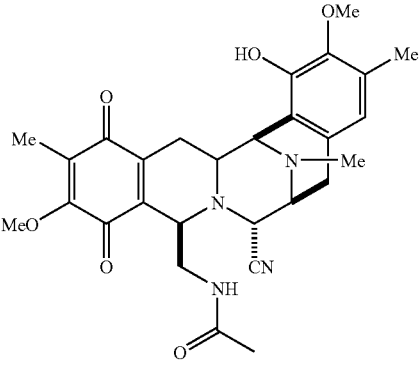

-continued
| Compound | IC$_{50}$ (μM) | | | | | |
|---|---|---|---|---|---|---|
| | P-388 | A-549 | HT-29 | MEL-28 | CV-1 | DU-145 |
| 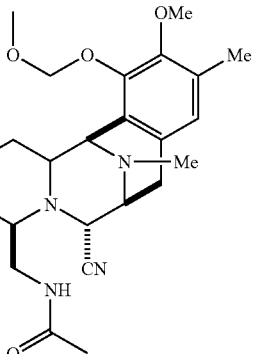 7 | 0.22 | 0.22 | 0.22 | 0.22 | 0.22 | |
| 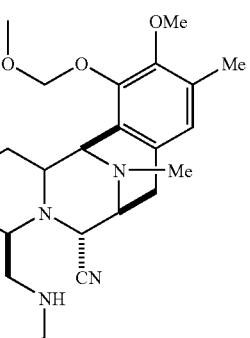 8 | >9 | >18.1 | >18.1 | >18.1 | >18.1 | |
| 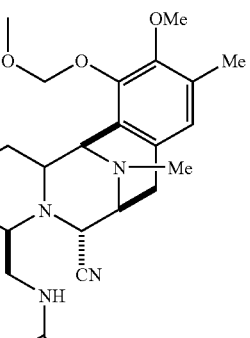 9 | >1.77 | >1.77 | >1.77 | >1.77 | | >1.77 |

-continued
| Compound | IC₅₀ (μM) | | | | | |
|---|---|---|---|---|---|---|
| | P-388 | A-549 | HT-29 | MEL-28 | CV-1 | DU-145 |
| 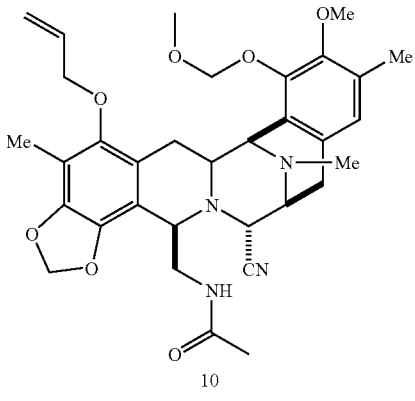<br>10 | >1.65 | >1.65 | >1.65 | >1.65 | | >1.65 |
| 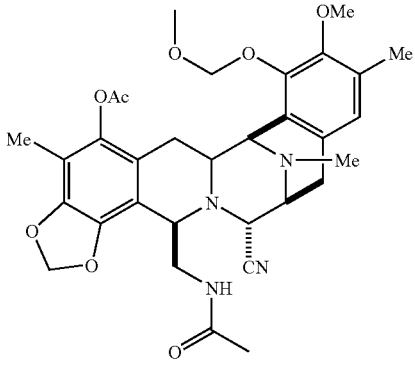<br>46 | 0.016 | 0.016 | 0.016 | 0.016 | | 0.016 |
| 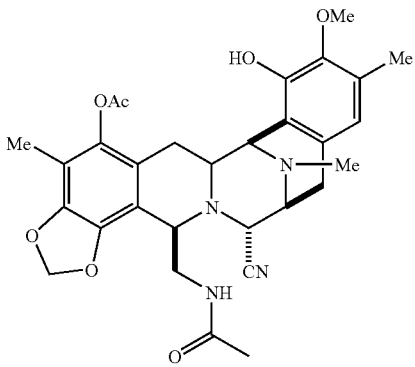<br>47 | 0.001 | 0.001 | 0.001 | 0.001 | | 0.001 |

-continued
| Compound | IC$_{50}$ (µM) | | | | | |
|---|---|---|---|---|---|---|
| | P-388 | A-549 | HT-29 | MEL-28 | CV-1 | DU-145 |
| 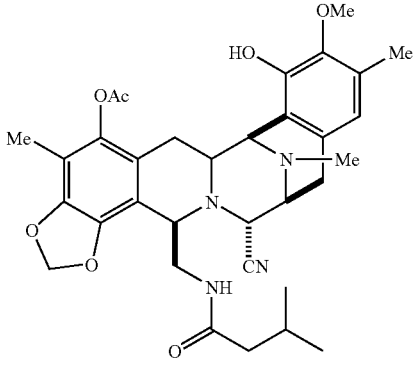 48 | 0.0008 | 0.001 | 0.0008 | 0.0008 | | 0.001 |
| 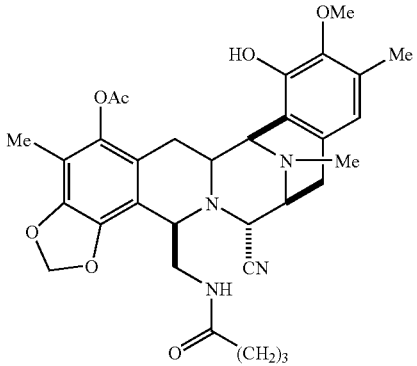 49 | 0.007 | 0.007 | 0.007 | 0.007 | | 0.007 |
| 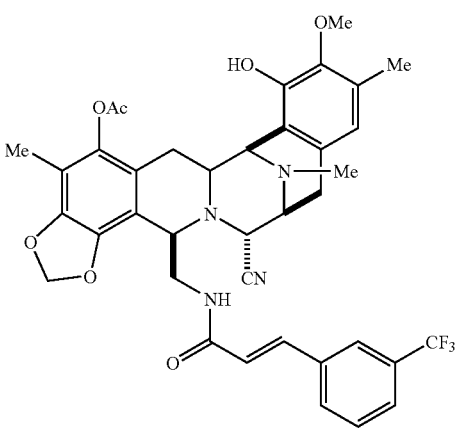 50 | 0.0001 | 0.0001 | 0.0001 | 0.0001 | | 0.0001 |

| Compound | IC$_{50}$ (μM) | | | | | |
|---|---|---|---|---|---|---|
| | P-388 | A-549 | HT-29 | MEL-28 | CV-1 | DU-145 |
| 51 | 0.0001 | 0.0001 | 0.0001 | 0.0001 | | 0.0001 |
| 52 | 0.001 | 0.001 | 0.001 | 0.001 | | 0.001 |
| 53 | 0.0001 | 0.0001 | 0.0001 | 0.0001 | | 0.0001 |

-continued
| Compound | IC$_{50}$ (μM) | | | | | |
|---|---|---|---|---|---|---|
| | P-388 | A-549 | HT-29 | MEL-28 | CV-1 | DU-145 |
| 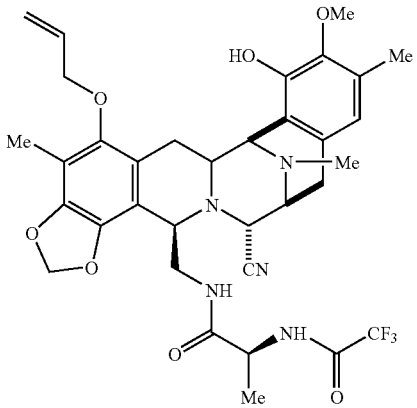 54 | 0.001 | 0.001 | 0.001 | 0.001 | | 0.001 |
| 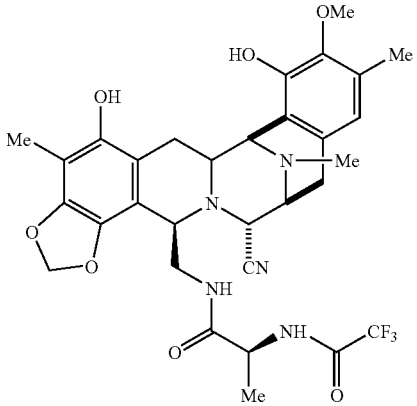 55 | 0.01 | 0.01 | 0.01 | 0.01 | | 0.01 |
| 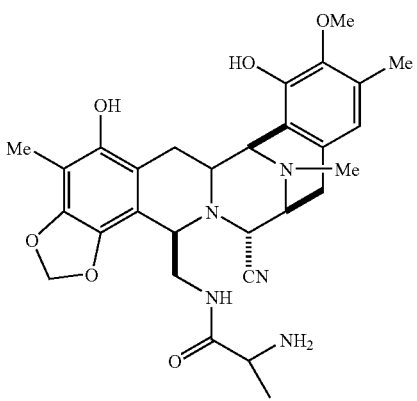 56 | 0.18 | 0.9 | 0.18 | 0.8 | | 0.9 |

-continued
| Compound | IC$_{50}$ (μM) | | | | | |
|---|---|---|---|---|---|---|
| | P-388 | A-549 | HT-29 | MEL-28 | CV-1 | DU-145 |
| 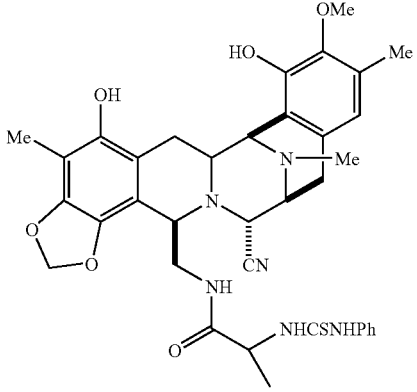 57 | 0.14 | 0.14 | 0.14 | 0.14 | | 0.14 |
| 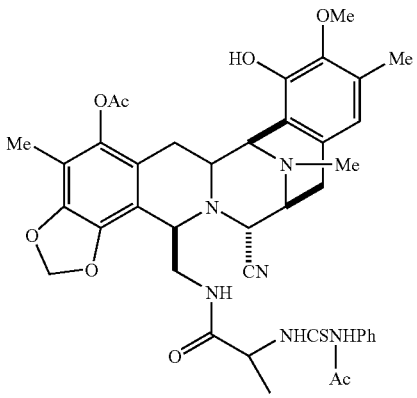 58 | 0.001 | 0.001 | 0.001 | 0.001 | | 0.001 |
| 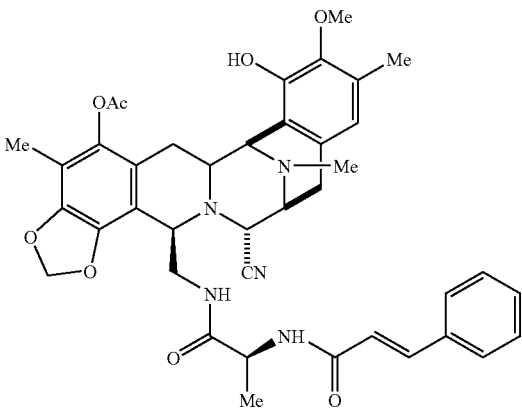 60 | 0.001 | 0.001 | 0.0001 | 0.001 | | 0.0005 |

-continued
| | IC$_{50}$ (μM) | | | | | |
|---|---|---|---|---|---|---|
| Compound | P-388 | A-549 | HT-29 | MEL-28 | CV-1 | DU-145 |
| 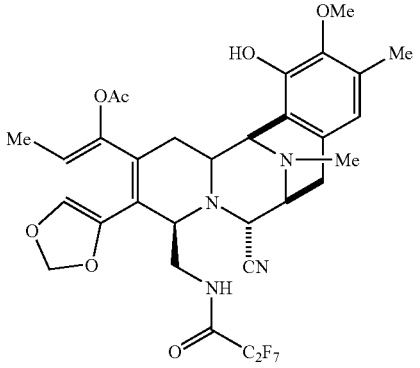 61 | 0.001 | 0.001 | 0.001 | 0.001 | | 0.001 |
| 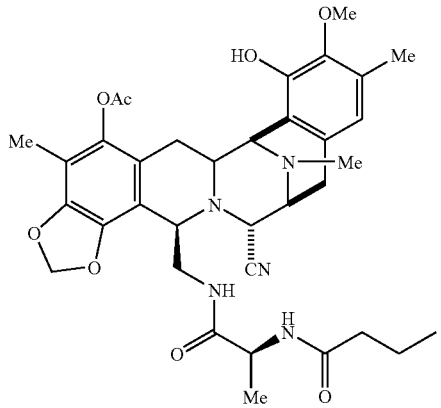 62 | 0.001 | 0.001 | | 0.0005 | | 0.001 |
| 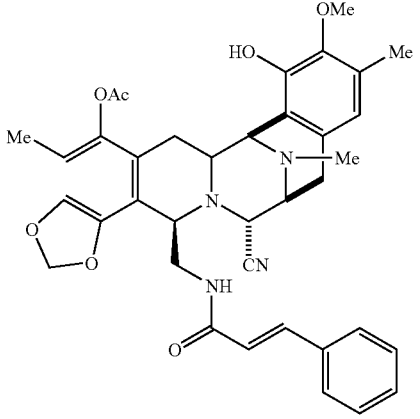 63 | 0.0001 | 0.0001 | 0.0001 | 0.0001 | | 0.0001 |

| | IC$_{50}$ (μM) | | | | | |
|---|---|---|---|---|---|---|
| Compound | P-388 | A-549 | HT-29 | MEL-28 | CV-1 | DU-145 |
| 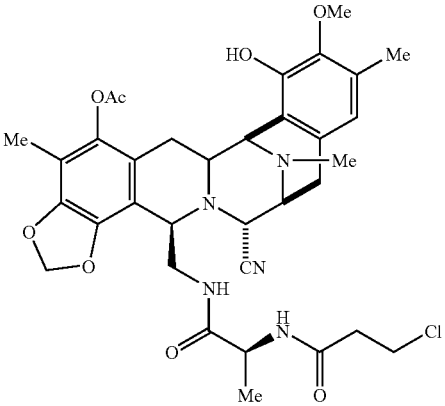<br>64 | 0.001 | 0.001 | | 0.001 | | 0.001 |
| 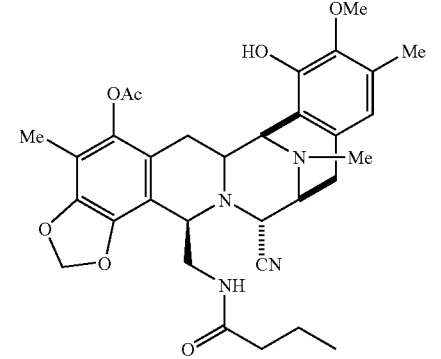<br>65 | 0.0001 | 0.0001 | 0.0001 | | 0.0001 | |
| 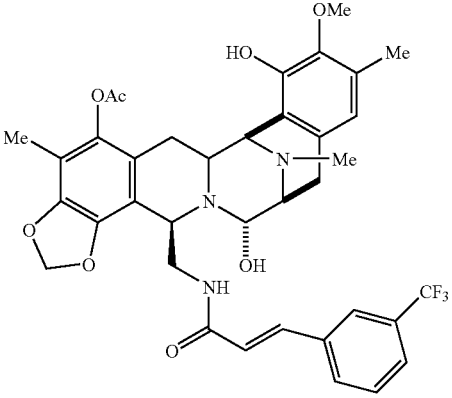<br>66 | 0.0001 | 0.0001 | 0.0001 | | 0.0001 | |

-continued
| Compound | IC$_{50}$ (μM) | | | | | |
|---|---|---|---|---|---|---|
| | P-388 | A-549 | HT-29 | MEL-28 | CV-1 | DU-145 |
| 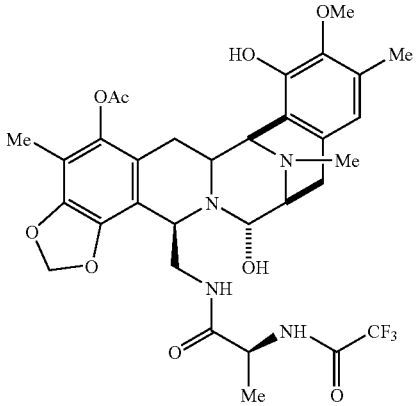 67 | 0.0001 | 0.0001 | 0.0001 | | 0.0001 | |
| 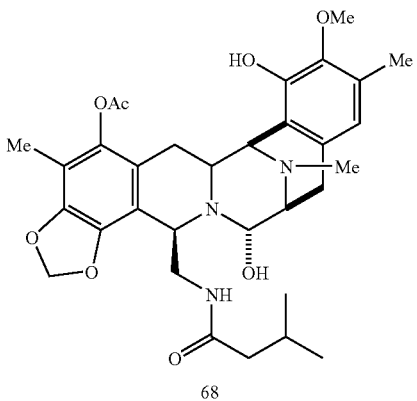 68 | 0.0008 | 0.001 | 0.0008 | 0.0008 | | 0.001 |
| 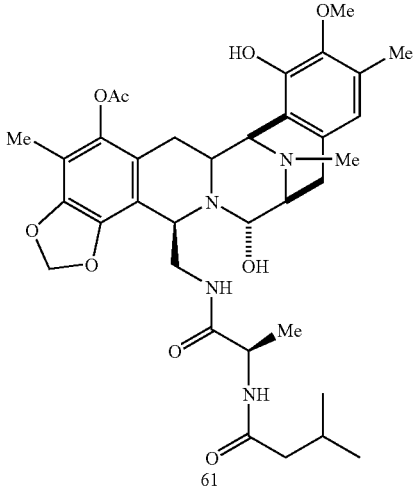 61 | 0.001 | 0.001 | 0.001 | 0.001 | | 0.001 |

-continued

| Compound | IC₅₀ (μM) | | | | | |
|---|---|---|---|---|---|---|
| | P-388 | A-549 | HT-29 | MEL-28 | CV-1 | DU-145 |
| 70 | 0.0001 | 0.0001 | 0.0001 | 0.0001 | | 0.0001 |
| 71 | 0.0008 | 0.0008 | 0.0001 | 0.0008 | | 0.0001 |
| 72 | 0.0001 | 0.0001 | 0.0001 | 0.0001 | | 0.0001 |

-continued

| Compound | IC₅₀ (µM) | | | | | |
|---|---|---|---|---|---|---|
| | P-388 | A-549 | HT-29 | MEL-28 | CV-1 | DU-145 |
| 73 | 0.0001 | 0.0001 | 0.0001 | 0.0001 | | 0.0001 |
| 74 | 0.0001 | 0.0001 | 0.0001 | 0.0001 | | 0.0001 |
| 75 | 0.1 | 0.1 | 0.1 | 0.1 | | 0.1 |

-continued
| Compound | IC$_{50}$ (μM) | | | | | |
|---|---|---|---|---|---|---|
| | P-388 | A-549 | HT-29 | MEL-28 | CV-1 | DU-145 |
| 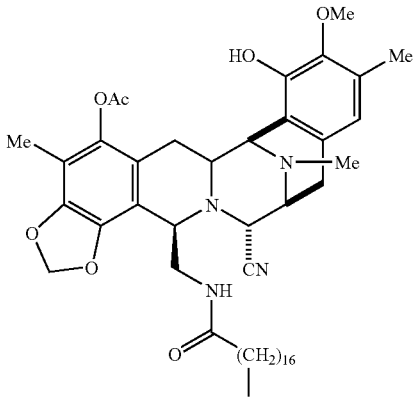76 | 0.1 | 0.1 | 0.1 | 0.1 | | 0.1 |
| 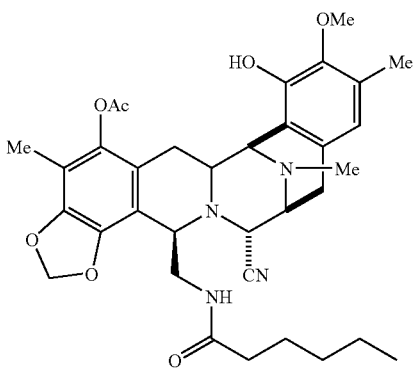77 | 0.0001 | 0.0001 | 0.0001 | 0.0001 | 0.0001 | 0.0001 |
| 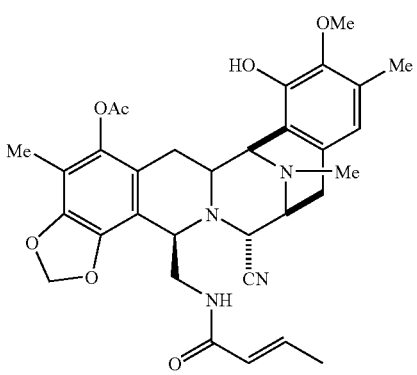78 | 0.0001 | 0.0008 | 0.0001 | 0.0001 | | 0.0008 |

-continued
| Compound | IC$_{50}$ (μM) | | | | | |
|---|---|---|---|---|---|---|
| | P-388 | A-549 | HT-29 | MEL-28 | CV-1 | DU-145 |
| 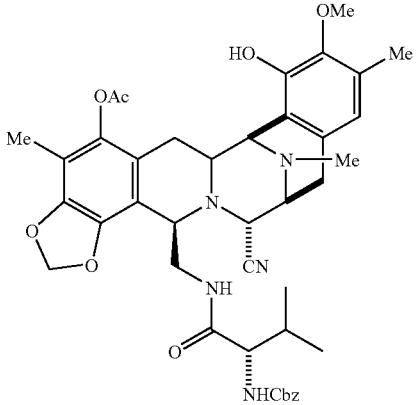79 | 0.001 | 0.001 | 0.001 | 0.001 | | 0.001 |
| 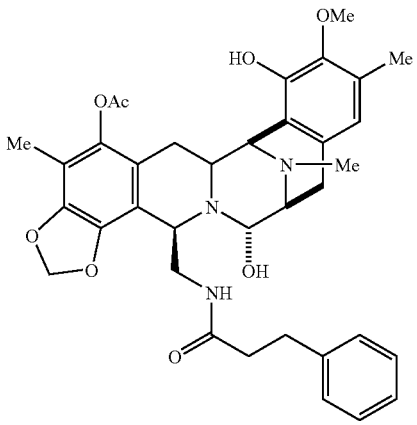80 | 0.0001 | 0.0001 | 0.0001 | 0.0001 | | 0.0001 |
| 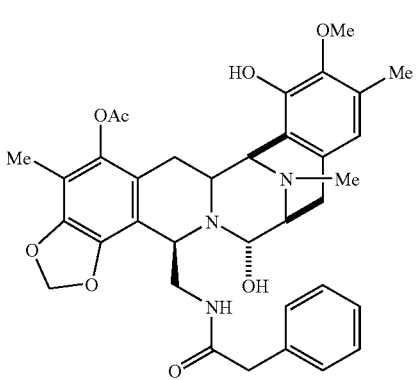81 | 0.0007 | 0.0007 | 0.0007 | 0.0007 | | 0.0007 |

-continued

| Compound | IC$_{50}$ (μM) | | | | | |
| --- | --- | --- | --- | --- | --- | --- |
| | P-388 | A-549 | HT-29 | MEL-28 | CV-1 | DU-145 |
| 82 | 0.0001 | 0.0001 | 0.0001 | 0.0001 | | 0.0001 |
| 83 | 0.0001 | 0.0001 | 0.0001 | 0.0001 | 0.0001 | 0.0001 |
| 84 | 0.0001 | 0.0008 | 0.0001 | 0.0001 | | 0.0008 |

-continued
| Compound | IC$_{50}$ (μM) | | | | | |
|---|---|---|---|---|---|---|
| | P-388 | A-549 | HT-29 | MEL-28 | CV-1 | DU-145 |
| 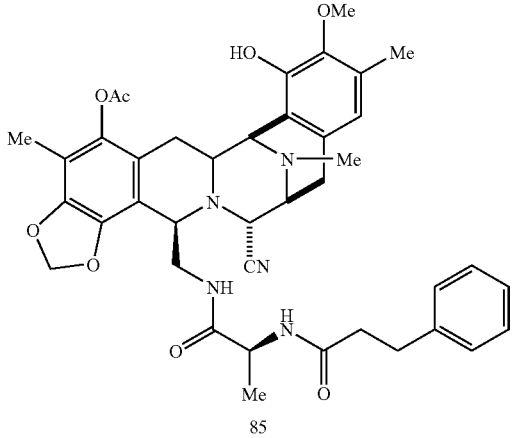<br>85 | 0.0006 | 0.001 | 0.0006 | 0.001 | | 0.0006 |
| 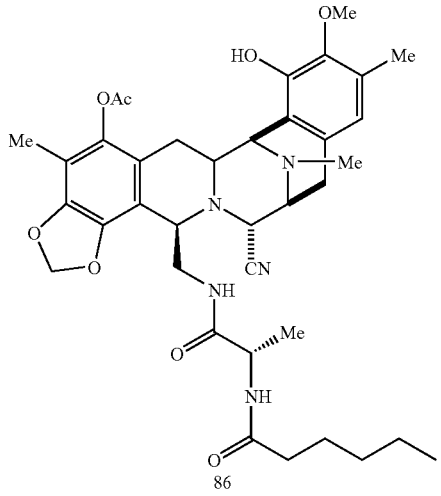<br>86 | 0.001 | 0.001 | 0.001 | 0.001 | 0.001 | 0.001 |
| 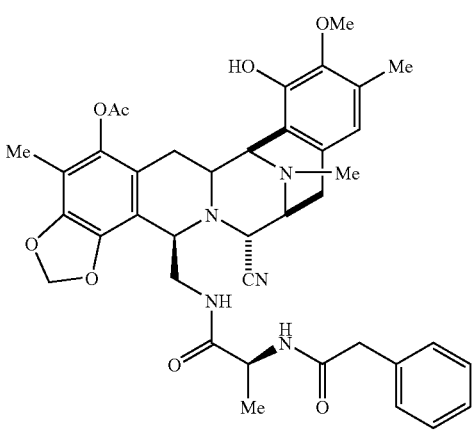<br>87 | 0.0001 | 0.0001 | 0.0001 | 0.0001 | | 0.0001 |

-continued

| Compound | IC$_{50}$ (μM) | | | | | |
|---|---|---|---|---|---|---|
| | P-388 | A-549 | HT-29 | MEL-28 | CV-1 | DU-145 |
| 88 | 0.0007 | 0.0007 | 0.0007 | 0.0007 | | 0.0007 |
| 89 | 0.001 | 0.007 | 0.001 | 0.001 | | 0.007 |
| 90 | 0.01 | 0.01 | 0.01 | 0.01 | | 0.01 |

-continued
| Compound | IC$_{50}$ (μM) | | | | | |
|---|---|---|---|---|---|---|
| | P-388 | A-549 | HT-29 | MEL-28 | CV-1 | DU-145 |
| 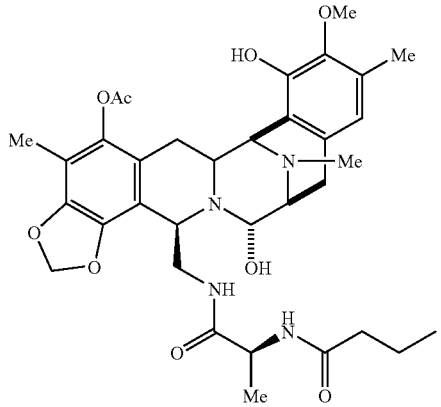<br>91 | 0.001 | 0.001 | 0.001 | 0.001 | | 0.001 |
| 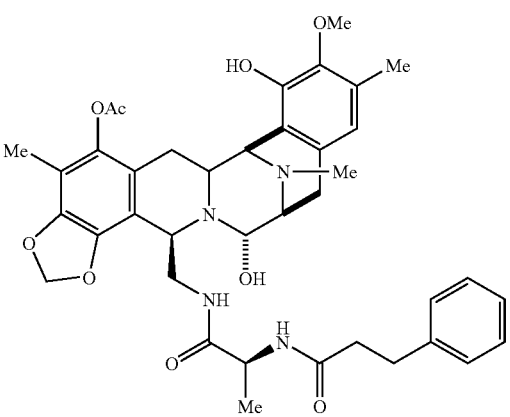<br>92 | 0.0001 | 0.0001 | 0.0001 | 0.0001 | | 0.0001 |
| 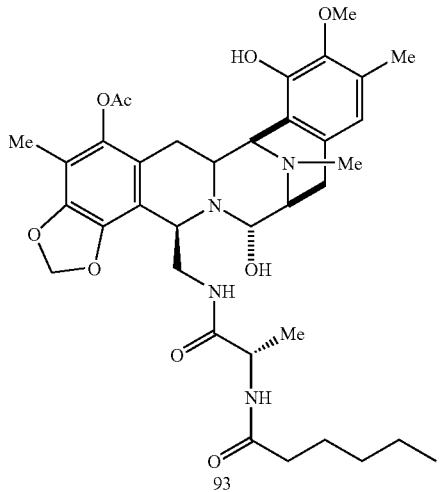<br>93 | 0.001 | 0.001 | 0.001 | 0.001 | 0.001 | 0.001 |

-continued
| Compound | IC$_{50}$ (μM) | | | | | |
|---|---|---|---|---|---|---|
| | P-388 | A-549 | HT-29 | MEL-28 | CV-1 | DU-145 |
| 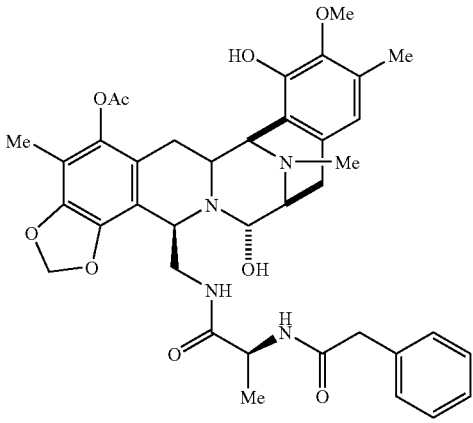<br>94 | 0.0007 | 0.0007 | 0.0007 | 0.0007 | | 0.0007 |
| 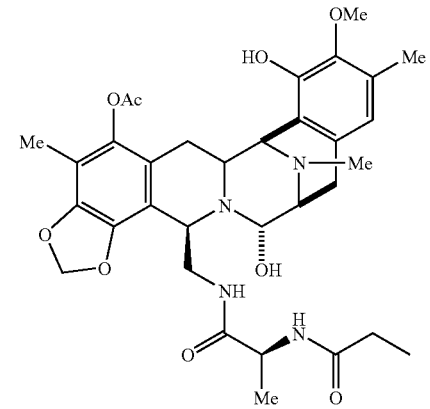<br>95 | 0.0001 | 0.0001 | 0.0001 | 0.0001 | | 0.0001 |
| 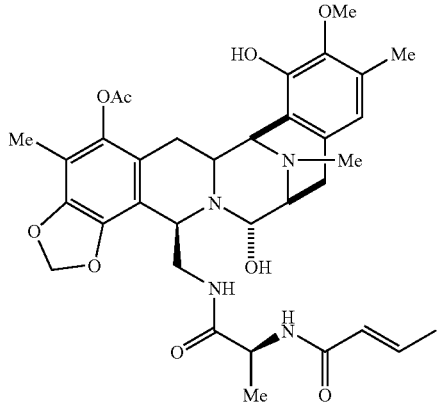<br>96 | 0.001 | 0.007 | 0.001 | 0.001 | | 0.007 |

-continued

| Compound | IC$_{50}$ (μM) | | | | | |
|---|---|---|---|---|---|---|
| | P-388 | A-549 | HT-29 | MEL-28 | CV-1 | DU-145 |
| 97 | >1 | >1 | >1 | >1 | | >1 |
| 98 | >1 | >1 | >1 | >1 | | >1 |
| 99 | 0.7 | 0.7 | 0.7 | 0.7 | 0.7 | 0.7 |

-continued
| Compound | IC$_{50}$ (μM) | | | | | |
|---|---|---|---|---|---|---|
| | P-388 | A-549 | HT-29 | MEL-28 | CV-1 | DU-145 |
| 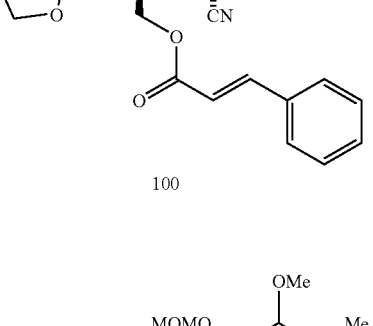
100 | 0.1 | 0.1 | 0.1 | 0.1 | | 0.1 |
| 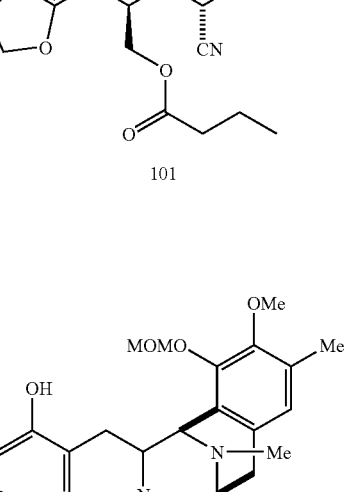
101 | 0.1 | 0.1 | 0.1 | 0.1 | | 0.1 |
| 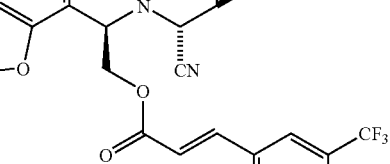
102 | 0.1 | 0.1 | 0.1 | 0.1 | | 0.1 |

-continued
| Compound | IC$_{50}$ (μM) | | | | | |
|---|---|---|---|---|---|---|
| | P-388 | A-549 | HT-29 | MEL-28 | CV-1 | DU-145 |
| 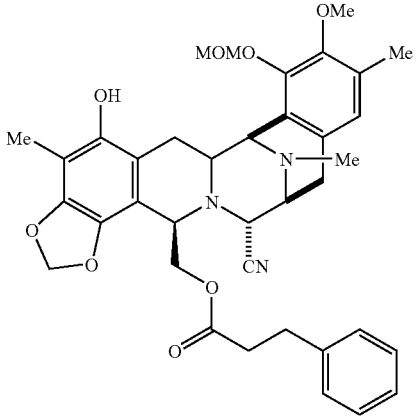 103 | 0.1 | 0.1 | 0.1 | 0.1 | | 0.1 |
| 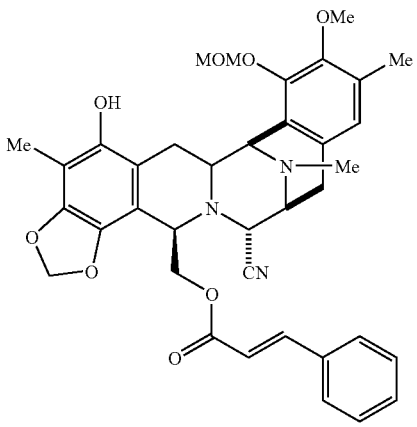 104 | 0.1 | 0.1 | 0.1 | 0.1 | | 0.1 |
| 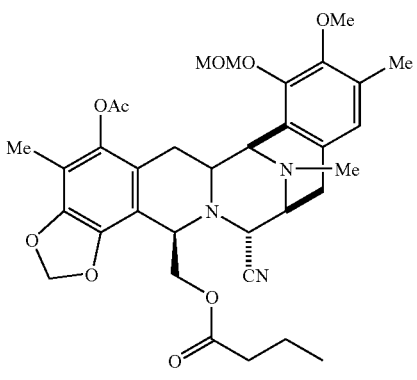 105 | 0.1 | 0.1 | 0.1 | 0.1 | | 0.1 |

| Compound | IC₅₀ (μM) | | | | | |
|---|---|---|---|---|---|---|
| | P-388 | A-549 | HT-29 | MEL-28 | CV-1 | DU-145 |
| 106 | 0.6 | 0.6 | 0.6 | 0.6 | | 0.6 |
| 107 | 0.1 | 0.1 | 0.1 | 0.1 | | 0.1 |
| 108 | 0.01 | 0.07 | 0.07 | 0.07 | | 0.07 |

-continued

| Compound | IC$_{50}$ (μM) | | | | | |
|---|---|---|---|---|---|---|
| | P-388 | A-549 | HT-29 | MEL-28 | CV-1 | DU-145 |
| 109 | 0.0001 | 0.0008 | 0.0008 | 0.0008 | | 0.0008 |
| 110 | 0.001 | 0.001 | 0.001 | 0.001 | | 0.001 |
| 111 | 0.0001 | 0.0001 | 0.0001 | 0.0001 | | 0.0001 |

-continued

| Compound | IC$_{50}$ (μM) | | | | | |
|---|---|---|---|---|---|---|
| | P-388 | A-549 | HT-29 | MEL-28 | CV-1 | DU-145 |
| 112 | 0.0007 | 0.0007 | 0.0007 | 0.0007 | | 0.0007 |
| 113 | 0.0001 | 0.0001 | 0.0001 | 0.0001 | | 0.0001 |
| 114 | 0.0001 | 0.0001 | 0.0001 | 0.0001 | | 0.0001 |

| Compound | IC$_{50}$ (μM) | | | | | |
|---|---|---|---|---|---|---|
| | P-388 | A-549 | HT-29 | MEL-28 | CV-1 | DU-145 |
| 115 | 0.0001 | 0.0001 | 0.0001 | 0.0001 | | 0.0001 |
| 116 | 0.0001 | 0.0007 | 0.0007 | 0.0007 | | 0.0007 |
| 117 | 0.06 | 0.06 | 0.06 | 0.06 | | 0.06 |

-continued

| Compound | IC₅₀ (μM) | | | | | |
|---|---|---|---|---|---|---|
| | P-388 | A-549 | HT-29 | MEL-28 | CV-1 | DU-145 |
| 118 | 0.001 | 0.001 | 0.001 | 0.001 | | 0.001 |
| 119 | 0.001 | 0.001 | 0.001 | 0.001 | | 0.001 |
| 120 | 0.06 | 0.06 | 0.06 | 0.06 | | 0.06 |

-continued
| Compound | IC$_{50}$ (μM) | | | | | |
|---|---|---|---|---|---|---|
| | P-388 | A-549 | HT-29 | MEL-28 | CV-1 | DU-145 |
| 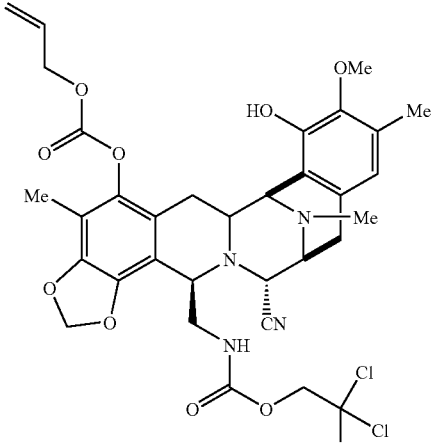 121 | 0.006 | 0.006 | 0.006 | 0.006 | | 0.006 |
| 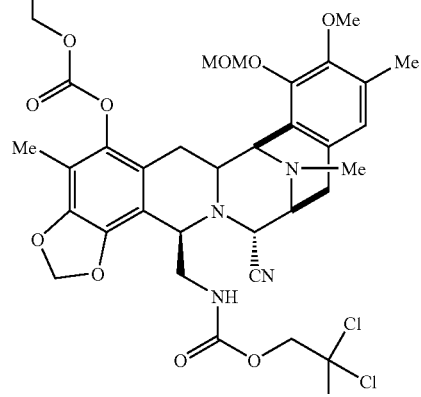 122 | 0.1 | 0.1 | 0.1 | 0.1 | | 0.1 |

-continued
| Compound | IC$_{50}$ (μM) | | | | | |
|---|---|---|---|---|---|---|
| | P-388 | A-549 | HT-29 | MEL-28 | CV-1 | DU-145 |
| 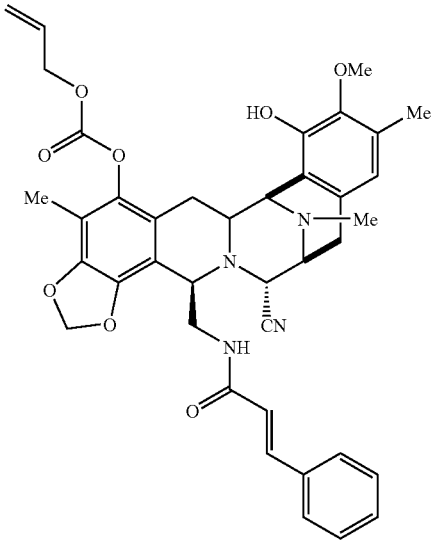<br>124 | 0.0001 | 0.0001 | 0.0001 | 0.0001 | | 0.0001 |
| 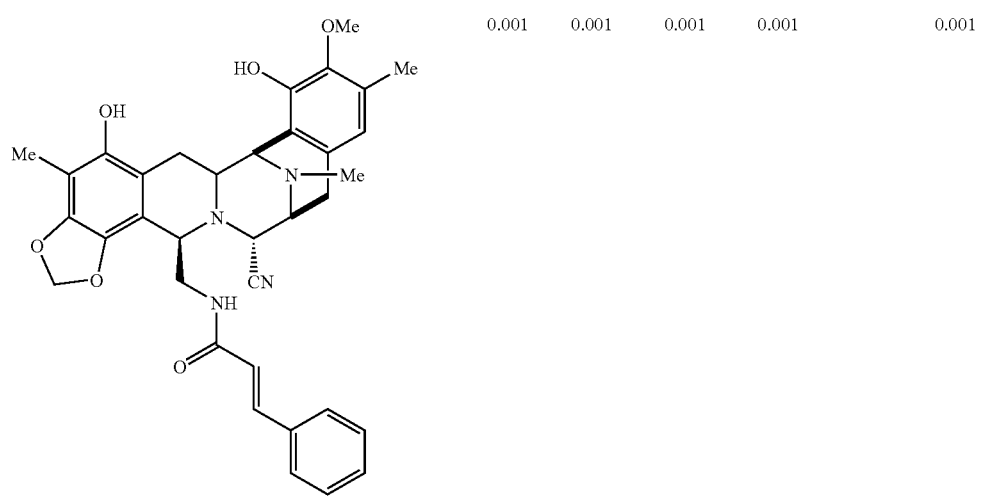<br>125 | 0.001 | 0.001 | 0.001 | 0.001 | | 0.001 |

-continued
| Compound | IC$_{50}$ (μM) | | | | | |
| --- | --- | --- | --- | --- | --- | --- |
| | P-388 | A-549 | HT-29 | MEL-28 | CV-1 | DU-145 |
| 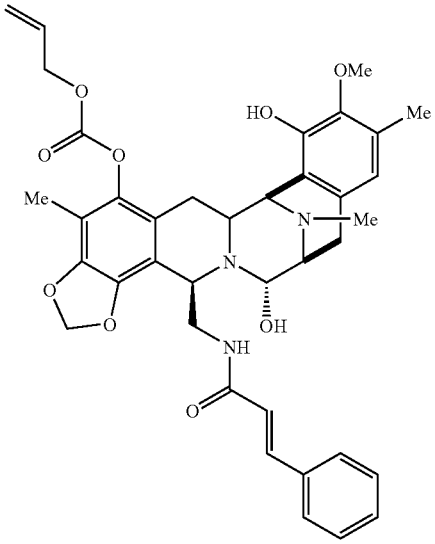<br>126 | 00001 | 0.0001 | 0.0001 | 0.0001 | | 0.0001 |
| 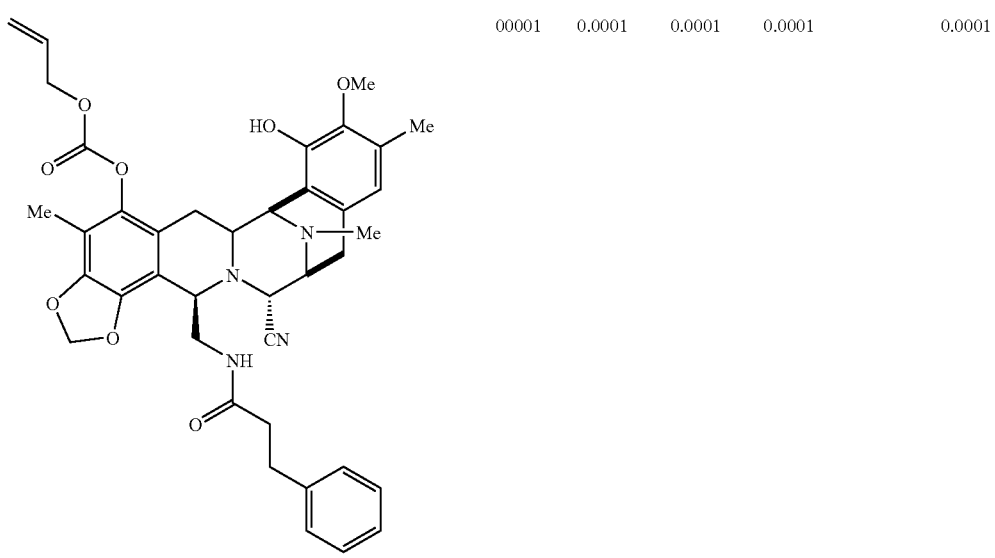<br>127 | 00001 | 0.0001 | 0.0001 | 0.0001 | | 0.0001 |

| Compound | IC₅₀ (μM) | | | | | |
|---|---|---|---|---|---|---|
| | P-388 | A-549 | HT-29 | MEL-28 | CV-1 | DU-145 |
| 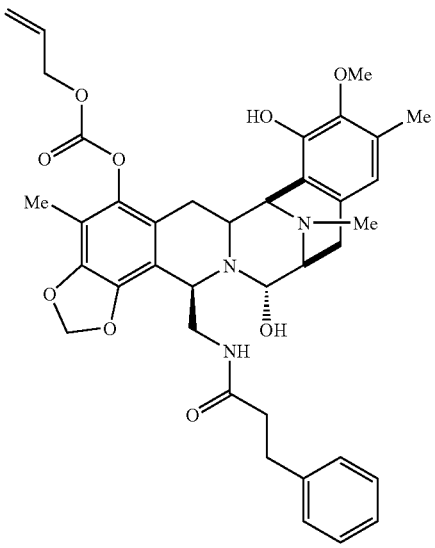<br>128 | 0.0001 | 0.0001 | 0.0001 | 0.0001 | | 0.0001 |
| 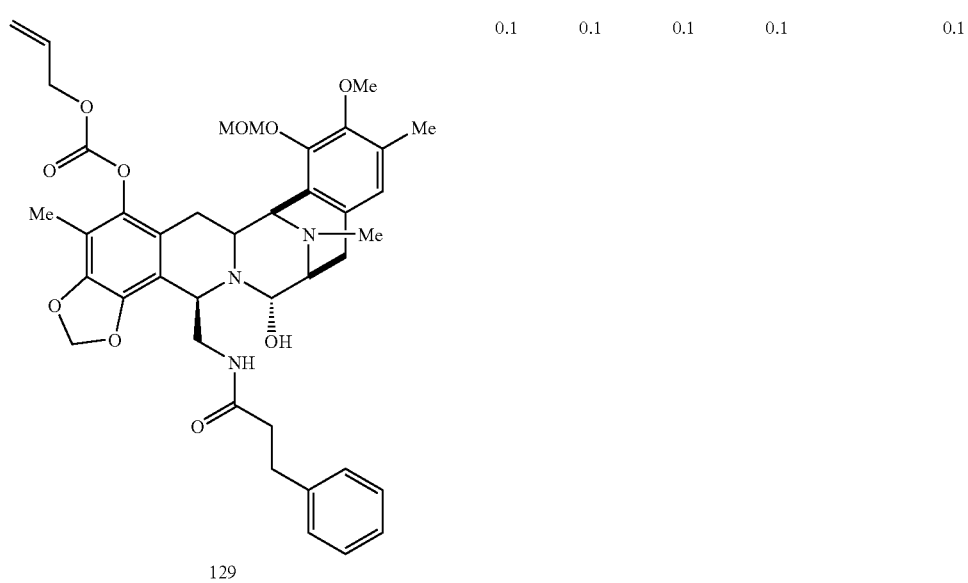<br>129 | 0.1 | 0.1 | 0.1 | 0.1 | | 0.1 |

| Compound | IC$_{50}$ (μM) | | | | | |
|---|---|---|---|---|---|---|
| | P-388 | A-549 | HT-29 | MEL-28 | CV-1 | DU-145 |
| 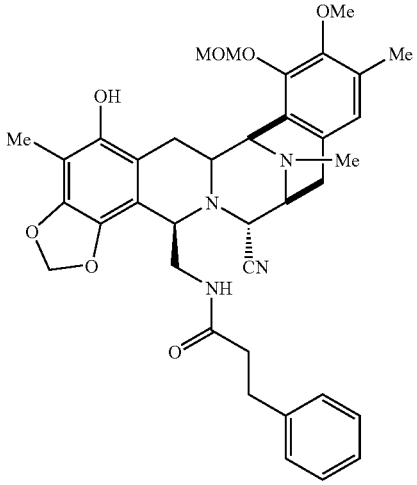<br>130 | 0.1 | 0.1 | 0.1 | 0.1 | | 0.1 |
| 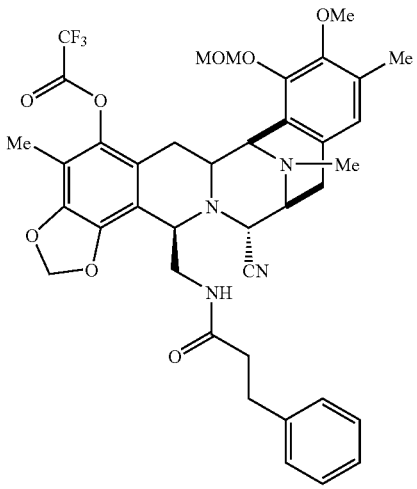<br>131 | 0.5 | 0.5 | 0.5 | 0.5 | | 0.5 |
| 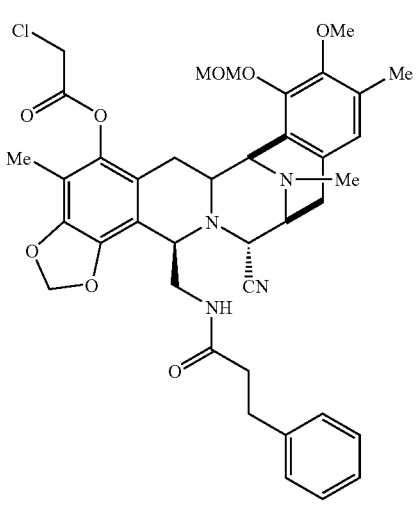<br>132 | 0.1 | 0.1 | 0.1 | 0.1 | | 0.1 |

-continued
| Compound | IC₅₀ (μM) | | | | | |
|---|---|---|---|---|---|---|
| | P-388 | A-549 | HT-29 | MEL-28 | CV-1 | DU-145 |
| 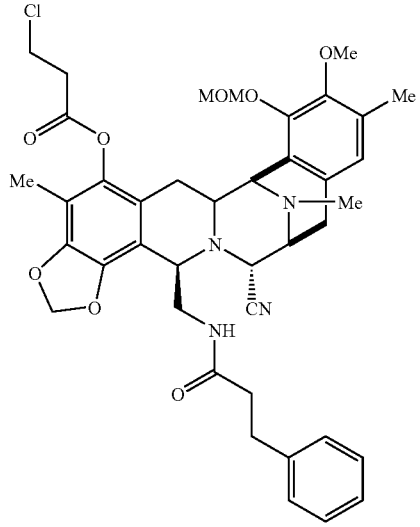 133 | 0.05 | 0.05 | 0.05 | 0.05 | | 0.05 |
| 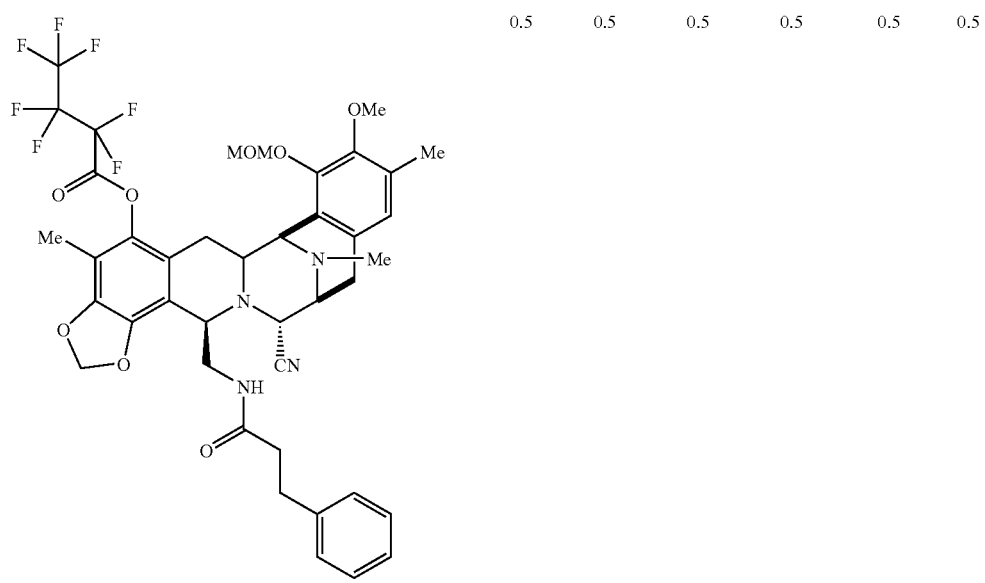 134 | 0.5 | 0.5 | 0.5 | 0.5 | 0.5 | 0.5 |

| Compound | IC$_{50}$ (μM) | | | | | |
|---|---|---|---|---|---|---|
| | P-388 | A-549 | HT-29 | MEL-28 | CV-1 | DU-145 |
| 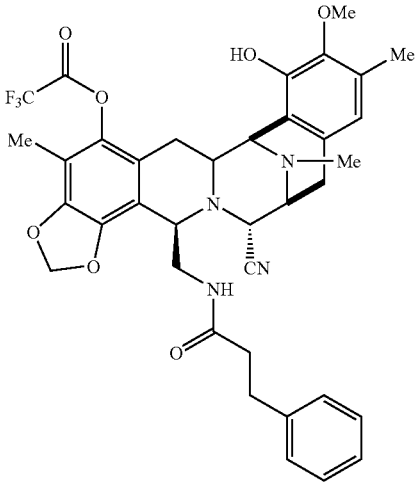 135 | 0.01 | 0.01 | 0.01 | 0.01 | | 0.01 |
| 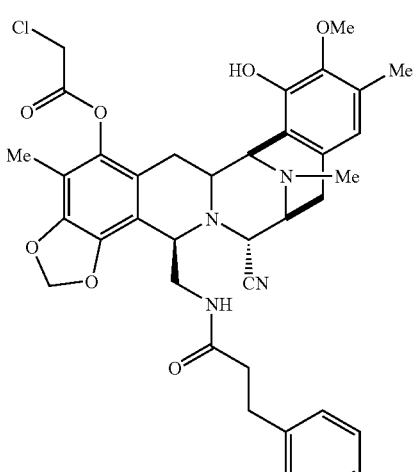 136 | 0.001 | 0.001 | 0.001 | 0.001 | | 0.001 |

| Compound | IC$_{50}$ (μM) | | | | | |
|---|---|---|---|---|---|---|
| | P-388 | A-549 | HT-29 | MEL-28 | CV-1 | DU-145 |
| 137 | 0.01 | 0.01 | 0.01 | 0.01 | | 0.01 |
| 138 | 0.006 | 0.006 | 0.006 | 0.006 | | 0.006 |
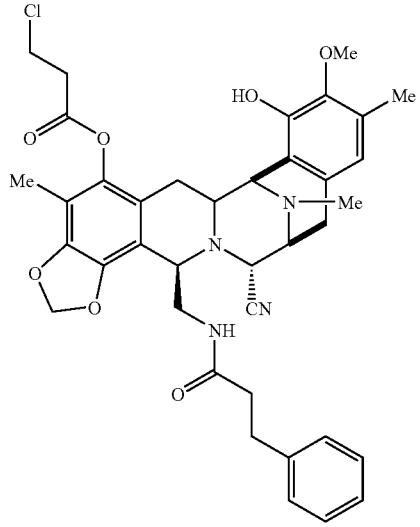

| Compound | IC$_{50}$ (μM) | | | | | |
|---|---|---|---|---|---|---|
| | P-388 | A-549 | HT-29 | MEL-28 | CV-1 | DU-145 |
| 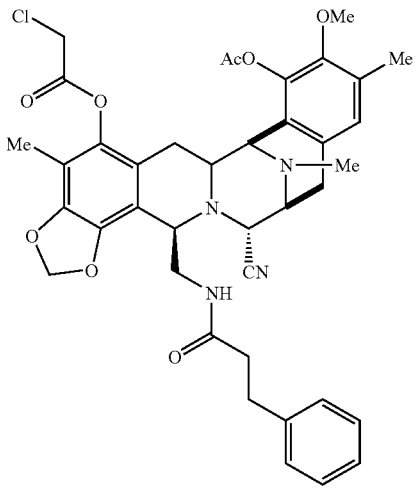 139 | 0.01 | 0.01 | 0.01 | 0.01 | | 0.01 |
| 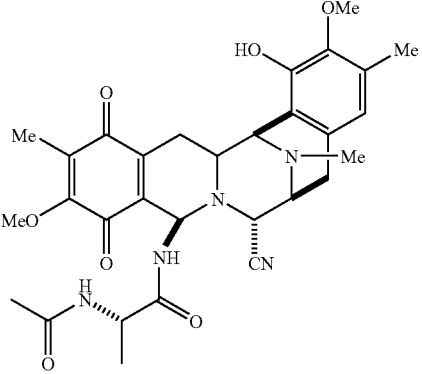 140 | 0.08 | 0.08 | 0.08 | 0.08 | | 0.08 |
| 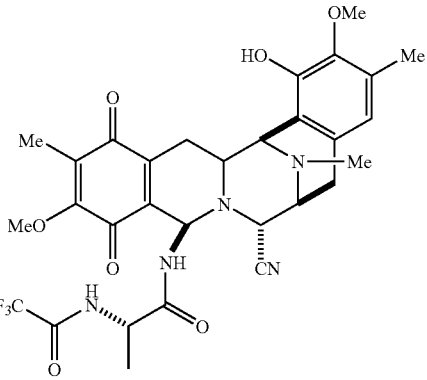 141 | 0.01 | 0.01 | 0.01 | 0.01 | 0.01 | 0.01 |

-continued
| Compound | IC$_{50}$ (μM) | | | | | |
|---|---|---|---|---|---|---|
| | P-388 | A-549 | HT-29 | MEL-28 | CV-1 | DU-145 |
| 174 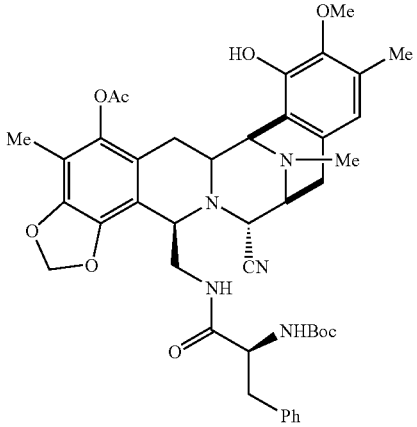 | 0.0013 | 0.0013 | | | | |
| 175 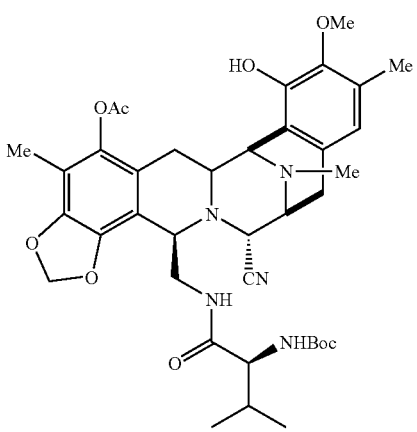 | 0.007 | 0.007 | | | | |
| 176 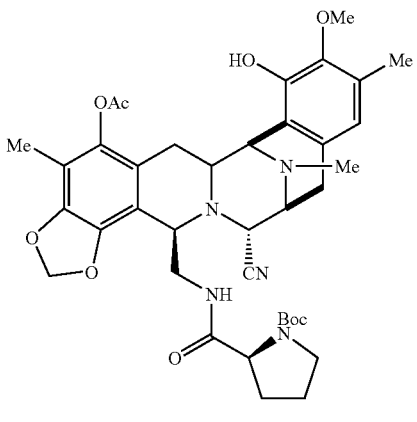 | 0.014 | 0.014 | | | | |

| Compound | IC₅₀ (μM) | | | | | |
|---|---|---|---|---|---|---|
| | P-388 | A-549 | HT-29 | MEL-28 | CV-1 | DU-145 |
| 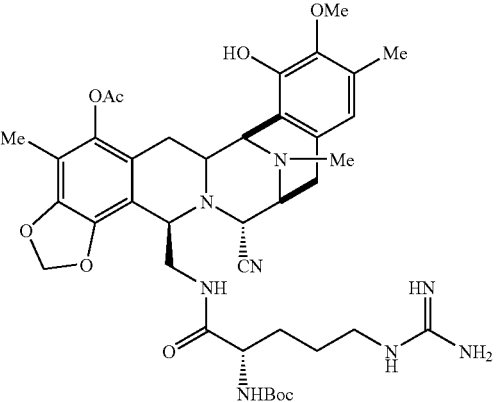177 | >1 | >1 | | | | |
| 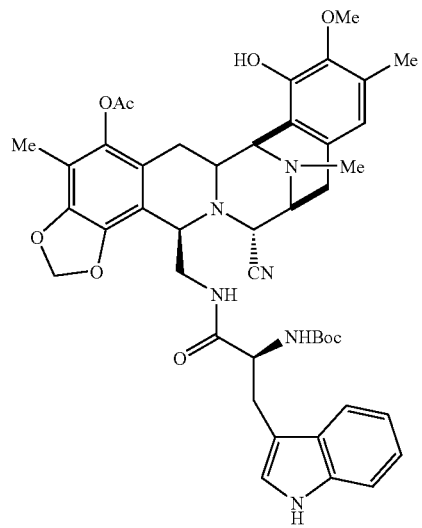178 | 0.00012 | 0.00012 | | | | |
| 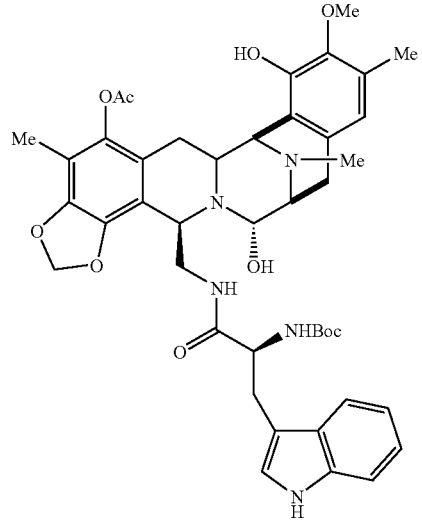179 | 0.012 | 0.012 | | | | |

| Compound | IC$_{50}$ (µM) | | | | | |
|---|---|---|---|---|---|---|
| | P-388 | A-549 | HT-29 | MEL-28 | CV-1 | DU-145 |
| 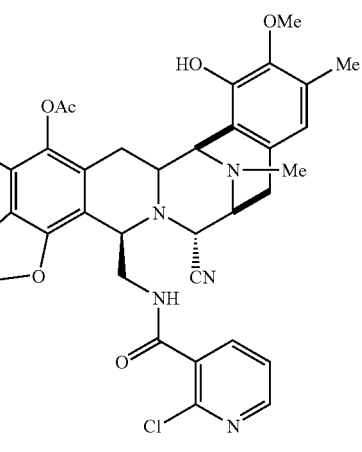 180 | 0.00015 | 0.00015 | | | | |
| 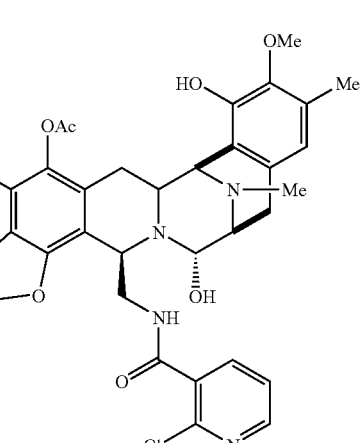 181 | 0.00015 | 0.00015 | | | | |
| 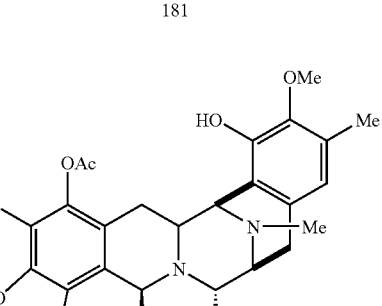 182 | 0.0015 | 0.0015 | | | | |

| | IC$_{50}$ (μM) | | | | | |
|---|---|---|---|---|---|---|
| Compound | P-388 | A-549 | HT-29 | MEL-28 | CV-1 | DU-145 |
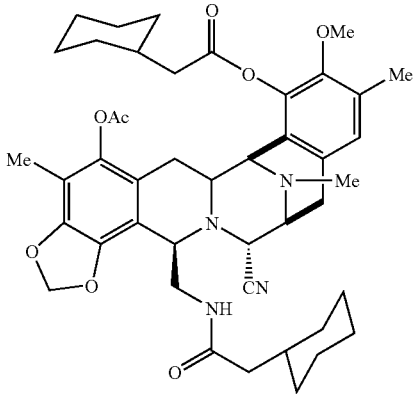
183
| | 0.013 | 0.013 | | | | |
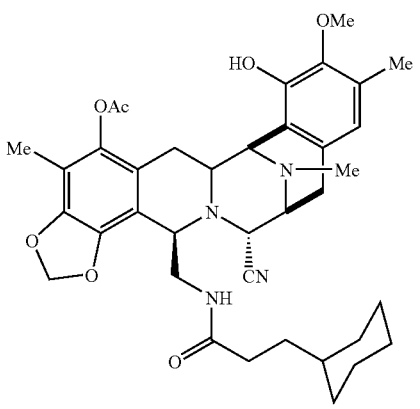
184
| | 0.0015 | 0.0015 | | | | |
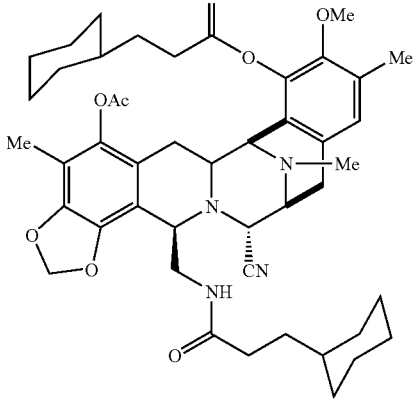
185
| | 0.12 | 0.12 | | | | |

-continued

| Compound | IC₅₀ (μM) | | | | | |
|---|---|---|---|---|---|---|
| | P-388 | A-549 | HT-29 | MEL-28 | CV-1 | DU-145 |
| 186 | 0.0014 | 0.0014 | | | | |
| 187 | 0.013 | 0.013 | | | | |
| 188 | 0.012 | 0.012 | | | | |

| Compound | IC$_{50}$ (μM) | | | | | |
|---|---|---|---|---|---|---|
| | P-388 | A-549 | HT-29 | MEL-28 | CV-1 | DU-145 |
| 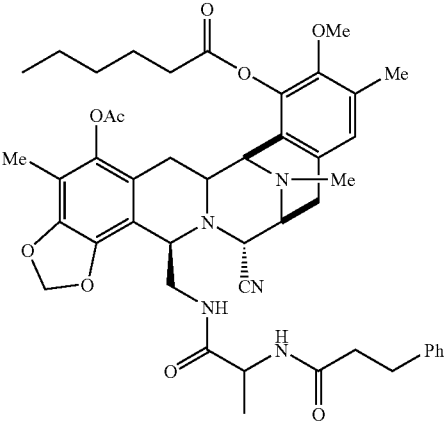 189 | | 0.06 | 0.06 | | | |
| 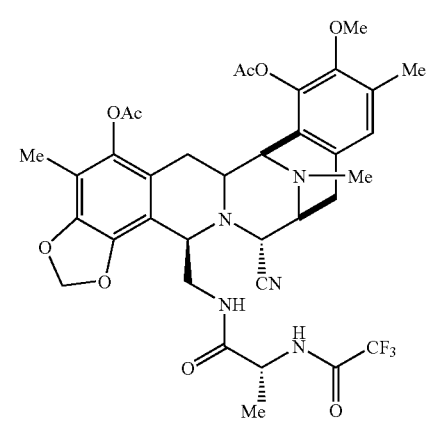 190 | | 0.013 | 0.013 | | | |
| 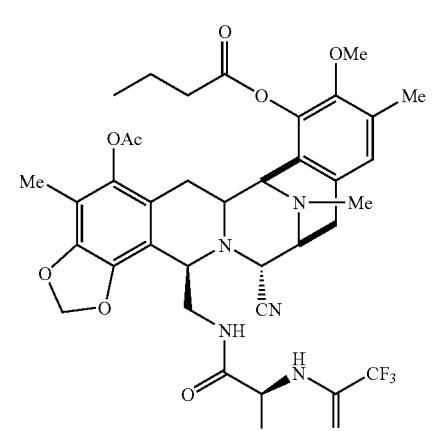 191 | | 0.13 | 0.13 | | | |

| Compound | IC₅₀ (µM) | | | | | |
|---|---|---|---|---|---|---|
| | P-388 | A-549 | HT-29 | MEL-28 | CV-1 | DU-145 |
| 192 | 0.12 | 0.12 | | | | |
| 193 | 0.11 | 0.11 | | | | |
| 194 | 0.012 | 0.012 | | | | |

| Compound | IC₅₀ (μM) | | | | | |
|---|---|---|---|---|---|---|
| | P-388 | A-549 | HT-29 | MEL-28 | CV-1 | DU-145 |
| 195 | 0.012 | 0.012 | | | | |
| 196 | 0.1 | 0.1 | | | | |
| 197 | 0.0018 | 0.0018 | | | | |

-continued
| Compound | IC$_{50}$ (μM) | | | | | |
|---|---|---|---|---|---|---|
| | P-388 | A-549 | HT-29 | MEL-28 | CV-1 | DU-145 |
| 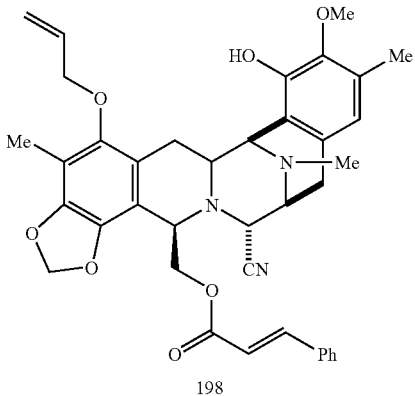 198 | 0.0015 | 0.0015 | | | | |
| 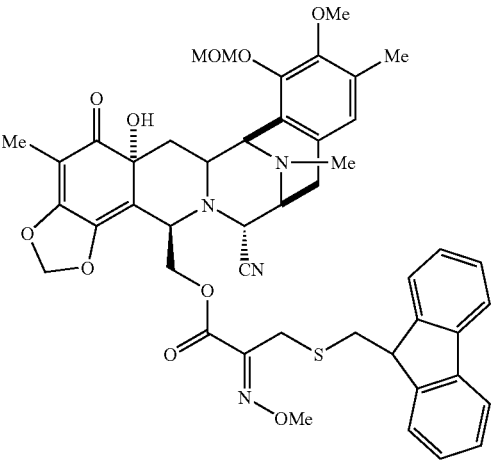 199 | >1 | >1 | | | | |
| 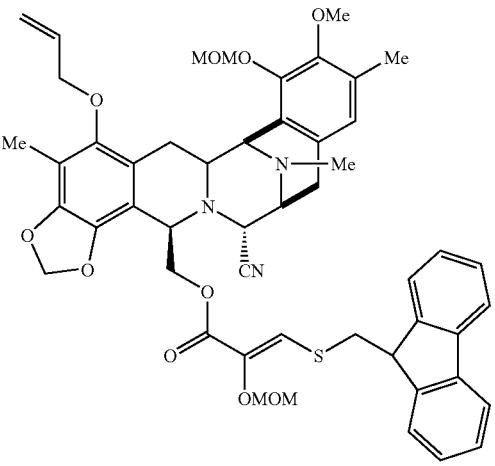 202 | 0.056 | 0.056 | | | | |

Cytotoxic Activity (M)

| SOLID TUMORS | LINE | | | |
|---|---|---|---|---|
| | | 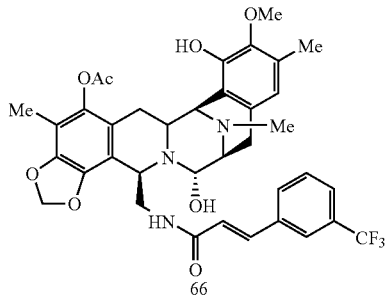 66 | | 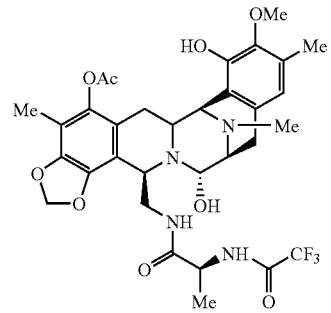 67 |
| Bladder | 5637 | 6.02E-10 | | 3.42E-10 |
| Breast | MX-1 | 1.65E-06 | | NA |
| Colon | HT-29 | 7.84E-10 | | 1.97E-08 |
| Gastric | Hs746t | 7.90E-12 | | 2.18E-09 |
| Liver | SK-HEP-1 | 1.79E-12 | | 6.01E-11 |
| NSCL | A549 | 3.25E-09 | | 7.68E-06 |
| Ovary | SK-OV-3 | 4.39E-11 | | 1.02E-07 |
| Pancreas | PANC-1 | 7.22E-11 | | 4.17E-09 |
| Pharnynx | FADU | 5.41E-11 | | 1.58E-09 |
| Prostate | PC3 | 6.65E-09 | | 2.15E-09 |
| Prostate | DU-145 | 5.73E-10 | | 1.83E-07 |
| Prostate | LNCAP | 5.45E-10 | | 2.17E-10 |
| Renal | 786-O | 6.58E-12 | | 1.59E-09 |
| SCL | NCI-H187 | 7.14E-14 | | 9.57E-10 |
| Retinoblastoma | Y-79 | 7.14E-14 | | 7.36E-10 |
| Melanoma | Mel-28 | 2.60E-10 | | 3.17E-09 |
| Fibrosarcoma | SW-694 | 9.91E-10 | | NA |
| Chondrosarcoma | CHSA | 3.24E-10 | | 6.77E-09 |
| Osteosarcoma | OSA-FH | 1.94E-09 | | 1.39E-09 |
| SOLID TUMORS | | | | |
| | | 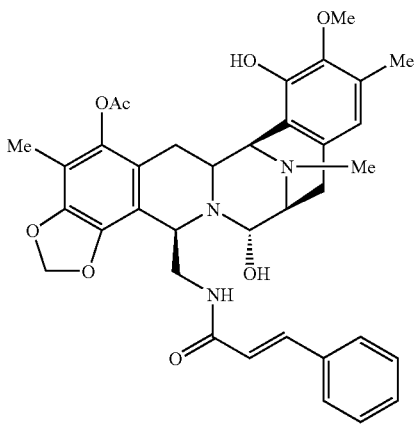 70 | | 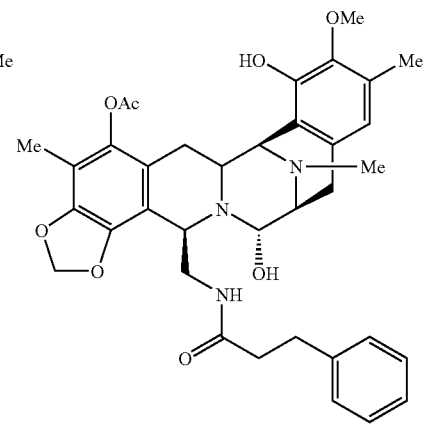 80 |
| | Bladder | 1.91E-10 | | 2.04E-11 |
| | Breast | 2.38E-09 | | NA |
| | Colon | 2.12E-09 | | 8.44E-12 |
| | Gastric | 7.10E-11 | | 2.21E-09 |
| | Liver | 3.15E-09 | | 9.91E-11 |
| | NSCL | NA | | NA |
| | Ovary | 8.74E-09 | | NA |
| | Pancreas | 1.29E-10 | | 1.19E-10 |
| | Pharnynx | 3.71E-10 | | 5.98E-09 |
| | Prostate | 4.70E-09 | | 1.52E-10 |
| | Prostate | 2.22E-09 | | NA |
| | Prostate | 3.94E-11 | | |
| | Renal | 1.72E-09 | | 1.03E-10 |
| | SCL | 7.78E-14 | | |
| | Retinoblastoma | 8.85E-11 | | |
| | Melanoma | 2.18E-09 | | 1.23E-10 |
| | Fibrosarcoma | 1.39E-06 | | NA |

|  | Chondrosarcoma | 1.39E-09 |  | 2.30E-10 |
|---|---|---|---|---|
|  | Osteosarcoma | 1.09E-09 |  | 1.11E-10 |

| SOLID TUMORS | LINE | | | |
|---|---|---|---|---|

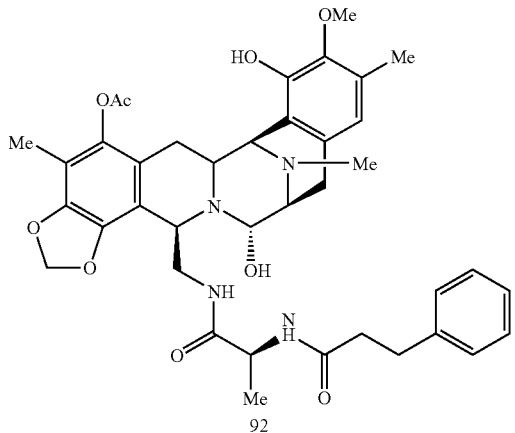

92

| Bladder | 5637 | 1.65E-10 |
|---|---|---|
| Breast | MX-1 | NA |
| Colon | HT-29 | 7.43E-10 |
| Gastric | Hs746t | 9.35E-10 |
| Liver | SK-HEP-1 | 1.40E-09 |
| NSCL | A549 | NA |
| Ovary | SK-OV-3 | |
| Pancreas | PANC-1 | 8.93E-10 |
| Pharnynx | FADU | 8.41E-10 |
| Prostate | PC3 | 8.13E-10 |
| Prostate | DU-145 | NA |
| Prostate | LNCAP | |
| Renal | 786-O | 7.88E-10 |
| SCL | NCI-H187 | |
| Retinoblastonia | Y-79 | |
| Melanoma | Mel-28 | 1.08E-09 |
| Fibrosarcoma | SW-694 | NA |
| Chondrosarcoma | CHSA | 1.08E-09 |
| Osteosarcoma | OSA-FH | 8.84E-10 |

| SOLID TUMORS | | | | |
|---|---|---|---|---|

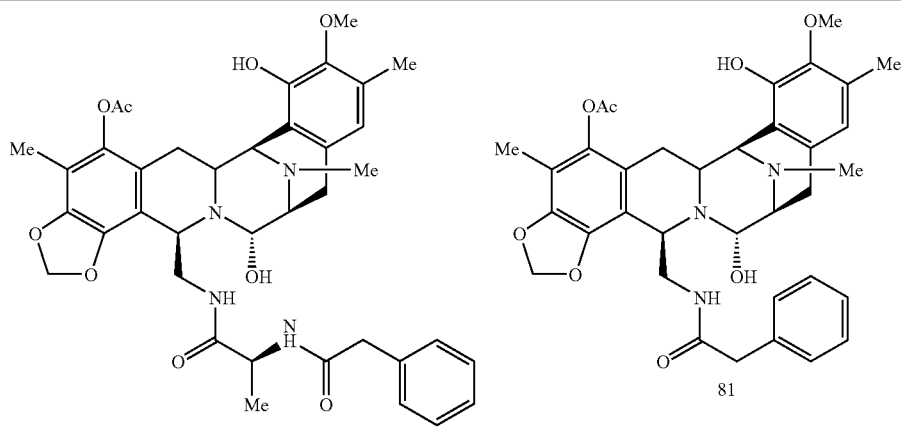

94   81

| Bladder | 7.85E-10 |  | 3.18-09 |
|---|---|---|---|
| Breast | 2.85E-06 |  | NA |
| Colon | 1.2E-10 |  | NA |
| Gastric | 6.25E-09 |  | 1.37E-07 |
| Liver | 9.03E-10 |  | 9.50E-09 |
| NSCL | NA |  | NA |
| Ovary | NA |  | NA |
| Pancreas | 2.58E-9 |  | 1.03E-08 |
| Pharnynx | 3.77E-08 |  | 1.14E-09 |
| Prostate |  |  | 9.34E-09 |
| Prostate | NA |  | NA |
| Prostate | NA |  |  |

| | | -continued | | |
|---|---|---|---|---|
| | Renal | 2.90E-09 | | 1.00E-08 |
| | SCL | 2.07E-12 | | |
| | Retinoblastoma | 1.31E-11 | | 7.78E-09 |
| | Melanoma | 1.13E-09 | | 4.48E-09 |
| | Fibrosarcoma | | | |
| | Chondrosarcoma | 2.25E-09 | | 1.09E-08 |
| | Osteosarcoma | 1.35-08 | | 9.50E-09 |
| LEUKEMIAS & LYMPHOMAS | LINE | 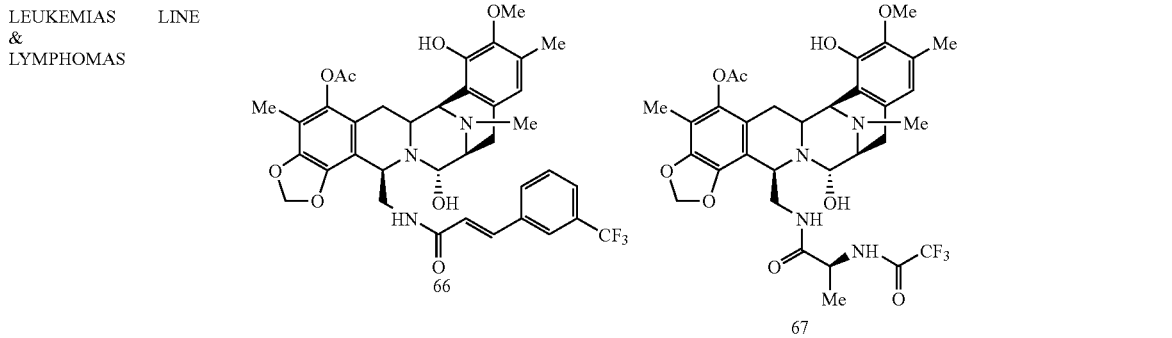 | | |
| ALL Promyelocytic leukemia | HL60 | | | |
| ALL Acute lymphoblastic | Molt 3 | 6.13E-10 | | 2.8E-09 |
| CML Chronic myelogenous Leukemia | K562 | | | |
| Hairy B-cell | Mo-B | | | |
| Lymphoma T cell | H9 | | | |
| Lymphoma Cutaneus T cell | Hut 78 | 5.50E-11 | | 2.57E-10 |
| Lymphoma undifferentiated | MC116 | 2.15E-10 | | 2.65E-10 |
| Lymphoma Burkitts B cell | RAMOS | | | |
| Lymphoma Histiocytic | U-937 | 1.77E-10 | | 5.27E-11 |
| | LEUKEMIAS & LYMPHOMAS | 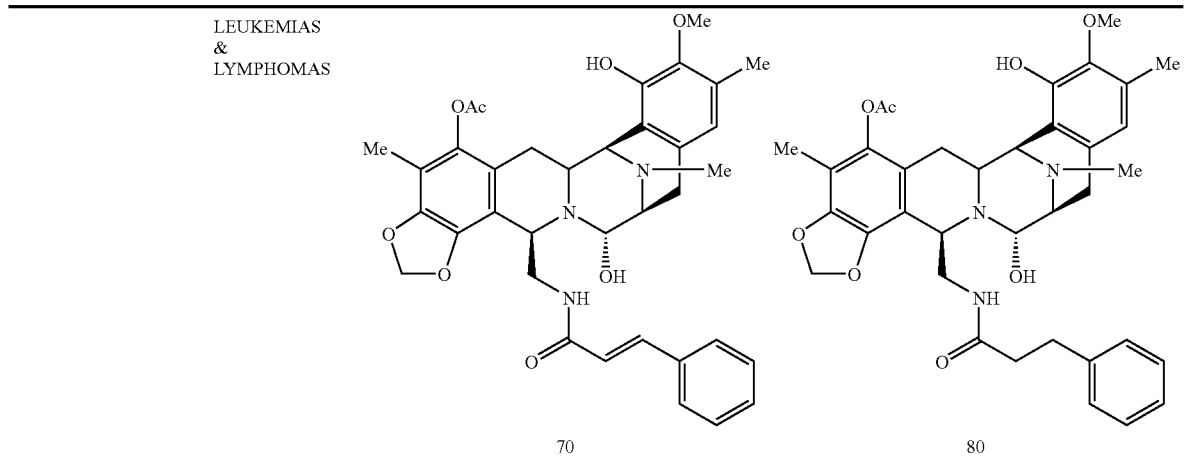 | | |
| | ALL Promyelocytic leukemia | | | 9.38E-09 |
| | ALL Acute lymphoblastic | 5.66E-10 | | 1.55E-14 |
| | CML Chronic myelogenous Leukemia | | | 2.33E-07 |
| | Hairy B-cell | | | |

-continued

| | | | | |
|---|---|---|---|---|
| | Lymphoma T cell | | | 1.99E-11 |
| | Lymphoma Cutaneus T cell | 4.62E-9 | | 6.21E-11 |
| | Lymphoma undifferentiated | 3.8E-09 | | NA |
| | Lymphoma Burkitts B cell | | | 7.77E-13 |
| | Lymphoma Histiocytic | 3.28E-11 | | 3.06E-11 |

| LEUKEMIAS & LYMPHOMAS | LINE | |
|---|---|---|

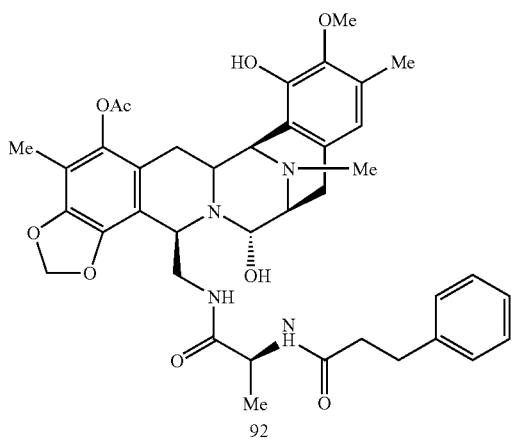

92

| ALL Promyelocytic leukemia | HL60 | 5.92E-09 |
|---|---|---|
| ALL Acute lymphoblastic | Molt 3 | 7.53E-12 |
| CML Chronic myelogenous | K562 | 1.09E-08 |
| Leukemia Hairy B-cell | Mo-B | |
| Lymphoma T-cell | H9 | 4.48E-09 |
| Lymphoma Cutaneus T cell | Hut 78 | 9.9E-10 |
| Lymphoma undifferentiated | MC116 | NA |
| Lymphoma Burkitts B celll | RAMOS | 5.26-11 |
| Lymphoma Histiocytic | U-937 | 5.15E-10 |

| LEUKEMIAS & LYMPHOMAS | | |
|---|---|---|

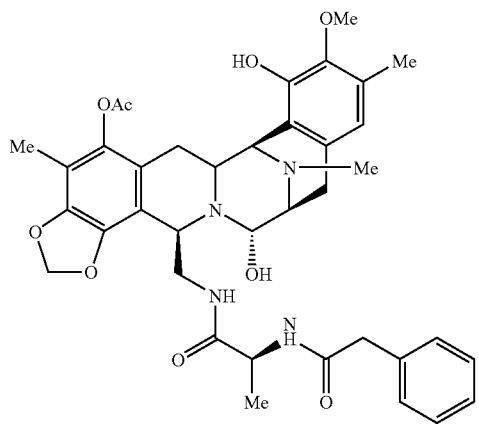

94

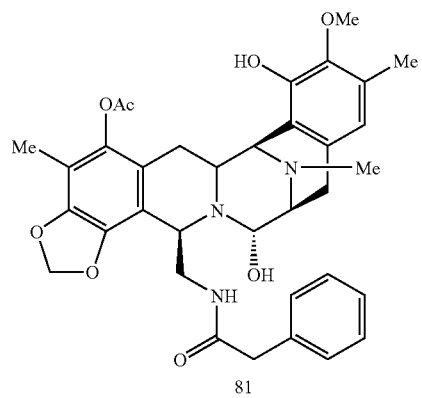

81

| ALL Promyelocytic leukemia | 1.23E-10 | 3.97E-10 |
|---|---|---|

-continued

| | | | | |
|---|---|---|---|---|
| ALL Acute lymphoblastic | | 8.85E-10 | | 2.54E-09 |
| CML Chronic myelogenous Leukemia | | 4.45E-08 | | |
| Hairy B-cell Lymphoma T cell | | 1.14E-08 | | |
| Lymphoma Cutaneus T cell | | 1.06E-08 | | 7.46E-09 |
| Lymphoma undifferentiated | | 1.41E-09 | | 1.13E-08 |
| Lymphoma Burkitts B cell | | 8.85E-10 | | 7.15E-09 |
| Lymphoma Histiocytic | | | | |

| SOLID TUMORS | LINE | | | |
|---|---|---|---|---|

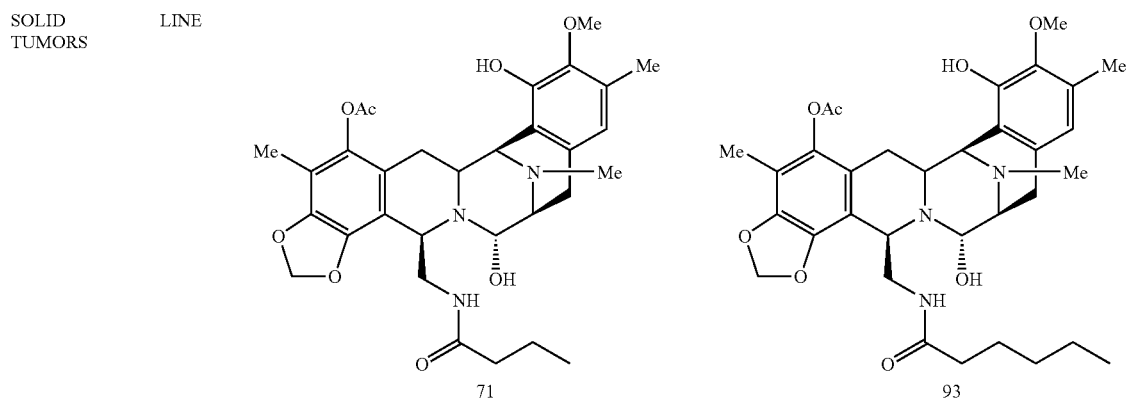

71, 93

| | | | | |
|---|---|---|---|---|
| Bladder | 5637 | 2.81E-09 | | 2.84E-10 |
| Breast | MX-1 | 2.50E-06 | | NA |
| Colon | HT-29 | NA | | 8.97E-09 |
| Gastric | Hs746t | 2.97E-08 | | 9.19E-09 |
| Liver | SK-HEP-1 | 5.07E-09 | | 1.08E-09 |
| NSCL | A549 | NA | | 9.41E-09 |
| Ovary | SK-OV-3 | 2.21E-07 | | NA |
| Pancreas | PANC-1 | 2.90E-09 | | 1.00E-09 |
| Pharnynx | FADU | 7.94E-09 | | 1.39E-08 |
| Prostate | PC3 | 1.46-08 | | 9.32E-10 |
| Prostate | DU-145 | NA | | NA |
| Prostate | LNCAP | 5.39E-09 | | |
| Renal | 786-0 | 6.55E-09 | | 1.72E-09 |
| SCL | NCI-H187 | 3.98E-11 | | |
| Retinoblastoma | Y-79 | 3.14E-09 | | |
| Melanoma | Mel-28 | 3.05E-08 | | 1.15E-09 |
| Fibrosarcoma | SW-694 | NA | | NA |
| Chondrosarcoma | CHSA | 1.73E-08 | | 2.10E-09 |
| Osteosarcoma | OSA-FH | 8.56E-08 | | 1.30E-09 |

-continued

| SOLID TUMORS | LINE | | |
|---|---|---|---|
| | | 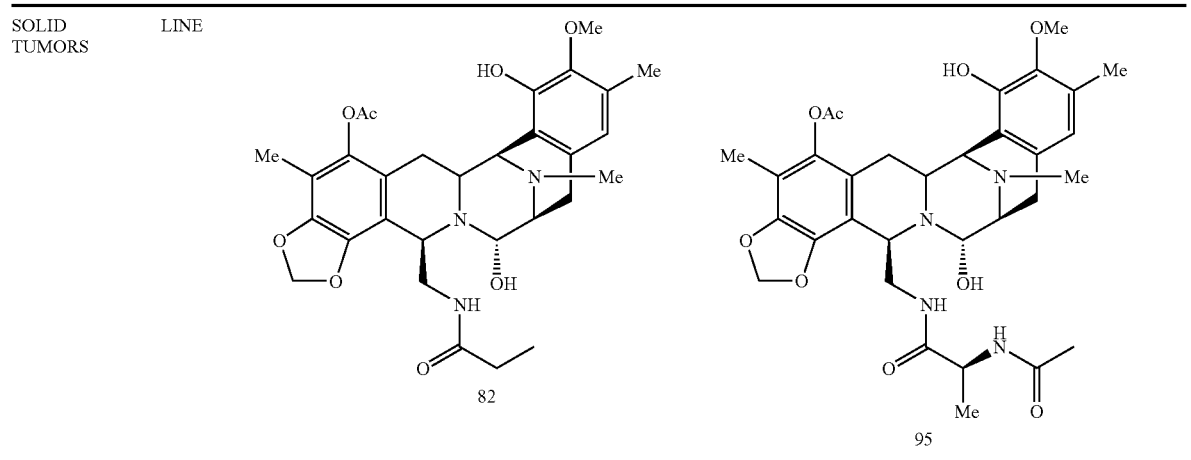 | |
| | | 82 | 95 |
| Bladder | 5637 | 9.91E-10 | 1.17E-09 |
| Breast | MX-1 | NA | 1.92E-09 |
| Colon | HT-29 | NA | NA |
| Gastric | Hs746t | 1.36E-09 | 8.15E-09 |
| Liver | SK-HEP-1 | 1.17E-09 | 6.21E-09 |
| NSCL | A549 | NA | NA |
| Ovary | SK-OV-3 | 2.90E-08 | NA |
| Pancreas | PANC-1 | 1.37E-09 | 8.61E-09 |
| Pharnynx | FADU | 3.05E-08 | 4.38E-08 |
| Prostate | PC3 | | |
| Prostate | DU-145 | NA | NA |
| Prostate | LNCAP | 2.38E-08 | 1.77E-08 |
| Renal | 786-O | 2.27E-09 | 1.54E-08 |
| SCL | NCI-H187 | 2.41E-11 | 9.89E-11 |
| Retinoblastoma | Y-79 | 3.08E-10 | 7.45E-10 |
| Melanoma | Mel-28 | 2.85E-09 | 1.42E-08 |
| Fibrosarcoma | SW-694 | | |
| Chondrosarcoma | CHSA | 1.63E-09 | 2.91E-08 |
| Osteosarcoma | OSA-FH | 4.37E-09 | 1.15E-08 |

| LEUKEMIAS & LYMPHOMAS | LINE | | |
|---|---|---|---|
| | | 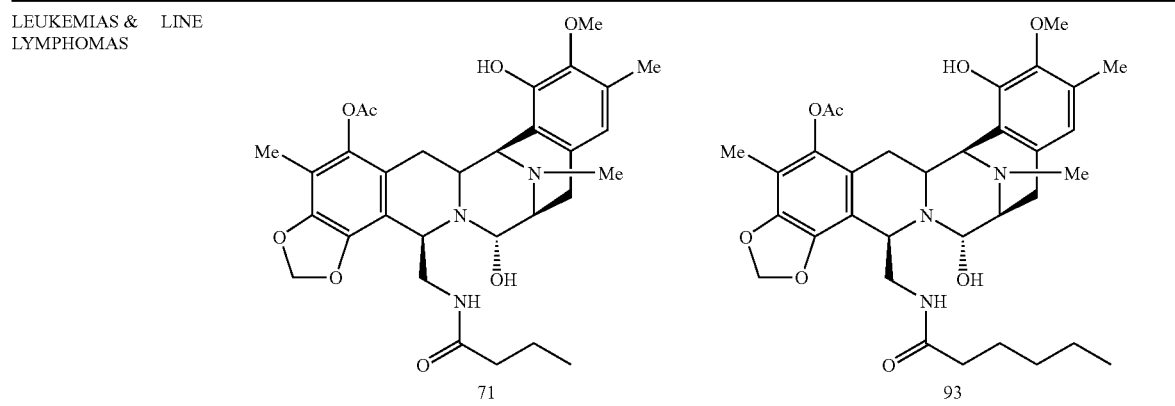 | |
| | | 71 | 93 |
| ALL Promyelocytic leukemia | HL60 | | 1.50E-08 |
| ALL Acute lymphoblastic | Molt 3 | 1.62E-09 | 3.87E-09 |
| CML Chronic myelogenous | K562 | | 6.89E-08 |
| Lymphoma T-cell | H9 | | 1.08E-08 |
| Lymphoma Cutaneus T cell | Hut 78 | 7.33E-09 | 1.97E-08 |
| Lymphoma undifferentiated | MC116 | 1.62E-08 | 3.81E-09 |
| Lymphoma Burkitts B celll | RAMOS | | 1.1E-09 |

| | | | | |
|---|---|---|---|---|
| Lymphoma Histiocytic | U-937 | 1.92E-09 | | 1.08E-09 |
| | | |
|---|---|---|
| LEUKEMIAS & LYMPHOMAS | LINE | 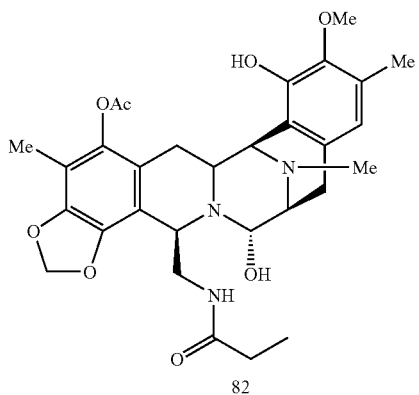 82     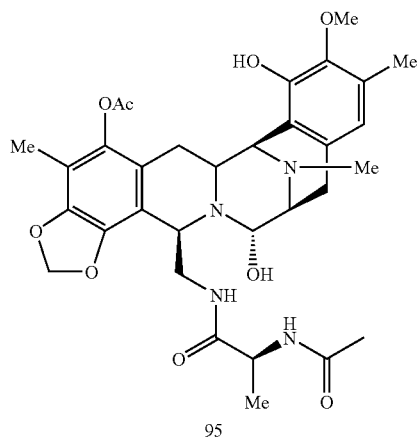 95 |
| | | | | |
|---|---|---|---|---|
| ALL Promyelocytic leukemia | HL60 | 4.93E-10 | | 7.36E-09 |
| ALL Acute lymphoblastic | Molt 3 | 9.86E-10 | | 9.86E-10 |
| CML Chronic myelogenous | K562 | 1.87E-08 | | 1.18E-08 |
| Lymphoma T-cell | H9 | 1.20E-08 | | 2.43-08 |
| Lymphoma Cutaneus T cell | Hut 78 | | | |
| Lymphoma undifferentiated | MC116 | 1.04E-09 | | 1.49E-09 |
| Lymphoma Burkitts B cell | RAMOS | | | 5.01E-09 |
| Lymphoma Histiocytic | U-937 | | | |
| | | |
|---|---|---|
| SOLID TUMORS | LINE | 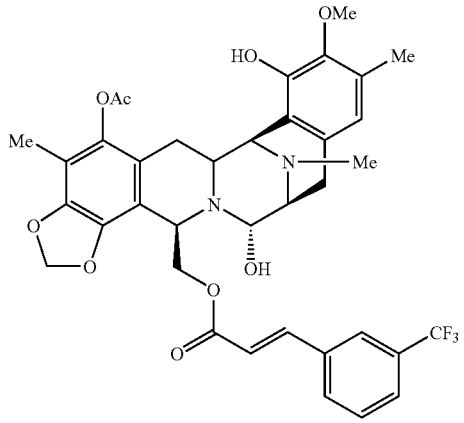 114     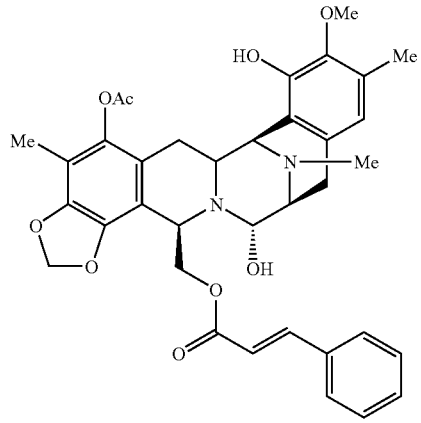 116 |
| | | | | |
|---|---|---|---|---|
| Bladder | 5637 | 1.14E-08 | | 1.71E-08 |
| Breast | MX-1 | 2.81E-08 | | 7.25E-13 |

| | | | |
|---|---|---|---|
| Colon | HT-29 | 4.08E-07 | 2.96E-07 |
| Gastric | Hs746t | 3.57E-08 | 1.24E-09 |
| Liver | SK-HEP-1 | 1.63-08 | 1.94E-09 |
| NSCL | A549 | 2.81E-06 | 1.56-05 |
| Ovary | SK-OV-3 | 7.03E-06 | 7.78E-08 |
| Pancreas | PANC-1 | 1.03E-08 | 9.47E-09 |
| Pharnynx | FADU | 4.59E-07 | 2.46E-08 |
| Prostate | PC3 | 7.88E-08 | |
| Prostate | DU-145 | 7.03E-08 | 1.56E-06 |
| Prostate | LNCAP | 5.98E-07 | 6.83E-08 |
| Renal | 786-O | 1.46E-08 | 5.26E-12 |
| SCL | NCI-H187 | 8.02E-10 | 7.78E-14 |
| Retinoblastoma | Y-79 | 8.85E-10 | 7.78E-14 |
| Melanoma | Mel-28 | 1.76E-08 | 5.89E-08 |
| Fibrosarcoma | SW-694 | 3.38E-06 | 6.69E-06 |
| Chondrosarcoma | CHSA | 2.53E-08 | 4.49E-08 |
| Osteosarcoma | OSA-FH | 6.34E-08 | 5.26E-07 |

| SOLID TUMORS | LINE | | |
|---|---|---|---|
| | | 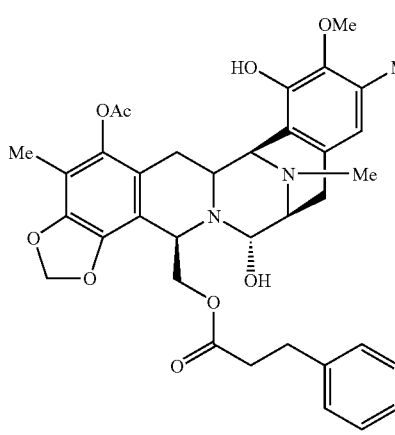 115 | 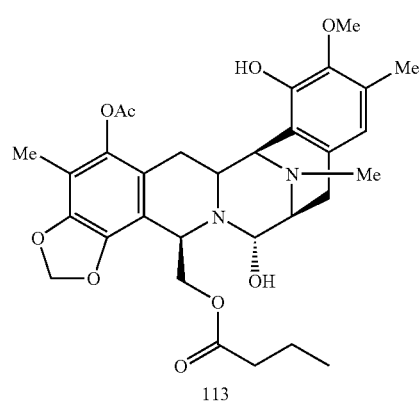 113 |
| Bladder | 5637 | 7.88E-10 | 3.02E-08 |
| Breast | MX-1 | NA | 4.75E-08 |
| Colon | HT-29 | 8.99E-09 | 1.34E-08 |
| Gastric | Hs746t | 2.95E-08 | 7.05E-07 |
| Liver | SK-HEP-1 | 1.29E-09 | 6.12E-08 |
| NSCL | A549 | 8.22E-06 | 8.49E-09 |
| Ovary | SK-OV-3 | | 3.55E-08 |
| Pancreas | PANC-1 | 5.68E-10 | 1.28E-08 |
| Pharnynx | FADU | 5.40E-11 | 2.47E-08 |
| Prostate | PC3 | 7.71E-10 | 6.18E-10 |
| Prostate | DU-145 | NA | 1.17E-O8 |
| Prostate | LNCAP | | 3.29E-07 |
| Renal | 786-O | 9.23E-10 | 1.13E-08 |
| SCL | NCI-H187 | | 2.33E-10 |
| Retinoblastoma | Y-79 | 1.03E-08 | 2.64E-09 |
| Melanoma | Mel-28 | 2.23E-08 | 1.25E-08 |
| Fibrosarcoma | SW-694 | 8.53E-06 | NA |
| Chondrosarcoma | CHSA | 1.55E-05 | 2.95E-08 |
| Osteosarcorna | OSA-FH | 1.29E-09 | 5.01E-08 |

| LEUKEMIAS & LYMPHOMAS | LINE | 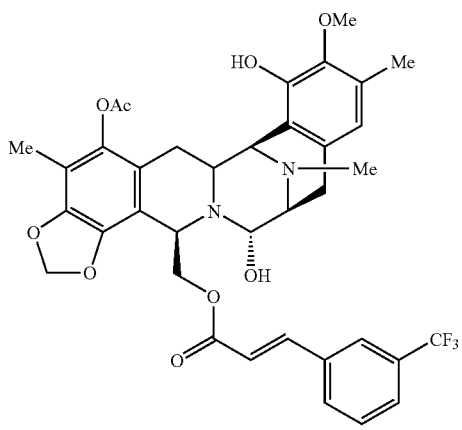 114 | | 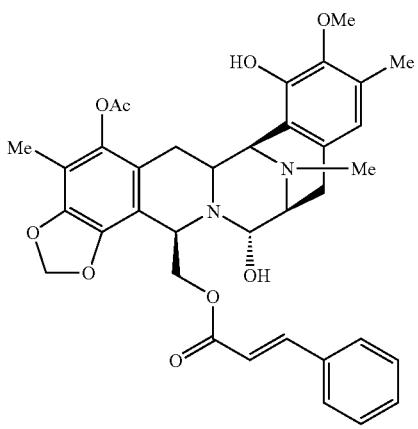 116 |
|---|---|---|---|---|
| ALL Promyelocytic leukemia | HL60 | | | 1.34E-08 |
| ALL Acute lymphoblastic | Molt 3 | 1.44E-08 | | 2.48E-09 |
| CML Chronic myelogenous | K562 | 1.56E-07 | | 6.13E-08 |
| Lymphoma T-cell | H9 | 1.56E-07 | | 1.91E-O8 |
| Lymphoma Cutaneus T cell | Hut 78 | 6.47E-08 | | 7.31E-09 |
| Lymphoma undifferentiated | MC116 | 1.69E-08 | | 6.38E-09 |
| Lymphoma Burkitts B celll | RAMOS | 8.86E-09 | | 7.15E-10 |
| Lymphoma Histiocytic | U-937 | 7.6E-08 | | |

| LEUKEMIAS & LYMPHOMAS | LINE | 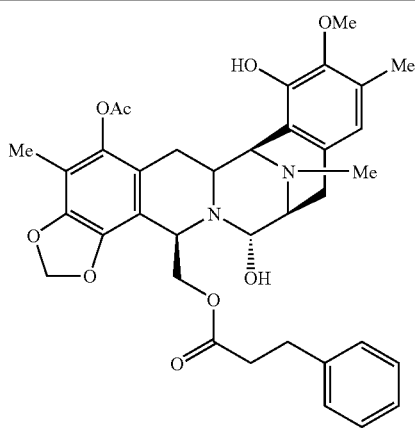 115 | | 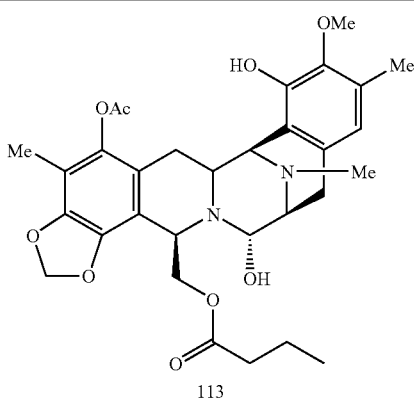 113 |
|---|---|---|---|---|
| ALL Promyclocytic leukemia | HL60 | 3.1E-09 | | |
| ALL Acute lymphoblastic | Molt 3 | 8.69E-11 | | 4.63E-08 |
| CML Chronic myelogenous | K562 | 2.11E-08 | | |
| Lymphoma T-cell | H9 | 2.17E-O8 | | 6.76E-08 |
| Lymphoma Cutaneus T cell | Hut 78 | 4.81E-08 | | 2.06E-08 |
| Lymphoma undifferentiated | MC116 | 5.27E-11 | | 1.51E-08 |

| | | | | |
|---|---|---|---|---|
| Lymphoma Burkitts B celll | RAMOS | 1.86E.09 | | 9.09E-09 |
| Lymphoma Histiocytic | U-937 | | | 1.03E-08 |

EXAMPLES OF THE INVENTION

The present invention is illustrated by the following examples.

Example 1

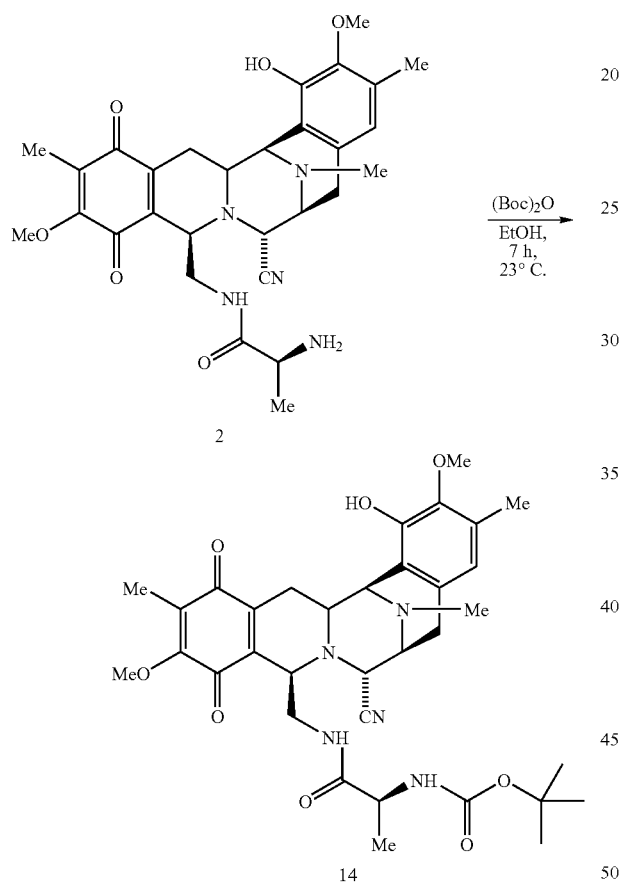

2

14

To a solution of 2 (21.53 g, 39.17 ml) in ethanol (200 ml), tert-butoxycarbonyl anhydride (7.7 g, 35.25 ml) was added and the mixture was stirred for 7 h at 23° C. Then, the reaction was concentrated in vacuo and the residue was purified by flash column chromatography (SiO$_2$, hexane:ethyl acetate 6:4) to give 14 (20.6 g, 81%) as a yellow solid.

Rf: 0.52 (ethyl acetate:CHCl$_3$ 5:2).

$^1$H NMR (300 MHz, CDCl$_3$): δ 6.49 (s, 1H), 6.32 (bs, 1H), 5.26 (bs, 1H), 4.60 (bs, 1H), 4.14 (d, J=2.4 Hz, 1H), 4.05 (d, J=2.4 Hz, 1H), 3.94 (s, 3H), 3.81 (d, J=4.8 Hz, 1H), 3.7 (s, 3H), 3.34 (br d, J=7.2 Hz, 1H), 3.18-3.00 (m, 5H), 2.44 (d, J=18.3 Hz 1H), 2.29 (s, 3H), 2.24 (s, 3H), 1.82 (s, 3H), 1.80-1.65 (m, 1H), 1.48 (s, 9H), 0.86 (d, J=5.7 Hz, 3H)

$^{13}$C NMR (75 MHz CDCl$_3$): δ 185.5, 180.8, 172.7, 155.9, 154.5, 147.3, 143.3, 141.5, 135.3, 130.4, 129.2, 127.5, 120.2, 117.4, 116.9, 80.2, 60.7, 60.3, 58.5, 55.9, 55.8, 54.9, 54.4, 50.0, 41.6, 40.3, 28.0, 25.3, 24.0, 18.1, 15.6, 8.5.

ESI-MS m/z: Calcd. for C$_{34}$H$_{43}$N$_5$O$_8$: 649.7. Found (M+H)$^+$: 650.3.

Example 2

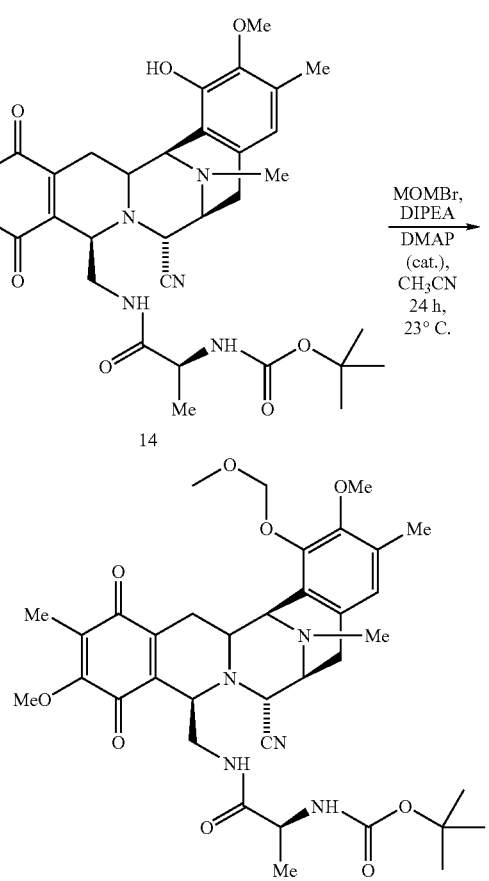

14

15

To a stirred solution of 14 (20.6 g, 31.75 ml) in CH$_3$CN (159 ml), diisopropylethylamine (82.96 ml, 476.2 ml), methoxymethylene bromide (25.9 ml, 317.5 ml) and dimethylaminopyridine (155 mg, 1.27 ml) were added at 0° C. The mixture was stirred at 23° C. for 24 h. The reaction was quenched at 0° C. with aqueous 0.1N HCl (750 ml) (pH=5), and extracted with CH$_2$Cl$_2$ (2×400 ml). The organic phase was dried (sodium sulphate) and concentrated in vacuo. The residue was purified by flash column chromatography (SiO$_2$, gradient hexane:ethyl acetate 4:1 to hexane:ethyl acetate 3:2) to give 15 (17.6 g, 83%) as a yellow solid.

Rf: 0.38 (hexane:ethyl acetate 3:7).

$^1$H NMR (300 MHz, CDCl$_3$): δ 6.73 (s, 1H), 5.35 (bs, 1H), 5.13 (s, 1H), 4.50 (bs, 1H), 4.25 (d, J=2.7 Hz, 1H), 4.03 (d,

J=2.7 Hz, 1H), 3.97 (s, 3H), 3.84 (bs, 1H), 3.82-3.65 (m, 1H), 3.69 (s, 3H), 3.56 (s, 3H), 3.39-3.37 (m, 1H), 3.20-3.00 (m, 5H), 2.46 (d, J=18 Hz, 1H), 2.33 (s, 3H), 2.23 (s, 3H), 1.85 (s, 3H), 1.73-1.63 (m, 1H), 1.29 (s, 9H), 0.93 (d, J=5.1 Hz, 3H).

$^{13}$C NMR (75 MHz, CDCl$_3$): δ 185.4, 180.9, 172.4, 155.9, 154.5, 149.0, 148.4, 141.6, 135.1, 131.0, 129.9, 127.6, 124.4, 123.7, 117.3, 99.1, 79.3, 60.7, 59.7, 58.4, 57.5, 56.2, 55.9, 55.0, 54.2, 50.0, 41.5, 39.9, 28.0, 25.2, 24.0, 18.1, 15.6, 8.5.

ESI-MS m/z: Calcd. for C$_{36}$H$_{47}$N$_5$O$_9$: 693.8. Found (M+H)$^+$: 694.3.

Example 3

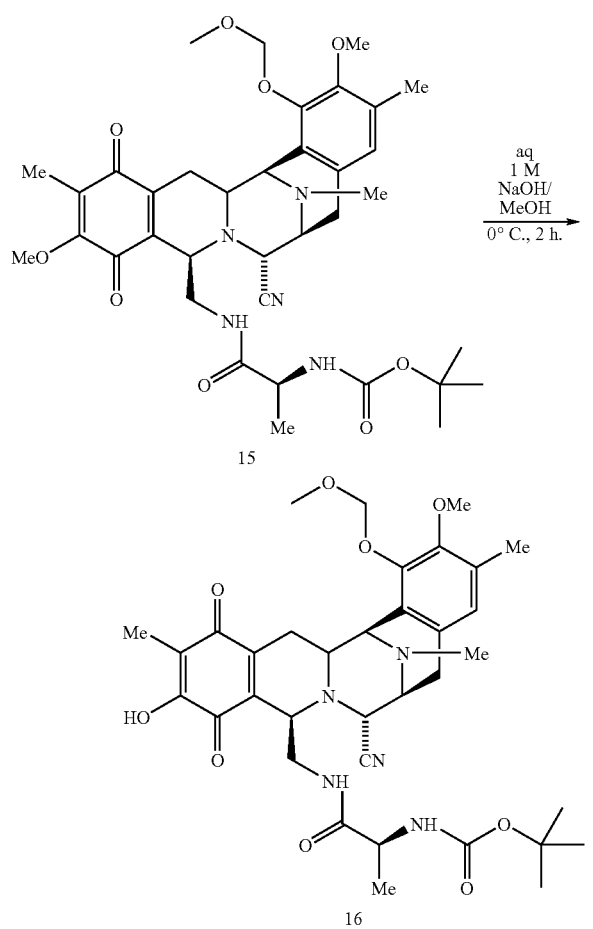

To a flask containing 15 (8 g, 1.5 ml) in methanol (1.6 l) an aqueous solution of 1M sodium hydroxide (3.2 l) was added at 0° C. The reaction was stirred for 2 h at this temperature and then, quenched with 6M HCl to pH=5. The mixture was extracted with ethyl acetate (3×1 l) and the combined organic layers were dried over sodium sulphate and concentrated in vacuo. The residue was purified by flash column chromatography (SiO$_2$, gradient CHCl$_3$ to CHCl$_3$:ethyl acetate 2:1) to afford 16 (5.3 mg, 68%).

Rf: 0.48 (CH$_3$CN:H$_2$O 7:3, RP-C18)

$^1$H NMR (300 MHz, CDCl$_3$): δ 6.73 (s, 1H), 5.43 (bs, 1H), 5.16 (s, 2H), 4.54 (bs, 1H), 4.26 (d, J=1.8 Hz, 1H), 4.04 (d, J=2.7 Hz 1H), 3.84 (bs, 1H), 3.80-3.64 (m, 1H), 3.58 (s, 3H), 3.41-3.39 (m, 1H), 3.22-3.06 (m, 5H), 2.49 (d, J=18.6 Hz 1H), 2.35 (s, 3H), 2.30-2.25 (m, 1H), 2.24 (s, 3H), 1.87 (s, 3H), 1.45-1.33 (m, 1H), 1.19 (s, 9H), 1.00 (br d, J=6.6 Hz 3H)

$^{13}$C NMR (75 MHz, CDCl$_3$): δ 184.9, 180.9, 172.6, 154.7, 151.3, 149.1, 148.6, 144.7, 132.9. 131.3, 129.8, 124.5, 123.7, 117.3, 116.8, 99.1, 79.4, 59.8, 58.6, 57.7, 56.2, 55.6, 54.9, 54.5, 50.1, 41.6, 40.1, 28.0, 25.3, 24.4, 18.1, 15.7, 8.0.

ESI-MS m/z: Calcd. for C$_{35}$H$_{45}$N$_5$O$_9$: 679.7. Found (M+H)$^+$: 680.3.

Example 4

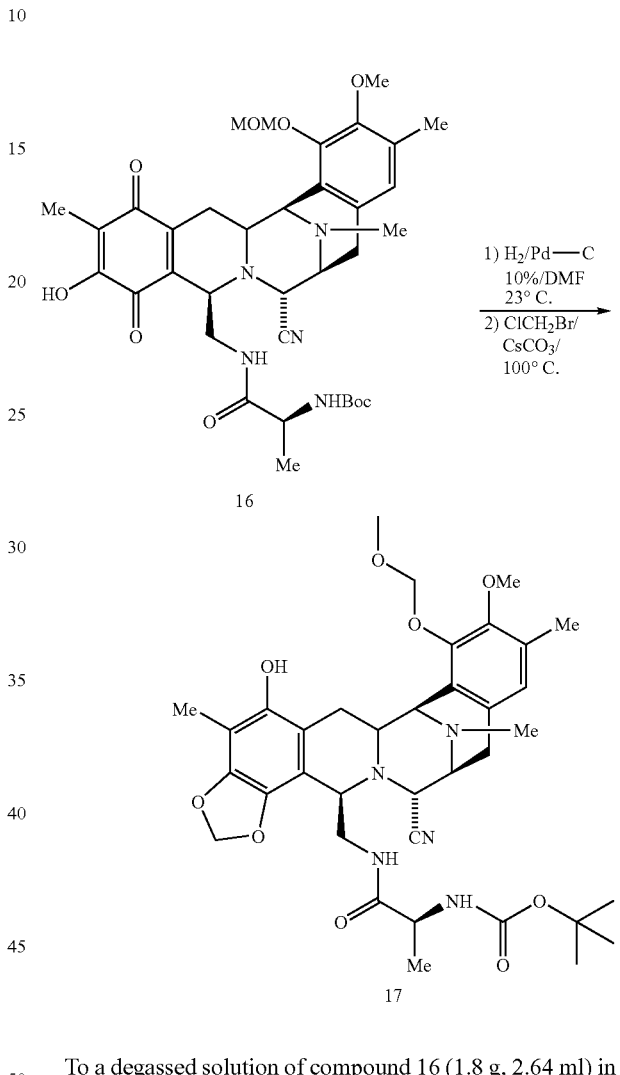

To a degassed solution of compound 16 (1.8 g, 2.64 ml) in DMF (221 ml) 10% Pd/C (360 mg) was added and stirred under H$_2$ (atmospheric pressure) for 45 min. The reaction was filtered through celite under argon, to a flask containing anhydrous Cs$_2$CO$_3$ (2.58 g, 7.92 ml). Then, bromochloromethane (3.40 ml 52.8 ml), was added and the tube was sealed and stirred at 100° C. for 2 h. The reaction was cooled, filtered through a pad of celite and washed with CH$_2$Cl$_2$. The organic layer was concentrated and dried (sodium sulphate) to afford 17 as a brown oil that was used in the next step with no further purification.

Rf: 0.36 (hexane:ethyl acetate 1:5, SiO$_2$).

$^1$H NMR (300 MHz, CDCl$_3$): δ 6.68 (s, 1H), 6.05 (bs, 1H), 5.90 (s, 1H), 5.79 (s, 1H), 5.40 (bs, 1H), 5.31-5.24 (m, 2H), 4.67 (d, J=8.1 Hz, 1H), 4.19 (d, J=2.7 Hz, 1H), 4.07 (bs, 1H), 4.01 (bs, 1H), 3.70 (s, 3H), 3.67 (s, 3H), 3.64-2.96 (m, 5H), 2.65 (d, J=18.3 Hz, 1H), 2.33 (s, 3H), 2.21 (s, 3H), 2.04 (s, 3H), 2.01-1.95 (m, 1H), 1.28 (s, 9H), 0.87 (d, J=6.3 Hz, 3H)

¹³C NMR (75 MHz, CDCl₃): δ 172.1, 162.6, 154.9, 149.1, 145.7, 135.9, 130.8, 130.7, 125.1, 123.1, 117.8, 100.8, 99.8, 76.6, 59.8, 59.2, 57.7, 57.0, 56.7, 55.8, 55.2, 49.5, 41.6, 40.1, 36.5, 31.9, 31.6, 29.7, 28.2, 26.3, 25.0, 22.6, 18.2, 15.8, 14.1, 8.8.

ESI-MS m/z: Calcd. for $C_{36}H_{47}N_5O_9$: 693.34. Found (M+H)⁺: 694.3.

Example 5

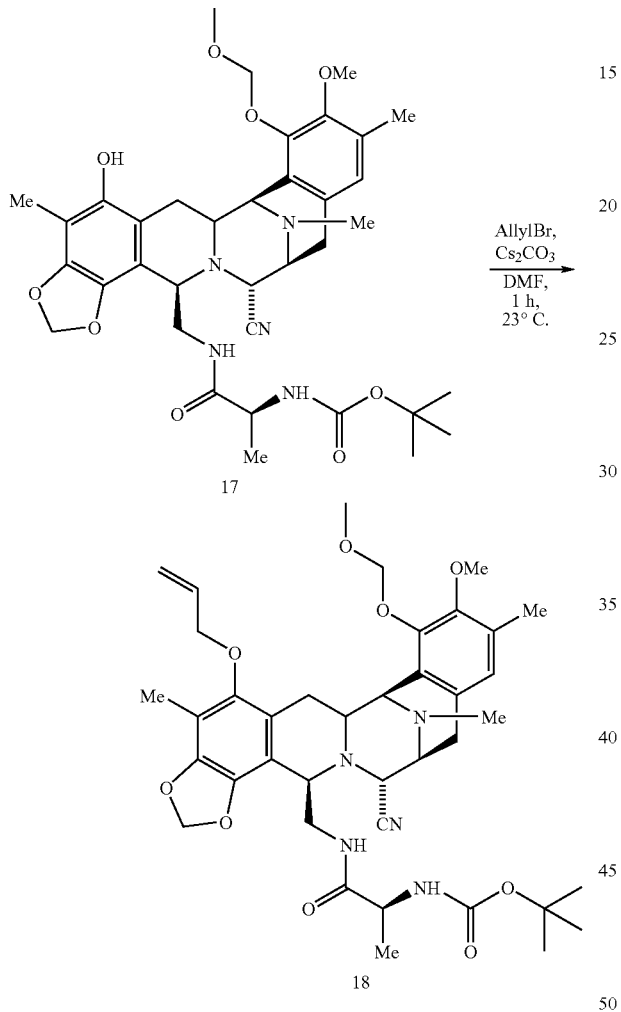

J=18 Hz, 1H), 2.30 (s, 3H), 2.21 (s, 3H), 2.09 (s, 3H), 1.91-1.80 (m, 1H), 1.24 (s, 9H), 0.94 (d, J=6.6 Hz, 3H)

¹³C NMR (75 MHz, CDCl₃): δ 172.0, 154.8, 148.8, 148.6, 148.4, 144.4, 138.8, 133.7, 130.9, 130.3, 125.1, 124.0, 120.9, 117.8, 117.4, 112.8, 112.6, 101.1, 99.2, 73.9, 59.7, 59.3, 57.7, 56.9, 56.8, 56.2, 55.2, 40.1, 34.6, 31.5, 28.1, 26.4, 25.1, 22.6, 18.5, 15.7, 14.0, 9.2.

ESI-MS m/z: Calcd. for $C_{39}H_{51}N_5O_9$: 733.4. Found (M+H)⁺: 734.4.

Example 6

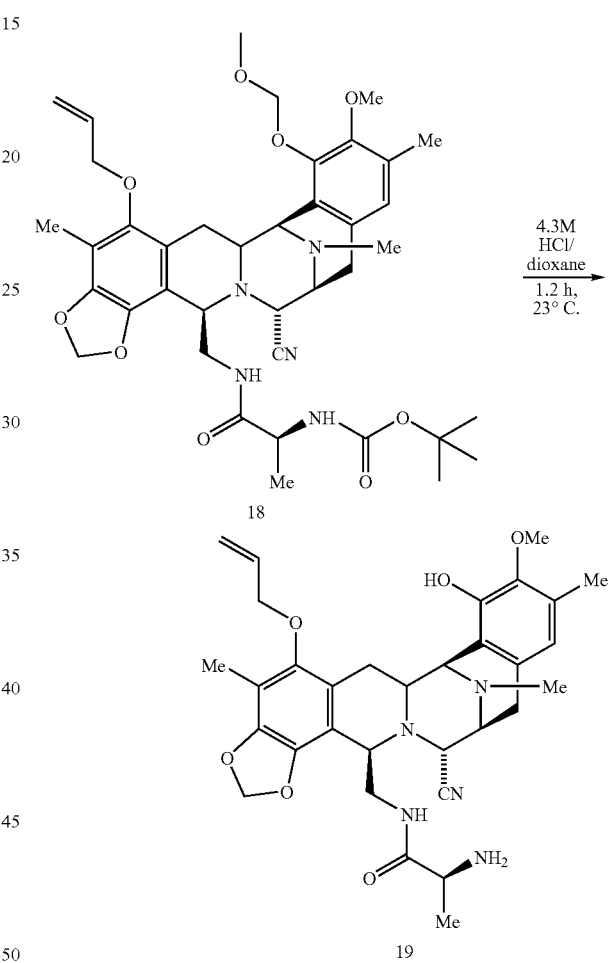

To a flask containing a solution of 17 (1.83 g, 2.65 ml) in DMF (13 ml). Cs₂CO₃ (2.6 g, 7.97 ml), and allyl bromide (1.15 ml, 13.28 ml) were added at 0° C. The resulting mixture was stirred at 23° C. for 1 h. The reaction was filtered through a pad of celite and washed with CH₂Cl₂. The organic layer was dried and concentrated (sodium sulphate). The residue was purified by flash column chromatography (SiO₂, CHCl₃: ethyl acetate 1:4) to afford 18 (1.08 mg, 56%) as a white solid.

Rf: 0.36 (CHCl₃:ethyl acetate 1:3).

¹H NMR (300 MHz, CDCl₃): δ 6.70 (s, 1H), 6.27-6.02 (m, 1H), 5.94 (s, 1H), 5.83 (s, 1H), 5.37 (dd, J₁=1.01 Hz, J₂=16.8 Hz, 1H), 5.40 (bs, 1H), 5.25 (dd, J₁=1.0 Hz, J₂=10.5 Hz, 1H), 5.10 (s, 2H), 4.91 (bs, 1H), 4.25-4.22 (m, 1H), 4.21 (d, J=2.4 Hz, 1H), 4.14-4.10 (m, 1H), 4.08 (d, J=2.4 Hz, 1H), 4.00 (bs, 1H), 3.70 (s, 3H), 3.59 (s, 3H), 3.56-3.35 (m, 2H), 3.26-3.20 (m, 2H), 3.05-2.96 (dd, J₁=8.1 Hz, J₂=18 Hz, 1H), 2.63 (d,

To a solution of 18 (0.1 g, 0.137 ml) in dioxane (2 ml), 4.2M HCl/dioxane (1.46 ml) was added and the mixture was stirred for 1.2 h at 23° C. The reaction was quenched at 0° C. with sat. Aqueous sodium bicarbonate (60 ml) and extracted with ethyl acetate (2×70 ml). The organic layers were dried (sodium sulphate) and concentrated in vacuo to afford 19 (267 mg, 95%) as a white solid that was used in subsequent reactions with no further purification.

Rf: 0.17 (ethyl acetate:methanol 10:1, SiO₂)

¹H NMR (300 MHz, CDCl₃): δ 6.49 (s, 1H), 6.12-6.00 (m, 1H), 5.94 (s, 1H), 5.86 (s, 1H), 5.34 (dd, J'1.0 Hz, J=17.4 Hz, 1H), 5.25 (dd, J=1.0 Hz, J=10.2 Hz, 1H), 4.18-3.76 (m, 5H), 3.74 (s, 3H), 3.71-3.59 (m, 1H), 3.36-3.20 (m, 4H), 3.01-2.90 (m, 1H), 2.60 (d, J=18.0 Hz, 1H), 2.29 (s, 3H), 2.24 (s, 3H), 2.11 (s, 3H), 1.97-1.86 (m, 1H), 0.93 (d, J=8.7 Hz, 3H)

$^{13}$C NMR (75 MHz, CDCl$_3$): δ 175.5, 148.4, 146.7, 144.4, 142.4, 138.9, 133.7, 131.3, 128.3, 120.8, 117.9, 117.4, 113.8, 112.4, 101.1, 74.2, 60.5, 59.1, 56.5, 56.1, 56.3, 56.0, 55.0, 50.5, 41.6, 39.5, 29.5, 26.4, 24.9, 21.1, 15.5, 9.33.

ESI-MS m/z: Calcd. for C$_{32}$H$_{39}$N$_5$O$_6$: 589. Found (M+H)$^+$: 590.

124.1, 120.9, 120.5, 117.7, 117.4, 116.7, 112.6, 112.5, 101.0, 74.0, 60.6, 59.0, 57.0, 56.2, 56.1, 55.0, 53.3, 41.4, 39.7, 26.3, 24.8, 18.3, 15.5, 9.2.

ESI-MS m/z: Calcd. for C$_{39}$H$_{44}$N$_6$O$_6$S: 724.8. Found (M+H)$^+$: 725.3.

Example 7

Example 8

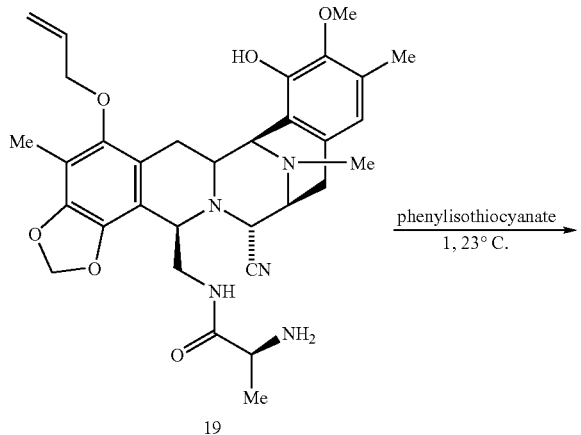

19

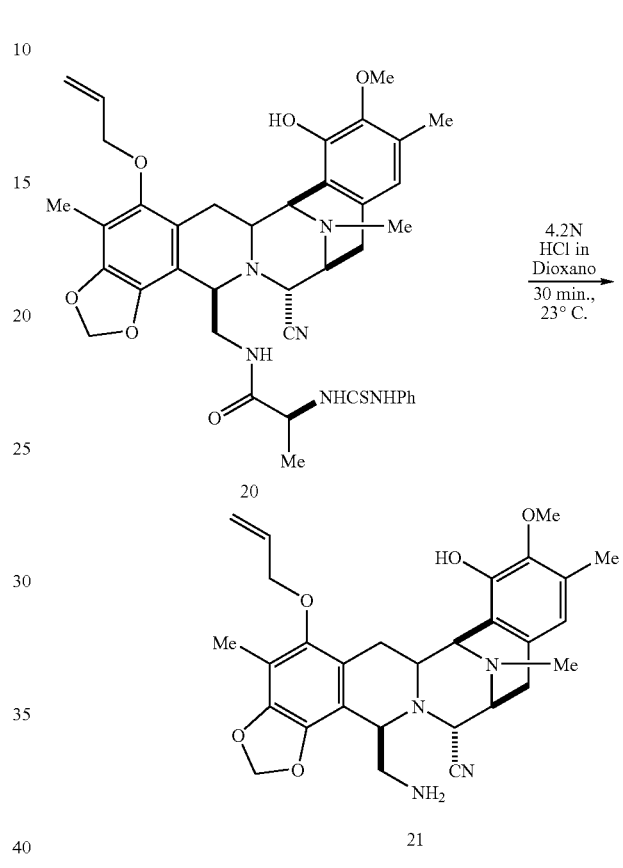

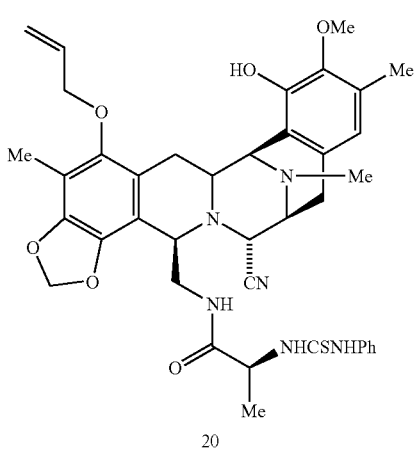

20

To a solution of 19 (250 mg, 0.42 ml) in CH$_2$Cl$_2$ (1.5 ml), phenyl isothiocyanate (0.3 ml, 2.51 ml) was added and the mixture was stirred at 23° C. for 1 h. The reaction was concentrated in vacuo and the residue was purified by flash column chromatography (SiO$_2$, gradient Hexane to 5:1 hexane:ethyl acetate) to afford 20 (270 mg, 87%) as a white solid.

Rf: 0.56 (CHCl$_3$:ethyl acetate 1:4).

$^1$H NMR (300 MHz, CDCl$_3$): δ 8.00 (bs, 1H), 7.45-6.97 (m, 4H), 6.10 (s, 1H), 6.08-6.00 (m, 1H), 5.92 (s, 1H), 5.89 (s, 1H), 5.82 (s, 1H), 5.40 (dd, J=1.5 Hz, J=17.1 Hz, 1H), 3.38 (bs, 1H), 5.23 (dd, J=1.5 Hz, J=10.5 Hz, 1H), 4.42-4.36 (m, 1H), 4.19-4.03 (m, 5H), 3.71 (s, 3H), 3.68-3.17 (m, 4H), 2.90 (dd, J=7.8 Hz, J=18.3 Hz, 1H), 2.57 (d, J=18.3 Hz, 1H), 2.25 (s, 3H), 2.12 (s, 3H), 2.10 (s, 3H), 1.90 (dd, J=12.3 Hz J=16.5 Hz, 1H), 0.81 (d, J=6.9 Hz, 3H).

$^{13}$C NMR (75 MHz, CDCl$_3$): δ 178.4, 171.6, 148.6, 146.8, 144.3, 142.7, 138.7, 136.2, 133.6, 130.7, 129.8, 126.6, 124.2,

To a solution of 20 (270 mg, 0.37 ml) in dioxane (1 ml), 4.2N HCl/dioxane (3.5 ml) was added and the reaction was stirred at 23° C. for 30 min. Then, ethyl acetate (20 ml) and H$_2$O (20 ml) were added and the organic layer was decanted. The aqueous phase was basified with saturated aqueous sodium bicarbonate (60 ml) (pH=8) at 0° C. and then, extracted with CH$_2$Cl$_2$ (2×50 ml). The combined organic extracts were dried (sodium sulphate), and concentrated in vacuo. The residue was purified by flash column chromatography (SiO$_2$, ethyl acetate:methanol 5:1) to afford compound 21 (158 mg, 82%) as a white solid.

Rf: 0.3 (ethyl acetate:methanol 1:1).

$^1$H NMR (300 MHz, CDCl$_3$): δ 6.45 (s, 1H), 6.12-6.03 (m, 1H), 5.91 (s, 1H), 5.85 (s, 1H), 5.38 (dd, J$_1$=1.2 Hz, J$_2$=17.1 Hz, 1H), 5.24 (dd, J$_1$=1.2 Hz, J$_2$=10.5 Hz, 1H), 4.23-4.09 (m, 4H), 3.98 (d, J=2.1 Hz, 1H), 3.90 (bs, 1H), 3.72 (s, 3H), 3.36-3.02 (m, 5H), 2.72-2.71 (m, 2H), 2.48 (d, J=18.0 Hz, 1H), 2.33 (s, 3H), 2.22 (s, 3H), 2.11 (s, 3H), 1.85 (dd, J$_1$=11.7 Hz, J$_2$=15.6 Hz, 1H)).

$^{13}$C NMR (75 MHz, CDCl$_3$): δ 148.4, 146.7, 144.4, 142.8, 138.8, 133.8, 130.5, 128.8, 121.5, 120.8, 118.0, 117.5, 116.9, 113.6, 112.2, 101.1, 74.3, 60.7, 59.9, 58.8, 56.6, 56.5, 55.3, 44.2, 41.8, 29.7, 26.5, 25.7, 15.7, 9.4.

ESI-MS m/z: Calcd. for C$_{29}$H$_{34}$N$_4$O$_5$: 518.3. Found (M+H)$^+$: 519.2.

Example 9

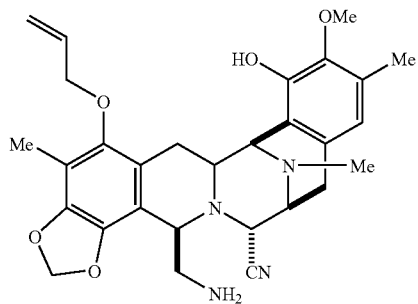

21

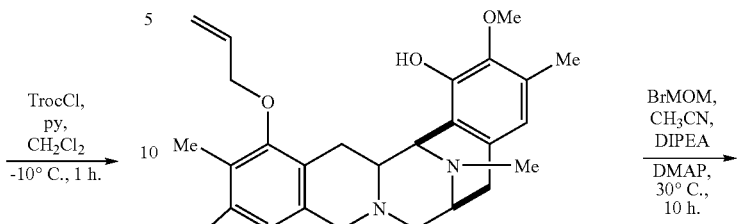

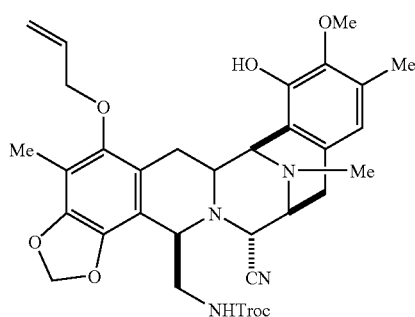

22

To a solution of 21 (0.64 g, 1.22 ml) in CH$_2$Cl$_2$ (6.13 ml), pyridine (0.104 ml, 1.28 ml) and 2,2,2-trichloroethyl chloroformate (0.177 ml, 1.28 ml) were added at −10° C. The mixture was stirred at this temperature for 1 h and then, the reaction was quenched by addition of 0.1N HCl (10 ml) and extracted with CH$_2$Cl$_2$ (2×10 ml). The organic layer was dried over sodium sulphate and concentrated in vacuo. The residue was purified by flash column chromatography (SiO$_2$, (hexane:ethyl acetate 1:2) to afford 22 (0.84 g, 98%) as a white foam solid.

Rf: 0.57 (ethyl acetate:methanol 5:1).

$^1$H NMR (300 MHz, CDCl$_3$): δ 6.50 (s, 1H), 6.10-6.00 (m, 1H), 6.94 (d, J=1.5Hz, 1H), 5.87 (d, J=1.5 Hz, 1H), 5.73 (bs, 1H), 5.37 (dq, J$_1$=1.5 Hz, J$_2$=17.1 Hz, 1H), 5.26 (dq, J$_1$=1.8 Hz, J$_2$=10.2 Hz, 1H), 4.60 (d, J=12 Hz, 1H), 4.22-4.10 (m, 4H), 4.19 (d, J=12 Hz, 1H), 4.02 (m, 2H), 3.75 (s, 3H), 3.37-3.18 (m, 5H), 3.04 (dd, J$_1$=8.1 Hz, J$_2$=18 Hz, 1H), 2.63 (d, J=18 Hz, 1H), 2.31 (s, 3H), 2.26 (s, 3H), 2.11 (s, 3H), 1.85 (dd, J$_1$=12.3 Hz, J$_2$=15.9 Hz, 1H).

$^{13}$C NMR (75 MHz, CDCl$_3$) δ 154.3, 148.5, 146.7, 144.5, 142.8, 139.0, 133.8, 130.7, 128.7, 121.3, 120.8, 117.8, 117.7, 116.8, 112.7, 101.2, 77.2, 74.3, 60.7, 59.9, 57.0, 56.4, 55.3, 43.3, 41.7, 31.6, 26.4, 25.3, 2.6, 15.9, 14.1, 9.4.

ESI-MS m/z: Calcd. for C$_{32}$H$_{35}$Cl$_3$N$_4$O$_7$: 694.17. Found (M+H)$^+$: 695.2.

Example 10

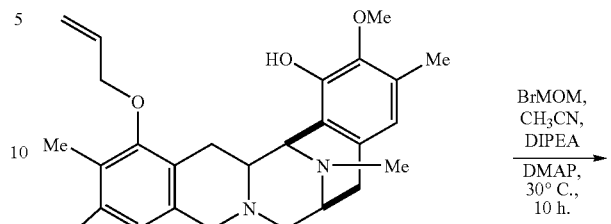

22

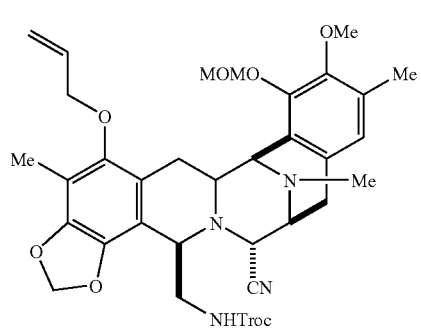

23

To a solution of 22 (0.32 g, 0.46 ml) in CH$_3$CN (2.33 ml), diisopropylethylamine (1.62 ml, 9.34 ml), bromomethyl methyl ether (0.57 ml, 7.0 ml) and dimethylaminopyridine (6 mg, 0.046 ml) were added at 0° C. The mixture was heated at 30° C. for 10 h. Then, the reaction was diluted with dichloromethane (30 ml) and poured in an aqueous solution of HCl at pH=5 (10 ml). The organic layer was dried over sodium sulphate and the solvent was eliminated under reduced pressure to give a residue which was purified by flash column chromatography (SiO$_2$, hexane:ethyl acetate 2:1) to afford 23 (0.304 g, 88%) as a white foam solid.

Rf: 0.62 (hexane:ethyl acetate 1:3).

$^1$H NMR (300 MHz, CDCl$_3$): δ 6.73 (s, 1H), 6.10 (m, 1H), 5.94 (d, J=1.5 Hz, 1H), 5.88 (d, J=1.5 Hz, 1H), 5.39 (dq, J$_1$=1.5 Hz, J$_2$=17.1 Hz, 1H), 5.26 (dq, J$_1$=1.8 Hz, J$_2$=10.2 Hz, 1H), 5.12 (s, 2H), 4.61 (d, J=12 Hz, 1H), 4.55 (t, J=6.6 Hz, 1H), 4.25 (d, J=12 Hz, 1H), 4.22-4.11 (m, 4H), 4.03 (m, 2H), 3.72 (s, 3H), 3.58 (s, 3H), 3.38-3.21 (m, 5H), 3.05 (dd, J$_1$=8.1 Hz, J$_2$=18 Hz, 1H), 2.65 (d, J=18 Hz, 1H), 2.32 (s, 3H), 2.23 (s, 3H), 2.12 (s, 3H), 1.79 (dd, J$_1$=12.3 Hz, J$_2$=15.9 Hz, 1H);

$^{13}$C NMR (75 MHz, CDCl$_3$) δ 154.3, 148.6, 148.4, 144.5, 139.0, 133.6, 130.6, 130.1, 125.07, 124.7, 124.0, 121.1, 117.7, 112.6, 101.2, 99.2, 77.2, 74.4, 74.1, 59.8, 59.8, 57.7, 57.0, 56.8, 56.68, 55.3, 43.2, 41.5, 26.4, 25.2, 15.9, 9.3.

ESI-MS m/z: Calcd. for C$_{34}$H$_{39}$Cl$_3$N$_4$O$_8$: 738.20. Found (M+H)$^+$: 739.0.

Example 11

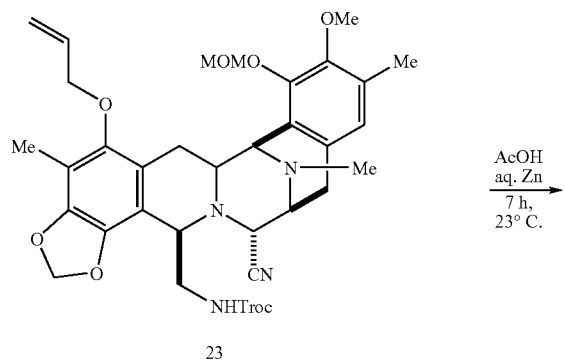

To a suspension of 23 (0.304 g, 0.41 ml) in 90% aqueous acetic acid (4 ml), powder zinc (0.2 g, 6.17 ml) was added and the reaction was stirred for 7 hour at 23° C. The mixture was filtered through a pad of celite which was washed with $CH_2Cl_2$. The organic layer was washed with an aqueous sat. solution of sodium bicarbonate (pH=9) (15 ml) and dried over sodium sulphate. The solvent was eliminated under reduced pressure to give 24 (0.191 g, 83%) as a white solid.

Rf: 0.3 (ethyl acetate:methanol 5:1).

$^1$H NMR (300 MHz, $CDCl_3$): δ 6.68 (s, 1H), 6.09 (m, 1H), 5.90 (d, J=1.5 Hz, 1H), 5.83 (d, J=1.5 Hz, 1H), 5.39 (dq, $J_1$=1.5 Hz, $J_2$=17.1 Hz, 1H), 5.25 (dq, $J_1$=1.5 Hz, $J_2$=10.2 Hz, 1H), 5.10 (s, 2H), 4.22-4.09 (m, 3H), 3.98 (d, J=2.4 Hz, 1H), 3.89 (m, 1H), 3.69 (s, 3H), 3.57 (s, 3H), 3.37-3.17 (m, 3H), 3.07 (dd, $J_1$=8.1 Hz, $J_2$=18 Hz, 1H), 2.71 (m, 2H), 2.48 (d, J=18 Hz, 1H), 2.33 (s, 3H), 2.19 (s, 3H), 2.17 (s, 3H), 1.80 (dd, $J_1$=12.3 Hz, $J_2$=15.9 Hz, 1H)

$^{13}$C NMR (75 MHz, $CDCl_3$): δ 148.5, 148.2, 144.3, 138.7, 133.7, 130.7, 129.9, 125.0, 123.9, 121.3, 117.9, 117.5, 113.6, 112.0, 101.0, 99.2, 74.0, 59.8, 59.7, 58.8, 57.6, 57.0, 56.2, 55.2, 44.2, 41.5, 31.5, 26.4, 25.6, 22.5, 16.7, 14.0, 9.2.

ESI-MS m/z: Calcd. for $C_{31}H_{38}N_4O_6$: 562.66. Found (M+H)$^+$: 563.1.

Example 12

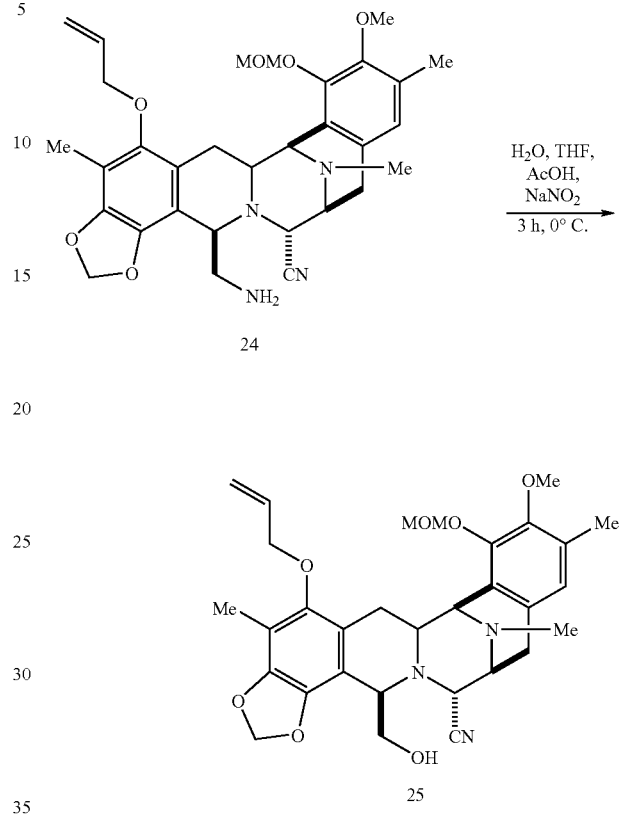

To a solution of 24 (20 mg, 0.035 ml), in $H_2O$ (0.7 ml) and THF (0.7 ml). $NaNO_2$ (12 mg, 0.17 ml) and 90% aqueous. AcOH (0.06 ml) were added at 0° C. and the mixture was stirred at 0° C. for 3 h. After dilution with $CH_2Cl_2$ (5 ml), the organic layer was washed with water (1 ml), dried over sodium sulphate and concentrated in vacuo. The residue was purified by flash column chromatography ($SiO_2$, hexane: ethyl acetate 2:1) to afford 25 (9.8 mg, 50%) as a white solid.

Rf: 0.34 (hexane:ethyl acetate 1:1).

$^1$H NMR (300 MHz, $CDCl_3$): δ 6.71 (s, 1H), 6.11 (m, 1H), 5.92 (d, J=1.5 Hz, 1H), 5.87 (d, J=1.5 Hz, 1H), 5.42 (dq, $J_1$=1.5 Hz, $J_2$=17.1 Hz, 1H), 5.28 (dq, $J_1$=1.5 Hz, $J_2$=10.2 Hz, 1H), 5.12 (s, 2H), 4.26-4.09 (m, 3H), 4.05 (d, J=2.4 Hz, 1H), 3.97 (t, J=3.0 Hz, 1H), 3.70 (s, 3H), 3.67-3.32 (m, 4H), 3.58 (s, 3H), 3.24 (dd, $J_1$=2.7 Hz, $J_2$=15.9 Hz, 1H), 3.12 (dd, $J_1$=8.1 Hz, $J_2$=18.0 Hz, 1H), 2.51 (d, J=18 Hz, 1H), 2.36 (s, 3H), 2.21 (s, 3H), 2.12 (s, 3H), 1.83 (dd, $J_1$=12.3 Hz, $J_2$=15.9 Hz, 1H)

$^{13}$C NMR (75 MHz, $CDCl_3$) δ 148.7, 148.4, 138.9, 133.7, 131.1, 129.4, 125.1, 123.9, 120.7, 117.6, 117.5, 113.2, 112.3, 101.1, 99.2, 74.0, 63.2, 59.8, 59.7, 57.9, 57.7, 57.0, 56.5, 55.2, 41.6, 29.6, 26.1, 25.6, 22.6, 15.7, 9.2.

ESI-MS m/z: Calcd. for $C_{31}H_{37}N_3O_7$: 563.64. Found (M+H)$^+$: 564.1.

Example 13

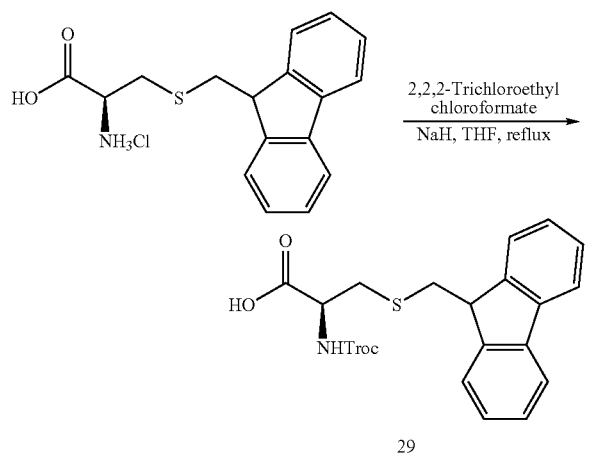

The starting material (2.0 g, 5.90 ml) was added to a suspension of sodium hydride (354 mg, 8.86 ml) in THF (40 ml) at 23° C., following the suspension was treated with allyl chloroformate (1.135 ml, 8.25 ml) at 23° C. and then refluxed for 3 hours. The suspension was cooled, filtered off, the solid washed with ethyl acetate (100 ml), and the filtrate was concentrated. The oil crude was ground with hexane (100 ml) and kept at 4° C. overnight. After, the solvent was decanted and the light yellow slurry was treated with $CH_2Cl_2$ (20 ml), and precipitated with hexane (100 ml). After 10 minutes, the solvent was decanted again. The operation was repeated until appearing a white solid. The white solid was filtered off and dried to afford compound 29 (1.80 g, 65%) as a white solid.

$^1$H-NMR (300 MHz, $CDCl_3$): δ 7.74 (d, J=7.5 Hz, 2H), 7.62 (d, J=6.9 Hz, 2H), 7.33 (t, J=7.5 Hz, 2H), 7.30 (t, J=6.3 Hz, 2H), 5.71 (d, J=7.8 Hz, 1H), 4.73 (d, J=7.8 Hz, 2H), 4.59 (m, 1H), 4.11 (t, J=6.0 Hz, 1H), 3.17 (dd, J=6.0 Hz, J=2.7 Hz, 2H), 3.20 (dd, J=5.4 Hz, J=2.1 Hz, 2H).

$^{13}$C-NMR (75 MHz, $CDCl_3$): δ 173.6, 152.7, 144.0, 139.7, 137.8, 126.0, 125.6, 123.4, 118.3, 73.4, 52.4, 45.5, 35.8, 33.7.

ESI-MS m/z: Calcd. for $C_{20}H_{18}Cl_3NO_4S$: 474.8. Found $(M+Na)^+$: 497.8.

Example 14

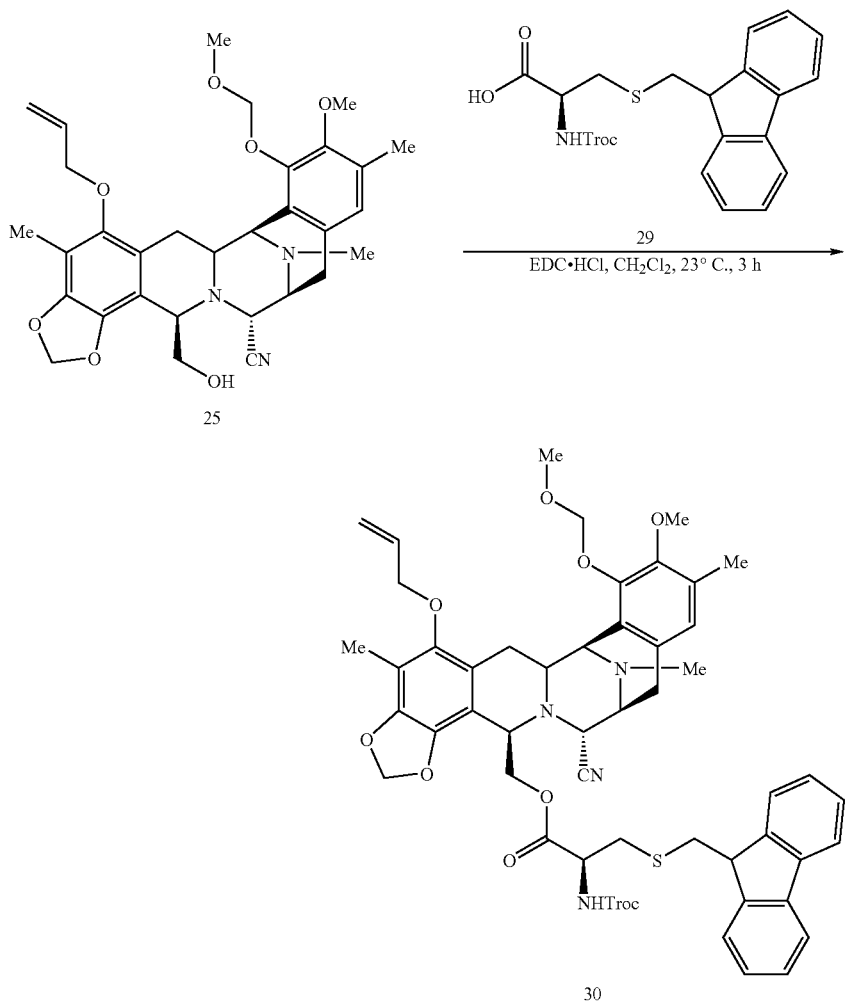

A mixture of compound 25 (585 mg, 1.03 ml) and compound 29 (1.47 mg, 3.11 ml) were azeotroped with anhydrous toluene (3×10 ml). To a solution of 25 and 29 in anhydrous CH$_2$Cl$_2$ (40 ml) was added DMAP (633 mg, 5.18 ml) and EDC.HCl (994 mg, 5.18 ml) at 23° C. The reaction mixture was stirred at 23° C. for 3 hours. The mixture was partitioned with saturated aqueous solution of sodium bicarbonate (50 ml) and the layers were separated. The aqueous layer was washed with CH$_2$Cl$_2$ (50 ml). The combined organic layers were dried over sodium sulphate, filtered and concentrated. The crude was purified by flash column chromatography (ethyl acetate/hexane 1:3) to obtain 30 (1.00 g, 95%) as a pale cream yellow solid.

$^1$H-NMR (300 MHz, CDCl$_3$): δ 7.72 (m, 2H), 7.52 (m, 2H), 7.38 (m, 2H), 7.28 (m, 2H), 6.65 (s, 1H), 6.03 (m, 1H), 5.92 (d, J=1.5 Hz, 1H), 5.79 (d, J=1.5 Hz, 1H), 5.39 (m, 1H), 5.29 (dq, J=10.3 Hz, J=1.5 Hz, 1H), 5.10 (s, 2H), 4.73 (d, J=11.9 Hz, 1H), 4.66 (d, J=11.9 Hz 1H), 4.53 (m, 1H), 4.36-3.96 (m, 9H), 3.89 (t, J=6.4 Hz, 1H), 3.71 (s, 3H), 3.55 (s, 3H), 3.33 (m, 1H), 3.20 (m, 2H), 2.94 (m, 3H), 2.59 (m, 1H), 2.29 (s, 3H), 2.23 (s, 3H), 2.02 (s, 3H), 1.83 (dd, J=16.0 Hz, J=11.9 Hz, 1H).

$^{13}$C-NMR (75 MHz, CDCl$_3$): δ 169.7, 154.0, 148.8, 148.4, 145.7, 144.5, 140.9, 139.0, 133.7, 130.9, 130.6, 127.6, 127.0, 124.8, 124.6, 124.1, 120.8, 119.9, 118.2, 117.7, 117.3, 112.7, 112.1, 101.3, 99.2, 74.7, 73.9, 64.4, 59.8, 57.7, 57.0, 56.8, 55.4, 53.3, 46.7, 41.4, 36.5, 34.7, 31.5, 26.4, 24.9, 22.6, 15.7, 14.0, 9.1.

ESI-MS m/z: Calcd. for C$_{51}$H$_{53}$Cl$_3$N$_4$O$_{10}$S: 1020.4. Found (M+H)$^+$: 1021.2.

To a solution of 30 (845 mg, 0.82 ml), acetic acid (500 mg, 8.28 ml) and (PPb$_3$)$_2$PdCl$_2$ (29 mg, 0.04 ml) in anhydrous CH$_2$Cl$_2$ 20 ml at 23° C. was added, dropwise, Bu$_3$SnH (650 mg, 2.23 ml). The reaction mixture was stirred at this temperature for 15 min., bubbling was. The crude was quenched with water (50 ml) and extracted with CH$_2$Cl$_2$ (3×50 ml). The organic layers were dried over sodium sulphate, filtered and concentrated. The crude was purified by flash column chromatography (ethyl acetate/hexane in gradient from 1:5 to 1:3) to obtain compound 31 (730 mg, 90%) as a pale cream yellow solid.

$^1$H-NMR (300 MHz, CDCl$_3$): δ 7.72 (m, 2H), 7.56 (m, 2H), 7.37 (m, 2H), 7.30 (m, 2H), 6.65 (s, 1H), 5.89 (s, 1H), 5.77 (s, 1H), 5.74 (s, 1H), 5.36 (d, J=5.9 Hz, 1H), 5.32 (d, J=5.9 Hz, 1H), 5.20 (d, J=9.0, 1H), 4.75 (d, J=12.0 Hz, 1H), 4.73 (m, 1H), 4.48 (d, J=11.9 Hz, 1H), 4.08 (m, 4H), 3.89 (m, 1H), 3.86, (t, J=6.2 Hz, 1H), 3.70 (s, 3H), 3.69 (s, 3H), 3.38 (m, 1H), 3.25 (m, 1H), 3.02-2.89 (m, 4H), 2.67 (s, 1H), 2.61 (s, 1H), 2.51 (dd, J=14.3 Hz, J=4.5 Hz, 1H), 2.29 (s, 3H), 2.23 (s, 3H), 1.95 (s, 3H), 1.83 (m, 1H).

$^{13}$C-NMR (75 MHz, CDCl$_3$): δ 168.2, 152.5, 148.1, 146.2, 144.4, 144.3, 143.3, 139.6, 134.6, 129.7, 129.6, 126.2, 125.6, 123.4, 123.3, 121.6, 118.5, 116.3, 110.7, 110.2, 105.1, 99.4, 98.5, 75.2, 73.3, 61.7, 58.4, 57.9, 56.3, 56.1, 55.1, 54.7, 53.9, 51.9, 45.2, 40.1, 35.6, 33.3, 24.8, 23.3, 14.5, 7.3.

ESI-MS m/z: Calcd. for C$_{48}$H$_{49}$Cl$_3$N$_4$O$_{10}$S: 980.3. Found (M+H)$^+$: 981.2.

Example 15

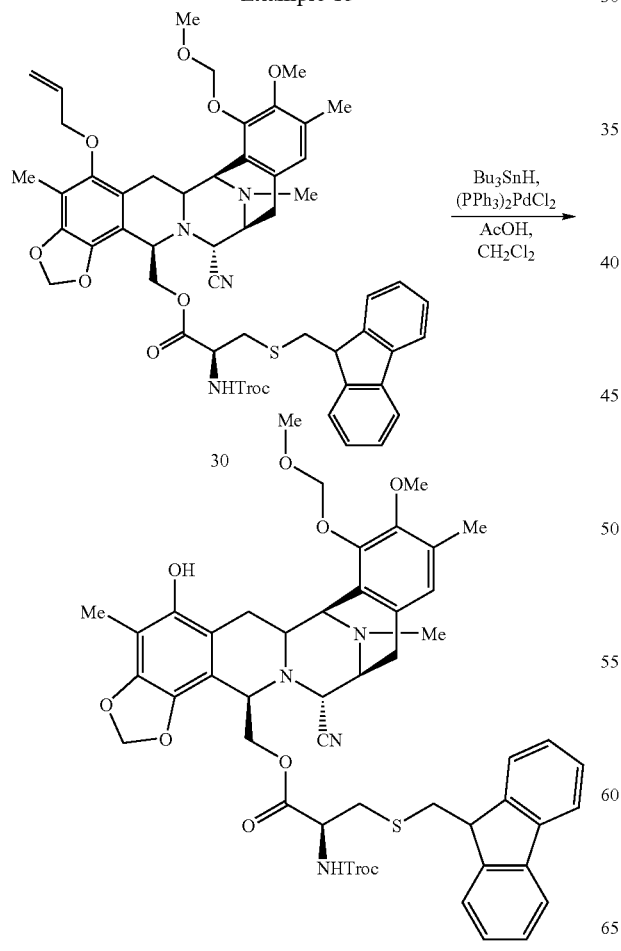

30

31

Example 16

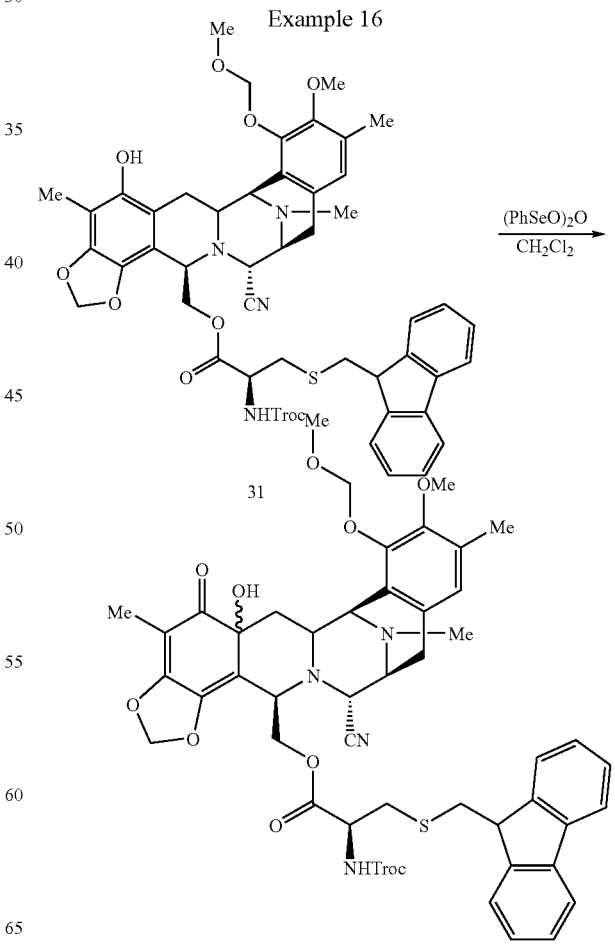

31

32

To a solution of 31 (310 mg, 0.32 ml), in anhydrous $CH_2Cl_2$ (15 ml) at −10° C. was added a solution of benzeneseleninic anhydride 70% (165 mg, 0.32 ml), in anhydrous $CH_2Cl_2$ (7 ml), via cannula, keeping the temperature at −10° C. The reaction mixture was stirred at −10° C. for 5 min. A saturated solution of sodium bicarbonate (30 ml) w % as added at this temperature. The aqueous layer was washed with more $CH_2Cl_2$ (40 ml). The organic layers were dried over sodium sulphate, filtered and concentrated. The crude was purified by flash column chromatography (ethyl acetate/hexane in gradient from 1:5 to 1:1) to obtain 32 (287 mg, 91%, HPLC: 91.3%) as a pale cream yellow solid and as a mixture of two isomers (65:35) which were used in the next step.

$^1$H-NMR (300 MHz, $CDCl_3$): δ (Mixture of isomers) 7.76 (m, 4H), 7.65 (m, 4H), 7.39 (m, 4H), 7.29 (m, 4H), 6.62 (s, 1H), 6.55 (s, 1H), 5.79-5.63 (m, 6H), 5.09 (s, 1H), 5.02 (d, J=6.0 Hz, 1H), 4.99 (d, J=6.0 Hz, 1H), 4.80-4.63 (m, 6H), 4.60 (m, 1H), 4.50 (m, 1H), 4.38 (d, J=12.8 Hz, J=7.5 Hz, 1H), 4.27 (dd, J=12.8 Hz, J=7.5 Hz, 1H), 4.16-3.90 (m, 10H), 3.84 (s, 3H), 3.62 (s, 3H), 3.50 (s, 3H), 3.49 (s, 3H), 3.33-2.83 (m, 14H), 2.45-2.18 (m, 2H), 2.21 (s, 6H), 2.17 (s, 6H), 1.77 (s, 6H), 1.67 (m, 2H).

$^{13}$C-NMR (75 MHz, $CDCl_3$): δ (Mixture of isomers) 168.6, 168.4, 158.6, 154.8, 152.8, 152.5, 147.3, 147.2, 146.8, 144.1, 144.0, 140.8, 139.7, 137.1, 129.8, 129.3, 128.4, 128.7, 126.5, 125.5, 123.7, 123.6, 123.5, 123.4, 122.2, 121.3, 118.3, 115.8, 115.5, 110.2, 106.9, 103.5, 103.2, 100.1, 99.6, 97.9, 97.7, 93.8, 73.4, 70.9, 69.2, 64.9, 62.5, 59.3, 58.9, 58.4, 56.7, 56.3, 56.2, 55.4, 55.2, 55.1, 54.9, 54.7, 54.3, 54.1, 53.8, 52.8, 45.5, 40.5, 40.0, 39.8, 35.8, 35.5, 33.9, 33.7, 30.1, 28.8, 24.2, 24.1, 21.2, 14.5, 14.4, 12.7, 6.0, 5.7.

ESI-MS m/z: Calcd. for $C_{48}H_{49}Cl_3N_4O_{11}S$: 996.3. Found $(M+H)^+$: 997.2.

Example 17

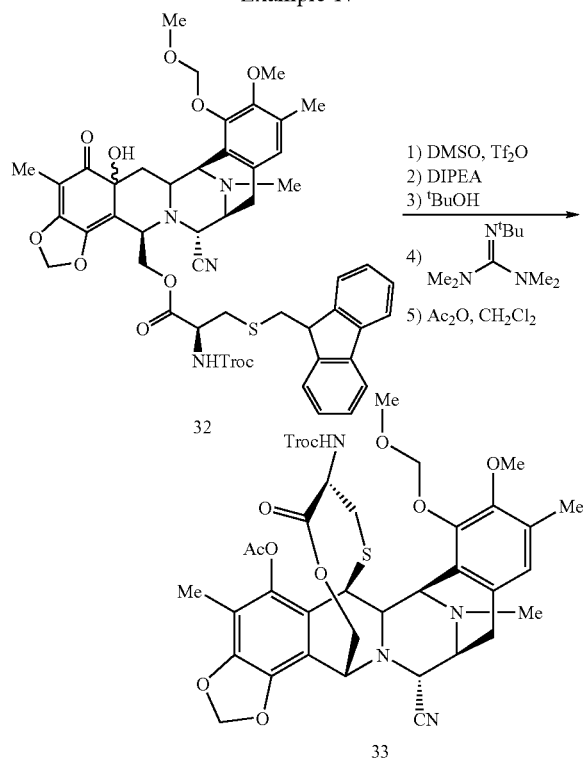

The reaction flask was flamed twice, purged vacuum/Argon several times and kept under Argon atmosphere for the reaction. To a solution of DMSO (39.1 ml, 0.55 ml, 5 equivalents.) in anhydrous $CH_2Cl_2$ (4.5 ml) was dropwise added triflic anhydride (37.3 ml, 0.22 ml, 2 equivalents.) at −78° C. The reaction mixture was stirred at −78° C. for 20 minutes, then a solution of 32 (110 mg, 0.11 ml. HPLC: 91.3%) in anhydrous $CH_2Cl_2$ (1 ml, for the main addition and 0.5 ml for wash) at −78° C. was added, via cannula. During the addition the temperature was kept at −78° C. in both flasks and the colour changed from yellow to brown. The reaction mixture was stirred at −40° C. for 35 minutes. During this period of time the solution was turned from yellow to dark green. After this time. $^iPr_2NEt$ (153 ml, 0.88 ml, 8 equivalents.) was dropwise added and the reaction mixture was kept at 0° C. for 45 minutes, the colour of the solution turned to brown during this time. Then t-butanol (41.6 ml, 0.44 ml, 4 equivalents.) and 2-$^t$Butyl-1,1,3,3-tetramethylguanidine (132.8 ml, 0.77 ml, 7 equivalents.) were dropwise added and the reaction mixture was stirred at 23° C. for 40 minutes. After this time, acetic anhydride (104.3 ml, 1.10 ml, 10 equivalents.) was dropwise added and the reaction mixture was kept at 23° C. for 1 hour more. Then the reaction mixture was diluted with $CH_2Cl_2$ (20 ml) and washed with aqueous saturated solution of $NH_4Cl$ (50 ml), sodium bicarbonate (50 ml), and sodium chloride (50 ml). The combined organic layers were dried over sodium sulphate, filtered and concentrated. The residue was purified by flash column chromatography (eluent: ethyl acetate/hexane gradient from 1:3 to 1:2) to afford compound 33 (54 mg, 58%) as a pale yellow solid.

$^1$H-NMR (300 MHz, $CDCl_3$): δ 6.85 (s, 1H), 6.09 (s, 1H), 5.99 (s, 1H), 5.20 (d, J=5.8 Hz, 1H), 5.14 (d, J=5.3 Hz, 1H), 5.03 (m, 1H), 4.82 (d, J=12.2, 1H), 4.63 (d, J=12.0 Hz, 1H), 4.52 (m, 1H), 4.35-4.17 (m, 4H), 3.76 (s, 3H), 3.56 (s, 3H), 3.45 (m, 2H), 2.91 (m, 2H), 2.32 (s, 3H), 2.28 (s, 3H), 2.21 (s, 3H), 2.12 (m, 2H), 2.03 (s, 3H).

$^{13}$C-NMR (75 MHz, $CDCl_3$): δ 168.5, 167.2, 152.7, 148.1, 147.1, 144.5, 139.6, 139.1, 130.5, 129.0, 123.7, 123.5, 123.3, 118.8, 116.5, 112.1, 100.6, 97.8, 73.3, 60.5, 59.4, 59.2, 58.3, 57.6, 57.4, 56.1, 53.3, 53.1, 40.6, 40.0, 31.0, 22.2, 18.9, 14.4, 8.1.

ESI-MS m/z: Calcd. for $C_{36}H_{39}Cl_3N_4O_{11}S$: 842.1. Found $(M+H)^{30}$: 843.1.

Example 18

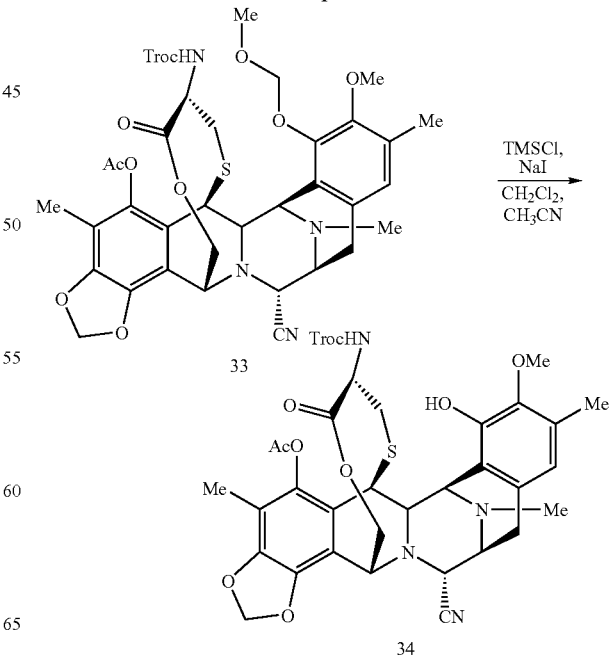

To a solution of 33 (12 mg, 0.014 ml) in dry dichloromethane (1.2 ml) and HPLC grade acetonitrile (1.2 ml) was added at 23° C. sodium iodide (21 mg, 0.14 ml) and freshly distilled (over calcium hydride at atmospheric pressure) trimethylsilyl chloride (15.4 mg, 0.14 ml). The reaction mixture turned to orange colour. After 15 min the solution was diluted with dichloromethane (10 ml) and was washed with a freshly aqueous saturated solution of $Na_2S_2O_4$ (3×10 ml). The organic layer was dried over sodium sulphate, filtered and concentrated. It was obtained compound 34 (13 mg, quantitative) as pale yellow solid which was used without further purification.

$^1$H-NMR (300 MHz, $CDCl_3$): δ 6.85 (s, 1H), 6.09 (s, 1H), 5.99 (s, 1H), 5.27 (d, J=5.8 Hz, 1H), 5.14 (d, J=5.3 Hz, 1H), 5.03 (d, J=11.9 Hz, 1H), 4.82 (d, J=12.2, 1H), 4.63 (d, J=13.0 Hz, 1H), 4.52 (m, 1H), 4.34 (m, 1H), 4.27 (bs, 1H), 4.18 (m, 2H), 3.76 (s, 3H), 3.56 (s, 3H), 3.44 (m, 1H), 3.42 (m, 1H), 2.91 (m, 2H), 2.32 (s, 3H), 2.28 (s, 3H), 2.21 (s, 3H), 2.03 (s, 3H).

ESI-MS m/z: Calcd. for $C_{34}H_{35}N_4O_{10}S$: 798.1. Found $(M+H)^+$: 799.1.

Example 19

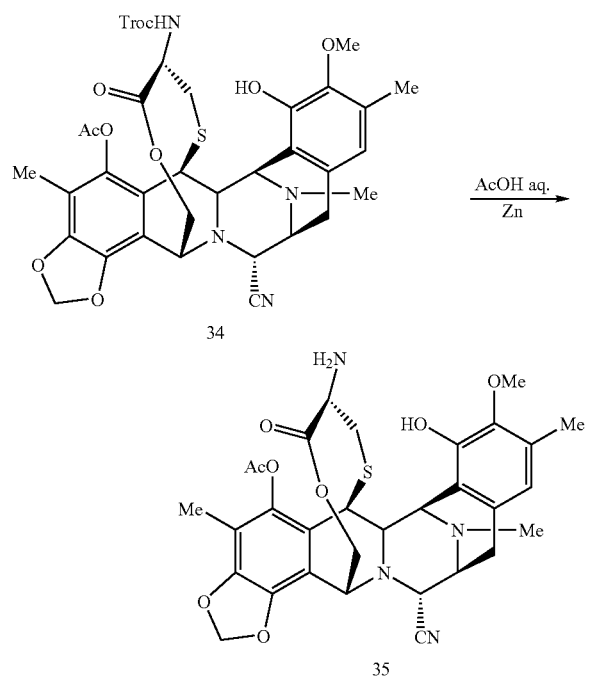

To a solution of 34 (13 mg, 0.016 ml) in a mixture of acetic acid/$H_2O$ (90:10, 1 ml) was added powder Zinc (5.3 mg, 0.081 ml) at 23° C. The reaction mixture was heated at 70° C. for 6 h. After this time, was cooled to 23° C. diluted with $CH_2Cl_2$ (20 ml) and washed with aqueous saturated solution of sodium bicarbonate (15 ml) and aqueous solution of $Et_3N$ (15 ml). The organic layer was dried over sodium sulphate, filtered and concentrated. The residue was purified by flash column chromatography with Silica-$NH_2$ (eluent: ethyl acetate/hexane gradient from 0:100 to 50:50) to afford compound 35 (6.8 mg, 77% for two steps) as a pale yellow solid.

$^1$H-NMR (300 MHz, $CDCl_3$): δ 6.51 (s, 1H) 6.03 (dd, J=1.3 Hz, J=26.5 Hz, 2H), 5.75 (bs, 1H), 5.02 (d, J=11.6 Hz, 1H), 4.52 (m, 1H), 4.25 (m, 2H), 4.18 (d, J=2.5 Hz, 1H), 4.12 (dd, J=1.9 Hz, J=11.5 Hz, 1H), 3.77 (s, 3H), 3.40 (m, 2H), 3.26 (t, J=6.4 Hz, 1H), 2.88 (m, 2H), 2.30-2.10 (m, 2H), 2.30 (s, 3H), 2.28 (s, 3H), 2.18 (s, 3H), 2.02 (s, 3H).

$^{13}$C-NMR (75 MHz, $CDCl_3$): δ 174.1, 168.4, 147.8, 145.4, 142.9, 140.8, 140.1, 131.7, 130.2, 129.1, 128.3, 120.4, 118.3, 117.9, 113.8, 111.7, 101.7, 61.2, 59.8, 59.2, 58.9, 54.4, 53.8, 54.4, 41.3, 41.5, 34.1, 23.6, 20.3, 15.5, 9.4.

ESI-MS m/z: Calcd. for $C_{31}H_{34}N_4O_8S$: 622.7. Found $(M+H)^+$: 623.2.

Example 20

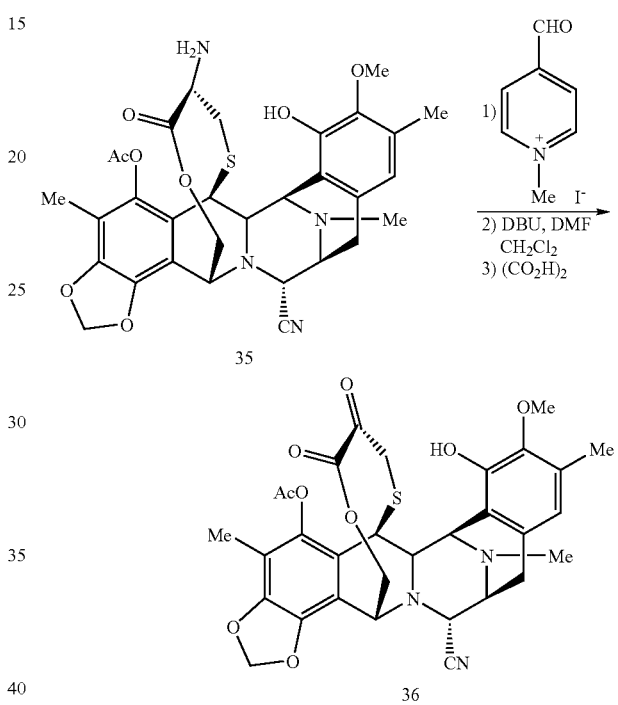

A solution of N-methylpyridine-4-carboxaldehyde iodide (378 mg, 1.5 mmol) in anhydrous DMF (5.8 mL) was treated with anhydrous toluene (2×10 mL) to eliminate the amount of water by azeotropic removal of the toluene. A solution of 35 (134 mg, 0.21 mmol), previously treated with anhydrous toluene (2×10 mL), in anhydrous $CH_2Cl_2$ (distilled over $CaH_2$, 7.2 mL) was added, via cannula, at 23° C. to this orange solution. The reaction mixture was stirred at 23° C. for 4 hours. After this time DBU (32.2 µL, 0.21 mmol) was dropwise added at 23° C. and it was stirred for 15 minutes at 23° C. A freshly aqueous saturated solution of oxalic acid (5.8 mL) was added to the reaction mixture and was stirred for 30 minutes at 23° C. Then the reaction mixture was cooled to 0° C. and $NaHCO_3$ was portionwise added followed by addittion of aqueous saturated solution of $NaHCO_3$. The mixture was extracted with $Et_2O$. $K_2CO_3$ was added to the aqueous layer and it was extrated with $Et_2O$. The combined organic layers were dried over $MgSO_4$ and the solvent was removed under reduced pressure. The crude was purified by flash column chromatography (AcOEt/hexane from 1/3 to 1/1) to afford compound 36 (77 mg, 57%) as pale yellow solid.

$^1$H-NMR (300 MHz, $CDCl_3$): δ 6.48 (s, 1H), 6.11 (d, J=1.3 Hz, 1H), 6.02 (d, J=1.3 Hz, 1H), 5.70 (bs, 1H), 5.09 (d, J=11.3 Hz, 1H), 4.66 (bs, 1H), 4.39 (m, 1H), 4.27 (d, J=5.6 Hz, 1H), 4.21 (d, J=10.5 Hz, 1H), 4.16 (d, J=2.6 Hz, 1H), 3.76 (s, 3H), 3.54 (d, J=5.1 Hz, 1H), 3.42 (d, J=8.5 Hz, 1H), 2.88-2.54 (m, 3H), 2.32 (s, 3H), 2.24 (s, 3H), 2.14 (s, 3H), 2.04 (s, 3H).
$^{13}$C-NMR (75 MHz, CDCl$_3$): δ 186.7, 168.5, 160.5, 147.1, 146.4, 142.9, 141.6, 140.7, 130.4, 129.8, 121.7 (2C), 120.0, 117.8, 117.1, 113.5, 102.2, 61.7, 61.4, 60.3, 59.8, 58.9, 54.6, 41.6, 36.9, 29.7, 24.1, 20.3, 15.8, 14.1, 9.6.

ESI-MS m/z: Calcd. for C$_{31}$H$_{31}$N$_3$O$_9$S: 621.7. Found (M+H)$^+$: 622.2.

Example 21

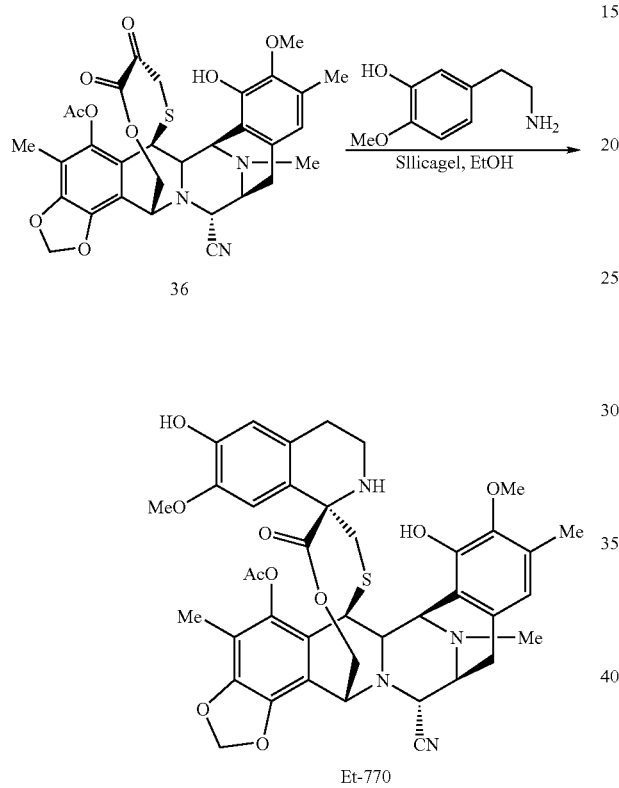

To a solution of 36 (49 mg, 0.08 ml) and 2-[3-hydroxy-4-methoxyphenyl]ethylamine (46.2 mg, 0.27 ml) in ethanol (2.5 ml) was added silica gel (105 mg) at 23° C. The reaction mixture was stirred at 23° C. for 14 h. It was diluted with hexane and poured into a column of chromatography (ethyl acetate/hexane from 1/3 to 1/1) to afford Et-770 (55 mg, 90%) as a pale yellow solid.

$^1$H-NMR (300 MHz, CDCl$_3$): δ 6.60 (s, 1H), 6.47 (s, 1H), 6.45 (s, 1H), 6.05 (s, 1H), 5.98 (s, 1H), 5.02 (d, J=11.4 Hz, 1H), 4.57 (bs, 1H), 4.32 (bs, 1H), 4.28 (d, J=5.3 Hz, 1H), 4.18 (d, J=2.5 Hz, 1H), 4.12 (dd, J=2.1 Hz, J=11.5 Hz, 1H), 3.78 (s, 3H), 3.62 (s, 3H), 3.50 (d, J=5.0 Hz, 1H), 3.42 (m, 1H), 3.10 (ddd, J=4.0 Hz, J=10.0 Hz, J=11.0 Hz, 1H), 2.94 (m, 2H), 2.79 (m, 1H), 2.61 (m, 1H), 2.47 (m, 1H), 2.35 (m, 1H), 2.32 (s, 3H), 2.27 (s, 3H), 2.20 (s, 3H), 2.09 (m, 1H), 2.04 (s, 3H).

ESI-MS m/z: Calcd. for C$_{40}$H$_{42}$N$_4$O$_{10}$S: 770.7. Found (M+H)$^{30}$: 771.2.

Example 22

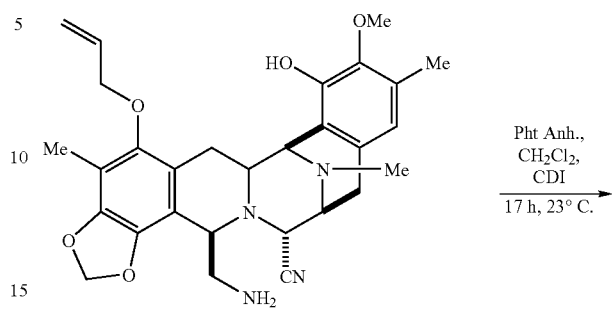

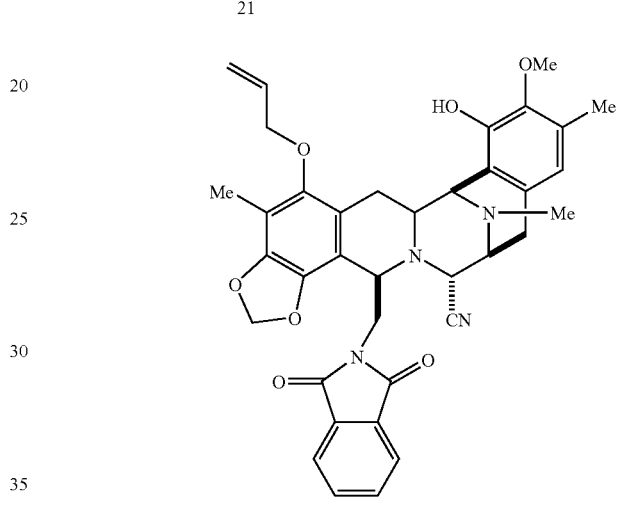

To a solution of 21 (22 mg, 0.042 ml) in CH$_2$Cl$_2$ (0.8 ml) was added phthalic anhydride (6.44 mg, 0.042 ml) and the reaction mixture was stirred for 2 h at 23° C. Then, carbonyldiimidazole (1 mg, 0.006 ml) was added and the mixture was stirred at 23° C. for 7 h. Then, carbonyldiimidazole (5.86 mg, 0.035 ml) was added and the reaction was stirred at 23° C. for an additional 17 h. The solution was diluted with CH$_2$Cl$_2$ (15 ml) and washed with 0.1 N HCl (15 ml). The organic layer was dried over sodium sulphate, filtered, and the solvent was eliminated under reduced pressure. The residue was purified b flash column chromatography (SiO$_2$, hexane:ethyl acetate 2:1) to afford 27 (26.4 mg, 96%) as a white solid.

Rf: 0.58 (ethyl acetate).

$^1$H NMR (300 MHz, CDCl$_3$): 7.73-7.64 (m, 4H), 6.40 (s, 1H), 6.12-6.01 (m, 1H), 5.63 (s, 1H), 5.58 (d, J=1.5 Hz, 1H), 5.37 (dd, J$_1$=1.8 Hz, J$_2$=17.4 Hz), 5.23 (dd, J$_1$=1.8 Hz, J$_2$=10.5 Hz, 1H), 5.12 (d, J=1.5 Hz, 1H), 4.22-4.15 (m, 3H), 4.08 (d, J=1.8 Hz, 1H), 3.68 (s, 3H), 3.59-3.55 (m 2H), 3.35 (d, J=8.1 Hz, 1H), 3.27-3.16 (m, 2H), 3.05 (dd, J$_1$=8.1 Hz, J$_2$=18.3 Hz, 1H), 2.64 (d, J=18.0 Hz, 1H), 2.30 (s, 3H), 2.24 (s, 3H), 2.09 (s, 3H), 1.80 (dd, J$_1$=11.4 Hz, J$_2$=15 Hz, 1H);

$^{13}$C NMR (75 MHz, CDCl$_3$): δ 167.7, 148.9, 146.4, 144.2, 142.6, 139.5, 134.0, 133.5, 132.0, 131.0, 128.3, 123.0, 121.3, 120.9, 118.1, 117.5, 116.8, 113.6, 112.4, 100.8, 74.5, 60.6, 60.5, 57.7, 56.6, 55.6, 55.5, 42.3, 41.7, 26.6, 25.5, 15.9, 9.46.

ESI-MS m/z: Calcd. for C$_{37}$H$_{35}$N$_4$O$_7$: 648.79. Found (M+H)$^+$: 649.3.

Example 23

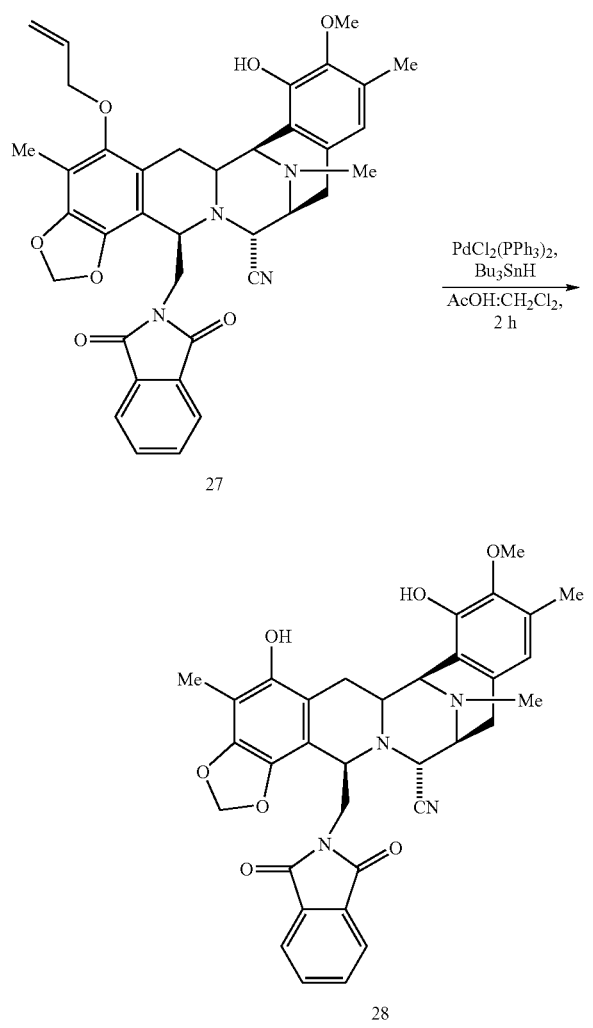

To a solution of 27 (26 mg, 0.041 ml) in CH$_2$Cl$_2$ (11 ml), acetic acid (11 ml), (PPh$_3$)$_2$PdCl$_2$ (2.36 mg) and Bu$_3$SnH (28 ml, 0.10 ml) were added at 23° C. After stirring at that temperature for 2 h the reaction was poured into a pad of flash column (SiO$_2$, gradient Hex to hexane:ethyl acetate 2:1) to afford 28 (24.7 mg, 99%) as a white solid.

Rf: 0.33 (hexane:ethyl acetate 2:1).

$^1$H NMR (300 MHz, CDCl$_3$): δ 7.75-7.70 (m, 2H), 7.69-7.65 (m, 2H), 6.39 (s, 1H), 5.82 (bs, 1H), 5.50 (d, J=1.5 Hz, 1H), 5.0 (d, J=1.5 Hz, 1H), 4.45 (bs, 1H), 4.23-4.19 (m, 2H), 4.10-4.09 (m, 1H), 3.73 (s, 3H), 3.60-3.48 (m, 2H), 3.36-3.33 (m, 1H), 3.26-3.20 (m, 1H), 3.14-3.08 (m, 1H), 3.98 (d, J=14.4 Hz, 1H), 2.61 (d, J=18.3 Hz, 1H), 2.30 (s, 3H), 2.23 (s, 3H), 2.06 (s, 3H), 1.85 (dd, J$_1$=12 Hz, J$_2$=15.3 Hz);

$^{13}$C NMR (75 MHz, CDCl$_3$): δ 167.8, 146.4, 145.1, 143.9, 142.7, 137.1, 133.5, 131.9, 130.8, 128.4, 122.9, 120.8, 118.0, 116.8, 114.0, 113.4, 106.4, 100.4, 60.6, 60.5, 57.8, 56.6, 55.5, 55.2, 42.6, 41.5, 25.6, 25.5, 15.8, 8.9.

ESI-MS m/z: Calcd. for C$_{34}$H$_{32}$N$_4$O$_7$: 608.6. Found (M+H)$^+$: 609.2.

Example 24

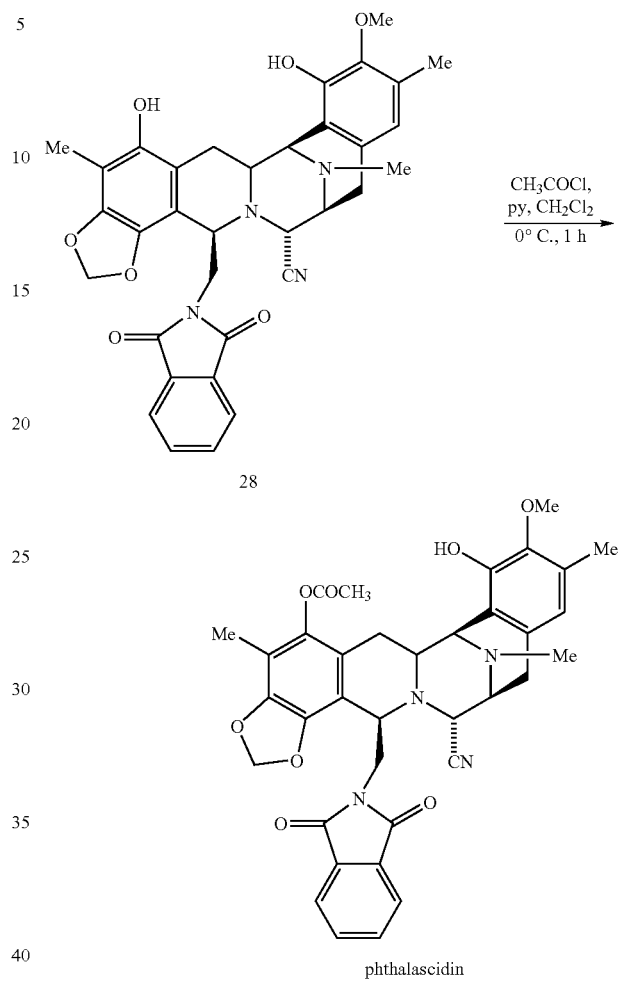

To a solution of 28 (357 mg, 0.058 ml) in CH$_2$Cl$_2$ (3 ml), acetyl chloride (41.58 ml, 0.58 ml) and pyridine (47.3 ml, 0.58 ml) were added at 0° C. The reaction mixture was stirred for 1 h and then, the solution was diluted with CH$_2$Cl$_2$ (15 ml) and washed with 0.1 N HCl (15 ml). The organic layer was dried over sodium sulphate, filtered, and the solvent was eliminated under reduced pressure. The residue was purified by flash column chromatography (RP-18, CH$_3$CN:H$_2$O 60:40) to afford phthalascidin (354 mg, 94%) as a white solid.

Rf: 0.37 (CH$_3$CN:H$_2$O 7:3, RP-18).

$^1$H NMR (300 MHz, CDCl$_3$): δ 7.72-7.68 (m, 2H), 7.67-7.63 (m, 2H), 6.38 (s, 1H), 5.69 (d, J=1.2 Hz, 1H), 5.64 (d, J=1.2 Hz, 1H), 5.30 (bs, 1H), 4.25-4.21 (m, 2H), 4.02 (d, J=2.1 Hz, 1H), 3.64-3.62 (m, 5H), 3.33 (d, J=8.4 Hz, 1H), 3.21-3.16 (m, 1H), 3.02 (dd, J$_1$=8.1 Hz, J$_2$=18 Hz, 1H), 2.76 (dd, J$_1$=1.8 Hz, J$_2$=15.6 Hz, 1H), 2.63 (d, J=17.7 Hz, 1H), 2.29 (s, 3H), 2.28 (s, 3H), 2.21 (s, 3H), 2.0 (s, 3H), 1.73 (dd, J$_1$=12.0 Hz, J$_2$=15.3 Hz, 1H))

$^{13}$C NMR (75 MHz, CDCl$_3$)): δ 168.5, 167.6, 146.2, 144.2, 142.5, 141.0, 140.5, 133.4, 131.8, 130.7, 128.2, 120.9, 120.8, 117.9, 116.4, 113.6, 101.1, 60.4, 60.0, 57.0, 56.3, 55.6, 55.4, 41.6, 41.5, 26.5, 25.2, 20.2, 15.7, 9.4.

ESI-MS m/z: Calcd. for C$_{36}$H$_{34}$N$_4$O$_8$: 650. Found (M+H)$^+$: 651.2.

Example 25

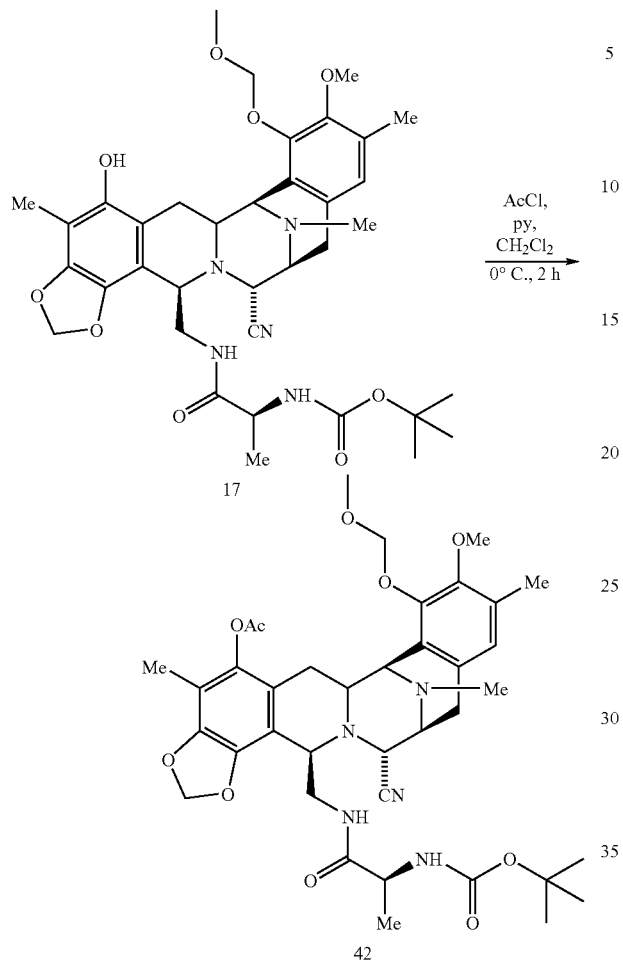

To a solution of 17 (300 mg, 0.432 ml) in CH$_2$Cl$_2$ (2 ml), acetyl chloride (30.7 ml, 0.432 ml) and pyridine (34.9 ml, 0.432 ml) were added at 0° C. The reaction mixture was stirred for 2 h at that temperature and then, the solution was diluted with CH$_2$Cl$_2$ (15 ml) and washed with 0.1 N HCl (15 ml). The organic layer was dried over sodium sulphate, filtered, and the solvent was eliminated under reduced pressure to afford 42 (318 mg, 100%) as a white solid that was used in subsequent reactions with no further purification.

Rf: 0.5 (ethyl acetate:methanol 5:1).

$^1$H NMR (300 MHz, CDCl$_3$). δ 6.66 (s, 1H), 5.93 (d, J=1.2 Hz, 1H), 5.83 (d, J=1.2 Hz, 1H), 5.42 (t, J=6.6 Hz, 1H), 5.07 (d, J=5.7 Hz, 1H), 4.98 (d, J=5.7 Hz, 1H), 4.16 (d, J=1.8 Hz, 1H), 4.11 (d, J=2.7 Hz, 1H), 3.98 (bs, 1H), 3.73-3.61 (m, 2H), 3.64 (s, 3H), 3.52-3.48 (m, 1H), 3.50 (s, 3H), 3.33 (d, J=9.6 Hz, 1H), 3.17-3.14 (m, 1H), 2.97-2.87 (m, 1H), 2.75-2.70 (d, J=16.8 Hz, 1H), 2.26 (s, 6H), 2.16 (s, 3H), 1.96 (s, 3H), 1.70 (dd, J$_1$=11.7 Hz, J$_2$=15.6 Hz, 1H), 1.33 (s, 9H), 0.59 (d, J=6.0 Hz, 3H).

$^{13}$C NMR (75 MHz, CDCl$_3$)): δ 172.0, 168.3, 162.3, 148.2, 144.4, 140.4, 140.2, 130.9, 130.5, 125.3, 123.4, 120.8, 117.6, 112.7, 111.7, 101.4, 99.1, 79.2, 59.5, 58.8, 57.5, 57.4, 56.4, 55.5, 55.0, 41.3, 39.0, 28.2, 26.4, 24.6, 19.9, 18.4, 15.4, 9.1.

ESI-MS m/z: Calcd. for C$_{38}$H$_{49}$N$_5$O$_{10}$: 735.82. Found (M+H)$^+$: 736.3.

Example 26

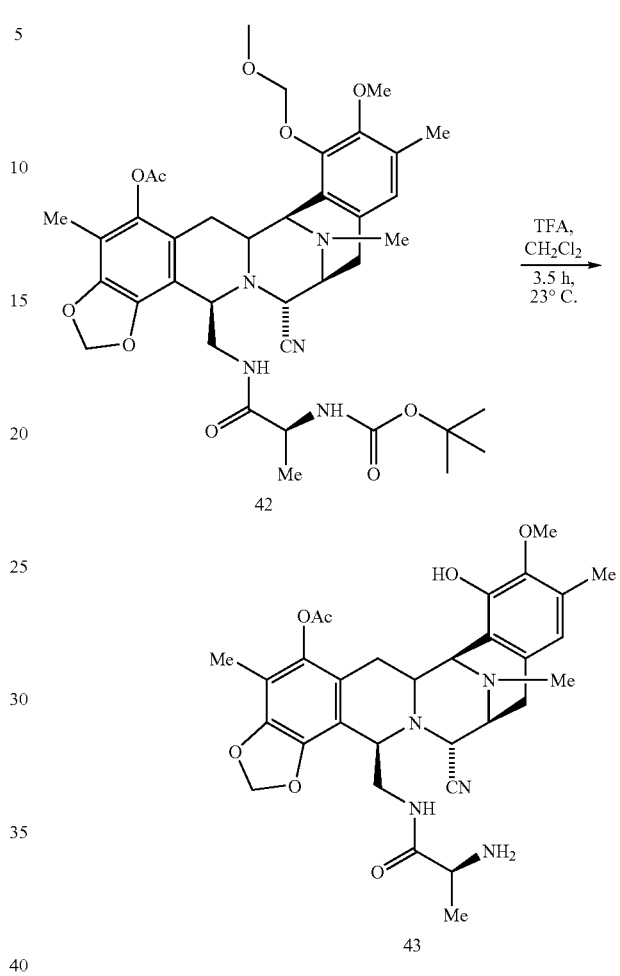

To a solution of 42 (318 mg, 0.432 ml) in CH$_2$Cl$_2$ (2.16 ml), trifluoroacetic acid (1.33 ml, 17.30 ml) was added and the reaction mixture was stirred for 3.5 h at 23° C. The reaction was quenched at 0° C. with saturated aqueous sodium bicarbonate (60 ml) and extracted with CH$_2$Cl$_2$ (2×70 ml). The combined organic layers were dried (sodium sulphate) and concentrated in vacuo. The residue was purified by flash column chromatography (SiO$_2$, ethyl acetate:methanol 20:1) to afford 43 (154 mg, 60%) as a white solid.

Rf: 0.22 (ethyl acetate:methanol 5:1).

$^1$H NMR (300 MHz, CDCl$_3$). δ 6.47 (s, 1H), 6.22 (bs, 1H), 5.95 (d, J=1.2 Hz, 1H), 5.88 (d, J=1.2 Hz, 1H), 4.08-4.06 (m, 2H), 4.01 (bs, 1H), 3.69 (s, 3H), 3.49 (d, J=3.6 Hz, 1H), 3.33 (d, J=8.1 Hz, 1H), 3.26-3.22 (m, 1H), 2.95 (dd, J$_1$=8.1 Hz, J$_2$=18 Hz, 1H), 2.80-2.76 (m, 2H), 2.58 (d, 118 Hz, 1H), 2.29 (s, 3H), 2.27 (s, 3H), 2.21 (s, 3H), 1.96 (s, 3H), 1.77 (dd, J$_1$=12.3 Hz, J$_2$=15.6 Hz, 1H), 0.90 (d, J=6.9 Hz, 3H).

$^{13}$C NMR (75 MHz, CDCl$_3$)): δ 174.8, 169.0, 146.8, 144.4, 142.8, 140.5, 140.2, 131.1, 128.8, 120.8, 120.5, 117.1, 112.9, 111.6, 101.5, 60.3, 59.0, 56.5, 56.3, 55.6, 55.1, 50.2, 41.6, 39.5, 26.8, 26.3, 24.9, 20.2, 15.4, 9.2.

ESI-MS m/z: Calcd. for C$_{31}$H$_{37}$N$_5$O$_7$: 591.65. Found (M+H)$^+$: 592.3.

Example 27

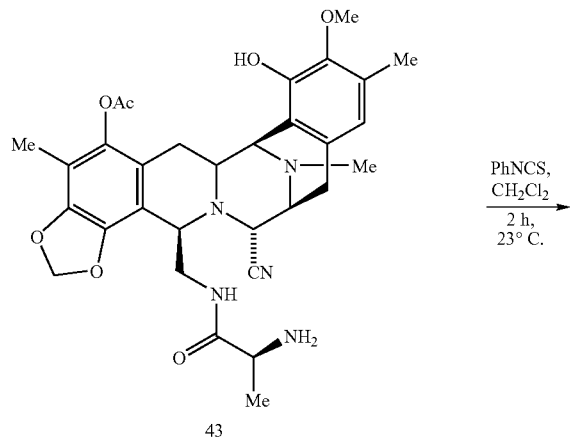

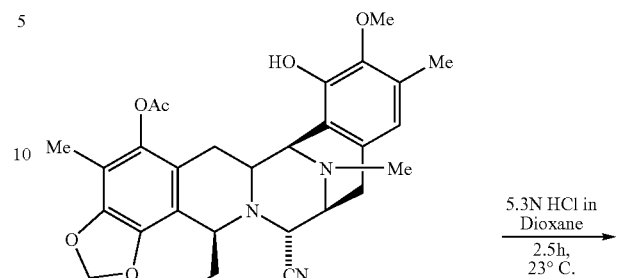

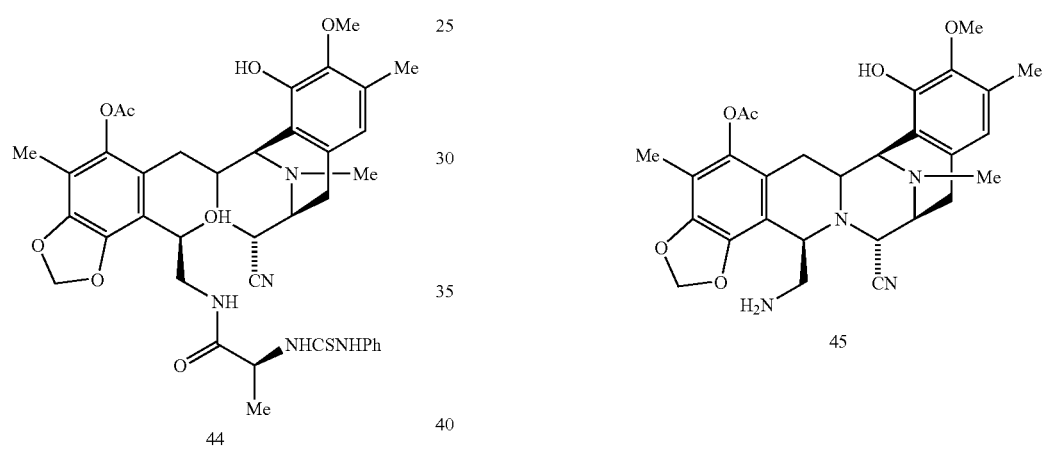

To a solution of 43 (154 mg, 0.26 ml) in CH$_2$Cl$_2$ (1.3 ml), phenyl isothiocyanate (186 ml, 1.56 ml) was added and the mixture was stirred at 23° C. for 2 h. The reaction was concentrated in vacuo and the residue was purified by flash column chromatography (SiO$_2$, gradient Hexane to hexane:ethyl acetate 1:1) to afford 44 (120 mg, 63%) as a white solid.

Rf: 0.41 (ethyl acetate:methanol 5:1).

$^1$H NMR (300 MHz, CDCl$_3$). δ 8.17 (s, 1H), 7.49-7.44 (m, 3H), 7.31-7.24 (m, 3H), 7.05 (d, J=6.9 Hz, 1H), 5.98 (d, J=1.2 Hz, 1H), 5.87 (d, J=1.2 Hz, 1H), 5.52 (bs, 1H), 4.54 (t, J=6.6 Hz, 1H), 4.15 (d, J=2.1 Hz, 1H), 4.03 (d, J=2.7 Hz, 2H), 3.80 (bs, 1H), 3.66 (s, 3H), 3.40 (bs, 1H), 3.32 (d, J=7.8 Hz, 1H), 3.16 (d, J=11.7 Hz, 1H), 2.82-2.61 (m, 3H), 2.29 (s, 3H), 2.20 (s, 3H), 2.01 (s, 3H), 1.99 (s, 3H), 1.80 (dd, J$_1$=12.0 Hz, J$_2$=15.9 Hz, 1H), 0.62 (d, J=6.0 Hz, 3H).

$^{13}$C NMR (75 MHz, CDCl$_3$) δ 178.5, 171.9, 168.7, 146.7, 144.5, 142.6, 140.6, 140.3, 136.3, 131.0, 129.9, 128.9, 126.7, 124.4, 120.9, 120.6, 117.7, 116.6, 112.7, 111.9, 101.4, 60.4, 58.7, 57.5, 56.1, 55.7, 55.1, 53.3, 41.4, 38.8, 26.3, 24.4, 20.2, 18.1, 15.3, 9.2.

ESI-MS m/z: Calcd. for C$_{38}$H$_{42}$N$_6$O$_7$S: 726.3. Found (M+H)$^+$: 727.3.

Example 28

To a solution of 44 (120 mg, 0.165 ml) in dioxane (0.9 ml), 5.3N HCl/dioxane (1.8 ml) was added and the reaction was stirred at 23° C. for 2.5 h. Then, CH$_2$Cl$_2$ (10 ml) and H$_2$O (5 ml) were added to this reaction and the organic layer was decanted. The aqueous phase was basified with saturated aq sodium bicarbonate (20 ml) (pH=8) at 0° C. and then, extracted with CH$_2$Cl$_2$ (2×15 ml). The combined organic extracts were dried (sodium sulphate), and concentrated in vacuo to afford 45 (75 mg, 87%) as a white solid that was used in subsequent reactions with no further purification.

Rf: 0.23 (ethyl acetate:methanol 5:1).

$^1$H NMR (300 MHz, CDCl$_3$): δ 6.43 (s, 1H), 5.94 (d, J=1.2 Hz, 1H), 5.87 (d, J=1.2 Hz, 1H), 4.10 (d, J=2.1 Hz, 1H), 3.98 (d, J=2.4 Hz, 1H), 3.91 (bs, 1H), 3.69 (s, 3H), 3.34-3.25 (m, 2H), 3.05 (dd, J$_1$=1.8 Hz, J$_2$=8.1 Hz, 1H), 2.80-2.73 (m, 3H), 2.46 (d, J=18 Hz, 1H), 2.30 (s, 3H), 2.28 (s, 3H), 2.20 (s, 3H), 1.98 (s, 3H), 1.79 (dd, J$_1$=12.6 Hz, J$_2$=16.2 Hz, 1H);

$^{13}$C NMR (75 MHz, CDCl$_3$)): δ 168.7, 146.7, 144.4, 142.9, 140.4, 130.4, 128.9, 121.1, 120.8, 117.8, 116.8, 113.6, 111.5, 101.4, 67.6, 60.5, 59.8, 58.4, 56.6, 55.8, 55.3, 43.6, 41.8, 31.3, 25.6, 20.2, 15.6, 9.2.

ESI-MS m/z: Calcd. for C$_{28}$H$_{32}$N$_4$O$_6$: 520.58. Found (M+H)$^+$: 521.3.

Example 29

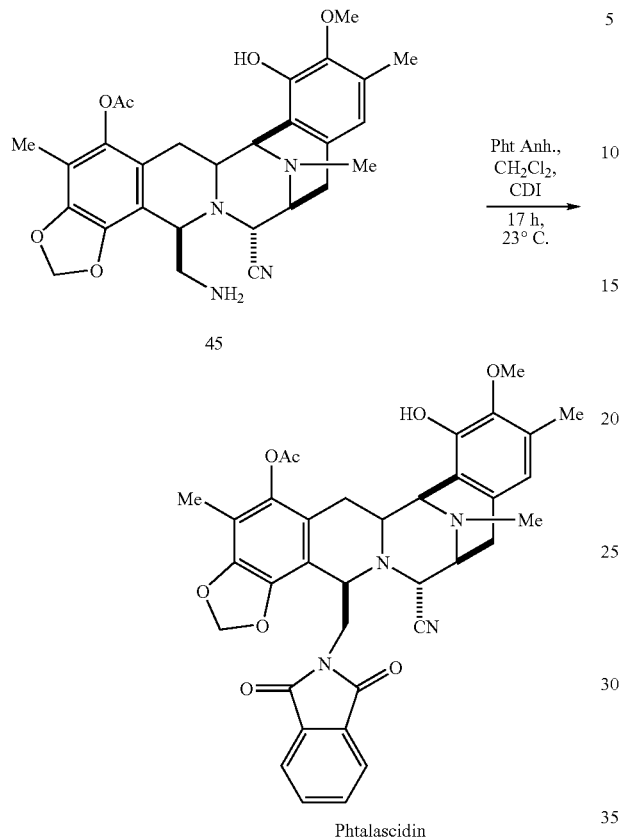

To a solution of 45 (10 mg, 0.02 ml) in $CH_2Cl_2$ (0.4 ml) was added phthalic anhydride (2.84 mg, 0.02 ml) and the reaction mixture was stirred for 2 h at 23° C. Then, carbonyldiimidazole (0.5 mg, 0.003 ml) was added and the mixture was stirred at 23° C. for 7 h. Then, carbonyldiimidazole (2.61 mg, 0.016 ml) was added and the reaction was stirred at 23° C. for an additional 17 h. The solution was diluted with $CH_2Cl_2$ (10 ml) and washed with 0.1 N HCl (5 ml). The organic layer was dried over sodium sulphate, filtered, and the solvent was eliminated under reduced pressure. The residue was purified by flash column chromatography (RP-18, $CH_3CN:H_2O$ 60:40) to afford phthalascidin (11.7 mg, 93%) as a white solid.

Rf: 0.37 ($CH_3CN:H_2O$ 7:3, RP-18).

$^1$H NMR (300 MHz, $CDCl_3$): δ 7.72-7.68 (m, 2H), 7.67-7.63 (m, 2H), 6.38 (s, 1H), 5.69 (d, J=1.2 Hz, 1H), 5.64 (d, J=1.2 Hz, 1H), 5.30 (bs, 1H), 4.25-4.21 (m, 2H), 4.02 (d, J=2.1 Hz, 1H), 3.64-3.62 (m, 5H), 3.33 (d, J=8.4 Hz, 1H), 3.21-3.16 (m, 1H), 3.02 (dd, $J_1$=8.1 Hz, $J_2$=18 Hz, 1H), 2.76 (dd, $J_1$=1.8 Hz, $J_2$=15.6 Hz, 1H), 2.63 (d, J=17.7 Hz, 1H), 2.29 (s, 3H), 2.28 (s, 3H), 2.21 (s, 3H), 2.0 (s, 3H), 1.73 (dd, $J_1$=12.0 Hz, $J_2$=15.3 Hz, 1H));

$^{13}$C NMR (75 MHz, $CDCl_3$)): δ 168.5, 167.6, 146.2, 144.2, 142.5, 141.0, 140.5, 133.4, 131.8, 130.7, 128.2, 120.9, 120.8, 117.9, 116.4, 113.6, 101.1, 60.4, 60.0, 57.0, 56.3, 55.6, 55.4, 41.6, 41.5, 26.5, 25.2, 20.2, 15.7, 9.4.

ESI-MS m/z: Calcd. for $C_{36}H_{34}N_4O_8$: 650. Found $(M+H)^+$: 651.2.

Example 30

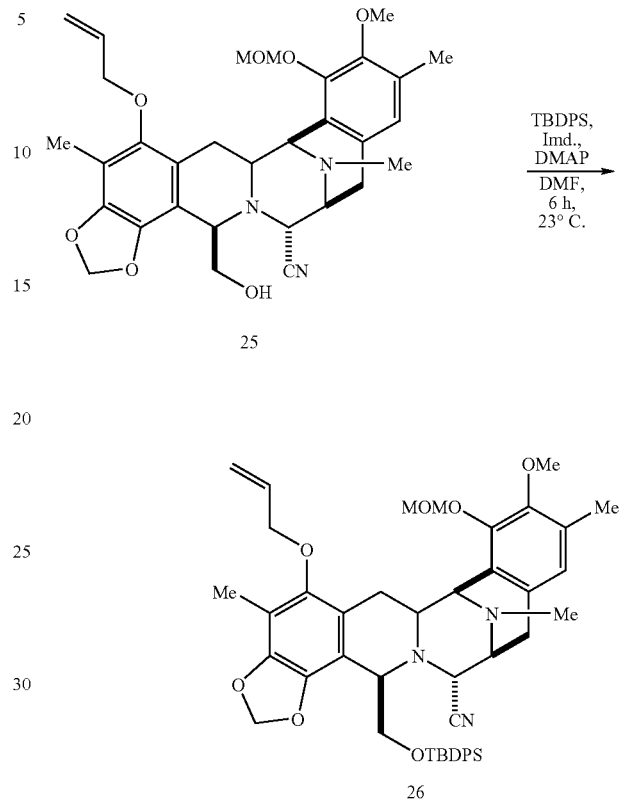

To a solution of 25 (18 mg, 0.032 ml) in DMF (0.05 ml), cat. DMAP (0.5 mg, 0.004 ml), imidazole (5 mg, 0.08 ml) and tert-Butyldiphenylsilyl chloride (12.5 ml, 0.048 ml) were added at 0° C. and the reaction mixture was stirred for 6 h at 23° C. Water (10 ml) was added at 0° C. and the aqueous phase was extracted with hexane:ethyl acetate 1:10 (2×10 ml). The organic layer was dried (sodium sulphate), filtered, and the solvent was removed under reduced pressure. The crude was purified by flash column chromatography ($SiO_2$, hexane:ethyl acetate 3:1) to afford 26 (27 mg, 88%) as a white solid.

Rf: 0.29 (hexane:ethyl acetate 3:1).

$^1$H NMR (300 MHz, $CDCl_3$) δ 7.61-7.58 (m, 2h), 7.42-7.28 (m, 8H), 6.71 (s, 1H), 6.19-6.02 (m, 1H), 5.78 (d, J=1.2 Hz, 1H), 5.64 (d, J=1.2 Hz, 1H), 5.40 (dd, $J_1$=1.2 Hz, $J_2$=17.1 Hz, 1H), 5.27 (dd, $J_1$=1.2 Hz, $J_2$=10.2 Hz, 1H), 5.13 (s, 2H), 4.45 (d, J=2.4 Hz, 1H), 4.24 (d, J=2.1 Hz, 1H), 4.17-4.06 (m, 3H), 3.75 (s, 3H), 3.64 (dd, $J_1$=2.4 Hz, $J_2$=9.9 Hz, 1H), 3.59 (s, 3H), 3.42-3.21 (m, 4H), 3.10 (dd, $J_1$=8.1 Hz, $J_2$=17.7 Hz, 1H), 2.70 (d, J=17.7 Hz, 1H), 2.33 (s, 3H), 2.26 (s, 3H), 2.11 (s, 3H), 2.08-1.89 (m, 1H), 0.87 (s, 9H);

$^{13}$C NMR (75 MHz, $CDCl_3$): δ 148.5, 148.3, 148.1, 144.0, 139.0, 135.6, 135.4, 133.8, 133.1, 132.6, 130.5, 130.3, 129.6, 129.4, 127.5, 127.4, 125.1, 124.3, 121.6, 118.5, 117.5, 112.9, 111.7, 100.8, 99.2, 74.0, 67.7, 61.5, 59.6, 59.0, 57.7, 57.1, 55.4, 41.6, 29.6, 26.6, 25.5, 18.8, 15.8, 9.2.

ESI-MS m/z: Calcd. for $C_{47}H_{55}N_3O_7Si$: 801.3. Found $(M+H)^+$: 802.3.

Example 31

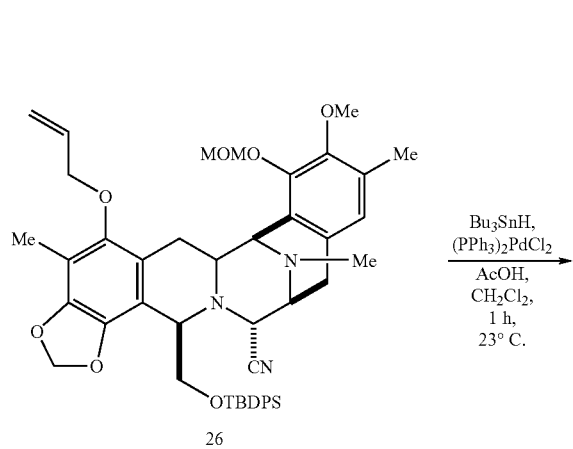

To a solution of 26 (7 mg, 0.0087 ml) in CH$_2$Cl$_2$ (0.15 ml), acetic acid (2.5 ml, 0.044 ml), (PPh$_3$)$_2$PdCl$_2$ (0.5 mg, 6.96× 10$^{-4}$ ml) and Bu$_3$SnH (3.5 ml, 0.013 ml) were added at 23° C. The reaction mixture was stirred at that temperature for 1 h. The solution was diluted with a mixture of hexane:ethyl acetate 5:1 (0.5 ml) and poured into a pad of flash column (SiO$_2$, gradient 5:1 to 1:1 hexane:ethyl acetate) affording ET-11 (5 mg, 75%) as a white solid.

Rf: 0.36 (hexane:ethyl acetate 1:5, silica).

$^1$H NMR (300 MHz, CDCl$_3$): δ 7.56 (m, 2H), 7.41-7.25 (m, 8H), 6.67 (s, 1H), 5.72 (d, J=1.0 Hz, 1H), 5.58 (d, J=1.0 Hz, 1H), 5.51 (s, 1H), 5.38 (d, J=5.75 Hz, 1H), 5.16 (d, J=5.7 Hz, 1H), 4.57 (d, J=2.9 Hz, 1H), 4.21 (m, 1H), 4.09 (m, 1H), 3.72 (s, 3H), 3.71 (s, 3H), 3.68 (dd, J$_1$=2.1 Hz, J$_2$=10.4 Hz, 1H), 3.38-3.26 (m, 3H), 3.11 (dd, J$_1$=2.5 Hz, J$_2$=15.7 Hz, 1H), 3.01 (dd, J$_1$=8.9 Hz, J$_2$=17.9 Hz, 1H), 2.70 (d, J=17.9 Hz, 1H), 2.31 (s, 3H), 2.25 (s, 3H), 2.06 (s, 3H), 1.89 (dd, J$_1$=12.1 Hz, J$_2$=15.7 Hz, 1H), 0.9 (s, 9H).);

$^{13}$C NMR (75 MHz, CDCl$_3$): δ 149.0, 147.4, 145.3, 144.3, 136.3, 135.7, 135.4, 133.2, 130.9, 130.5, 129.6, 129.5, 127.5, 125.0, 118.6, 112.5, 112.1, 105.7, 100.5, 99.8, 68.5, 61.5, 59.7, 58.8, 57.7, 56.9, 56.5, 55.4, 41.7, 26.6, 26.2, 25.5, 18.9, 15.8, 14.2, 8.7.

ESI-MS m/z: Calcd. for C$_{44}$H$_{51}$N$_3$O$_7$Si: 761. Found (M+H)$^+$: 762.

Example 32

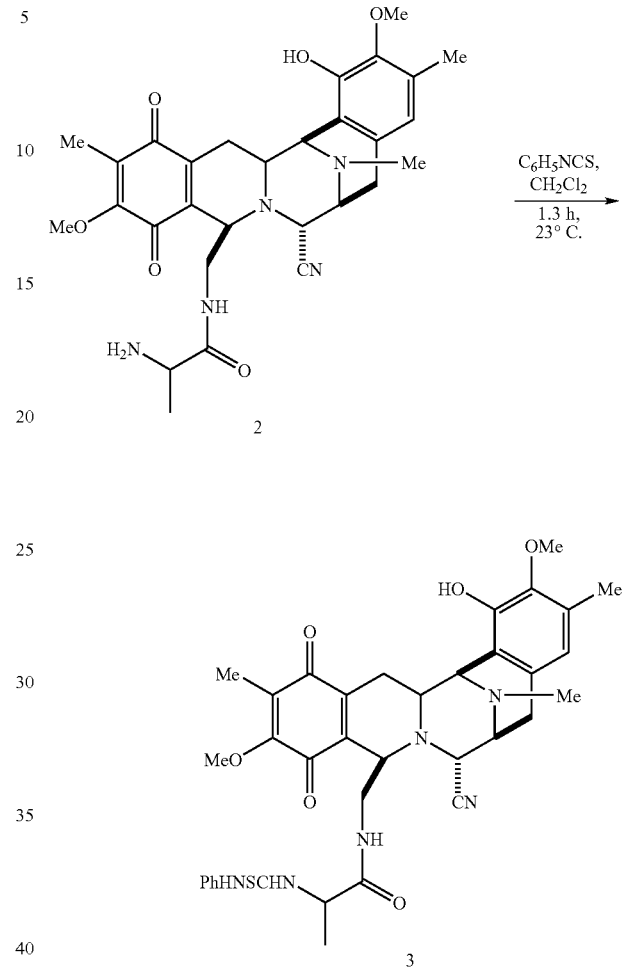

A solution of 2 (3.0 g, 5.46 ml) and phenyl isothiocyanate (3.92 mL, 32.76 ml) in CH$_2$Cl$_2$ (27 ml) was stirred at 23° C. for 1.5 h. The reaction mixture was partitioned between CH$_2$Cl$_2$ (10 ml) and H$_2$O (5 ml). The organic layer was dried over sodium sulphate, filtered and concentrated. The residue was purified by flash column chromatography (SiO$_2$, gradient Hex to 2:3 hexane:ethyl acetate) to give 3 (3.29 g, 88%) as a yellow solid.

Rf: 0.27 (ACN:H$_2$O 3:2, RP-C18);

$^1$H NMR (300 MHz, CDCl$_3$): δ 7.77 (bs, 1H), 7.42-7.11 (m, 5H), 6.65 (d, 1H), 6.29 (s, 1H), 5.6-5.5 (m, 1H), 4.19-4.14 (m, 2H), 4.08 (d, 1H), 3.92 (s, 3H), 3.87-3.65 (m, 6H), 3.77 (s, 3H), 3.37-2.98 (m, 8H), 2.50 (d, 1H), 2.31 (s, 3H), 2.20 (s, 3H), 1.96 (d, 1H), 1.87 (s, 3H), 1.81-1.75 (m, 1H), 0.96 (d, 3H);

$^{13}$C NMR (75 MHz, CDCl$_3$): δ 185.7, 180.9, 178.9, 172.0, 155.7, 147.1, 143.2, 142.4, 142.0, 135.1, 130.5, 129.9, 129.3, 128.5, 126.9, 124.4, 120.2, 117.4, 116.3, 77.1, 60.9, 58.6, 56.2, 55.8, 55.0, 54.6, 53.5, 41.7, 40.3, 25.1, 24.5, 18.4, 15.8, 8.7

ESI-MS m/z: Calcd. for C$_{36}$H$_{40}$N$_6$O$_6$S: 684.8. Found (M+H)$^+$: 685.2.

Example 33

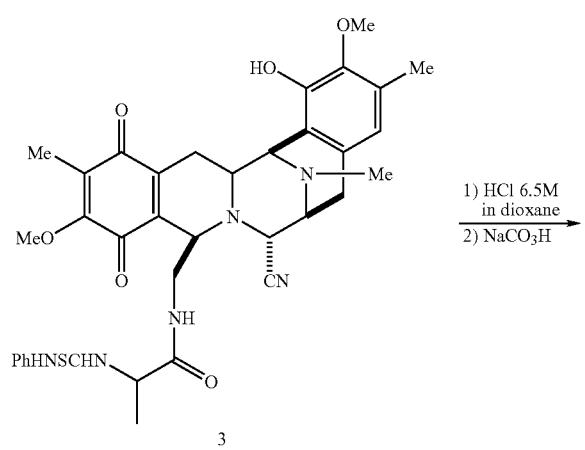

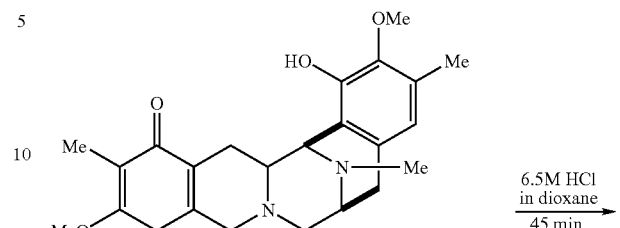

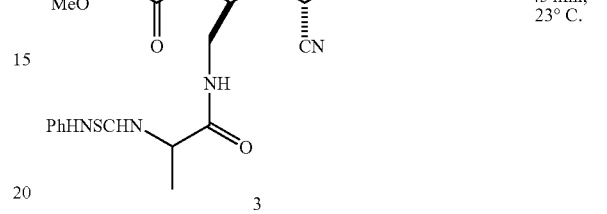

Example 34

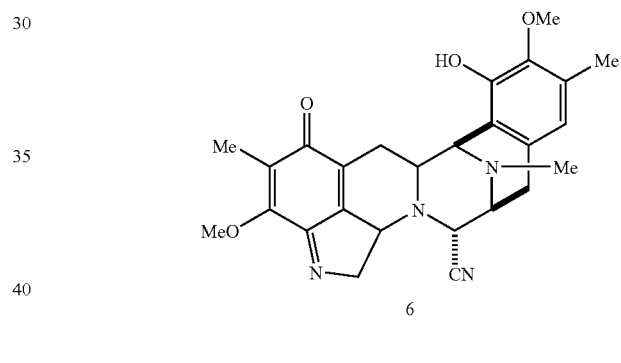

A solution of 3 (0.143 g, 0.208 ml) in 6.5 M HCl/dioxane (150 ml) was stirred at 23° C. for 6 h. Then, toluene (3 ml) was added to this reaction and the organic layer was decanted. The residue was partitioned between saturated aqueous sodium bicarbonate (3 ml) and CHCl$_3$ (3×3 ml) The organic layers were dried and concentrated to afford title compound as a mixture of 4 and 6 (4:6 90:10) which slowly cyclizes to 6 on standing.

Rf: 0.4 (ethyl acetate:methanol 5:1, silica);

$^1$H NMR (300 MHz, CDCl$_3$): δ 6.45 (s, 1H), 4.16 (m, 1H), 4.02 (d, 1H), 3.96 (s, 3H), 3.79 (m, 2h), 3.75 (s, 3H), 3.35 (m, 1H), 3.20-3.00 (m, 3H), 2.87 (d, 1H), 2.75 (d, 1H), 2.43 (d, 1H), 2.34 (s, 3H), 2.30 (s, 3H), 1.93 (s, 3H), 1.72-1.5 (m, 3H);

ESI-MS m/z: Calcd. for C$_{26}$H$_{30}$N$_4$O$_5$: 478.5. Found (M+H)$^+$: 479.2.

A solution of 3 (0.143 g, 0.208 ml) in 6.5M HCl/dioxane (150 ml) was stirred at 23° C. for 1 h. Evaporation of the solvent gave a residue which was purified by flash column chromatography (ethyl acetate/methanol/triethylamine 100:25:0.1) to give 6 (80 mg, 83%) as a yellow solid.

Rf: 0.26 (ACN:H$_2$O 3:2, RP-C18);

$^1$H NMR (500 MHz, CDCl$_3$): δ 6.46 (s, 1H), 5.9 (bs, 1H), 4.67 (dd, 18.3 Hz, J=7.8 Hz, 1H), 4.24 (d, 1H), 4.16 (s, 3H), 3.93 (d, J=2.7 Hz, 1H), 3.8 (m, 2h), 3.77 (s, 3H), 3.45 (m, 2 h), 3.08 (dd, J=17.9 Hz, J=3.6 Hz, 1H), 2.78 (m, 1H), 2.55 (d, 1H), 2.3 (m, 1H), 2.3 (s, 3H), 2.28 (s, 3H), 1.90 (s, 3H);

$^{13}$C NMR (75 MHz, CDCl$_3$): δ 186.2, 162.1, 154.9, 146.9, 145.3, 143.0, 130.1, 129.4, 128.1, 125.0, 121.4, 116.4, 116.2, 66.6, 60.7, 60.7, 60.1, 59.6, 58.8, 55.6, 54.9, 41.9, 25.3, 24.7, 15.7, 8.9.

ESI-MS m/z: Calcd. for C$_{26}$H$_{28}$N$_4$O$_4$: 460.5. Found (M+H)$^+$: 461.1.

Example 35

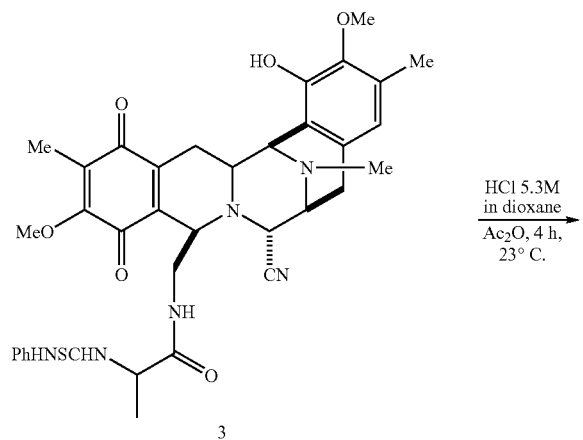

3

HCl 5.3M in dioxane
Ac₂O, 4 h,
23° C.

Example 36

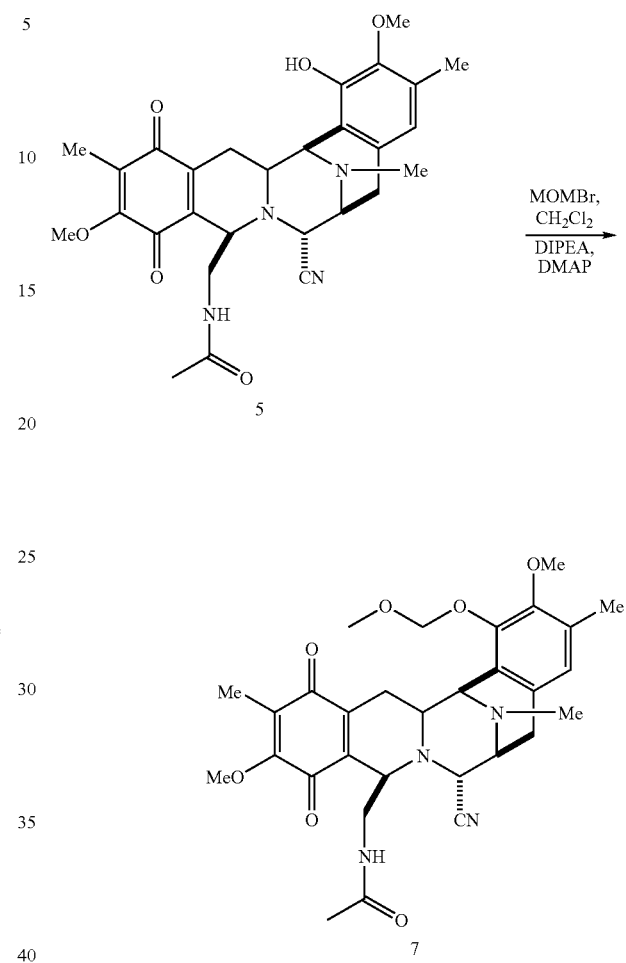

To a solution of 3 (2.38 g, 3.47 ml) in dioxane (5 ml) 5.3 M HCl in dioxane (34 ml) was added and the reaction was stirred at 23° C. for 45 minutes. Then Ac₂O (51 ml, 539.5 ml) was added and the mixture was stirred for 4 h. The reaction was cooled at 0° C. and partitioned between aqueous saturated Na₂CO₃ (300 ml) and ethyl acetate (300 ml) at this temperature. The organic phase was dried over sodium sulphate, filtered and concentrated. The residue was purified by flash column chromatography (SiO₂, gradient CH₂Cl₂ to CH₂Cl₂: ethyl acetate 1:2) to give 5 (1.75 g, 97%) as a yellow solid.

Rf: 0.53 (ACN:H₂O 3:2, RP-C18);

$^1$H NMR (300 MHz, CDCl$_3$): δ 6.51 (s, 1H), 5.98 (bs, 1H), 4.84 (dd, 1H), 4.17 (d, 1H), 4.00 (d, 1H), 3.99 (s, 3H), 3.85 (bs, 1H), 3.81 (m, 1H), 3.74 (s, 3H), 3.70 (d, 1H), 3.23 (m, 1H), 3.11 (dd, 1H), 3.09 (m, 1H), 2.93 (m, 2H), 2.44 (d, 1H), 3.67 (s, 3H), 2.25 (s, 3H), 1.70 (s, 3H), 1.60-1.50 (m, 2H), 1.29 (s, 3H);

$^{13}$C NMR (75 MHz, CDCl$_3$): δ 185.9, 180.8, 169.9, 160.2, 156.2, 147.0, 143.1, 140.4, 136.1, 130.6, 129.6, 127.9, 120.4, 117.2, 61.0, 60.7, 58.6, 56.1, 55.7, 55.1, 54.3, 41.8, 41.1, 25.7, 23.9, 22.2, 15.7, 8.7.

ESI-MS m/z: Calcd. for $C_{28}H_{32}N_4O_6$: 520.6. Found (M+H)$^+$: 521.1.

To a solution of 5 (1.75 g, 3.36 ml) in CH₂Cl₂ (17 ml) diisopropylethylamine (11.71 ml, 67.23 ml), DMAP (20 mg, 0.17 ml) and bromomethyl methyl ether (4.11 ml, 50.42 ml) were added at 0° C. After 6 h at 23° C. the reaction was partitioned between CH₂Cl₂ (50 ml) and aqueous saturated sodium bicarbonate (25 ml). The organic layer was dried over sodium sulphate and the solvent was eliminated under reduced pressure. The crude was purified by flash column chromatography (RP-18, CH₃CN/H₂O 1/1) to give 7 (1.32 g, 70%) as a yellow solid.

Rf: 0.34 (ACN:H₂O 2:3, RP-C 18);

$^1$H NMR (300 MHz, CDCl$_3$): δ 6.74 (s, 1H), 5.14 (s, 2H), 4.82 (m, 1H), 4.22 (d, 1H), 4.00 (s, 3H), 4.0 (m, 1H), 3.83 (m, 2H), 3.7 (s, 3H), 3.58 (s, 3H), 3.4 (m, 1H), 3.2-2.95 (m, 6H), 2.43 (d, 1H), 2.37 (s, 3H), 2.22 (s, 3H), 1.89 (s, 3H), 1.5-1.4 (m, 2H), 1.31 (s, 3H);

$^{13}$C NMR (75 MHz, CDCl$_3$): δ 185.9, 180.7, 169.6, 156.2, 148.9, 148.5, 140.3, 136.2, 131.3, 130.1, 127.7, 124.6, 123.7, 117.3, 99.5, 99.2, 60.9, 59.7, 58.8, 57.7, 56.4, 55.7, 55.0, 54.2, 51.0, 41.6, 41.0, 40.5, 25.5, 23.9, 22.3, 19.3, 15.6, 14.6, 8.6.

ESI-MS m/z: Calcd. for $C_{30}H_{36}N_4O_7$: 564.6. Found (M+H)$^+$: 565.3.

Example 37

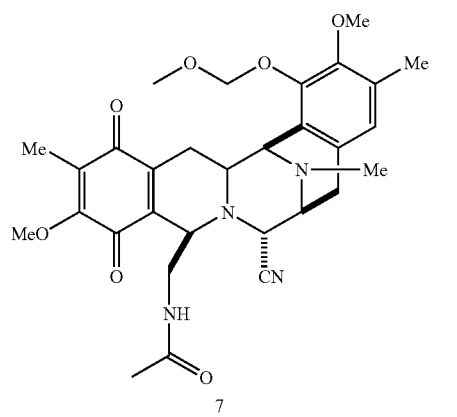

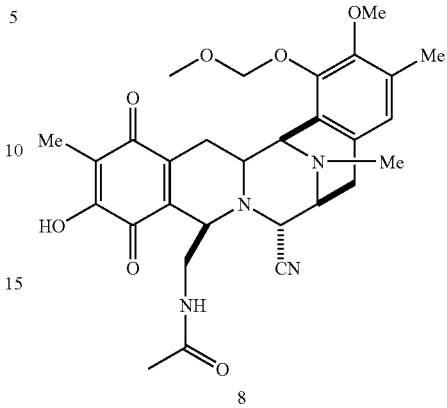

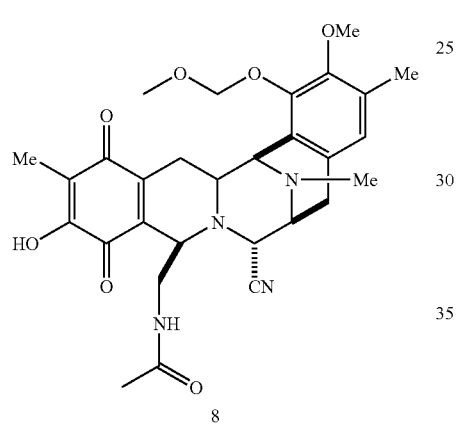

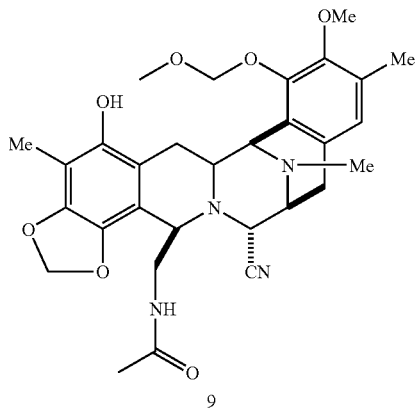

Example 38

To a solution of 7 (0.37 g, 0.65 ml) in methanol (74 ml) at 0° C. was added 1M sodium hydroxide (130 ml). The reaction was stirred for 15 minutes and then, quenched at 0° C. with 6M HCl to pH=5. The mixture was extracted with ethyl acetate (3×50 ml) and the combined organic layers were dried over sodium sulphate and concentrated in vacuo. The residue was purified by flash column chromatography (RP-C18 CH$_3$CN:H$_2$O 1/:1) to afford 8 (232 mg, 65%) as a yellow oil.

Rf: 0.5 (ACN:H$_2$O 3:2, RP-C18);

$^1$H NMR (300 MHz, CDCl$_3$): δ 6.75 (s, 1H), 5.15 (s, 2H), 4.86 (m, 1H), 4.26 (d, 1H),), 4.01 (d, 1H), 3.88-3.81 (m, 2H), 3.70 (s, 3H), 3.58 (s, 3H), 3.39 (m, 1H), 3.27-3.21 (m, 1H), 3.18-3.08 (m, 2H), 3.03-2.97 (m, 1H), 2.47 (d, 1H), 2.37 (s, 3H), 2.22 (s, 3H), 1.90 (s, 3H), 1.57-1.46 (m, 2h), 1.33 (s, 3H);

$^{13}$C NMR (75 MHz, CDCl$_3$): δ 185.3, 180.6, 175.9, 170.1, 151.5, 148.9, 148.6, 143.3, 133.7, 131.5, 129.9, 124.7, 123.5, 117.1, 117.0, 99.2, 59.8, 58.7, 57.8, 56.3, 55.3, 54.9, 54.3, 41.5, 40.7, 29.6, 25.5, 24.4, 22.2, 20.7, 15.7, 8.0.

ESI-MS m/z: Calcd. for C$_{29}$H$_{34}$N$_4$O$_7$: 550.6. Found (M+H)$^+$: 551.2.

To a degassed solution of compound 8 (240 mg, 0.435 ml) in DMF (30 ml) 10% Pd/C (48 mg) was added and the reaction was stirred under H$_2$ (atmospheric pressure.) for 1 h. The reaction was filtered through a pad of celite under Argon to a Schlenk tube, as a colourless solution, containing anhydrous Cs$_2$CO$_3$ (240 mg, 0.739 ml). Then, bromochloromethane (0.566 ml, 8.71 ml) was added. The tube was sealed and stirred at 90° C. for 3 h. The reaction was cooled and filtrated through celite and washed with CH$_2$Cl$_2$. The organic layer was concentrated and dried (sodium sulphate) to afford 9 as a brown oil that was used in the next step with no further purification.

Rf: 0.36 (SiO$_2$, hexane:ethyl acetate 1:5)

$^1$H NMR (300 MHz, CDCl$_3$): δ 6.71 (s, 3H), 5.89 (d, 1H), 5.81 (d, 1H), 5.63 (bs, 1H), 5.33 (d, 1H), 5.17 (d, 1H), 4.97 (m, 1H), 4.20 (d, 1H), 4.09 (m, 1H), 3.99 (m, 1H), 3.68 (m, 1H), 3.65 (s, 6H), 3.59-3.47 (m, 4H), 3.37-3.27 (m, 2H), 3.14-2.97 (m, 2H), 2.62 (d, 1H), 2.32 (s, 3H), 2.20 (s, 3H), 2.08 (s, 3H), 1.72 (m, 1H), 1.36 (s, 3H);

$^{13}$C NMR (75 MHz, CDCl$_3$): δ 169.8, 149.1, 147.4, 145.5, 136.2, 130.9, 130.8, 125.0, 122.9, 117.7, 112.6, 111.8, 106.4, 100.8, 99.8, 59.8, 58.9, 57.7, 56.6, 56.4, 55.5, 55.2, 41.6, 40.1, 29.6, 25.9, 25.0, 22.6, 15.6, 8.8.

ESI-MS m/z: Calcd. for C$_{30}$H$_{36}$SiN$_4$O$_7$: 564.6. Found (M+H)$^+$: 565.3.

Example 39

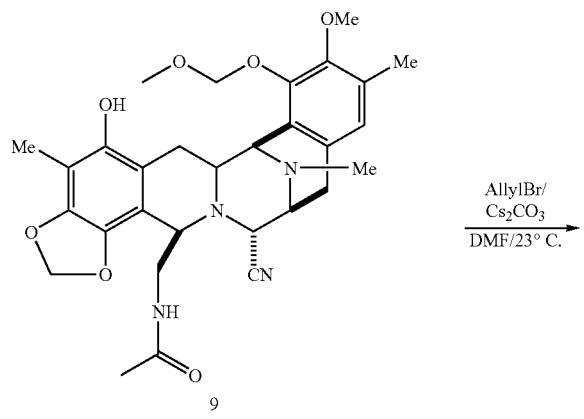

Example 40

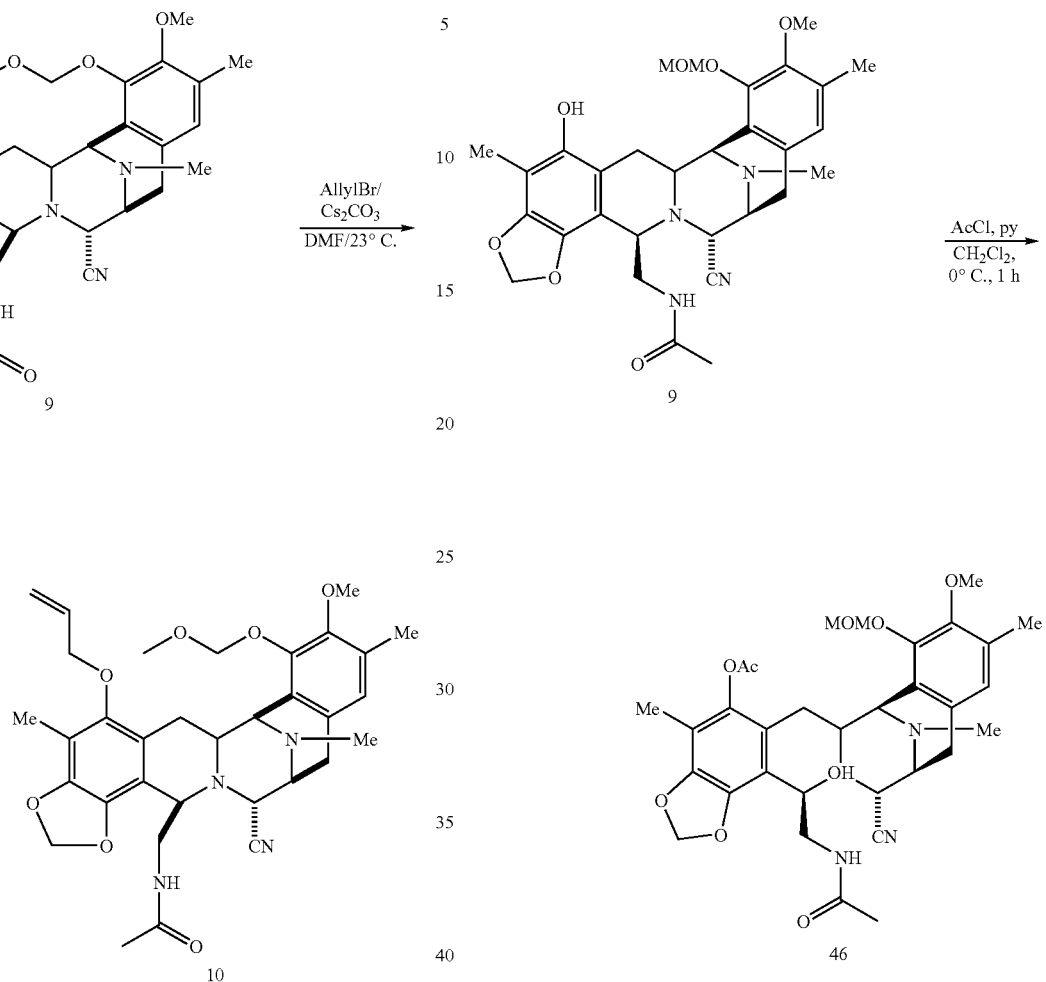

To a flask containing 9 (245 mg, 0.435 ml) in DMF, (4 ml), cesium carbonate (425 mg, 1.30 ml) and allyl bromide (376 ml, 4.35 ml) were added at 0° C. and the mixture was stirred at 23° C. for 1 h. The reaction was filtered though a pad of celite and partitioned between $CH_2Cl_2$ (25 ml) and $H_2O$ (10 ml). The organic phase was dried (sodium sulphate) and concentrated at reduced pressure to afford a residue that was purified by flash column chromatography ($SiO_2$, $CHCl_3$:ethyl acetate 1:2) to give 10 as a yellow oil. (113 mg, 43%).

Rf: 0.36 (hexane:ethyl acetate 1:5)

$^1$H NMR (300 MHz, $CDCl_3$): δ 6.74 (s, 1H), 6.3-6.0 (m, 1H), 5.94 (d, 1H), 5.87 (d, 1H), 5.43-5.36 (m, 2h), 5.22 (s, 2H), 5.00 (m, 1H), 4.22 (m, 1H), 4.17-4.01 (m, 1H), 3.98 (m, 2 h), 3.71-3.67 (m, 1H), 3.69 (s, 3H), 3.62-3.51 (m, 3H), 3.58 (s, 3H), 3.39-3.37 (m, 1H), 3.31-3.26 (m, 3H), 3.09 (dd, 1H), 2.56 (d, 1H), 2.36 (s, 3H), 2.21 (s, 3H), 2.11 (s, 3H), 2.24-2.10 (m, 1H), 1.82-1.73 (m, 1H), 1.24 (bs, 3H)

$^{13}$C NMR (75 MHz, $CDCl_3$): δ 169.4, 148.8, 148.3, 139.1, 133.7, 130.9, 130.3, 125.2, 120.2, 117.7, 113.1, 112.6, 101.3, 99.3, 74.1, 59.7, 59.3, 57.8, 57.0, 56.1, 56.1, 55.2, 41.6, 41.0, 40.9, 29.7, 26.3, 22.5, 15.6, 9.3

ESI-MS m/z: Calcd. for $C_{33}H_{40}N_4O_7$: 604.7. Found (M+H)$^+$: 605.3.

To a solution of 9 (22 mg, 0.039 ml) in $CH_2Cl_2$ (0.2 ml), acetyl chloride (2.79 ml, 0.039 ml) and pyridine (3.2 ml, 0.039 ml) were added at 0° C. The reaction mixture was stirred for 1 h and then, the solution was diluted with $CH_2Cl_2$ (10 ml) and washed with 0.1 N HCl (5 ml). The organic layer was dried over sodium sulphate, filtered, and the solvent was eliminated under reduced pressure to afford 46 (22 mg, 93%) as a white solid.

Rf: 0.4 (hexane:ethyl acetate 1:5).

$^1$H NMR (300 MHz, $CDCl_3$). δ 6.74 (s, 1H) 5.97 (d, J=0.9 Hz, 1H) 5.91 (d, J=0.9 Hz, 1H), 5.12 (d, J=5.7 Hz, 2H), 5.04 (d, J=5.7 Hz, 1H), 4.90 (t, J=6 Hz, 1H), 4.17 (d, J=2.7 Hz, 1H), 4.05 (d, J=2.7 Hz, 1H), 4.01 (bs, 1H), 3.71 (s, 3H), 3.57 (s, 3H), 3.50-3.44 (m, 2 h), 3.38-3.36 (m, 1H), 3.30-3.26 (m, 1H), 3.00 (dd, $J_1$=7.8 Hz, $J_2$=18.0 Hz, 1H), 2.79 (d, J=12.9 Hz, 1H), 2.60 (d, J=18.0 Hz, 1H), 2.35 (s, 3H), 2.32 (s, 3H), 2.21 (s, 3H), 2.00 (s, 3H), 1.68 (dd, $J_1$=11.7 Hz, $J_2$=15.6 Hz, 1H).

ESI-MS m/z: Calcd. for $C_{32}H_{38}N_4O_8$: 606.67. Found (M+H)$^+$: 607.3.

Example 41

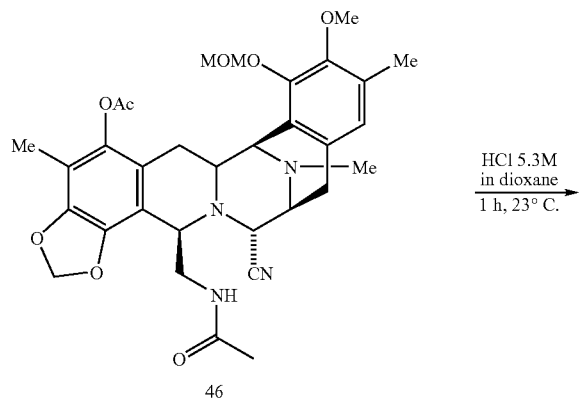

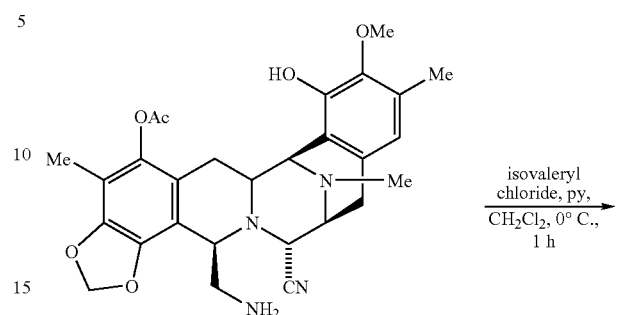

Example 42

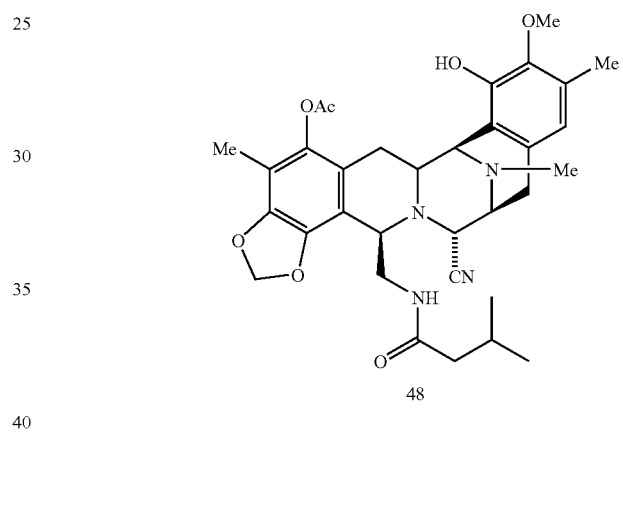

To a solution of 46 (8 mg, 0.013 ml) in dioxane (0.1 ml), 5.3N HCl/dioxane (0.5 ml) was added and the reaction was stirred at 23° C. for 1 h. Then, the solution was diluted with $CH_2Cl_2$ (5 ml) and washed with 0.1 N HCl (3 ml). The organic layer was dried over sodium sulphate, filtered, and the solvent was eliminated under reduced pressure to afford 47 (5 mg, 70%) as a white solid.

Rf: 0.4 (hexane:ethyl acetate 1:5).

$^1$H NMR (300 MHz, CDCl$_3$). δ 6.51 (s, 1H), 5.97 (d, J=1.2 Hz, 1H), 5.91 (d, J=1.2 Hz, 1H), 4.97 (bs, 1H), 4.11 (bs, 1H), 4.04-4.02 (m, 2H), 3.75 (s, 3H), ), 3.65 (d, J=2.1 Hz, 2h), 3.56-3.30 (m, 2h), 3.04 (dd, J$_1$=7.5 Hz, J$_2$=18 Hz, 1H), 2.80 (d, J=14.4 Hz 1H), 2.59 (d, J=18.3 Hz, 1H), 2.33 (s, 3H), 2.24 (s, 3H), 2.00 (s, 3H), 1.76 (dd, J$_1$=12.0 Hz, J$_2$=15.9 Hz, 1H), 1.33 (s, 3H), 1.25 (s, 3H).

ESI-MS m/z: Calcd. for $C_{30}H_{34}N_4O_7$: 562.61. Found (M+H)$^+$: 563.3.

To a solution of 45 (10 mg, 0.0192 ml) in $CH_2Cl_2$ (0.3 ml), isovaleryl chloride (2.34 ml, 0.0192 ml) and pyridine (1.55 ml, 0.0192 ml) were added at 0° C. The reaction mixture was stirred for 1 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography (SiO$_2$, Hex:ethyl acetate 1:2) to afford 48 (11 mg, 95%) as a white solid.

Rf: 0.12 (Hex:ethyl acetate 1:2).

$^1$H NMR (300 MHz, CDCl$_3$): δ 6.50 (s, 1H), 5.98 (d, J=1.5 Hz, 1H), 5.91 (d, J=1.5 Hz, 1H), 5.75 (s, 1H), 5.02 (t, J=5.4 Hz, 1H), 4.10 (d, J=1.5 Hz, 1H), 4.06 (d, J=2.7 Hz, 1H), 4.02 (d, J=2.7 Hz, 1H), 3.77 (s, 3H), 3.76-3.71 (m, 1H), 3.86-3.28 (m, 3H), 3.04 (dd, J$_1$=8.1 Hz, J$_2$=18.3 Hz, 1H), 2.78 (d, J=15.9 Hz, 1H), 2.55 (d, J=18 Hz, 1H), 2.32 (s, 6H), 2.26 (s, 3H), 1.98 (s, 3H), 1.84-1.68 (m, 2h), 1.36 (d, J=7.2 Hz, 2h), 0.69 (d, J=6.6 Hz, 3H), 0.62 (d, J=6.6 Hz, 3H).

ESI-MS m/z: Calcd. for $C_{33}H_{40}N_4O_7$: 604.69. Found (M+H)$^+$: 605.3.

Example 43

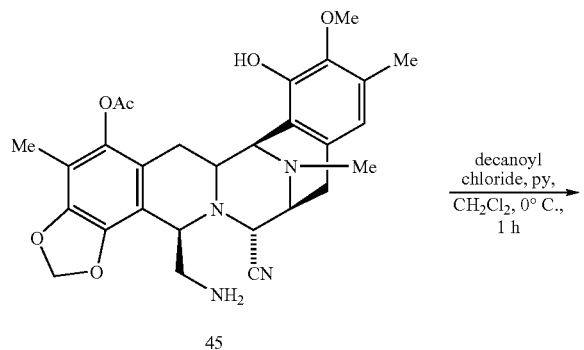

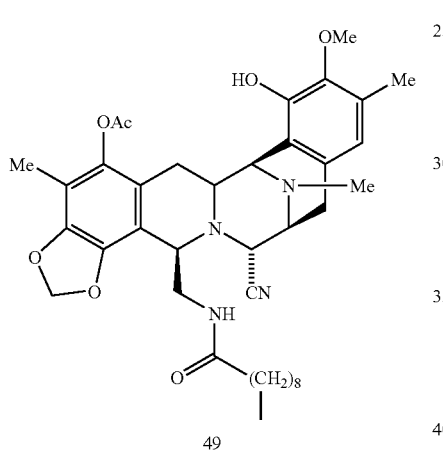

To a solution of 45 (10 mg, 0.0192 ml) in CH$_2$Cl$_2$ (0.3 ml), isovaleryl chloride (3.98 ml, 0.0192 ml) and pyridine (1.55 ml, 0.0192 ml) were added at 0° C. The reaction mixture was stirred for 1 h and then, the solution was diluted with CH$_2$Cl$_2$ (5 ml) and washed with 0.1 N HCl (3 ml). The organic layer was dried over sodium sulphate, filtered, and the solvent was eliminated under reduced pressure. The residue was purified by flash column chromatography (SiO$_2$, Hex:ethyl acetate 1:2) to afford 49 (12.4 mg, 96%) as a white solid.

Rf: 0.7 (ethyl acetate:methanol 10:1).

$^1$H NMR (300 MHz, CDCl$_3$): δ 6.50 (s, 1H), 5.98 (d, J=1.5 Hz, 1H), 5.91 (d, J=1.5 Hz, 1H), 5.73 (s, 1H), 5.08 (t, J=5.4 Hz, 1H), 4.10 (d, J=1.5 Hz, 1H), 4.05 (m, 1H), 4.01 (m, 1H), 3.76 (s, 3H), 3.65-3.61 (m, 1H), 3.40-3.27 (m, 3H), 3.03 (dd, J$_1$=8.1 Hz J$_2$=18.6 Hz, 1H), 2.78 (d, J=13.2 Hz, 1H), 2.57 (d, J=18.3 Hz, 1H), 2.32 (s, 3H), 2.31 (s, 3H), 2.25 (s, 3H), 1.99 (s, 3H), 1.79 (dd, J$_1$=12.0 Hz, J$_2$=16.5 Hz, 1H), 1.73-1.42 (m, 4H), 1.33-1.18 (m, 10H), 1.03 (m, 2H), 0.87 (t, J=6.6 Hz, 3H).

ESI-MS m/z: Calcd. for C$_{38}$H$_{50}$N$_4$O$_7$: 674.83. Found (M+H)$^+$: 675.5.

Example 44

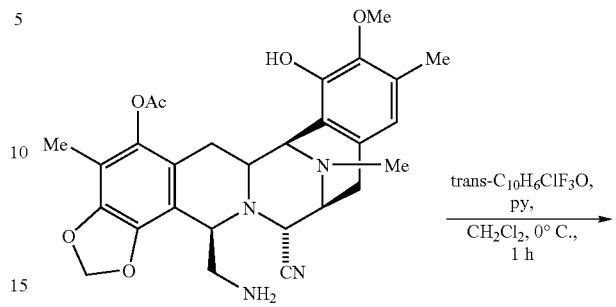

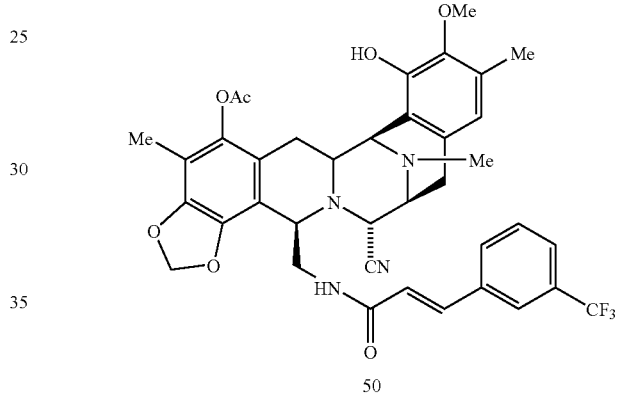

To a solution of 45 (14.5 mg, 0.0278 ml) in CH$_2$Cl$_2$ (0.3 ml), trans-3-trifluoromethyl cinnamoyl chloride (4.76 ml, 0.0278 ml) and pyridine (2.25 ml, 0.0278 ml) were added at 0° C. The reaction mixture was stirred for 1b and then, the solution was diluted with CH$_2$Cl$_2$ (5 ml) and washed with 0.1 N HCl (3 ml). The organic layer was dried over sodium sulphate, filtered, and the solvent was eliminated under reduced pressure. The residue was purified by flash column chromatography (SiO$_2$, Hex:ethyl acetate 1:1) to afford 50 (18.7 mg, 94%) as a white solid.

Rf: 0.64 (ethyl acetate:methanol 5:1).

$^1$H NMR (300 MHz, CH$_3$OD). δ 7.74-7.55 (m, 4H), 7.23 (d, J=16.0 Hz, 1H), 6.34 (s, 1H), 6.12 (d, J=16.0 Hz, 1H), 6.07 (d, J=0.9 Hz, 1H), 5.96 (d, J=0.9 Hz, 1H), 4.39 (d, J=2.4 Hz, 1H), 4.07-4.05 (m, 1H), 3.81 (bs, 1H), 3.46-3.51 (m, 3H), 3.42 (s, 3H), 3.09 (br d, J=12.0 Hz, 1H), 2.94-2.85 (m, 2h), 2.74 (d, J=18.3 Hz, 1H), 2.38 (s, 3H), 2.23 (s, 3H), 2.02 (s, 3H), 1.80 (s, 3H), 1.84-1.75 (m, 1H).

$^{13}$C NMR (75 MHz, CDCl$_3$)): δ 168.7, 165.3, 146.5, 144.7, 142.6, 140.6, 138.0, 135.9, 131.0, 130.9, 129.1, 128.6, 125.8, 125.7, 124.5, 124.4, 122.7, 121.2, 117.8, 116.5, 113.0, 112.0, 101.7, 60.4, 59.1, 56.5, 56.4, 55.6, 55.3, 41.8, 40.3, 26.6, 25.1, 20.3, 15.4, 9.3.

ESI-MS m/z: Calcd. for C$_{38}$H$_{37}$F$_3$N$_4$O$_7$: 718.72. Found (M+H)$^+$: 719.3.

Example 45

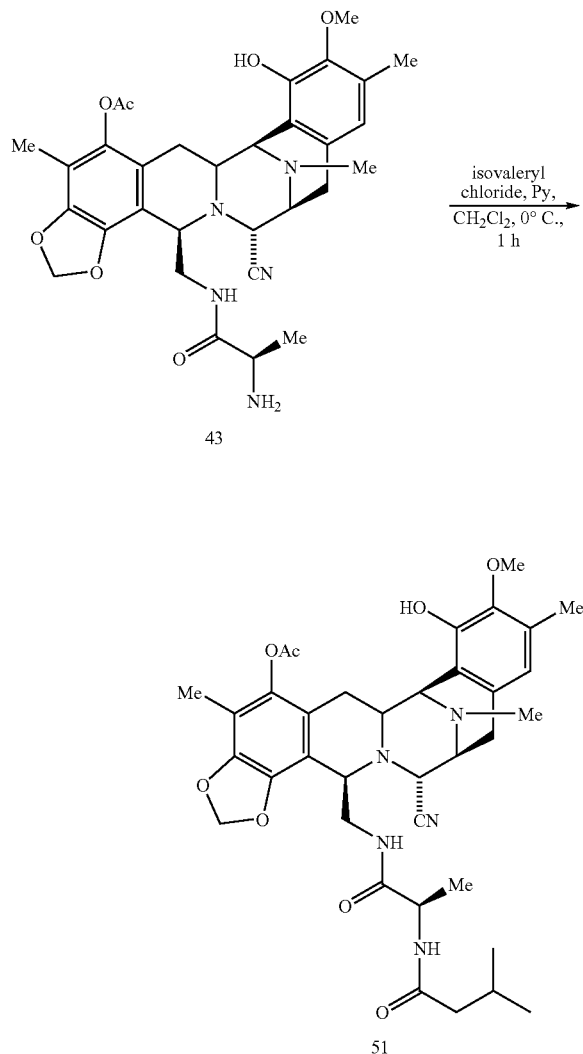

To a solution of 43 (33 mg, 0.0557 ml) in CH$_2$Cl$_2$ (0.4 ml), isovaleryl chloride (6.79 ml, 0.0557 ml) and pyridine (4.5 ml, 0.0557 ml) were added at 0° C. The reaction mixture was stirred for 1 h and then, the solution was diluted with CH$_2$Cl$_2$ (5 ml) and washed with 0.1 N HCl (3 ml). The organic layer was dried over sodium sulphate, filtered, and the solvent was eliminated under reduced pressure. The residue was purified by flash column chromatography (SiO$_2$, Hex:ethyl acetate 1:2) to afford 51 (34 mg, 91%) as a white solid.

Rf: 0.09 (Hex:ethyl acetate 1:2).

$^1$H NMR (300 MHz, CDCl$_3$): δ 6.46 (s, 1H), 6.10 (bs, 1H), 5.99 (d, J=0.9 Hz, 1H), 5.90 (d, J=0.9 Hz, 1H), 5.30 (t, J=6.0 Hz, 1H), 4.10-4.05 (m, 3H), 3.81 (bs, 1H), 3.74 (s, 3H), 3.54 (bs, 1H), 3.38-3.36 (m, 1H), 3.29-3.21 (m, 1H), 3.00 (dd, J$_1$=8.0 Hz, J$_2$=18.0 Hz, 1H), 2.25 (s, 3H), 2.20 (s, 3H), 2.00 (s, 3H), 1.95-1.90 (m, 3H), 0.87 (d, J=6.6 Hz, 6H), 0.76 (d, J=6.0 Hz, 3H).

ESI-MS m/z: Calcd. for C$_{36}$H$_{45}$N$_5$O$_8$: 675.77. Found (M+H)$^+$: 676.3.

Example 46

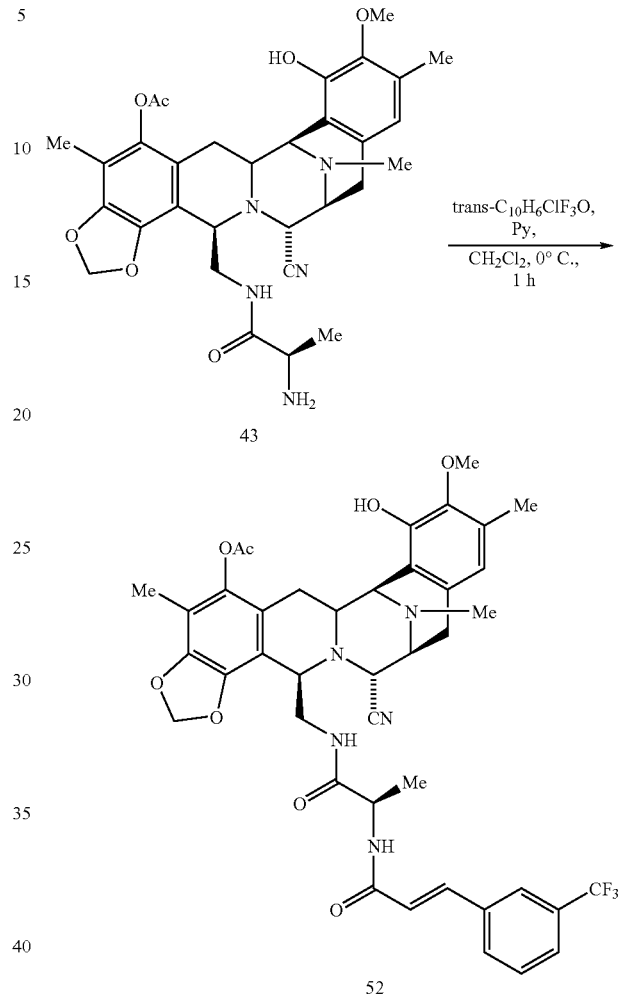

To a solution of 43 (33 mg, 0.0557 ml) in CH$_2$Cl$_2$ (0.4 ml), trans-3-trifluoromethyl cinnamoyl chloride (9.52 ml, 0.0557 ml) and pyridine (4.5 ml, 0.0557 ml) were added at 0° C. The reaction mixture was stirred for 1 h and then, the solution was diluted with CH$_2$Cl$_2$ (5 ml) and washed with 0.1 N HCl (3 ml). The organic layer was dried over sodium sulphate, filtered, and the solvent was eliminated under reduced pressure. The residue was purified by flash column chromatography (SiO$_2$, Hex:ethyl acetate 1:2) to afford 52 (40 mg, 92%) as a white solid.

Rf: 0.21 (hexane:ethyl acetate 1:2).

$^1$H NMR (300 MHz, CD$_3$OD). δ 7.74-7.47 (m, 4H), 6.49 (s, 1H), 6.40 (d, J=15.6 Hz, 1H), 6.00 (d, J=1.5 Hz, 1H), 5.90 (d, J=1.5 Hz, 1H), 5.47 (t, J=6 Hz, 1H), 4.12-4.09 (m, 3H), 3.93 (bs, 1H), 3.71 (s, 3H), 3.59-3.58 (m, 1H), 3.38 (d, J=7.8 Hz, 1H), 3.29 (d, J=12.0 Hz, 1H) 3.00 (dd, J$_1$=8.1 Hz, J$_2$=18.3 Hz, 1H), 2.79-2.78 (m, 1H), 2.65 (d, J=18.3 Hz, 1H) 2.29 (s, 6H), 2.28 (s, 3H), 2.22 (s, 3H), 1.84-1.80 (m, 1H), 0.85-0.84 (m, 3H).

$^{13}$C NMR (75 MHz, CDCl$_3$) δ 171.9, 168.8, 164.4, 146.9, 144.6, 143.0, 140.5, 140.5, 139.3, 135.7, 131.1, 131.0, 129.4, 129.1, 126.0, 124.1, 124.0, 122.4, 121.1, 120.7, 120.6, 117.7, 116.9, 112.8, 112.0, 101.6, 60.6, 59.3, 57.1, 56.3, 55.9, 55.2, 49.0, 41.7, 49.9, 26.5, 25.1, 20.2, 18.4, 15.7, 9.3.

ESI-MS m/z: Calcd. for $C_{41}H_{42}F_3N_5O_8$: 789.8. Found $(M+H)^+$: 790.3.

Example 47

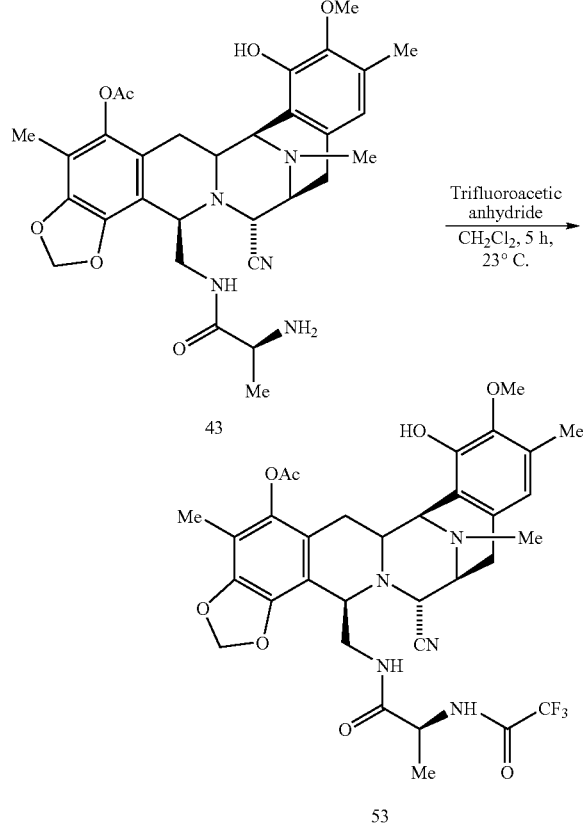

Example 48

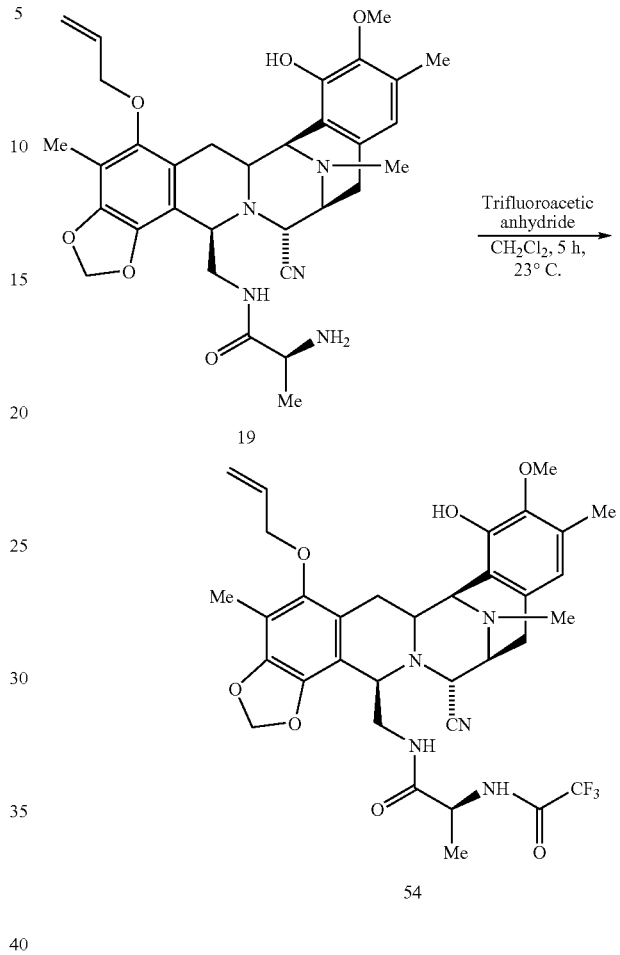

To a solution of 43 (10 mg, 0.0169 ml) in $CH_2Cl_2$ (0.2 ml) trifluoroacetic anhydride (2.38 μl, 0.0169 ml) was added at 23° C. The reaction mixture was stirred for 5 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography ($SiO_2$, Hex:ethyl acetate 3:2) to afford 53 (10.7 mg, 93%) as a white solid.

Rf: 0.57 (ethyl acetate:methanol 5:1).

$^1$H NMR (300 MHz, $CDCl_3$) δ 6.45 (s, 1H), 6.00 (d, J=1.2 Hz, 1H), 5.90 (d, J=1.2 Hz, 1H), 5.87 (bs, 1H), 5.32 (bs, 1H), 4.12 (d, J=2.1 Hz, 1H), 4.08 (d, J=1.8 Hz, 1H), 3.78-3.56 (m, 3H), 3.72 (s, 3H), 3.40 (d, J=8.1 Hz, 1H), 3.25 (d, J=9.3 Hz, 1H), 3.00 (dd, $J_1$=8.4 Hz, $J_2$=18.0 Hz, 1H), 2.77 (dd, $J_1$=2.1 Hz, $J_2$=15.9 Hz 1H), 2.68 (d, J=18.6 Hz, 1H), 2.30 (s, 3H), 2.28 (s, 3H), 2.22 (s, 3H), 2.00 (s, 3H), 1.75 (dd, $J_1$=11.4 Hz, $J_2$=15.9 Hz, 1H), 0.69 (d, J=6.3 Hz, 3H).

$^{13}$C NMR (75 MHz, $CDCl_3$) δ 170.1, 168.6, 156.0, 147.0, 144.3, 143.0, 140.6, 140.4, 131.0, 129.4, 120.9, 120.7, 117.6, 116.8, 112.4, 112.1, 101.6, 60.5, 59.0, 57.1, 56.3, 55.6, 55.2, 48.7, 41.6, 39.4, 26.5, 24.9, 20.2, 17.8, 15.4, 9.2.

ESI-MS m/z: Calcd. for $C_{33}H_{36}F_3N_5O_8$: 687.63. Found $(M+H)^+$: 688.66.

To a solution of 19 (11 mg, 0.0169 ml) in $CH_2Cl_2$ (0.2 ml) trifluoroacetic anhydride (2.38 ml, 0.0169 ml) was added at 23° C. The reaction mixture was stirred for 5 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography ($SiO_2$, Hex:ethyl acetate 3:2) to afford 54 (10.7 mg, 93%) as a white solid.

Rf: 0.6 (ethyl acetate:methanol 5:1).

$^1$H NMR (300 MHz, $CDCl_3$) δ 7.33 (d, J=6.3 Hz, 1H), 6.45 (s, 1H), 6.04 (m, 1H), 5.95 (d, J=1.5 Hz, 1H), 5.84 (d, J=1.5 Hz, 1H), 5.32 (m, 2h), 5.21 (m, 1H), 4.11 (m, 4H), 3.73 (s, 3H), 3.64 (m, 2H), 3.51 (m, 1H), 3.37 (d, J=7.8 Hz, 1H), 3.22 (m, 2H), 3.03 (dd, 1H, $J_1$=8.1 Hz, $J_2$=18.3 Hz, 1H), 2.60 (d, J=18.3 Hz, 1H), 2.29 (s, 3H), 2.24 (s, 3H), 2.08 (s, 3H), 1.86 (dd, $J_1$=12 Hz, $J_2$=16.2 Hz, 1H), 0.82 (d, J=7.2 Hz, 3H).

$^{13}$C NMR (75 MHz, $CDCl_3$) δ 170.0, 156.0, 148.4, 147.1, 144.3, 143.0, 138.7, 133.8, 130.5, 129.4, 120.6, 120.4, 117.6, 117.5, 117.0, 113.5, 112.5, 112.4, 101.1, 74.1, 66.8, 60.4, 59.3, 56.9, 56.6, 56.3, 55.4, 48.7, 41.6, 40.1, 26.2, 25.0, 17.6, 15.4, 9.1.

ESI-MS m/z: Calcd. for $C_{35}H_{39}F_3N_5O_7$: 685.69. Found $(M+H)^+$: 686.3.

Example 49

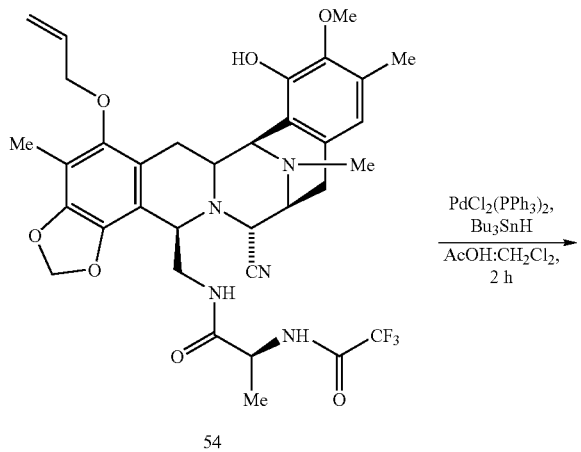

Example 50

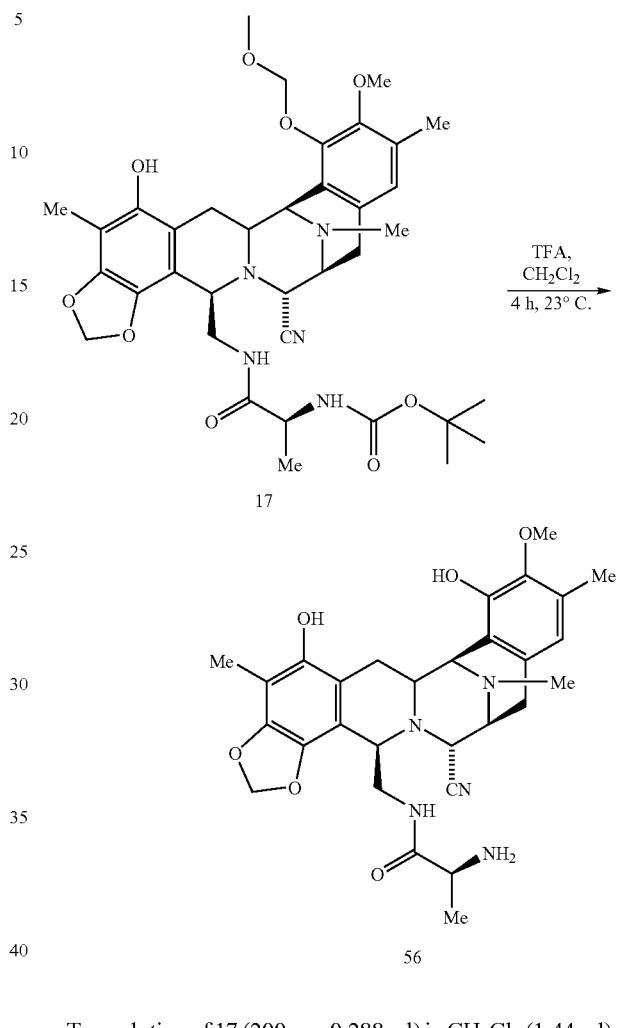

To a solution of 54 (100 mg, 0.415 ml) in CH$_2$Cl$_2$ (4 ml), acetic acid (40 ml), (PPh$_3$)$_2$PdCl$_2$ (8.4 mg, 0.012 ml) and Bu$_3$SnH (157 ml, 0.56 ml) were added at 23° C. After stirring at that temperature for 2 h the reaction was poured into a pad of flash column (SiO$_2$, gradient Hex to hexane:ethyl acetate 2:1) to afford 55 (90 mg, 96%) as a white solid.

Rf: 0.6 (hexane:ethyl acetate 1:2).

$^1$H NMR (300 MHz, CDCl$_3$) δ 7.55 (d, J=7.2 Hz, 1H), 6.45 (s, 1H), 5.90 (d, J=1.2 Hz, 1H), 5.82 (d, J=1.2 Hz, 1H), 5.37 (t, J=6.0 Hz, 1H), 4.15 (d, J=2.1 Hz 1H), 4.04 (d, J=1.8 Hz, 1H), 3.70 (s, 3H), 3.66-3.53 (m, 2H), 3.37-3.31 (m, 2H), 3.19-3.15 (d, J=11.7 Hz, 1H), 3.08-3.00 (m, 2H), 2.56 (d, J=18.3 Hz, 1H), 2.30 (s, 3H), 2.24 (s, 3H), 2.04 (s, 3H), 1.91 (dd, J$_1$=12.0 Hz, J$_2$=15.6 Hz, 1H), 0.84 (d, J=6.9 Hz, 3H).

$^{13}$C NMR (75 MHz, CDCl$_3$) δ 170.1, 156.3, 147.3, 144.9, 144.4, 143.3, 136.7, 130.7, 129.3, 120.6, 117.6, 117.4, 114.4, 112.1, 107.7, 101.0, 85.8, 60.5, 59.3, 56.5, 56.4, 56.2, 55.2, 48.9, 41.6, 40.9, 25.7, 25.3, 18.0, 15.6, 8.7.

ESI-MS m/z: Calcd. for C$_{32}$H$_{35}$F$_3$N$_5$O$_7$: 645.63. Found (M+H)$^+$: 646.2.

To a solution of 17 (200 mg, 0.288 ml) in CH$_2$Cl$_2$ (1.44 ml), trifluoroacetic acid (888 ml, 11.53 ml) was added and the reaction mixture was stirred for 4 h at 23° C. The reaction was quenched at 0° C. with saturated aqueous sodium bicarbonate (60 ml) and extracted with ethyl acetate (2×70 ml). The combined organic layers were dried (sodium sulphate) and concentrated in vacuo to afford 56 (147 mg, 93%) as a white solid that was used in subsequent reactions with no further purification.

Rf: 0.19 (ethyl acetate:methanol 5:1).

$^1$H NMR (300 MHz, CD$_3$OD). δ 6.48 (s, 1H), 5.88, d, J=0.9 Hz, 1H), 5.81 (d, J=0.9 Hz, 1H), 4.35 (d, J=2.4 Hz, 1H), 4.15 (d, J=1.8 Hz, 1H), 3.99-3.98 (m, 1H), 3.70 (s, 3H), 3.52-2.96 (m, 7H), 2.68 (d, J=18.3 Hz 1H), 2.24 (s, 3H), 2.23 (s, 3H), 2.06 (s, 3H), 1.85 (dd, J$_1$=11.7 Hz, J$_2$=15.6 Hz, 1H), 0.91 (d, J=6.6 Hz, 3H).

$^{13}$C NMR (75 MHz, CD$_3$OD): δ 173.2, 149.1, 145.6, 144.9, 138.0, 132.2, 130.6, 121.4, 119.6, 117.4, 114.3, 109.2, 102.5, 82.3, 60.4, 58.4, 58.3, 57.8, 56.6, 50.1, 42.3, 41.6, 27.8, 26.2, 19.5, 15.5, 9.8.

ESI-MS m/z: Calcd. for C$_{29}$H$_{35}$N$_5$O$_6$: 549.62. Found (M+H)$^+$: 550.3.

Example 51

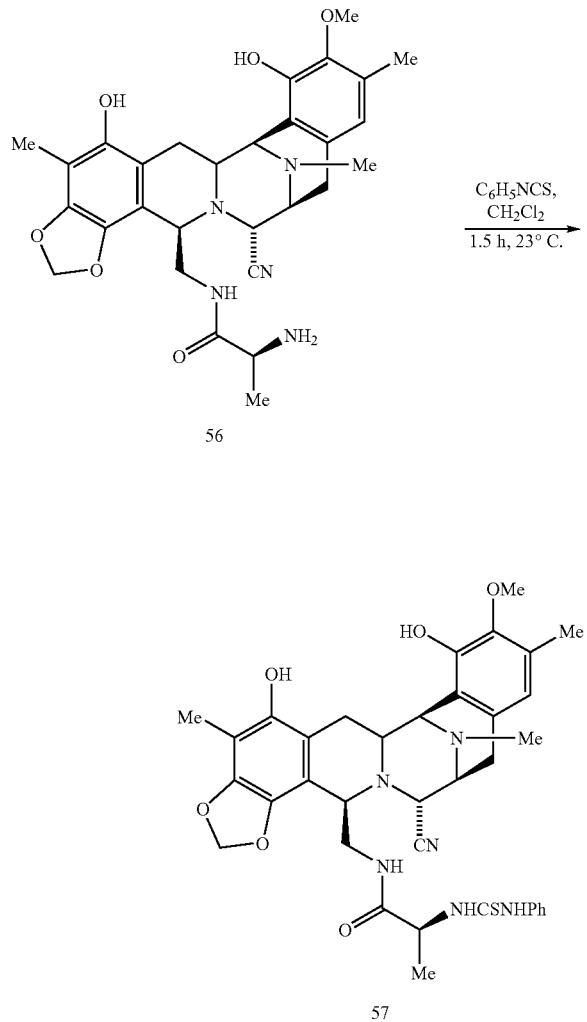

To a solution of 56 (10 mg, 0.018 ml) in CH$_2$Cl$_2$ (0.4 ml), phenyl isothiocyanate (13 ml, 0.109 ml) was added and the reaction was stirred at 23° C. for 1.5 h. The mixture was concentrated in vacuo and the residue was purified by flash column chromatography (SiO$_2$, gradient Hexane to 1:1 hexane:ethyl acetate) to afford 57 (8 mg, 65%) as a white solid.

Rf: 0.57 (ethyl acetate:methanol 10:1).

$^1$H NMR (300 MHz, CDCl$_3$): δ 7.88 (bs, 1H), 7.41-7.36 (m, 2H), 7.27-7.22 (m, 1H), 7.02-7.00 (d, J=7.8 Hz, 2H), 6.71 (d, J=7.2 Hz, 1H), 6.31 (s, 1H), 6.17 (bs, 1H), 5.93 (d, J=1.2 Hz, 1H), 5.83 (d, J=1.2 Hz, 1H), 5.55 (bs, 1H), 5.20-5.17 (m, 1H), 4.16 (d, J=1.8 Hz, 1H), 4.05 (bs, 1H), 4.02 (d, J=2.4 Hz, 1H), 3.79 (s, 3H), 3.75-3.71 (m, 1H), 3.35 (d, J=7.8 Hz, 1H), 3.28-3.19 (m, 2H), 3.12-2.97 (m, 2H), 2.50 (d, J=18.3 Hz, 1H), 2.32 (s, 3H), 2.21 (s, 3H), 2.15-2.09 (dd, J$_1$=11.4 Hz, J$_2$=15.9 Hz, 1H), 1.95 (s, 3H), 0.88 (d, J=6.9 Hz, 3H).

$^{13}$C NMR (75 MHz, CDCl$_3$): δ 178.5, 171.7, 147.2, 145.0, 144.3, 143.3, 137.0, 135.7, 130.6, 130.4, 129.6, 127.5, 124.3, 120.6, 117.7, 117.2, 115.3, 112.1, 108.3, 100.9, 60.9, 59.5, 56.7, 56.5, 56.2, 55.2, 54.1, 41.7, 41.1, 26.3, 25.4, 18.5, 15.8, 9.0.

ESI-MS m/z: Calcd. for C$_{36}$H$_{40}$N$_6$O$_6$S: 684.81. Found (M+H)$^+$: 685.3.

Example 52

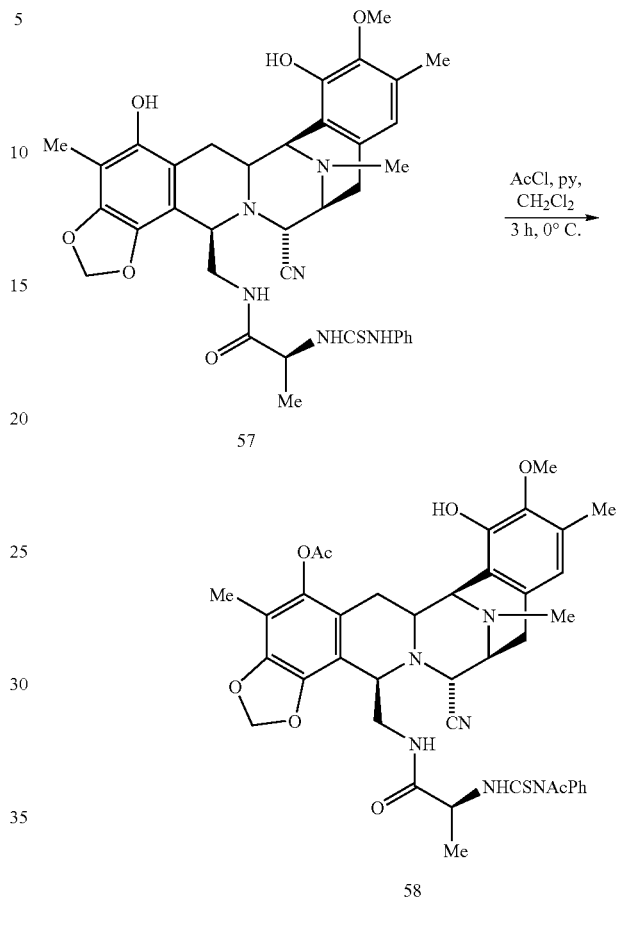

To a solution of 57 (45 mg, 0.065 ml) in CH$_2$Cl$_2$ (0.5 ml), acetyl chloride (4.67 ml, 0.065 ml) and pyridine (5.3 ml, 0.065 ml) were added at 0° C. The reaction mixture was stirred for 3 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (RP-18, CH$_3$CN:H$_2$O 40:60) to afford 58 (14 mg, 28%) as a white solid.

Rf: 0.34 (CH$_3$CN:H$_2$O 7:15).

$^1$H NMR (300 MHz, CDCl$_3$). δ 11.90 (d, J=6.6 Hz, 1H), 7.45-7.40 (m, 3H), 7.18-7.15 (m, 2H), 6.58 (s, 1H), 6.00 (d, J=1.2 Hz, 1H), 5.89 (d, J=1.2 Hz, 1H), 5.70 (s, 1H), 5.37 (t, J=4.8 Hz, 1H), 4.48 (m, 1H), 4.23 (bs, 1H), 4.07 (bs, 2H), 3.85-3.75 (m, 1H), 3.70 (s, 3H), 3.46-3.41 (m, 2H), 3.24-3.20 (m, 1H), 3.00-2.95 (m, 1H), 2.87-2.75 (m, 1H), 2.31 (s, 3H), 2.28 (s, 3H), 2.24 (s, 3H), 2.00 (s, 3H), 1.85 (dd, J$_1$=11.4 Hz, J$_2$=15.6 Hz, 1H), 1.66 (s, 3H), 0.82 (d, J=6.0 Hz, 3H).

$^{13}$C NMR (75 MHz, CDCl$_3$)): δ 182.6, 174.3, 171.0, 146.6, 144.6, 142.7, 142.3, 140.7, 140.2, 131.3, 129.8, 129.3, 128.9, 128.8, 121.5, 120.4, 117.3, 116.6, 112.8, 112.0, 111.3, 101.5, 60.5, 59.0, 57.6, 56.2, 55.9, 55.3, 55.1, 41.6, 39.4, 27.8, 26.5, 24.8, 20.2, 17.1, 15.5, 9.3.

ESI-MS m/z: Calcd. for C$_{40}$H$_{44}$N$_6$O$_8$S: 768.88. Found (M+H)$^+$: 769.2.

Example 53

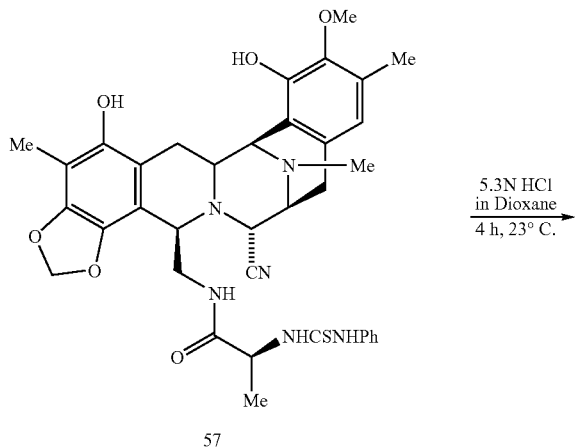

Example 54

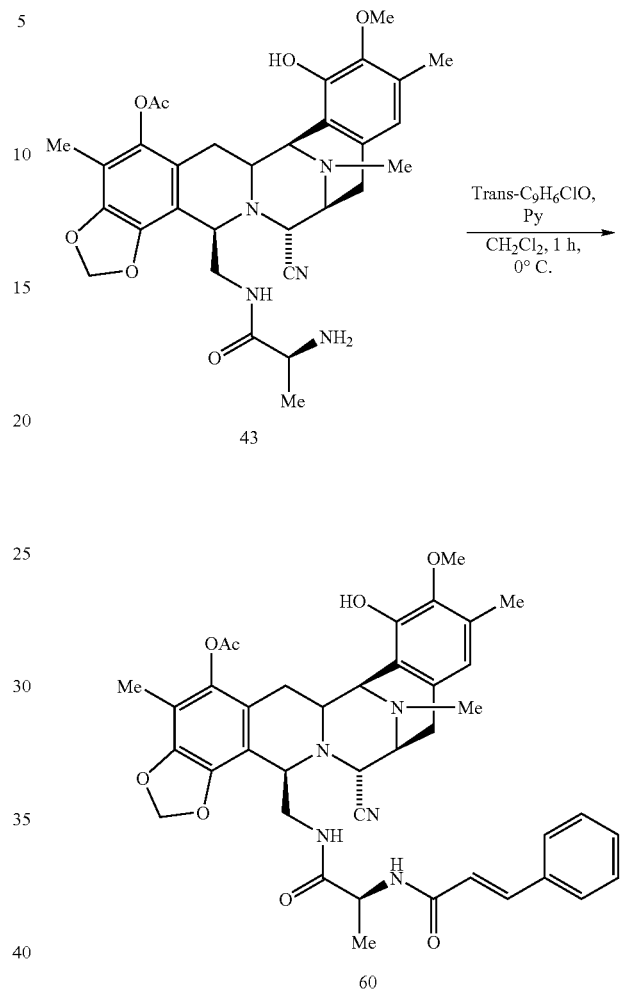

A solution of 57 (130 mg, 0.189 ml) in dioxane (1 ml), 5.3N HCl/dioxane (1.87 ml) was added and the reaction was stirred at 23° C. for 4 h. Then, CH$_2$Cl$_2$ (15 ml) and H$_2$O (10 ml) were added to this reaction and the organic layer was decanted. The aqueous phase was basified with saturated aq sodium bicarbonate (60 ml) (pH=8) at 0° C. and then, extracted with ethyl acetate (2×50 ml). The combined organic extracts were dried (sodium sulphate), and concentrated in vacuo to afford 59 (63 mg, 70%) as a white solid.

Rf: 0.15 (ethyl acetate:methanol 5:1).

$^1$H NMR (300 MHz, CDCl$_3$). δ 6.67 (s, 1H), 5.99 (d, J=0.9 Hz, 1H), 5.91 (d, J=1.2 Hz, 1H), 5.10 (bs, 1H), 4.32 (d, J=7.2 Hz, 1H), 4.25 (dd, J$_1$=3.6 Hz, J$_2$=9.3 Hz, 1H), 3.7 (s, 3H), 3.71-3.64 (m, 2h), 3.50 (dd, J$_1$=2.4 Hz, J$_2$=15.9 Hz, 1H), 3.42-3.37 (m, 2 H), 3.16 (dd, J$_1$=3.6 Hz, J$_2$=12.9 Hz, 1H), 2.57 (dd, J$_1$=9.3 Hz, J$_2$=12.9 Hz, 1H), 2.27 (s, 3H), 2.11 (s, 3H), 1.91 (dd, J$_1$=12.0 Hz, J$_2$=15.9 Hz, 1H).

ESI-MS m/z: Calcd. for C$_{26}$H$_{30}$N$_4$O$_5$: 478.5. Found (M+H)$^+$: 479.3.

A solution of 43 (20 mg, 0.0338 mmol) in CH$_2$Cl$_2$ (0.3 ml), cinnamoyl chloride (5.63 mg, 0.0338 mmol) and pyridine (2.73 ml, 0.0338 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc: MeOH 20:1) to afford 60 (22 mg, 90%) as a white solid.

Rf: 0.56 (EtOAc:MeOH 5:1).

$^1$H NMR (300 MHz, CDCl$_3$), 7.51 (s, 1H, 7.50-7.47 (m, 2H), 7.36-7.35 (m, 2H), 6.43 (s, 1H), 6.36 (brd, J=15.9 Hz, 2H), 6.01 (d, J=1.5 Hz, 1H), 5.90 (brd, J=1.5 Hz, 2H), 5.42 (t, J=6.0 Hz 1H), 4.12-4.07 (m, 3H), 3.96-3.95 (m, 1H), 3.73 (bs, 3H), 3.58 (bs, 2H), 3.39 (d, J=8.7 Hz, 1H), 3.25 (d, J=11.7 Hz, 1H), 3.0 (dd, J$_1$=7.5 Hz, J$_2$=17.7 Hz, 1H), 2.78 (d, J=15.9 Hz, 1H), 2.67 (d, J=16.5 Hz, 1H), 2.29 (s, 6H), 2.23 (s, 3H), 1.99 (s, 3H), 1.82 (dd, J$_1$=11.4 Hz, J$_2$=15.6 Hz, 1H), 0.83 (d, J=6.0 Hz, 3H).

$^{13}$C NMR (75 MHz, CDCl$_3$)): δ 172.0, 165.0, 146.9, 144.6, 143.1, 141.0, 140.5, 134.8, 131.0, 129.7, 129.1, 128.8, 127.8, 125.5, 123.8, 123.0, 121.1, 120.5, 117.7, 116.9, 112.8, 112.0, 101.9, 60.6, 59.2, 57.1, 56.4, 55.9, 55.3, 48.8, 41.7, 40.0, 26.5, 25.1, 20.3, 18.5, 15.7, 9.3.

ESI-MS m/z: Calcd. for $C_{40}H_{43}N_5O_8$: 721.8. Found (M+H)$^+$: 722.3.

Example 55

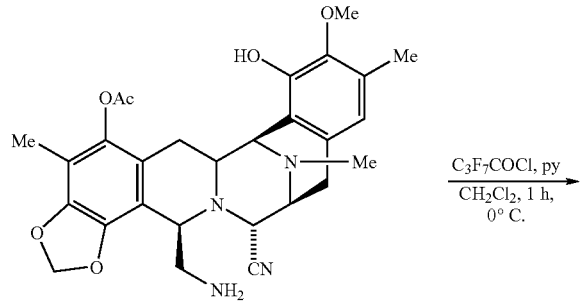

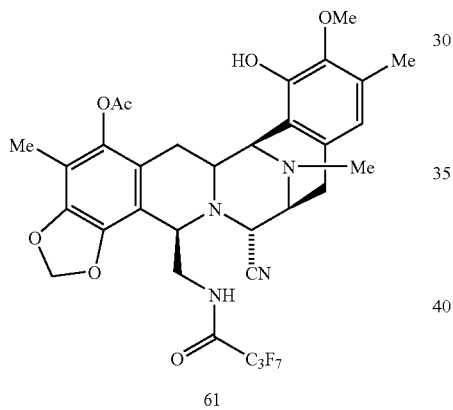

A solution of 45 (19 mg, 0.0364 mmol) in $CH_2Cl_2$ (0.3 ml), heptafluorobutyryl chloride (5.44 ml, 0.0364 mmol) and pyridine (2.95 ml, 0.0364 mmol) were added at 0° C. The reaction mixture was stirred for 1 h and then, the solution was diluted with $CH_2Cl_2$ (10 ml) and washed with 0.1 N HCl (5 ml). The organic layer was dried over sodium sulphate, filtered, and the solvent was eliminated under reduced pressure. The residue was purified by flash column chromatography ($SiO_2$, EtOAc:MeOH 20:1) to afford 61 (11.7 mg, 45%) as a white solid.

Rf: 0.76 (EtOAc:MeOH 5:1).

$^1$H NMR (300 MHz, CDCl$_3$), δ 6.46 (s, 1H), 6.12 (bs, 1H), 5.98 (d, J=1.2 Hz, 1H), 5.93 (d, J=1.2 Hz, 1H), 5.72 (bs, 1H), 4.13-4.11 (m, 2H), 4.0 (d, J=2.4 Hz, 1H), 3.98-3.96 (m, 1H), 3.73 (s, 3H), 3.39 (d, J=7.5 Hz, 1H), 3.39-3.28 (m, 2H), 3.09 (dd, J$_1$=8.1 Hz, J$_2$=18.0 Hz, 1H), 2.80 (d, J=16.2 Hz, 1H), 2.46 (d, J=18.3 Hz, 1H), 2.32 (s, 6H), 2.21 (s, 3H), 1.99 (s, 3H), 1.80 (dd, J$_1$=12.0 Hz, J$_2$=16.2 Hz, 1H).

ESI-MS m/z: Calcd. for $C_{32}H_{31}F_7N_4O_7$: 716.6. Found (M+H)$^+$: 717.2.

Example 56

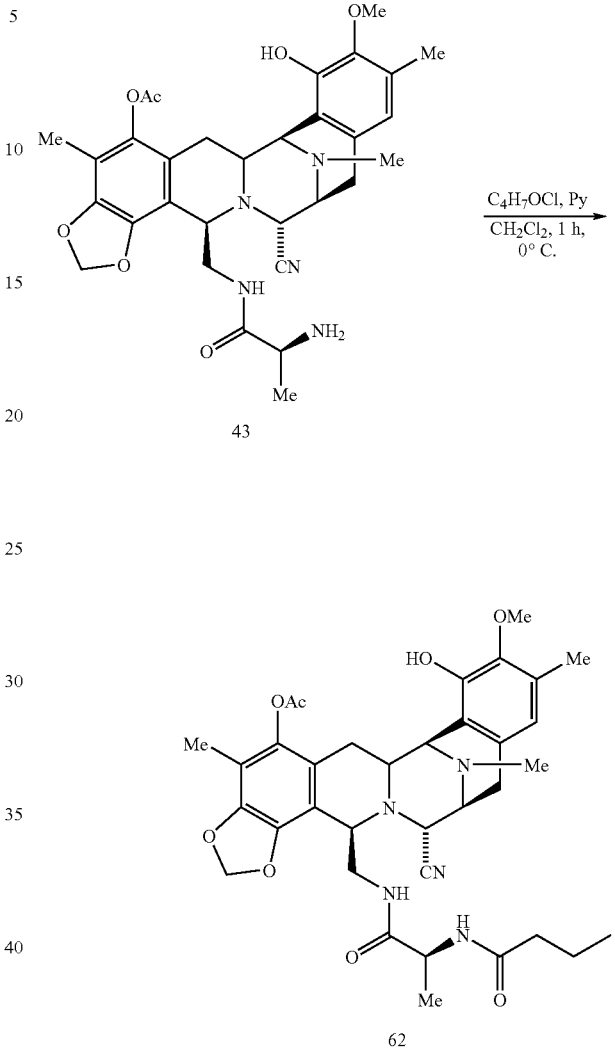

A solution of 43 (24 mg, 0.04 mmol) in $CH_2Cl_2$ (0.3 ml), butyryl chloride (4.15 ml, 0.04 mmol) and pyridine (3.28 ml, 0.04 mmol) were added at 0° C. The reaction mixture was stirred for 1 h and then, the solution was diluted with $CH_2Cl_2$ (10 ml) and washed with 0.1 N HCl (5 ml). The organic layer was dried over sodium sulphate, filtered, and the solvent was eliminated under reduced pressure. The residue was purified by flash column chromatography ($SiO_2$, EtOAc:MeOH 20:1) to afford 62 (24 mg, 90%) as a white solid.

Rf: 0.35 (EtOAc:MeOH 5:1).

$^1$H NMR (300 MHz, CDCl$_3$) δ 6.47 (s, 1H), 6.10 (d, J=6.5 Hz, 1H), 6.0 (d, J=1.5 Hz, 1H), 5.91 (d, J=1.5 Hz, 1H), 5.86 (bs, 1H), 5.31 (d, J=6.9 Hz, 1H), 4.11-4.06 (m, 3H), 3.85-3.81 (m, 1H), 3.75 (s, 3H), 3.59-3.53 (m, 2H), 3.38 (d, J=7.5 Hz, 1H), 3.27-3.22 (m, 1H), 3.0 (dd, J$_1$=7.8 Hz, J$_2$=17.4 Hz, 1H), 2.79 (d, J=15.3 Hz, 1H), 2.63 (d, J=17.7 Hz, 1H), 2.31 (s, 3H), 2.0 (s, 3H), 1.80 (dd, J$_1$=12.0 Hz, J$_2$=15.9 Hz, 1H), 1.58 (q, J=7.2 Hz, 2H), 0.89 (t, J=7.2 Hz, 3H), 0.76 (d, J=6.6 Hz, 3H).

ESI-MS m/z: Calcd. for $C_{35}H_{43}N_5O_8$: 661.64. Found (M+H)$^+$: 662.3.

Example 57

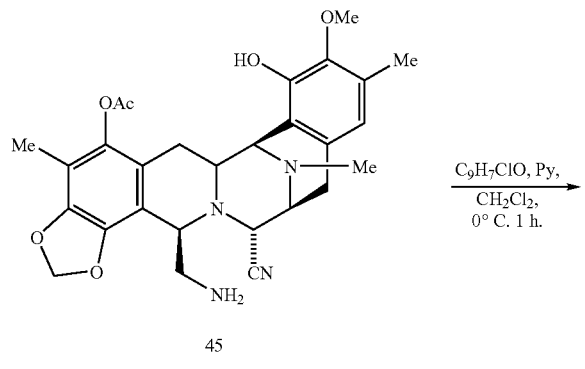

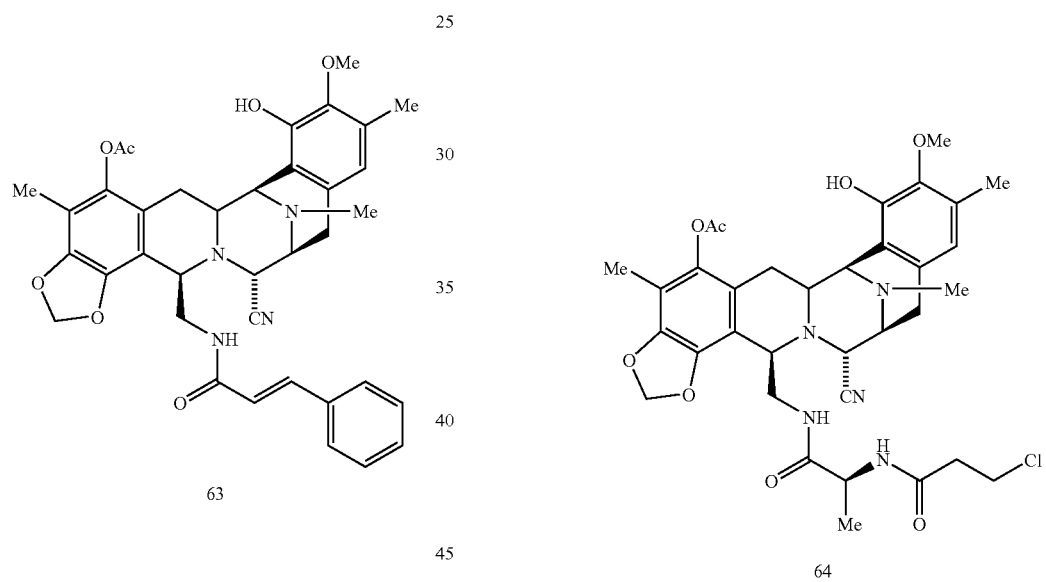

A solution of 43 (19 mg, 0.0364 mmol) in CH$_2$Cl$_2$ (0.3 ml), cinnamoyl chloride (6.06 mg, 0.0364 mmol) and pyridine (2.95 ml, 0.0364 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc: MeOH 20:1) to afford 63 (20.1 mg, 85%) as a white solid.

Rf: 0.65 (EtOAc:MeOH 5:1).

$^1$H NMR (300 MHz, CDCl$_3$) δ 7.39-7.29 (m, 5H), 6.42, (s, 1H), 6.01 (d, J=1.5 Hz, 1H), 5.92 (d, J=1.5 Hz, 1H), 5.73 (bs, 1H), 5.24 (t, J=6.8 Hz, 1H), 4.12-4.08 (m, 3H), 3.66-3.64 (m, 2H), 3.58 (bs, 3H), 3.36 (d, J=8.7 Hz, 1H), 3.29 (d, J=12.0 Hz, 1H), 2.98 (dd, J$_1$=8.1 Hz, J$_2$=18 Hz, 1H), 2.33 (s, 6H), 2.29 (s, 3H), 2.01 (s, 3H), 1.84 (dd, J$_1$=12.0 Hz, J$_2$=15.9 Hz, 1H).).

ESI-MS m/z: Calcd. for C$_{37}$H$_{38}$N$_4$O$_7$: 650.72. Found (M+H)$^+$: 651.2.

Example 58

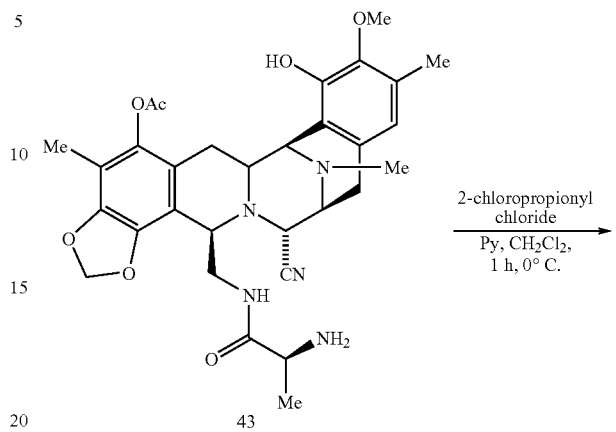

A solution of 43 (20 mg, 0.0338 mmol) in CH$_2$Cl$_2$ (0.3 ml), 3-chloropropionyl chloride (3.22 ml, 0.0338 mmol) and pyridine (2.73 ml, 0.0338 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc: MeOH 20:1) to afford 64 (20.5 mg, 89%) as a white solid.

Rf: 0.32 (EtOAc:Hexane 5:1).

$^1$HNMR (300 MHz, CDCl$_3$) 6.48 (s, 3H), 6.28 (m, 1H), 5.99 (d, J=1.2 Hz, 1H), 5.91 (d, J=1.2 Hz, 1H), 5.86 (bs, 1H), 5.31 (m, 1H), 4.08-4.07 (m, 3H), 3.75 (s, 3H), 3.72-3.53 (m, 5H), 3.39 (d, J=8.1 Hz, 1H), 3.24 (d, J=12.0 Hz, 1H), 3.00 (dd, J$_1$=8.1 Hz, J$_2$=18.0 Hz, 1H), 2.79 (d, J=13.5 Hz, 1H), 2.50 (t, J=6.3 Hz, 2H), 2.32 (s, 3H), 2.28 (s, 3H), 2.0 (s, 3H), 1.79 (dd, J$_1$=12.3 Hz, J$_2$=14.8 Hz, 1H), 0.81 (d, J=6.3 Hz, 3H).

Example 59

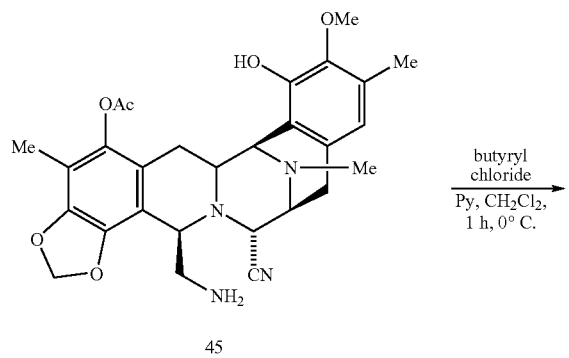

Example 60

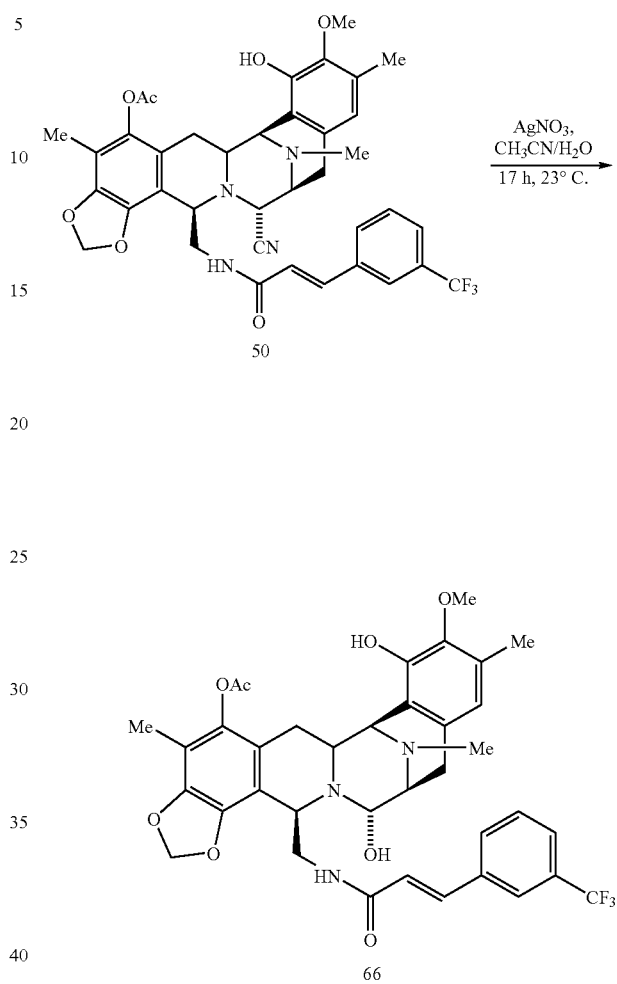

A solution of 43 (19 mg, 0.0364 mmol) in CH$_2$Cl$_2$ (0.3 ml), butyryl chloride (3.78 ml, 0.0364 mmol) and pyridine (2.95 ml, 0.0364 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc:MeOH 20:1) to afford 64 (19 mg, 87%) as a white solid.

Rf: 0.60 (EtOAc:MeOH 5:1).

$^1$H NMR (300 MHz, CDCl$_3$) 6.50 (s, 1H), 5.98 (d, J=1.5 Hz, 1H), 5.91 (d, J=1.5 Hz, 1H, 5.75 (s, 1H), 5.01 (t, J=6.4 Hz, 1H), 4.10-4.09 (m, 1H), 4.06 (d, J=2.1 Hz, 1H), 4.03-4.02 (m, 1H), 3.76 (s, 3H), 3.67-3.60 (m, 1H), 3.42-3.35 (m, 2H), 3.29 (d, J=12.0 Hz, 1H), 3.02 (dd, J=7.8 Hz, J=17.7 Hz, 1H), 2.79 (d, J=14.1 Hz, 1H), 2.56 (d, J=18.3 Hz, 1H), 2.32 (s, 3H), 2.31 (s, 3H), 2.25 (s, 3H), 1.78 (dd, J$_1$=12.0 Hz, J$_2$=15.9 Hz, 1H), 1.63 (s, 3H), 1.53-1.46 (m, 2H), 1.28-1.16 (m, 2H), 0.68 (t, J=7.2 Hz, 3H).

ESI-MS m/z: Calcd. for C$_{32}$H$_{38}$N$_4$O$_7$: 590.67. Found (M+H)$^+$: 591.2.

To a solution of 50 (31.7 mg, 0.044 mmol) in CH$_3$CN/H$_2$O (1.5 ml/0.5 ml), AgNO$_3$ (225 mg, 1.32 mmol) was added and the reaction was stirred at 23° C. for 17 h. Then brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 66 (16 mg, 51%) as a white solid.

Rf: 0.26 (EtOAc:MeOH 5:1).

$^1$H NMR (300 MHz, CDCl$_3$) δ 7.66-7.42 (m, 4H), 7.20 (bs, 1H), 6.44 (s, 1H), 5.97 (b, J=1.2 Hz, 1H), 5.90 (d, J=1.2 Hz, 1H), 5.76 (bs, 1H), 5.28 (bs, 1H), 4.54 (bs, 1H), 4.43 (bs, 1H), 4.00 (bs, 1H), 3.68-3.57 (m, 4H), 3.47 (d, J=3.3 Hz, 1H), 3.40 (d, J=11.7 Hz, 1H), 3.17 (d, J=6.9 Hz, 1H), 2.92 (dd, J$_1$=8.1 Hz, J$_2$=17.7 Hz, 1H), 2.74 (d, J=17.1 Hz 1H), 2.48 (d, J=18.6 Hz, 1H), 2.32 (s, 6H), 2.28 (s, 3H), 1.99 (s, 3H), 1.76 (dd, J$_1$=12.0 Hz, J$_2$=16.2 Hz, 1H).

ESI-MS m/z: Calcd. for C$_{37}$H$_{38}$F$_3$N$_3$O$_8$: 709. Found (M$^+$–17): 692.3.

Example 61

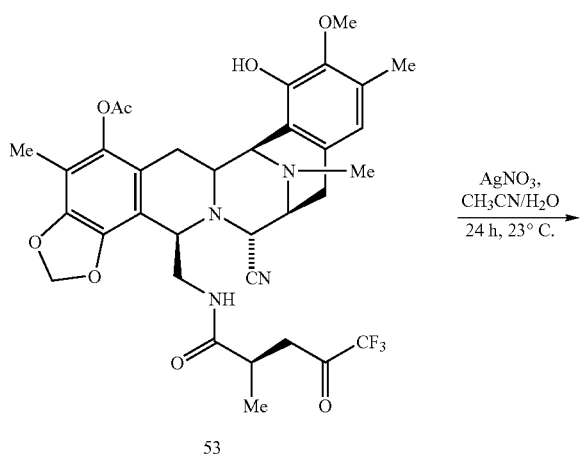

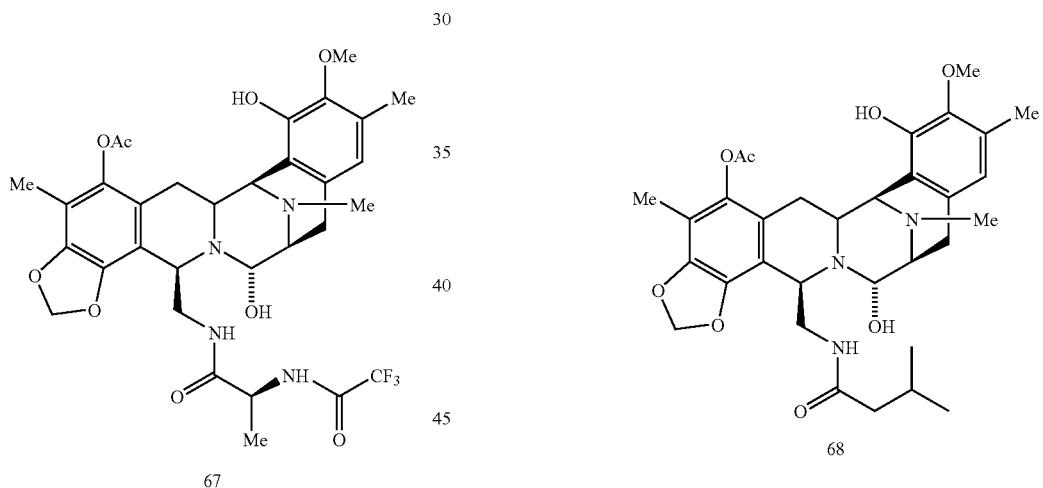

To a solution of 53 (57 mg, 0.0828 mmol) in CH$_3$CN/H$_2$O (1.5 mL/0.5 ml). AgNO$_3$ (650 mg, 3.81 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 67 (28 mg, 50%) as a white solid.

Rf: 0.28 (EtOAc:MeOH 10:1).

$^1$H NMR (300 MHz, CDCl$_3$) d 6.47 (s, 1H), 5.97 (s, 1H), 5.88 (s, 1H), 5.35 (bs, 1H), 4.51 (bs, 1H), 4.41 (bs, 1H), 4.12-4.05 (m, 1H), 4.00 (d, J=2.7 Hz, 1H), 3.77 (s, 3H), 3.64 (bs, 1H), 3.46 (d, 3.3 Hz, 1H), 3.34 (d, J=11.4 Hz, 1H), 3.18 (d, J=7.5 Hz, 1H), 2.95 (dd, J$_1$=8.4 Hz, J$_2$=18.3 Hz, 1H), 2.70 (d, J=15.6 Hz, 1H), 2.48 (d, J=17.7 Hz, 1H), 2.28 (s, 3H), 2.27 (s, 3H), 2.26 (s, 3H), 1.98 (s, 3H), 1.68 (dd, J$_1$=12 Hz, J$_2$=15.6 Hz, 1H), 0.86 (d, J=6.3 Hz, 3H).

ESI-MS m/z: Calcd. for C$_{32}$H$_{37}$F$_3$N$_4$O$_9$: 678.66. Found (M$^+$–17): 661.2.

Example 62

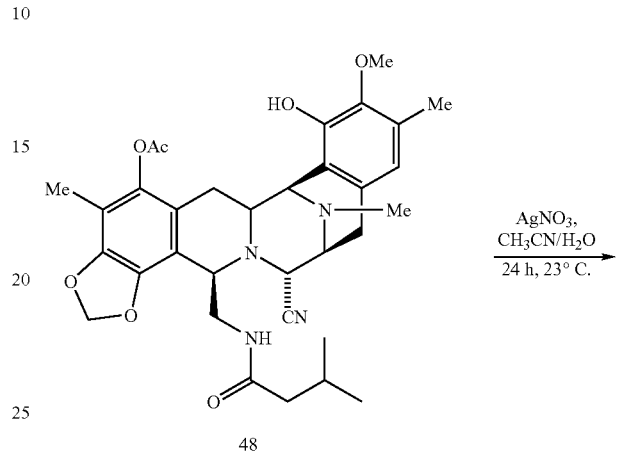

To a solution of 48 (32 mg, 0.0529 mmol) in CH$_3$CN/H$_2$O (1.5 ml/0.5 ml), AgNO$_3$ (270 mg, 1.58 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 68 (18 mg, 56%) as a white solid.

Rf: 0.40 (EtOAc:MeOH 5:1).

$^1$H NMR (300 MHz, CDCl$_3$) d 6.50 (s, 1H), 5.95 (d, J=1.2 Hz, 1H), 5.88 (d, J=1.2 Hz, 1H), 5.23 (d, J=6.9 Hz, 1H), 4.45 (d, J=3.3 Hz, 1H), 4.38 (s, 1H), 4.01 (d, J=2.4 Hz, 1H), 3.78 (m, 1H), 3.77 (s, 3H), 3.41-3.37 (m, 1H), 3.17-3.15 (m, 1H), 2.96 (dd, J$_1$=7.8 Hz, J$_2$=18.0 Hz, 1H), 2.70 (d, J=15.3 Hz, 1H), 2.40 (d, J=18.0 Hz, 1H), 2.30 (s, 6H), 2.27 (s, 3H), 1.76-1.65 (m, 1H), 1.35-1.25 (m, 1H), 0.89-0.82 (m, 1H), 0.69 (d, J=6.6 Hz, 3H), 0.58 (d, J=6.6 Hz, 3H)

Example 63

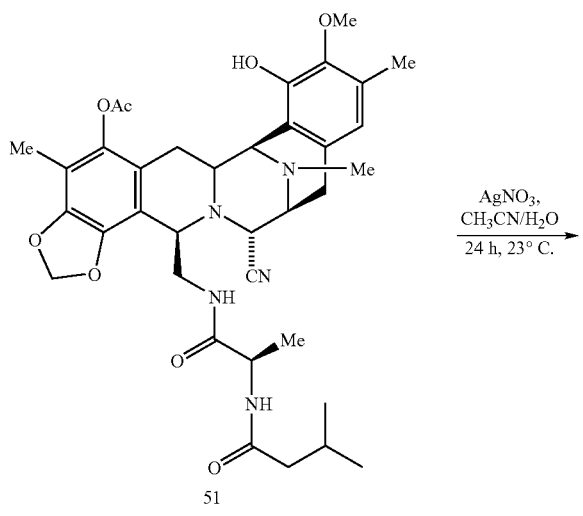

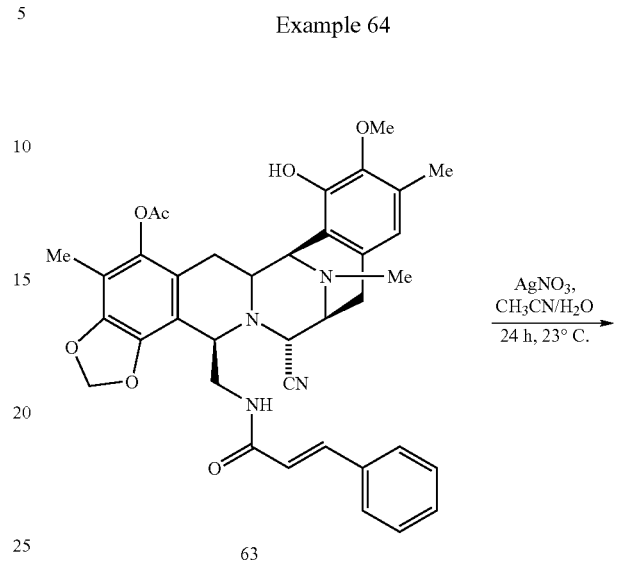

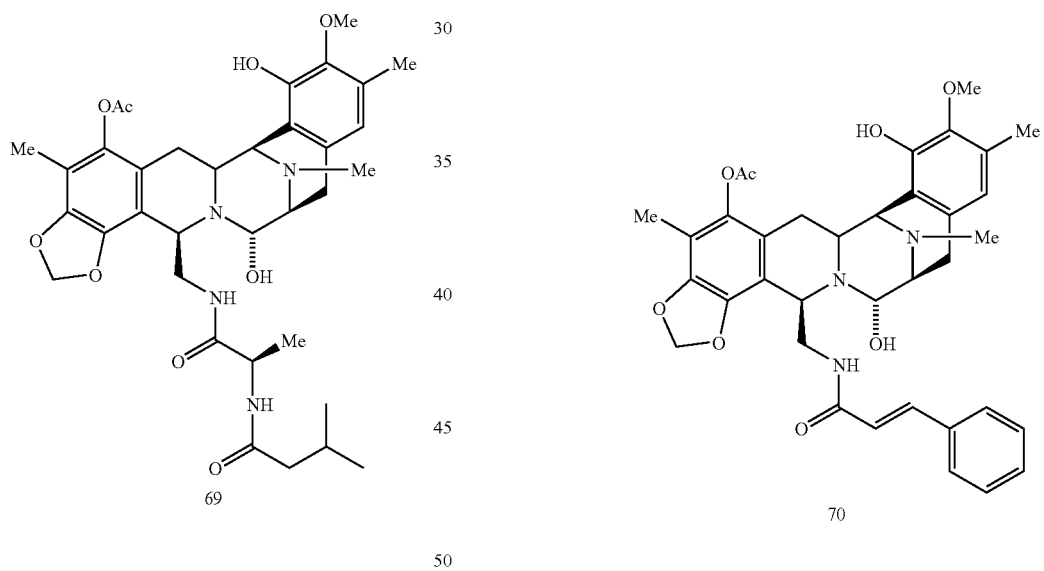

To a solution of 51 (27 mg, 0.04 mmol) in CH$_3$CN/H$_2$O (1.5 ml/0.5 ml). AgNO$_3$ (204 mg, 1.19 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 69 (10 mg 38%) as a white solid.

Rf: 0.38 (EtOAc:MeOH 5:1).

$^1$H NMR (300 MHz, CDCl$_3$) d 6.48 s, 1H), 6.16 (bs, 1H), 5.98 (d, J=1.5 Hz, 1H), 5.89 (d, J=1.5 Hz, 1H), 5.33 (t, J=6.0 Hz, 1H), 4.50 (m, 1H), 4.40 (m, 1H), 4.11-4.09 (m, 1H), 4.00 (d, J=2.6 Hz, 1H), 3.78 (s, 3H), 3.41-3.32 (m, 3H), 3.18 (d, J=8.4 Hz, 1H), 2.94 (dd, J$_1$=8.4 Hz, J$_2$=2=18.3 Hz, 1H), 2.70 (d, J=14.4 Hz, 1H), 4.45 (d, J=18.3 Hz, 1H), 2.31 (s, 3H), 2.28 (s, 3H), 2.27 (s, 3H), 2.04 (s, 3H), 2.00-1.86 (m, 3H), 1.73 (m, 1H), 0.87 (d, J=6.3 Hz, 6H).

Example 64

To a solution of 63 (15 mg, 0.023 mmol) in CH$_3$CN/H$_2$O (1.5 ml/0.5 ml). AgNO$_3$ (118 mg, 0.691 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 70 (20.1 mg, 85%) as a white solid.

Rf: 0.43 (EtOAc:MeOH 5:1).

$^1$HNMR (300 MHz, CDCl$_3$) d 7.38-7.28 (m, 5H), 6.48 (s, 1H), 5.98 (d, J=1.5 Hz, 1H), 5.91 (d, J=1.5 Hz, 1H), 5.75 (bs, 1H), 5.38 (brd, 1H), 5.30 (bs, 1H), 4.53 (m, 1H), 4.42 (m, 1H), 4.02 (d, J=2.7 Hz, 1H), 3.78-3.65 (m, 5H), 3.46-3.40 (m, 2H), 3.17 (d, J=7.8 Hz, 1H), 2.94 (dd, J$_1$=7.8 Hz, J$_2$=17.7 Hz, 1H), 2.73 (d, J=16.8 Hz, 1H), 2.45 (d, J=18.0 Hz, 1H), 2.31 (s, 6H), 2.28 (s, 3H), 1.97 (s, 3H), 1.77 (dd, J$_1$=12.0 Hz, J$_2$=15.3 Hz, 1H).

Example 65

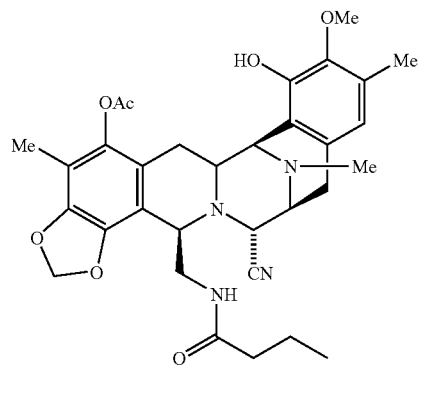

65

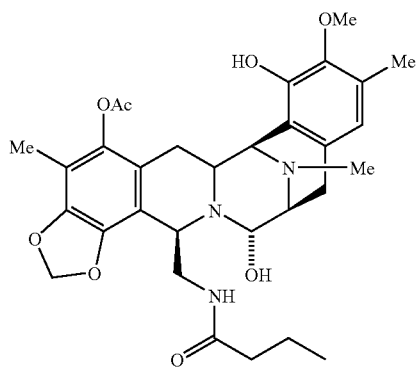

71

To a solution of 65 (25 mg, 0.042 mmol) in CH$_3$CN/H$_2$O (1.5 ml/0.5 ml), AgNO$_3$ (215.56 mg, 1.269 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:2) to afford 71 (16 mg, 65%) as a white solid.

Rf: 0.0.5 (EtOAc:MeOH 5:2).

$^1$H NMR (300 MHz, CDCl$_3$) d 6.50 (s, 1H), 5.95 (d, J=1.5 Hz, 1H), 5.78 (s, 1h), 5.19 (bs, 1H), 4.45 (d, J=3.3 Hz, 1H), 4.37 (bs, 1H), 4.11 (brd, J=4.8 Hz, 1H), 4.01 (d, J=2.1 Hz, 1H), 3.76 (s, 1H), 3.71-3.69 (m, 1H), 3.49-3.35 (m, 1H), 3.24 (d, J=13.5 Hz, 1H), 3.15 (d, J=9.3 Hz, 1H), 2.95 (dd, J$_1$=8.1 Hz, J=17.7 Hz, 1H), 2.70 (d, J=15.6 Hz, 1H), 2.40 (d, J=18.0 Hz, 1H), 2.31 (s, 3H), 2.29 (s, 3H), 2.26 (s, 3H), 1.96 (s, 3H), 1.75-1.66 (m, 1H), 1.52-1.17 (m, 2H), 0.66 (t, J=7.2 Hz, 3H).

Example 66

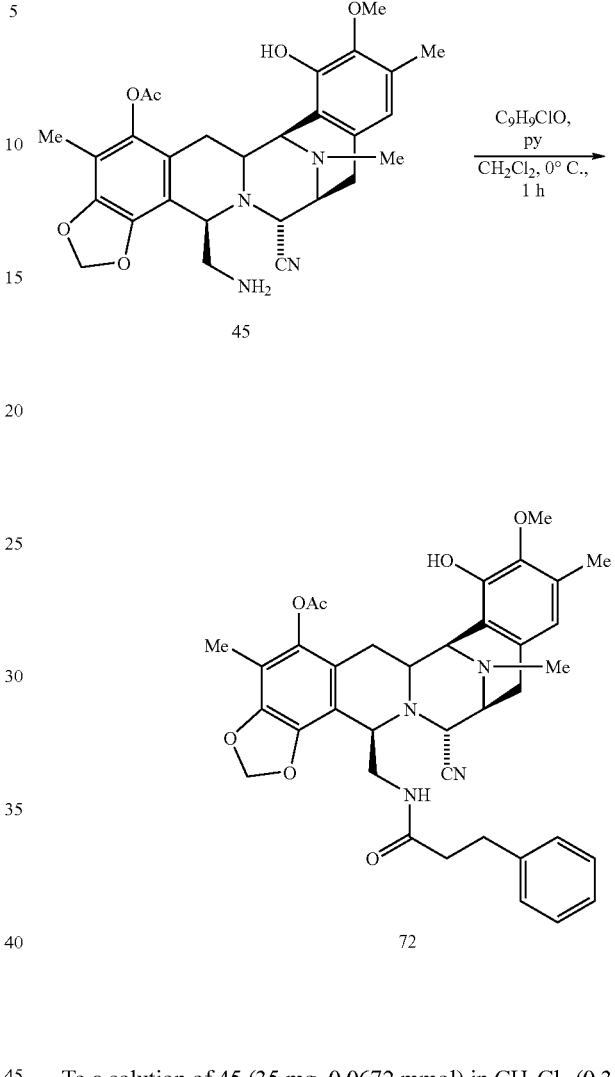

To a solution of 45 (35 mg, 0.0672 mmol) in CH$_2$Cl$_2$ (0.3 mL), hydrocinnamoyl chloride (11.58 μl, 0.0672 mmol) and pyridine (5.43 μL, 0.0672 mmol) were added at 0° C. The reaction mixture was stirred for 1.5 h and then, the solution was diluted with CH$_2$Cl$_2$ (10 mL) and washed with 0.1 N HCl (5 mL). The organic layer was dried over Na$_2$SO$_4$, filtered, and the solvent was eliminated under reduced pressure. The residue was purified by flash column chromatography (SiO$_2$, gradient Hex:ethyl acetate 2:1 to ethyl acetate) to afford 72 (30 mg, 68%) as a white solid.

Rf: 0.51 (ethyl acetate:MeOH 10:1).

$^1$H NMR (300 MHz, CDCl$_3$) δ 7.23-7.12 (m, 3H), 7.05-7.00 (m, 2H), 5.97 (d, J=1.2 Hz, 1H), 5.91 (d, J=1.2 Hz, 1H), 5.73 (s, 1H), 5.04 (brt, 1H), 4.08 (d, J=2.4 Hz, 1H), 4.02 (bs, 1H), 4.00 (d, J=2.4 Hz, 1H), 3.58 (dd, J$_1$=4.5 Hz, J$_2$=13.8 Hz, 1H), 3.47 (bs, 3H), 3.33 (d, J=7.5 Hz, 1H), 3.29 (dt, J$_1$=2.7 Hz, J$_2$=11.7 Hz, 1H), 3.00 (dd, J$_1$=7.8 Hz, J$_2$=18.3 Hz, 1H), 2.79 (d, J=14.1 Hz, 1H), 2.58-2.50 (m, 3H), 2.32 (s, 3H), 2.29 (s, 3H), 2.03 (s, 3H), 2.01 (s, 3H), 1.94-1.76 (m, 4H).

ESI-MS m/z: Calcd. for C$_{37}$H$_{40}$N$_4$O$_7$: 652.7. Found (M+Na)$^+$: 675.3.

Example 67

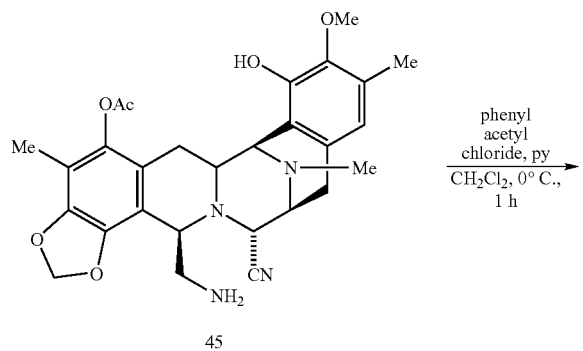

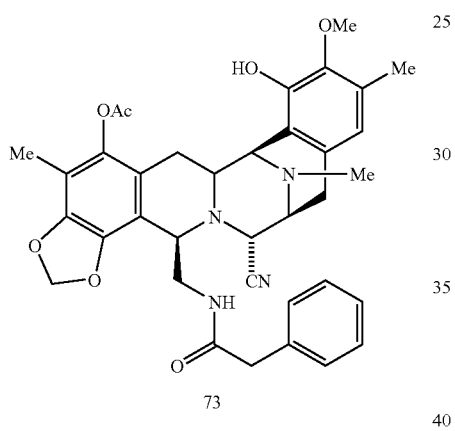

To a solution of 45 (45 mg, 0.0576 mmol) in $CH_2Cl_2$ (0.3 mL), phenyl acetyl chloride (7.61 μl, 0.0576 mmol) and pyridine (4.6 μL, 0.0576 mmol) were added at 0° C. The reaction mixture was stirred for 1 h and then, the solution was diluted with $CH_2Cl_2$ (10 mL) and washed with 0.1 N HCl (5 mL). The organic layer was dried over $Na_2SO_4$, filtered, and the solvent was eliminated under reduced pressure. The residue was purified by flash column chromatography ($SiO_2$, gradient Hex:ethyl acetate 3:1 to Hex:ethyl acetate 1:1) to afford 73 (25.8 mg, 70%) as a white solid.

Rf: 0.5 (Hex:ethyl acetate:MeOH 5:10:2).

$^1$H NMR (300 MHz, $CDCl_3$) δ 7.18-7.17 (m, 3H), 6.85 (bs, 1H), 6.54 (s, 1H), 5.89 (d, J=1.5 Hz, 1H), 5.83 (d, J=1.5 Hz, 1H), 5.76 (s, 1H), 5.08 (bs, 1H), 4.12 (d, J=2.1 Hz, 1H), 4.09 (d, J=2.1 Hz, 1H), 3.98 (bs, 1H), 3.73 (s, 3H), 3.51-3.46 (m, 2H), 3.35 (d, J=8.4 Hz, 1H), 3.25 (dt, $J_1$=2.7 Hz, $J_2$=12.0 Hz, 1H), 3.03 (d, J=8.7 Hz 1H), 3.02-2.94 (m, 2H), 2.75 (d, J=16.8 Hz, 1H), 2.63 (d, J=18.0 Hz, 1H), 2.35 (s, 3H), 2.30 (s, 3H), 2.22 (s, 3H9, 1.98 (s, 3H), 1.80 (dd, $J_1$=12.0 Hz, $J_2$=16.2 Hz, 1H).

ESI-MS m/z: Calcd. for $C_{36}H_{38}N_4O_7$: 638.7. Found (M+1)$^+$: 639.2.

Example 68

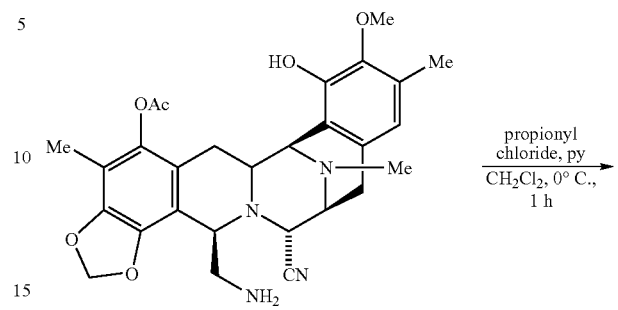

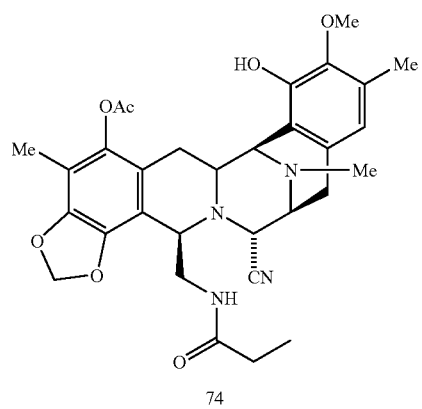

To a solution of 45 (30 mg, 0.0576 mmol) in $CH_2Cl_2$ (0.3 mL), propyonyl chloride (5 μL, 0.0576 mmol) and pyridine (4.6 μL, 0.0576 mmol) were added at 0° C. The reaction mixture was stirred for 1 h and then, the solution was diluted with $CH_2Cl_2$ (10 mL) and washed with 0.1 N HCl (5 mL). The organic layer was dried over $Na_2SO_4$, filtered, and the solvent was eliminated under reduced pressure. The residue was purified by flash column chromatography ($SiO_2$, gradient Hex:ethyl acetate 5:1 to Hex:ethyl acetate 1:1 to ethyl acetate) to afford 74 (23 mg, 70%) as a white solid.

Rf: 0.59 ((Hex:ethyl acetate:MeOH 5:10:2).

$^1$H NMR (300 MHz, $CDCl_3$) δ 6.50 (s, 1H), 5.97 (d, J=1.2 Hz, 1H), 5.91 (d, J=1.2 Hz, 1H), 5.76 (s, 1H), 5.00 (t, 1H), 4.09 (d, J=1.2 Hz, 1H), 4.04 (bs, 2H), 3.74 (s, 3H), 3.62 (dd, $J_1$=6.6 Hz, $J_2$=13.2 Hz, 1H), 3.43 (bs, 1H), 3.37 (d, J=8.4 Hz, 1H), 3.29 (d, J=12.0 Hz, 1H), 3.02 (dd, $J_1$=8.1 Hz, $J_2$=18.3 Hz, 1H), 2.80 (d, J=14.4 Hz, 1H), 2.55 (d, J=18.0 Hz, 1H), 2.31 (s, 3H), 2.24 (s, 3H), 2.00 (s, 3H), 1.78 (dd, $J_1$=12.0 Hz, $J_2$=15.6 Hz, 1H), 1.64-1.50 (m, 2H), 0.70 (t, J=7.8 Hz, 3H).

ESI-MS m/z: Calcd. for $C_{31}H_{36}N_4O_7$: 576.6. Found (M+1)$^+$: 577.2.

Example 69

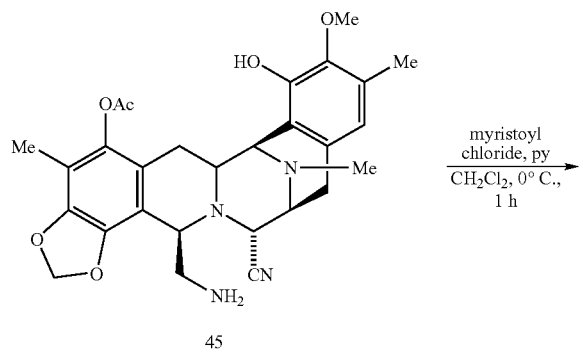

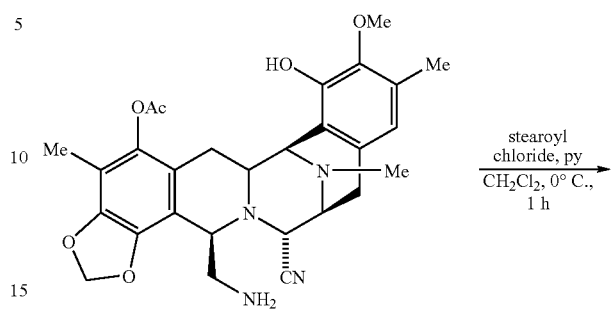

To a solution of 45 (15 mg, 0.0288 mmol) in CH$_2$Cl$_2$ (0.25 mL), myristoyl chloride (7.83 μL, 0.0288 mmol) and pyridine (2.3 μL, 0.0288 mmol) were added at 0° C. The reaction mixture was stirred for 1 h and then, the solution was diluted with CH$_2$Cl$_2$ (10 mL) and washed with 0.1 N HCl (5 mL). The organic layer was dried over Na$_2$SO$_4$, filtered, and the solvent was eliminated under reduced pressure. The residue was purified by flash column chromatography (SiO$_2$, gradient Hex: ethyl acetate 6:1 to Hex:ethyl acetate 1:1) to afford 75 (15 mg, 71%) as a white solid:

Rf: 0.65 (Hex:ethy acetate:MeOH 10:10:1).

$^1$H NMR (300 MHz, CDCl$_3$) δ 6.49 (s, 1H), 5.97 (d, J=1.2 Hz, 1H), 5.91 (d, J=1.2 Hz, 1H), 5.72 (s, 1H), 4.99 (t, 1H), 4.09 (d, J=1.5 Hz, 1H), 4.05 (d, J=1.5 Hz, 1H), 4.02 (bs, 1H), 3.76 (s, 3H), 3.61-3.59 (m, 1H), 3.39 (bs, 1H), 3.35 (d, J=7.8 Hz, 1H), 3.29 (d, J=12.3 Hz, 1H), 3.04 (dd, J$_1$=8.1 Hz, J$_2$=18.3 Hz, 1H), 2.78 (d, J=15.6 Hz, 1H), 2.55 (d, J=18.3 Hz, 1H), 2.32 (s, 6H), 2.25 (s, 3H), 1.99 (s, 3H), 1.78 (dd, J$_1$=12.3 Hz, J$_2$=15.0 Hz, 1H), 1.25-1.24 (m, 12H), 0.87 (d, J=6.0 Hz, 3H).

ESI-MS m/z: Calcd. for C$_{42}$H$_{58}$N$_4$O$_7$: 730.9. Found (M+1)$^+$: 731.4.

Example 70

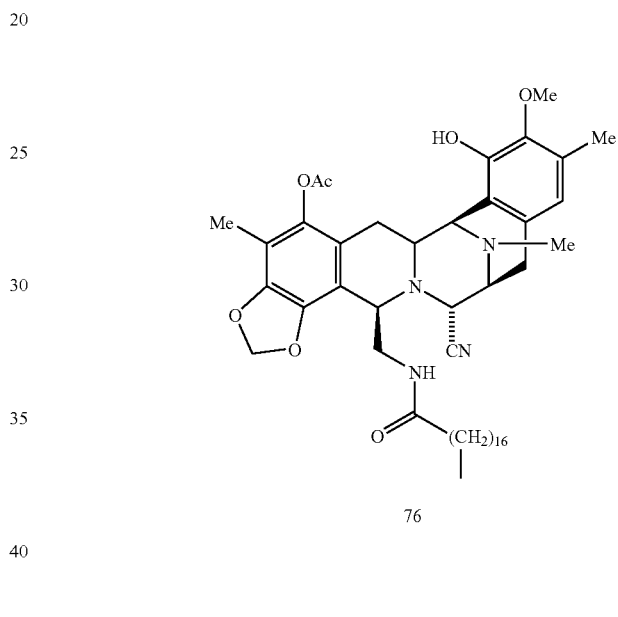

To a solution of 45 (15 mg, 0.0288 mmol) in CH$_2$Cl$_2$ (0.25 mL), stearoyl chloride (9.7 μL, 0.0288 mmol) and pyridine (2.3 μL, 0.0288 mmol) were added at 0° C. The reaction mixture was stirred for 1 h and then, the solution was diluted with CH$_2$Cl$_2$ (10 mL) and washed with 0.1 N HCl (5 mL). The organic layer was dried over Na$_2$SO$_4$, filtered, and the solvent was eliminated under reduced pressure. The residue was purified by flash column chromatography (SiO$_2$, gradient Hex: ethyl acetate 3:1 to Hex:ethyl acetate 1:1) to afford 76 (16 mg, 70%) as a white solid.

Rf: 0.46 (Hex:ethyl acetate:MeOH 10:10:1).

$^1$H NMR NMR (300 MHz, CDCl$_3$) δ 6.49 (s, 1H), 5.98 (d, J=1.5 Hz, 1H), 5.91 (d, J=1.15 Hz, 1H), 5.73 (s, 1H), 4.99 (t, J=5.7 Hz, 1H), 4.09 (d, J=1.8 Hz, 1H), 4.05 (d, J=2.4 Hz, 1H), 4.01 (bs, 1H), 3.76 (s, 3H), 3.61-3.59 (m, 1H), 3.38 (bs, 1H), 3.36 (d, J=7.2 Hz, 1H), 3.28 (d, J=12.0 Hz, 1H), 3.03 (dd, J$_1$=7.8 Hz, J$_2$=18.3 Hz, 1H), 2.78 (d, J=15.9 Hz, 1H), 2.57 (d, J=18.3 Hz, 1H), 2.32 (s, 3H), 2.31 (s, 3H), 2.24 (s, 3H), 1.99 (s, 3H), 1.77 (dd, J$_1$=11.7 Hz, J$_2$=15.6 Hz, 1H), 1.25-1.24 (m, 16H), 0.87 (d, J=6.3 Hz, 3H).

ESI-MS m/z: Calcd. for C$_{46}$H$_{66}$N$_4$O$_7$: 786.4. Found (M+22)$^+$: 809.5.

Example 71

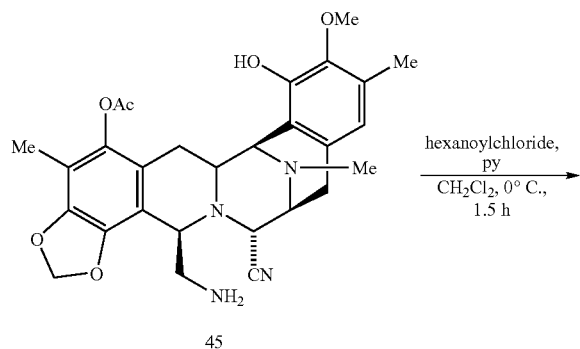

Example 72

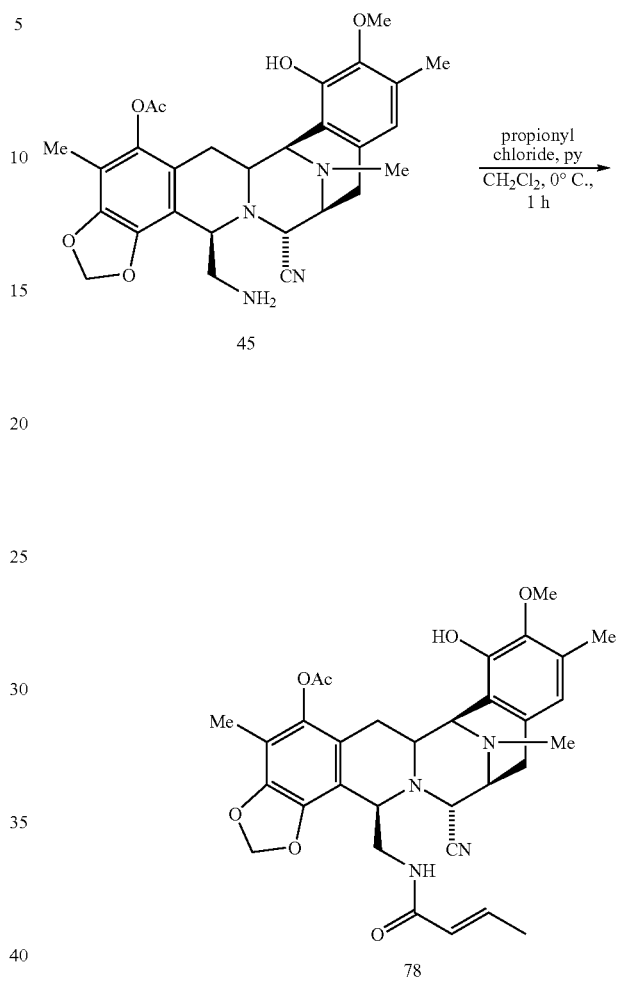

To a solution of 45 (31 mg, 0.0595 mmol) in $CH_2Cl_2$ (0.3 mL), hexanoyl chloride (8.32 μL, 0.0595 mmol) and pyridine (4.8 μL, 0.0595 mmol) were added at 0° C. The reaction mixture was stirred for 1.5 h and then, the solution was diluted with $CH_2Cl_2$ (10 mL) and washed with 0.1 N HCl (5 mL). The organic layer was dried over $Na_2SO_4$, filtered, and the solvent was eliminated under reduced pressure. The residue was purified by flash column chromatography ($SiO_2$, gradient Hex: ethyl acetate 3:2 to ethyl acetate) to afford 77 (26 mg, 70%) as a white solid.

Rf: 0.65 (ethyl acetate MeOH 10:1).

$^1$H NMR (300 MHz, $CDCl_3$) δ 6.50 (s, 1H), 5.98 (d, J=1.5 Hz, 1H), 5.91 (d, J=1.5 Hz, 1H), 5.74 (s, 1H), 5.00 (t, J=5.4 Hz, 1H), 4.09 (d, J=2.7 Hz, 1H), 4.05 (d, J=2.4 Hz, 1H), 4.01 (bs, 1H), 3.76 (s, 3H), 3.61-3.58 (m, 1H), 3.02 (dd, $J_1$=8.1 Hz, $J_2$=18.3 Hz, 1H), 2.78 (d, J=14.4 Hz, 1H), 2.56 (d, J=18.3 Hz, 1H), 2.31 (s, 6H), 2.25 (s, 3H), 2.00 (s, 3H), 1.78 (dd, $J_1$=12.0 Hz, $J_2$=15.9 Hz, 1H), 1.53-1.40 (m, 2H), 1.29-1.12 (m, 4H), 1.07-0.97 (m, 2H), 0.81 (t, J=7.5 Hz, 3H).

ESI-MS m/z: Calcd. for $C_{34}H_{42}N_4O_7$: 618.7. Found (M+1)$^+$: 619.3.

To a solution of 45 (20 mg, 0.0384 mmol) in $CH_2Cl_2$ (0.3 mL), trans-crotonyl chloride (3.68 μL, 0.0384 mmol) and pyridine (3.1 μL, 0.0384 mmol) were added at 0° C. The reaction mixture was stirred for 1 h and then, the solution was diluted with $CH_2Cl_2$ (10 mL) and washed with 0.1 N HCl (5 mL). The organic layer was dried over $Na_2SO_4$, filtered, and the solvent was eliminated under reduced pressure. The residue was purified by flash column chromatography ($SiO_2$, gradient Hex:ethyl acetate 4:1 to ethyl acetate) to afford 78 (16 mg, 71%) as a white solid.

Rf: 0.55 (ethyl acetate:MeOH 5:1).

$^1$H NMR (300 MHz, $CDCl_3$) δ 6.50-6.40 (m, 1H), 6.46 (s, 1H), 5.97 (d, J=1.5 Hz, 1H), 5.91 (d, J=1.5 Hz, 1H), 5.77 (s, 1H), 5.08 (bst, 1H), 4.10 (d, J=1.5 Hz, 1H), 4.05 (m, 2H), 3.78 (s, 3H), 3.67 (bs, 1H), 3.42-3.29 (m, 3H), 3.04 (dd, $J_1$=8.1 Hz, $J_2$=18.3 Hz, 1H), 2.78 (d, J=15.3 Hz, 1H), 2.53 (d, J=18.3 Hz, 1H), 2.32 (s, 3H), 2.26 (s, 3H), 1.98 (s, 3H), 1.79 (dd, $J_1$=12.0 Hz, $J_2$=15.6 Hz, 1H), 1.70 (dd, $J_1$=1.2 Hz, $J_2$=6.6 Hz, 3H).

ESI-MS m/z: Calcd. for $C_{32}H_{36}N_4O_7$: 588.6. Found (M+1)$^+$: 589.3.

Example 73

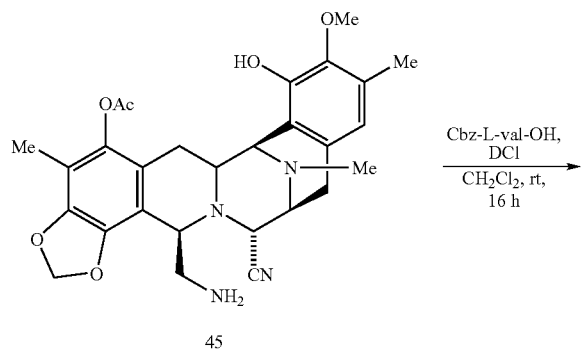

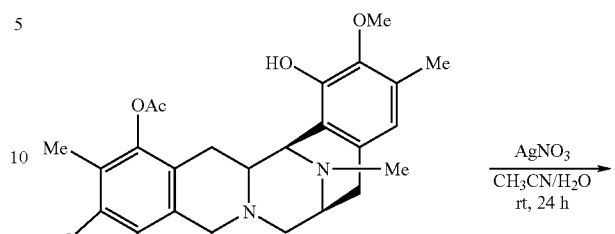

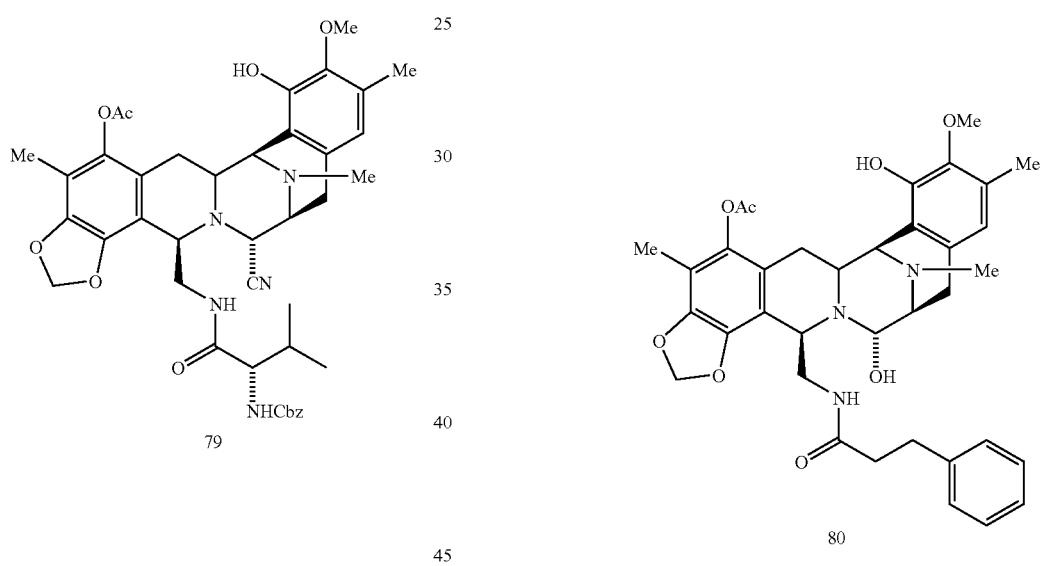

To a solution of 45 (50 mg, 0.096 mmol) in CH$_2$Cl$_2$ (0.5 mL). Cbz-L-Val-OH (24.12 mg, 0.096 mmol) and carbonyl diimidazole (18.7 mg, 0.115 mmol) were added at 0° C. The reaction mixture was stirred for 16 h at room temperature and then, the solution was diluted with CH$_2$Cl$_2$ (15 mL) and washed with 0.1 N HCl (10 mL). The organic layer was dried over Na$_2$SO$_4$, filtered, and the solvent was eliminated under reduced pressure. The residue was purified by flash column chromatography (SiO$_2$, Hex:EtOAc 4:1) to afford 79 (25 mg, 34%) as a white solid.

Rf: 0.7 (EtOAc:MeOH 5:1).

$^1$H NMR (300 MHz, CDCl$_3$) δ 7.33-7.28 (m, 5H), 6.45 (s, 1H), 5.96 (s, 1H), 5.90 (bs, 1H), 5.82 (s, 1H), 5.53 (bs, 1H), 5.09 (bs, 1H), 5.05 (d, J=3.3 Hz, 2H), 4.16 (bs, 1H), 4.09 (d, J=2.4 Hz, 1H), 4.02 (bs, 1H), 3.75 (s, 3H), 3.74 (m, 1H), 3.37-3.35 (m, 2H), 3.26-3.21 (m, 3H), 3.00 (dd, J$_1$=8.1 Hz, J$_2$=18.3 Hz, 1H), 2.77 (d, J=15.6 Hz, 1H), 2.55 (d, J=18.0 Hz, 1H), 2.30 (s, 3H), 2.27 (s, 3H), 2.25 (s, 3H), 1.98 (s, 3H), 1.70-1.66 (m, 1H), 0.65 (d, J=6.6 Hz, 3H).

ESI-MS m/z: Calcd. for C$_{41}$H$_{47}$N$_5$O$_9$: 753.8. Found (M+1)$^+$: 754.2.

Example 74

To a solution of 72 (18 mg, 0.0275 mmol) in CH$_3$CN/H$_2$O (1.5 mL/0.5 mL). AgNO$_3$ (140.5 mg, 0.827 mmol) was added and the reaction was stirred at 23° C. for 24 h. Then, brine (10 mL) and Aq sat NaHCO$_3$ (10 mL) were added at 0° C. and the mixture was stirred for 15 min, filtered through a pad of celite and washed with CH$_2$Cl$_2$ (20 mL). The solution was extracted and the organic layer was dried over Na$_2$SO$_4$, filtered and concentrated in vacuo. The residue was purified by flash column chromatography (SiO$_2$, EtOAc:MeOH 10:1) to afford 80 (13 mg, 74%) as a white solid.

Rf: 0.37 (EtOAc:MeOH 5:1).

$^1$HNMR (300 MHz, CDCl$_3$) δ 7.23-7.11 (m, 3H), 7.06-7.01 (m, 2H), 6.43 (s, 1H), 5.95 (d, J=1.2 Hz, 1H), 5.88 (d, J=1.2 Hz, 1H), 5.71 (bs, 1H), 5.19 (bs, 1H), 4.45 (d, J=3.0 Hz, 1H), 4.37 (bs, 1H), 4.02-3.96 (m, 1H), 3.75-3.68 (m, 2H), 3.48 (s, 3H), 3.41-3.36 (m, 2H), 3.28-3.24 (m, 1H), 3.15 (d, J=7.5 Hz, 1H), 3.01-2.88 (m, 2H), 2.70 (d, J=15.9 Hz, 1H), 2.57-2.51 (m, 2H), 2.31 (s, 3H), 2.27 (s, 3H), 2.00 (s, 6H), 1.77-1.68 (m, 1H).

ESI-MS m/z: Calcd. for C$_{36}$H$_{41}$N$_3$O$_8$: 643.3. Found (M−17)$^+$: 626.2.

Example 75

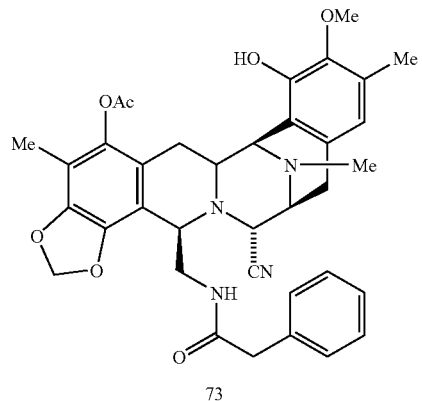

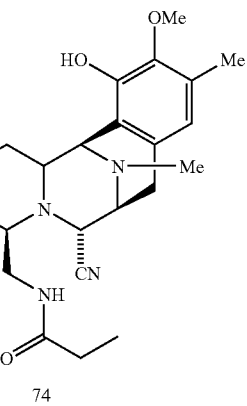

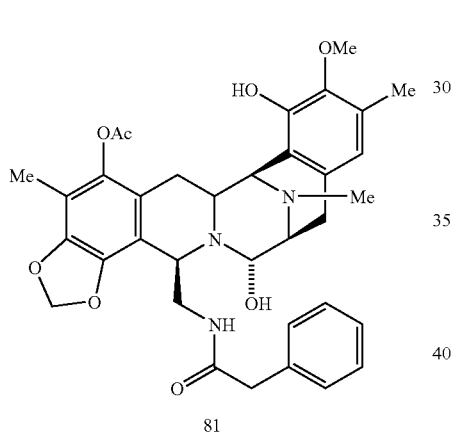

To a solution of 73 (23 mg, 0.036 mmol) in CH$_3$CN/H$_2$O (1.5 mL/1 mL), AgNO$_3$ (183 mg, 1.08 mmol) was added and the reaction was stirred at 23° C. for 24 h. Then, brine (10 mL) and Aq sat NaHCO$_3$ (10 mL) were added at 0° C. and the mixture was stirred for 15 min, filtered through a pad of celite and washed with CH$_2$Cl$_2$ (20 mL). The solution was extracted and the organic layer was dried over Na$_2$SO$_4$, filtered and concentrated in vacuo. The residue was purified by flash column chromatography (SiO$_2$, gradient EtOAc:MeOH 5:1 to MeOH) to afford 81 (9.3 mg, 41%) as a white solid.

Rf: 0.3 (EtOAc:MeOH 5:1).

$^1$HNMR (300 MHz, CDCl$_3$) δ 7.17-7.13 (m, 3H), 6.85 (m, 2H), 6.54 (s, 1H), 5.90 (d, J=1.5 Hz, 1H), 5.84 (d, J=1.5 Hz, 1H), 5.22 (m, 1H), 4.43 (bs, 1H), 4.39 (d, J=2.4 Hz, 1H), 4.00 (d, J=2.4 Hz, 1H), 3.71 (s, 3H), 3.64-3.29 (m, 2H), 3.16 (d, J=8.7 Hz, 1H), 2.98-2.88 (m, 3H), 2.67 (d, J=14.8 Hz, 1H), 2.45 (d, J=18.3 Hz, 1H), 2.33 (s, 3H), 2.28 (s, 3H), 2.22 (s, 3H), 1.97 (s, 3H), 1.68 (dd, J$_1$=12.8 Hz, J$_2$=14.7 Hz, 1H).

ESI-MS m/z: Calcd. for C$_{35}$H$_{39}$N$_3$O$_8$: 629.7. Found (M$^+$–OH): 612.3.

Example 76

To a solution of 74 (20 mg, 0.0346 mmol) in CH$_3$CN/H$_2$O (1.5 mL/1 mL). AgNO$_3$ (176.6 mg, 1.04 mmol) was added and the reaction was stirred at 23° C. for 24 h. Then, brine (10 mL) and Aq sat NaHCO$_3$ (10 mL) were added at 0° C. and the mixture was stirred for 15 min, filtered through a pad of celite and washed with CH$_2$Cl$_2$ (20 mL). The solution was extracted and the organic layer was dried over Na$_2$SO$_4$, filtered and concentrated in vacuo. The residue was purified by flash column chromatography (SiO$_2$, EtOAc:MeOH 1:1) to afford 82 (12.9 mg, 66%) as a white solid.

Rf: 0.3 (EtOAc:MeOH 5:1).

$^1$H NMR (300 MHz, CDCl$_3$) δ 6.50 (s, 1H), 5.95 (d, J=1.2 Hz, 1H), 5.89 (d, J=1.2 Hz, 1H), 5.19 (d, 1H), 4.46 (d, J=3.0 Hz, 1H), 4.38 (d, J=1.8 Hz, 1H), 4.00 (d, J=2.1 Hz, 1H), 3.74 (s, 3H), 3.70-3.66 (m, 1H), 3.38 (dt, J$_1$=2.7 Hz, J$_2$=13.2 Hz, 1H), 3.25 (d, J=13.8 Hz, 1H), 3.16 (d, J=7.5 Hz, 1H), 2.96 (dd, J$_1$=7.2 Hz, J$_2$=17.7 Hz, 1H), 2.71 (d, J=15.6 Hz, 1H), 2.40 (d, J=18.0 Hz, 1H), 2.30 (s, 3H), 2.29 (s, 3H), 2.24 (s, 3H), 1.97 (s, 3H), 1.71 (dd, J$_1$=11.7 Hz, J$_2$=15.3 Hz, 1H), 1.60-1.48 (m, 2H), 0.67 (t, J=7.5 Hz, 3H).

ESI-MS m/z: Calcd. for C$_{30}$H$_{37}$N$_3$O$_8$: 567.6. Found (M–17)$^+$: 550.2.

Example 77

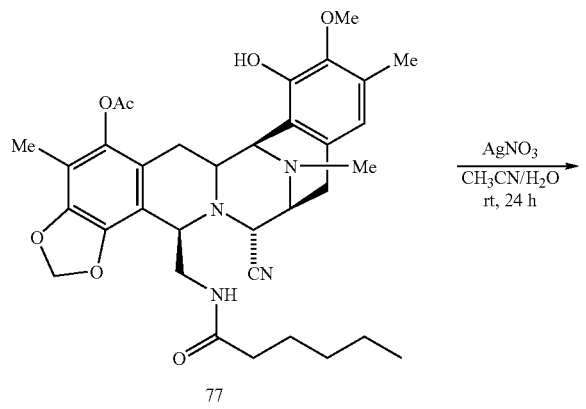

Example 78

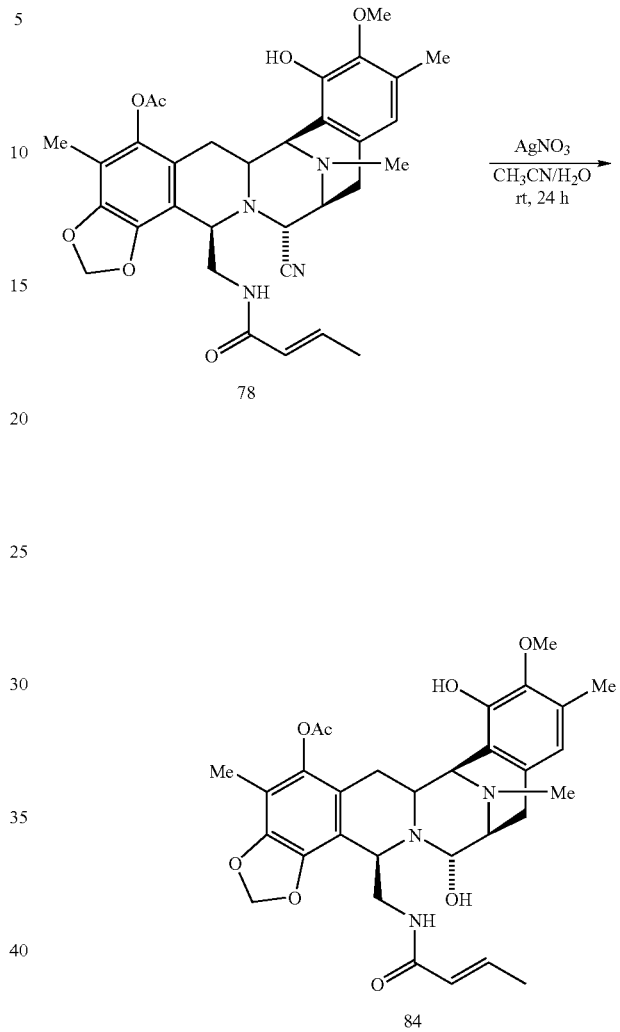

To a solution of 77 (14 mg, 0.0226 mmol) in CH$_3$CN/H$_2$O (1.5 mL/1 mL). AgNO$_3$ (115.3 mg, 0.68 mmol) was added and the reaction was stirred at 23° C. for 24 h. Then, brine (10 mL) and Aq sat NaHCO$_3$ (10 mL) were added at 0° C. and the mixture was stirred for 15 min, filtered through a pad of celite and washed with CH$_2$Cl$_2$ (15 mL). The solution was extracted and the organic layer was dried over Na$_2$SO$_4$, filtered and concentrated in vacuo. The residue was purified by flash column chromatography (SiO$_2$, EtOAc:MeOH 5:1) to afford 83 (9 mg, 65%) as a white solid.

Rf: 0.25 (EtOAc:MeOH 5:1).

$^1$H NMR (300 MHz, CDCl$_3$) δ 6.50 (s, 1H), 5.96 (d, J=1.5 Hz, 1H), 5.89 (d, J=1.5 Hz, 1H), 5.73 (bs, 1H), 4.44 (d, J=3.6 Hz, 1H), 4.37 (s, 1H), 4.01 (d, J=2.4 Hz, 1H), 3.77 (s, 3H), 3.73-3.64 (m, 1H), 3.39 (dt, J$_1$=3.0 Hz, J$_2$=9.3 Hz, 1H), 3.22 (d, J=14.5 Hz, 1H), 3.16 (d, J=7.5 Hz, 1H), 2.95 (dd, J$_1$=8.1 Hz, J$_2$=17.4 Hz, 1H), 2.70 (d, J=14.5 Hz, 1H), 2.41 (d, J=18.3 Hz, 1H), 2.30 (s, 3H), 2.29 (s, 3H), 2.25 (s, 3H), 1.96 (s, 3H), 1.71 (dd, J$_1$=12.0 Hz, J$_2$=15.6 Hz, 1H), 1.48-1.46 (m, 2H), 1.24-1.10 (m, 4H), 1.00-0.95 (m, 2H), 0.80 (t, J=7.2 Hz, 3H).

ESI-MS m/z: Calcd. for C$_{33}$H$_{43}$N$_3$O$_8$: 609.7. Found (M−17)$^+$: 592.3.

To a solution of 78 (15 mg, 0.025 mmol) in CH$_3$CN/H$_2$O (1.5 mL/1 mL). AgNO$_3$ (130 mg, 0.764 mmol) was added and the reaction was stirred at 23° C. for 24 h. Then, brine (10 mL) and Aq sat NaHCO$_3$ (10 mL) were added at 0° C. and the mixture was stirred for 15 min, filtered through a pad of celite and washed with CH$_2$Cl$_2$ (15 mL). The solution was extracted and the organic layer was dried over Na$_2$SO$_4$, filtered and concentrated in vacuo. The residue was purified by flash column chromatography (SiO$_2$, gradient EtOAc to EtOAc:MeOH 1:1) to afford 84 (10 mg, 71%) as a white solid.

Rf: 0.19 (EtOAc:MeOH 5:1).

$^1$H NMR (300 MHz, CDCl$_3$) δ 6.49 (s, 1H), 6.47-6.37 (m, 1H), 5.94 (d, J=1.5 Hz, 1H), 5.88 (d, J=1.5 Hz, 1H), 5.77 (bs, 1H), 5.26 (d, J=5.7 Hz, 1H), 4.93 (d, J=14.7 Hz, 1H), 4.48 (d, J=11.1 Hz, 1H), 4.38 (d, J=2.7 Hz, 1H), 4.02 ((d, J=2.1 Hz, 1H), 3.79 (s, 3H), 3.76-3.72 (m, 1H), 3.42 (dt, J$_1$=2.7 Hz, J$_2$=12.0 Hz, 1H), 3.28 (d, J=13.2 Hz, 1H), 3.15 (d, J=6.6 Hz, 1H), 2.96 (dd, J$_1$=8.7 Hz, J$_2$=18.0 Hz, 1H), 2.70 (d, J=15.0 Hz, 1H), 2.38 (d, J=18.0 Hz, 1H), 2.30 (s, 3H), 2.28 (s, 3H), 1.95 (s, 3H), 1.72 (dd, J$_1$=12.3 Hz, J$_2$=17.4 Hz, 1H), 1.98 (dd, J$_1$=1.5 Hz, J$_2$=6.9 Hz, 3H).

ESI-MS m/z: Calcd. for C$_{31}$H$_{37}$N$_3$O$_8$: 579.6. Found (M−17)$^+$: 562.3.

Example 79

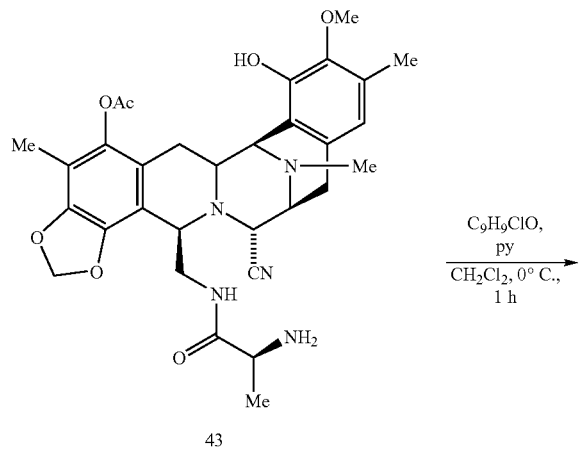

Example 80

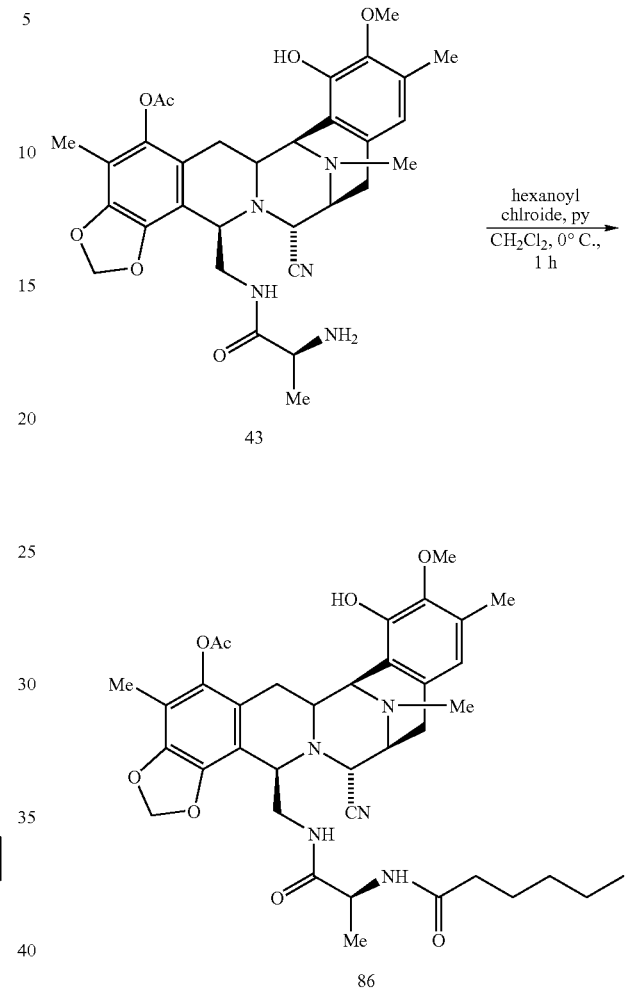

To a solution of 43 (25 mg, 0.422 mmol) in CH$_2$Cl$_2$ (0.3 mL), hydrocinnamoyl chloride (6.27 µL, 0.422 mmol) and pyridine (3.41 µL, 0.422 mmol) were added at 0° C. The reaction mixture was stirred for 1 h and then, the solution was diluted with CH$_2$Cl$_2$ (10 mL) and washed with 0.1 N HCl (5 mL). The organic layer was dried over Na$_2$SO$_4$, filtered, and the solvent was eliminated under reduced pressure. The residue was purified by flash column chromatography (SiO$_2$, gradient Hex:EtOAc 4:1 to EtOAc) to afford 85 (30 mg, 68%) as a white solid.

Rf: 0.54 (EtOAcMeOH 10:1).

$^1$H NMR (300 MHz, CDCl$_3$) δ 7.28-7.14 (m, 5H), 6.45 (s, 1H), 6.07 (brd, 1H), 5.99 (d, J=1.2 Hz, 1H), 5.90 (d, J=1.2 Hz, 1H), 5.88 (s, 1H), 5.31 (brt, 1H), 4.09-4.06 (m, 3H), 3.80-3.75 (m, 1H), 3.73 (s, 3H), 3.57-3.51 (m, 2H), 3.38 (d, J=7.5 Hz, 1H), 3.24 (m, 1H), 3.00 (dd, J$_1$=8.4 Hz, J$_2$=18.0 Hz, 1H), 2.89-2.85 (m, 2H), 2.79 (d, J=16.5 Hz, 1H), 2.61 (d, J=18.0 Hz, 1H), 2.31 (s, 3H), 2.28 (s, 3H), 2.22 (s, 3H), 2.00 (s, 3H), 1.79 (dd, J$_1$=12.3 Hz, J$_2$=16.2 Hz, 1H), 0.72 (d, J=6.6 Hz, 3H).

ESI-MS m/z: Calcd. for C$_{40}$H$_{45}$N$_5$O$_8$: 723.8. Found (M+23)$^+$: 746.3.

To a solution of 43 (20 mg, 0.0338 mmol) in CH$_2$Cl$_2$ (0.25 mL), hexanoyl chloride (4.72 µL, 0.0338 mmol) and pyridine (2.73 µL, 0.0338 mmol) were added at 0° C. The reaction mixture was stirred for 1 h and then, the solution was diluted with CH$_2$Cl$_2$ (10 mL) and washed with 0.1 N HCl (5 mL). The organic layer was dried over Na$_2$SO$_4$, filtered, and the solvent was eliminated under reduced pressure. The residue was purified by flash column chromatography (SiO$_2$, gradient Hex: EtOAc 1:1 to EtOAc) to afford 86 (10 mg, 43%) as a white solid.

Rf: 0.74 (EtOAc:MeOH 10:1).

$^1$H NMR (300 MHz, CDCl$_3$) δ 6.47 (s, 1H), 6.12 (brd, 1H), 6.00 (d, J=1.2 Hz, 1H), 5.91 (d, J=1.2 Hz, 1H), 5.30 (m, 1H), 4.09-3.99 (m, 3H), 3.84-3.82 (m, 1H), 3.75 (s, 3H), 3.57-3.55 (m, 2H), 3.39 (d, J=6.9 Hz, 1H), 3.24 (d, J=12.0 Hz, 1H), 3.04 (dd, J$_1$=9.0 Hz, J$_2$=18.3 Hz, 1H), 2.77 (d, J=115.3 Hz, 1H), 2.63 (d, J=18.0 Hz, 1H), 2.32 (s, 3H), 2.28 (s, 3H), 2.25 (s, 3H), 2.00 (s, 3H), 1.80 (dd, J$_1$=11.7 Hz, J$_2$=15.6 Hz, 1H), 1.55-1.50 (m, 2H), 1.30-1.22 (m, 6H), 0.87 (t, J=6.9 Hz, 3H), 0.75 (d, J=6.6 Hz, 3H).

ESI-MS m/z: Calcd. for C$_{37}$H$_{47}$N$_5$O$_8$: 689.8. Found (M+1)$^+$: 690.3.

Example 81

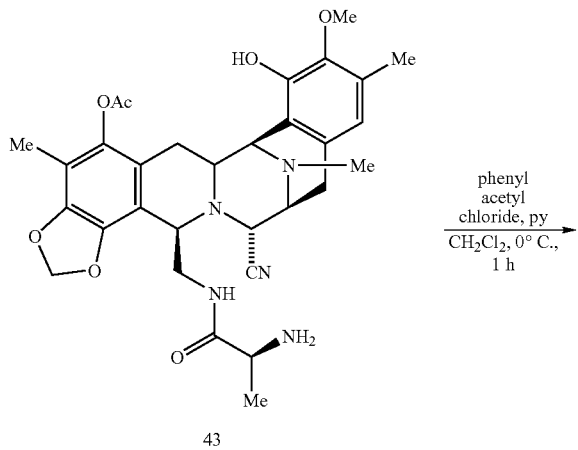

Example 82

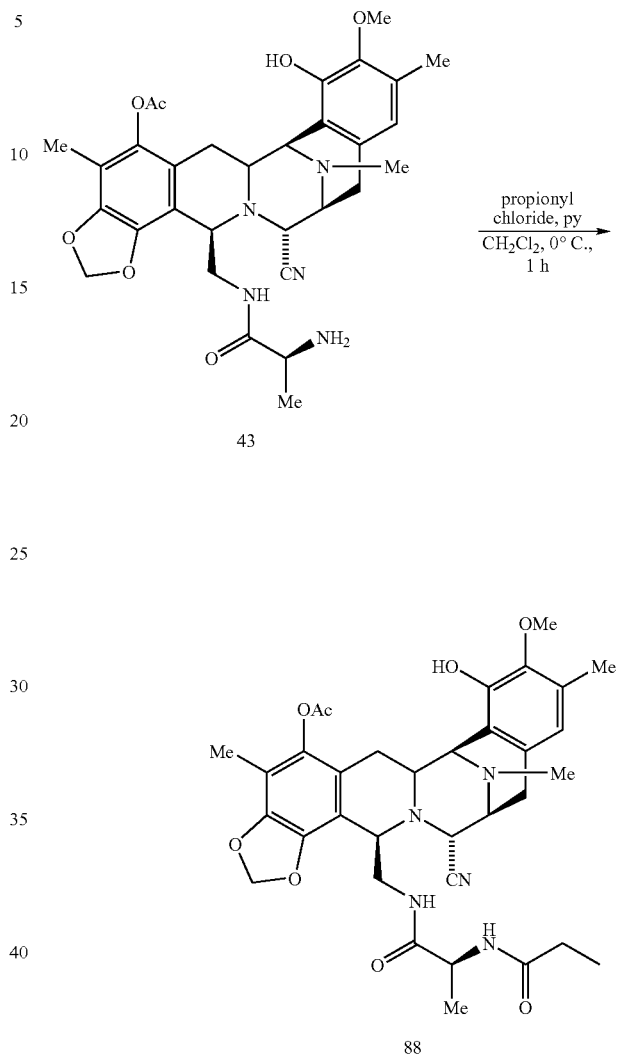

To a solution of 43 (33 mg, 0.0557 mmol) in $CH_2Cl_2$ (0.4 mL), phenyl acetyl chloride (7.36 µL, 0.0557 mmol) and pyridine (4.5 µL, 0.0557 mmol) were added at 0° C. The reaction mixture was stirred for 1 h and then, the solution was diluted with $CH_2Cl_2$ (10 mL) and washed with 0.1 N HCl (5 mL). The organic layer was dried over $Na_2SO_4$, filtered, and the solvent was eliminated under reduced pressure. The residue was purified by flash column chromatography ($SiO_2$, gradient Hex:EtOAc 2:1) to afford 87 (13 mg, 32%) as a white solid.

Rf: 0.63 (Hex:EtOAc:MeOH 5:10:2).

$^1$H NMR (300 MHz, $CDCl_3$) δ 7.37-7.20 (m, 5H), 6.26 (s, 1H), 6.14 (d, J=6.6 Hz, 1H), 5.98 (d, J=1.2 Hz, 1H), 5.83 (s, 1H), 5.27 (t, J=6.2 Hz, 1H), 4.11 (d, J=2.1 Hz, 1H), 4.07 (d, J=3.0 Hz, 1H), 4.04 (s, 1H), 3.86-3.81 (m, 1H), 3.70 (s, 3H), 3.54-3.53 (m, 2H), 3.44 (bs, 2H), 3.36 (d, J=8.1 Hz, 1H), 3.22 (dt, $J_1$=2.7 Hz, $J_2$=12.0 Hz, 1H), 2.93 (dd, $J_1$=7.2 Hz, $J_2$=18.3 Hz, 1H), 2.77 (d, J=14.4 Hz, 1H), 2.59 (d, J=18.0 Hz, 1H), 2.31 (s, 3H), 2.26 (s, 3H), 2.17 (s, 3H), 2.01 (s, 3H), 1.78 (dd, $J_1$=10.8 Hz, $J_2$=15.6 Hz, 1H), 0.65 (d, J=6.3 Hz, 1H).

ESI-MS m/z: Calcd. for $C_{39}H_{43}N_5O_8$: 709.8. Found (M+1)$^+$: 710.3.

To a solution of 43 (30 mg, 0.05 mmol) in $CH_2Cl_2$ (0.3 mL), propionyl chloride (4.40 µL, 0.05 mmol) and pyridine (4.04 µL, 0.05 mmol) were added at 0° C. The reaction mixture was stirred for 1 h and then, the solution was diluted with $CH_2Cl_2$ (15 mL) and washed with 0.1 N HCl (10 mL). The organic layer was dried over $Na_2SO_4$, filtered, and the solvent was eliminated under reduced pressure. The residue was purified by flash column chromatography ($SiO_2$, gradient Hex: EtOAc 1:1 to EtOAc) to afford 88 (18 mg, 56%) as a white solid.

Rf: 0.49 (Hex:EtOAc:MeOH 1:10:2).

$^1$H NMR (300 MHz, $CDCl_3$) δ 6.46 (s, 1H), 6.16 (brd, 1H), 5.99 (d, J=1.2 Hz, 1H), 5.95 (s, 1H), 5.90 (d, J=1.2 Hz, 1H), 5.34 brt, 1H), 4.12-4.06 (m, 3H), 3.84 (bs, 1H), 3.74 (s, 3H), 3.63 (dd, $J_1$=6.3 Hz, $J_2$=12.9 Hz, 1H), 3.50-3.48 (m, 1H), 3.39 (d, J=8.1 Hz, 1H), 3.23 (d, J=11.7 Hz, 1H), 3.00 (dd, $J_1$=8.4 Hz, $J_2$=18.3 Hz, 1H), 2.78 (d, J=15.6 Hz, 1H), 2.63 (d, J=18.3 Hz, 1H), 2.31 (s, 3H), 2.27 (s, 3H), 1.87-1.80 (m, 1H), 1.06 (t, J=7.5 Hz, 3H), 0.74 (d, J=6.9 Hz, 3H).

ESI-MS m/z: Calcd; for $C_{34}H_{41}N_5O_8$: 647.7. Found (M+1)$^+$: 648.2.

Example 83

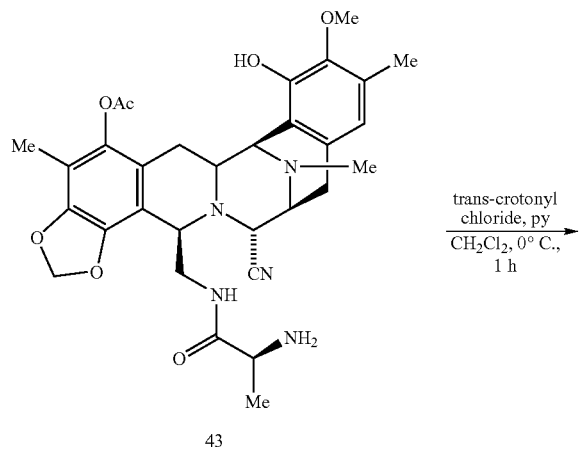

Example 84

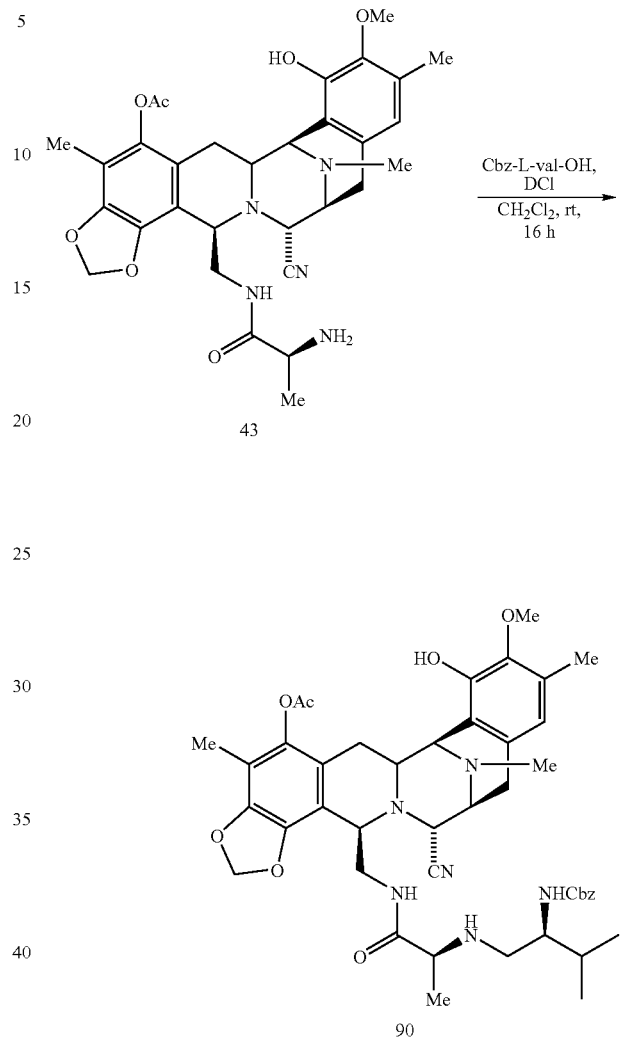

To a solution of 43 (20 mg, 0.0338 mmol) in CH$_2$Cl$_2$ (0.3 mL), propionyl chloride (3.238 μL, 0.0338 mmol) and pyridine (2.73 μL, 0.0338 mmol) were added at 0° C. The reaction mixture was stirred for 1 h and then, the solution was diluted with CH$_2$Cl$_2$ (10 mL) and washed with 0.1 N HCl (5 mL). The organic layer was dried over Na$_2$SO$_4$, filtered, and the solvent was eliminated under reduced pressure. The residue was purified by flash column chromatography (SiO$_2$, gradient Hex:EtOAc 3:1 to AcOEt) to afford 89 (11.5 mg, 52%) as a white solid.

Rf: 0.57 (EtOAc:MeOH 10:1).

$^1$H NMR (300 MHz, CDCl$_3$) δ 6.82-6.70 (m, 1H), 6.46 (s, 1H), 6.11 (d, 1H), 6.00 (d, J=1.5 Hz, 1H), 5.89 (d, J=1.5 Hz, 1H), 5.85 (s, 1H), 5.77 (dd, J$_1$=1.5 Hz, J$_2$=15.3 Hz, 1H), 5.37 (bst, 1H), 4.13-4.06 (m, 3H), 3.19 (m, 1H), 3.73 (s, 3H), 3.55 (m, 2H), 3.38 (d, J=1.5 Hz, 1H), 3.23 (d, J=11.4 Hz, 1H), 3.00 (dd, J$_1$=8.4 Hz, J$_2$=18.3 Hz, 1H), 2.78 (d, J=15.0 Hz, 1H), 2.65 (d, J=18.0 Hz, 1H), 2.31 (s, 3H), 2.28 (s, 3H), 2.22 (s, 3H), 2.00 (s, 3H), 1.85-1.82 (m, 4H), 0.77 (d, J=6.3 Hz, 3H).

ESI-MS m/z: Calcd. for C$_{35}$H$_{41}$N$_5$O$_8$: 659.7. Found (M+1)$^+$: 660.3.

To a solution of 43 (15 mg, 0.0253 mmol) in CH$_2$Cl$_2$ (0.3 mL) Cbz-L-Val-OH (6.39 mg, 0.0253 mmol) and carbonyl diimidazole (4.86 mg, 0.03 mmol) were added at 0° C. The reaction mixture was stirred for 16 h at room temperature and then, the solution was diluted with CH$_2$Cl$_2$ (15 mL) and washed with 0.1 N HCl (10 mL). The organic layer was dried over Na$_2$SO$_4$, filtered, and the solvent was eliminated under reduced pressure. The residue was purified by flash column chromatography (SiO$_2$, gradient Hex:EtOAc 1:1 to EtOAc) to afford 90 (6.7 mg, 32%) as a white solid.

Rf: 0.79 (EtOAc:MeOH 5:1).

$^1$H NMR (300 MHz, CDCl$_3$) δ 7.35 ms, 5H), 6.46 (s, 1H), 6.28 (d, J=6.0 Hz, 1H), 5.98 (d, J=1.2 Hz, 1H), 5.89 (d, J=1.2 Hz, 1H), 5.77 (s, 1H), 5.44 (bs, 1H), 5.30 (bs, 1H), 5.08 (s, 2H), 4.09-4.06 (m, 3H), 3.94-3.89 (m, 1H), 3.70-3.66 (m, 5H), 3.38 (d, J=11.7 Hz, 1H), 3.01 96 (dd, J$_1$=7.8 Hz, J$_2$=18.3 Hz, 1H), 2.79 (d, J=14.1 Hz, 1H), 2.63 (d, J=18.0 Hz, 1H), 2.30 (s, 3H), 2.28 (s, 3H), 2.20 (s, 3H), 1.99 (s, 3H9, 1.97-1.81 (m, 2H), 0.83 (d, J=6.6 Hz, 3H), 0.80 (d, J=6.6 Hz, 3H), 0.75 (d, J=6.9 Hz, 3H).

ESI-MS m/z: Calcd. for C$_{44}$H$_{52}$N$_6$O$_{10}$: 824.9. Found (M+1)$^+$: 825.4.

Example 85

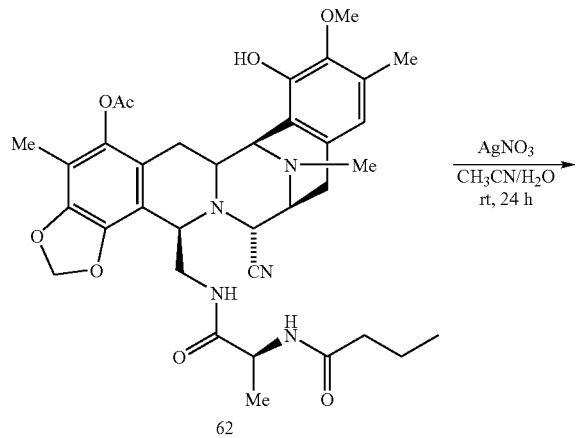

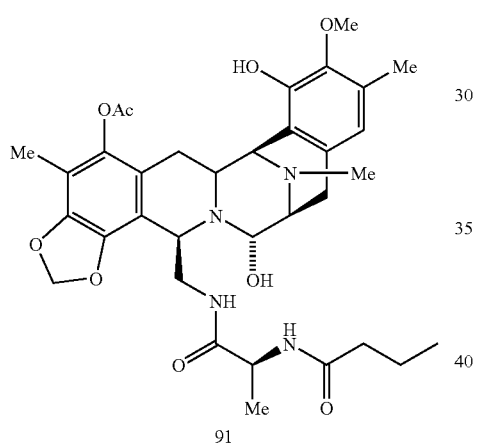

To a solution of 62 (20 mg, 0.030 mmol) in CH₃CN/H₂O (1.5 mL/1 mL). AgNO₃ (154 mg, 0.90 mmol) was added and the reaction was stirred at 23° C. for 24 h. Then, brine (10 mL) and Aq sat NaHCO₃ (10 mL) were added at 0° C. and the mixture was stirred for 15 min, filtered through a pad of celite and washed with CH₂Cl₂ (15 mL). The solution was extracted and the organic layer was dried over Na₂SO₄, filtered and concentrated in vacuo. The residue was purified by flash column chromatography (SiO₂, gradient EtOAc to EtOAc: MeOH 3:1) to afford 91 (13 mg, 66%) as a white solid.

Rf: 0.18 (EtOAc:MeOH 10:1).

$^1$H NMR (300 MHz, CDCl₃) δ 6.49 (s, 1H), 6.16 (d, 1H), 5.98 (d, J=1.5 Hz, 1H), 5.89 (d, J=1.5 Hz, 1H), 5.32 (bs, 1H), 4.41 (bs, 1H), 4.00 (bs, 1H), 3.79 (s, 3H), 3.70-3.65 (m, 2H), 3.37-3.32 (m, 2H), 3.19-3.17 (m, 1H), 2.94 (dd, J$_1$=9.0 Hz, J$_2$=15.0 Hz, 1H), 2.74 (d, J=15.9 Hz, 1H), 2.46 (d, J=17.1 Hz, 1H), 2.31 (s, 3H), 2.28 (s, 3H), 2.27 (s, 3H), 2.04-2.01 (m, 2H), 1.98 (s, 3H), 1.64-1.62 (m, 1H), 1.54-1.52 (m, 2H), 0.89-0.84 (m, 6H).

ESI-MS m/z: Calcd. for C₃₄H₄₄N₄O₉: 652.7. Found (M−17)⁺: 635.3.

Example 86

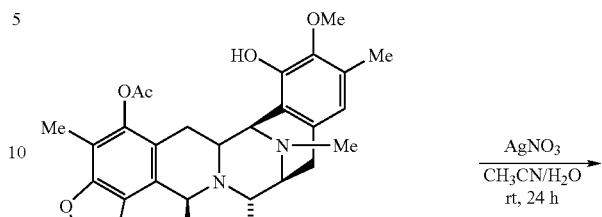

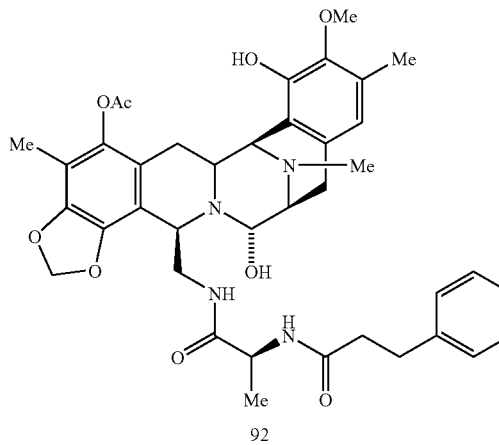

To a solution of 85 (10 mg, 0.0138 mmol) in CH₃CN/H₂O (1.5 mL/1 mL), AgNO₃ (70.4 mg, 0.414 mmol) was added and the reaction was stirred at 23° C. for 24 h. Then, brine (10 mL) and Aq sat NaHCO₃ (10 mL) were added at 0° C. and the mixture was stirred for 15 min, filtered through a pad of celite and washed with CH₂Cl₂ (15 mL). The solution was extracted and the organic layer was dried over Na₂SO₄, filtered and concentrated in vacuo. The residue was purified by flash column chromatography (SiO₂, gradient EtOAc to EtOAc: MeOH 4:1) to afford 92 (7 mg, 71%) as a white solid.

Rf: 0.20 (EtOAc:MeOH 5:1).

$^1$H NMR (300 MHz, CDCl₃) δ 7.25-7.13 (m, 5H), 6.47 (s, 1H), 6.13 (brd, 1H), 5.97 (d, J=1.2 Hz, 1H), 5.88 (d, 3=1.2 Hz, 1H), 5.34 (brt, 1H), 4.50 (bs, 1H), 4.40 (bs, 1H), 4.00 (bs, 1H), 3.76 (s, 3H), 3.70-3.65 (m, 3H), 3.34 (d, J=11.7 Hz, 1H), 3.17 (d, J=5.1 Hz, 1H), 2.98-2.83 (m, 3H), 2.72 (d, J=14.4 Hz, 1H), 2.44 (d, J=19.2 Hz, 1H), 2.30 (s, 3H), 2.27 (s, 6H), 1.97 (s, 3H), 1.72 (m, 1H), 0.82 (d, J=6.6 Hz, 3H).

ESI-MS m/z: Calcd. for C₃₉H₄₆N₄O₉: 714.8. Found (M−17)⁺: 697.3.

Example 87

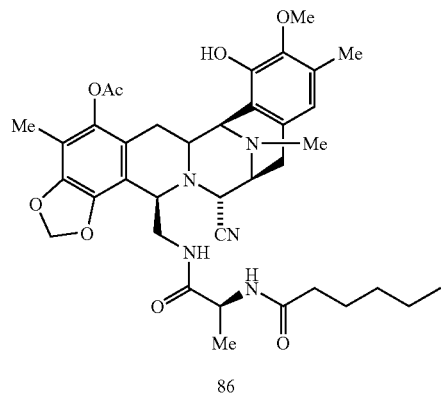

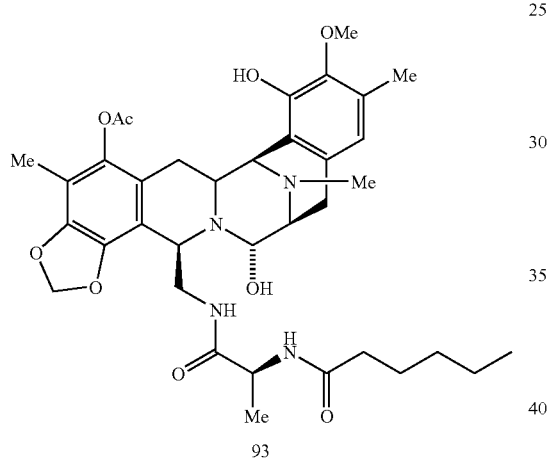

Example 88

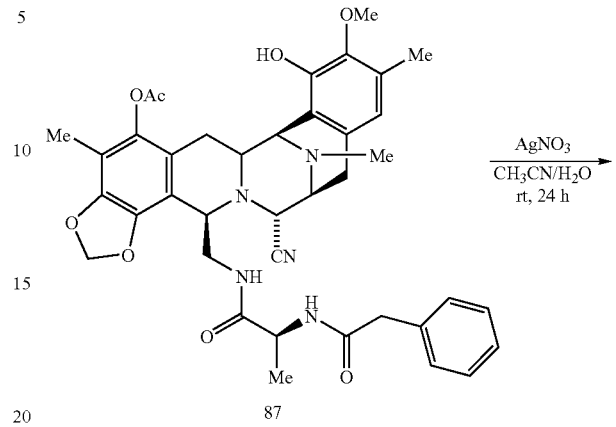

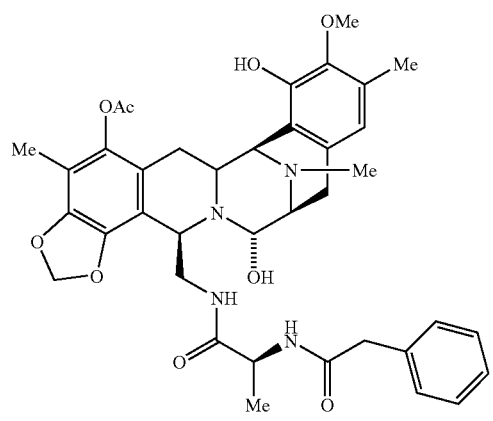

To a solution of 86 (6 mg, 0.0087 mmol) in CH$_3$CN/H$_2$O (1.5 mL/1 mL). AgNO$_3$ (44 mg, 0.26 mmol) was added and the reaction was stirred at 23° C. for 24 h. Then brine (10 mL) and Aq sat NaHCO$_3$ (10 mL) were added at 0° C. and the mixture was stirred for 15 min. filtered through a pad of celite and washed with CH$_2$Cl$_2$ (15 mL). The solution was extracted and the organic layer was dried over Na$_2$SO$_4$, filtered and concentrated in vacuo. The residue was purified by flash column chromatography (SiO$_2$, gradient EtOAc to EtOAc: MeOH 5:1) to afford 93 (5 mg, 85%) as a white solid.

Rf: 0.018 (EtOAc:MeOH 5:1).

$^1$H NMR (300 MHz, CDCl$_3$) δ 6.48 (s, 1H), 6.17 (d, 1H), 5.98 (d, J=1.5 Hz, 1H)) 5.89 (d, J=1.5 Hz, 1H), 5.33 (bs, 1H), 4.51 (d, 1H), 4.40 (d, 1H), 4.00 (d, 1H), 3.78 (s, 3H), 3.76-3.65 (m, 2H), 3.36-3.32 (m, 2H), 3.18 (d, J=6.9 Hz, 1H), 2.98-2.89 (m, 1H), 2.71 (d, J=15.0 Hz, 1H), 2.45 (d, J=17.7 Hz, 1H), 2.31 (s, 3H), 2.27 (s, 3H), 2.26 (s, 3H), 1.98 (s, 3H), 1.68-1.50 (m, 3H), 1.29-1.19 (m, 6H), 0.88-0.84 (m, 6H).

ESI-MS m/z: Calcd. for C$_{36}$H$_{48}$N$_4$O$_9$: 680.7. Found (M−17)$^+$: 663.3.

To a solution of 87 (12 mg, 0.0169 mmol) in CH$_3$CN/H$_2$O (1.5 mL/1 mL), AgNO$_3$ (86 mg, 0.507 mmol) was added and the reaction was stirred at 23° C. for 24 h. Then, brine (10 mL) and Aq sat NaHCO$_3$ (10 mL) were added at 0° C. and the mixture was stirred for 15 min, filtered through a pad of celite and washed with CH$_2$Cl$_2$ (15 mL). The solution was extracted and the organic layer was dried over Na$_2$SO$_4$, filtered and concentrated in vacuo. The residue was purified by flash column chromatography (SiO$_2$, gradient EtOAc to EtOAc: MeOH 5:1) to afford 94 (8.8 mg, 74%) as a white solid.

Rf: 0.28 (EtOAc:MeOH 5:1).

$^1$H NMR (300 MHz, CDCl$_3$) δ 7.34-7.18 (m, 5H), 6.37 (s, 1H), 6.20 (d, 1H), 5.96 (d, J=1.5 Hz, 1H), 5.88 (d, J=1.5 Hz, 1H), 5.30 (t, 1H), 4.50 (bs, 1H), 4.39 (d, J=1.8 Hz, 1H), 3.99 (d, J=2.1 Hz, 1H), 3.73 (s, 3H), 3.69-3.60 (m, 3H), 3.37-3.30 (m, 3H), 3.17 (d, J=18.1 Hz, 1H), 2.89 (dd, J$_1$=7.5 Hz, J$_2$=18.3 Hz, 1H), 2.31 (s, 3H), 2.25 (s, 3H), 2.21 (s, 3H), 1.99 (s, 3H), 1.71 (dd, J$_1$=11.7 Hz, J$_2$=15.0 Hz, 1H), 0.77 (d, J=6.6 Hz, 1H).

ESI-MS m/z: Calcd. for C$_{38}$H$_{44}$N$_4$O$_9$: 700.7. Found (M−17)$^+$: 683.2.

Example 89

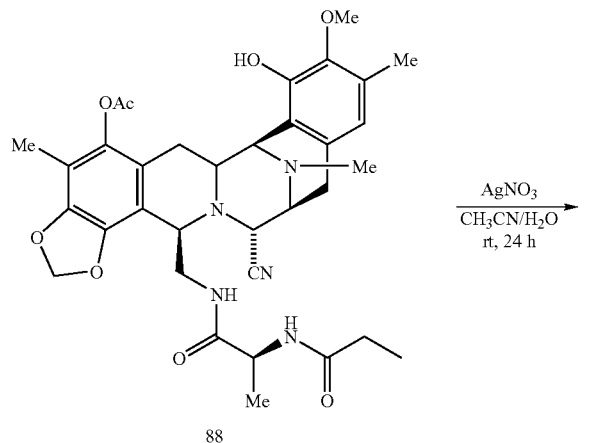

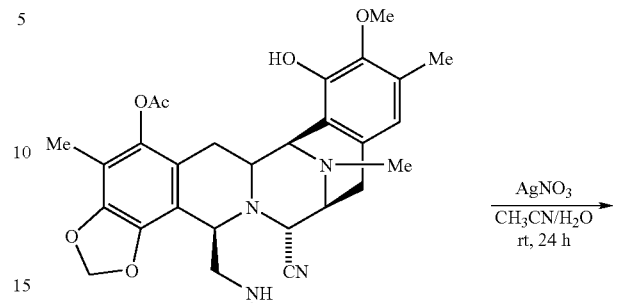

Example 90

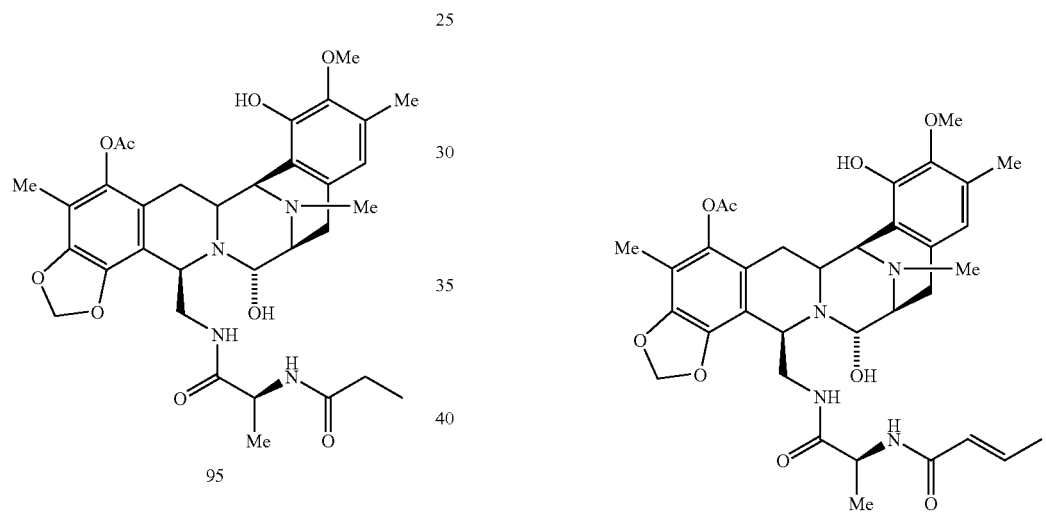

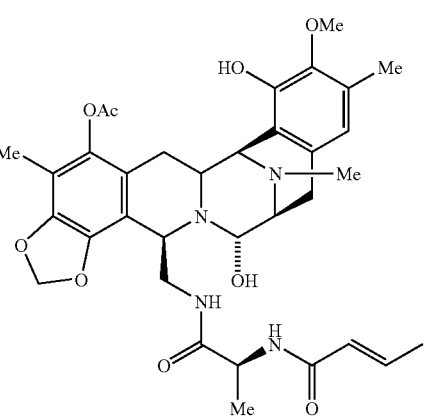

To a solution of 88 (14 mg, 0.0216 mmol) in CH₃CN/H₂O (1.5 mL/1 mL). AgNO₃ (110 mg, 0.648 mmol) was added and the reaction was stirred at 23° C. for 24 h. Then, brine (10 mL) and Aq sat NaHCO₃ (10 mL) were added at 0° C. and the mixture was stirred for 15 min, filtered through a pad of celite and washed with CH₂Cl₂ (15 mL). The solution was extracted and the organic layer was dried over Na₂SO₄, filtered and concentrated in vacuo. The residue was purified by flash column chromatography (SiO₂, gradient EtOAc to EtOAc: MeOH 5:1) to afford 95 (9.7 mg, 70%) as a white solid.

Rf: 0.16 (EtOAc:MeOH 5:1).

$^1$H NMR (300 MHz, CDCl₃) δ 6.48 (s, 1H), 6.10 (d, 1H), 5.97 (d, J=1.2 Hz, 1H), 5.89 (d, J=1.2 Hz, 1H), 5.36 (bs, 1H), 4.51 (bs, 1H), 4.40 (d, J=2.1 Hz, 1H), 4.00 (d, J=2.1 Hz, 1H), 3.78 (s, 3H), 3.76-3.62 (m, 3H), 3.33 (d, J=11.7 Hz, 1H), 3.18 (d, J=8.4 Hz, 1H), 2.94 (dd, $J_1$=8.4 Hz, $J_2$=16.5 Hz, 1H), 2.72 (d, J=15.0 Hz, 1H), 2.45 (d, J=18.3 Hz, 1H), 2.31 (s, 3H), 2.27 (s, 3H), 2.22 (s, 3H), 1.97 (s, 3H), 1.86 (m, 2H), 1.73 (dd, $J_1$=12.0 Hz, J=15.0 Hz, 1H), 1.05 (t, J=7.8 Hz, 3H), 0.83 (d, J=6.9 Hz, 3H).

ESI-MS m/z: Calcd. for C₃₃H₄₂N₄O₉: 638.7. Found (M−17)⁺: 621.2.

To a solution of 89 (10 mg, 0.015 mmol) in CH₃CN/H₂O (1.5 mL/1 mL). AgNO₃ (77.2 mg, 0.454 mmol) was added and the reaction was stirred at 23° C. for 24 h. Then, brine (10 mL) and Aq sat NaHCO₃ (10 mL) were added at 0° C. and the mixture was stirred for 15 min, filtered through a pad of celite and washed with CH₂Cl₂ (15 mL). The solution was extracted and the organic layer was dried over Na₂SO₄, filtered and concentrated in vacuo. The residue was purified by flash column chromatography (SiO₂, gradient EtOAc to EtOAc: MeOH 1:1) to afford 96 (9 mg, 92%) as a white solid.

Rf: 0.016 (EtOAc:MeOH 5:1).

$^1$H NMR (300 MHz, CDCl₃) δ 6.76-6.69 (m, 1H), 6.47 (s, 1H), 6.18 (brd, 1H), 5.97 (d, J=1.5 Hz, 1H), 5.88 (d, J=1.5 Hz, 1H), 5.71 (dd, $J_1$=1.5 Hz, $J_2$=16.2 Hz, 3H), 5.32 (bs, 1H), 4.50 (m, 1H), 4.41 (m, 1H), 3.99 (m, 1H), 3.78 (m, 4H), 3.64-3.58 (m, 2H), 3.34 (d, J=11.1 Hz, 1H), 3.17 (d, J=8.6 Hz, 1H), 2.95 (dd, $J_1$=7.5 Hz, $J_2$=17.4 Hz, 1H), 2.70 (d, J=16.2 Hz, 1H), 2.48 (d, J=17.7 Hz, 1H), 2.31 (s, 3H), 2.27 (s, 3H), 2.17 (s, 6H), 1.97 (s, 3H), 1.82-1.74 (m, 4H), 0.88 (t, J=5.2 Hz, 3H).

ESI-MS m/z: Calcd. for C₃₄H₄₂N₄O₉: 650.7. Found (M−17)⁺: 633.3.

Example 91

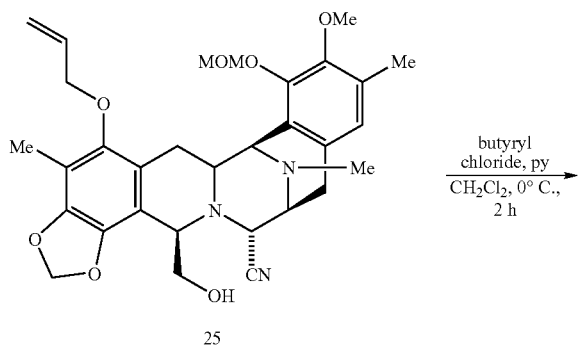

Example 92

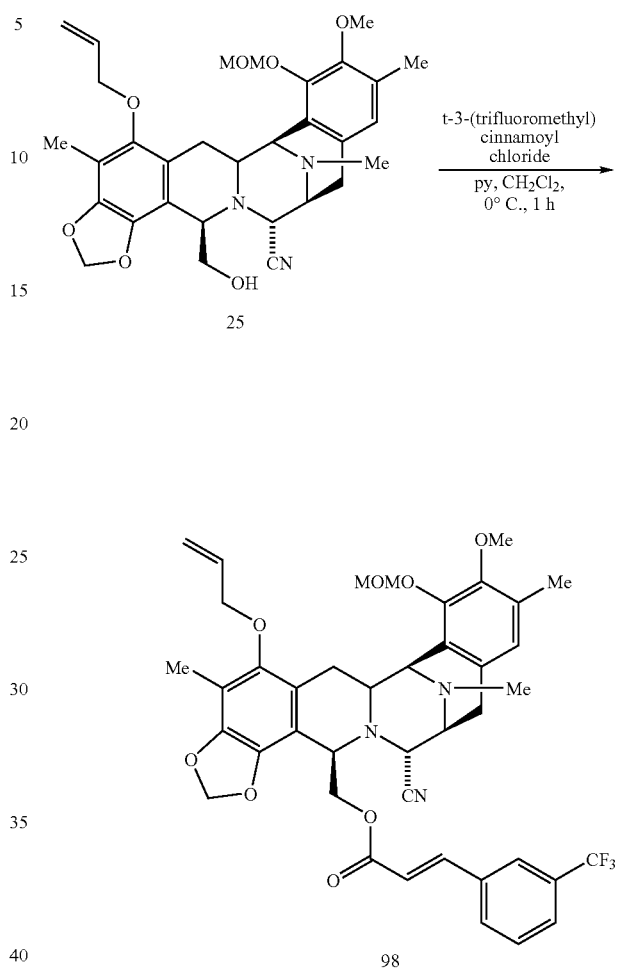

To a solution of 25 (100 mg, 0.177 mmol) in CH$_2$Cl$_2$ (0.5 mL), butyryl chloride (24 µL, 0.23 mmol) and pyridine (17 Lµ, 0.212 mmol) were added at 0° C. The reaction mixture was stirred for 2 h at room temperature and then, the solution was diluted with CH$_2$Cl$_2$ (30 mL) and washed with 0.1 N HCl (20 mL). The organic layer was dried over Na$_2$SO$_4$, filtered, and the solvent was eliminated under reduced pressure. The residue was purified by flash column chromatography (SiO$_2$, Hex:EtOAc 3:1) to afford 97 (99 mg, 88%) as a colorless oil.

Rf: 0.64 (Hex:EtOAc 1:1).

$^1$H NMR (300 MHz, CDCl$_3$) δ 6.66 (s, 1H), 6.16-6.05 (m, 1H), 5.93 (d, J=1.2 Hz, 1H), 5.87 (d, J=1.2 Hz, 1H), 5.40 (dd, J$_1$=1.2 Hz, J$_2$=17.1 Hz, 1H), 5.26 (dd, J$_1$=1.2 Hz, J$_2$=10.2 Hz, 1H), 5.13-5.08 (m, 2H), 4.44 (dd, J$_1$=3.6 Hz, J$_2$=11.1 Hz, 1H), 4.21-4.07 (m, 5H), 3.74 (m, 1H), 3.72 (s, 1H), 3.57 (s, 3H), 3.35 (d, J=10.5 Hz, 1H), 3.26-3.21 (m, 2H), 3.98 (dd, J$_1$=8.7 Hz, J$_2$=18.0 Hz, 1H), 2.54 (d, J=18.0 Hz), 2.30 (s, 3H), 2.21 (s, 3H), 2.13 (s, 3H), 1.92-1.65 (m, 3H), 1.42-1.34 (m, 2H), 0.80 (t, J=7.5 Hz, 3H).

ESI-MS m/z: Calcd. for C$_{35}$H$_{43}$N$_3$O$_9$: 633.7. Found (M+1)$^+$: 634.3.

To a solution of 25 (100 mg, 0.177 mmol) in CH$_2$Cl$_2$ (0.4 mL), trans-3-(trifluoromethyl)cinnamoyl chloride (35 µL, 0.23 mmol) and pyridine (17 µL, 0.212 mmol) were added at 0° C. The reaction mixture was stirred for 1 h at room temperature and then, the solution was diluted with CH$_2$Cl$_2$ (30 mL) and washed with 0.1 N HCl (20 mL). The organic layer was dried over Na$_2$SO$_4$, filtered, and the solvent was eliminated under reduced pressure. The residue was purified by flash column chromatography (SiO$_2$, gradient Hex:EtOAc 6:1 to Hex:EtOAc 1:1) to afford 98 (122 mg, 90%) as a white solid. Rf: 0.478 (Hex:EtOAc 1:1).

$^1$H NMR (300 MHz, CDCl$_3$) δ 7.64-7.48 (m, 4H), 7.37 (d, J=15.6 Hz, 1H), 6.62 (s, 1H), 6.16-6.07 (m, 1H), 6.12 (d, J=15.6 Hz, 1H), 5.94 (d, J=1.2 Hz, 1H), 5.89 (d, J=1.2 Hz, 1H), 5.41 (dd, J$_1$=1.8 Hz, J$_2$=17.1 Hz, 1H), 5.28 (dd, J$_1$=1.8 Hz, J$_2$=12.0 Hz, 1H), 5.04 (q, J=6.0 Hz, 1H), 4.60 (dd, J$_1$=3.3 Hz, J$_2$=11.1 Hz, 1H), 4.22-4.15 (m, 5H), 3.90 (dd, J$_1$=4.2 Hz, J$_2$=11.1 Hz, 1H), 3.55 (s, 3H), 3.38 (s, 3H), 3.35-3.34 (m, 1H), 3.27-3.25 (m, 1H), 3.22 (bs, 1H), 2.98 (dd, J$_1$=7.8 Hz, J$_2$=18.0 Hz, 1H), 2.61 (d, J=17.7 Hz, 1H), 2.29 (s, 3H), 2.16 (s, 3H), 2.00 (s, 3H), 1.80 (dd, J$_1$=11.7 Hz, J$_2$=15.6 Hz, 1H).

ESI-MS m/z: Calcd. for C$_{41}$H$_{42}$F$_3$N$_3$O$_8$: 761.7. Found (M+1)$^+$: 762.3.

Example 93

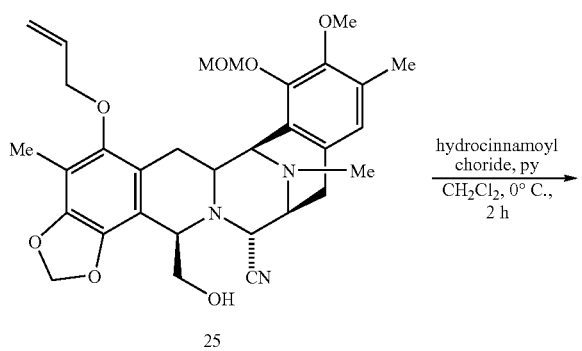

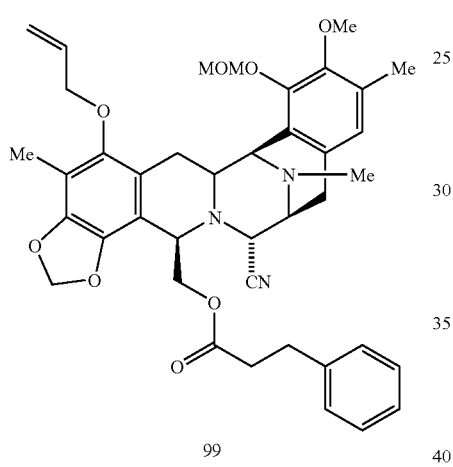

To a solution of 25 (68 mg, 0.12 mmol) in CH$_2$Cl$_2$ (0.4 mL), hydrocynnamoyl chloride (20 μL, 1.12 mmol) and pyridine (10 μL, 1.01 mmol) were added at 0° C. The reaction mixture was stirred for 2 h at room temperature and then, the solution was diluted with CH$_2$Cl$_2$ (30 mL) and washed with 0.1 N HCl (20 mL). The organic layer was dried over Na$_2$SO$_4$, filtered, and the solvent was eliminated under reduced pressure. The residue was purified by flash column chromatography (SiO$_2$, gradient Hex:EtOAc 5:1 to Hex:EtOAc 2:1) to afford 99 (41 mg, 49%) as a white solid. Rf: 0.47 (Hex:EtOAc 1:1).

$^1$H NMR (300 MHz, CDCl$_3$) δ 7.29-7.18 (m, 3H), 7.04-7.02 (m, 2H), 6.66 (s, 1H), 6.16-6.07 (m, 1H), 5.93 (d, J=1.2 Hz, 1H), 5.87 (d, J=1.2 Hz, 1H), 5.40 (dd, J$_1$=1.7 Hz, J$_2$=17.4 Hz, 1H), 5.26 (dd, J$_1$=1.7 Hz, J$_2$=10.2 Hz, 1H), 5.09 (dd, J$_1$=6.0 Hz, J$_2$=8.7 Hz, 2H), 4.43 (dd, J$_1$=3.3 Hz, J$_2$=11.1 Hz, 1H), 4.20-4.14 (m, 3H), 4.06 (t, J=3.7 Hz, 1H), 4.02 (d, J=2.4 Hz, 1H), 3.72 (dd, J$_1$=4.5 Hz, J$_2$=11.1 Hz, 1H), 3.56 (s, 3H), 3.55 (s, 3H), 3.32 (brd, J=8.7 Hz, 1H), 3.26 (dd, J$_1$=1.9 Hz, J$_2$=8.1 Hz, 1H), 3.23-3.20 (m, 1H), 3.01 (brd, J=8.1 Hz, 1H), 3.23-3.20 (m, 1H), 3.26 (dd, J$_1$=1.9 Hz, J$_2$=8.1 Hz, 1H), 2.95 (d, J=1.8 Hz, 1H), 2.71-2.64 (m, 3H), 2.53 (d, J=17.7 Hz, 1H), 2.26 (s, 3H), 2.14 (s, 6H), 1.83 (dd, J$_1$=12.3 Hz, J$_2$=15.9 Hz, 1H).

ESI-MS m/z: Calcd. for C$_{40}$H$_{45}$F$_3$N$_3$O$_8$: 695.3. Found (M+1)$^+$: 696.3.

Example 94

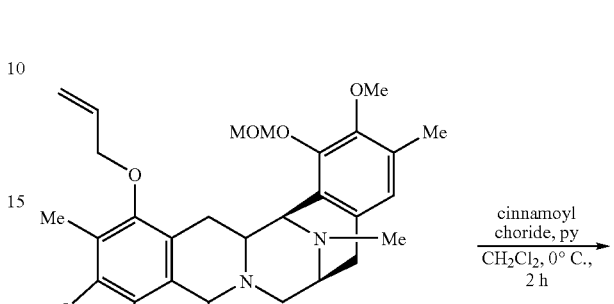

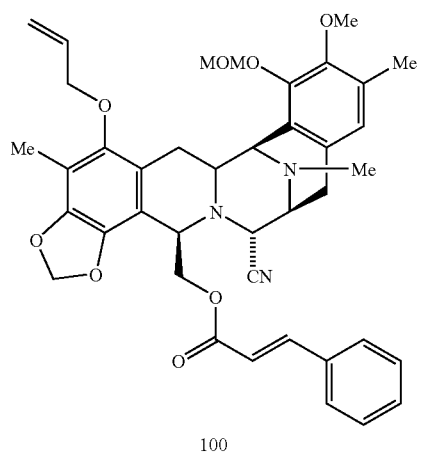

To a solution of 25 (100 mg, 0.177 mmol) in CH$_2$Cl$_2$ (0.4 mL), cynnamoyl chloride (35 mg, 0.21 mmol) and pyridine (17 μL, 0.21 mmol) were added at 0° C. The reaction mixture was stirred for 2 h at room temperature and then, the solution was diluted with CH$_2$Cl$_2$ (30 mL) and washed with 0.1 N HCl (20 mL). The organic layer was dried over Na$_2$SO$_4$, filtered, and the solvent was eliminated under reduced pressure. The residue was purified by flash column chromatography (SiO$_2$, Hex:EtOAc 6:1) to afford 100 (94 mg, 76%) as a white solid. Rf: 0.49 (Hex:EtOAc 1:1).

$^1$H NMR (300 MHz, CDCl$_3$) δ 7.42-7.33 (m, 6H), 6.62 (s, 1H), 6.16-6.05 (m, 1H), 6.10 (d, J=15.9 Hz, 1H), 5.94 (d, J=1.2 Hz, 1H), 5.88 (d, J=1.2 Hz, 1H), 5.43 (dd, J$_1$=3.0 Hz, J$_2$=17.1 Hz, 1H), 5.27 (dd, J$_1$=3.0 Hz, J$_2$=12.0 Hz, 1H), 5.04 (q, J=6.0 Hz, 1H), 4.55 (dd, J$_1$=3.9 Hz, J$_2$=11.1 Hz, 1H), 4.22-4.15 (m, 5H), 3.87 (dd, J$_1$=4.5 Hz, J$_2$=11.1 Hz, 1H), 3.55 (s, 3H), 3.39 (s, 3H), 3.36-3.33 (m, 1H), 3.26-3.22 (m, 2H), 2.98 (dd, J$_1$=8.1 Hz, J$_2$=17.7 Hz, 1H), 2.63 (d, J=17.7 Hz, 1H), 2.29 (s, 3H), 2.03 (s, 3H), 1.82 (dd, J$_1$=11.7 Hz, J$_2$=15.3 Hz, 1H).

ESI-MS m/z: Calcd. for C$_{40}$H$_{43}$N$_3$O$_8$: 693.3. Found (M+1)$^+$: 694.3.

Example 95

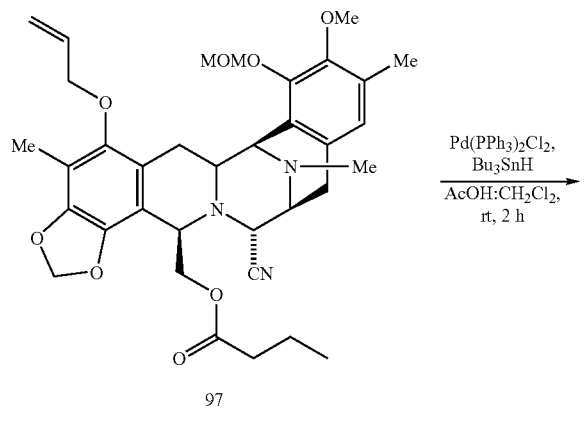

Example 96

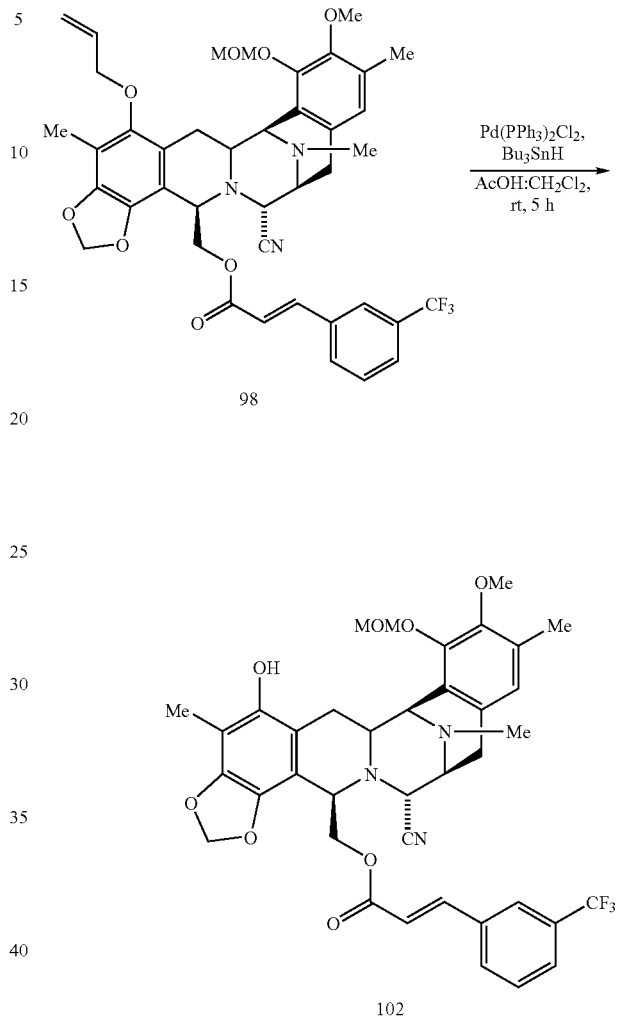

To a solution of 97 (40 mg, 0.063 mmol) in $CH_2Cl_2$ (0.7 mL), acetic acid (17.8 µL), $Pd(PPh_3)_2Cl_2$ (3.64 mg, 0.0052 mmol) and $Bu_3SnH$ (67.9 µL, 0.252 mmol) were added at 23° C. The reaction mixture was stirred for 2 h at that temperature and then, the solution was poured into a pad of flash column ($SiO_2$, gradient Hex:EtOAc 5:1 to Hex:EtOAc 3:1) to afford 101 (30 mg, 80%) as a white solid. Rf: 0.4 (Hex:EtOAc 1:1).

$^1$H NMR (300 MHz, CDCl$_3$) δ 6.65 (s, 1H), 5.90 (d, J=1.5 Hz, 1H), 5.82 (d, J=1.5 Hz, 1H), 5.54 (s, 1H), 5.33 (d, J=6.0 Hz, 1H), 5.13 (d, J=6.0 Hz, 1H), 4.54 (dd, $J_1$=3.6 Hz, $J_2$=11.4 Hz, 1H), 4.18 (d, J=2.1 Hz, 1H), 4.13 (d, J=2.4 Hz, 1H), 4.07 (t, J=3.3 Hz, 1H), 3.75 (dd, $J_1$=3.9 Hz, $J_2$=11.1 Hz, 1H), 3.70 (s, 3H), 3.35 (d, J=8.4 Hz, 1H), 3.24 (dd, $J_1$=2.7 Hz, $J_2$=8.7 Hz, 1H), 3.10 (dd, $J_1$=2.4 Hz, $J_2$=15.0 Hz, 1H), 3.01 (d, J=8.1 Hz, 1H), 2.95 (d, J=7.8 Hz, 1H), 2.58 (d, J=18.3 Hz, 1H), 2.29 (s, 3H), 2.21 (s, 3H), 2.10 (s, 3H), 1.89-1.66 (m, 3H), 1.36-1.25 (m, 2H), 0.77 (t, J=7.5 Hz, 3H).

ESI-MS m/z: Calcd. for $C_{32}H_{39}N_3O_8$: 593.6. Found (M+1)$^+$: 594.8.

To a solution of 98 (37 mg, 0.0485 mmol) in $CH_2Cl_2$ (0.7 mL), acetic acid (20 µL). $Pd(PPh_3)_2Cl_2$ (4 mg, 0.0057 mmol) and $Bu_3SnH$ (53 µL, 0.194 mmol) were added at 23° C. The reaction mixture was stirred for 5 h at that temperature and then, the solution was poured into a pad of flash column ($SiO_2$, gradient Hex:EtOAc 6:1 to Hex:EtOAc 2:1) to afford 102 (25 mg, 71%) as a white solid. Rf: 0.38 (Hex:EtOAc 1:1).

$^1$H NMR (300 MHz, CDCl$_3$) δ 7.63-7.60 (M, 2H), 7.50-7.49 (M, 2H), 7.24 (d, J=15.9 Hz, 1H), 6.59 (s, 1H), 5.98 (d, J=15.9 Hz, 1H), 5.92 (d, J=1.5 Hz, 1H), 5.84 (d, J=1.5 Hz, 1H), 5.66 (s, 1H), 5.20 (d, J=6.0 Hz, 1H), 4.87 (d, J=6.0 Hz, 1H), 4.71 (dd, $J_1$=2.7 Hz, $J_2$=10.8 Hz, 1H), 4.16-4.15 (m, 3H), 3.93 (dd, $J_1$=3.3 Hz, $J_2$=11.1 Hz, 1H), 3.66 (s, 3H), 3.36 (brd, J=10.2 Hz, 1H), 3.26 (brd, J=11.7 Hz, 1H), 3.10 (brd, J=15.0 Hz, 1H), 2.96 (dd, $J_1$=7.8 Hz, $J_2$=17.7 Hz, 1H), 2.62 (d, J=17.7 Hz, 1H), 2.27 (s, 3H), 2.14 (s, 3H), 1.97 (s, 3H), 1.79 (dd, $J_1$=12.0 Hz, $J_2$=15.8 Hz, 1H).

ESI-MS m/z: Calcd. for $C_{38}H_{38}F_3N_3O_8$: 721.7. Found (M+1)$^+$: 722.2.

Example 97

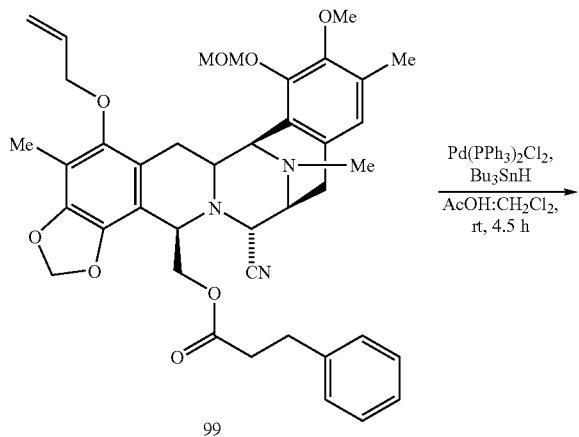

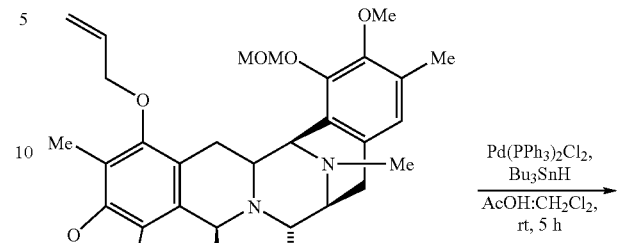

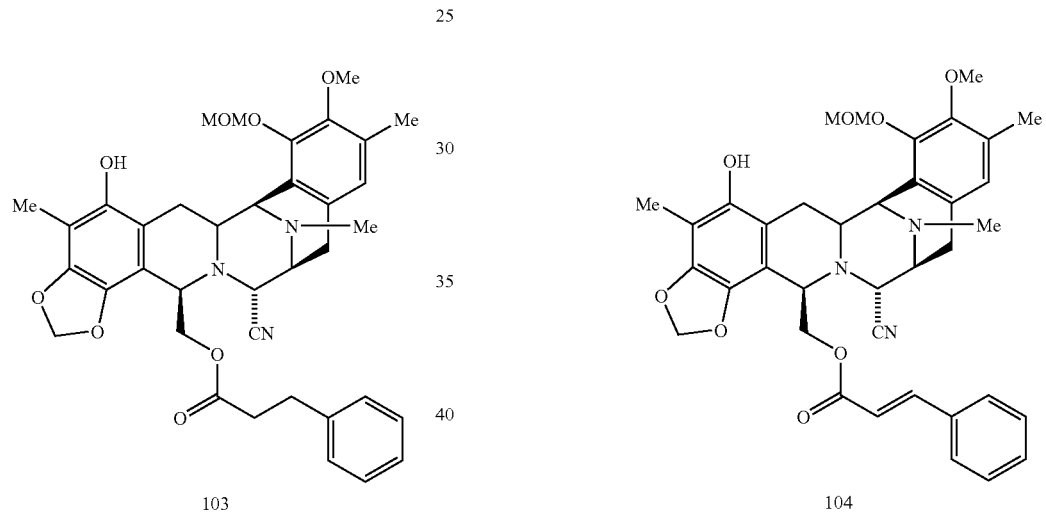

Example 98

To a solution of 99 (41 mg, 0.059 mmol) in CH$_2$Cl$_2$ (1 mL), acetic acid (25 μL), Pd(PPh$_3$)$_2$Cl$_2$ (5 mg, 0.0071 mmol) and Bu$_3$SnH (63 μL, 0.235 mmol) were added at 23° C. The reaction mixture was stirred for 4.5 h at that temperature and then, the solution was poured into a pad of flash column (SiO$_2$, gradient Hex:EtOAc 6:1 to Hex:EtOAc 1:1) to afford 103 (34.2 mg, 89%) as a white solid. Rf: 0.49 (Hex:EtOAc 1:1).

$^1$H NMR (300 MHz, CDCl$_3$) δ 7.24-7.15 (m, 3H), 7.03-7.01 (m, 2H), 6.65 (s, 1H), 5.89 (bs, 1H), 5.82 (bs, 1H), 5.49 (s, 1H), 5.31 (d, J=6.0 Hz, 1H), 5.12 (d, J=6.0 Hz, 1H), 4.53 (dd, J$_1$=3.3 Hz, J$_2$=11.1 Hz, 1H), 4.18 (d, J=2.7 Hz, 1H), 4.07 (m, 2H), 3.75 (dd, J$_1$=3.9 Hz, J$_2$=11.1 Hz, 1H), 3.69 (s, 3H), 3.62 (s, 3H), 3.32 (d, J=7.8 Hz, 1H), 3.25 (d, J=10.8 Hz, 1H), 3.12 (d, J=14.7 Hz, 1H), 3.00 (d, J=7.8 Hz, 1H), 2.94 (d, J=8.1 Hz, 1H), 2.66-2.60 (m, 3H), 2.57 (d, J=18.0 Hz, 1H), 2.28 (s, 3H), 2.14 (s, 3H), 2.10 (bs, 3H), 1.83-1.74 (m, 1H).

ESI-MS m/z: Calcd. for C$_{37}$H$_{41}$N$_3$O$_8$: 655.7. Found (M+1)$^+$: 656.3.

To a solution of 100 (40 mg, 0.0576 mmol) in CH$_2$Cl$_2$ (1 mL), acetic acid (25 μL). Pd(PPh$_3$)$_2$Cl$_2$ (4.8 mg, 0.007 mmol) and Bu$_3$SnH (62 μL, 0.23 mmol) were added at 23° C. The reaction mixture was stirred for 5 h at that temperature and then, the solution was poured into a pad of flash column (SiO$_2$, gradient Hex:EtOAc 4:1 to Hex:EtOAc 1:1) to afford 104 (30 mg, 82%) as a white solid. Rf: 0.41 (Hex:EtOAc 1:1).

$^1$H NMR (300 MHz, CDCl$_3$) δ 7.36 (s, 5H), 7.30 (d, J=16.2 Hz, 1H), 6.59 (s, 1H), 5.99 (d, J=16.2 Hz, 1H), 5.91 (d, J=1.2 Hz, 1H), 5.84 (d, J=1.2 Hz, 1H), 5.60 (s, 1H), 5.20 (d, J=5.6 Hz, 1H), 4.94 (d, J=5.6 Hz, 1H), 4.63 (dd, J$_1$=3.3 Hz, J$_2$=11.4 Hz, 1H), 4.18-4.15 (m, 3H), 3.91 (dd, J$_1$=3.9 Hz, J$_2$=11.1 Hz, 1H), 3.66 (s, 3H), 3.49 (s, 3H), 3.35 (brd, J=15.0 Hz, 1H), 3.26 (brd, J=11.4 Hz, 1H), 3.10 (brd, J=15.0 Hz, 1H), 2.96 (dd, J$_1$=8.4 Hz, J$_2$=18.0 Hz, 1H), 2.63 (d, J=18.0 Hz, 1H), 2.27 (s, 3H), 2.13 (s, 3H), 2.00 (s, 3H), 1.80 (dd, J$_1$=12.0 Hz, J$_2$=14.4 Hz, 1H).

ESI-MS m/z: Calcd. for C$_{37}$H$_{39}$N$_3$O$_8$: 653.7. Found (M+23)$^+$: 676.2.

Example 99

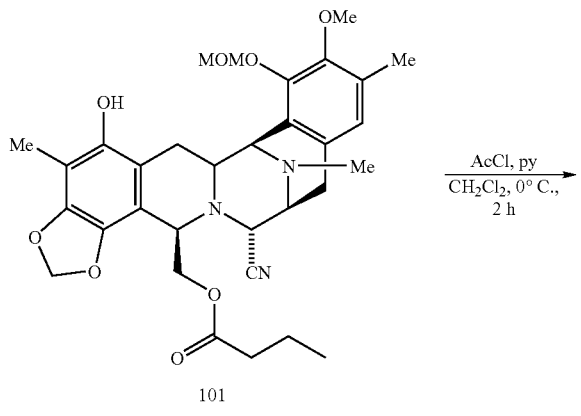

Example 100

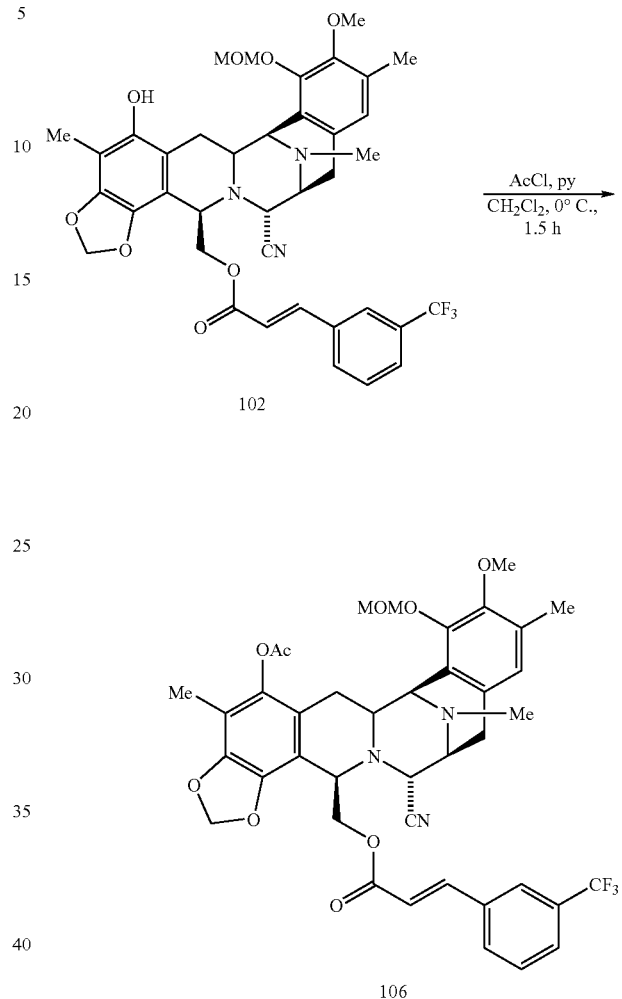

To a solution of 101 (24 mg, 0.041 mmol) in CH$_2$Cl$_2$ (0.4 mL), acetyl chloride (3 μL, 0.041 mmol), and pyridine (3.3 μL, 0.041 mmol) were added at 0° C. The reaction mixture was stirred for 2 h and then, the solution was diluted with CH$_2$Cl$_2$ (15 mL) and washed with 0.1 N HCl (5 mL). The organic layer was dried over sodium sulphate, filtered, and the solvent was eliminated under reduced pressure. The residue was purified by flash column chromatography (SiO$_2$, gradient Hex:EtOAc 5:1 to Hex:EtOAc 1:1) to afford 105 (23 mg, 88%) as a white solid. Rf: 0.40 (Hex:EtOAc 1:1).

$^1$H NMR (300 MHz, CDCl$_3$) δ 6.66 (s, 1H), 5.97 (d, J=1.2 Hz, 1H), 5.91 (d, J=1.2 Hz, 1H), 4.58 (d, J=3.0 Hz, 1H), 4.54 (d, J=3.0 Hz, 1H), 4.07 (t, J=3.3 Hz, 1H), 3.77 (dd, J$_1$=3.9 Hz, J$_2$=11.4 Hz, 1H), 3.73 (s, 3H), 3.57 (s, 3H), 3.35 (d, J=10.2 Hz, 1H), 3.22 (dt. J$_1$=2.7 Hz, J$_2$=11.7 Hz, 1H), 2.98 (dd, J$_1$=8.1 Hz, J$_2$=18.0 Hz, 1H), 2.80 (d, J=13.5 Hz, 1H), 2.58 (d, J=18.0 Hz, 1H), 2.33 (s, 3H), 2.30 (s, 3H), 2.21 (s, 3H), 2.02 (s, 3H), 1.89-1.76 (m, 2-H), 1.72-1.66 (m, 1H), 1.37-1.25 (m, 2H), 0.78 (t, J=7.5 Hz, 3H).

ESI-MS m/z: Calcd. for C$_{34}$H$_{41}$N$_3$O$_9$: 635.7. Found (M+1)$^+$: 636.8.

To a solution of 102 (16 mg, 0.022 mmol) in CH$_2$Cl$_2$ (0.2 mL), acetyl chloride (1.9 μL, 0.0266 mmol), and pyridine (2.15 μL, 0.0266 mmol) were added at 0° C. The reaction mixture was stirred for 1.5 h and then, the solution was diluted with CH$_2$Cl$_2$ (10 mL) and washed with 0.1 N HCl (7 mL). The organic layer was dried over sodium sulphate, filtered, and the solvent was eliminated under reduced pressure. The residue was purified by flash column chromatography (SiO$_2$, gradient Hex:EtOAc 4:1 to EtOAc) to afford 106 (12 mg, 71%) as a white solid. Rf: 0.60 (Hex:EtOAc 1:1).

$^1$H NMR (300 MHz, CDCl$_3$) δ 7.83 (bs, 1H), 7.65-7.58 (m, 2H), 7.49-7.44 (m, 1H), 7.14 (d, J=16.2 Hz, 1H), 6.62 (s, 1H), 6.06 (d, 16.2 Hz, 1H), 6.00 (d, J=1.2 Hz, 1H), 5.95 (d, J=1.2 Hz, 1H), 5.02 (d, J=5.7 Hz, 1H), 4.96 (bs, 1H), 4.92 (d, J=5.7 Hz, 1H), 4.15-4.11 (m, 3H), 3.88 (dd, J$_1$=3.3 Hz, J$_2$=11.1 Hz, 1H), 3.08 (bs, 3H), 2.93 (dd, J$_1$=8.1 Hz, J$_2$=18.3 Hz, 1H), 2.80 (d, J=13.2 Hz, 1H), 2.64 (d, J=18.0 Hz, 1H), 2.31 (s, 3H), 2.27 (s, 3H), 2.08 (s, 3H), 1.91 (s, 3H), 1.69 (dd, J$_1$=11.7 Hz, J$_2$=15.9 Hz, 1H).).

ESI-MS m/z: Calcd. for C$_{40}$H$_{40}$F$_3$N$_3$O$_9$: 763.7. Found (M+1)$^+$: 764.2.

Example 101

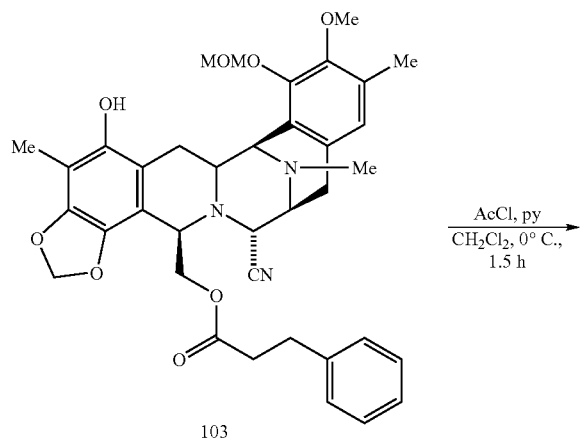

Example 102

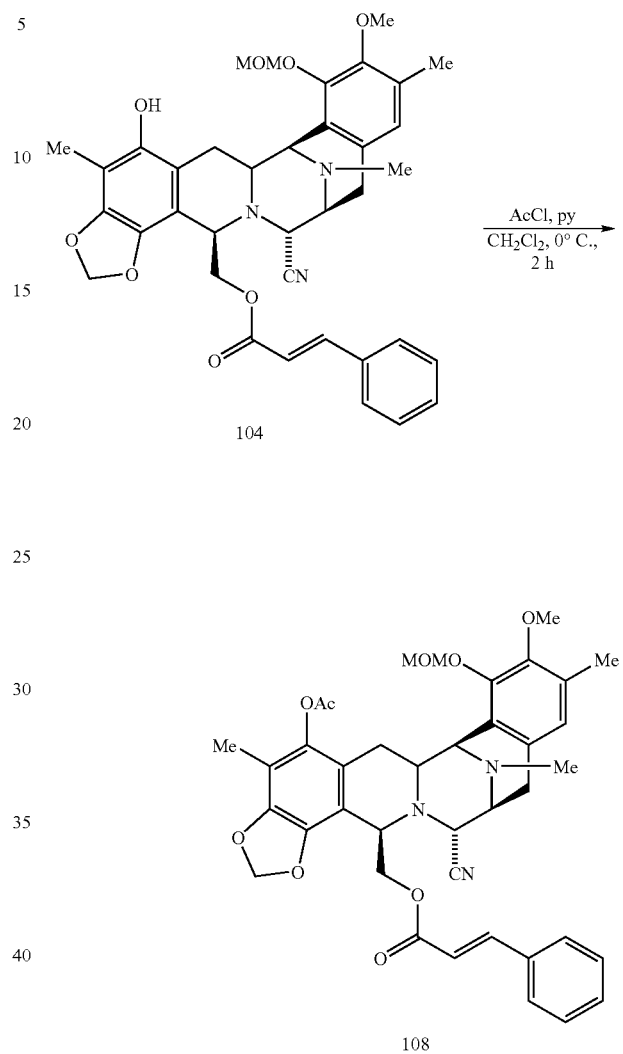

To a solution of 103 (34 mg, 0.052 mmol) in CH$_2$Cl$_2$ (0.2 mL), acetyl chloride (4.4 µL, 0.062 mmol), and pyridine (5 µL, 0.062 mmol) were added at 0° C. The reaction mixture was stirred for 1.5 h and then, the solution was diluted with CH$_2$Cl$_2$ (10 mL) and washed with 0.1 N HCl (7 mL). The organic layer was dried over sodium sulphate, filtered, and the solvent was eliminated under reduced pressure. The residue was purified by flash column chromatography (SiO$_2$, gradient Hex:EtOAc 4:1 to EtOAc) to afford 107 (25.5 mg, 70%) as a white solid. Rf: 0.48 (Hex:EtOAc 1:1).

$^1$H NMR (300 MHz, CDCl$_3$) δ 7.25-7.14 (m, 3H), 7.06-7.04 (m, 2H), 6.66 (s, 1H), 5.96 (d, J=1.2 Hz, 1H), 5.91 (d, J=1.2 Hz, 1H), 5.11 (d, J=5.4 Hz, 1H), 4.14 (d, J=3.3 Hz, 1H), 4.07 (d, J=3.6 Hz, 1H), 4.04 (d, J=2.7 Hz, 1H), 3.78 (dd, J$_1$=3.3 Hz, J$_2$=10.8 Hz, 1H), 3.55 (s, 3H), 3.51 (s, 3H), 3.33 (brd, J=8.1 Hz, 1H), 3.23 (dt, J$_1$=2.7 Hz, J$_2$=11.7 Hz, 1H), 2.97 (dd, J$_1$=8.1 Hz, J$_2$=18.0 Hz, 1H), 2.81 (d, J=14.1 Hz, 1H), 2.63-2.52 (m, 3H), 2.33 (s, 3H), 2.29 (s, 3H), 2.26-202 (m, 2H), 2.09 (s, 3H), 2.04 (s, 3H), 1.74 (dd, J$_1$=12.0 Hz, J$_2$=15.6 Hz, 1H).

ESI-MS m/z: Calcd. for C$_{39}$H$_{13}$N$_3$O$_9$: 697.7. Found (M+1)$^+$: 698.3.

To a solution of 104 (29 mg, 0.0443 mmol) in CH$_2$Cl$_2$ (0.3 mL), acetyl chloride (3.77 µL, 0.053 mmol), and pyridine (4.3 µL, 0.053 mmol) were added at 0° C. The reaction mixture was stirred for 2 h and then, the solution was diluted with CH$_2$Cl$_2$ (15 mL) and washed with 0.1 N HCl (10 mL). The organic layer was dried over sodium sulphate, filtered, and the solvent was eliminated under reduced pressure. The residue was purified by flash column chromatography (SiO$_2$, gradient Hex:EtOAc 4:1 to EtOAc) to afford 108 (21.6 mg, 70%) as a white solid. Rf: 0.58 (Hex:EtOAc 1:1).

$^1$H NMR (300 MHz, CDCl$_3$) δ 7.47-7.44 (m, 2H), 7.35-7.34 (m, 3H), 7.29 (d, J=15.9 Hz, 1H), 6.62 (s, 1H), 5.99 (d, J=1.2 Hz, 1H), 5.93 (d, J=1.2 Hz, 1H), 5.05 (d, J=5.7 Hz, 1H), 4.94 (d, J=5.7 Hz, 1H), 4.81 (d, J=11.5 Hz, 1H), 4.16-4.11 (m, 3H), 3.34 (brd, J=5.4 Hz, 1H), 3.24 (bs, 3H), 3.22-3.20 (m, 2H), 2.94 (dd, J$_1$=8.1 Hz, J$_2$=18.0 Hz, 1H), 2.80 (d, J=14.1 Hz, 1H), 2.64 (d, J=18.0 Hz, 1H), 2.32 (s, 3H), 2.28 (s, 3H), 2.09 (s, 3H), 1.94 (s, 3H), 1.71 (dd, J$_1$=11.7 Hz, J$_2$=15.6 Hz, 1H).

ESI-MS m/z: Calcd. for C$_{39}$H$_{41}$N$_3$O$_9$: 695.7. Found (M+1)$^+$: 696.2.

Example 103

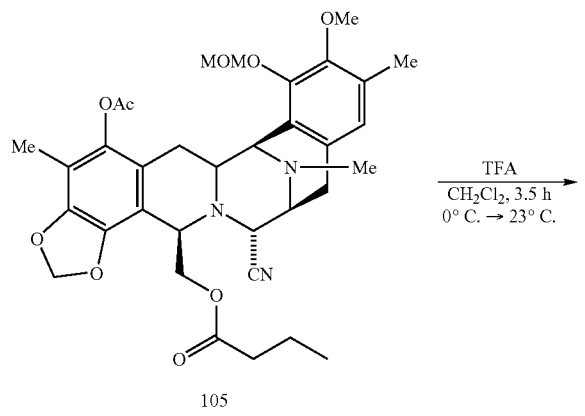

Example 104

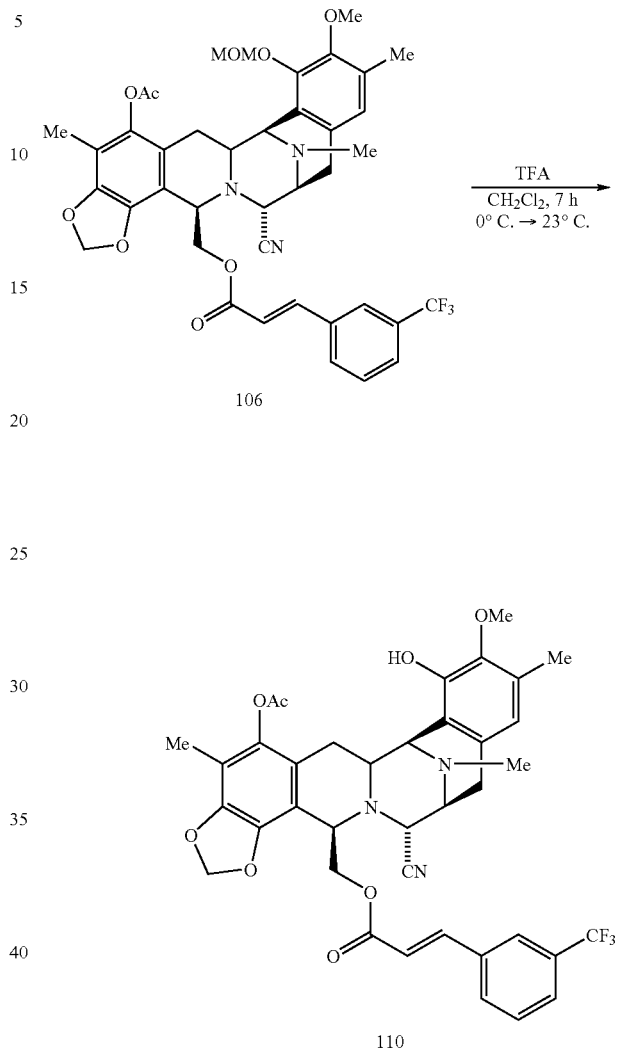

To a solution of 105 (16 mg, 0.025 mmol) in CH$_2$Cl$_2$ (0.2 mL), trifluoroacetic acid (77 µL, 1 mmol) was added at 0° C. and the reaction mixture was stirred for 3.5 h at 23° C. The reaction was quenched at 0° C. with saturated aqueous sodium bicarbonate (15 mL) and extracted with ethyl acetate (2×10 mL). The combined organic layers were dried over sodium sulphate, filtered, and the solvent was eliminated under reduced pressure. The residue was purified by flash column chromatography (SiO$_2$, Hex:EtOAc 1:1) to afford 109 (12 mg, 81%) as a white solid. Rf: 0.32 (Hex:EtOAc 1:1).

$^1$H NMR (300 MHz, CDCl$_3$) δ 6.43 (s, 1H), 5.97 (d, J=1.5 Hz, 1H), 5.91 (d, J=1.5 Hz, 1H), 5.69 (s, 1H), 4.51 (dd, J$_1$=3.3 Hz, J$_2$=11.1 Hz, 1H), 4.10-4.05 (m, 3H), 3.78-3.77 (m, 1H), 3.75 (s, 3H), 3.33 (d, J=8.1 Hz, 1H), 3.22 (dt, J=2.7 Hz, J=12.0 Hz, 1H), 2.96 (dd, J$_1$=8.4 Hz, J$_2$=17.7 Hz, 1H), 2.80 (d, J=15.6 Hz, 1H), 2.55 (d, J=18.0 Hz, 1H), 2.33 (s, 3H), 2.24 (s, 3H), 2.01 (s, 3H), 1.87-1.66 (m, 3H), 1.37-1.27 (m, 2H), 0.77 (t, J=7.5 Hz, 3H).

ESI-MS m/z: Calcd. for C$_{32}$H$_{31}$N$_3$O$_8$: 591.6. Found (M+1)$^+$: 592.8.

To a solution of 106 (90 mg, 0.1178 mmol) in CH$_2$Cl$_2$ (0.3 mL), trifluoroacetic acid (750 µL, 4.71 mmol) was added at 0° C. and the reaction mixture was stirred for 7 h at 23° C. The reaction was quenched at 0° C. with saturated aqueous sodium bicarbonate (20 mL) and extracted with ethyl acetate (2×15 mL). The combined organic layers were dried over sodium sulphate, filtered, and the solvent was eliminated under reduced pressure. The residue was purified by flash column chromatography (SiO$_2$, Hex:EtOAc 1:1) to afford 110 (71 mg, 84%) as a white solid. Rf: 0.6 (Hex:EtOAc 1:1).

$^1$H NMR (300 MHz, CDCl$_3$) δ 7.76 (bs, 1H), 7.62-7.57 (m, 2H), 7.48-7.45 (m, 1H), 7.12 (d, J=16.2 Hz, 1H), 6.37 (s, 1H), 6.00 (d, J=16.2 Hz, 1H), 5.98 (d, J=1.2 Hz, 1H), 5.92 (d, J=1.2 Hz, 1H), 5.60 (bs, 1H), 4.88 (d, J=10.2 Hz, 1H), 4.14 (bs, 1H), 4.10 (d, J=2.4 Hz, 1H), 4.03 (d, J=2.4 Hz, 1H), 3.89 (dd, J$_1$=2.7 Hz, J$_2$=11.4 Hz, 1H), 3.32 (d, J=8.4 Hz, 1H), 3.26-3.21 (m, 4H), 2.91 (dd, J$_1$=8.1 Hz, J$_2$=18.0 Hz, 1H), 2.82 (d, J=13.8 Hz, 1H), 2.58 (d, J=18.0 Hz, 1H), 2.33 (s, 3H), 2.24 (s, 3H), 2.05 (s, 3H), 1.89 (s, 3H), 1.84 (dd, J$_1$=12.0 Hz, J$_2$=15.6 Hz, 1H).

ESI-MS m/z: Calcd. for C$_{38}$H$_{36}$F$_3$N$_3$O$_8$: 719.7. Found (M+1): 720.3.

Example 105

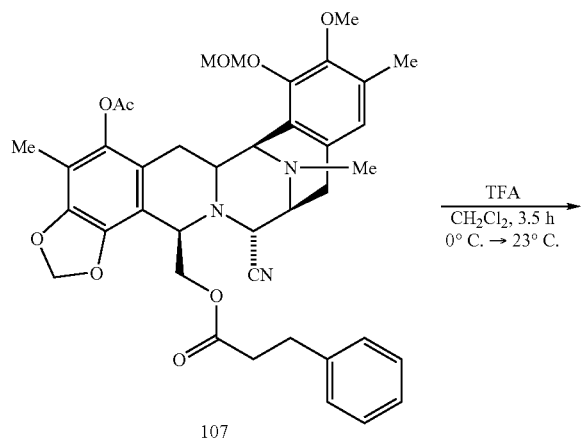

Example 106

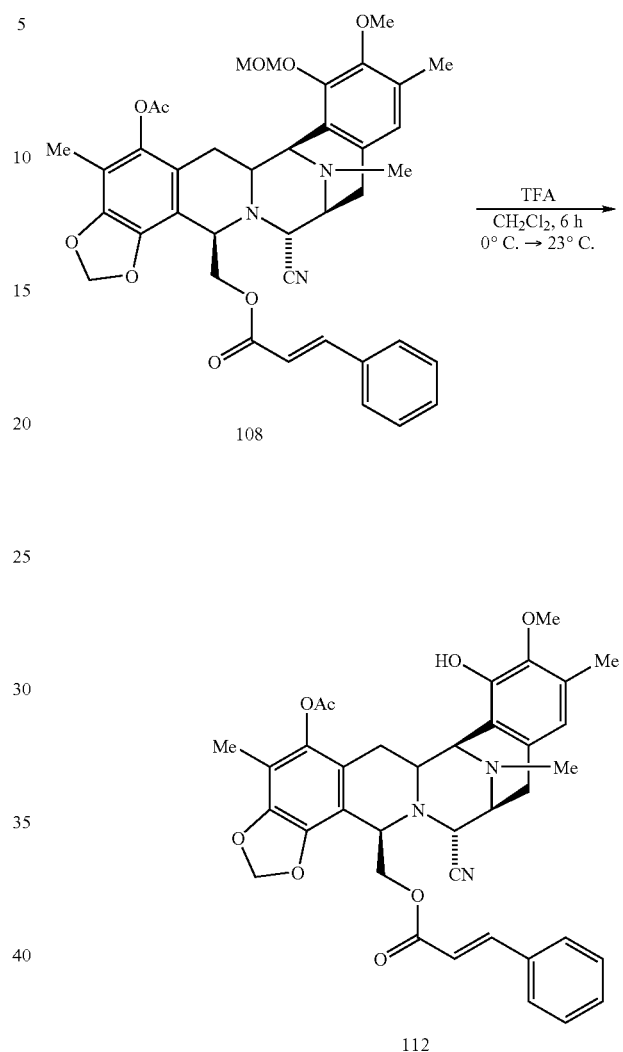

To a solution of 107 (20 mg, 0.286 mmol) in CH$_2$Cl$_2$ (0.2 mL), trifluoroacetic acid (88 μL, 1.144 mmol) was added at 0° C. and the reaction mixture was stirred for 4 h at 23° C. The reaction was quenched at 0° C. with saturated aqueous sodium bicarbonate (15 mL) and extracted with ethyl acetate (2×10 mL). The combined organic layers were dried over sodium sulphate, filtered, and the solvent was eliminated under reduced pressure. The residue was purified by flash column chromatography (SiO$_2$, Hex:EtOAc 1:1) to afford 111 (18 mg, 96%) as a white solid. Rf: 0.39 (Hex:EtOAc 1:1).

$^1$H NMR (300 MHz, CDCl$_3$) δ 7.23-7.16 (m, 3H), 7.06-7.04 (m, 2H), 6.43 (s, 1H), 5.96 (d, J=1.5 Hz, 1H), 5.90 (d, J=1.5 Hz, 1H), 6.66 (s, 1H), 4.52 (dd, J$_1$=3.3 Hz, J$_2$=11.1 Hz, 1H), 4.07 (s, 1H), 4.05 (d, J=3.3 Hz, 1H), 4.03 (d, J=2.4 Hz, 1H), 3.76 (dd, J$_1$=3.6 Hz, J$_2$=11.1 Hz, 1H), 3.56 (s, 3H), 3.31 (d, J=7.5 Hz, 1H), 3.23 (d, J=12.0 Hz, 1H), 2.95 (dd, J$_1$=8.1 Hz, J$_2$=18.0 Hz, 1H), 2.80 (d, J=15.3 Hz, 1H), 2.63-2.58 (m, 2H), 2.53 (d, J=18.0 Hz, 1H), 2.33 (s, 3H), 2.61 (s, 3H), 2.21-2.09 (m, 2H), 2.13 (s, 3H), 2.02 (s, 3H), 1.85 (dd, J$_1$=11.7 Hz, J$_2$=115.3 Hz, 1H). ESI-MS m/z: Calcd. for C$_{37}$H$_{39}$N$_3$O$_8$: 653.7. Found (M+1)$^+$: 654.3.

To a solution of 108 (14 mg, 0.02 mmol) in CH$_2$Cl$_2$ (0.4 mL), trifluoroacetic acid (61.5 μL, 0.8 mmol) was added at 0° C. and the reaction mixture was stirred for 6 h at 23° C. The reaction was quenched at 0° C. with saturated aqueous sodium bicarbonate (15 mL) and extracted with ethyl acetate (2×10 mL). The combined organic layers were dried over sodium sulphate, filtered, and the solvent was eliminated under reduced pressure. The residue was purified by flash column chromatography (SiO$_2$, Hex:EtOAc 2:1) to afford 112 (12 mg, 92%) as a white solid. Rf: 0.36 (Hex:EtOAc 1:1).

$^1$H NMR (300 MHz, CDCl$_3$) δ 7.46-7.45 (m, 2H), 7.35-7.20 (m, 4H), 6.38 (s, 1H), 6.05 (d, J=15.9 Hz, 1H), 5.98 (d, J=1.2 Hz, 1H), 5.93 (d, J=1.2 Hz, 1H), 5.57 (s, 1H), 4.71 (d, J=9.3 Hz, 1H), 4.17-4.13 (m, 2H), 4.08 (d, J=1.9 Hz, 1H), 3.89 (dd, J$_1$=3.6 Hz, J$_2$=11.4 Hz, 1H), 3.33 (m, 5H), 3.26-3.22 (m, 1H), 2.93 (dd, J$_1$=9.0 Hz, J$_2$=17.4 Hz, 1H), 2.34 (s 3H) 2.25 (s, 3H), 2.05 (s, 3H), 1.97 (s, 3H), 1.81 (dd, J$_1$=12.0 Hz, J$_2$=15.6 Hz, 1H).

ESI-MS m/z: Calcd. for C$_{37}$H$_{37}$N$_3$O$_8$: 651. Found (M+1)$^+$: 652.2.

Example 107

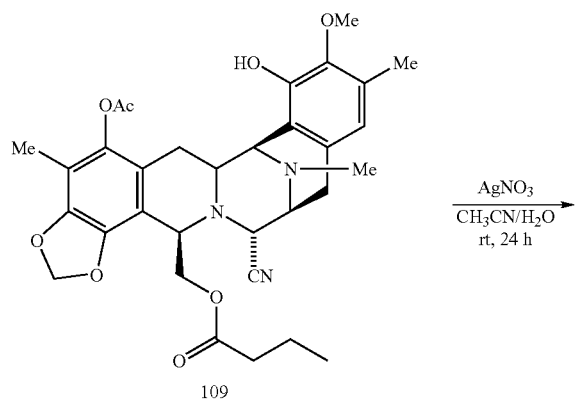

109

Example 108

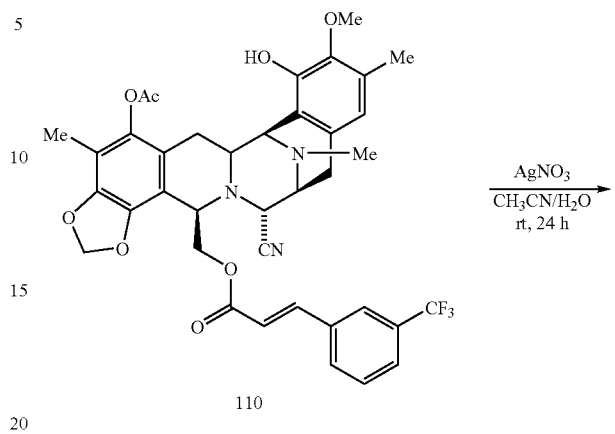

110

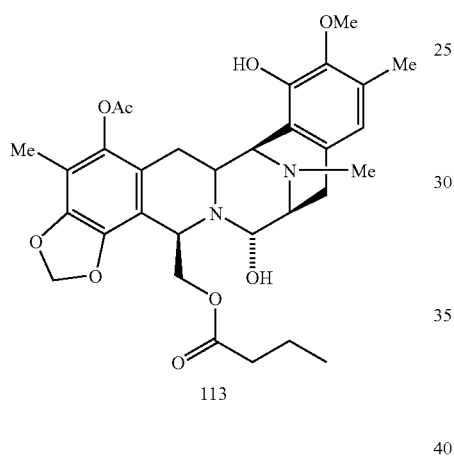

113

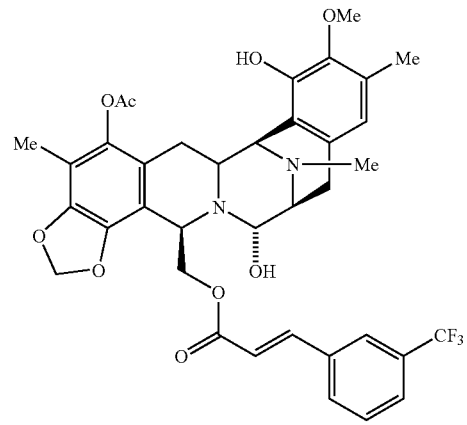

114

To a solution of 109 (10 mg, 0.017 mmol) in CH$_3$CN/H$_2$O (1.5 mL/1 mL), AgNO$_3$ (86 mg, 0.5 mmol) was added and the reaction was stirred at 23° C. for 24 h. Then, brine (10 mL) and Aq sat NaHCO$_3$ (10 mL) were added at 0° C. and the mixture was stirred for 15 min, filtered through a pad of celite and washed with CH$_2$Cl$_2$ (15 mL). The solution was extracted and the organic layer was dried over Na$_2$SO$_4$, filtered and concentrated in vacuo. The residue was purified by flash column chromatography (SiO$_2$, gradient EtOAc to EtOAc:MeOH 3:1) to afford 113 (7 mg, 71%) as a white solid.

Rf: 0.41 (EtOAc:MeOH 5:1).

$^1$H NMR (300 MHz, CDCl$_3$) δ 6.45 (s, 1H), 5.95 (d, J=1.5 Hz, 1H), 5.88 (d, J=1.5 Hz, 1H), 5.65 (bs, 1H), 4.50-4.48 (m, 2H), 4.44 (d, J=2.1 Hz, 1H), 3.96 (d, J=3.0 Hz, 1H), 3.76 (s, 3H), 3.74-3.70 (m, 1H), 3.30 (d, J=12.3 Hz, 1H), 3.13 (d, J=7.5 Hz, 1H), 2.86 (dd, J$_1$=5.7 Hz, J$_2$=18.3 Hz, 1H), 2.73 (d, J=14.7 Hz, 1H), 2.48 (d, J=17.7 Hz, 1H), 2.33 (s, 3H), 2.24 (s, 3H), 2.17 (s, 3H), 2.00 (s, 3H), 1.86-1.55 (m, 3H), 1.42-1.23 (m, 2H), 0.75 (t, J=7.5 Hz, 3H).

ESI-MS m/z: Calcd. for C$_{31}$H$_{38}$N$_2$O$_9$: 582.6. Found (M−17)$^+$: 565.3.

To a solution of 110 (42.8 mg, 0.059 mmol) in CH$_3$CN/H$_2$O (1.5 mL/1 mL). AgNO$_3$ (303 mg, 1.78 mmol) was added and the reaction was stirred at 23° C. for 24 h. Then, brine (10 mL) and Aq sat NaHCO$_3$ (10 mL) were added at 0° C. and the mixture was stirred for 15 min, filtered through a pad of celite and washed with CH$_2$Cl$_2$ (20 mL). The solution was extracted and the organic layer was dried over Na$_2$SO$_4$, filtered and concentrated in vacuo. The residue was purified by flash column chromatography (SiO$_2$, gradient EtOAc to EtOAc:MeOH 5:1) to afford 114 (30 mg, 71%) as a white solid.

Rf: 0.30 (EtOAc:MeOH 5:1).

$^1$H NMR (300 MHz, CDCl$_3$) δ 7.75 (bs, 1H), 7.61-7.56 (m, 2H), 7.45-7.42 (m, 1H), 7.12 (d, J=16.2 Hz, 1H), 6.38 (s, 1H), 6.02 (d, J=16.2 Hz, 1H), 5.97 (d, J=1.5 Hz, 1H), 5.90 (d, J=1.5 Hz, 1H), 5.50 (bs, 1H), 4.87 (bs, 1H), 4.56 (m, 1H), 4.45 (bs, 1H), 3.92 (d, J=2.4 Hz, 1H), 3.31 (dt, J$_1$=3.6 Hz, J$_2$=12.9 Hz, 1H), 3.21 (bs, 3H), 3.13 (d, J=7.8 Hz, 1H), 2.82 (dd, J$_1$=8.1 Hz, J$_2$=18.0 Hz, 1H), 2.75 (d, J=14.7 Hz, 1H), 2.49 (d, J=18.0 Hz, 1H), 2.33 (s, 3H), 2.21 (s, 3H), 2.05 (s, 3H), 1.89 (s, 3H), 1.78 (dd, J$_1$=12.0 Hz, J$_2$=15.6 Hz, 1H).

ESI-MS m/z: Calcd. for C$_{37}$H$_{37}$F$_3$N$_2$O$_9$: 710.6. Found (M−17)$^+$: 693.2.

Example 109

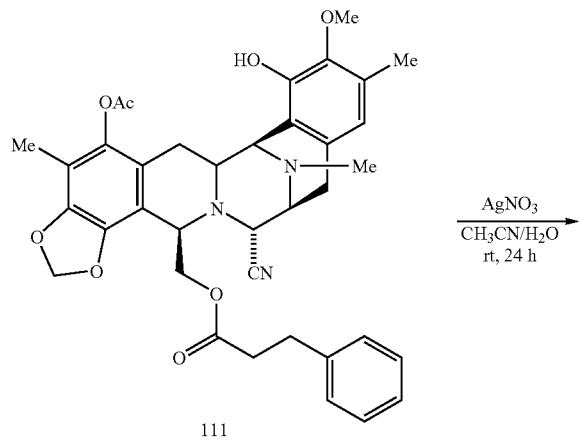

Example 110

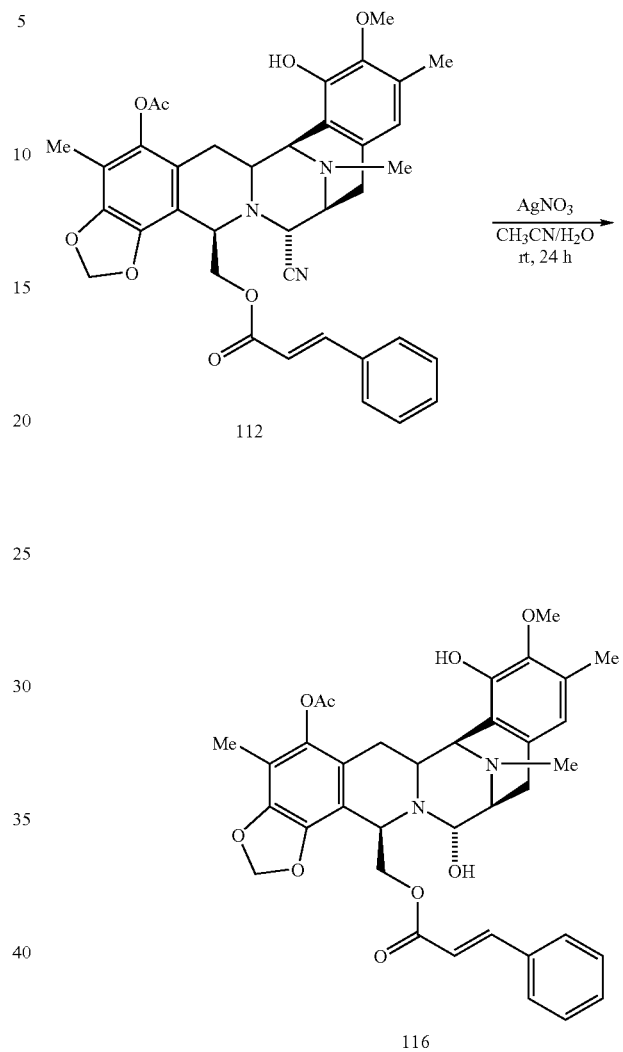

To a solution of 111 (12 mg, 0.018 mmol) in CH₃CN/H₂O (1.5 mL/1 mL). AgNO₃ (93.5 mg, 0.55 mmol) was added and the reaction was stirred at 23° C. for 24 h. Then, brine (10 mL) and Aq sat NaHCO₃ (10 mL) were added at 0° C. and the mixture was stirred for 15 min, filtered through a pad of celite and washed with CH₂Cl₂ (15 mL). The solution was extracted and the organic layer was dried over Na₂SO₄, filtered and concentrated in vacuo. The residue was purified by flash column chromatography (SiO₂, gradient EtOAc to EtOAc: MeOH 1:1) to afford 115 (10 mg, 86%) as a white solid.

Rf: 0.43 (EtOAc:MeOH 5:1).

$^1$H NMR (300 MHz, CDCl₃) δ 7.23-7.14 (m, 3H), 7.05-7.03 (m, 2H), 6.45 (s, 1H), 5.93 (d, J=1.2 Hz, 1H), 5.88 (d, J=1.2 Hz, 1H), 5.63 (brd, 1H), 4.55-4.49 (m, 2H), 4.43 (d, J=2.7 Hz, 1H), 3.96 (d, J=3.1 Hz, 1H), 3.80-3.73 (m, 1H), 3.56 (bs, 3H), 3.32 (dt, J₁=3.3 Hz, J₂=12.6 Hz, 1H), 3.13 (d, J=6.0 Hz, 1H), 2.86 (dd, J₁=7.5 Hz, J₂=18.3 Hz, 1H), 2.74 (d, J=14.7 Hz, 1H), 2.61-2.56 (m, 2H), 2.47 (d, J=18.0 Hz, 1H), 2.33 (s, 3H), 2.23 (s, 3H), 2.13 (s, 3H), 2.01 (s, 3H), 1.99-1.94 (m, 2H), 1.78 (dd, J₁=11.7 Hz, J₂=15.0 Hz, 1H).

ESI-MS m/z: Calcd. for C₃₆H₄₀N₂O₉: 644.7. Found (M−17)⁺: 627.2.

To a solution of 112 (12 mg, 0.018 mmol) in CH₃CN/H₂O (1.5 mL/1 mL), AgNO₃ (93 mg, 0.55 mmol) was added and the reaction was stirred at 23° C. for 24 h. Then, brine (10 mL) and Aq sat NaHCO₃ (10 mL) were added at 0° C. and the mixture was stirred for 15 min, filtered through a pad of celite and washed with CH₂Cl₂ (15 mL). The solution was extracted and the organic layer was dried over Na₂SO₄, filtered and concentrated in vacuo. The residue was purified by flash column chromatography (SiO₂, gradient EtOAc to EtOAc: MeOH 1:1) to afford 116 (8 mg, 70%) as a white solid.

Rf: 0.41 (EtOAc:MeOH 5:1).

$^1$H NMR (300 MHz, CDCl₃) δ 7.44-7.43 (m, 2H), 7.34-7.27 (m, 4H), 6.39 (s, 1H), 6.03 (d, J=15.9 Hz, 1H), 5.96 (d, J=1.5 Hz, 1H), 5.90 (d, J=1.5 Hz, 1H), 5.55 (m, 1H), 4.47 (m, 1H), 4.50 (m, 1H), 3.94 (d, J=3.6 Hz, 1H), 3.85 (dd, J₁=3.3 Hz, J₂=11.1 Hz, 1H), 3.66 (bs, 3H), 3.34-3.31 (m, 2H), 3.13 (d, J=5.1 Hz, 1H), 2.93-2.73 (m, 2H), 2.53 (d, J=18.0 Hz, 1H), 2.33 (s, 3H), 2.22 (s, 3H), 2.03 (s, 3H), 1.94-1.82 (m, 1H).

ESI-MS m/z: Calcd. for C₃₆H₃₈N₂O₉: 642.7. Found (M−17)⁺: 625.2.

Example 111

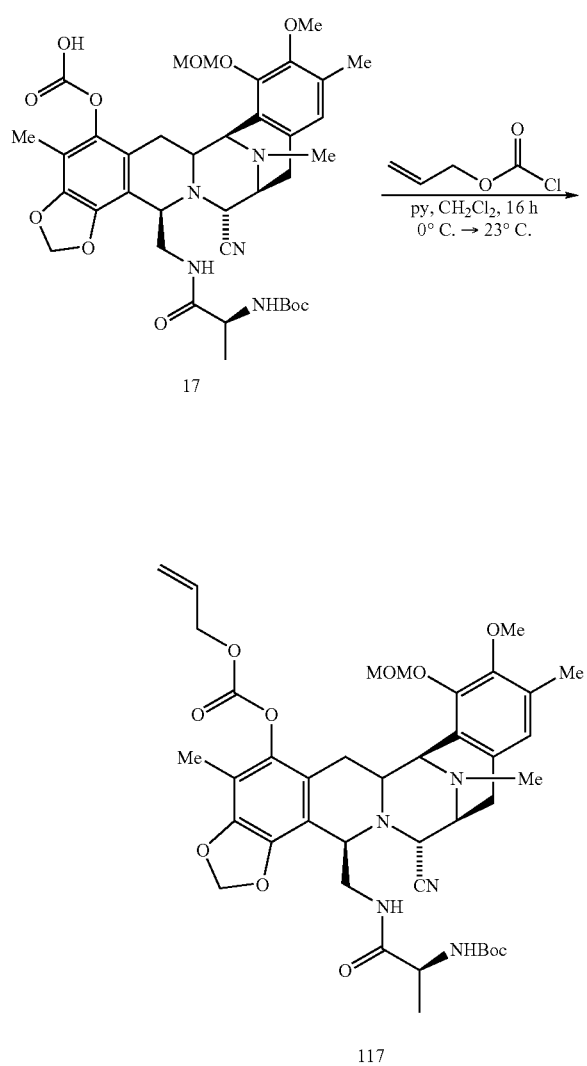

17

117

To a solution of 17 (6.28 g, 9.06 mmol) in CH$_2$Cl$_2$ (45.3 mL), allyl chloroformiate (3.85 mL, 36.24 mmol) and pyridine (2.93 mL, 36.24 mmol) were added at 0° C. The reaction mixture was stirred for 16 h at 23° C. and then, the solution was diluted with CH$_2$Cl$_2$ (150 mL) and washed with 0.1 N HCl (2×100 mL). The organic layer was dried over Na$_2$SO$_4$, filtered, and the solvent was eliminated under reduced pressure to give 117 (5.96 g, 84%) which was used in following steps with no further purification.

Rf: 0.56 (CH$_2$Cl$_2$:EtOAc 1:1).

$^1$H NMR (300 MHz, CDCl$_3$) δ 6.72 (s, 1H), 6.05-5.94 (m, 1H), 6.01 (s, 1H), 5.91 (s, 1H), 5.44 (dd, J1=1.2 Hz, J2=17.1 Hz, 1H), 5.35 (dd, J1=1.2 Hz, J2=10.5 Hz, 1H), 5.34 (m, 1H), 5.10 (d, J=5.7 Hz, 1H), 5.05 (d, J=5.7 Hz, 1H), 4.68 (d, J=5.7 Hz, 1H), 4.65 (dt, J1=1.2 Hz, J2=6 Hz, 1H), 4.18 (brd, J=9 Hz, 2H), 4.04 (bs, 1H), 3.70 (s, 3H), 3.67-3.60 (m, 1H), 3.55 (s, 3H), 3.43-3.41 (m, 2H), 3.29-3.25 (m, 2H), 3.00 (dd, J1=8.7 Hz, J2=18.3 Hz, 1H), 2.90 (dd, J1=2.4 Hz, J2=16.2 Hz, 1H), 2.75 (d, J=18.3 Hz, 1H), 2.35 (s, 3H), 2.22 (s, 3H), 2.06 (s, 3H), 1.83 (dd, J1=11.4 Hz, J2=15.9 Hz, 1H), 1.39 (s, 9H), 0.73 (d, J=6.9 Hz, 3H).

$^{13}$C NMR (75 MHz, CDCl$_3$) δ 172.1, 152.8, 148.6, 148.3, 144.6, 140.7, 140.6, 131.5, 131.2, 131.1, 130.4, 125.3, 125.0, 123.3, 120.9, 119.1, 118.8, 117.6, 112.9, 112.0, 101.6, 99.2, 71.8, 69.0, 68.4, 59.7, 59.2, 57.6, 57.3, 56.7, 55.8, 55.2, 41.4, 39.9, 28.2, 26.0, 25.0, 18.6, 15.6, 9.0.

ESI-MS m/z: Calcd. for C$_{40}$H$_{51}$N$_5$O$_{11}$: 777.8. Found (M+1)$^+$: 778.3.

Example 112

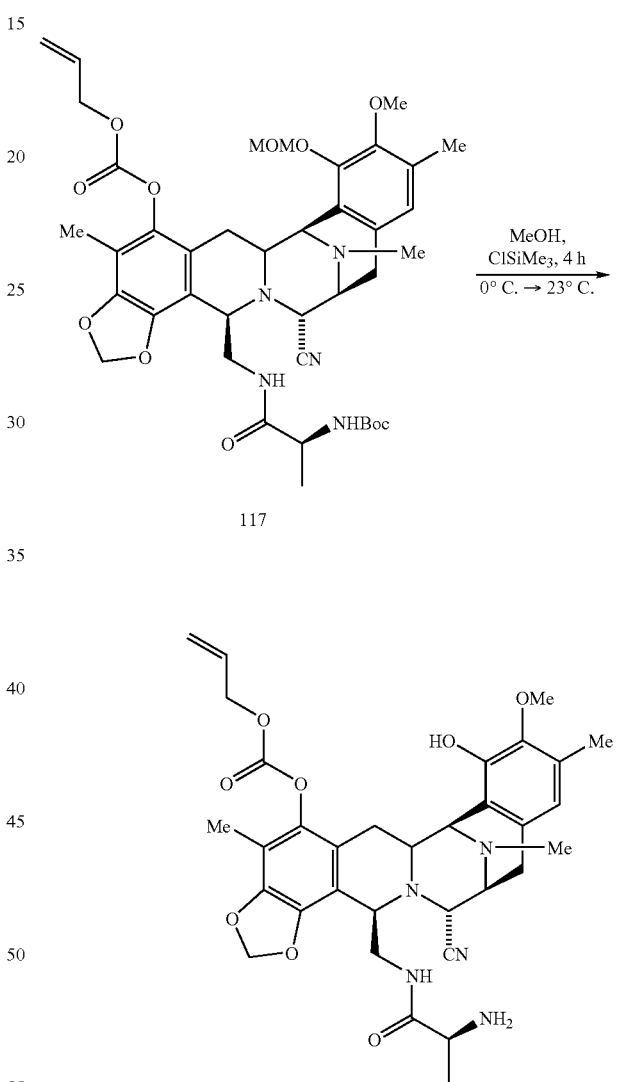

117

118

To a solution of 117 (3.96 g, 5.09 mmol) in MeOH (37.4 mL), trimetylchlorosilane (6.5 mL, 50.9 mmol) was added at 0° C. The reaction mixture was stirred for 4 h at 23° C. and then, the solvent was eliminated under reduced pressure. The residue was diluted with EtOAc (70 mL) and washed with a saturated aqueous solution of NaHCO$_2$ (2×45 mL). The organic layer was dried over Na$_2$SO$_4$, filtered, and the solvent was eliminated in vacuo to give 118 (2.77 g, 86%) which was used in following steps with no further purification.

Rf: 0.61 (Hex:EtOAc 1:1).

¹H NMR (300 MHz, CDCl₃) δ 6.50 (s, 1H), 6.45 (m, 1H), 6.10-6.03 (m, 1H), 6.00 (s, 1H), 5.93 (s, 1H), 5.47 (dd, J1=1.2 Hz, J2=17.1 Hz, 1H), 5.38 (dd, J1=1.2 Hz J2=10.5 Hz, 1H), 4.81-4.64 (m, 2H), 4.10-4.03 (m, 3H), 3.75 (s, 3H), 3.70-3.44 (m, 2H), 3.35 (d, J=8.1 Hz, 1H), 3.28 (dt, J1=2.7 Hz, J2=9 Hz, 1H), 2.98 (dd, J1=7.8 Hz, J2=18 Hz, 1H), 2.90 (dd, J1=2.7 Hz, J2=16.2 Hz, 1H), 2.78 (dd, J1=6.9 Hz, J2=14.1 Hz, 1H), 2.63 (d, J=18.3 Hz, 1H), 2.30 (s, 3H), 2.25 (s, 3H), 2.04 (s, 3H), 1.88 (dd, J1=13.2 Hz, J2=15.6 Hz, 1H), 0.95 (d, J=6.9 Hz, 3H).

¹³C NMR (75 MHz, CDCl₃) δ 175.8, 152.9, 146.6, 144.6, 142.5, 140.8, 140.6, 131.5, 131.3, 128.5, 121.1, 120.8, 118.9, 117.8, 117.0, 113.2, 111.9, 101.7, 68.9, 60.6, 59.1, 56.6, 56.4, 55.7, 55.2, 50.5, 41.7, 39.4, 26.1, 25.0, 21.0, 15.6, 9.2.

ESI-MS m/z: Calcd for C₃₃H₃₉N₅O₈: 633.6. Found (M+1)⁺: 634.2.

Example 113

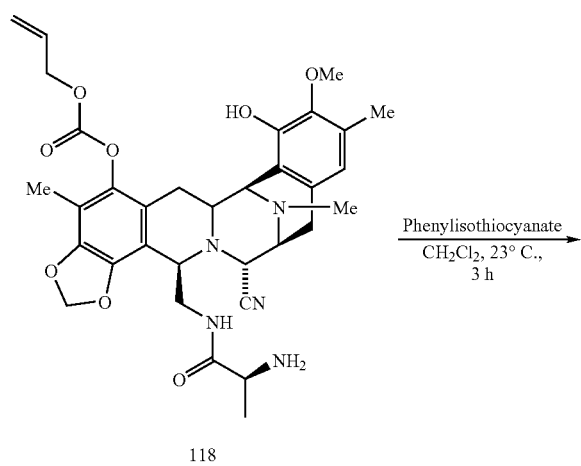

118

To a solution of 118 (3.52 g, 5.56 mmol) in CH₂Cl₂ (28 mL), phenylisothiocyanate (3.99 mL, 33.36 mmol) was added at 23° C. The reaction mixture was stirred for 3 and then, the solvent was eliminated under reduced pressure. The residue was purified by flash column chromatography to afford 119 (3.5 g, 82%) as a white solid.

Rf: 0.52 (CH₂Cl₂:EtOAc 1:5).

¹H NMR (300 MHz, CDCl₃) δ 7.69 (bs, 1H), 7.49-7.46 (m, 2H), 7.34-7.21 (m 2H), 6.96 (d, J=6.9 Hz, 1H), 6.06-5.97 (m, 1H), 6.03 (s, 1H), 5.96 (bs, 1H), 5.91 (s, 1H), 5.66 (s, 1H), 5.47 (dd, J1=1.5 Hz, J2=17.1 Hz, 1H), 5.37 (dd, J1=1.5 Hz, J2=10.5 Hz, 1H), 5.36 (s, 1H), 4.75-4.70 (m, 2H), 4.54-4-49 (m, 1H), 4.14 (d, J=2.4 Hz, 1H), 4.07-4.06 (m, 2H), 3.70 (s, 3H), 3.44 (m, 1H), 3.35 (d, J=8.1 Hz, 1H), 3.21 (dt, J1=2.7 Hz, J2=6.6 Hz, 1H), 2.94-2.82 (m, 2H), 2.63 (d, J=18 Hz, 1H), 2.24 (s, 3H), 2.06 (s, 3H), 2.06 (s, 3H), 1.90 (dd, J1=11.7 Hz, J2=15.9 Hz, 1H), 0.71 (d, J=6.9 Hz, 3H).

¹³C NMR (75 MHz, CDCl₃) δ 178.6, 171.9, 152.8, 146.7, 144.5, 142.6, 140.8, 140.5, 136.3, 131.3, 131.0, 129.9, 129.8, 128.9, 126.7, 125.2, 124.3, 121.1, 120.6, 118.9, 117.7, 116.5, 112.8, 112.1, 101.6, 68.9, 60.5, 58.9, 57.3, 56.1, 55.9, 55.1, 53.3, 41.5, 39.2, 25.9, 24.6, 20.9, 15.4, 9.1.

ESI-MS m/z: Calcd. for C₄₀H₄₄N₃O₈S: 768.8. Found (M+1)⁺: 769.3.

Example 114

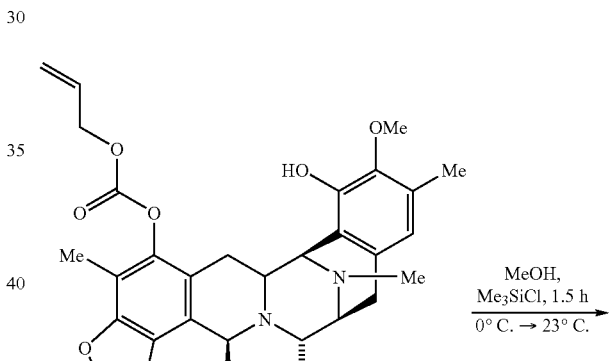

119

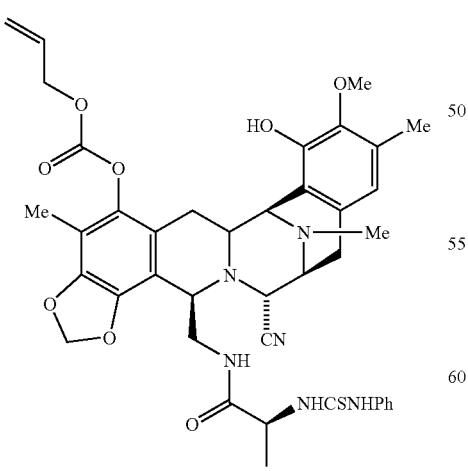

119

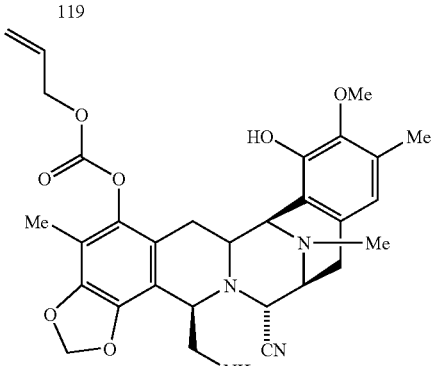

120

To a solution of 119 (3.38 g, 4.4 mmol) in MeOH (22 mL), trimetylchlorosilane (2.3 mL, 22 mmol) was added at 0° C. The reaction mixture was stirred for 1.5 h at 23° C. and then, the solvent was eliminated under reduced pressure. The residue was diluted with EtOAc (100 mL) and washed with 0.1 N HCl (2×75 mL). The aqueous phase was basified with a saturated aqueous solution of NaHCO$_2$ and extracted with CH$_2$Cl$_2$ (2×100 mL). The combined organic layers were dried over Na$_2$SO$_4$, filtered, and the solvent was eliminated under reduced pressure to afford 120 (2.47 g, 100%) as a white solid which was used in following steps with no further purification.

Rf: 0.26 (EtOAc:MeOH 5:1).

$^1$H NMR (300 MHz, CDCl$_3$) δ 6.45 (s, 1H), 6.05-5.98 (m, 1H), 5.97 (d, J=1.2 Hz, 1H), 5.90 (d, J=1.2 Hz, 1H), 5.44 (dd, J1=1.2 Hz, J2=17.1 Hz, 1H), 5.35 (dd, J1=1.2 Hz, J2=10.2 Hz, 1H), 4.75-4.71 (m, 2H), 4.12-4.10 (m, 1H), 3.99 (d, J=2.4 Hz, 1H), 3.92 (bs, 1H), 3.73 (s, 3H), 3.36-3.26 (m, 2H), 3.06 (dd, J1=8.4 Hz, J2=18 Hz, 1H), 2.89 (dd, J1=2.7 Hz, J2=15.9 Hz, 1H), 2.75-2.73 (m, 2H), 2.48 (d, J=18 Hz, 1H), 2.32 (s, 3H), 2.23 (s, 3H), 2.05 (s, 3H), 1.85 (dd, J1=11.7 Hz, J2=15.6 Hz, 1H).

$^{13}$C NMR (75 MHz, CDCl$_3$) δ 153.0, 146.6, 144.5, 142.8, 140.7, 131.5, 130.5, 128.9, 121.3, 120.9, 119.1, 117.9, 116.7, 113.8, 111.6, 101.5, 69.0, 60.6, 59.8, 58.7, 56.5, 56.0, 55.3, 44.2, 41.8, 31.6, 26.1, 25.7, 15.7, 9.2.

ESI-MS m/z: Calcd. for C$_{30}$H$_{34}$N$_4$O$_7$: 562.6. Found (M+1)$^+$: 563.2.

To a solution of 120 (2.57 g, 4.4 mmol) in CH$_2$Cl$_2$ (44 mL), TrocCl (0.91 mL, 6.6 mmol) and pyridine (0.53 mL, 6.6 mmol) were added at −20° C. The reaction mixture was stirred for 30 min at 0° C. and then, the solution was diluted with CH$_2$Cl$_2$ (50 mL) and washed with 0.1 N HCl (2×25 mL). The organic layer was dried over Na$_2$SO$_4$, filtered, and the solvent was eliminated under reduced pressure to give 121 (3.24 g, 100%) which was used in following steps with no further purification.

Rf: 0.62 (EtOAc:MeOH 5:1).

$^1$H NMR (300 MHz, CDCl$_3$) δ 6.50 (s, 1H), 6.07-6.01 (m, 1H), 5.99 (d, J=1.2 Hz, 1H), 5.93 (d, J=1.2 Hz, 1H), 5.68 (s, 1H), 5.46 (dd, J1=1.2 Hz, J2=17.1 Hz, 1H), 5.37 (dd, J1=1.2 Hz, J2=10.5 Hz, 1H), 4.74 (t, J=5.7 Hz, 2H), 4.63-4.62 (m, 1H), 4.54 (d, J=12 Hz, 1H), 4.30 (d, J=12 Hz, 1H), 4.14-4.11 (m, 2H), 4.02-4.01 (m, 2H), 3.75 (s, 3H), 3.36-3.26 (m, 3H), 3.04 (dd, J1=8.1 Hz, J2=17.7 Hz, 1H), 2.91 (dd, J1=2.4 Hz, J2=15.6 Hz, 1H), 2.60 (d, J=17.7 Hz, 1H), 2.31 (s, 3H), 2.25 (s, 3H), 2.04 (s, 3H), 1.84 (dd, J1=12 Hz, J2=15.9 Hz, 1H).

ESI-MS m/z: Calcd. for C$_{33}$H$_{35}$Cl$_3$N$_4$O$_9$: 738.0. Found (M+1)$^+$: 737.2.

Example 116

Example 115

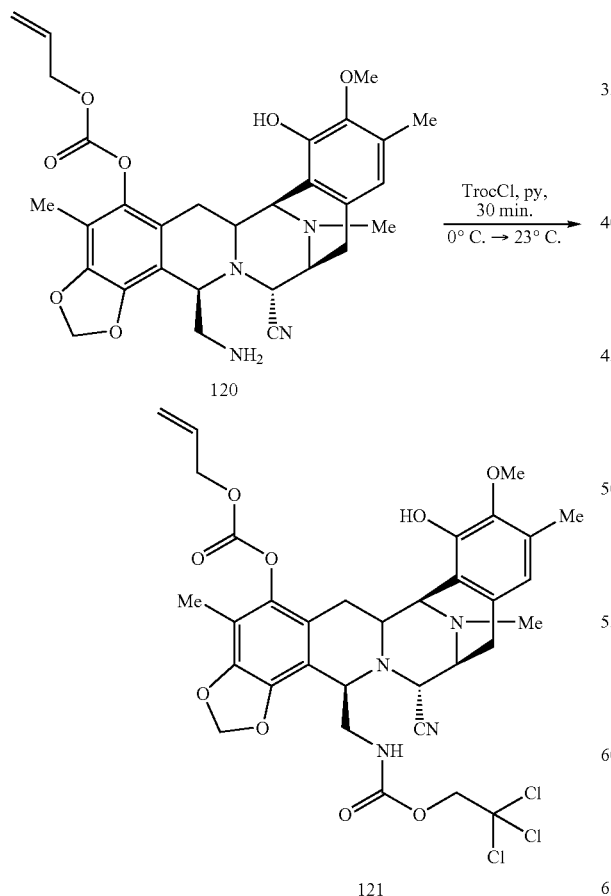

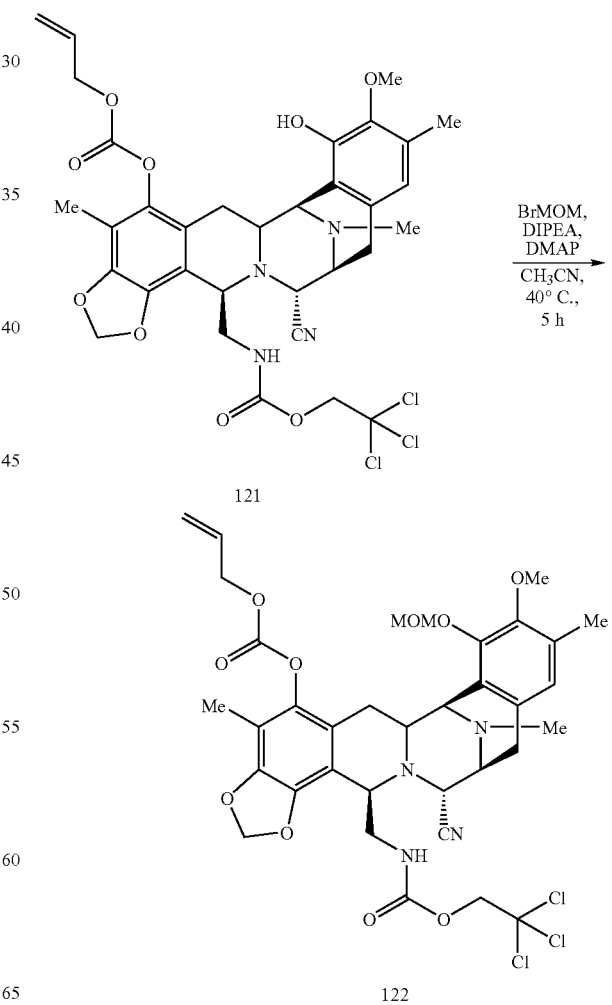

To a solution of 121 (0.45 g, 0.60 mmol) in $CH_3CN$ (4 mL), diisopropylethylamine (2.17 mL, 12.46 mmol), bromomethyl methyl ether (0.76 mL, 9.34 mmol) and dimethylaminopyridine (8 mg, 0.062 mmol) were added at 0° C. The reaction mixture was heated at 40° C. for 5 h. Then, the reaction was diluted with $CH_2Cl_2$ (50 mL) and washed with 0.1 N HCl (2×25 mL). The organic layer was dried over $Na_2SO_4$, filtered, and the solvent was eliminated under reduced pressure to give 122 (0.453 g, 95%) which was used in following steps with no further purification.

Rf: 0.31 (RP-18 $CH_3CN$—$H_2O$ 8:2).

$^1$H NMR (300 MHz, $CDCl_3$) δ 6.70 (s, 1H), 6.05-5.99 (m, 1H), 5.97 (s, 1H), 5.92 (s, 1H), 5.43 (dd, J1=1.2 Hz, J2=117.1 Hz, 1H), 5.34 (dd, J1=1.2 Hz, J2=110.5 Hz, 1H), 5.10-5.04 (m, 2H), 4.72-4.68 (m, 2H), 4.60 (t, J=5.7 Hz, 1H), 4.49 (d, J=12.3 Hz, 1H), 4.38 (d, J=12.3 Hz, 1H), 4.18 (d, J=2.7 Hz, 1H), 4.03-4.00 (m, 2H), 3.71 (s, 3H), 3.54 (s, 3H), 3.38-3.22 (m, 4H), 3.04 (dd, J1=7.8 Hz, J2=18.3 Hz, 1H), 2.91 (dd, J1=2.4 Hz, J2=15.9 Hz, 1H), 2.61 (d, J=18 Hz, 1H), 2.31 (s, 3H), 2.20 (s, 3H), 2.03 (s, 3H), 1.76 (dd, J1=11.7 Hz, J2=15.6 Hz, 1H).

ESI-MS m/z: Calcd. for $C_{33}H_{39}Cl_3N_4O_{10}$: 782.0. Found $(M+1)^+$: 783.2.

the mixture was filtered through a pad of celite which was washed with $CH_2Cl_2$ (25 mL). The organic layer was washed with an aqueous sat. solution of sodium bicarbonate (pH=9) (2×15 mL), dried over $Na_2SO_4$, filtered, and the solvent was eliminated under reduced pressure to give 123 (0.351 g, 100%) which was used in following steps with no further purification.

Rf: 0.38 ($SiO_2$, EtOAc:MeOH 5:1).

$^1$H NMR (300 MHz, $CDCl_3$) δ 6.68 (s, 1H), 6.06-5.99 (m, 1H), 5.97 (d, J=1.5 Hz, 1H), 5.91 (d, J=1.25 Hz, 1H), 5.44 (dd, J1=1.5 Hz, J2=17.4 Hz, 1H), 5.36 (dd, J1=1.5 Hz, J2=10.2 Hz, 1H), 5.08 (q, J=5.7 Hz, 2H), 5.74-4.70 (m, 2H), 4.02 (d, J=3 Hz, 1H), 4.00 (d, J=2.4 Hz, 1H), 3.91 (m, 1H), 3.71 (s, 3H), 3.56 (s, 3H), 3.37-3.35 (m, 1H), 3.29 (t, J=2.7 Hz, 1H), 3.08 (dd, J1=7.5 Hz, J2=18 Hz, 1H), 2.90 (dd, J1=2.7 Hz, J2=15.9 Hz, 1H), 2.74 (dd, J1=2.4 Hz, J2=5.1 Hz, 2H), 2.48 (d, J=18 Hz, 1H), 2.35 (s, 3H), 2.20 (s, 3H), 2.05 (s, 3H), 1.80 (dd, J1=12 Hz, J2=15.9 Hz, 2H).

ESI-MS m/z: Calcd. for $C_{32}H_{38}N_4O_8$: 606.6. Found $(M+1)^+$: 607.3.

Example 117

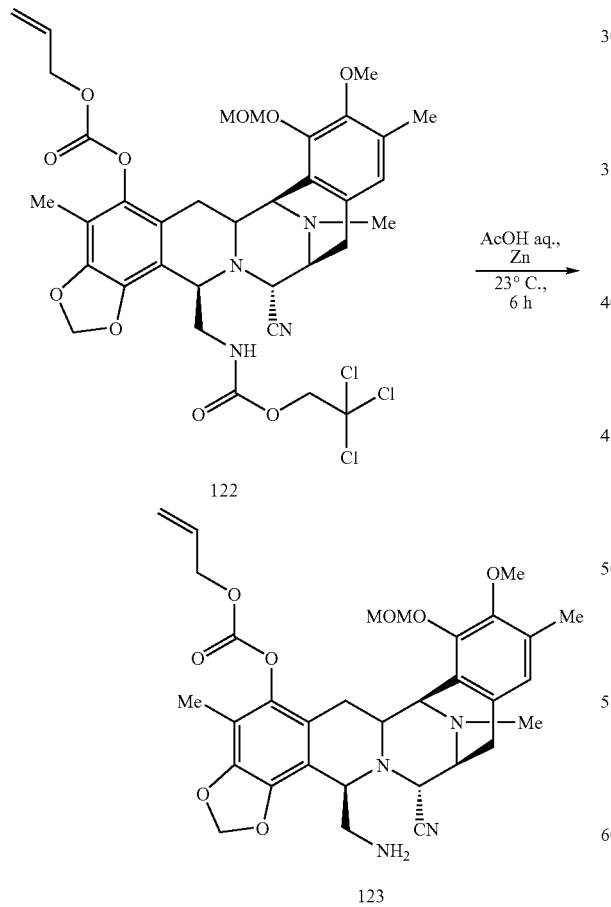

Example 118

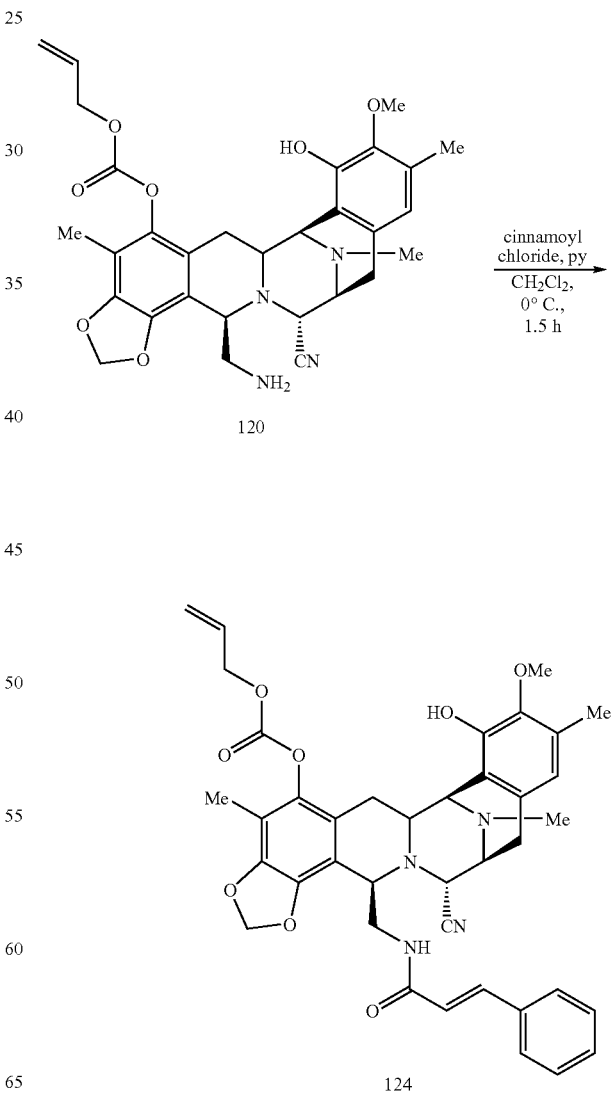

To a suspension of 122 (0.45 g, 0.579 mmol) in 90% aqueous acetic acid (6 mL), powder zinc (0.283 g, 4.34 mmol) was added and the reaction was stirred for 6 h at 23° C. Then, To a solution of 120 (100 mg, 0.177 mmol) in CH$_2$Cl$_2$ (0.7 mL), cinnamoyl chloride (29.5 mg, 0.177 mmol) and pyridine (14.37 μL, 0.177 mmol) were added at 0° C. The reaction mixture was stirred for 1.5 h and then, the solution was diluted with CH$_2$Cl$_2$ (15 mL) and washed with 0.1 N HCl (10 mL). The organic layer was dried over Na$_2$SO$_4$, filtered, and the solvent was eliminated under reduced pressure. The residue was purified by flash column chromatography (SiO$_2$, gradient Hex:EtOAc 2:1 to Hex:EtOAc 1:3) to afford 124 (86 mg, 70%) as a white solid.

Rf: 0.77 (EtOAc:MeOH 5:1).

$^1$H NMR (300 MHz, CDCl$_3$) δ 7.39-7.26 (m, 5H), 7.25 (d, J=15.6 Hz, 1H), 6.44 (s, 1H), 6.01 (d, J=1.2 Hz, 1H), 5.94 (d, J=1.2 Hz, 1H), 5.68 (s, 1H), 5.65 (d, J=15.6 Hz, 1H), 5.44 (dd, J1=1.2 Hz, J2=17.1 Hz, 1H), 5.35 (dd, J1=1.2 Hz, J2=10.5 Hz, 1H), 5.18 (t, J=6 Hz, 1H), 4.73-4.69 (m, 2H), 4.11-4.09 (m, 3H), 3.66-3.58 (m, 2H), 3.65 (s, 3H), 3.38-3.31 (n, 3H), 3.02 (dd, J1=8.4 Hz, J2=18.3 Hz, 1H), 2.92 (dd, J1=2.7 Hz, J2=15.6 Hz, 1H), 2.59 (d, J=18.3 Hz, 1H), 2.31 (s, 3H), 2.05 (s, 3H), 2.02 (s, 3H), 1.89 (dd, J1=12.3 Hz, J2=16.2 Hz, 1H).

$^{13}$C NMR (75 MHz, CDCl$_3$) δ 165.5, 152.7, 146.6, 144.4, 142.6, 140.7, 140.5, 140.1, 134.7, 131.2, 130.6, 129.3, 128.7, 128.4, 127.6, 120.8, 120.5, 120.3, 118.9, 117.6, 116.5, 113.2, 111.8, 101.6, 68.8, 60.4, 59.0, 56.2, 56.1, 55.7, 55.0, 41.5, 40.6, 25.9, 25.1, 15.5, 9.0.

ESI-MS m/z: Calcd. for C$_{39}$H$_{40}$N$_4$O$_8$: 692.7. Found (M+1)$^+$: 693.2.

The reaction mixture was stirred for 2 h at 23° C. and then, the solution was poured into a pad of flash column (SiO$_2$, gradient Hex:EtOAc 1:1 to EtOAc) to afford 125 (435 mg, 100%) as a white solid. Rf: 0.22 (Hex:EtOAc 1:2).

$^1$H NMR (300 MHz, CDCl$_3$) δ 7.36-7.33 (m, 5H), 7.28 (d, J=15.9 Hz, 1H), 6.45 (s, 1H), 5.90 (s, 1H), 5.83 (s, 1H), 5.55 (d, J=15.6 Hz, 1H), 5.24 (t, J=12.9 Hz, 1H), 4.17 (d, J=1.8 Hz, 1H), 4.10-4.07 (m, 2H), 3.72 (s, 3H), 3.46-3.32 (m, 3H), 3.14-3.00 (m, 2H), 2.54 (d, J=18 Hz, 1H), 2.32 (s, 3H), 2.05 (s, 6H), 1.89 (dd, J$_1$=12 Hz, J2=15.3 Hz, 1H).

$^{13}$C NMR (75 MHz, CDCl$_3$) δ 165.7, 146.9, 145.1, 144.2, 143.0, 140.8, 136.5, 134.5, 130.6, 129.4, 128.9, 127.9, 127.7, 120.8, 119.8, 117.8, 114.1, 112.9, 107.1, 100.8, 60.5, 59.2, 56.4, 56.0, 55.1, 41.4, 30.7, 25.5, 25.3, 15.5, 8.9.

ESI-MS m/z: Calcd. for C$_{35}$H$_{36}$N$_4$O$_6$: 608.6. Found (M+1)$^+$: 609.2.

Example 120

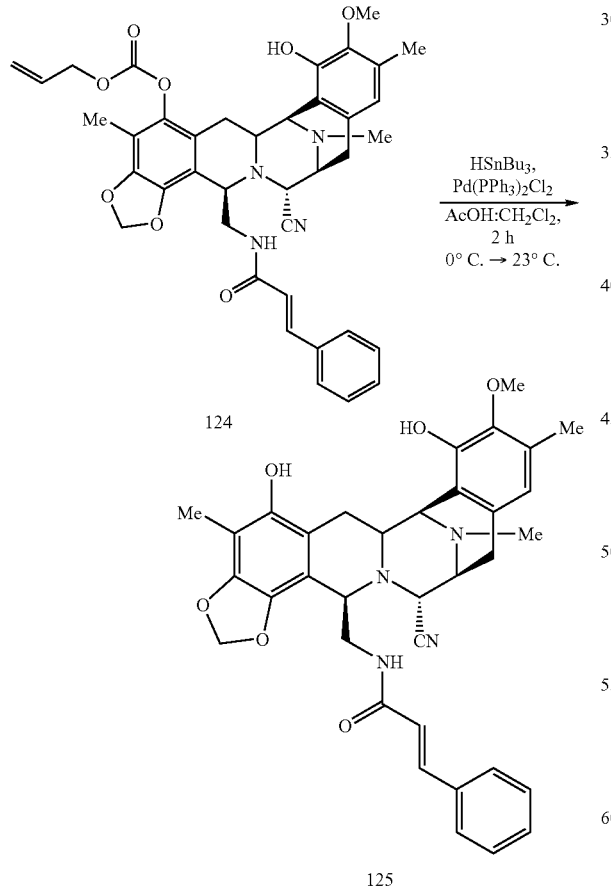

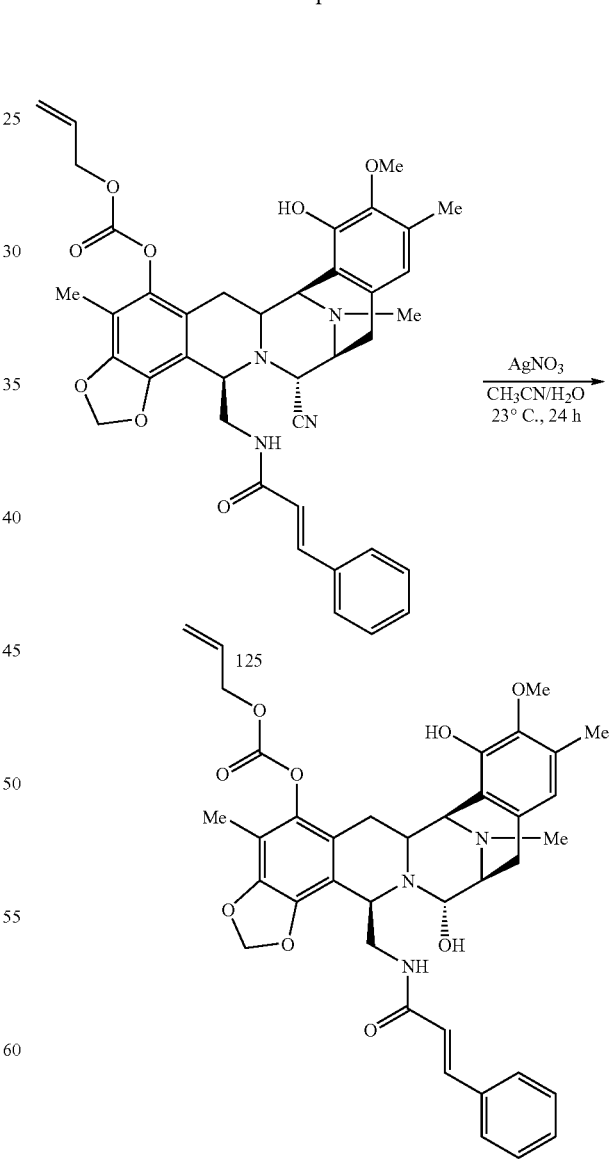

To a solution of 124 (495 mg, 0.713 mmol) in CH$_2$Cl$_2$ (28 mL), acetic acid (163 μL), Pd(PPh$_3$)$_2$Cl$_2$ (50 mg, 0.0713 mmol) and Bu$_3$SnH (384 μL, 1.42 mmol) were added at 0° C.

To a solution of 125 (86 mg, 0.124 mmol) in CH$_3$CN/H$_2$O (1.5 mL/1 mL) AgNO$_3$ (632 mg, 3.72 mmol) was added and the reaction was stirred at 23° C. for 24 h. Then, brine (10 mL) and Aq sat NaHCO$_3$ (10 mL) were added at 0° C. and the mixture was stirred for 15 min, filtered through a pad of celite and washed with CH$_2$Cl$_2$ (20 mL). The solution was extracted and the organic layer was dried over Na$_2$SO$_4$, filtered and concentrated in vacuo. The residue was purified by flash column chromatography (SiO$_2$, gradient EtOAc to EtOAc: MeOH 2:1) to afford 126 (70 mg, 83%) as a white solid.

Rf: 0.07 (EtOAc:MeOH 5:1).

$^1$H NMR (300 MHz, CDCl$_3$) δ 7.40-7.28 (m, 5H), 7.25 (d, J=15.6 Hz, 1H), 6.48 (s, 1H), 6.00-5.94 (m, 1H), 5.96 (s, 1H), 5.92 (s, 1H), 5.89 (s, 1H), 5.53 (d, J=15.6 Hz, 1H), 5.42-5.36 (m, 2H), 5.31 (dd, J$_1$=1.2 Hz, J2=10.8 Hz, 1H), 4.71-4.65 (m, 2H), 4.51 (d, J=3 Hz, 1H), 4.42 (bs, 1H), 4.07 (bs, 1H), 3.79 (dd, J$_1$=6.9 Hz, J2=12.9 Hz, 1H), 3.68 (s, 3H), 3.62-3.59 (m, 1H), 3.41-3.37 (m, 1H), 3.16 (d, J=7.8 Hz, 1H), 2.95 (dd, J$_1$=7.5 Hz, J2=17.4 Hz, 1H), 2.88-2.83 (m, 1H), 2.43 (d, J=18 Hz, 1H), 2.28 (s, 3H), 2.10 (s, 3H), 2.00 (s, 3H), 1.81 (dd, J$_1$=11.7 Hz, J2=15.3 Hz, 1H).

$^{13}$C NMR (75 MHz, CDCl$_3$) δ 165.5, 152.9, 146.7, 144.5, 144.4, 142.7, 141.0, 140.0, 134.6, 131.4, 130.7, 129.2, 128.8, 128.5, 127.8, 127.7, 124.6, 121.2, 120.9, 118.9, 116.5, 114.9, 114.7, 111.3, 101.6, 93.3, 92.3, 83.2, 68.9, 60.6, 57.8, 56.8, 56.6, 56.3, 52.5, 52.2, 41.6, 26.1, 24.6, 15.6, 9.1.

ESI-MS m/z: Calcd. for C$_{38}$H$_{41}$N$_3$O$_9$: 683.7. Found (M−17)$^+$: 666.3.

was stirred for 1.5 h and then, the solution was diluted with CH$_2$Cl$_2$ (50 mL) and washed with 0.1 N HCl (30 mL). The organic layer was dried over Na$_2$SO$_4$, filtered, and the solvent was eliminated under reduced pressure. The residue was purified by flash column chromatography (SiO$_2$, gradient Hex: EtOAc 2:1 to EtOAc) to afford 127 (1.64 g, 83%) as a white solid.

Rf: 0.63 (EtOAc:MeOH 5:1).

$^1$H NMR (300 MHz, CDCl$_3$) δ 7.26-7-14 (m, 3H), 7.04-7.01 (m, 2H), 6.44 (s, 1H), 6.07-5.99 (m, 1H), 5.97 (d, J=1.5 Hz, 1H), 5.91 (d, J=1.5 Hz, 1H), 5.75 (bs, 1H), 5.45 (dd, J$_1$=1.5 Hz, J2=17.4 Hz, 1H), 5.36 (dd, J$_1$=1.5 Hz, J2=10.2 Hz, 1H), 5.03 (t, J=5.7 Hz, 1H), 5.74-5.66 (m, 2H), 4.09 (d, J=2.4 Hz, 1H), 4.01 (bs, 1H), 3.97 (d, J=2.7 Hz, 1H), 3.62 (dd, J$_1$=8.4 Hz, J2=13.5 Hz, 1H), 3.42 (s, 3H), 3.37-3.28 (m, 3H), 3.04-2.87 (m, 3H), 2.67-2.46 (m, 4H), 2.29 (s, 3H), 2.05 (s, 3H), 2.03 (s, 3H), 1.83-1.79 (m, 1H).

$^{13}$C NMR (75 MHz, CDCl$_3$) δ 171.8, 152.8, 146.7, 144.5, 144.4, 142.7, 140.9, 140.8, 140.6, 131.4, 130.7, 128.9, 128.4, 128.2, 128.1, 126.0, 120.8, 120.4, 118.9, 117.6, 116.6, 113.0, 111.9, 101.6, 68.9, 60.3, 59.0, 56.3, 56.2, 55.6, 55.1, 41.6, 40.3, 37.7, 31.0, 25.9, 25.2, 15.5, 9.1.

ESI-MS m/z: Calcd. for C$_{39}$H$_{42}$N$_4$O$_8$: 694.3. Found (M+1)$^+$: 695.3.

Example 122

Example 121

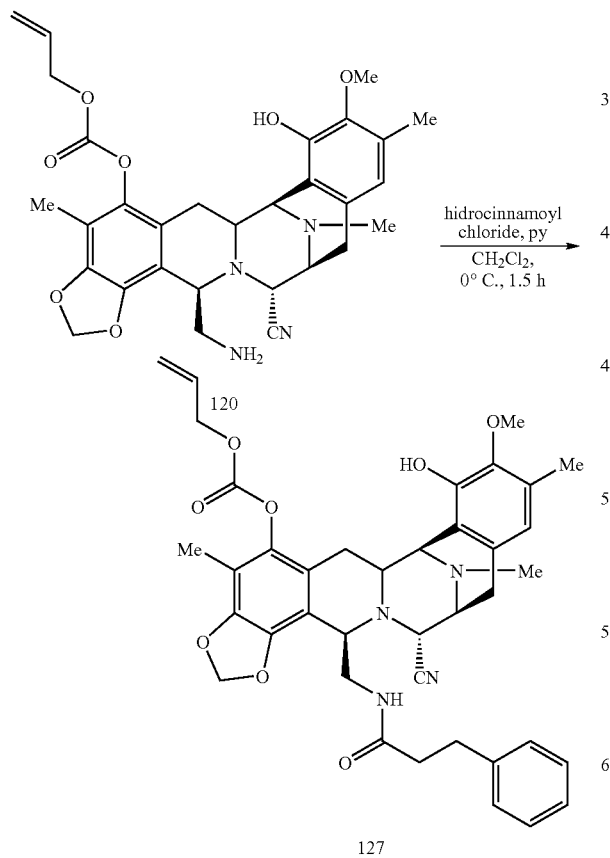

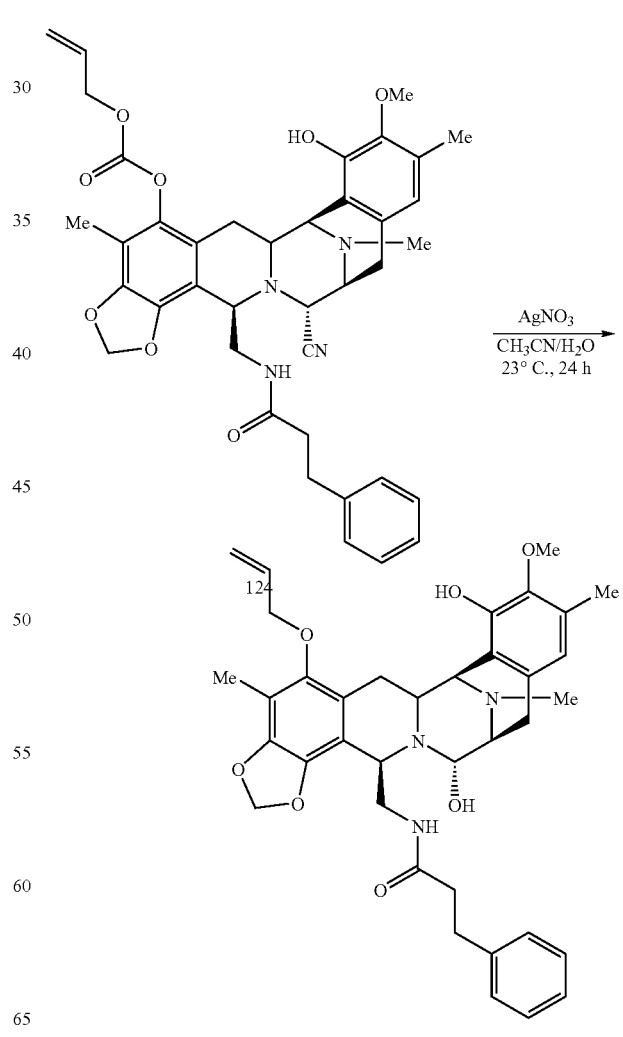

To a solution of 120 (1.61 g, 2.85 mmol) in CH$_2$Cl$_2$ (4 mL), hydrocinnamoyl chloride (423 μL, 2.85 mmol) and pyridine (230 μL, 2.85 mmol) were added at 0° C. The reaction mixture To a solution of 127 (50 mg, 0.072 mmol) in CH$_3$CN/H$_2$O (1.5 mL/1 mL), AgNO$_3$ (444 mg, 2.16 mmol) was added and the reaction was stirred at 23° C. for 24 h. Then, brine (10 mL) and Aq sat NaHCO$_3$ (10 mL) were added at 0° C. and the mixture was stirred for 15 min, filtered through a pad of celite and washed with CH$_2$Cl$_2$ (15 mL). The solution was extracted and the organic layer was dried over Na$_2$SO$_4$, filtered and concentrated in vacuo. The residue was purified by flash column chromatography (SiO$_2$, gradient EtOAc to EtOAc: MeOH 3:1) to afford 128 (30 mg, 61%) as a white solid.

Rf: 0.65 (EtOAc:MeOH 5:1).

$^1$H NMR (300 MHz, CDCl$_3$) δ 7.22-7.11 (m, 3H), 7.06-7.03 (m, 2H), 6.43 (s, 1H), 6.08-5.98 (m, 1H), 5.96 (d, J=1.5 Hz, 1H), 5.90 (d, J=1.5 Hz, 1H), 5.66 (bs, 1H), 5.44 (dd, J$_1$=1.5 Hz, J2=17.4 Hz, 1H), 5.36 (dd, J$_1$=1.5 Hz, J2=10.5 Hz, 1H), 4.78-4.65 (m, 2H), 4.44 (d, J=3 Hz, 1H), 4.36 (bs, 1H), 3.99 (td, J1=2.1 Hz, J2=9.9 Hz, 1H), 3.78-3.67 (m, 1H), 3.56 (dt, J1=1.5 Hz, J2=11.1 Hz, 1H), 3.43 (s, 3H), 3.30-3.12 (m, 2H), 3.02-2.89 (m, 1H), 2.83 (dd, J1=2.7 Hz, J2=15.9 Hz, 1H), 2.62-2.51 (m, 2H), 2.36 (d, J=18.6 Hz, 1H), 2.27 (s, 3H), 2.02 (s, 3H), 2.00 (s, 3H), 1.86-1.66 (m, 3H).

$^{13}$C NMR (75 MHz, CDCl$_3$) δ 171.6, 146.7, 141.2, 141.1, 131.5, 130.5, 128.9, 128.3, 128.2, 128.2, 125.9, 124.7, 121.1, 121.0, 118.8, 111.3, 101.6, 94.0, 83.2, 68.8, 60.3, 57.9, 56.6, 56.3, 52.3, 52.0, 41.7, 41.6, 41.1, 37.9, 31.1, 31.0, 26.1, 24.6, 15.5, 9.2.

ESI-MS m/z: Calcd. for C$_{38}$H$_{43}$N$_3$O$_9$: 685.7. Found (M−17)$^+$: 668.3.

Example 123

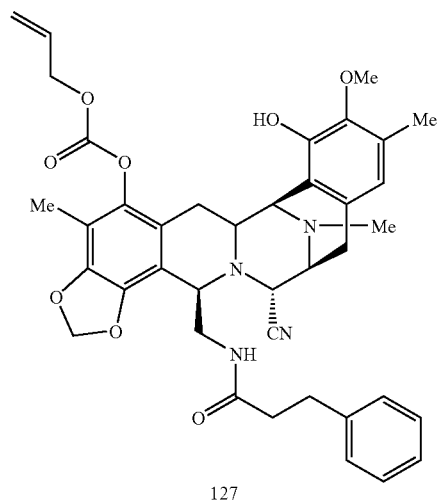

127

BrMOM, DIPEA, DMAP
CH$_3$CN, 40° C., 5 h

-continued

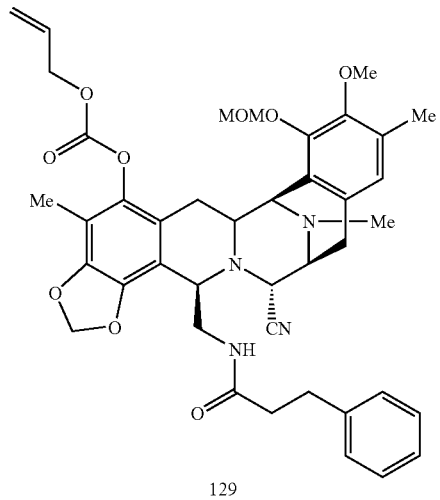

129

To a solution of 127 (1.64 g, 2.36 mmol) in CH$_3$CN (12 mL), diisopropylethylamine (8.22 mL, 47.2 mmol), bromomethyl methyl ether (2.89 mL, 35.4 mmol) and dimethylaminopyridine (29 mg, 0.236 mmol) were added at 0° C. The reaction mixture was heated at 40° C. for 5 h. Then, the reaction was diluted with CH$_2$Cl$_2$ (80 mL) and washed with 0.1 N HCl (3×25 mL). The organic layer was dried over Na$_2$SO$_4$, filtered, and the solvent was eliminated under reduced pressure to give 129 (1.46 g, 84%) which was used in following steps with no further purification.

Rf: 0.24 (RP-18 CH$_3$CN—H$_2$O 8:2).

$^1$H NMR (300 MHz, CDCl$_3$) δ 7.27-7.11 (m, 3H), 7.05-7.02 (m, 2H), 6.67 (s, 1H), 6.08-5.98 (m, 1H), 5.96 (d, J=1.2 Hz, 1H), 5.90 (d, J=1.2 Hz, 1H), 5.44 (dd, J1=1.2 Hz, J2=17.1 Hz, 1H), 5.34 (dd, J1=1.2 Hz, J2=10.5 Hz, 1H), 5.05 (d, J=6 Hz, 1H), 5.00 (d, J=6 Hz, 1H), 4.97 (t, J=5.1 Hz, 1H), 4.75-4.68 (m, 2H), 4.16 (d, J=2.7 Hz, 1H), 3.98-3.97 (m, 1H), 3.68-3.67 (m, 1H), 3.65-3.61 (m, 1H), 3.52 (s, 3H), 3.35 (s, 3H), 3.32-3.26 (m, 3H), 3.05-2.86 (m, 3H), 2.59-2.48 (m, 2H), 2.30 (s, 3H), 2.02 (s, 3H), 1.94 (s, 3H), 1.91-1.67 (m, 3H).

$^{13}$C NMR (75 MHz, CDCl$_3$) δ 171.4, 152.7, 148.5, 148.3, 144.5, 140.9, 140.8, 140.4, 131.1, 130.9, 130.4, 130.1, 128.4, 128.2, 126.0, 124.6, 123.7, 120.3, 119.0, 112.9, 111.8, 101.6, 99.1, 68.9, 59.4, 59.1, 57.5, 56.7, 56.3, 55.4, 55.1, 41.5, 40.2, 37.7, 30.9, 25.8, 25.2, 15.5, 9.0.

ESI-MS m/z: Calcd. for C$_{41}$H$_{46}$N$_4$O$_9$: 738.8. Found (M+23)$^+$: 761.2.

Example 124

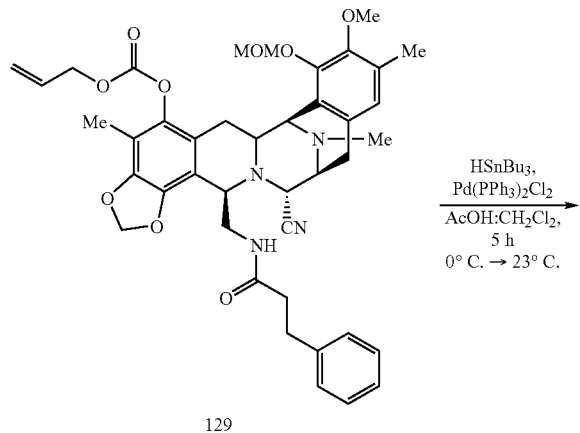

Example 125

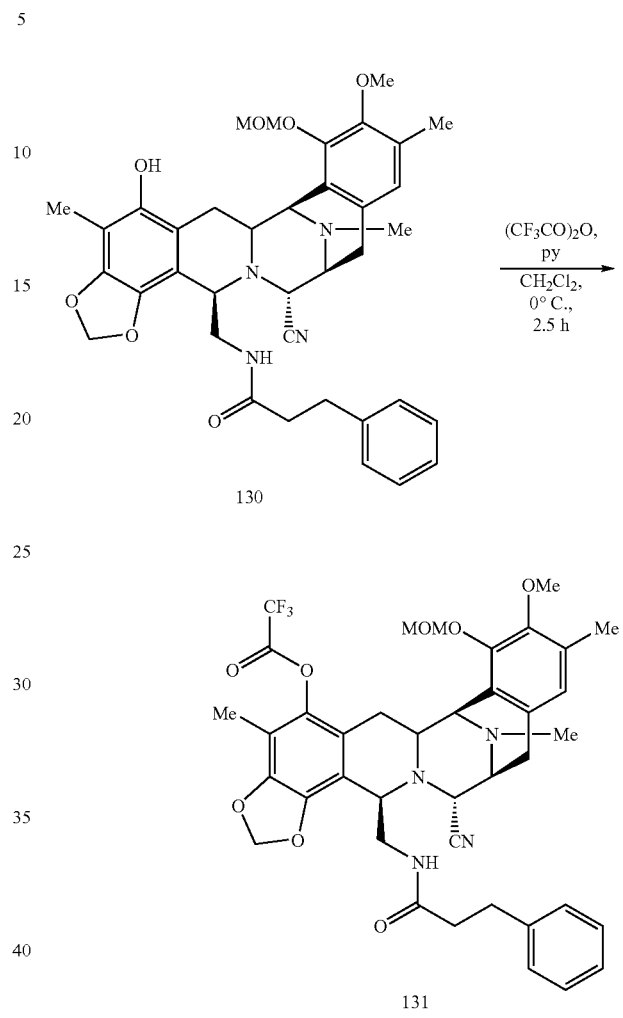

To a solution of 129 (1.46 g, 1.97 mmol) in CH$_2$Cl$_2$ (40 mL), acetic acid (450 µL), Pd(PPh$_3$)$_2$Cl$_2$ (138 mg, 0.197 mmol) and Bu$_3$SnH (1.06 mL, 3.95 mmol) were added at 0° C. The reaction mixture was stirred for 5 h at 23° C. and then, the solution was poured into a pad of flash column (SiO$_2$, gradient Hex:EtOAc 1:1 to EtOAc) to afford 130 (1.1 g, 85%) as a white solid. Rf: 0.22 (Hex:EtOAc 1:2).

$^1$H NMR (300 MHz, CDCl$_3$) δ 7.21-7.12 (m, 3H), 6.98-6.95 (m, 2H), 5.86 (s, 1H), 5.84 (s, 1H), 5.79 (bs, 1H), 5.26 (d, J=6 Hz, 1H), 5.11 (d, J=6 Hz, 1H), 5.05 (t, J=5.7 Hz, 1H), 4.19 (d, J=2.4 Hz, 1H), 4.03 (d, J=2.4 Hz, 1H), 3.99 (bs, 1H), 3.65 (s, 3H), 3.56 (s, 3H), 3.53-3.42 (m, 2H), 3.34 (d, J=8.7 Hz, 1H), 3.27 (brd, J=11.7 Hz, 1H), 3.11 (d, J=15 Hz, 1H), 2.99 (dd, J1=8.4 Hz, J2=18.3 Hz, 1H), 2.64-2.52 (m, 3H), 2.29 (s, 3H), 2.08 (s, 3H), 2.06 (s, 3H), 1.84 (t, J=7.8 Hz, 2H), 1.71 (dd, J1=12.9 Hz, J2=13.5 Hz, 1H).

$^{13}$C NMR (75 MHz, CDCl$_3$) δ 171.7, 149.0, 147.6, 140.6, 132.1, 131.9, 130.9, 130.5, 128.5, 128.4, 128.3, 128.0, 126.0, 124.9, 124.6, 123.1, 117.6, 100.8, 99.6, 59.6, 58.9, 57.6, 56.6, 56.5, 55.6, 55.1, 41.5, 37.8, 31.5, 31.1, 25.9, 25.1, 22.6, 15.5, 8.8.

ESI-MS m/z: Calcd. for C$_{37}$H$_{42}$N$_4$O$_7$: 654.7. Found (M$^+$+Na): 655.1.

To a solution of 130 (130 mg, 0.198 mmol) in CH$_2$Cl$_2$ (1 mL), trifluoroacetyl anhydride (41.9 µL, 0.297 mmol) and pyridine (24 µL, 0.297 mmol) were added at 0° C. The reaction mixture was stirred for 2.5 h and then, the solution was diluted with CH$_2$Cl$_2$ (10 mL) and washed with 0.1 N HCl (7 mL). The organic layer was dried over Na$_2$SO$_4$, filtered, and the solvent was eliminated under reduced pressure. The residue was purified by flash column chromatography (SiO$_2$, gradient Hex:EtOAc 4:1 to Hex:EtOAc 1:4) to afford 131 (93 mg, 62%) as a white solid.

Rf: 0.30 (Hex:EtOAc 1:2).

$^1$H NMR (300 MHz, CDCl$_3$) δ 7.25-7.16 (m, 3H), 7.04-7.02 (m, 2H), 6.78 (s, 1H), 6.02 (d, J=1.2 Hz, 1H), 5.95 (d, J=1.2 Hz, 1H), 5.11 (d, J=6.6 Hz, 1H), 4.98 (d, J=6.6 Hz, 1H), 4.95 (t, J=6.3 Hz, 1H), 4.61 (bs, 1H), 4.30 (s, 1H), 4.08 (s, 1H), 3.96 (d, J=7.2 Hz, 1H), 3.66-3.54 (m, 1H), 3.50 (s, 3H), 3.39 (s, 3H), 3.19 (dd, J1=7.8 Hz, J2=18.3 Hz, 1H), 2.88 (d, J=18.6 Hz, 1H), 2.79 (dd, J1=2.7 Hz, J2=15.9 Hz, 1H), 2.66-2.62 (m, 1H), 2.57 (s, 3H), 2.06 (s, 6H), 1.94-1.87 (m, 1H), 1.77-1.68 (m, 2H).

ESI-MS m/z: Calcd. for C$_{39}$H$_{41}$F$_3$N$_4$O$_8$: 750.7. Found (M+Na)$^+$: 751.2.

Example 126

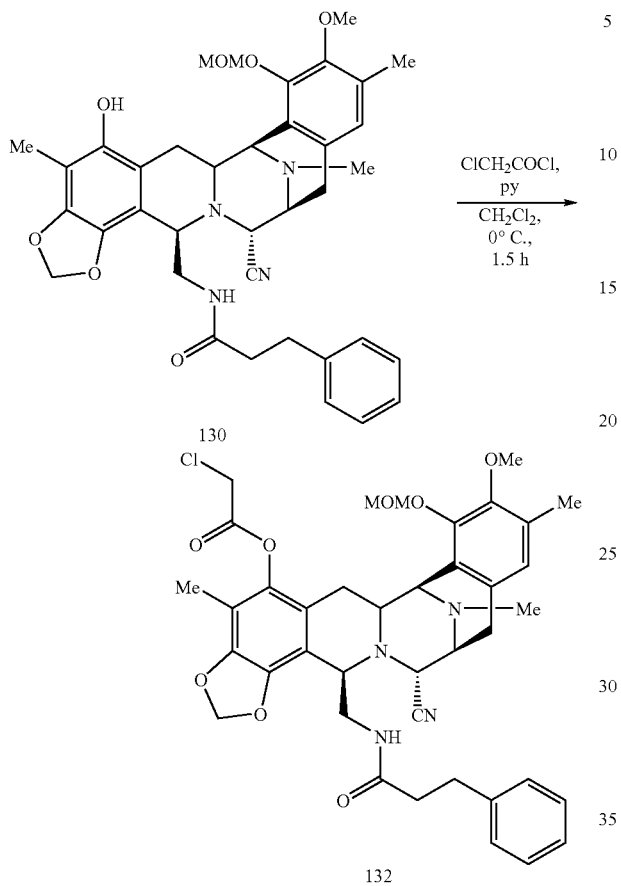

To a solution of 130 (130 mg, 0.198 mmol) in $CH_2Cl_2$ (2 mL), chloroacetyl chloride (23.65 μL, 0.297 mmol) and pyridine (24 μL, 0.297 mmol) were added at 0° C. The reaction mixture was stirred for 1.5 h and then, the solution was diluted with $CH_2Cl_2$ (10 mL) and washed with 0.1 N HCl (7 mL). The organic layer was dried over $Na_2SO_4$, filtered and the solvent was eliminated under reduced pressure. The residue was purified b flash column chromatography ($SiO_2$, gradient Hex:EtOAc 2:1 to Hex:EtOAc 1:1) to afford 132 (130 mg, 90%) as a white solid.

Rf: 0.31 (Hex:EtOAc 1:2).

$^1$H NMR (300 MHz, $CDCl_3$) δ 7.24-7.15 (m, 3H), 7.07-7.05 (m, 2H), 6.69 (s, 1H), 6.00 (d, J=1.5 Hz, 1H), 5.94 (d, J=1.5 Hz, 1H), 5.11 (d, J=5.7 Hz, 1H), 5.04 (d, J=5.7 Hz, 1H), 4.93 (m, 1H), 4.36 (s, 2H), 4.16 (d, J=2.7 Hz, 1H), 4.01 (m, 2H), 3.64 (dd, J1=6.9 Hz, J2=12.3 Hz, 1H), 3.54 (s, 3H), 3.40 (s, 3H), 3.38-3.35 (m, 2H), 2.29 (dt, J1=3 Hz, J2=12 Hz, 1H), 3.03 (dd, J1=7.8 Hz, J2=18 Hz, 1H), 2.77 (dd, J1=2.4 Hz, J2=16.2 Hz, 1H), 2.58-2.52 (m, 3H), 2.32 (s, 3H), 2.02 (s, 3H), 1.92-1.85 (m, 1H), 1.76-1.65 (m, 2H).

$^{13}$C NMR (75 MHz, $CDCl_3$) δ 171.6, 164.9, 148.3, 144.6, 140.9, 140.8, 139.8, 132.1, 131.9, 131.1, 130.0, 128.2, 126.0, 125.0, 124.6, 123.5, 120.1, 117.5, 113.0, 111.5, 101.7, 99.1, 64.9, 59.7, 58.9, 57.7, 56.6, 56.4, 55.2, 55.1, 41.5, 40.2, 39.9, 37.7, 30.9, 26.3, 25.1, 15.4, 9.1.

ESI-MS m/z: Calcd. for $C_{39}H_{43}ClN_4O_8$: 730.2. Found $(M+1)^+$: 731.1.

Example 127

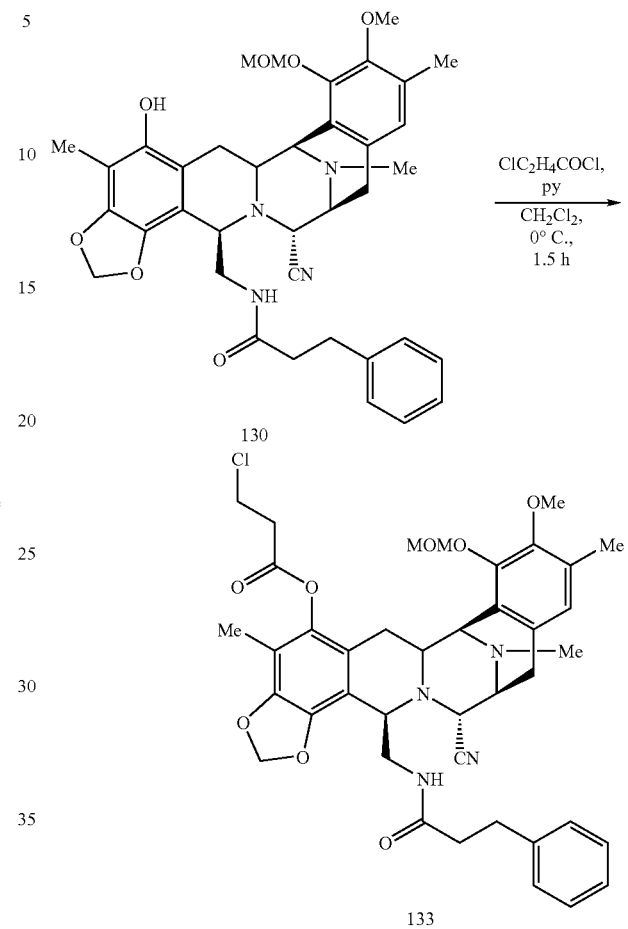

To a solution of 130 (130 mg, 0.198 mmol) in $CH_2Cl_2$ (2 mL), chloropropionyl chloride (28.35 μL, 0.297 mmol) and pyridine (24 μL, 0.297 mmol) were added at 0° C. The reaction mixture was stirred for 1.5 h and then, the solution was diluted with $CH_2Cl_2$ (10 mL) and washed with 0.1 N HCl (7 mL). The organic layer was dried over $Na_2SO_4$, filtered, and the solvent was eliminated under reduced pressure. The residue was purified by flash column chromatography ($SiO_2$, Hex:EtOAc 1:1) to afford 133 (94 mg, 64%) as a white solid.

Rf: 0.43 (Hex:EtOAc 1:2).

$^1$H NMR (300 MHz, $CDCl_3$) δ 7.23-7.12 (m, 3H), 7.06-7.04 (m, 2H), 6.69 (s, 1H), 5.97 (s, 1H), 5.92 (s, 1H), 5.08 (d, J=6 Hz, 1H), 5.00 (d, J=6 Hz, 1H), 4.97 (m, 1H), 4.16 (bs, 1H), 4.00 (m, 1H), 3.88 (t, J=6.9 Hz, 2H), 3.75 (t, J=6.9 Hz, 2H), 3.59 (dd, J1=6.3 Hz, J2=12.3 Hz, 1H), 3.53 (s, 3H), 3.37 (s, 3H), 3.03-3.26 (m, 1H), 3.17-2.97 (m, 3H), 2.83-2.73 (m, 2H), 2.58-2.52 (m, 3H), 2.31 (s, 3H), 2.03 (s, 6H), 1.93-1.86 (m, 1H), 1.79-1.64 (m, 2H).

$^{13}$C NMR (75 MHz, $CDCl_3$) δ 171.9, 167.8, 148.3, 144.7, 140.8, 132.1, 132.0, 131.1, 130.2, 128.2, 126.1, 125.2, 124.6, 123.7, 122.2, 120.2, 117.6, 114.7, 112.9, 111.8, 101.7, 99.3, 74.9, 65.0, 59.6, 59.0, 57.7, 56.7, 56.4, 55.4, 55.1, 41.5, 38.5, 37.8, 37.2, 31.0, 26.4, 25.2, 15.5, 9.3.

ESI-MS m/z: Calcd. for $C_{40}H_{45}ClN_4O_8$: 744.2. Found $(M+1)^+$: 745.0.

Example 128

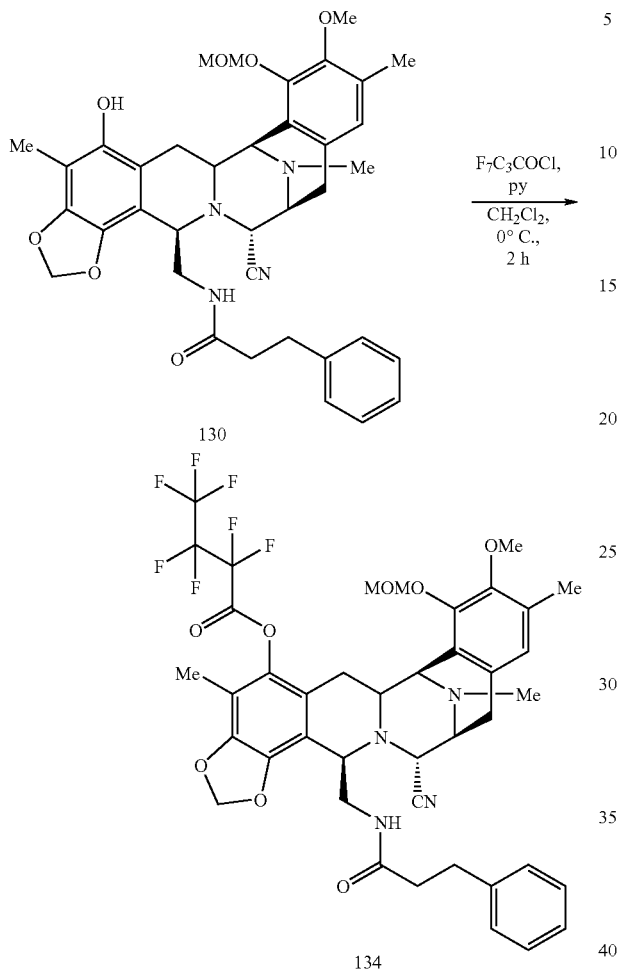

Example 129

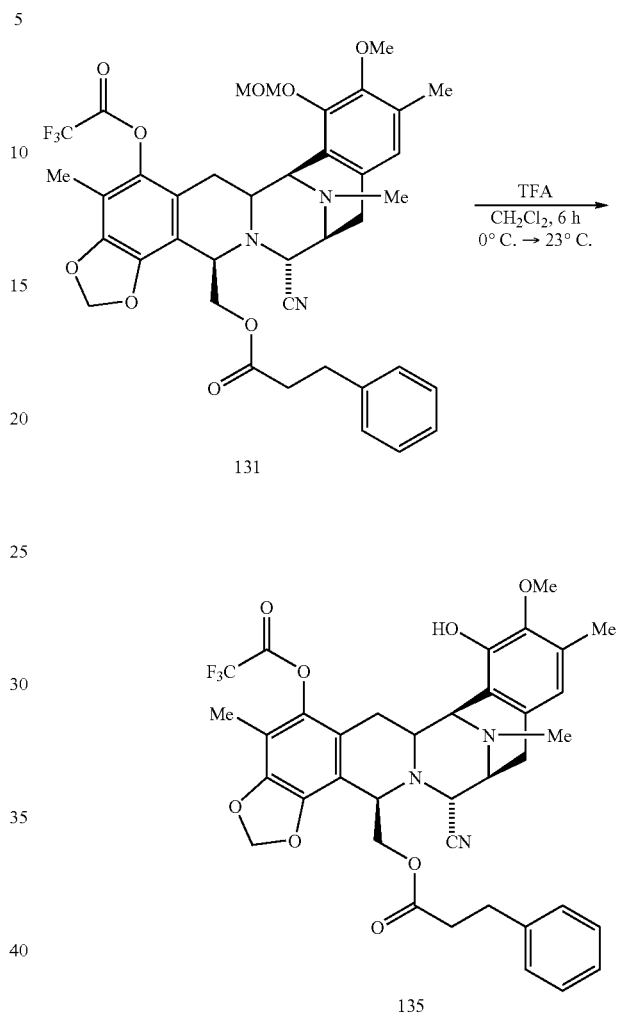

To a solution of 130 (160 mg, 0.244 mmol) in CH$_2$Cl$_2$ (2 mL), heptafluorobutyryl chloride (54.5 μL, 0.366 mmol) and pyridine (40 μL, 0.49 mmol) were added at 0° C. The reaction mixture was stirred for 2 h and then, the solution was diluted with CH$_2$Cl$_2$ (15 mL) and washed with 0.1 N HCl (10 mL). The organic layer was dried over Na$_2$SO$_4$, filtered, and the solvent was eliminated under reduced pressure. The residue was purified by flash column chromatography (SiO$_2$, gradient Hex:EtOAc 2:1 to Hex:EtOAc 1:4) to afford 134 (120 mg, 63%) as a white solid.

Rf: 0.40 (Hex:EtOAc 1:2).

$^1$H NMR (300 MHz, CDCl$_3$) δ 7.25-7.16 (m, 3H), 7.04-7.02 (m, 2H), 6.77 (s, 1H), 6.02 (d, J=1.5 Hz, 1H), 5.96 (d, J=1.5 Hz, 1H), 5.11 (d, J=6.6 Hz, 1H), 4.95 (d, J=6.6 Hz, 1H), 4.94 (m, 1H), 4.58 (m, 1H), 4.25 (bs, 1H), 4.06 (bs, 1H), 3.88 (d, J=6.9 Hz, 1H), 3.64 (dd, J1=7.5 Hz, J2=12.9 Hz, 1H), 3.55-3.53 (m, 1H), 3.49 (s, 3H), 3.38 (s, 3H), 3.17 (dd, J1=8.1 Hz, J2=18.9 Hz, 1H), 2.85 (d, J=18.3 Hz, 1H), 2.77 (dd, J1=2.7 Hz J2=16.2 Hz, 1H), 2.60-2.57 (m, 3H), 2.56 (s, 3H), 2.06 (s, 3H), 2.03 (s, 3H), 1.96-1.88 (m, 1H), 1.79-1.69 (m, 2H).

ESI-MS m/z: Calcd. for C$_{41}$H$_{41}$F$_7$N$_4$O$_8$: 850.7. Found (M+1)$^+$: 851.3.

To a solution of 131 (93 mg, 0.123 mmol) in CH$_2$Cl$_2$ (1 mL), trifluoroacetic acid (381 μL, 4.95 mmol) was added at 0° C. and the reaction mixture was stirred for 6 h at 23° C. The reaction was quenched at 0° C. with saturated aqueous sodium bicarbonate (15 mL) and extracted with ethyl acetate (2×10 mL). The combined organic layers were dried over sodium sulphate, filtered, and the solvent was eliminated under reduced pressure to give 135 (65 mg, 75%) as a white solid which was used in following steps with no further purification. Rf: 0.26 (Hex:EtOAc 1:1).

$^1$H NMR (300 MHz, CDCl$_3$) δ 7.24-7.15 (m, 3H), 7.04-7.01 (m, 2H), 6.45 (s, 1H), 6.03 (d, J=1.5 Hz, 1H), 5.97 (d, J=1.5 Hz, 1H), 5.62 (s, 1H), 4.97 (m, 1H), 4.09 (d, J=1.8 Hz, 1H), 4.03 (bs, 1H), 3.99 (d, J=2.4 Hz, 1H), 3.73 (dd, J1=7.5 Hz, J2=12 Hz, 1H), 3.38 (s, 3H), 3.34-3.28 (m, 3H), 3.05 (dd, J1=8.4 Hz, J2=18.3 Hz, 1H), 2.75 (dd, J$_1$=3.3 Hz, J2=16.5 Hz, 1H), 2.60-2.47 (m, 3H), 2.30 (s, 3H), 2.05 (s, 3H), 2.02 (s, 3H), 1.91-1.65 (m, 3H).

ESI-MS m/z: Calcd. for C$_{37}$H$_{37}$F$_3$N$_4$O$_7$: 706.2. Found (M+1)$^+$: 707.2.

Example 130

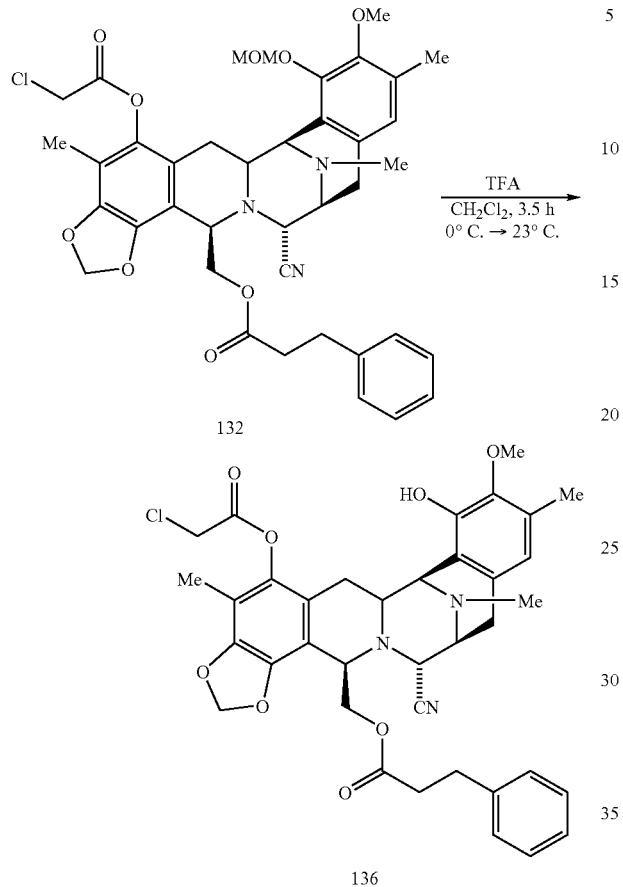

To a solution of 132 (130 mg, 0.177 mmol) in CH$_2$Cl$_2$ (1 mL), trifluoroacetic acid (545 µL, 7.08 mmol) was added at 0° C. and the reaction mixture was stirred for 3.5 h at 23° C. The reaction was quenched at 0° C. with saturated aqueous sodium bicarbonate (15 mL) and extracted with ethyl acetate (2×10 mL). The combined organic layers were dried over sodium sulphate, filtered, and the solvent was eliminated under reduced pressure to give 136 (118 mg, 97%) as a white solid which was used in following steps with no further purification. Rf: 0.27 (Hex:EtOAc 1:1).

$^1$H NMR (300 MHz, CDCl$_3$) δ 7.23-7.13 (m, 3H), 7.06-7.03 (m, 2H), 6.45 (s, 1H), 5.98 (d, J=1.2 Hz, 1H), 5.91 (d, J=1.2 Hz, 1H), 5.04 (t, J=4.5 Hz, 1H), 4.37 (bs, 2H), 4.13 (d, J=2.1 Hz, 1H), 4.03 (bs, 2H), 3.68-3.61 (dd, J1=7.2 Hz, J2=12.3 Hz 1H), 3.40 (s 3H), 3.37-3.28 (m, 3H), 3.02 (dd, J1=8.4 Hz, J2=18.6 Hz 1H), 2.75 (dd, J1=2.7 Hz, J2=15.9 Hz 1H), 2.58-2.50 (m, 3H), 2.32 (s, 3H), 2.01 (s, 6H), 1.94-1.67 (m, 3H).

$^{13}$C NMR (75 MHz, CDCl$_3$) δ 171.8, 165.0, 146.8, 144.6, 142.9, 141.0, 140.9, 139.8, 132.0, 130.3, 129.4, 128.5, 128.3, 126.0, 120.8, 120.1, 117.4, 116.1, 113.0, 111.5, 101.7, 60.5, 58.7, 56.3, 56.2, 55.2, 55.0, 41.5, 40.4, 39.5, 37.7, 31.0, 29.6, 26.4, 25.3, 15.5, 9.2.

ESI-MS m/z: Calcd. for C$_{37}$H$_{39}$ClN$_4$O$_7$: 686.2. Found (M+1)$^+$: 687.2.

Example 131

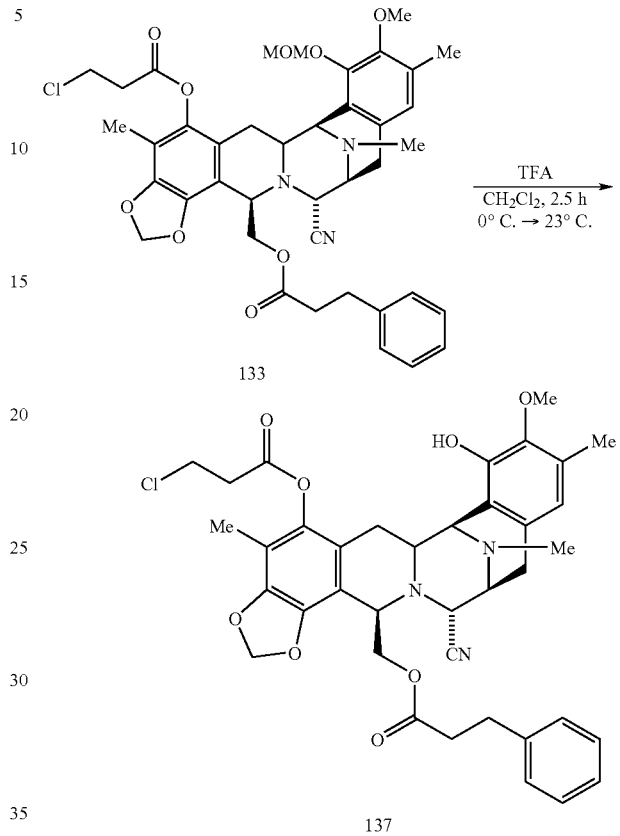

To a solution of 133 (94 mg, 0.126 mmol) in CH$_2$Cl$_2$ (1 mL), trifluoroacetic acid (385 µL, 5.0 mmol) was added at 0° C. and the reaction mixture was stirred for 2.5 h at 23° C. The reaction was quenched at 0° C. with saturated aqueous sodium bicarbonate (15 mL) and extracted with ethyl acetate (2×10 mL). The combined organic layers were dried over sodium sulphate, filtered, and the solvent was eliminated under reduced pressure to give 137 (118 mg, 97%) as a white solid which was used in following steps with no further purification. Rf: 0.24 (Hex:EtOAc 1:1).

$^1$H NMR (300 MHz, CDCl$_3$) δ 7.25-7.14 (m, 3H), 7.05-7.03 (m, 2H), 6.44 (s, 1H), 5.98 (d, J=1.5 Hz, 1H), 5.92 (d, J=1.5 Hz, 1H), 5.82 (s, 1H), 5.20 (t, J=4.8 Hz, 1H), 4.07 (d, J=2.1 Hz, 1H), 5.82 (s, 1H), 5.20 (t, J=4.8 Hz, 1H), 4.07 (d, =2.1 Hz, 1H), 4.01 (bs, 1H), 3.98 (d, J=2.4 Hz, 1H), 3.93-3.84 (m, 2H), 3.63 (ddd, J1=1.5 Hz, J2=6.9 Hz, J3=12 Hz, 1H), 3.44 (bs, 3H), 3.37-3.26 (m, 3H), 3.11-3.06 (m, 2H), 3.01 (dd, J1=8.4 Hz, J2=18.3 Hz, 1H), 2.80 (brd, J=13.8 Hz, 1H), 2.58-2.47 (m, 3H), 2.29 (s, 3H), 2.03 (s, 3H), 2.01 (s, 3H), 1.93-1.68 (m, 3H).

$^{13}$C NMR (75 MHz, CDCl$_3$) δ 171.7, 168.0, 146.7, 144.6, 142.8, 142.1, 141.0, 140.8, 140.1, 130.7, 129.0, 128.2, 126.0, 122.2, 120.9, 116.7, 114.7, 113.1, 111.7, 102.3, 101.7, 72.0, 60.4, 59.1, 56.4, 56.3, 55.7, 55.2, 41.7, 40.3, 38.8, 37.8, 37.1, 31.0, 26.4, 25.2, 15.5, 9.4.

ESI-MS m/z: Calcd. for C$_{38}$H$_{41}$ClN$_4$O$_7$: 700.2. Found (M+23)$^+$: 723.1.

Example 132

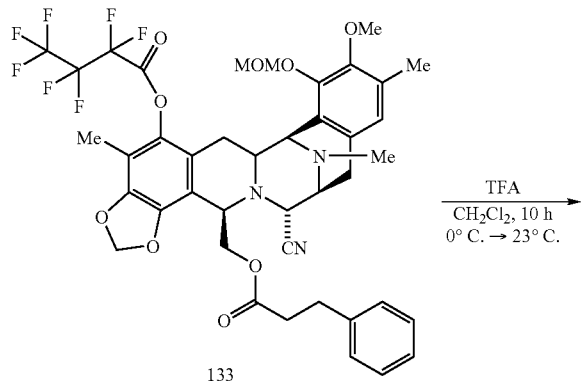

133

TFA
CH$_2$Cl$_2$, 10 h
0° C. → 23° C.

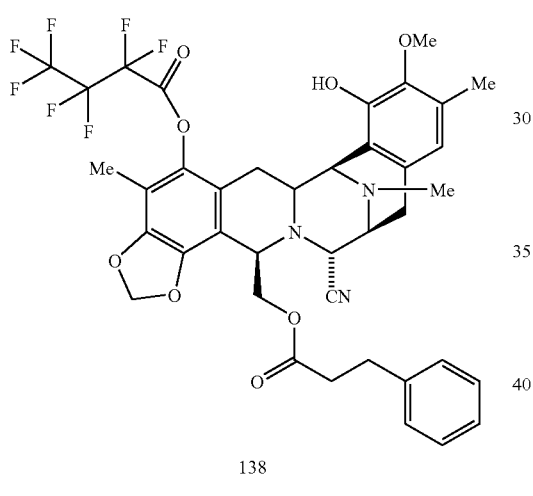

138

Example 133

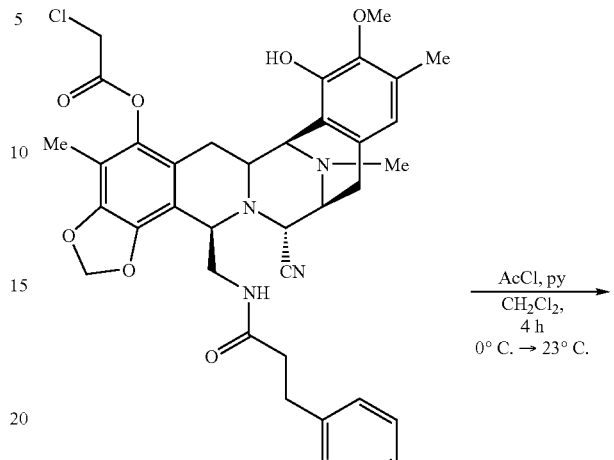

136

AcCl, py
CH$_2$Cl$_2$,
4 h
0° C. → 23° C.

139

To a solution of 134 (46 mg, 0.054 mmol) in CH$_2$Cl$_2$ (1 mL), trifluoroacetic acid (166 µL, 2.16 mmol) was added at 0° C. and the reaction mixture was stirred for 10 h at 23° C. The reaction was quenched at 0° C. with saturated aqueous sodium bicarbonate (15 mL) and extracted with ethyl acetate (2×10 mL). The combined organic layers were dried over sodium sulphate, filtered, and the solvent was eliminated under reduced pressure to give 138 (35 mg, 80%) as a white solid which was used in following steps with no further purification. Rf: 0.26 (Hex:EtOAc 1:1).

$^1$H NMR (300 MHz, CDCl$_3$) δ 7.23-7.12 (m, 3H), 7.04-7.01 (m, 2H), 6.45 (s, 1H), 6.03 (d, J=1.5 Hz, 1H), 5.97 (d, J=1.5 Hz, 1H), 5.64 (s, 1H), 4.98 (m, 1H), 4.09 (d, J=2.1 Hz, 1H), 4.03 (bs, 1H), 3.98 (d, J=2.4 Hz, 1H), 3.75 (dd, J1=9.6 Hz, J2=14.1 Hz 1H), 3.35 (s, 3H), 3.29-3.24 (m, 3H), 3.04 (dd, J1=7.8 Hz, J2=18.0 Hz, 1H), 2.74 (dd, J1=3.0 Hz, J2=16.8 Hz, 1H), 2.57-2.45 (m, 3H), 2.30 (s, 3H), 2.03 (s, 6H), 1.92-1.64 (m, 3H). ESI-MS m/z: Calcd. for C$_{39}$H$_{37}$F$_7$N$_4$O$_7$: 806.7. Found (M+1)$^+$: 807.3.

To a solution of 136 (45 mg, 0.065 mmol) in CH$_2$Cl$_2$ (0.3 mL), acetyl chloride (4.65 µL, 0.065 mmol), and pyridine (5.2 µL, 0.065 mmol) were added at 0° C. The reaction mixture was stirred for 4 h and then, the solution was diluted with CH$_2$Cl$_2$ (15 mL) and washed with 0.1 N HCl (7 mL). The organic layer was dried over sodium sulphate, filtered, and the solvent was eliminated under reduced pressure. The residue was purified by flash column chromatography (SiO$_2$, gradient Hex:EtOAc 5:1 to EtOAc) to afford 139 (27 mg, 57%) as a white solid.

Rf: 0.36 (Hex:EtOAc 1:2).

$^1$H NMR (300 MHz, CDCl$_3$) δ 7.26-7.14 (m, 3H), 7.07-7.04 (m, 2H), 6.84 (s, 1H), 6.00 (d, J=1.2 Hz, 1H), 5.94 (d, J=1.2 Hz, 1H), 4.94 (t, J=5.1 Hz, 1H), 4.39-4.38 (m, 2H), 4.02 (bs, 2H), 3.67 (d, J=3 Hz, 1H), 3.60-3.54 (m, 1H), 3.47-3.35 (m, 3H), 3.42 (s, 3H), 3.26 (dt, J$_1$=4.8 Hz, J$_2$=8.7 Hz 1H), 3.02

(dd, J$_1$=8.1 Hz, J$_2$=18.3 Hz, 1H), 2.64-2.38 (m, 3H), 2.35 (s, 3H), 2.25 (s, 3H), 2.06 (s, 3H), 2.03 (s, 3H), 1.95-1.69 (m, 3H).

ESI-MS m/z: Calcd. for C$_{39}$H$_{41}$ClN$_4$O$_8$: 729.2. Found (M+23)$^+$: 752.3.

1H), 3.04 (dd, J$_1$=3.6 Hz, J$_2$=18.6 Hz, 1H), 2.92 (dt, J$_1$=3.3 Hz, J$_2$=14.1 Hz, 1H), 2.43 (d, J=18.0 Hz, 1H), 2.37 (s, 3H), 2.29 (s, 3H), 1.89 (s, 3H), 1.79 (s, 3H), 1.75 (dd, J$_1$=2.7 Hz, J$_2$=6.9 Hz, 1H), 0.99 (d, J=7.5 Hz, 3H).

ESI-MS m/z: Calcd. for C$_{31}$H$_{37}$N$_5$O$_7$: 591.6. Found (M+1)$^+$: 592.3.

Example 134

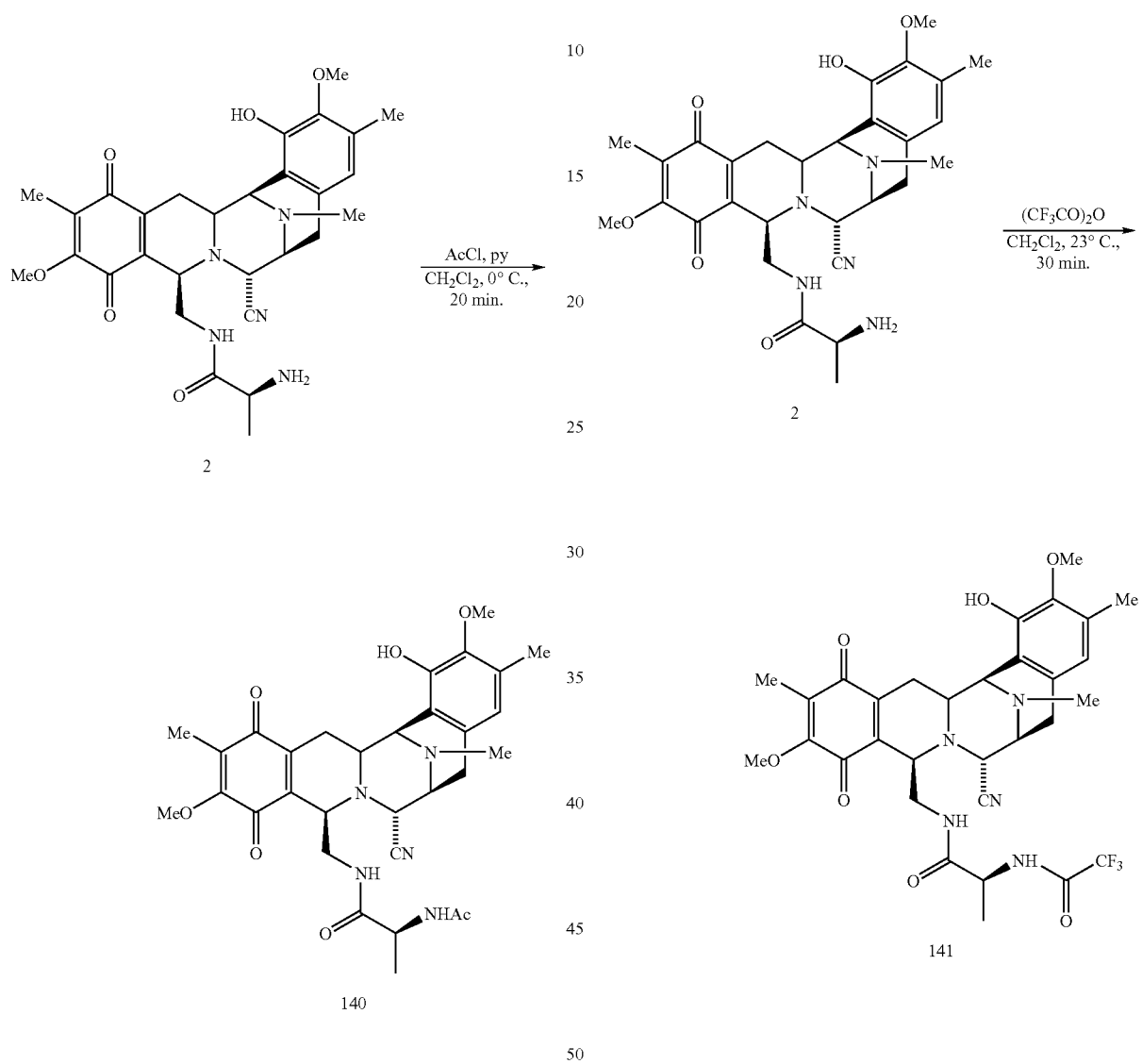

Example 135

To a solution of 2 (15 mg, 0.0273 mmol) in CH$_2$Cl$_2$ (0.2 mL), acetyl chloride (1.94 μL, 0.0273 mmol), and pyridine (2.20 μL, 0.0273 mmol) were added at 0° C. The reaction mixture was stirred for 20 minutes and then, the solution was diluted with CH$_2$Cl$_2$ (15 mL) and washed with 0.1 N HCl (5 mL). The organic layer was dried over sodium sulphate, filtered, and the solvent was eliminated under reduced pressure. The residue was purified by flash column chromatography (SiO$_2$, gradient EtOAc to EtOAcMeOH 5:1) to afford 140 (9 mg, 56%) as a light yellow solid. Rf: 0.56 (EtOAc:MeOH 5:1).

$^1$H NMR (300 MHz, CDCl$_3$) δ 6.52 (s, 1H), 6.40 (s, 1H), 5.73 (d, J=7.5 Hz, 1H), 4.95 (d, J=6.9 Hz, 1H), 4.20 (d, J=1.5 Hz, 1H), 4.00 (s, 3H), 3.86 (d, J=4.5 Hz, 1H), 3.79 (s, 3H), 3.78-3.77 (m, 1H), 3.40-3.35 (m, 2H), 3.24 (dt, J$_1$=3.6 Hz, J$_2$=11.4 Hz, 1H), 3.17 (d, J=7.8 Hz, 1H), 3.11 (d, J=7.5 Hz,

To a solution of 2 (15 mg, 0.0273 mmol) in CH$_2$Cl$_2$ (0.2 mL), trifluoroacetyl anhydride (3.85 μL, 0.0273 mmol was added at 23° C. The reaction mixture was stirred for 30 minutes and then, the solution was diluted with CH$_2$Cl$_2$ (15 mL) and washed with 0.1 N HCl (5 mL). The organic layer was dried over sodium sulphate, filtered, and the solvent was eliminated under reduced pressure. The residue was purified by flash column chromatography (SiO$_2$, gradient EtOAc to EtOAcMeOH 4:1) to afford 141 (12.1 mg, 69%) as a light yellow solid. Rf: 0.73 (EtOAc:MeOH 5:1).

$^1$H NMR (300 MHz, CDCl$_3$) δ 6.90 (d, J=6.6 Hz, 1H), 6.56 (s, 1H), 5.11 (d, J=6.6 Hz, 1H), 4.47 (bs, 1H), 4.23 (bs, 1H), 3.97 (s, 3H), 3.93 (bs, 1H), 3.85-3.81 (m, 1H), 3.77 (s, 3H), 3.40-3-36 (m, 2H), 3.23 (dd, $J_1$=7.2 Hz, $J_2$=18.6 Hz, 1H), 3.13-3.08 (m, 3H), 1.86 (s, 3H), 1.74 (dd, $J_1$=10.8 Hz, $J_2$=16.8 Hz, 1H), 1.07 (d, J=6.9 Hz, 3H).

ESI-MS m/z: Calcd. for $C_{31}H_{34}F_3N_5O_7$: 645.6. Found (M+1)$^+$: 646.3.

Example 136

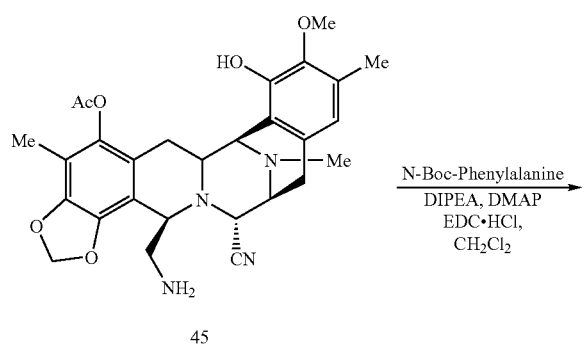

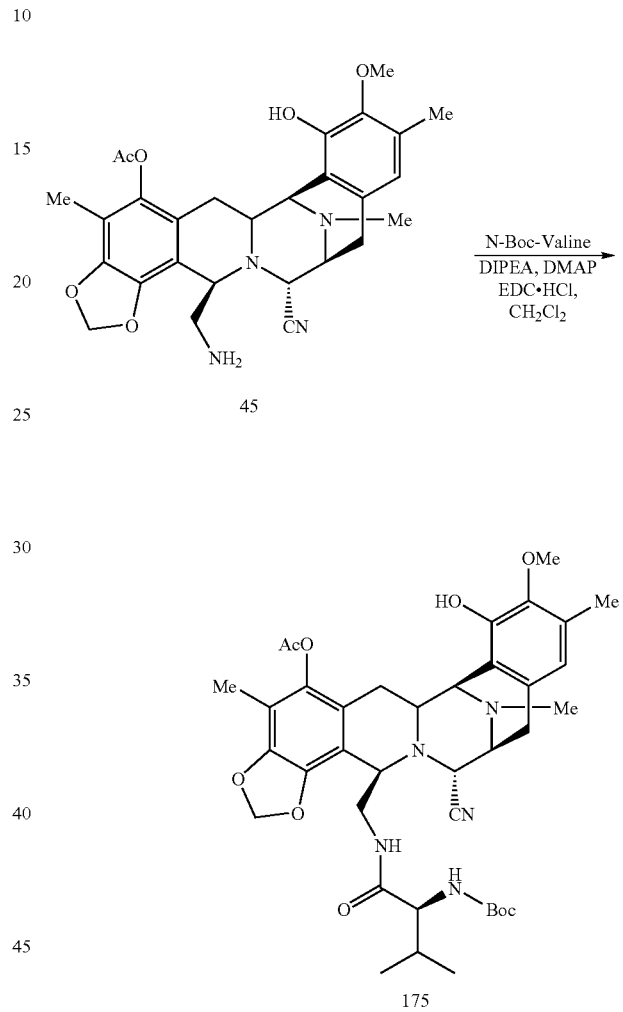

174

To a solution of 45 (30 mg, 0.058 mmol) in $CH_2Cl_2$ (0.87 mL), DIPEA (15.0 mL, 0.086 mmol), EDC.HCl (27.6 mg, 0.145 mmol), N-Boc-Phenylalanine (22.9 mg, 0.086 mmol) and DMAP (0.7 mg, 0.006 mmol) were added at room temperature and the reaction mixture was stirred for 4 h. Then, the solution was diluted with $CH_2Cl_2$ (10 mL) and washed successively with 0.1 N HCl (5 mL) and a solution of 10% NaHCO$_3$ (5 ml). The organic layer was dried over $Na_2SO_4$, filtered, and the solvent was eliminated under reduced pressure. The residue was purified by flash column chromatography (SiO$_2$, Hex:EtOAc 1:2) to afford 174 (17 mg, 38%) as a white solid.

Rf=0.35 Hex:AcOEt 1:2.

$^1$H NMR (300 MHz, CDCl$_3$) 7.24-7.15 (m, 3H), 7.05-7.02 (m, 2H), 6.43 (s, 1H), 5.88 (s, 1H), 5.78 (s, 1H), 5.64 (s, 1H), 5.63 (bs, 1H), 4.80 (bs, 1H), 3.98 (s, 1H), 3.85 (bs, 2H), 3.75 (bs, 1H), 3.58 (bs, 1H), 3.53 (bs, 3H), 3.38 (m, 1H), 3.17-3.10 (m, 3H), 2.90 (dd, $J_1$=8.7 Hz, $J_2$=17.7 Hz, 1H), 2.73 (d, J=14.4 Hz, 1H), 2.57 (m, 1H), 2.43-2.37 (m, 1H), 2.25 (s, 3H), 2.24 (s, 3H), 2.10 (s, 3H), 1.94 (s, 3H), 1.76 (dd, $J_1$=12.3 Hz, $J_2$=15.6 Hz, 1H), 1.19 (bs, 9H). $^{13}$C NMR (75 MHz, CDCl$_3$) 171.2, 168.8, 146.6, 144.6, 142.8, 140.6, 137.0, 130.7, 129.5, 129.0, 128.4, 126.8, 121.1, 121.0, 117.8, 116.7, 113.3, 111.8, 101.5, 60.5, 59.7, 57.0, 56.4, 55.3, 41.9, 41.6, 38.7, 31.6, 29.7, 28.2, 26.5, 25.2, 22.6, 20.3, 15.7, 14.1, 9.3.

ESI-MS m/z: Calcd. for $C_{42}H_{49}N_5O_9$: 767.87. Found (M+1)$^+$: 768.3.

Example 137

175

To a solution of 45 (30 mg, 0.058 mmol) in $CH_2Cl_2$ (0.87 mL), DIPEA (15.0 mL, 0.086 mmol), EDC.HCl (27.6 mg, 0.145 mmol), N-Boc-Valine (18.8 mg, 0.086 mmol) and DMAP (0.7 mg, 0.006 mmol) were added at room temperature and the reaction mixture was stirred for 4 h. Then, the solution was diluted with $CH_2Cl_2$ (10 mL) and washed successively with 0.1 N HCl (5 mL) and a solution of 10% NaHCO$_3$ (5 ml). The organic layer was dried over $Na_2SO_4$, filtered, and the solvent was eliminated under reduced pressure. The residue was purified by flash column chromatography (SiO$_2$. Hex:EtOAc 1:2) to afford 175 (18 mg, 43%) as a white solid.

Rf=0.25 Hex:EtOAc 1:1.

$^1$H NMR (300 MHz, CDCl$_3$) δ 6.42 (s, 1H), 5.97 (s, 1H), 5.82 (s, 1H), 5.73 (bs, 1H), 5.50 (bs, 1H), 4.82 (bs, 1H), 4.15 (bs, 1H), 4.03 (bs, 1H), 3.96 (bs, 1H), 3.72 (s, 3H), 3.61 (m, 1H), 3.41-3.15 (m, 3H), 2.96 (dd, $J_1$=8.4 Hz, $J_2$=18.3 Hz, 1H), 2.72 (d, J=16.5 Hz, 1H), 2.53 (d, J=18 Hz, 1H), 2.25 (s, 3H), 2.21 (s, 3H), 1.93 (s, 3H), 1.81 (dd, J₁=14.1 Hz, J₂=14.7 Hz, 1H), 1.34 (s, 9H), 0.83-0.76 (m, 2H), 0.61 (d, J=6.3 Hz, 3H), 0.54 (d, J=6.3 Hz, 3H).

¹³C NMR (75 MHz, CDCl₃) δ 171.6, 168.7, 155.4, 146.8, 144.5, 142.9, 140.7, 130.7, 128.8, 121.0, 120.6, 117.7, 116.8, 113.3, 111.9, 101.4, 60.6, 60.0, 59.3, 57.2, 56.3, 55.2, 41.7, 29.7, 29.3, 28.2, 26.2, 25.2, 22.6, 20.3, 18.9, 17.7, 15.7, 14.1, 9.3.

ESI-MS m/z: Calcd. for $C_{38}H_{49}N_5O_9$: 719.82. Found (M+1)⁺: 720.3.

Example 138

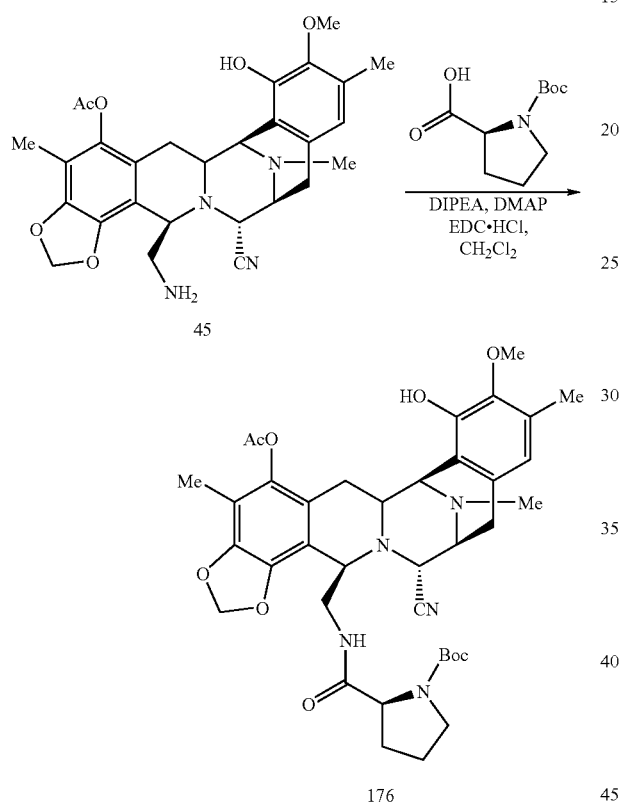

176

To a solution of 45 (38 mg, 0.073 mmol) in CH₂Cl₂ (1.09 mL), DIPEA (19.0 mL, 0.109 mmol), EDC.HCl (34.9 mg, 0.182 mmol), N-Boc-Proline (23.5 mg, 0.109 mmol) and DMAP (0.8 mg, 0.007 mmol) were added at 23° C. and the reaction mixture was stirred for 4.5 h. Then, the solution was diluted with CH₂Cl₂ (10 mL) and washed successively with 0.1 N HCl (5 mL) and a solution of 10% NaHCO₃ (5 ml). The organic layer was dried over Na₂SO₄, filtered, and the solvent was eliminated under reduced pressure. The residue was purified by flash column chromatography (SiO₂, Hex:EtOAc 1:1) to afford 176 (33 mg, 63%) as a white solid.

Rf=0.14 Hex:EtOAc 1:2.

¹H NMR (300 MHz, CDCl₃) δ 6.49 (s, 1H), 6.02 (bs, 1H), 5.90 (s, 1H), 5.74 (s, 1H), 4.19 (bs, 1H), 4.09 (bs, 1H), 3.98 (bs, 1H), 3.76 (s, 3H), 3.38 (d, J=6 Hz, 2H), 3.22 (d, J=11.7 Hz, 1H), 3.15-2.99 (m, 2H), 2.80 (d, J=15.3 Hz, 1H), 2.63-2.58 (m, 1H), 2.32 (s, 3H), 2.26 (s, 6H), 1.99 (s, 3H), 1.78-1.62 (m, 1H), 1.50-0.83 (m, 7H), 1.21 (s, 9H).

ESI-MS m/z: Calcd. for $C_{38}H_{47}N_5O_9$: 717.81. Found (M+1)⁺: 718.3.

Example 139

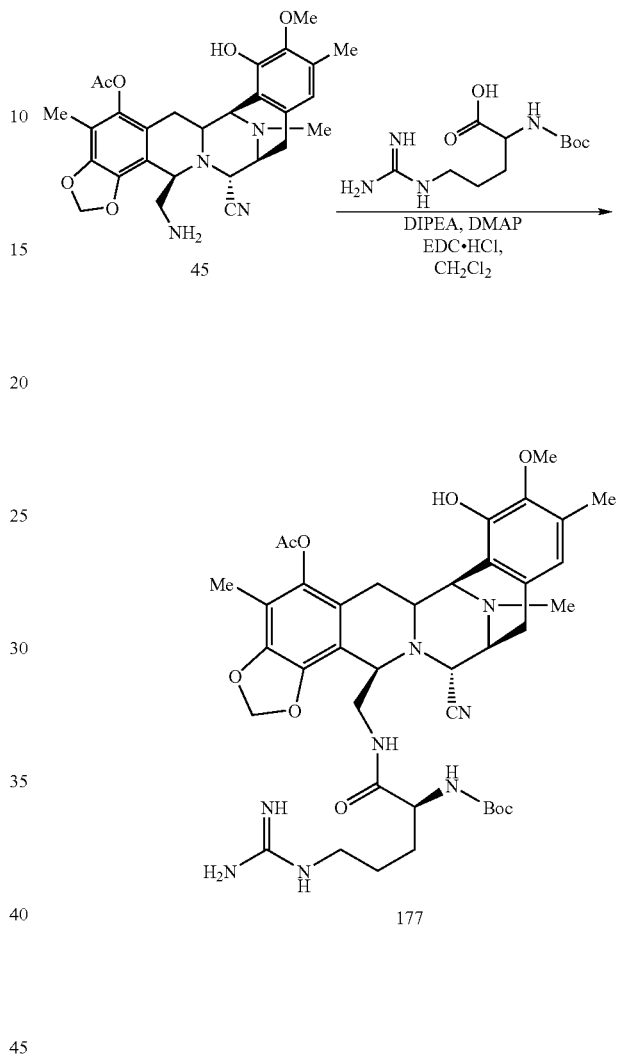

177

To a solution of 45 (50 mg, 0.144 mmol) in CH₂Cl₂ (0.96 mL), DIPEA (41.8 mL, 0.240 mmol), EDC.HCl (46.0 mg, 0.240 mmol), N-Boc-Arginine hidrochloride hydrate (47.2 mg, 0.144 mmol) and DMAP (1.1 mg, 0.01 mmol) were added at 23° C. and the reaction mixture was stirred for 4 h. Then, the solvent was removed under vacuum and the residue was purified by flash column chromatography (SiO₂, Hex: EtOAc 1:2) to afford 177 (58 mg, 78%) as a white solid.

Rf=0.40 MeOH:EtOAc 1:5.

¹H NMR (300 MHz, CDCl₃) δ 7.53 (bs, 1H), 6.95 (bs, 3H), 6.54 (bs, 1H), 6.48 (s, 1H), 6.07 (s, 1H), 6.00 (bs, 1H), 5.88 (s, 1H), 5.11 (bs, 1H), 4.23 (s, 1H), 4.08 (s, 1H), 4.02 (s, 1H), 3.76 (s, 3H), 3.70 (bs, 1H), 3.48 (bs, 1H), 3.37 (d, J=6.9 Hz, 1H), 3.18 (d, J=10.2 Hz, 1H), 3.00-2.94 (m, 3H), 2.82-2.70 (m, 2H), 2.34 (s, 3H), 2.25 (s, 6H), 1.99 (s, 3H), 1.73 (brt, J=14.1 Hz, 1H), 1.40 (s, 9H), 1.25 (bs, 3H), 0.95-0.85 (m, 2H).

ESI-MS m/z: Calcd. for $C_{39}H_{52}N_8O_9$: 776.88. Found (M+1)⁺: 777.3.

Example 140

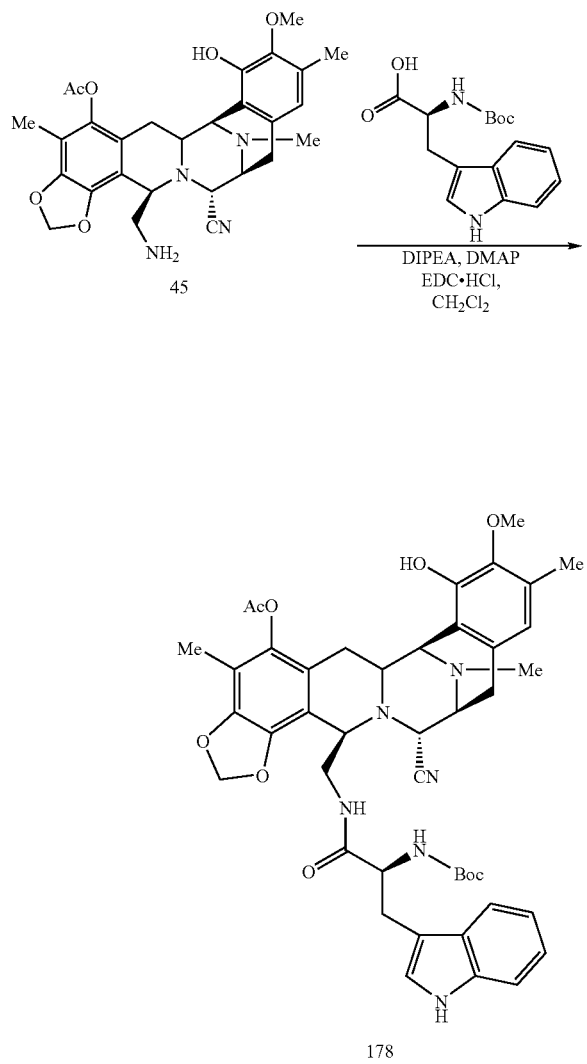

To a solution of 45 (50 mg, 0.096 mmol) in CH$_2$Cl$_2$ (1.44 mL), DIPEA (25.8 mL, 0.144 mmol), EDC.HCl (46.0 mg, 0.240 mmol), N-Boc-Tryptophan (43.8 mg, 0.144 mmol) and DMAP (1.2 mg, 0.009 mmol) were added at 23° C. and the reaction mixture was stirred for 4 h. Then, the solution was diluted with CH$_2$Cl$_2$ (10 mL) and washed successively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by flash column chromatography (SiO$_2$, Hex:EtOAc 1:2) to afford 178 (57 mg, 74%) as a white solid.

Rf=0.12 Hex:EtOAc 1:1.

$^1$H NMR (300 MHz, CDCl$_3$) δ 8.50 (bs, 1H), 7.73-7.71 (m, 1H), 7.13-7.12 (m, 3H), 6.51 (s, 1H), 5.72 (s, 1H), 5.36 (bs, 1H), 5.28 (bs, 1H), 4.95 (bs, 1H), 4.41 (bs, 1H), 4.05 (s, 1H), 3.70 (s, 3H), 3.50 (bs, 2H), 3.30-3.17 (m, 4H), 2.89-2.82 (m, 3H), 2.40 (s, 3H), 2.29 (s, 3H), 2.19 (s, 3H), 2.03 (s, 3H), 1.49 (s, 9H), 1.26-1.25 (m, 2H).

ESI-MS m/z: Calcd. for C$_{44}$H$_{50}$N$_6$O$_9$: 806.90. Found (M+1)$^+$: 807.3.

Example 141

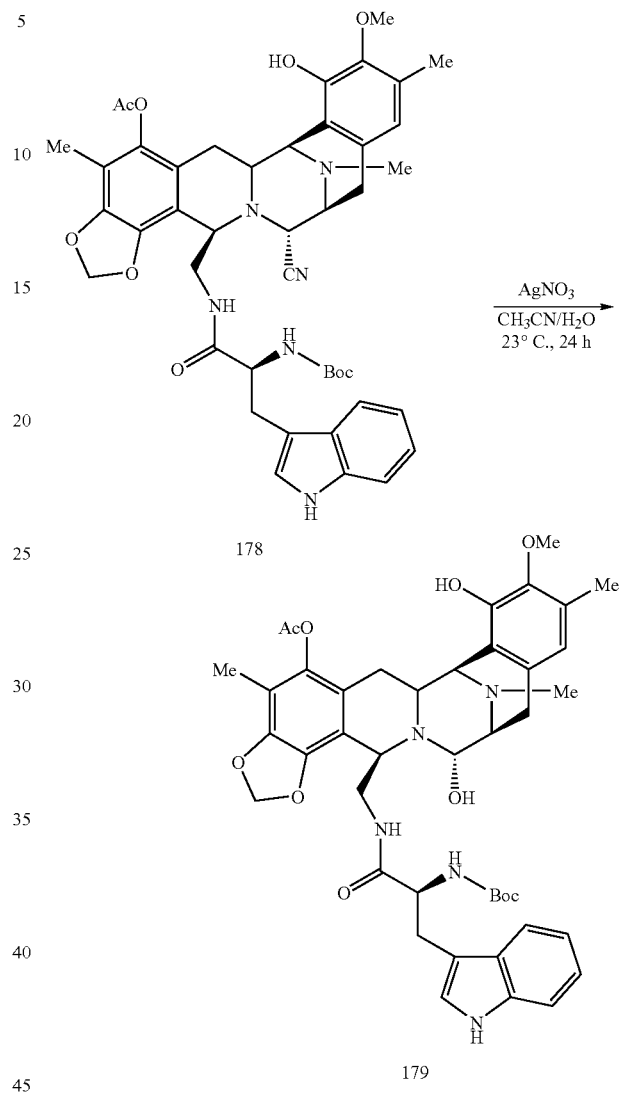

To a solution of 178 (43 mg, 0.053 mmol) in CH$_3$CN/H$_2$O (3 mL/2 mL), AgNO$_3$ (271 mg, 1.60 mmol) was added and the reaction was stirred at 23° C. for 17 h. Then, Aq sat NaCl (10 mL) and Aq sat NaHCO$_3$ (10 mL) were added at 0° C. and the mixture was stirred for 15 min, filtered through a pad of celite and washed with CH$_2$Cl$_2$ (20 mL). The solution was decanted and the organic layer was dried and concentrated in vacuo. The residue was purified by flash column chromatography (SiO$_2$, EtOAc:MeOH 5:1) to afford 179 (24 mg, 56%) as a white solid.

Rf=0.38 EtOAc:MeOH 5:1.

$^1$H NMR (300 MHz, CDCl$_3$) δ 8.40 (s, 1H), 7.66 (bs, 1H), 7.25-7.21 (m, 1H), 7.16-7.09 (m, 2H), 6.45 (s, 1H), 5.75 (bs, 1H), 5.55 (bs, 1H), 5.45 (s, 1H), 5.25 (bs, 1H), 4.36 (bs, 1H), 4.16 (bs, 1H), 4.05 (bs, 1H), 3.95 (s, 1H), 3.69 (s, 3H), 3.35-3.02 (m, 6H), 2.83-2.73 (m, 3H), 2.35 (s, 3H), 2.24 (s, 3H), 2.19 (s, 3H), 1.99 (s, 3H), 1.77 (dd, J$_1$=12 Hz, J$_2$=15.3 Hz 1H).

ESI-MS m/z: Calcd. for C$_{43}$H$_{51}$N$_5$O$_{10}$: 797.89. Found (M−17)$^+$: 780.

Example 142

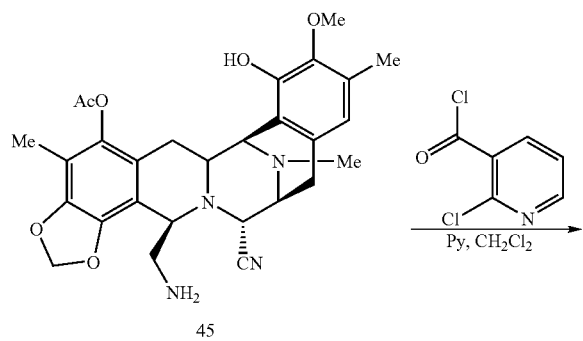

To a solution of 45 (50 mg, 0.0960 mmol) in CH$_2$Cl$_2$ (0.7 mL), 2-Chloronicotinoyl chloride (17.7 mg, 0.101 mmol) and pyridine (8.1 mL, 0.101 mmol) were added at 0° C. The reaction mixture was stirred for 1.5 h and then, the solution was diluted with CH$_2$Cl$_2$ (5 mL) and washed with 0.1 N HCl (3 mL). The organic layer was dried over Na$_2$SO$_4$, filtered, and the solvent was eliminated under reduced pressure. The residue was purified by flash column chromatography (SiO$_2$, Hex:EtOAc 1:1) to afford 180 (45 mg, 71%) as a white solid.

Rf=0.18 Hex:EtOAc 1:2.

$^1$H NMR (300 MHz, CDCl$_3$) δ 8.32-8.29 (m, 1H), 7.38-7.34 (m, 1H), 7.14-7.09 (m, 1H), 6.14 (s, 1H), 5.97 (d, J=1.2 Hz, 1H), 5.92-5.91 (m, 2H), 5.75 (d, J=2.1 Hz, 1H), 4.18 (d, J=2.1 Hz, 1H), 4.15 (s, 1H), 4.07 (s, 1H), 3.91-3.73 (m, 2H), 3.68 (s, 3H), 3.36 (d, J=7.5 Hz, 1H), 3.31 (dt, J$_1$=2.4 Hz, J$_2$=11.7 Hz, 1H), 2.92 (dd, J$_1$=8.1 Hz, J$_2$=18 Hz, 1H), 2.80 (d, J=16.2 Hz, 1H), 2.58 (d, J=18 Hz, 1H), 2.31 (s, 3H), 2.27 (s, 3H), 1.99 (s, 3H), 1.91 (s, 3H) 1.97-1.83 (m, 1H).

$^{13}$C NMR (75 MHz, CDCl$_3$) δ 168.6, 164.8, 150.3, 147.2, 146.5, 144.6, 142.5, 140.6, 139.0, 130.9, 130.5, 128.8, 122.3, 120.8, 120.3, 117.6, 116.3, 112.7, 112.1, 101.6, 60.6, 58.8, 56.5, 56.3, 55.6, 55.1, 41.6, 39.8, 31.5, 26.2, 24.9, 20.3, 15.5, 9.3.

ESI-MS m/z: Calcd. for C$_{34}$H$_{34}$ClN$_5$O$_7$: 659.2. Found (M+1)$^+$: 660.1.

Example 143

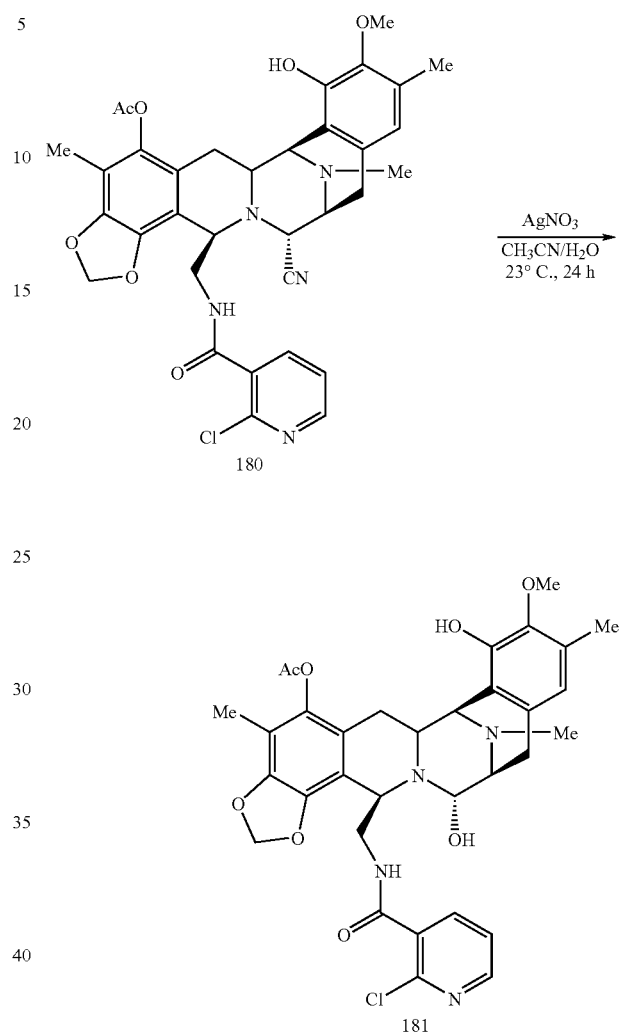

To a solution of 180 (39 mg, 0.059 mmol) in CH$_3$CN/H$_2$O (3 mL/2 mL), AgNO$_3$ (301 mg, 1.77 mmol) was added and the reaction was stirred at 23° C. for 17 h. Then, Aq sat NaCl (10 mL) and Aq sat NaHCO$_3$ (10 mL) solutions were added at 0° C. and the mixture was stirred for 15 min, filtered through a pad of celite and washed with CH$_2$Cl$_2$ (20 mL). The solution was decanted and the organic layer was dried and concentrated in vacuo. The residue was purified by flash column chromatography (SiO$_2$, EtOAc:MeOH 5:1) to afford 181 (28 mg, 73%) as a white solid.

Rf=0.24, EtOAc:MeOH 5:1.

$^1$H NMR (300 MHz, CDCl$_3$) δ 8.33-8.31 (m, 1H), 7.40-7.35 (m, 1H), 7.16-7.09 (m, 2H), 6.20 (s, 1H), 5.98 (d, J=1.2 Hz, 1H), 5.96 (s, 1H), 5.92 (d, J=1.2 Hz, 1H), 5.63 (bs, 1H), 4.60 (bs, 1H), 4.47 (bs, 1H), 4.02-3.95 (m, 2H), 3.69 (s, 3H), 3.65-3.56 (m, 1H), 3.48 (s, 3H), 3.43-3.38 (m, 1H), 3.17 (brd, J=7.2 Hz, 1H), 2.88 (dd, J$_1$=8.7 Hz, J$_2$=18.3 Hz, 1H), 2.74 (d, J=15.3 Hz, 1H), 2.40 (d, J=18.3 Hz, 1H), 2.32 (s, 3H), 2.26 (s, 3H), 2.00 (s, 3H), 1.99 (s, 3H), 1.77 (dd, J$_1$=12 Hz, J$_2$=15 Hz, 1H).

$^{13}$C NMR (75 MHz, CDCl$_3$) δ 168.1, 165.0, 150.0, 147.2, 146.5, 144.4, 142.5, 140.9, 138.7, 131.5, 130.2, 128.9, 122.3, 121.1, 120.7, 116.1, 114.4, 111.4, 101.5, 82.6, 60.6, 57.8, 56.2, 52.1, 41.6, 31.5, 26.4, 24.5, 22.6, 20.3, 15.6, 14.1, 9.3.

ESI-MS m/z: Calcd. for C$_{33}$H$_{35}$ClN$_4$O$_8$: 650.2. Found (M−17)$^+$: 633.3.

Example 144

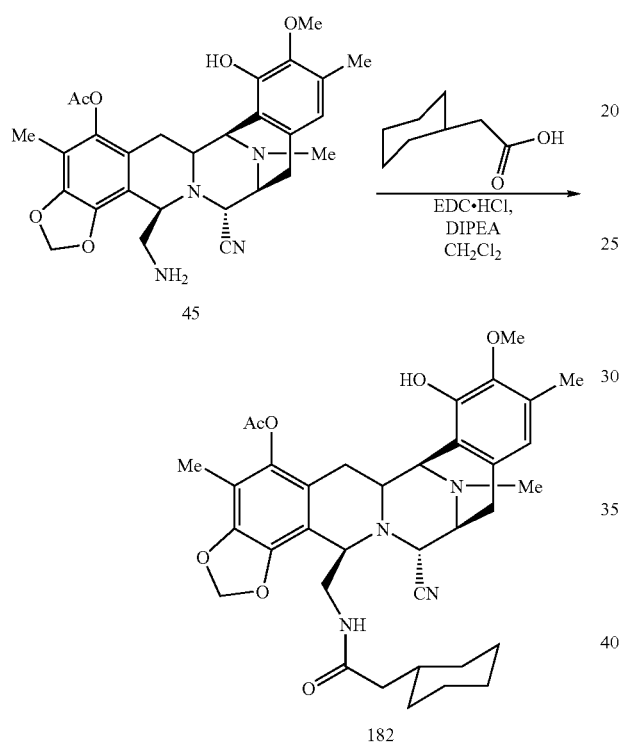

Example 145

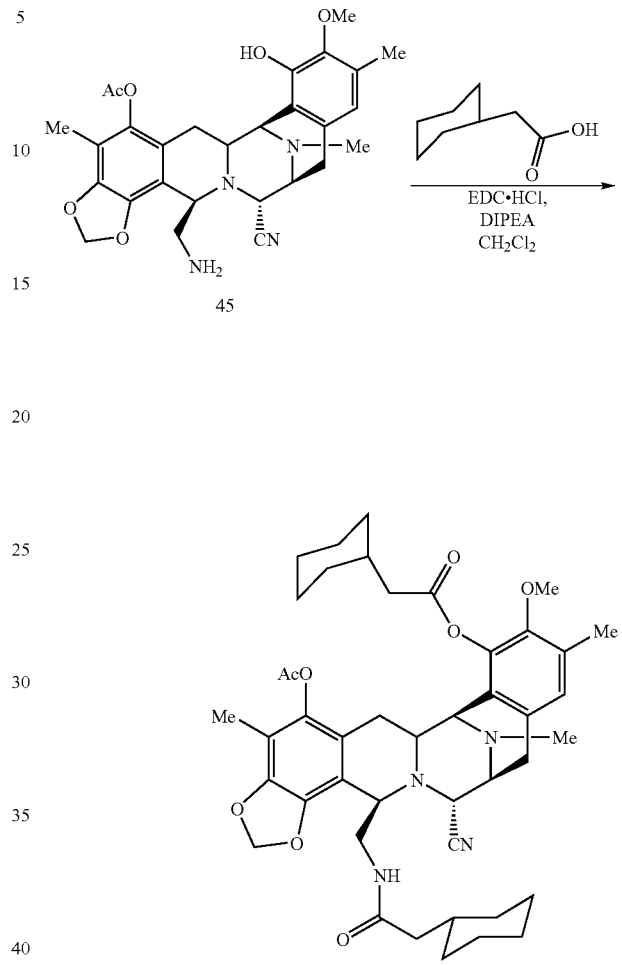

To a solution of 45 (30 mg, 0.058 mmol) in CH$_2$Cl$_2$ (0.87 mL). DIPEA (15.0 mL, 0.086 mmol), EDC.HCl (27.6 mg, 0.145 mmol), cyclohexylacetic acid (12.2 mg, 0.086 mmol) and DMAP (0.7 mg, 0.006 mmol) were added at 0° C. and the reaction mixture was stirred for 5 h. Then, the solution was diluted with CH$_2$Cl$_2$ (10 mL) and washed successively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by flash column chromatography (SiO$_2$, Hex:EtOAc 1:2) to afford 182 (10 mg, 27%) as a white solid.

Rf=0.11 Hex:EtOAc 1:1.

$^1$H NMR (300 MHz, CDCl$_3$) δ 6.50 (s, 1H), 5.98 (d, J=1.2 Hz, 1H), 5.91 (d, J=1.2 Hz, 1H), 5.75 (s, 1H), 5.02-4.91 (m, 1H), 4.11 (bs, 1H), 4.04 (d, J=2.1 Hz, 1H), 4.01 (bs, 1H), 3.78 (s, 3H), 3.72-3.69 (m, 1H), 3.38-3.29 (m, 3H), 3.05 (dd, J$_1$=7.8 Hz, J$_2$=18.0 Hz, 1H), 2.77 (d, J=15.6 Hz, 1H), 2.54 (d, J=18.6 Hz, 1H), 2.33 (s, 3H), 2.32 (s, 3H), 2.27 (s, 3H), 1.98 (s, 3H), 1.79 (dd, J$_1$=11.7 Hz, J$_2$=15.6 Hz, 1H), 1.59-0.61 (m, 13H).

ESI-MS m/z: Calcd. for C$_{36}$H$_{44}$N$_4$O$_7$: 644.76. Found (M+1)$^+$: 645.3.

To a solution of 45 (30 mg, 0.058 mmol) in CH$_2$Cl$_2$ (0.87 mL), DIPEA (15.0 mL, 0.086 mmol), EDC.HCl (27.6 mg, 0.145 mmol), cyclohexylacetic acid (12.2 mg, 0.086 mmol) and DMAP (0.7 mg, 0.006 mmol) were added at 0° C. and the reaction mixture was stirred for 5 h. Then, the solution was diluted with CH$_2$Cl$_2$ (10 mL) and washed successively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by flash column chromatography (SiO$_2$, Hex:EtOAc 1:2) to afford 183 (17 mg, 38%) as a white solid.

Rf=0.13 Hex:EtOAc 1:1.

$^1$H NMR (300 MHz, CDCl$_3$) δ 6.87 (s, 1H), 5.99 (d, J=1.2 Hz, 1H), 5.92 (d, J=1.2 Hz, 1H), 4.95 (t, J=5.7 Hz, 1H), 4.08 (bs, 1H), 4.00 (bs, 1H), 3.71 (s, 3H), 3.64 (d, J=1.8 Hz, 2H), 3.38 (d, J=6.6 Hz, 1H), 3.33-3.32 (m, 1H), 3.27 (d, J=11.7 Hz, 1H), 3.06 (dd, J$_1$=7.8 Hz, J$_2$=18.0 Hz, 1H), 2.65-2.59 (m, 1H), 2.50-2.47 (m, 1H), 2.35 (s, 3H), 2.27 (s, 6H), 1.99 (s, 3H), 1.78-1.74 (m, 1H) 1.60-0.62 (m, 26H).

ESI-MS m/z: Calcd. for C$_{44}$H$_{56}$N$_4$O$_8$: 768.94. Found (M+1)$^+$: 769.3.

Example 146

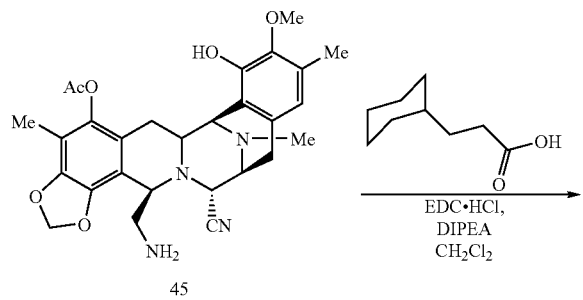

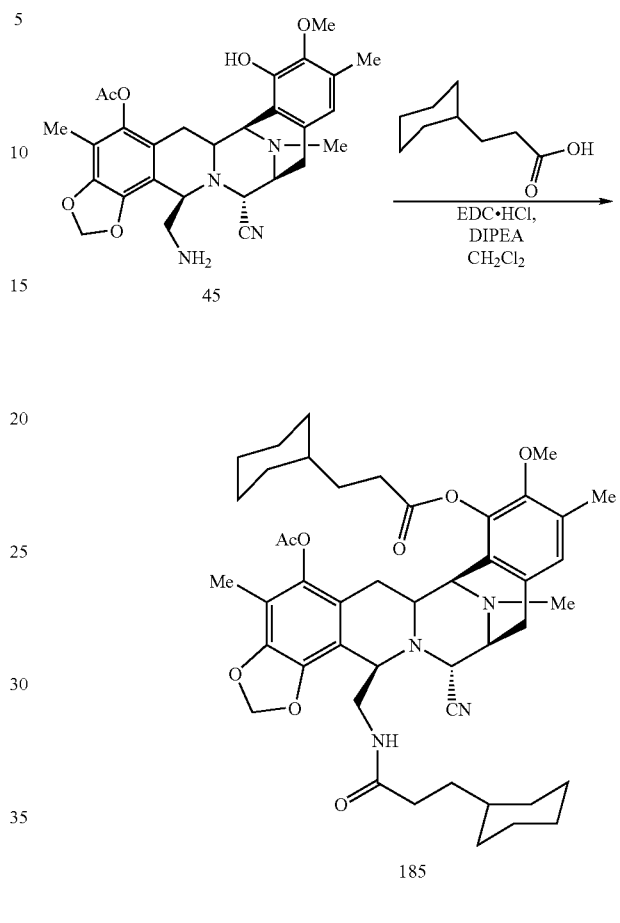

184

To a solution of 45 (30 mg, 0.058 mmol) in $CH_2Cl_2$ (0.87 mL), DIPEA (15.0 mL, 0.086 mmol), EDC.HCl (27.6 mg, 0.145 mmol), cyclohexylpropionic acid (13.5 mg, 0.086 mmol) and DMAP (0.7 mg, 0.006 mmol) were added at 0° C. and the reaction mixture was stirred at 23° C. for 6 h. Then, the solution was diluted with $CH_2Cl_2$ (10 mL) and washed successively with 0.1 N HCl (5 mL) and a solution of 10% $NaHCO_3$ (5 ml). The organic layer was dried over $Na_2SO_4$, filtered, and the solvent was eliminated under reduced pressure. The residue was purified by flash column chromatography ($SiO_2$, Hex:EtOAc 1:2) to afford 184 (15 mg, 39%) as a white solid.

Rf=0.15 Hex:EtOAc 1:1.

$^1$H NMR (300 MHz, $CDCl_3$) δ 6.50 (s, 1H), 5.98 (s, 1H), 5.91 (s, 1H), 5.74 (s, 1H) 5.01 (t, J=5.1 Hz, 1H), 4.09 (bs, 1H), 4.06 (s, 1H), 4.02 (bs, 1H), 3.76 (s, 3H), 3.64-3.58 (m, 1H), 3.42-3.41 (m, 1H), 3.36 (d, J=7.5 Hz, 1H), 3.28 (d, J=12.3 Hz, 1H), 3.05 (dd, $J_1$=8.6 Hz, $J_2$=18 Hz, 1H), 2.79 (d, J=14.7 Hz, 1H), 2.57 (d, J=18 Hz, 1H), 2.32 (s, 3H), 2.30 (s, 3H), 2.25 (s, 3H), 1.99 (s, 3H), 1.77 (dd, $J_1$=12.0 Hz, $J_2$=15.9 Hz, 1H), 1.62-0.71 (m, 15H). ESI-MS m/z: Calcd. for $C_{37}H_{46}N_4O_7$: 658.78. Found (M+1)$^+$: 659.3.

Example 147

To a solution of 45 (30 mg, 0.058 mmol) in $CH_2Cl_2$ (0.87 mL), DIPEA (15.0 mL, 0.086 mmol), EDC.HCl (27.6 mg, 0.145 mmol), cyclohexylpropionic acid (13.5 mg, 0.086 mmol) and DMAP (0.7 mg, 0.006 mmol) were added at 0° C. and the reaction mixture was stirred for 6 h. Then, the solution was diluted with $CH_2Cl_2$ (10 mL) and washed successively with 0.1 N HCl (5 mL) and a solution of 10% $NaHCO_3$ (5 ml). The organic layer was dried over $Na_2SO_4$, filtered, and the solvent was eliminated under reduced pressure. The residue was purified by flash column chromatography ($SiO_2$, Hex:EtOAc 1:2) to afford 185 (21 mg, 46%) as a white solid.

Rf=0.17 Hex:EtOAc 1:1.

$^1$H NMR (300 MHz, $CDCl_3$) δ 6.86 (s, 1H), 5.99 (s, 1H), 5.92 (s, 1H), 4.97 (t, J=5.4 Hz, 1H), 4.10 (d, J=2.4 Hz, 1H), 4.01 (bs, 1H), 3.70 (s, 3H), 3.64 (d, J=2.4 Hz, 1H), 3.51 (bs, 1H), 3.37 (d, J=8.1 Hz, 1H), 3.23 (d, J=11.1 Hz, 1H), 3.02 (dd, $J_1$=7.8 Hz, $J_2$=18 Hz, 1H), 2.69-2.59 (m, 4H), 2.35 (s, 3H), 2.26 (s, 6H), 2.00 (s, 3H), 1.76-0.72 (m, 30H).

$^{13}$C NMR (75 MHz, $CDCl_3$) δ 173.1, 171.5, 168.2, 147.9, 144.7, 142.5, 140.7, 140.3, 130.9, 130.6, 127.7, 123.3, 120.0, 117.5, 113.1, 111.9, 101.6, 60.5, 59.0, 57.3, 56.7, 55.2, 55.0, 41.6, 39.9, 37.2, 33.5, 33.0, 32.9, 32.9, 32.8, 32.5, 32.4, 31.9, 31.7, 29.7, 29.3, 26.6, 26.5, 26.2, 24.9, 20.3, 15.8, 14.1, 9.4.

ESI-MS m/z: Calcd. for $C_{46}H_{60}N_4O_8$: 796.4. Found (M+1)$^+$: 797.5.

Example 148

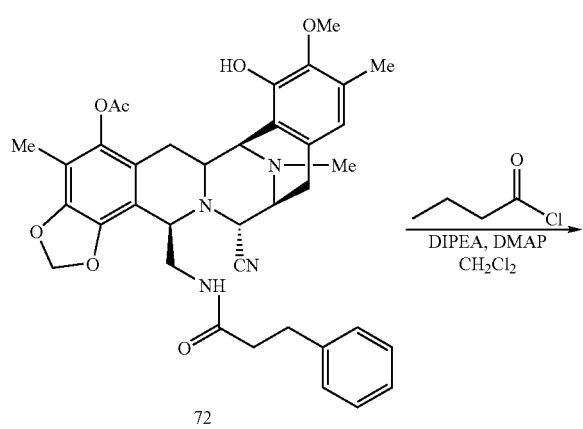

To a solution of 72 (111 mg, 0.162 mmol) in $CH_2Cl_2$ (0.81 mL). DIPEA (56.3 mL, 0.324 mmol), butyryl chloride (33.6 mL, 0.324 mmol) and DMAP (1.96 mg, 0.016 mmol) were added at 0° C. and the reaction mixture was stirred for 5 h at this temperature. Then, the solution was diluted with $CH_2Cl_2$ (10 mL) and washed successively with 0.1 N HCl (5 mL) and a solution of 10% $NaHCO_3$ (5 ml). The organic layer was dried over $Na_2SO_4$, filtered, and the solvent was eliminated under reduced pressure. The residue was purified by flash column chromatography (RP-18, $CH_3CN:H_2O$ 1:1) to afford 186 (65.4 mg, 54%) as a white solid.

Rf=0.21 Hex:EtOAc 1:2.

$^1$H NMR (300 MHz, $CDCl_3$) δ 7.24-7.15 (m, 3H), 7.12-7.04 (m, 2H), 6.84 (s, 1H), 5.98 (d, J=1.2 Hz, 1H), 5.92 (d, J=1.2 Hz, 1H), 4.97 (t, J=5.7 Hz, 1H), 4.03 (m, 3H), 3.63 (d, J=2.7 Hz, 1H), 3.50 (m, 2H), 3.44 (s, 3H), 3.37 (d, J=8.4 Hz, 1H), 3.24 (dt, $J_1$=2.7 Hz, $J_2$=11.7 Hz, 1H), 3.02 (dd, $J_1$=8.1 Hz, $J_2$=18.3 Hz, 1H), 2.65-2.54 (m, 7H), 2.35 (s, 3H), 2.25 (s, 3H), 2.07 (s, 3H), 2.02 (s, 3H), 1.87-1.75 (m, 3H), 1.08 (t, J=7.5 Hz, 3H).

$^{13}$C NMR (75 MHz, $CDCl_3$) δ 171.7, 170.8, 168.2, 147.8, 144.7, 142.5, 140.8, 140.6, 140.3, 131.1, 130.5, 128.3, 128.2, 127.6, 126.0, 123.2, 117.5, 112.9, 111.8, 101.6, 60.2, 59.0, 57.3, 56.6, 55.1, 54.9, 41.5, 39.9, 37.8, 36.0, 31.0, 26.5, 24.8, 22.6, 20.2, 18.5, 15.6, 13.7, 9.3.

ESI-MS m/z: Calcd. for $C_{41}H_{46}N_4O_8$: 722.83. Found (M+1)$^+$: 723.2.

Example 149

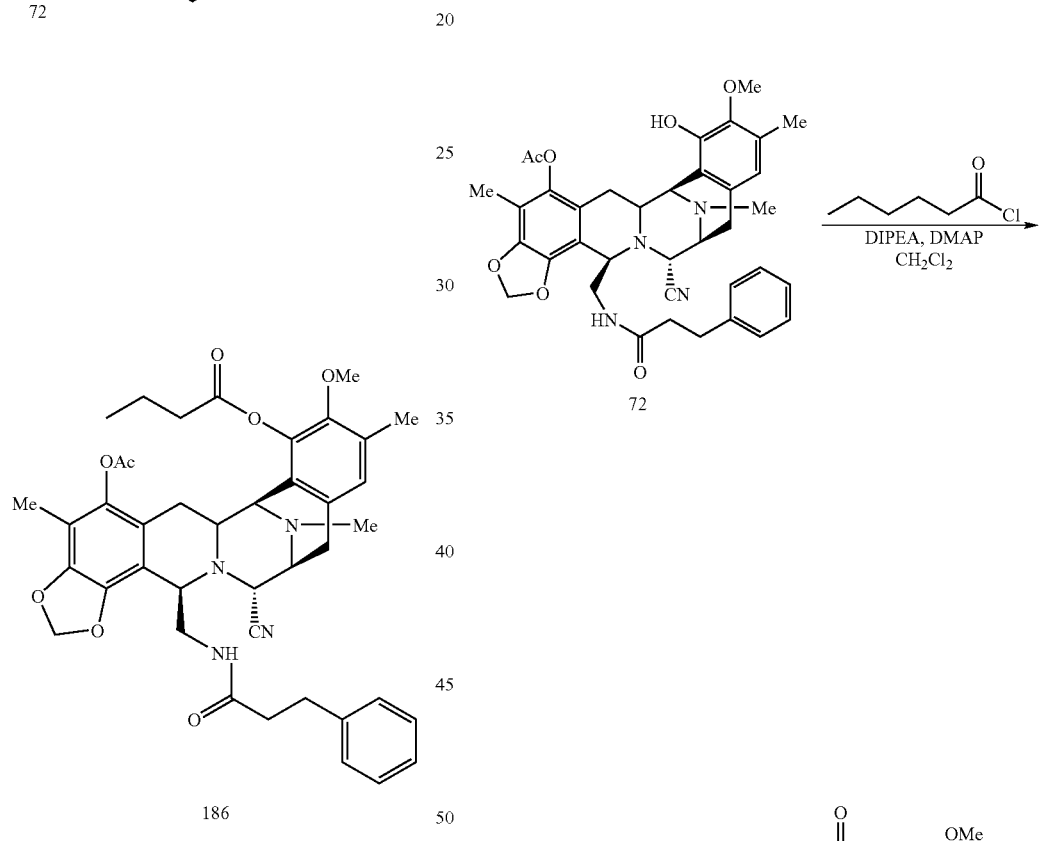

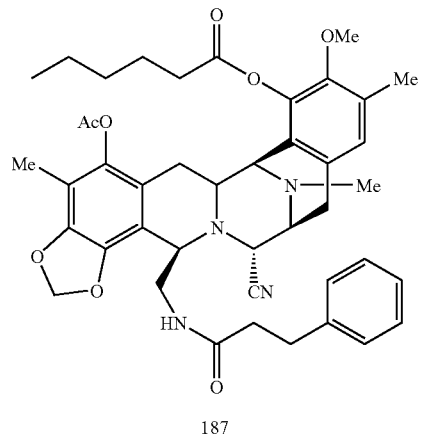

To a solution of 72 (80 mg, 0.122 mmol) in CH$_2$Cl$_2$ (0.61 mL). DIPEA (64.0 mL, 0.367 mmol), hexanoyl chloride (49.5 mL, 0.367 mmol) and DMAP (1.50 mg, 0.012 mmol) were added at 0° C. and the reaction mixture was stirred at this temperature for 5 h. Then, the solution was diluted with CH$_2$Cl$_2$ (10 mL) and washed successively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by flash column chromatography (RP-18, CH$_3$CN:H$_2$O 6:4) to afford 187 (86.1 mg, 94%) as a white solid.

Rf=0.25 Hex:EtOAc 1:2

$^1$H NMR (300 MHz, CDCl$_3$) δ 7.20-7.06 (m, 3H), 6.99-6.97 (m, 2H), 6.77 (s, 1H), 5.91 (s, 1H), 5.85 (s, 1H), 4.90 (m, 1H), 3.96 (d, J=3 Hz, 2H), 3.57-3.55 (m, 1H), 3.43 (bs, 2H), 3.36 (bs, 3H), 3.29 (brd, J=10.5 Hz, 1H), 3.18 (d, J=11.7 Hz, 1H), 2.97 (dd, J$_1$=4.8 Hz, J$_{2=12}$ Hz, 1H), 2.58-2.46 (m, 6H), 2.28 (s, 3H), 2.18 (s, 3H), 2.00 (s, 3H), 1.95 (s, 3H), 1.86-1.66 (m, 7H), 1.41-1.38 (m, 2H), 0.86-0.81 (m, 3H).

$^{13}$C NMR (75 MHz, CDCl$_3$) δ 171.7, 171.0, 168.2, 147.8, 144.7, 142.5, 140.8, 140.6, 140.3, 131.1, 130.5, 128.3, 128.2, 127.6, 126.0, 117.5, 112.9, 111.8, 101.6, 60.2, 59.0, 57.3, 56.6, 55.1, 55.0, 41.5, 39.9, 37.8, 34.1, 31.3, 31.1, 29.6, 24.8, 24.7, 22.3, 20.2, 15.6, 13.8.

ESI-MS m/z: Calcd. for C$_{43}$H$_{50}$N$_4$O$_8$: 750.88. Found (M+1)$^+$: 751.3.

Example 150

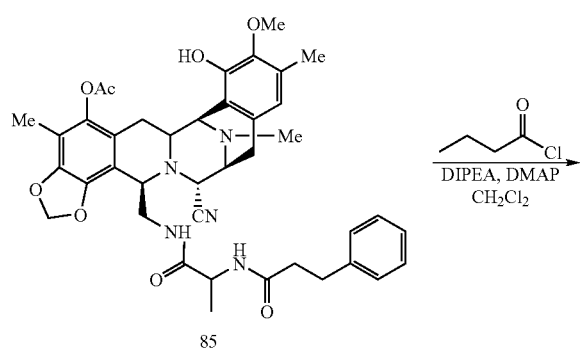

85

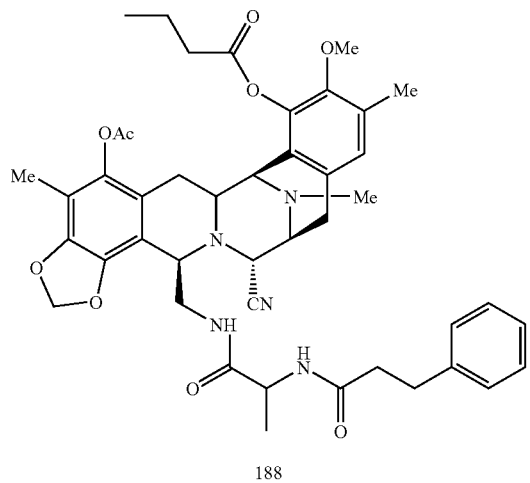

188

To absolution of 85 (80 mg, 0.110 mmol) in CH$_2$Cl$_2$ (0.55 mL), DIPEA (57.7 mL, 0.331 mmol), butyryl chloride (34.4 mL, 0.331 mmol) and DMAP (1.30 mg, 0.011 mmol) were added at 0° C. and the reaction mixture was stirred at 23° C. for 5 h. Then, the solution was diluted with CH$_2$Cl$_2$ (10 mL) and washed successively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by flash column chromatography (RP-18, CH$_3$CN:H$_2$O 1:1) to afford 188 (70.1 mg, 80%) as a white solid.

Rf=0.54 MeOH:EtOAc 1:5.

$^1$H NMR (300 MHz, CDCl$_3$) δ 7.28-7.14 (m, 5H), 6.80 (s, 1H), 6.07 (d, J=6.6 Hz, 1H), 6.00 (d, J=1.5 Hz, 1H), 5.90 (d, J=1.5 Hz, 1H), 5.35 (t, J=5.4 Hz, 1H), 4.12 (d, J=2.4 Hz, 1H), 4.05 (bs, 1H), 3.89 (brt, J=6.9 Hz, 1H), 3.66 (s, 3H), 3.64-3.63 (m, 1H), 3.59-3.45 (m, 2H), 3.40 (brd, J=7.8 Hz, 1H), 3.20 (dt, J$_1$=2.7 Hz, J$_2$=12 Hz, 1H), 3.00 (dd, J$_1$=8.1 Hz, J$_2$=18 Hz, 1H), 2.87 (t, J=8.1 Hz, 2H), 2.71 (d, J=18.6 Hz, 1H), 2.66-2.61 (m, 1H), 2.58 (t, J=7.2 Hz, 2H), 2.41-2.35 (m, 2H), 2.33 (s, 3H), 2.23 (s, 3H), 2.21 (s, 3H), 2.00 (s, 3H), 1.90-1.77 (m, 3H), 1.08 (t, J=7.2 Hz, 3H), 0.69 (d, J=6.9 Hz, 3H).

$^{13}$C NMR (75 MHz, CDCl$_3$) δ 172.0, 171.3, 170.8, 168.5, 147.7, 144.7, 142.5, 140.6, 140.5, 140.3, 131.0, 130.7, 128.4, 128.2, 127.7, 126.1, 123.1, 120.3, 117.5, 112.7, 111.8, 101.6, 60.3, 59.1, 57.3, 57.2, 55.4, 54.9, 48.2, 41.5, 39.5, 38.0, 36.0, 31.4, 26.8, 26.6, 24.6, 20.1, 18.5, 18.1, 15.7, 13.7, 9.2.

ESI-MS m/z: Calcd. for C$_{44}$H$_{51}$N$_5$O$_9$: 793.9. Found (M+1)$^+$: 794.3.

Example 151

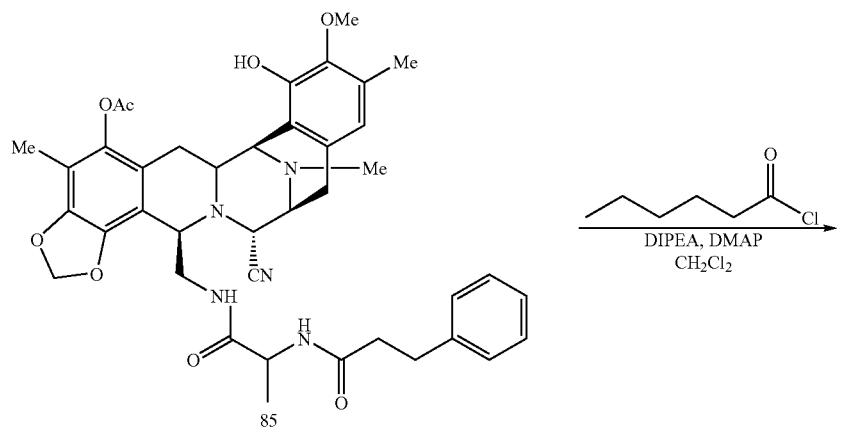

To a solution of 85 (80 mg, 0.110 mmol) in CH$_2$Cl$_2$ (0.55 mL), DIPEA (57.7 mL, 0.331 mmol), hexanoyl chloride (46.3 mL, 0.331 mmol) and DMAP (1.30 mg, 0.011 mmol) were added at 0° C. and the reaction mixture was stirred at 23° C. for 5 h. Then, the solution was diluted with CH$_2$Cl$_2$ (10 mL) and washed succesively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by column chromatography (RP-18, CH$_3$CN:H$_2$O 1:1) to afford 189 (80 mg, 88%) as a white solid.

Rf=0.23 Hex:EtOAc 1:3.

$^1$H NMR (300 MHz, CDCl$_3$) δ 7.21-7.08 (m, 5H), 6.74 (s, 1H), 6.00 (d, J=6.9 Hz, 1H), 5.94 (d, J=1.5 Hz, 1H), 5.84 (d, J=1.5 Hz, 1H), 5.24 (t, J=5.4 Hz, 1H), 4.06 (bs, 1H), 4.00 (bs, 1H), 3.83 (t, J=6 Hz, 1H), 3.59 (s, 3H), 3.57 (m, 1H), 3.53-3.40 (m, 2H), 3.33 (d, J=7.8 Hz, 1H), 3.14 (d, J=11.7 Hz, 1H), 2.94 (dd, J$_1$=8.4 Hz, J$_2$=18 Hz, 1H), 2.81 (t, J=7.5 Hz, 2H), 2.65 (d, J=18 Hz, 1H), 2.60-2.54 (m, 1H), 2.52 (t, J=7.2 Hz, 2H), 2.35-2.29 (m, 2H), 2.27 (s, 3H), 2.17 (s, 3H), 2.15 (s, 3H), 1.95 (s, 3H), 1.76-1.60 (m, 3H), 1.35-1.29 (m, 2H), 1.84 (m, 2H), 0.85-0.78 (m, 3H), 0.62 (t, J=6.6 Hz, 3H).

$^{13}$C NMR (75 MHz, CDCl$_3$) δ 172.0, 171.3, 171.1, 168.4, 147.8, 144.8, 142.6, 140.7, 140.5, 131.2, 130.6, 128.4, 128.3, 127.7, 126.2, 123.1, 120.3, 117.5, 112.6, 112.0, 101.7, 60.4, 59.1, 57.4, 57.2, 55.4, 54.9, 48.3, 41.5, 39.6, 38.1, 34.1, 33.6, 31.5, 31.3, 26.7, 24.7, 22.3, 20.2, 18.2, 15.7, 13.9, 9.3.

ESI-MS m/z: Calcd. for C$_{46}$H$_{55}$N$_5$O$_9$: 821.96. Found (M+1)$^+$: 822.3.

Example 152

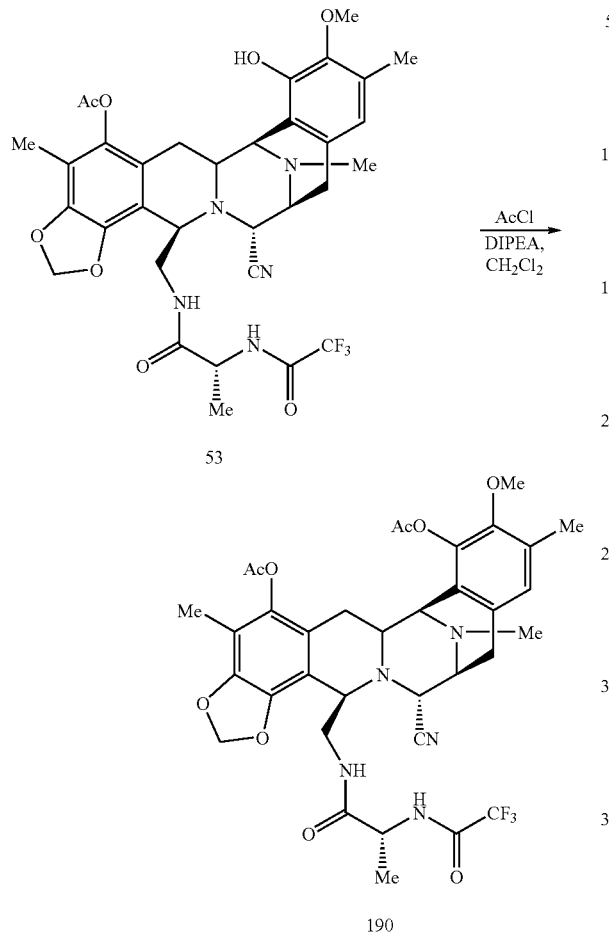

To a solution of 53 (100 mg, 0.145 mmol) in CH$_2$Cl$_2$ (0.72 mL), DIPEA (50.6 mL, 0.291 mmol) and acetyl chloride (20.7 mL, 0.291 mmol) were added at 0° C. and the reaction mixture was stirred for 4 h at 23° C. Then, the solution was diluted with CH$_2$Cl$_2$ (10 mL), and washed successively with 0.1 N HCl (5 mL), and a solution of 10% NaHCO$_3$ (5 ml). The organic layer was dried over Na$_2$SO$_4$, filtered, and the solvent was eliminated under reduced pressure. The residue was purified by flash column chromatography (SiO$_2$, Hex:EtOAc 1:2) to afford 190 (27 mg, 25%) as a white solid.

Rf=0.24 Hex:EtOAc 1:1.

$^1$H NMR (300 MHz, CDCl$_3$) δ 6.82 (s, 1H), 6.02 (d, J=0.9 Hz, 1H), 5.92 (d, J=0.9 Hz, 1H), 5.30 (bs, 1H), 4.14 (d, J=2.7 Hz, 1H), 4.10 (s, 1H), 3.90-3.73 (m, 2H), 3.68 (s, 3H), 3.67 (bs, 1H), 3.49 (bs, 1H), 3.42 (brd, J=8.1 Hz, 1H), 3.24-3.20 (m, 1H), 3.01 (dd, J$_1$=8.4 Hz, J$_2$=18.3 Hz, 1H), 2.78 (d, J=18 Hz, 1H), 2.64 (brd, J=15.6 Hz, 1H), 2.36 (s, 3H), 2.34 (s, 3H), 2.24 (s, 3H), 2.20 (s, 3H), 2.02 (s, 3H), 1.77 (dd, J$_1$=11.7 Hz, J$_2$=15.6 Hz, 1H), 0.65 (d, J=6.6 Hz, 3H).

$^{13}$C NMR (75 MHz, CDCl$_3$) δ 170.2, 168.6, 168.1, 167.6, 147.9, 144.9, 142.8, 140.5, 131.5, 131.0, 127.7, 123.2, 120.3, 117.5, 112.3, 112.2, 101.7, 60.4, 59.0, 57.4, 57.2, 55.2, 54.9, 48.6, 41.5, 39.1, 36.6, 29.7, 26.7, 24.6, 20.7, 20.2, 17.6, 15.5, 9.2.

ESI-MS m/z: Calcd. for C$_{35}$H$_{38}$F$_3$N$_5$O$_9$: 729.70. Found (M+1)$^+$: 730.3.

Example 153

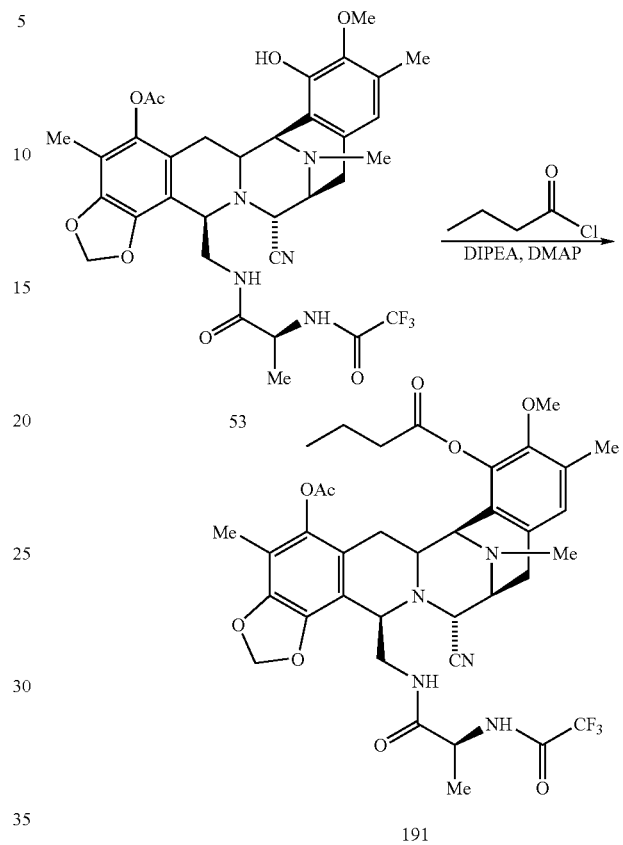

To a solution of 53 (150 mg, 0.218 mmol) in CH$_2$Cl$_2$ (1.09 mL). DIPEA (151.9 mL, 0.87 mmol), butyryl chloride (90.6 mL, 0.87 mmol) and DMAP (2.70 mg, 0.02 mmol) were added at 0° C. and the reaction mixture was stirred at 23° C. for 4 h. Then, the solution was diluted with CH$_2$Cl$_2$ (10 mL) and washed successively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by flash column chromatography (RP-18, CH$_3$CN:H$_2$O 4:1) to afford 191 (20.2 mg, 12%) as a white solid.

Rf=0.3 Hex:EtOAc 1:1.

$^1$H NMR (300 MHz, CDCl$_3$) δ 6.81 (s, 1H), 6.03 (d, J=1.2 Hz, 1H), 5.92 (d, J=1.2 Hz, 1H), 5.16 (t, J=5.4 Hz, 1H), 4.13 (d, J=2.1 Hz, 1H), 4.10 (bs, 1H), 3.87-3.82 (m, 1H), 3.80-3.74 (m, 1), 3.68 (s, 3H), 3.64 (d, J=3 Hz, 1H), 3.52-3.47 (m, 1H), 3.42 (brd, J=7.2 Hz, 1H), 3.24-3.20 (m, 1H), 3.02 (dd, J$_1$=8.1 Hz, J$_2$=18.3 Hz, 1H), 2.77 (d, J=17.7 Hz, 1H), 2.64 (brd, J=16.2 Hz, 1H), 2.58 (t, J=7.2 Hz, 2H), 2.33 (s, 3H), 2.25 (s, 3H), 2.22 (s, 3H), 2.02 (s, 3H), 1.87-1.73 (m, 3H), 1.08 (t, J=7.2 Hz, 3H), 0.68 (d, J=6.6 Hz, 3H).

$^{13}$C NMR (75 MHz, CDCl$_3$) δ 172.8, 172.1, 170.4, 157.8, 150.0, 146.9, 144.8, 142.6, 142.5, 133.3, 132.8, 129.6, 125.3, 122.3, 119.5, 118.4, 115.7, 114.3, 114.2, 103.8, 62.4, 61.0, 59.4, 59.2, 57.2, 57.0, 50.6, 43.6, 41.2, 38.1, 31.7, 28.7, 26.6, 22.2, 20.6, 19.7, 17.5, 15.7, 11.2.

ESI-MS m/z: Calcd. for C$_{37}$H$_{12}$F$_3$N$_5$O$_9$: 757.75. Found: 758.5 (M+1)$^+$, 780.5 (M+23)$^+$.

Example 154

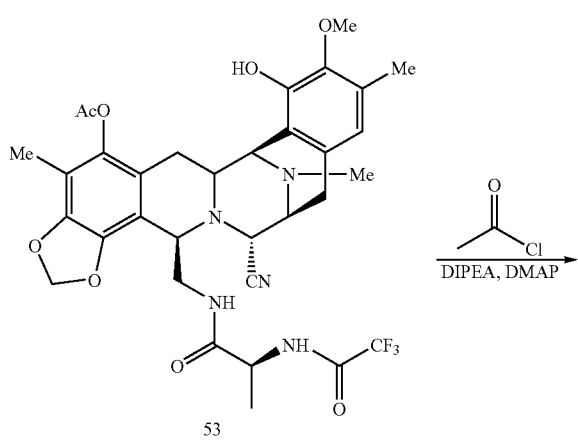

Rf=0.25 Hex:EtOAc 1:1.

$^1$H NMR (300 MHz, CDCl$_3$) δ 6.80 (s, 1H), 5.87 (s, 1H), 5.81 (s, 1H), 4.70 (dd, J$_1$=2.4 Hz, J$_2$=9.9 Hz, 1H), 4.20 (d, J=6.3 Hz, 1H), 4.09 (s, 1H), 3.74 (s, 3H), 3.60 (s, 1H), 3.28 (d, J=7.5 Hz, 1H), 3.17 (d, J=12 Hz, 1H), 3.07 (dd, J$_1$=7.2 Hz, J$_2$=18.3 Hz, 1H), 2.93 (d, J=13.2 Hz, 1H), 2.66 (d, J=15.3 Hz, 1H), 2.53 (d, J=17.7 Hz, 1H), 2.47-2.20 (m, 1H), 2.37 (s, 1H), 2.33 (s, 3H), 2.26 (s, 3H), 2.24 (s, 3H), 2.08 (s, 3H), 2.00 (s, 3H), 1.96 (s, 3H), 1.72 (t, J=14.4 Hz, 1H), 1.53 (d, J=6.9 Hz, 3H).

$^{13}$C NMR (75 MHz, CDCl$_3$) δ 174.1, 168.6, 168.4, 167.5, 147.7, 144.8, 142.2, 140.4, 131.1, 130.5, 126.9, 123.3, 120.4, 117.5, 112.4, 111.8, 101.1, 60.7, 60.6, 57.6, 57.2, 56.6, 55.3, 52.7, 48.3, 41.5, 31.6, 29.7, 26.4, 25.5, 23.0, 22.6, 20.7, 20.5, 20.2, 17.8, 15.9, 14.1, 9.5.

ESI-MS m/z: Calcd. for C$_{39}$H$_{42}$F$_3$N$_5$O$_{11}$: 813.7. Found (M+1)$^+$: 814.3.

Example 155

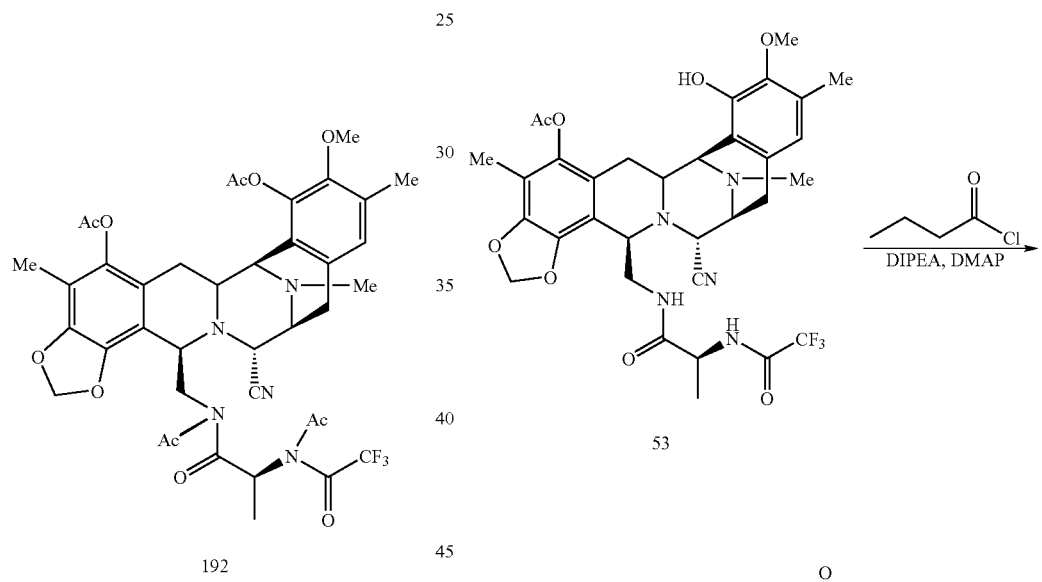

To a solution of 53 (150 mg, 0.218 mmol) in CH$_2$Cl$_2$ (1.09 mL). DIPEA (151.9 mL, 0.87 mmol), acetyl chloride (62.0 mL, 0.87 mmol) and DMAP (2.70 mg, 0.02 mmol) were added at 0° C. and the reaction mixture was stirred at 23° C. for 5 h. Then, the solution was diluted with CH$_2$Cl$_2$ (10 mL) and washed successively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by flash column chromatography (RP-18, CH$_3$CN:H$_2$O 1:1) to afford 192 (111 mg, 62%) as a white solid.

To a solution of 53 (150 mg, 0.218 mmol) in CH$_2$Cl$_2$ (1.09 mL), DIPEA (151.9 mL, 0.87 mmol), butyryl chloride (90.6 mL, 0.87 mmol) and DMAP (2.70 mg, 0.02 mmol) were added at 0° C. and the reaction mixture was stirred at 23° C. for 4 h. Then, the solution was diluted with CH$_2$Cl$_2$ (10 mL) and washed successively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by flash column chromatography (RP-18, CH$_3$CN:H$_2$O 4:1) to afford 193 (58 mg, 30%) as a white solid.

Rf=0.38 Hex:EtOAc 1:1.

$^1$H NMR (300 MHz, CDCl$_3$) δ 6.85 (s, 1H), 5.99 (d, J=1.2 Hz, 1H), 5.90 (d, J=1.2 Hz, 1H), 5.47-5.42 (m, 2H), 4.09-4.08 (m, 2H), 3.69 (s, 3H), 3.66 (m, 1H), 3.41 (d, J=7.5 Hz, 1H), 3.28-3.18 (m, 2H), 3.07 (dd, J$_1$=8.1 Hz, J$_2$=18 Hz, 1H), 2.66 (d, J=18.6 Hz, 1H), 2.61-2.39 (m, 3H), 2.34 (s, 3H), 2.26 (s, 3H), 2.21 (s, 3H), 2.01 (s, 3H), 1.95-1.79 (m, 6H), 1.72-1.59 (m, 6H) 1.09 (t, J=7.5 Hz, 3H), 0.99-0.94 (m, 6H), 0.85 (d, J=6.9 Hz, 3H).

$^{13}$C NMR (75 MHz, CDCl$_3$) δ 171.2, 170.7, 169.1, 168.4, 148.1, 145.0, 142.7, 140.9, 140.6, 131.2, 130.5, 128.4, 123.4, 119.9, 117.6, 113.0, 112.1, 101.9, 60.7, 59.5, 57.6, 56.5, 55.7, 55.2, 41.8, 41.4, 36.3, 35.8, 29.9, 27.0, 25.3, 20.5, 20.0, 18.8, 18.3, 15.8, 14.0, 13.8, 13.4, 12.7, 9.6.

ESI-MS m/z: Calcd. for C$_{45}$H$_{54}$F$_3$N$_5$O$_{11}$: 897.93. Found (M+1)$^+$: 898.3.

Example 156

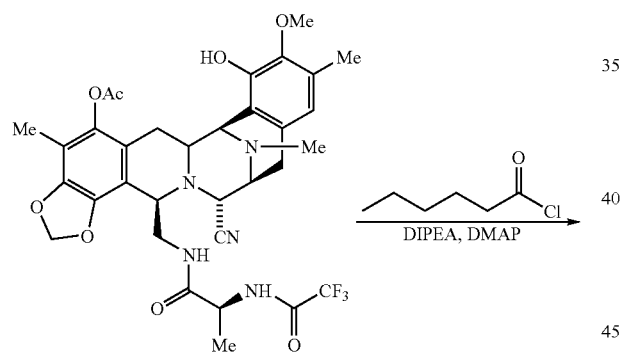

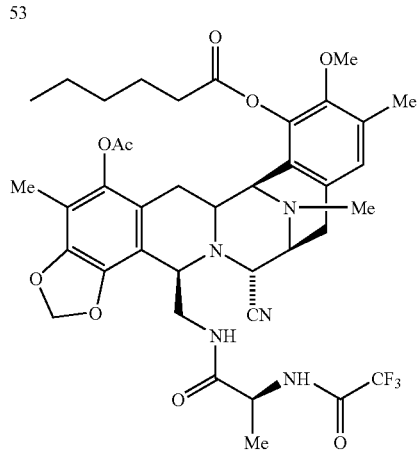

194

To a solution of 53 (150 mg, 0.218 mmol) in CH$_2$Cl$_2$ (1.09 mL). DIPEA (151.9 mL, 0.87 mmol), hexanoyl chloride (121.9 mL, 0.87 mmol) and DMAP (2.70 mg, 0.02 mmol) were added at 0° C. and the reaction mixture was stirred at 23° C. for 4 h. Then, the solution was diluted with CH$_2$Cl$_2$ (10 mL) and washed successively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by flash column chromatography (RP-18, CH$_3$CN:H$_2$O 4:1) to afford 194 (37.5 mg, 22%) as a white solid.

Rf=0.32 Hex:EtOAc 1:1.

$^1$H NMR (300 MHz, CDCl$_3$) δ 6.80 (s, 1H), 6.02 (d, J=1.2 Hz, 1H), 5.92 (d, J=1.2 Hz, 1H), 5.22 (t, J=5.7 Hz, 1H), 4.13 (d, J=2.4 Hz, 1H), 4.09 (s, 1H), 3.88-3.81 (m, 1H), 3.80-3.71 (m, 1H), 3.67 (s, 3H), 3.64 (d, J=3 Hz, 1H), 3.52-3.43 (m, 1H), 3.41 (brd, J=6.6 Hz, 1H), 3.23-3.19 (m, 1H), 3.00 (dd, J$_1$=8.7 Hz, J$_2$=18.6 Hz, 1H), 2.77 (d, J=18 Hz, 1H), 2.67-2.56 (m, 3H), 2.33 (s, 3H), 2.24 (s, 3H), 2.22 (s, 3H), 2.01 (s, 3H), 1.82-1.74 (m, 4H), 1.43-1.38 (m, 3H), 0.97-0.88 (m, 3H), 0.67 (d, J=6.9 Hz, 3H).

$^{13}$C NMR (75 MHz, CDCl$_3$) δ 171.2, 170.3, 168.6, 148.2, 145.1, 143.0, 140.8, 140.7, 131.7, 131.1, 127.8, 123.5, 120.6, 117.7, 112.5, 102.0, 60.7, 59.2, 57.6, 57.4, 55.4, 55.2, 48.9, 41.8, 34.4, 31.8, 31.6, 29.9, 26.9, 25.0, 24.8, 22.9, 22.5, 20.4, 17.9, 15.8, 14.3, 14.1, 9.5.

ESI-MS m/z: Calcd. for C$_{39}$H$_{46}$F$_3$N$_5$O$_9$: 785.81. Found: 786 (M+1)$^+$, 805.5 (M+23)$^+$.

Example 157

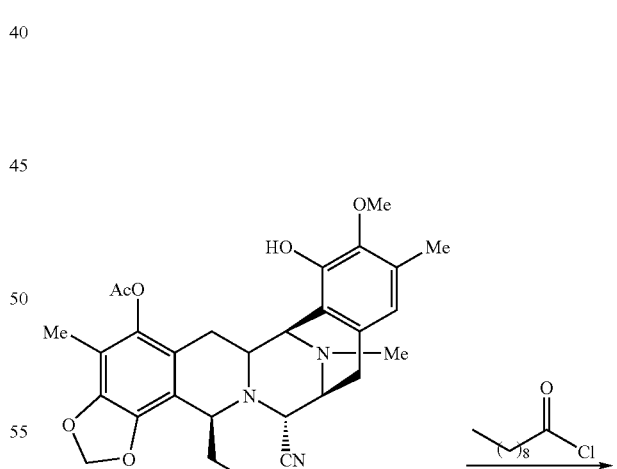

53

-continued

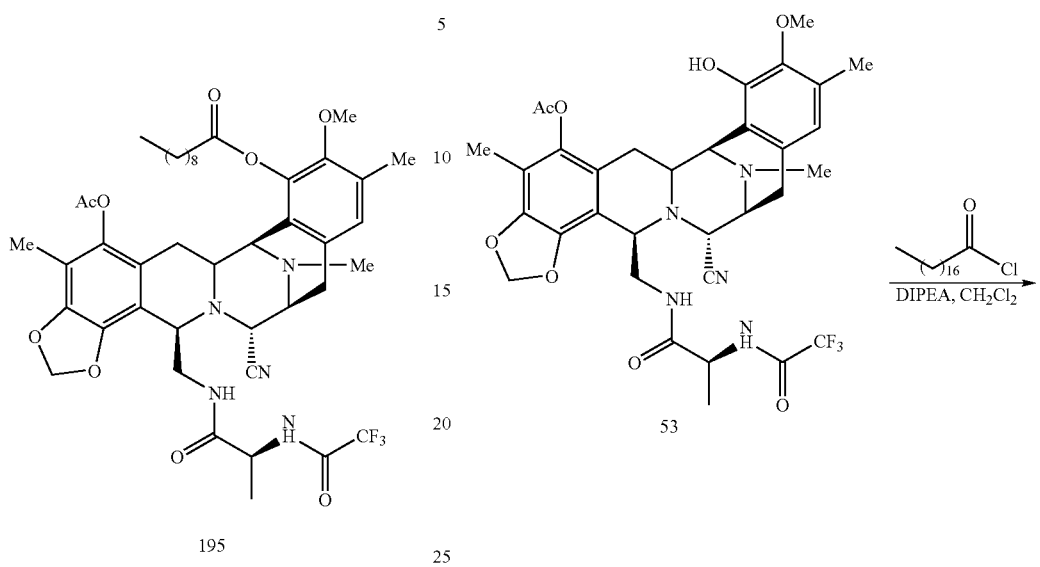

195

To a solution of 53 (150 mg, 0.218 mmol) in CH$_2$Cl$_2$ (1.09 mL), DIPEA (75.9 mL, 0.436 mmol), and decanoyl chloride (92.7 mL, 0.436 mmol) were added at 0° C. and the reaction mixture was stirred at 23° C. for 4 h. Then, the solution was diluted with CH$_2$Cl$_2$ (10 mL) and washed successively with 0.1 N HCl (5 mL), and a solution of 10% NaHCO$_3$ (5 ml). The organic layer was dried over Na$_2$SO$_4$, filtered, and the solvent was eliminated under reduced pressure. The residue was purified by flash column chromatography (RP-18, CH$_3$CN:H$_2$O 1:1) to afford 195 (75 mg, 41%) as a white solid.

Rf=0.32 Hex:EtOAc 1:1.

$^1$H NMR (300 Hz, CDCl$_3$) δ 6.82 (s, 1H), 6.03 (d, J=1.5 Hz, 1H), 5.93 (d, J=1.5 Hz, 1H), 5.26 (bs, 1H), 4.15 (s, 1H), 4.11 (s, 1H), 3.89-3.75 (m, 2H), 3.68 (s, 3H), 3.65 (bs, 1H), 3.52-3.44 (m, 1H), 3.43 (d, J=8.1 Hz, 1H), 3.22 (brd, J=11.4 Hz, 1H), 3.03 (dd, J$_1$=7.8 Hz, J$_{2=17.4}$ Hz, 1H), 2.78 (d, J=17.7 Hz, 1H), 2.69-2.56 (m, 3H), 2.34 (s, 3H), 2.26 (s, 3H), 2.23 (s, 3H), 2.03 (s, 3H), 1.83-1.74 (m, 3H), 1.83-1.74 (m, 12H), 0.90-8.88 (m, 3H), 0.68 (d, J=6 Hz, 3H).

$^{13}$C NMR (75 Hz, CDCl$_3$) δ 171.0, 170.1, 168.4, 148.0, 144.8, 142.8, 140.5, 131.5, 130.8, 127.5, 123.3, 120.3, 117.5, 112.3, 112.2, 101.7, 60.4, 59.0, 57.4, 57.2, 55.1, 55.0, 48.6, 41.5, 39.1, 34.2, 31.8, 29.4, 29.2, 26.7, 25.0, 24.6, 22.6, 20.2, 17.6, 15.5, 14.0, 9.2.

ESI-MS m/z: Calcd. for C$_{43}$H$_{54}$F$_3$N$_5$O$_9$: 841.91. Found (M+1)$^+$: 842.3.

Example 158

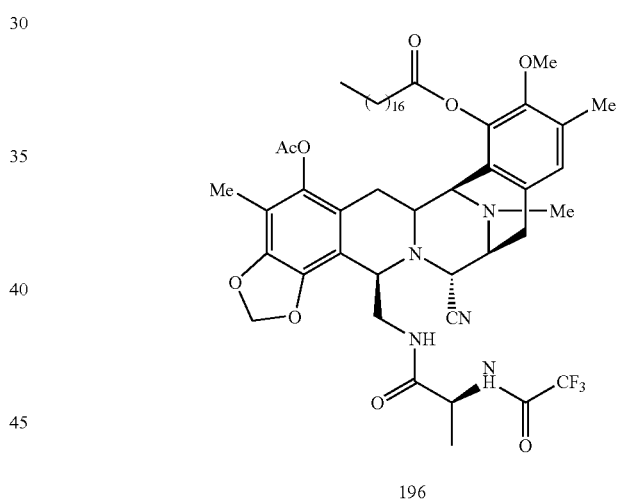

53

196

To a solution of 53 (150 mg, 0.218 mmol) in CH$_2$Cl$_2$ (1.09 mL). DIPEA (75.9 mL, 0.436 mmol), and stearoyl chloride (147.3 mL, 0.436 mmol) were added at 0° C. and the reaction mixture was stirred at 23° C. for 4 h. Then, the solution was diluted with CH$_2$Cl$_2$ (10 mL) and washed successively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by flash column chromatography (RP-18, CH$_3$CN:H$_2$O 1:1) to afford 196 (86 mg, 41%) as a white solid.

Rf=0.42 Hex:EtOAc 1:1.

$^1$H NMR (300 Hz, CDCl$_3$) δ 6.81 (s, 1H), 6.03 (s, 1H), 5.92 (s, 1H), 5.21 (bs, 1H), 4.14 (s, 1H), 4.10 (s, 1H), 3.88-3.74 (m, 2H), 3.67 (s, 3H), 3.64 (d, J=3 Hz, 1H), 3.49 (brd, J=14.7 Hz, 1H), 3.42 (d, J=8.1 Hz, 1H), 3.22 (brd, J=11.4 Hz, 1H), 3.02 (dd, J$_1$=8.7 Hz, J$_2$=18.6 Hz, 1H), 2.78 (d, J=18 Hz, 1H), 2.68-2.56 (m, 3H), 2.33 (s, 3H), 2.25 (s, 3H), 2.02 (s, 3H), 1.82-1.73 (m, 3H), 1.42-1.19 (m, 28H), 0.87 (t, J=7.2 Hz, 3H), 0.67 (d, J=6.6 Hz, 3H).

$^{13}$C NMR (75 MHz, CDCl$_3$) δ 171.0, 170.2, 168.5, 147.9, 144.8, 142.8, 140.4, 131.4, 130.9, 127.5, 123.3, 120.4, 117.5, 112.4, 112.1, 101.7, 60.4, 58.9, 57.4, 57.2, 55.2, 55.0, 48.6, 41.5, 39.0, 34.2, 31.9, 29.7, 29.6, 29.4, 29.3, 29.2, 26.7, 25.1, 24.6, 22.7, 20.2, 17.6, 15.5, 14.1, 9.2. ESI-MS m/z: Calcd. for C$_{51}$H$_{70}$F$_3$N$_5$O$_9$: 953.5. Found (M+1)$^+$: 954.4.

Example 159

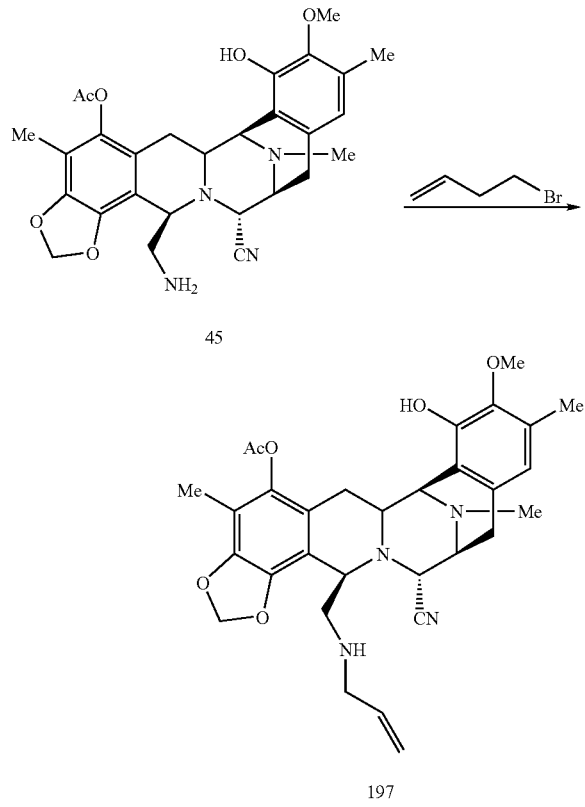

To a solution of 45 (10 mg, 0.019 mmol) in CH$_2$Cl$_2$ (0.095 mL), triethylamine (2.94 mL, 0.021 mmol) and allyl bromide (2.0 mL, 0.023 mmol) were added at 23° C. The reaction mixture was stirred for 6 h and then, the solvent was removed under reduced pressure. The residue was purified by flash column chromatography (SiO$_2$, MeOH:EtOAc 1:5) to afford 197 (3.8 mg, 35%) as a white solid.

Rf=0.19 EtOAc:MeOH 5:1.

$^1$H NMR (300 MHz, CDCl$_3$) δ 6.43 (s, 1H), 5.95 (s, 1H), 5.89 (s, 1H), 5.62-5.59 (m, 1H), 4.94-4.84 (m, 2H), 4.19 (s, 1H), 4.08 (s, 1H), 3.98 (t, J=4.5 Hz, 1H), 3.76 (s, 3H), 3.32-3.26 (m, 2H), 3.07 (dd, J$_1$=7.5 Hz, J$_2$=17.4 Hz, 1H), 2.89 (d, J=6 Hz, 2H), 2.80 (d, J=3.9 Hz, 1H), 2.76 (d, J=3.3 Hz, 1H), 2.57-2.52 (m, 2H), 2.33 (s, 6H), 2.24 (s, 3H), 1.99 (s, 3H), 1.88-1.79 (dd, J$_1$=12.9 Hz, J$_2$=15.9 Hz, 1H).

ESI-MS m/z: Calcd. for C$_{31}$H$_{36}$N$_4$O$_6$: 560.64. Found (M+1)$^+$: 561.3.

Example 160

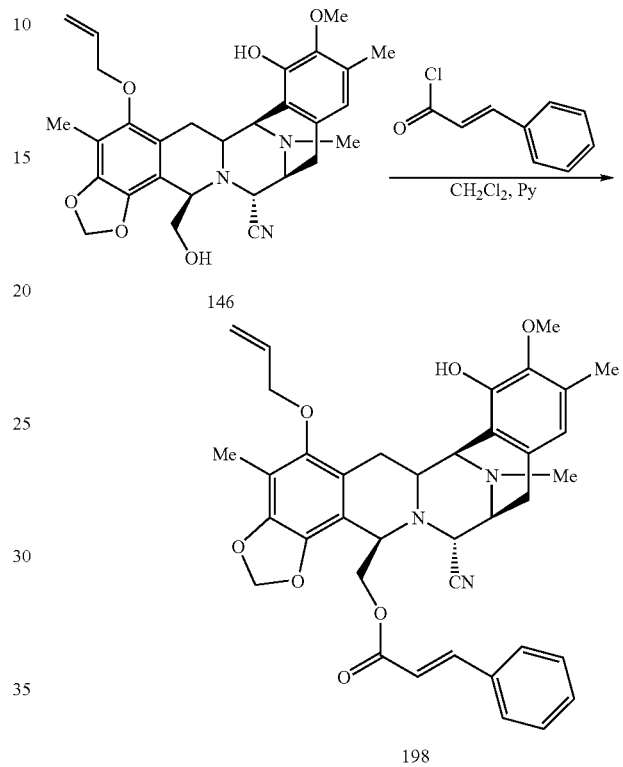

To a solution of 146 (50 mg, 0.096 mmol) in CH$_2$Cl$_2$ (0.96 mL), pyridine (11.7 mL, 0.144 mmol), and cinnamoyl chloride (24.0 mg, 0.144 mmol) were added at 23° C. and the reaction mixture was stirred for 18 h at that temperature. Then, the solution was diluted with CH$_2$Cl$_2$ (10 mL) and washed successively with 0.1 N HCl (5 mL) and a solution of 10% NaHCO$_3$ (5 ml). The organic layer was dried over Na$_2$SO$_4$, filtered, and the solvent was eliminated under reduced pressure. The residue was purified by flash column chromatography (SiO$_2$, Hex:EtOAc 1:2) to afford 198 (54 mg, 86%) as a white solid.

Rf=0.45 Hex:EtOAc 1:1.

$^1$H NMR (300 MHz, CDCl$_3$) δ 7.41-7.37 (m, 6H), 6.38 (s, 1H), 6.19-6.03 (m, 1H), 6.08 (d, J=15.9 Hz, 1H), 5.93 (d, J=1.5 Hz, 1H), 5.88 (d, J=1.5 Hz, 1H), 5.62 (s, 1H), 5.38 (dd, J$_1$=1.5 Hz, J$_2$=17.1 Hz, 1H), 5.26 (dd, J=1.5 Hz, J=10.5 Hz, 1H), 4.47 (dd, J$_1$=3.6 Hz, J$_{2=10.8}$ Hz, 1H), 4.23-4.11 (m, 5H), 3.89 (dd, J$_1$=4.8 Hz, J$_2$=11.1 Hz, 1H), 3.51 (s, 3H), 3.34 (brd, J=8.4 Hz, 1H), 3.27-3.21 (m, 2H), 2.97 (dd, J$_1$=7.8 Hz, J$_2$=17.7 Hz, 1H), 2.28 (s, 3H), 2.15 (s, 3H), 2.04 (s, 3H), 1.91 (dd, J$_1$=12 Hz, J$_2$=15.6 Hz, 1H).

$^{13}$C NMR (75 MHz, CDCl$_3$) δ 166.5, 148.8, 146.7, 144.7, 144.5, 142.7, 139.5, 134.4, 134.1, 131.1, 130.6, 129.1, 128.7, 128.2, 121.9, 121.2, 118.5, 117.8, 116.8, 112.9, 112.7, 101.5, 74.7, 65.2, 60.7, 60.6, 57.4, 56.8, 56.6, 55.7, 41.9, 31.8, 26.7, 25.5, 22.9, 15.9, 14.4, 9.7.

ESI-MS m/z: Calcd. for C$_{38}$H$_{39}$N$_3$O$_7$: 649.7. Found (M+1)$^+$: 650.3.

Example 161

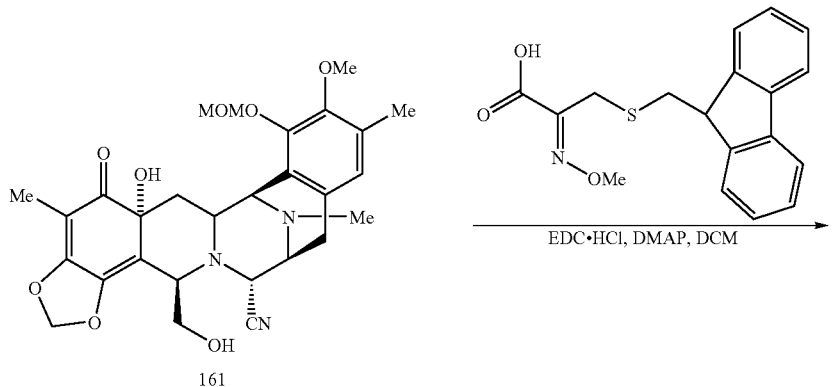

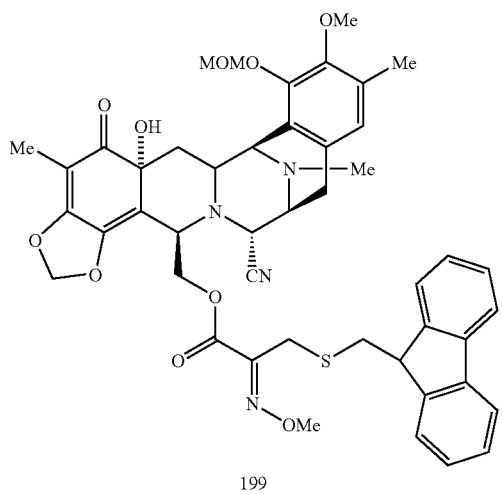

To a solution of 161 (78.5 mg 0.146 mmol) and the cysteine derivative (81.1 mg, 0.247 mmol) in anhydrous $CH_2Cl_2$ (7.3 mL), DMAP (50 mg, 0.41 mmol) and EDC.HCl (78.1 mg, 0.41 mmol) were added at 23° C. The reaction mixture was stirred at 23° C. under Argon atmosphere for 1.5 h. The mixture was diluted with $CH_2Cl_2$ (20 mL) and extracted with an aqueous saturated solution of sodium bicarbonate (25 mL). The aqueous phase was extracted with additional $CH_2Cl_2$ (20 mL) and the combined organic extracts were dried over $Na_2SO_4$, filtered and the solvent was eliminated under reduced pressure. The crude of the reaction was purified by flash column chromatography (inner diameter of the column 2 cm, height of silica 10 cm) with mixtures of ethyl acetate/hexane in a gradient manner, from 1:4 to 3:1 as eluent. Compound 199 (113 mg, 88%) was obtained as a pale yellow solid.

Rf=0.36 Hex:EtOAc 1:1.

$^1$H NMR (300 MHz, CDCl$_3$) δ: 7.76 (d, J=7.8 Hz, 2H), 7.63 (d, J=7.8 Hz, 2H), 7.40 (t, J=7.6 Hz, 2H), 7.29 (t, J=7.6 Hz, 2H), 6.54 (s, 1H), 5.80 (s, 1H), 5.74 (s, 1H), 5.10 (d, J=5.7 Hz, 1H), 5.08 (d, J=5.7 Hz, 1H), 4.50 (dd, J=4.9 Hz, J=11.8 Hz, 1H), 4.20-4.05 (m, 4H), 4.02 (s, 3H), 3.81 (s, 3H), 3.61 (d, J=13.8 Hz, 1H), 3.55 (d, J=13.8 Hz, 1H), 3.50 (s, 3H), 3.21 (m, 1H), 3.06 (m, 1H), 3.00 (d, J=6.0 Hz, 2H), 2.90 (dd, J=8.9 Hz, J=17.4 Hz, 1H), 2.79 (s, 1H), 2.56 (m, 1H), 2.50 (dd, J=4.8 Hz, J=14.9 Hz, 1H), 2.21 (s, 3H), 2.18 (s, 3H), 1.80 (s, 3H), 1.75 (m, 2H).

ESI-MS m/z: Calcd. for $C_{46}H_{48}N_4O_{10}S$: 848.3. Found: 849.3 (M+1)$^+$, 871.3 (M+23)$^+$. HPLC: Conditions: Column: Simmetry C18, Mobile phase: $CH_3CN/H_2O$ in gradient from 50 to 100% in 25 minutes. φ=1 mL/min, t=40° C. Retention time: 16.04 minutes. HPLC purity in area: 89.29%.

Example 162

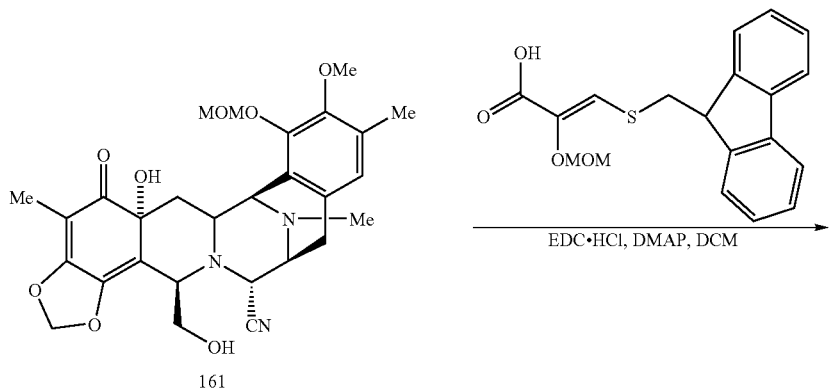

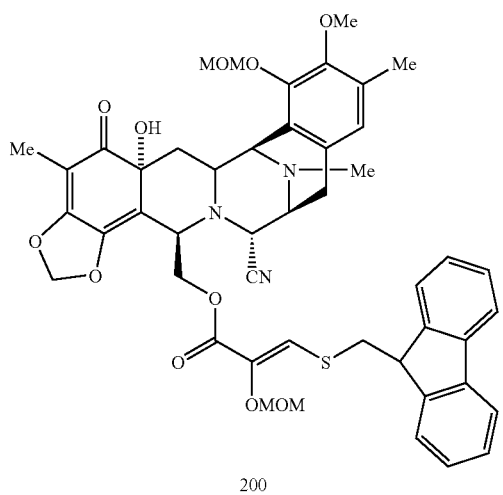

To a solution of 161 (80 mg, 0.148 mmol) and the cysteine derivative (76 mg, 0.223 mmol) in anhydrous $CH_2Cl_2$ (6.8 mL), DMAP (45 mg, 0.37 mmol) and EDC.HCl (71 mg, 0.37 mmol) were added at 23° C. The reaction mixture was stirred at 23° C. under Argon atmosphere for 2.5 h Then, the mixture was diluted with $CH_2Cl_2$ (20 mL) and extracted with an aqueous saturated solution of sodium bicarbonate (25 mL). The aqueous phase was extracted with additional $CH_2Cl_2$ (20 mL) and the combined organic extracts were dried over $Na_2SO_4$, filtered and the solvent was eliminated under reduced pressure. The crude of the reaction was purified by flash column chromatography (inner diameter of the column 2 cm, height of silica 10 cm) with mixtures of ethyl acetate/hexane in gradient from 1:4 to 3:1 as eluent. Compound 200 (83 mg, 65%) was obtained as a pale yellow solid.

Rf=0.5 Hex:EtOAc 1:1.

$^1$H NMR (300 MHz, CDCl$_3$) δ: 7.71 (m, 3H), 7.49 (d, J=7.3 Hz, 1H), 7.36 (t, J=7.3 Hz, 2H), 7.32-7.23 (m, 2H), 6.65 (s, 1H), 5.80 (s, 1H), 5.79 (s, 1H), 5.13 (d, J=6.1 Hz, 1H), 5.11 (d, J=6.1 Hz, 1H), 5.05 (d, J=6.1 Hz, 1H), 5.01 (d, J=6.3 Hz, 1H), 4.76 (dd, J=3.9 Hz, J=11.9 Hz, 1H), 4.15-4.03 (m, 4H), 3.96 (t, J=4.0 Hz, 1H), 3.87 (s, 3H), 3.55 (s, 3H), 3.51 (s, 3H), 3.34-3.29 (m, 2H), 3.24 (dd, J=5.5 Hz, J=13.5 Hz, 1H), 3.03 (m, 1H), 2.97 (t, J=7.5 Hz, 1H), 2.44-2.35 (m, 3H), 2.29 (s, 3H), 2.14 (s, 3H), 1.98 (dd, J=8.06, J=15.1 Hz, 2H), 1.75 (s, 3H).

$^{13}$C NMR (75 MHz, CDCl$_3$) δ 196.98, 161.13, 158.21, 149.01, 148.78, 145.05, 144.91, 141.01, 140.69, 140.07, 137.53, 132.76, 131.15, 129.41, 127.70, 127.67, 127.21, 126.83, 125.28, 125.05, 124.94, 122.51, 119.84, 119.73, 116.61, 110.26, 104, 57, 101.40, 99.23, 96.70, 70.25, 63.15, 60.40, 58.89, 57.52, 56.98, 56.72, 56.15, 55.06, 47.22, 41.37, 38.26, 35.22, 29.57, 25.34, 15.62, 7.26.

ESI-MS m/z: Calcd. for $C_{47}H_{49}N_3O_{11}S$: 863.97. Found: 865.0 (M+1)$^+$, 887.1 (M+23)$^+$. HPLC: Conditions: Column: Simmetry C18. Mobile phase: $CH_3CN/H_2O$ in gradient from 50 to 100% in 25 minutes. φ=1 mL/min, t=40° C. Retention time: 15.36 minutes. HPLC purity in area: 91.56%.

Example 163

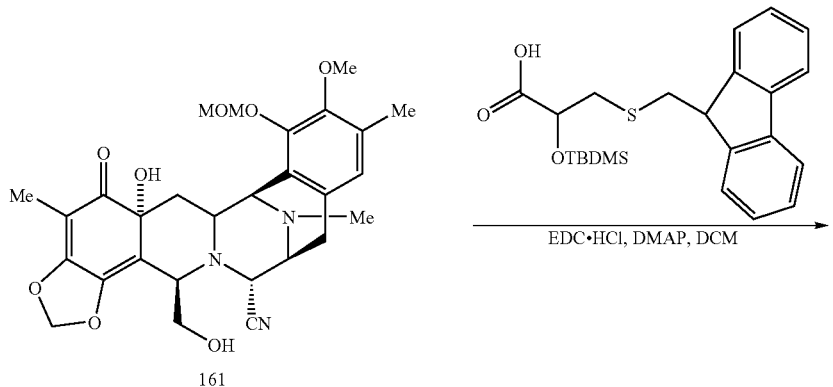

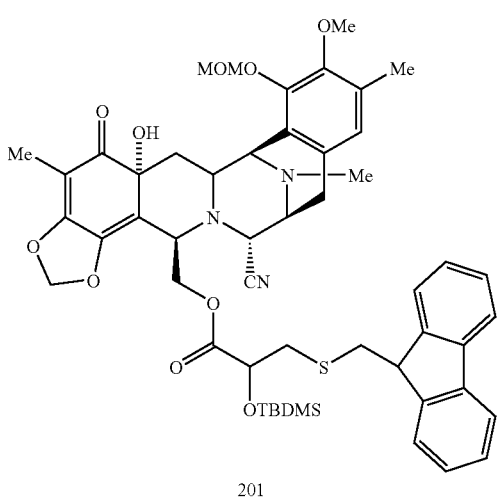

To a solution of 161 (418 mg, 0.77 mmol) and the cysteine derivative (321 mg, 0.77 mmol) in anhydrous CH$_2$Cl$_2$ (35 mL), DMAP (235 mg, 1.92 mmol) and EDC.HCl (369 mg, 1.92 mmol) were added at 23° C. and the reaction was stirred under Argon atmosphere for 2 h. The mixture was diluted with CH$_2$Cl$_2$ (20 mL) and extracted with an aqueous saturated solution of sodium bicarbonate (25 mL). The aqueous phase was extracted with additional CH$_2$Cl$_2$ (20 mL) and the combined organic extracts were dried over Na$_2$SO$_4$, filtered and the solvent was eliminated under reduced pressure. The crude of the reaction was purified by flash column chromatography (inner diameter of the column 3 cm, height of silica 11 cm) with mixtures of ethyl acetate/hexane in a gradient manner, from 1:3 to 3:1 as eluent. Compound 201 (372 mg, 52%) was obtained as a pale yellow solid.

Rf=0.41 Hex:EtOAc 1:1.

$^1$H-RMN (CDCl$_3$, 300 MHz) δ 7.76-7.64 (m, 4H), 7.41-7.30 (m, 4H), 6.54 (s, 1H major isomer), 6.51 (s, 1H, minor isomer), 5.69 (s, 1H, minor isomer), 5.67 (s, 1H, major isomer), 5.60 (s, 1H minor isomer), 5.57 (s, 1H major isomer), 5.08 (s, 2H), 4.26 (t, J=5.1 Hz, 1H minor isomer), 4.23 (t, J=4.9 Hz, 1H major isomer), 4.07-4.03 (m, 3H), 3.98-3.88 (n, 3H), 3.84 (s, 3H), 3.71 (dt, J$_1$=5.6 Hz, J$_2$=10.0 Hz, 1H), 3.49 (s, 3H, major isomer), 3.49 (s, 3H, minor isomer), 3.40 (dt, J$_1$=5.6 Hz, J$_2$=9.5 Hz, 1H), 3.18 (m, 3H), 3.11 (m, 1H), 2.91-2.82 (m, 1H), 2.48-2.28 (m, 2H), 2.24 (s, 3H), 2.16 (s, 3H, major isomer), 2.14 (s, 3H, minor isomer), 2.03 (s, 3H), 1.91 (dt, J$_1$=8.8 Hz, J$_2$=14.4 Hz, 1H), 1.76 (s, 3H, minor isomer), 1.76 (s, 3H major isomer), 0.85 (s, 9H minor isomer), 0.85 (s, 9H major isomer), 0.04 and 0.01 (s, 6H both isomers).

ESI-MS m/z: Calcd. for C$_{51}$H$_{61}$N$_3$O$_{10}$SSi: 935.4. Found: 936.4 (M+1)$^+$, 958.3 (M+23)$^+$.

Example 164

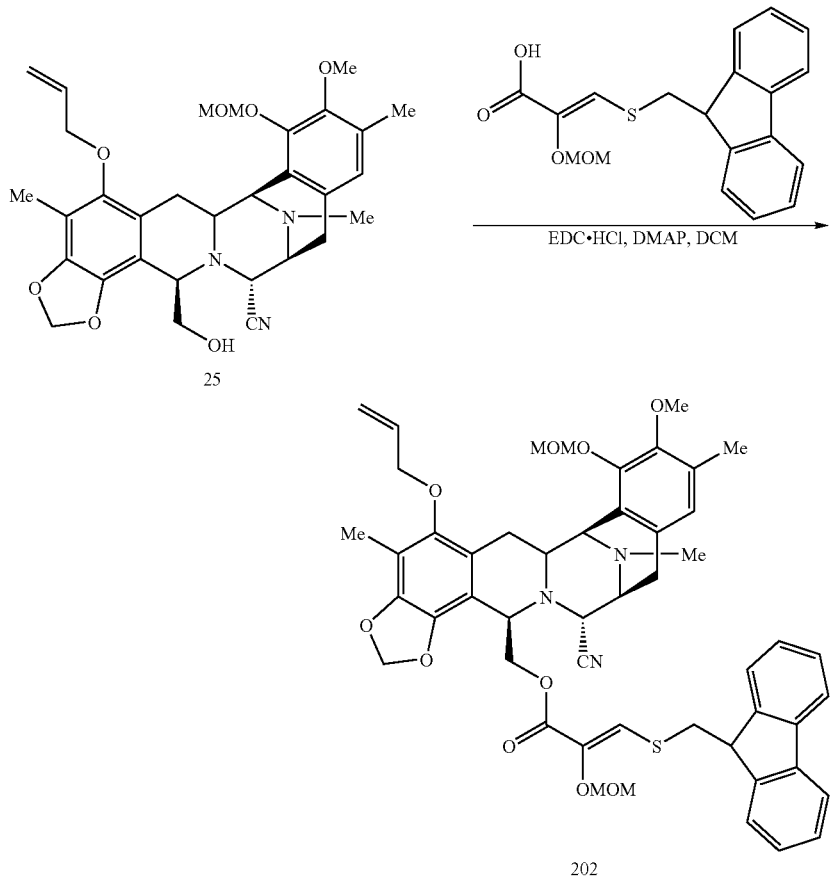

To a solution of 25 (2 mg, 0.0035 mmol) and an excess amount of the cysteine derivative in anhydrous $CH_2Cl_2$ (0.2 mL), an excess amounts of DMAP and EDC.HCl were added at 23° C. The reaction mixture was stirred at 23° C. under Argon atmosphere for 14 h. Then, the mixture was diluted with $CH_2Cl_2$ (10 mL) and washed with a saturated aqueous solution of sodium bicarbonate (10 mL). The aqueous phase was extracted with additional $CH_2Cl_2$ (10 mL). The combined organic layers were dried over $Na_2SO_4$, filtered and the solvent was eliminated under reduced pressure. The crude of the reaction was purified by flash column chromatography ($SiO_2$, Hex:EtOAc 4:1) to afford 202 as a pale yellow solid.

$^1$H NMR (300 MHz, $CDCl_3$) (poor resolution) δ 7.78.7.62 (m, 4H), 7.41-7.26 (m, 4H), 6.73 (s, 1H), 6.10 (m, 1H), 5.92 (d, J=1.3 Hz, 1H), 5.88 (d, J=1.3 Hz, 1H), 5.40-5.22 (m, 2H), 5.11 (s, 3H), 5.02 (d, J=13.8 Hz 1H), 4.29-4.02 (m, 6H), 3.97 (m, 1H), 3.72 (d, J=12.5 Hz, 2H), 3.70 (s, 3H), 3.58 (s, 3H), 3.51 (d, J=12.3 Hz, 2H), 3.50 (s, 3H), 3.49-3.20 (m, 4H), 2.54-2.28 (m, 4H), 2.40 (s, 3H), 2.21 (s, 3H), 2.16 (s, 3H).

Fermentation Procedures

Example A

Seed medium YMP3 containing 1% glucose; 0.25% beef extract; 0.5% bacto-peptone; 0.25% NaCl; 0.8% $CaCO_3$ was inoculated with 0.1% of a frozen vegetative stock of the microorganism, strain A2-2 of *Pseudomonas fluorescens*, and incubated on a rotary shaker (250 rpm) at 27° C. After 30 h of incubation, the seed culture was added to a agitated-vessel fermentor with a production medium composed of 2% dextrose; 4% mannitol, 2% dried brewer's yeast (Vitalevor® Biolux, Belgium); 1% $(NH_4)_2SO_4$: 0.04% $K_2HPO_4$; 0.8 KCl; 0.001% $FeCl_3$; 0.1% L-Tyr; 0.8% $CO_3Ca$; 0.05% PPG-2000; 0.2% anti-foam silicone (ASSAF-100, RHODIA UK). The sterilisation was carried out at 122° C. 30 minutes. The volume inoculated was a 2% (v/v). The temperature was 27° C. (0 to 16 h) and 24° C. from 16 h to final process (41 hours). The dissolve oxygen-pressure was upper to 25%. The pH was controlled at 6.0 with diluted sulphuric acid since 28 hours till final process. The overpressure was 0.5 bar. A 1% mannitol or sorbitol was added from 16 h to final process (for two days running) and 2% for three days fermentation-process.

After 41 or 64 hours, the fermentation broth must be extracted for recovery safracin B or KCN treatment in the clarified broth for recovery safracin B-cyano.

Example B

Obtention of Safracin B Cyano from the Crude Extract.

A clarification or filtration from the fermentation broth at pH 6 removes the solids. The clarified broth was adjusted a pH 9.5 with diluted sodium hydroxide and extracted twice with 2:1 (v/v) ethyl acetate, methylene chloride or butyl acetate. The extraction was carried out into an agitated-vessel during 20', the temperature of the mixture was maintained at 8 to 10° C. The two phases were separated by a liquid-liquid centrifuge. The organic phase was dried with sodium sulphate anhydrous or frozen and then filtered for removing ice. This organic phase (ethyl acetate layer) was evaporated until obtention of an oil-crude extract.

Example C

Obtention of Safracin B Cyano from the Clarified Broth.

A clarification or filtration from the fermentation broth at pH 6 removes the solids. The clarified broth was adjusted at pH 3.9 with concentrated acetic acid. 0.5 grams per litre of KCN are added to the clarified broth an incubated at 20° C. during 1 hour with agitation. Then, the temperature was decreased at 15° C. and the pH was adjusted at 9.5 with diluted sodium hydroxide and extracted with 2:1.5 (v/v) ethyl acetate. The extraction was carried out into an agitated-vessel during 20 minutes, the temperature of the mixture was maintained at 8 to 10° C. The two phases were separated by a liquid-liquid centrifuge. The organic phase was dried with sodium sulphate anhydrous. This organic phase (ethyl acetate layer) was evaporated until obtention of an oil-crude extract. This extract was purified by flash column chromatography ($SiO_2$, gradient 20:1 to 10: to 5:1 ethyl acetate:methanol) to afford quantitatively compound 2 as a light yellow solid.

Rf: 0.55 (ethyl acetate:methanol 5:1); $t_R$=19.9 min [HPLC, Delta Pack C4, 5 μm, 300 A, 150×3 mm, λ=215 nm, flow=0.7 ml/min, temp=50° C., grad.: $CH_3CN$-aq. NaOAc (10 mM) 85%-70% (20')];

$^1$H NMR (300 Mhz, $CDCl_3$): δ 6.54 (dd, $J_1$=4.4 Hz, $J_2$=8.4 Hz, 1H), 6.44 (s, 1H), 4.12 (d, J=2.4 Hz, 1H), 4.04 (d, J=2.4 Hz, 1H), 4.00 (s, 3H), 3.87 (bs, 1H), 3.65 (ddd, $J_1$=1.5 Hz, $J_{2=8.7}$ Hz, $J_3$=9.9 Hz, 1H), 3.35 (br. D, J=8.4 Hz, 1H), 3.15-2.96 (m, 4H), 2.92 (q, J=7.2 Hz, 1H), 2.47 (d, J=18.3 Hz, 1H), 2.29 (s, 3H), 2.18 (s, 3H) 1.83 (s, 3H), 1.64 (ddd, $J_1$=2.7 Hz, $J_2$=11.1 Hz, $J_3$=14.1 Hz, 1H), 0.79 (d, J=7.2 Hz, 3H);

$^{13}$C NMR (75 Mhz, $CDCl_3$): δ 186.0 (q), 175.9 (q), 156.2 (q), 146.8 (q), 142.8 (q), 140.7 (q), 136.6 (q), 130.5 (q), 128.8 (q), 127.0 (q), 120.5 (s), 117.4 (q), 116.5 (q), 60.8 (t), 60.4 (s), 58.7 (t), 56.2 (s), 55.7 (s), 54.8 (s), 54.8 (s), 54.4 (s), 50.0 (s), 41.6 (t), 39.8 (d), 25.2 (d), 24.4 (d), 21.2 (t), 15.5 (t), 8.4 (t).

ESI-MS m/z: Calcd for $C_{29}H_{35}N_5O_6$: 549.6. Found (M+Na)$^+$: 572.3.

Example D

A medium (50 l) composed of dextrose (2%), mannitol (4%), dry brewer's yeast (2%), ammonium sulphate (1%), potassium secondary phosphate (0.04%), potassium chloride (0.8%), iron (III) chloride 6-hydrate (0.001%), L-tyrosine (0.1%), calcium carbonate (0.8%), poly-(propylene glycol) 2000 (0.05%) and antifoam ASSAF 1000 (0.2%) was poured into a jar-fermentor with 75 l total capacity and, after sterilisation, inoculated with seed culture (2%) of A2-2 strain (FERM BP-14) and aerated cultivation under agitation was carried out at 27° C. to 24° C. for 64 hours (aeration of 75 l per minute and agitation from 350 to 500 rpm). The pH was controlled by automatic feeding of diluted sulphuric acid from 27 hours to final process. A 2% mannitol was added from 16 hours to final process. The cultured medium (45 l) thus obtained was, after removal of cells by centrifugation, adjusted to pH 9.5 with diluted sodium hydroxide, extracted with 25 litres of ethyl acetate twice. The mixture was carried out into an agitated-vessel at 8° C. for 20 minutes. The two phases were separated by a liquid-liquid centrifuge. The organic phases were frozen at −20° C. and filtered for removing ice and evaporated ice and evaporated until obtention of a 40 g oil-dark-crude extract. After introduction of the cyanide group and purification, 3.0 grams of safracin B cyano were obtained.

Example E

A medium (50 l) composed of dextrose (2%), mannitol (4%), dry brewer's yeast (2%), ammonium sulphate (1%), potassium secondary phosphate (0.02%, potassium chloride (0.2%), Iron (III) chloride 6-hydrate (0.001%, L-tyrosine (0.1%), calcium carbonate (0.8%, poly-(propylene glycol) 2000 (0.05%) and antifoam ASSAF 1000 (0.2%) was poured into a jar-fermentor with 75 l total capacity and, after sterilisation, inoculated with seed culture (2%) of A2-2 strain (FERM BP-14) and aerated cultivation under agitation was carried out at 27° C. to 24° C. for 41 hours (aeration of 75 l per minute and agitation from 350 to 500 rpm). The pH was controlled by automatic feeding of diluted sulphuric acid from 28 hours to final process. A 1% mannitol was added from 16 hours to final process. The cultured medium (45 l) thus obtained was, after removal of cells by centrifugation, adjusted to pH 3.9 with 200 ml of conc. acetic acid. 25 grams of potassium cyanide 97% were added and after 1 hour of agitation at 20° C., the pH was adjusted to 9.5 with 1500 ml of a solution 10% sodium hydroxide. Then, extracted with 35 litres of ethyl acetate. The mixture was carried out into an agitated-vessel at 8° C. for 20 minutes. The two phases were separated by a liquid-liquid centrifuge. The organic phase was dried by sodium sulphate anhydrous and evaporated until obtention of a 60 g oil-dark-crude extract.

After chromatography, 4.9 grams of safracin B cyano were obtained.

REFERENCES

European Patent 309,477.
U.S. Pat. No. 5,721,362.
Sakai, R., Jares-Erijman, E. A., Manzanares, I., Elipe, M. V. S., and Rinehart, K. L. J. Am.
Chem. Soc. (1996) 118, 9017-9023
Martinez, E. J., Owa, T., Schreiber, S. L. and Corey, E. J. *Proc. Nail. Acad. Sci.* USA. 1999, 96, 3496-3501.
Japanese Kokai JP-A2 59/225189.
Japanese Kokai JP-A2 60/084,288.
Arai, T,; Kubo, A. In *The Alkaloids, Chemistry and Pharmacology*; Brossi, A. Ed.;
Academic: New York, 1983, Vol 21; pp 56-110.
Remers, W. A.: In *The Chemistry of Antitumor Antibiotics*; Vol. 2; Wiley; New York, 1988, pp 93-118.
Gulavita N. K.; Scheuer, P. J.: Desilva, E. D. Abst. Indo-United States Symp. on Bioactive
Compounds from Marine Organisms, Goa, India, Feb. 23-27, 1989, p 28.
Arai, T; Takahashi, K; Kubo, A. *J. Antibiot*, 1977, 30, 1015-1018.
Arai. T.; Takahashi, K.; Nakahara, S.; Kubo, A. *Experientia* 1980, 36, 1025-1028.
Mikami, Y.; Takahashi, K; Yazawa, K.; Hour-Young, C.; Arai, T.; Saito, N.; Kubo, A. *J.*
Antibiot. 1988, 41, 734-740.
Arai, T.; Takahashi, K.; Ishiguro, K.; Yazawa, K. *J. Antibiot.* 1980, 33, 951-960.

Yazawa, K.; Takahashi, K.; Mikami, Y.; Arai, T.; Saito, N.; Kubo, A. *J. Antibiot.* 1986, 39, 1639-1650.

Arai, T.; Yazawa, K.; Takahashi, K.; Maeda, A.; Mikami, Y. *Antimicrob. Agent Chemother.* 1985, 28, 5-11.

Takahashi, K.; Yazawa, K.; Kishi, K.; Mikami, Y.; Arai, T.; Kubo, A. *J. Antibiot.* 1982, 35, 196-201.

Yazawa, K.; Asaoka, T.; Takahashi, K.; Mikami, Y.; Arai, T. *J. Antibiot.* 1982, 35, 915-917.

Frincke, J. M.; Faulkner, D. J. *J. Am. Chem. Soc.* 1982, 104, 265-269.

He, H.-Y.; Faulkner, D. J. *J. Org. Chem.* 1989, 54, 5822-5824.

Kubo, A.; Saito, N.; Kitahara, Y.; Takahashi, K.; Tazawa, K.; Arai, T. *Chem Pharm. Bull.* 1987, 35, 440-442.

Trowitzsch-Kienast, W.; Irschik, H.; Reichenback, H.; Wray, V.; Höfle, G. *Liebigs Ann. Chem.* 1988, 475-481.

Ikeda, Y.; Idemoto, H.; Hirayama, F.; Yamamoto, K.; Iwao, K.; Asano, T.; Munakata, T. *J. Antibiot.* 1983, 36, 1279-1283.

Asaoka, T.; Yazawa, K.; Mikami, Y. Arai, T.; Takahashi, K. *J Antibiot.* 1982, 35, 1708-1710.

Lown, J. W.; Hanstock, C. C.; Joshua, A. V.; Arai, T; Takahashi, K. *J. Antibiot.* 1983, 36, 1184-1194.

Munakata et al. U.S. Pat. No. 4,400,752, 1984.

Y. Ikeda et al. The Journal of Antibiotics. VOL XXXVI, No. 10, 1284, 1983.

R. Cooper, S. Unger. The Journal of Antibiotics. VOL XXXVIII, No. 1, 1985.

Corey et al. U.S. Pat. No. 5,721,362, 1998.

Corey et al. J. Am. Chem. Soc. vol 118 pp 9202-92034, 1996.

Proc. Natl. Acad. Sci. USA. Vol. 96, pp 3496-3501, 1999.

The invention claimed is:

1. A compound of the formula:

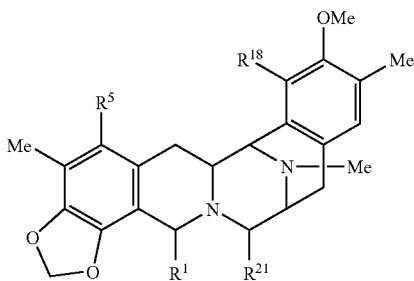

wherein:
  $R^1$ is selected from the group consisting of —$CH_2$—$NHR^a$ and —$CH_2$—$OR^a$, where $R^a$ is selected from the group consisting of alkyl-CO—; haloalkyl-CO—; haloalkyl-O—CO—; arylalkenyl-CO—; heteroaryl-CO—; alkenyl-CO—; and amino acid acyl;
  $R^5$ is —OR", where R" is selected from the group consisting of H and $C_1$-$C_4$ alkyl-CO—;
  $R^{18}$ is —OH; and
  $R^{21}$ is —CN;
or a pharmaceutically acceptable salt thereof.

2. A compound as claimed in claim 1, which is of the formula:

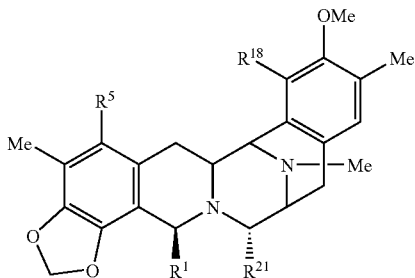

wherein $R^1$, $R^5$, $R^{18}$, and $R^{21}$ are as defined in claim 1.

3. A compound as claimed in claim 1 or 2, wherein $R^1$ is —$CH_2$—$NHR^a$.

4. A compound as claimed in claim 1 or 2, wherein $R^a$ is -aa-$R^b$ where aa is amino acid acyl and $R^b$ is selected from the group consisting of H; alkyl-CO—; haloalkyl-CO—; haloalkyl-O—CO—; arylalkyl-CO—; arylalkenyl-CO—; heteroaryl-CO—; alkenyl-CO—; and amino acid acyl.

5. A compound as claimed in claim 4, wherein said amino acid acyl is further substituted with at least one $R^a$ group.

6. A compound as claimed in claim 4, wherein $R^1$ is —$CH^2$—NH-aa-$R^b$ where aa is an amino acid acyl and $R^b$ is selected from the group consisting of hydrogen; arylalkenyl-CO—; haloalkyl-CO—; alkyl-CO—; arylalkyl-CO—; and amino acid acyl.

7. A compound as claimed in claim 6, wherein $R^1$ is —$CH^2$—NH-aa-$R^b$ where aa is alanine and $R^b$ is selected from the group consisting of hydrogen, $CF_3CO$—, trans(trifluoromethyl)cinnamoyl, cinnamoyl, $C_3F_7CO$—, butyryl, 3-chioroprionoyl, hydrocinnamoyl, phenylacetyl, and acetyl.

8. A compound as claimed in claim 3, wherein $R^1$ is —$CH^2$—$NHR^a$ where $R^a$ is selected from the group consisting of alkyl-CO—; alkenyl-CO—; arylalkenyl-CO—; and heteroaryl-CO.

9. A compound as claimed in claim 8, wherein $R^1$ is —$CH^2$—$NHR^a$ where $R^a$ is selected from the group consisting of acetyl, isovaleryl, decanoyl, and cinnamoyl.

10. A compound as claimed in claim 1 or 2, wherein $R^1$ is —$CH_2$—$OR^a$ where $R^a$ is selected from the group consisting of a protected cysteine; alkyl-CO—; and arylalkenyl-CO.

11. A compound as claimed in claim 10, wherein $R^1$ is —$CH^2$—$OR^a$ where $R^a$ is selected from the group consisting of butyryl; trans(trifluoromethyl)cinnamoyl; and cinnamoyl.

12. A compound as claimed in claim 1 or 2 wherein $R^5$ is —$OCOCH_3$.

13. A compound as claimed in claim 12, wherein $R^1$ is —$CH^2$—$NHR^a$ where $R^a$ is selected from the group consisting of acetyl, isovaleryl, decanoyl, cinnamoyl, propionyl, myristoyl, stearoyl, hexanoyl, crotonyl, and chloronicotinoyl.

14. A compound as claimed in claim 12, wherein $R^1$ is —$CH^2$—$OR^a$ where $R^a$ is selected from the group consisting of butyryl; trans(trifluoromethyl)cinnamoyl; and cinnamoyl.

15. A compound as claimed in claim 8, wherein $R^1$ is —$CH^2$—$NHR^a$ where $R^a$ is selected from the group consisting of propionyl, myristoyl, stearoyl, hexanoyl, crotonyl, and chloronicotinoyl.

16. A compound of general structure:

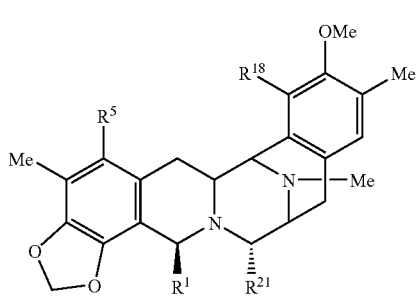
(I)

wherein $R^{21}$ is —CN, and $R^a$, $R^5$, $R^{18}$, and $R^1$, and are each independently selected from the groups defined below:

17. A compound of general structure I:

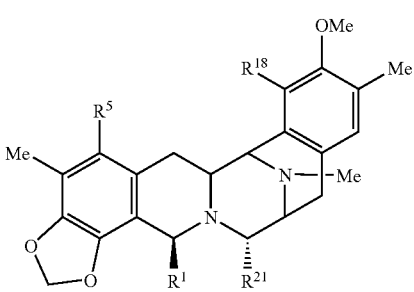

| $R^a$ | $X^5$ | $R^{18}$ | $R^1$ |
|---|---|---|---|
| | OH | OH | |
| | OAc | | $CH_2NHR^a$ |
| | | | $CH_2OR^a$ |
| $COCH_2CH_2CH_3$ | | | |
| $COCH{=}CHPh$ | | | |
| $COCH{=}CHArCF_3$ | | | |
| $COCH(CH_3)NHCOCH_2CH_2Ph$ | | | |
| $CO\text{-}(S)\text{-}CH(CH_3)NHCOCF_3$ | | | |
| $CO\text{-}(R)\text{-}CH(CH_3)NHCOCF_3$ | | | |
| $CO\text{-}(S)\text{-}CH(NHCbz)CH(CH_3)_2$ | | | |
| CSNHPh | | | |
| 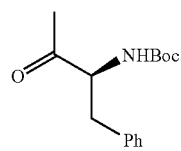 | | | |
| 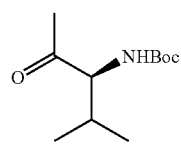 | | | |
| 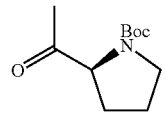 | | | |
| 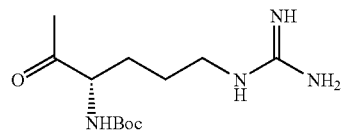 | | | |
| 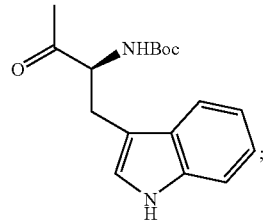 ; | | | | or a pharmaceutically acceptable salt thereof.

wherein $R^b$, $R^5$, $R^1$, $R^{18}$, and $R^{21}$ are each independently selected from the groups defined below:
$R^1$ is —$CH_2$—NH—CO—$CHCH_3$—$NHR^b$
| $R^b$ | $R^5$ | $R^{18}$ | $R^{21}$ |
|---|---|---|---|
| H | OH | OH | CN |
|  | OAc |  |  |
| $COCH_2CH_2CH_3$ |  |  |  |
| $COCH_2Ph$ |  |  |  |
| $COCH_2CH_2Ph$ |  |  |  |
| COCH=CHPh |  |  |  |
| ![structure with CF3] |  |  |  |
| Boc |  |  |  |
| CSNHPh; |  |  |  |
or a pharmaceutically acceptable salt thereof.
18. A compound selected from the following formulae:
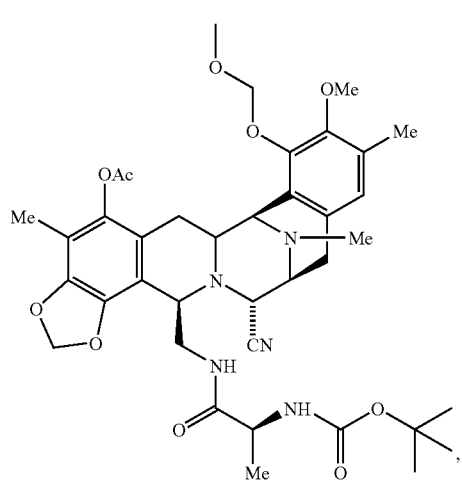
42
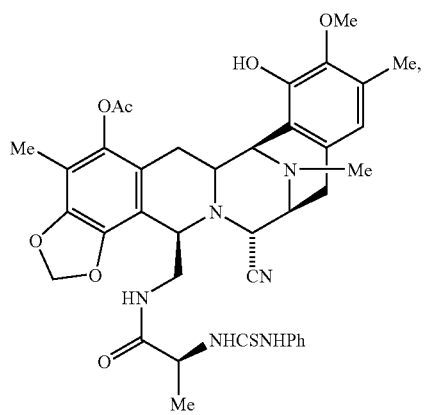
44
-continued
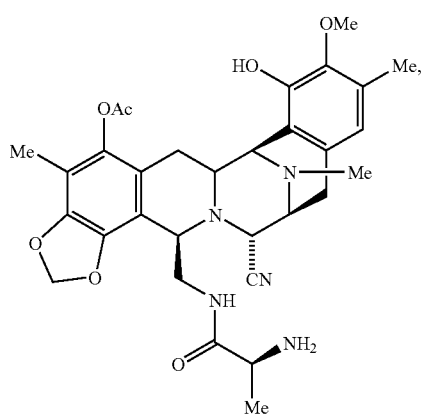
43
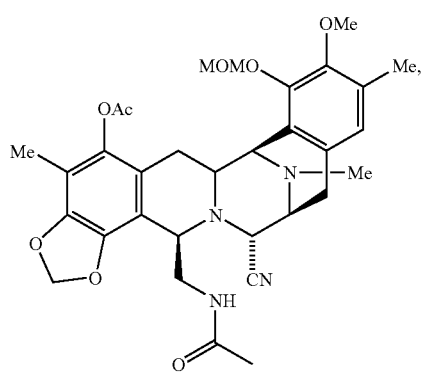
46

47
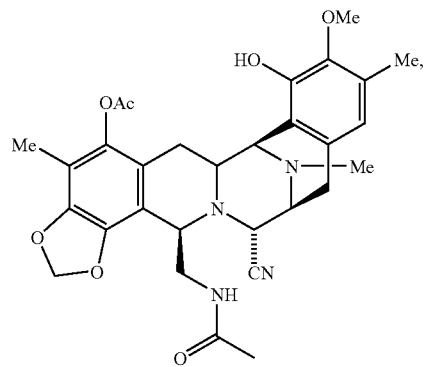
48
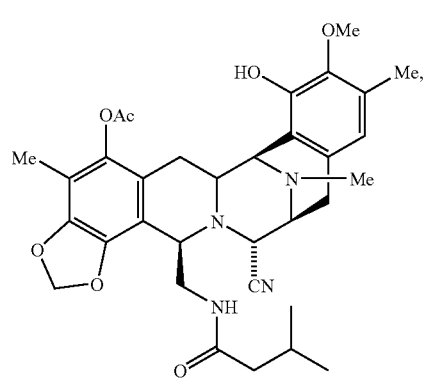
49
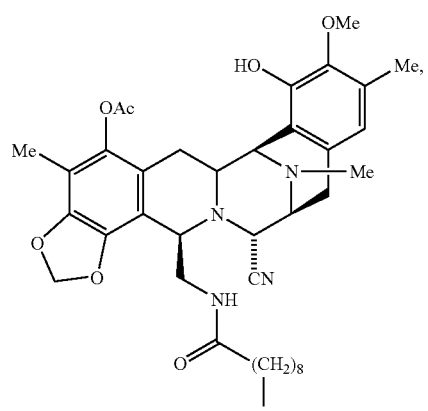
50
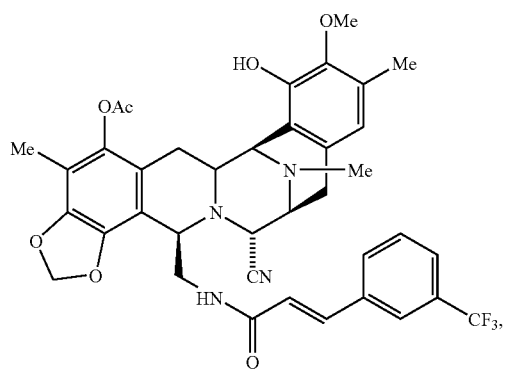
53
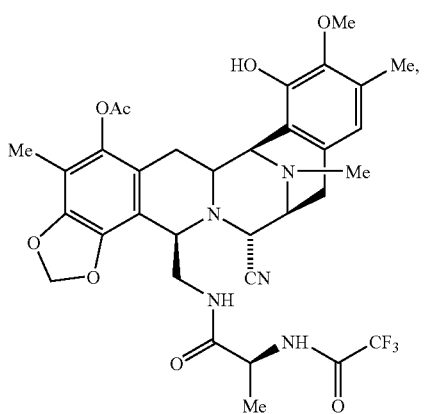
54
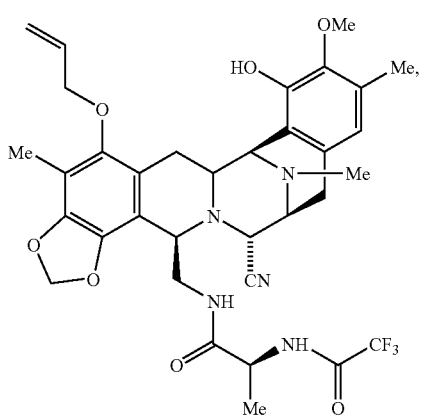
55
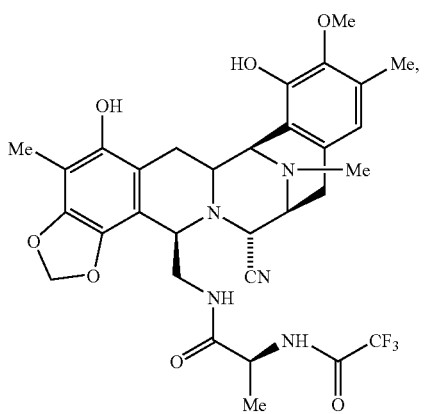

56
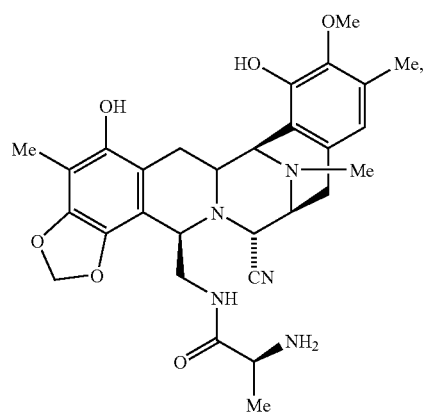
57
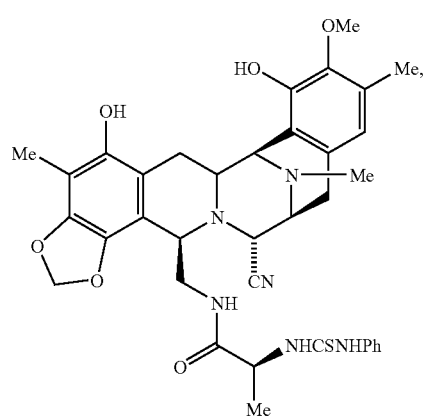
58
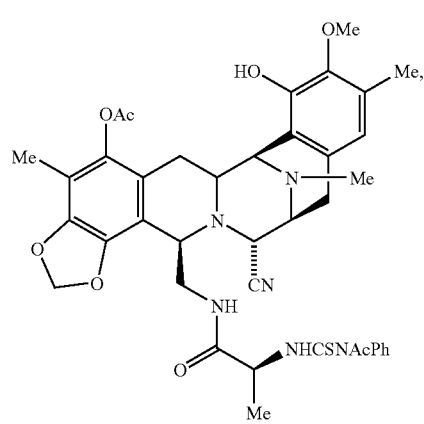
60
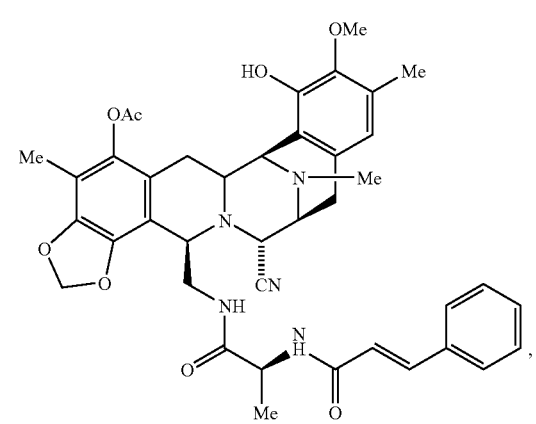
61
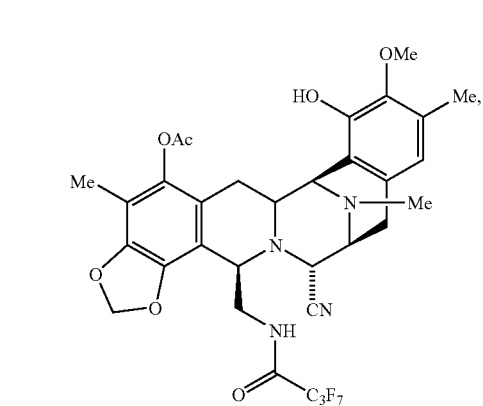
62
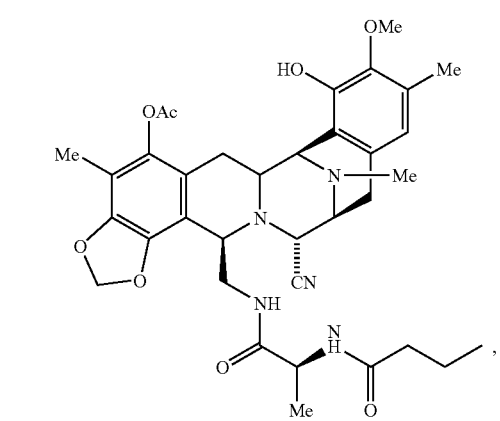

-continued
63
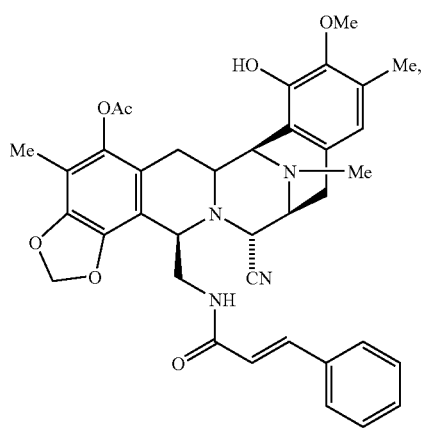
64
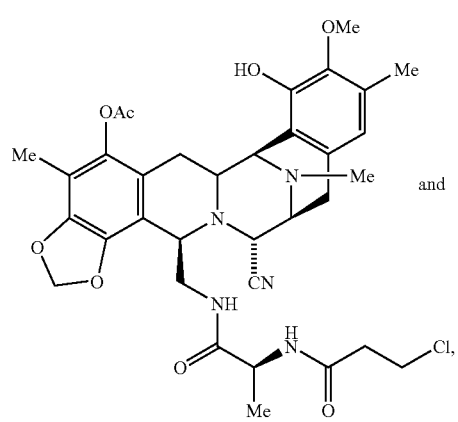
65
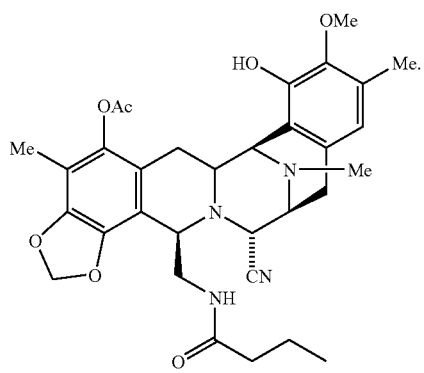
or a pharmaceutically acceptable salt thereof.
19. The compound of claim 2, wherein the compound is of the formula:
50
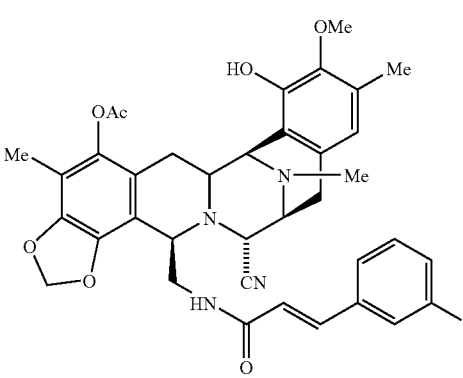
or a pharmaceutically acceptable salt thereof.
20. The compound of claim 2, wherein the compound is of the formula:
112
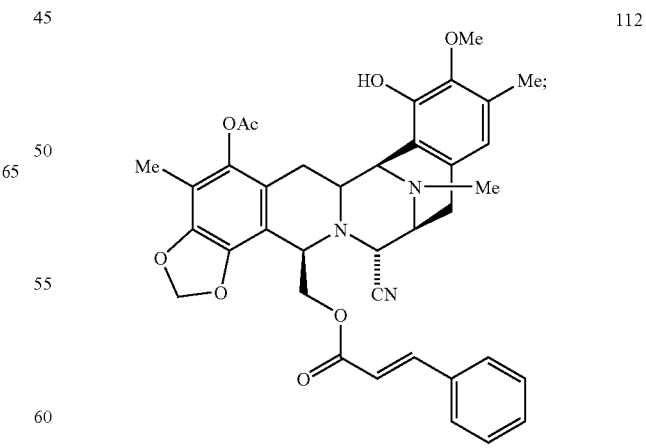
or a pharmaceutically acceptable salt thereof.

21. A pharmaceutical composition comprising a compound of the formula:

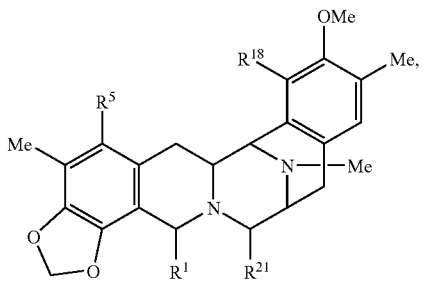

wherein:
R$^1$ is selected from the group consisting of —CH$_2$—NHR$^a$ and —CH$_2$—OR$^a$, where R$^a$ is selected from the group consisting of alkyl-CO—; haloalkyl-CO—; haloalkyl-O—CO—; arylalkenyl-CO—; heteroaryl-CO—; alkenyl-CO—; and amino acid acyl;
R$^5$ is —OR", where R" is selected from the group consisting of H and C$_1$-C$_4$ alkyl-CO—;
R$^{18}$ is —OH; and
R$^{21}$ is —CN;
or a pharmaceutically acceptable salt thereof;
together with a pharmaceutical acceptable carrier.

22. A composition as claimed in claim 21, wherein said compound is of the formula:

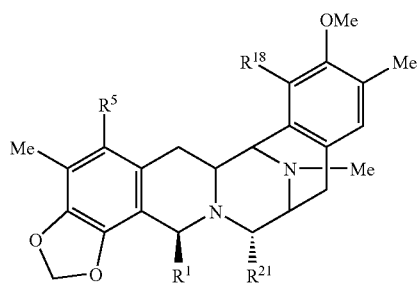

wherein R$^1$, R$^5$, R$^{18}$, and R$^{21}$ are as defined in claim 21.

23. A method of treating a mammal affected by lung cancer, colon cancer, kidney cancer, prostate cancer, melanoma or leukemia which comprises administering to the affected mammal a therapeutically effective amount of a compound of the formula:

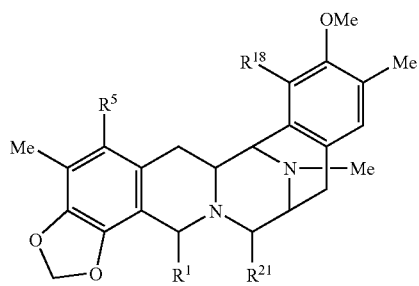

wherein:
R$^1$ is selected from the group consisting of —CH$_2$—NHR$^a$ and —CH$_2$—OR$^a$, where R$^a$ is selected from the group consisting of alkyl-CO—; haloalkyl-CO—; haloalkyl-O—CO—; arylalkenyl-CO—; heteroaryl-CO—; alkenyl-CO—; and amino acid acyl;
R$^5$ is —OR", where R" is selected from the group consisting of H and C$_1$-C$_4$ alkyl-CO—;
R$^{18}$ —OH; and
R$^{21}$ is —CN;
or a pharmaceutically acceptable salt thereof.

24. The method of claim 23, wherein said mammal is a human.

25. The method of claim 24, wherein said compound is administered by intravenous infusion.

26. The method as claimed in claim 23, wherein said compound is of the formula:

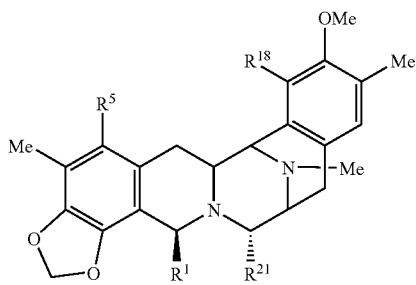

wherein R$^1$, R$^5$, R$^{18}$, and R$^{21}$ are as defined in claim 23.

27. A compound having the formula

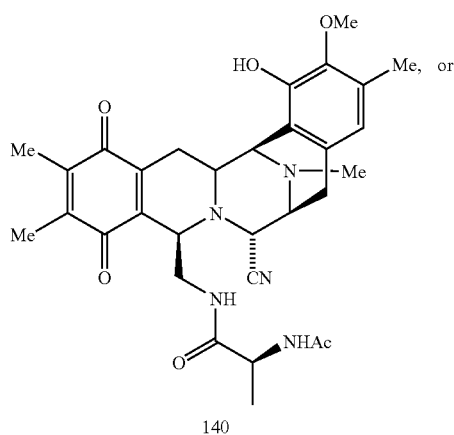

140

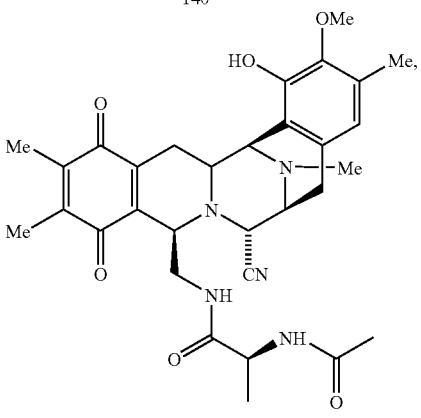

141 or a pharmaceutically acceptable salt thereof.

28. A compound as defined in claim 1, which is of the formula:

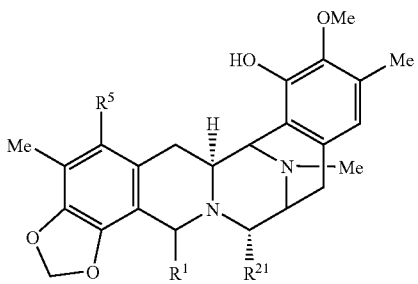

wherein $R^1$, $R^5$, and $R^{21}$ are as defined in claim 1.

29. A compound as claimed in claim 28, wherein $R^1$ is —CH$_2$—NHR$^a$.

30. A compound as claimed in claim 28, wherein $R^a$ is -aa-R$^b$ where aa is amino acid acyl and R$^b$ is selected from the group consisting of H; alkyl-CO—; haloalkyl-CO—; haloalkyl-O—CO—; arylalkyl-CO—; arylalkenyl-CO—; heteroaryl-CO—; alkenyl-CO—; amino acid acyl.

31. A compound as claimed in claim 30, wherein said amino acid acyl is further substituted with at least one R$^a$ group.

32. A compound as claimed in claim 30, wherein $R^1$ is —CH$^2$—NH-aa-R$^b$ where aa is an amino acid acyl and R$^b$ is selected from the group consisting of hydrogen; arylalkenyl-CO—; haloalkyl-CO—; alkyl-CO—; arylalkyl-CO—; and amino acid acyl.

33. A compound as claimed in claim 32, wherein $R^1$ is —CH$^2$—NH-aa-R$^b$ where aa is alanine and R$^b$ is selected from the group consisting of hydrogen, CF$_3$CO—, trans(trifluoromethyl)cinnamoyl, cinnamoyl, C$_3$F$_7$CO—, butyryl, 3-chloropropionoyl, hydrocinnamoyl, phenylacetyl, and acetyl.

34. A compound as claimed in claim 29, wherein $R^1$ is —CH$^2$—NHR$^a$ where R$^a$ is selected from the group consisting of alkyl-CO—; alkenyl-CO—; arylalkenyl-CO—; and heteroaryl-CO—.

35. A compound as claimed in claim 34, wherein $R^1$ is —CH$^2$—NHR$^a$ where R$^a$ is selected from the group consisting of acetyl, isovaleryl, decanoyl, and cinnamoyl.

36. A compound as claimed in claim 28, wherein $R^1$ is —CH$^2$—OR$^a$ where R$^a$ is selected from the group consisting of a protected cysteine; alkyl-CO— and arylalkenyl-CO—.

37. A compound as claimed in claim 36, wherein $R^1$ is —CH$^2$—OR$^a$ where R$^a$ is selected from the group consisting of butyryl; trans(trifluoromethyl)cinnamoyl and cinnamoyl.

38. A compound as claimed in claim 28, wherein $R^5$ is —OCOCH$_3$.

39. A compound as claimed in claim 38, wherein $R^1$ is —CH$^2$—NHR$^a$ where R$^a$ is selected from the group consisting of acetyl, isovaleryl, decanoyl, cinnamoyl, propionyl, myristoyl, stearoyl, hexanoyl, crotonyl, and chloronicotinoyl.

40. A compound as claimed in claim 38, wherein $R^1$ is —CH$^2$—OR$^a$ where R$^a$ is selected from the group consisting of butyryl; trans(trifluoromethyl)cinnamoyl; and cinnamoyl.

41. A compound as claimed in claim 34, wherein $R^1$ is —CH$^2$—NHR$^a$ where R$^a$ is selected from the group consisting of propionyl, myristoyl, stearoyl, hexanoyl, crotonyl, and chloronicotinoyl.

42. A compound of general structure (II):

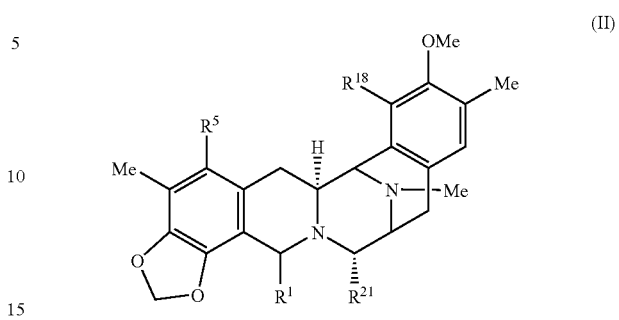

wherein $R^a$, $R^5$, $R^{18}$, $R^1$, and $R^{21}$ are each independently selected from the groups defined below:

| R$^a$ | R$^5$ | R$^{18}$ | R$^1$ | R$^{21}$ |
|---|---|---|---|---|
| COCH$_2$CH$_2$CH$_3$ | | OH | OH | CH$_2$NHR$^a$ | CN |
| | | | OAc | CH$_2$OR$^a$ | |
| COCH=CHPh | | | | | |

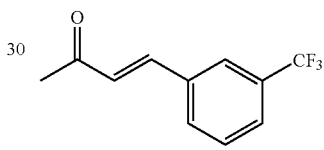

COCH(CH$_3$)NHCOCH$_2$CH$_2$Ph
CO—(S)—CH(CH$_3$)NHCOCF$_3$
CO—(R)—CH(CH$_3$)NHCOCF$_3$
CO—(S)—CH(NHCbz)CH(CH$_3$)$_2$
CSNHPh

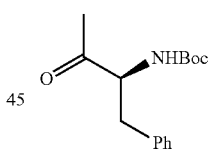

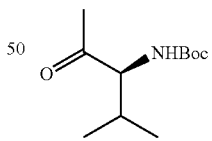

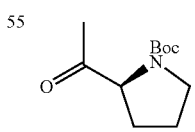

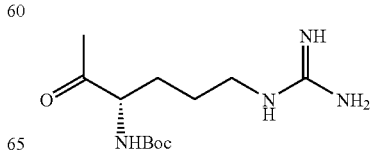

-continued

| $R^a$ | $R^5$ | $R^{18}$ | $R^1$ | $R^{21}$ |
|---|---|---|---|---|
| 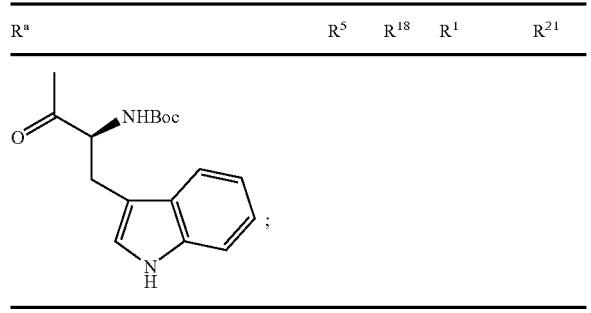 | | | | | or a pharmaceutically acceptable salt thereof.

43. A compound of general structure II:

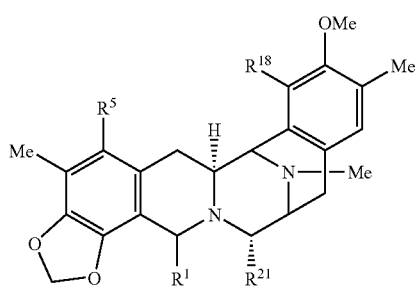

(II)

wherein $R^b$, $R^5$, $R^1$, $R^{18}$ and $R^{21}$ are each independently selected from the groups defined below:

$R^1$ is —CH$_2$—NH—CO—CHCH$_3$—NHR$^b$

| $R^b$ | $R^5$ | $R^{18}$ | $R^{21}$ |
|---|---|---|---|
| H | OH | OH | CN |
| COCH$_2$CH$_2$CH$_3$ | OAc | | |
| COCH$_2$Ph | | | |
| COCH$_2$CH$_2$Ph | | | |
| COCH=CHPh | | | |

-continued

| $R^b$ | $R^5$ | $R^{18}$ | $R^{21}$ |
|---|---|---|---|
| 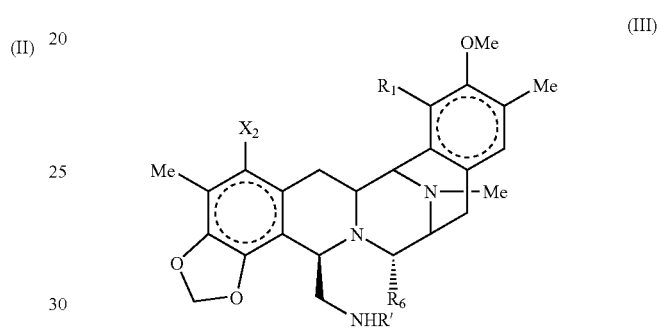 | | | |
| Boc | | | |
| CSNHPh; | | | | or a pharmaceutically acceptable salt thereof.

44. A compound of a formula selected from the following general structures (III) and (IV):

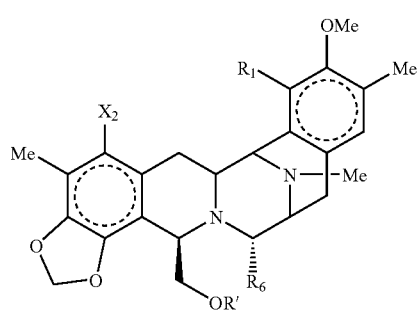

(III)

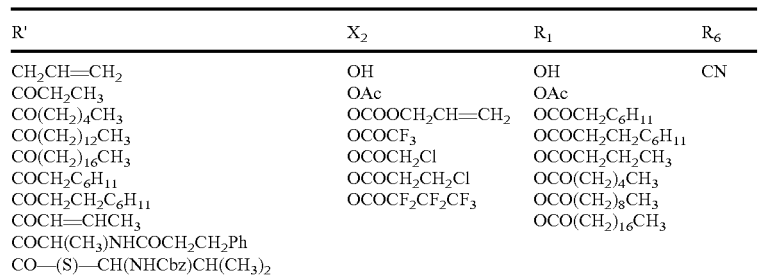

(IV)

wherein R', X$_2$, R$_1$, and R$_6$ are each independently selected from the groups defined below:

| R' | X$_2$ | R$_1$ | R$_6$ |
|---|---|---|---|
| CH$_2$CH=CH$_2$ | OH | OH | CN |
| COCH$_2$CH$_3$ | OAc | OAc | |
| CO(CH$_2$)$_4$CH$_3$ | OCOOCH$_2$CH=CH$_2$ | OCOCH$_2$C$_6$H$_{11}$ | |
| CO(CH$_2$)$_{12}$CH$_3$ | OCOCF$_3$ | OCOCH$_2$CH$_2$C$_6$H$_{11}$ | |
| CO(CH$_2$)$_{16}$CH$_3$ | OCOCH$_2$Cl | OCOCH$_2$CH$_2$CH$_3$ | |
| COCH$_2$C$_6$H$_{11}$ | OCOCH$_2$CH$_2$Cl | OCO(CH$_2$)$_4$CH$_3$ | |
| COCH$_2$CH$_2$C$_6$H$_{11}$ | OCOCF$_2$CF$_2$CF$_3$ | OCO(CH$_2$)$_8$CH$_3$ | |
| COCH=CHCH$_3$ | | OCO(CH$_2$)$_{16}$CH$_3$ | |
| COCH(CH$_3$)NHCOCH$_2$CH$_2$Ph | | | |
| CO—(S)—CH(NHCbz)CH(CH$_3$)$_2$ | | | |
| 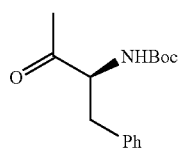 | | | |

| R' | X₂ | R₁ | R₆ |
|---|---|---|---|
-continued
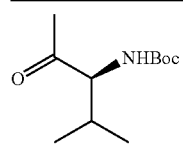
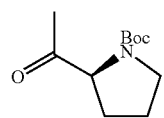
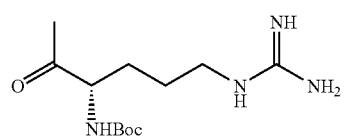
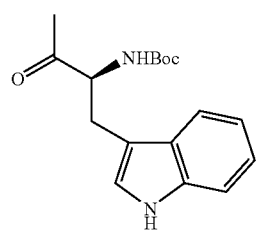
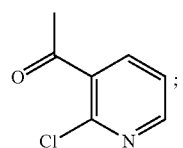
or a pharmaceutically acceptable salt thereof.

45. A compound of general structure V:

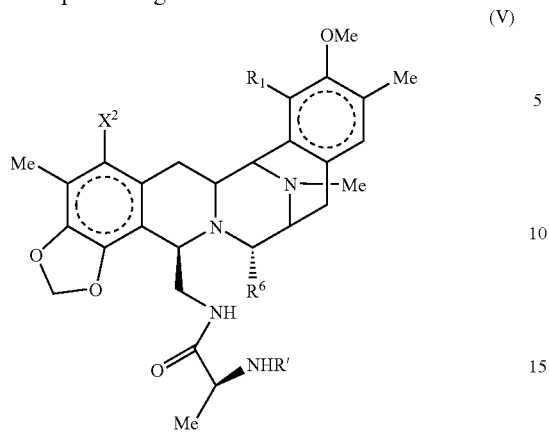

wherein $X_2$, $R_1$, $R_6$, and R are each independently selected from the groups defined below:

| R' | $X_2$ | $R_1$ | $R_6$ |
|---|---|---|---|
| | OH | OH | CN |
| $CH_2CH=CH_2$ | OAc | OAc | |
| $COCH_2CH_3$ | | | |
| | $OCOOCH_2CH=CH_2$ | $OCOCH_2C_6H_{11}$ | |
| $CO(CH_2)_4CH_3$ | $OCOCF_3$ | $OCOCH_2CH_2C_6H_{11}$ | |
| $CO(CH_2)_{12}CH_3$ | $OCOCH_2Cl$ | $OCOCH_2CH_2CH_3$ | |
| $CO(CH_2)_{16}CH_3$ | $OCOCH_2CH_2Cl$ | $OCO(CH_2)_4CH_3$ | |
| $COCH_2CH_2C_6H_{11}$ | $OCOCF_2CF_2CF_3$ | $OCO(CH_2)_8CH_3$ | |
| $COCH_2CH_2C_6H_{11}$ | | $OCO(CH_2)_{16}CH_3$ | |
| $COCH_2Ph$ | | | |
| $COCH_2CH_2Ph$ | | | |
| $COCH=CHCH_3$ | | | |
| $COCH(CH_3)NHCOCH_2CH_2Ph$ | | | |
| $CO-(S)-CH(CH_3)NHCOCF_3$ | | | |
| $CO-(R)-CH(CH_3)NHCOCF_3$ | | | |
| $CO-(S)-CH(NHCbz)CH(CH_3)_2$ | | | |
| Boc | | | |

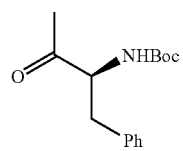

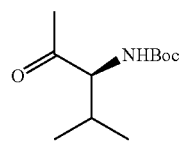

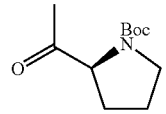

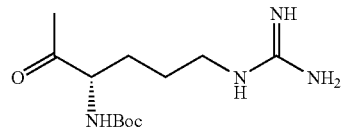

-continued
| R' | X₂ | R₁ | R₆ |
|---|---|---|---|
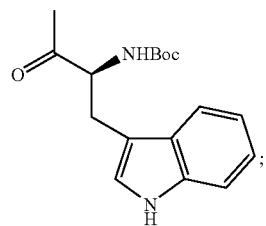
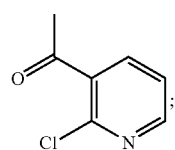
or a pharmaceutically acceptable salt thereof.
46. A compound selected from the following formulae:
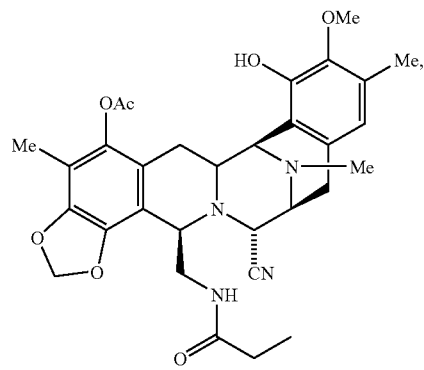
74
-continued
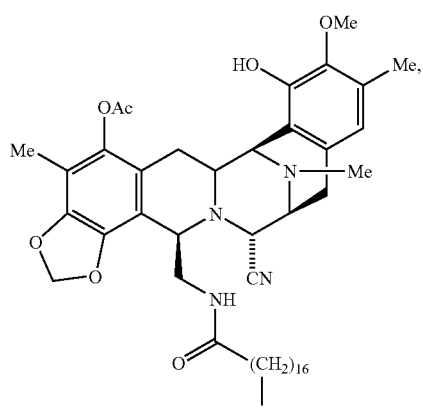
76
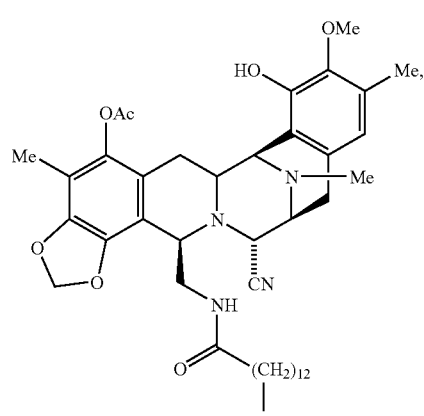
75
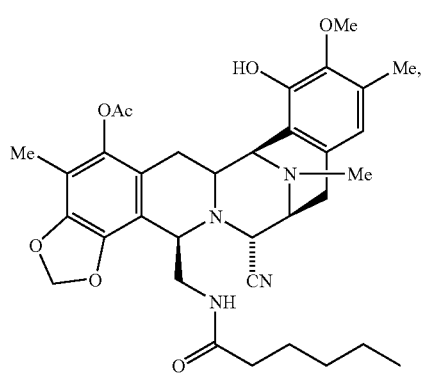
77

-continued
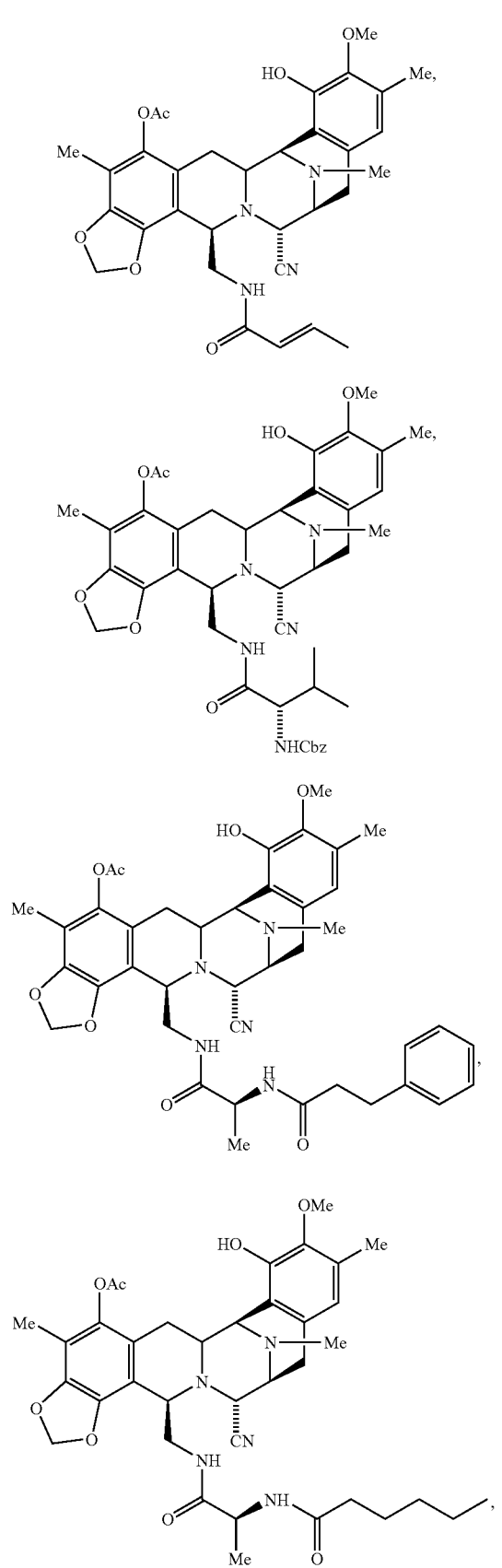
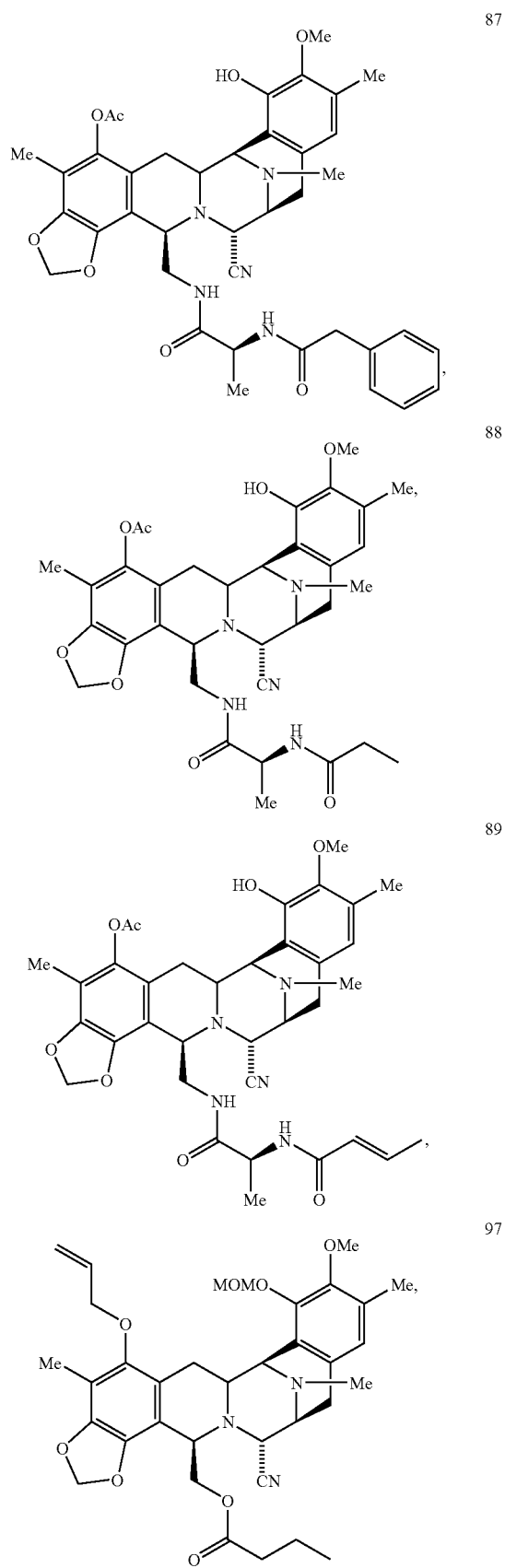

-continued
98
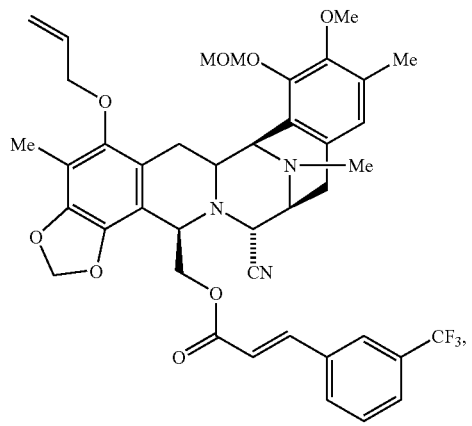
100
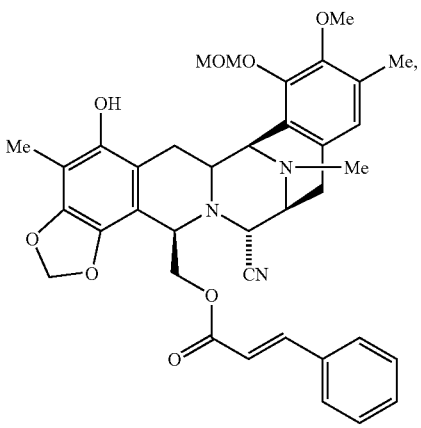
101
102
-continued
104
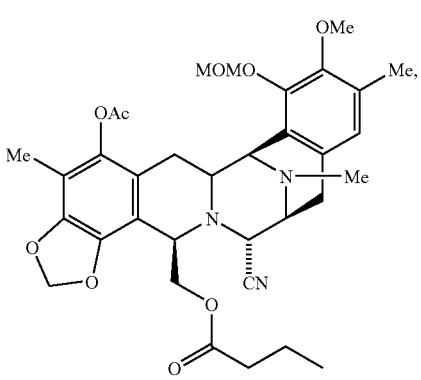
105
106
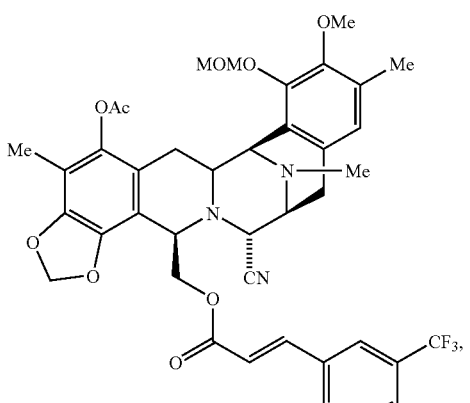
108
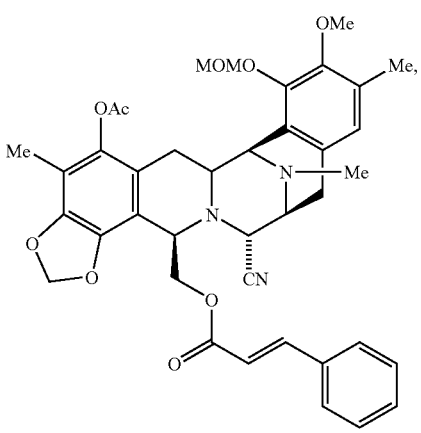

-continued
109
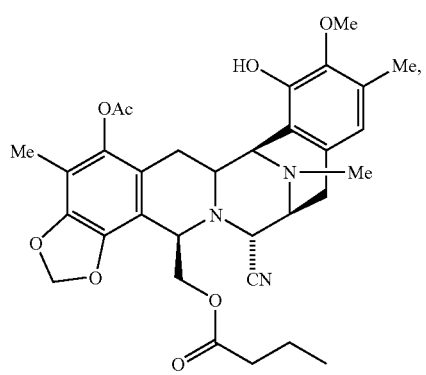
110
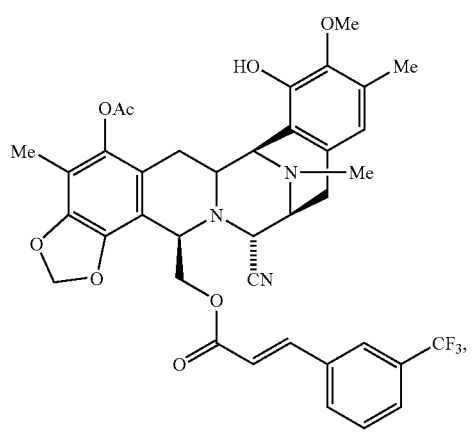
112
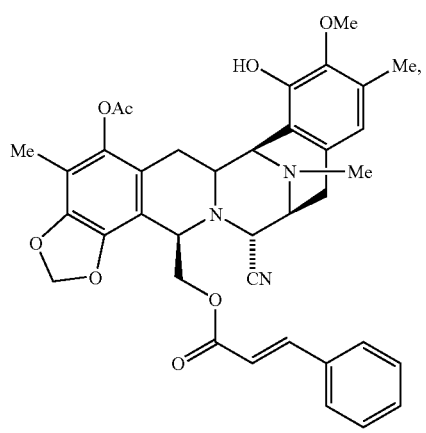
-continued
117
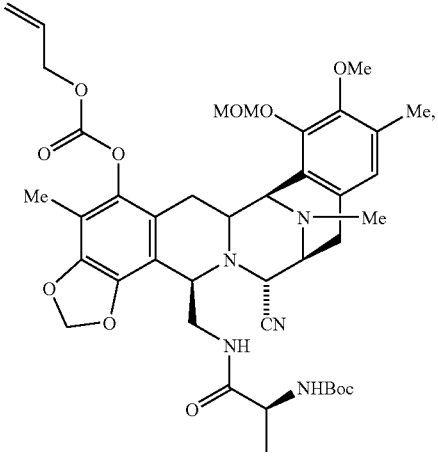
118
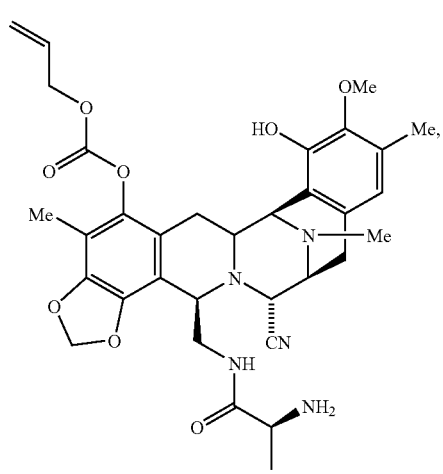
119
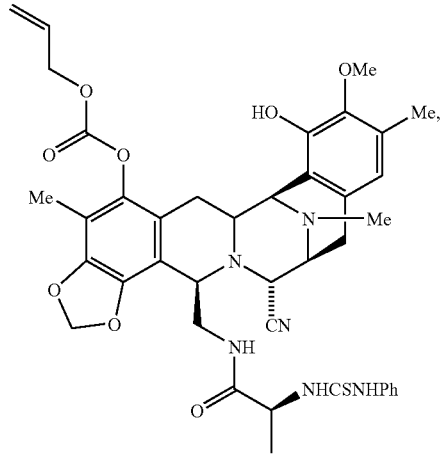

389
-continued
124
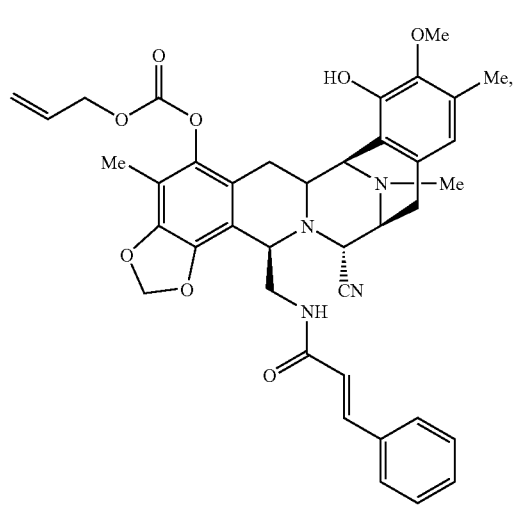
125
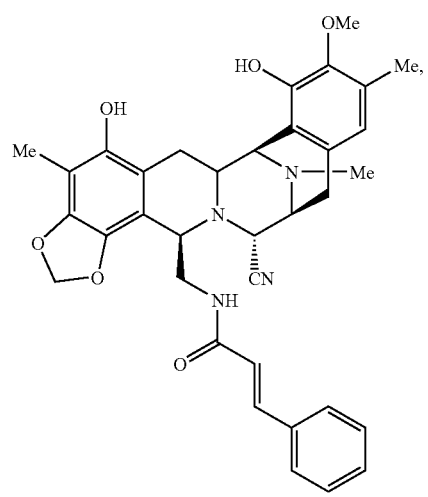
174
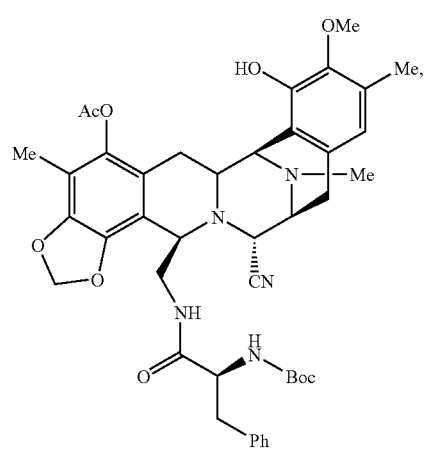
390
-continued
175
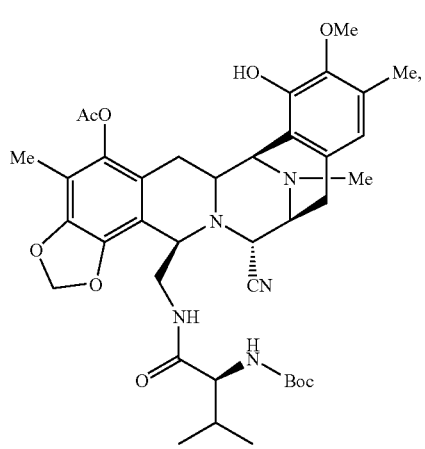
176
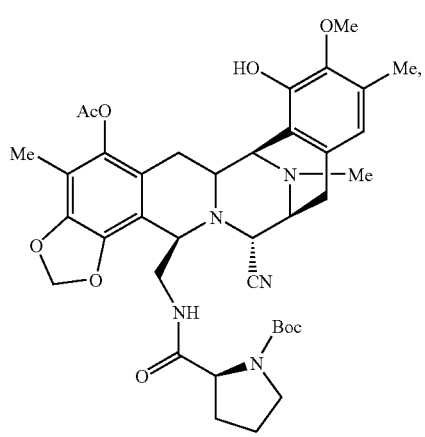
177
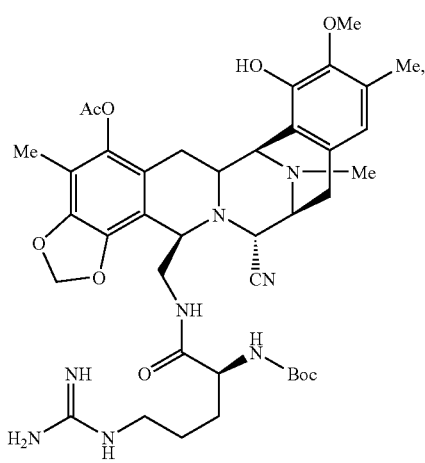

391
-continued
178
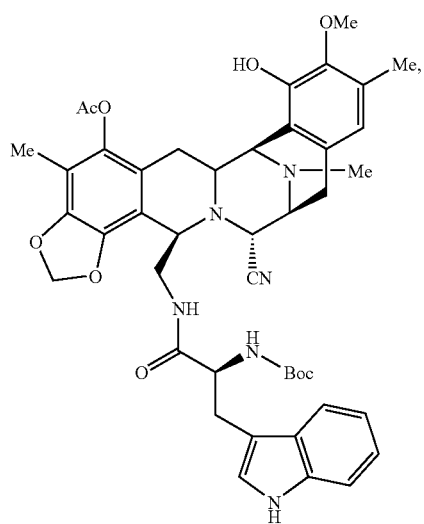
180
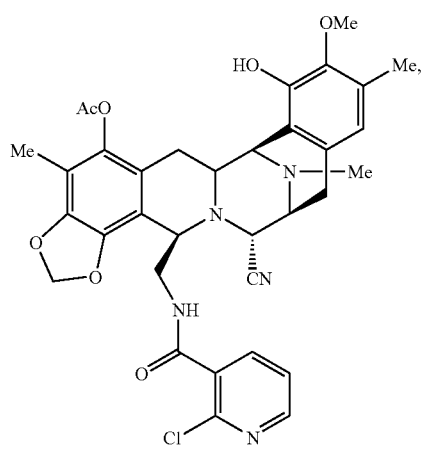
182
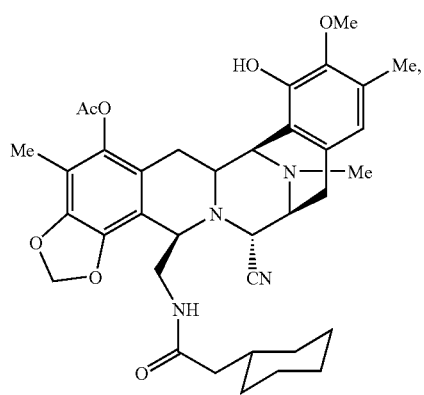
392
-continued
183
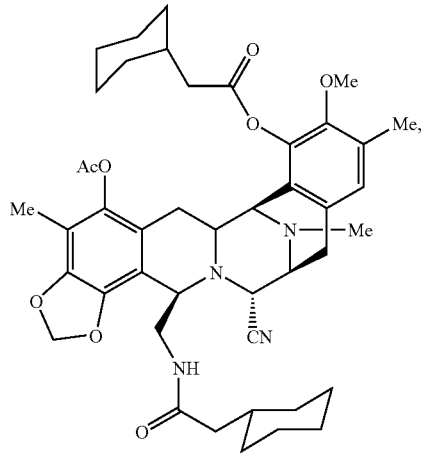
184
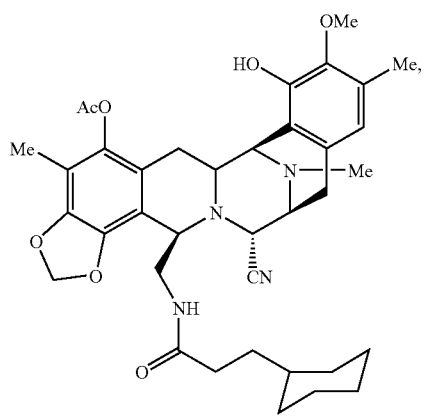
185
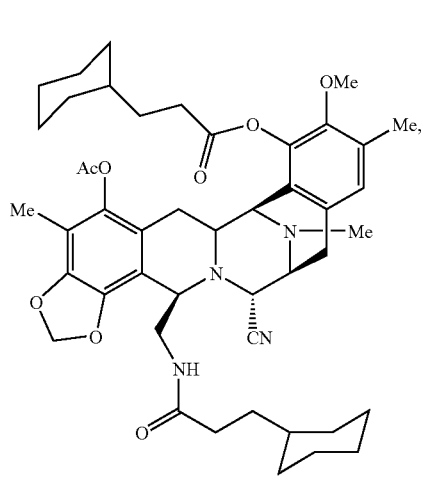

-continued
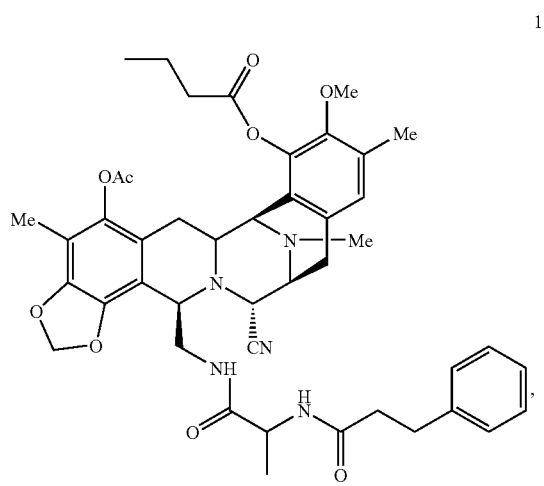
188
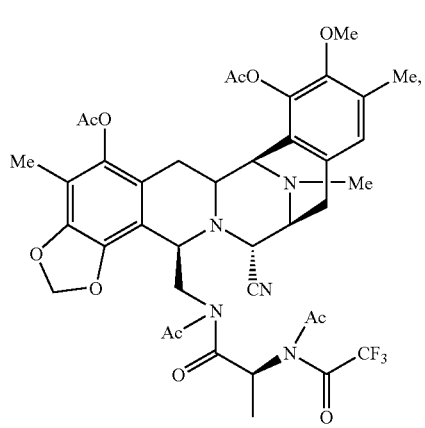
192
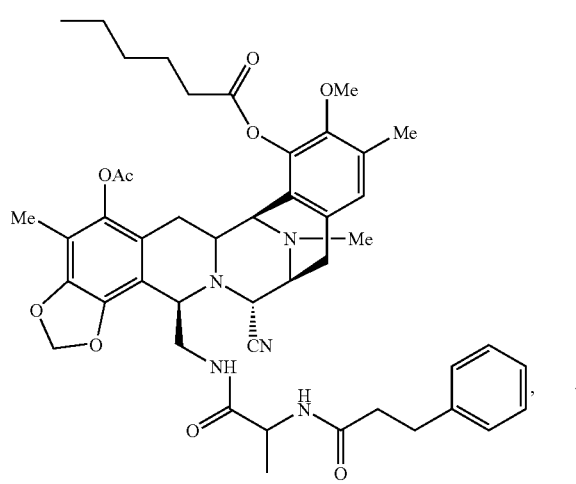
189
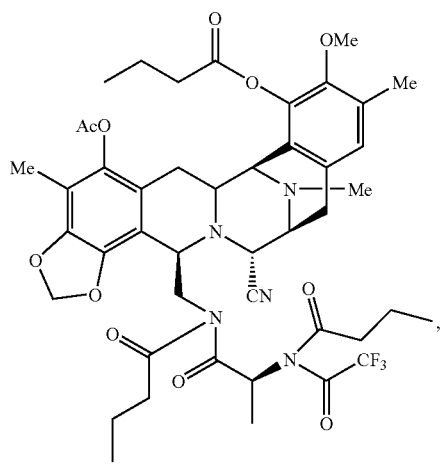
193
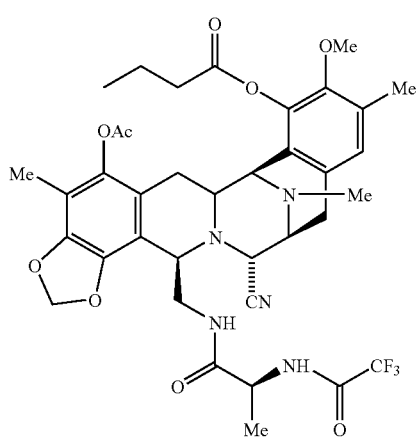
191
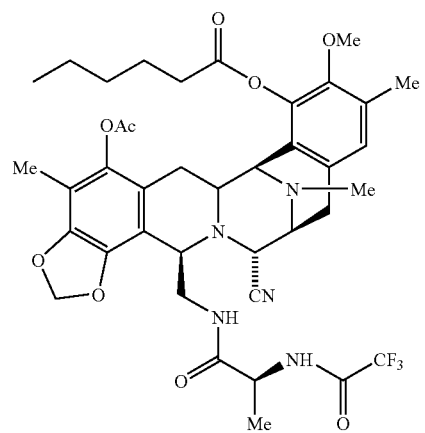
194

195
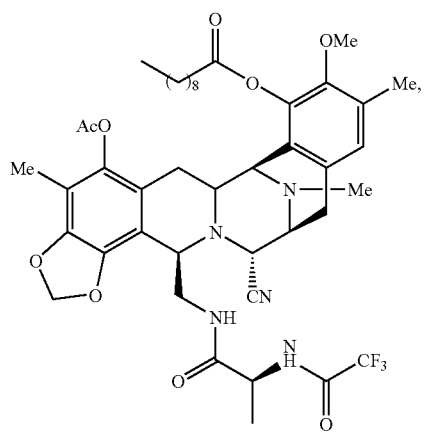
196
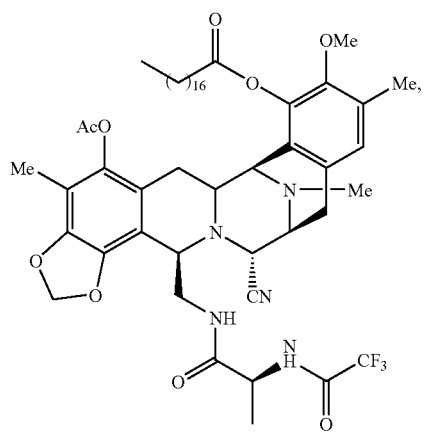
197
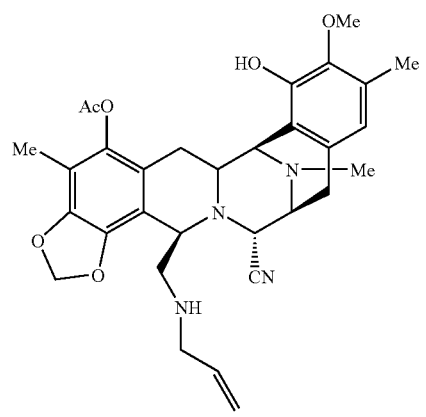
198
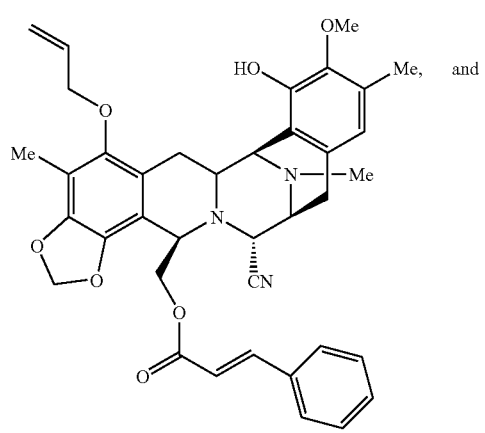
and
202
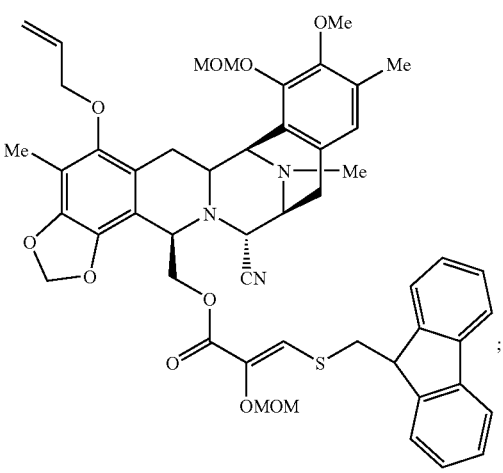
or a pharmaceutically acceptable salt thereof.
47. The compound of claim 46 which is of the formula:
100
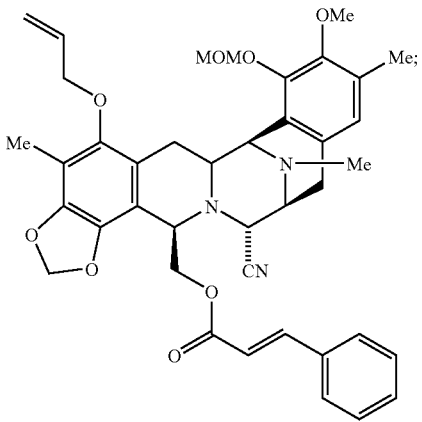
or a pharmaceutically acceptable salt thereof.

48. The compound of claim 46, which is of the formula:

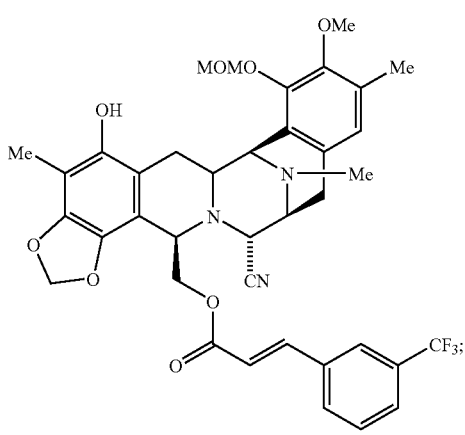

102 or a pharmaceutically acceptable salt thereof.

49. The compound of claim 46, which is of the formula:

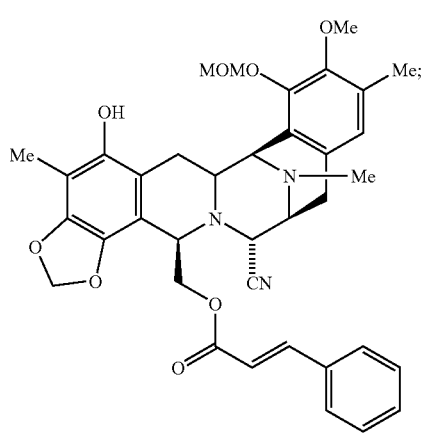

104 or a pharmaceutically acceptable salt thereof.

50. The compound of claim 46, which is of the formula:

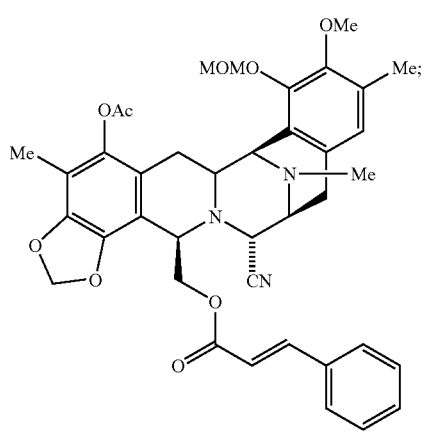

108 or a pharmaceutically acceptable salt thereof.

51. The compound of claim 46, which is of the formula:

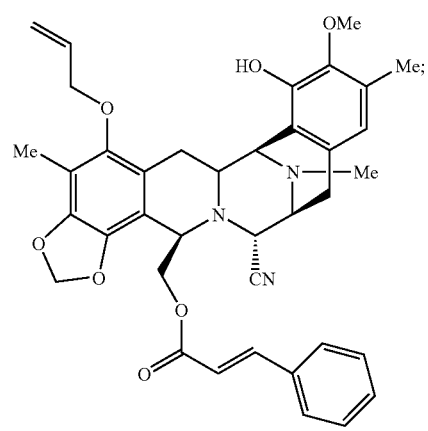

198 or a pharmaceutically acceptable salt thereof.

52. A compound of the formula:

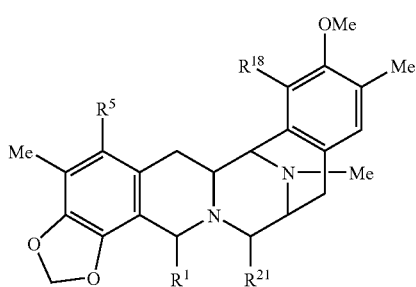

wherein:

$R^1$ is —$CH_2$—$OR^a$,
where $R^a$ is selected from the group consisting of alkyl-CO—; haloalkyl-CO—; cycloalkylalkyl-CO—; haloalkyl-O—CO—; arylalkenyl-CO—; heteroaryl-CO—; alkenyl-CO—; alkenyl; and amino acid acyl;

$R^5$ is —OR", where R" is selected from the group consisting of H; alkyl-CO—; cycloalkyl-CO—; and haloalkyl-CO—;

$R^{18}$ is —OR, where R is selected from the group consisting of H, alkyl-CO—; cycloalkylalkyl-CO—; and $R^{21}$ is —CN;

or a pharmaceutically acceptable salt thereof.

53. A compound according to claim 52, which is of the formula:

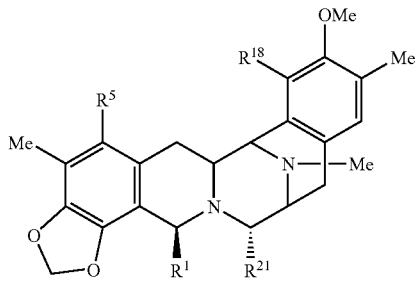

wherein $R^1$, $R^5$, $R^{18}$, and $R^{21}$ are as defined in claim 52.

54. A compound according to claim 52, which is of the formula:

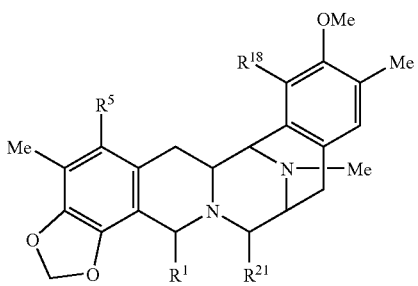

wherein $R^1$, $R^5$, $R^{18}$, and $R^{21}$ are as defined in claim 52.

55. A compound according to claim 53 or 54, wherein $R^1$ is —CH$_2$—OR$^a$ where R$^a$ is selected from the group consisting of a protected cysteine; alkyl-CO—; arylalkenyl-CO—; a cysteine derivative of the formula Prot$^{SH}$-S—CH$_2$—C(=NOProt$^{OH}$)-CO— where Prot$^{SH}$ is a protecting group for thiol and Prot$^{OH}$ is a protecting group hydroxy; and a cysteine derivative of formula Prot$^{SH}$-S—CH=C(—OProt$^{OH}$)-CO—, where Prot$^{SH}$ is a protecting group for thiol and Prot$^{OH}$ is a protecting group for hydroxy.

56. A compound according to claim 55, wherein $R^1$ is —CH$^2$—OR$^a$ where R$^a$ is selected from the group consisting of S—Fm—O-TBDMS-cysteine; butyryl; (trifluoromethyl) cinnamoyl; cinnamoyl; a cysteine derivative of the formula Prot$^{SH}$-S—CH$_2$—C(=NOProt$^{OH}$)-CO—, where Prot$^{SH}$ is Fm and Prot$^{OH}$ is methoxy; and a cysteine derivative of formula Prot$^{SH}$-S—CH$_2$=C(—OProt$^{OH}$)-CO—, where Prot$^{SH}$ is Fm and Prot$^{OH}$ is MOM.

57. A composition as claimed in claim 21, wherein said compound is of the formula:

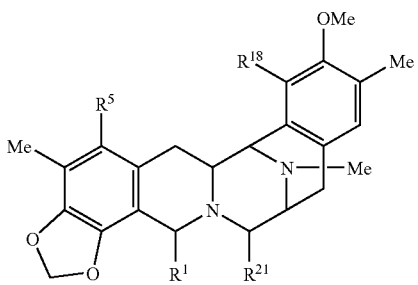

wherein $R^1$, $R^5$, and $R^{21}$ are as defined in claim 21.

58. A pharmaceutical composition comprising a compound of the formula:

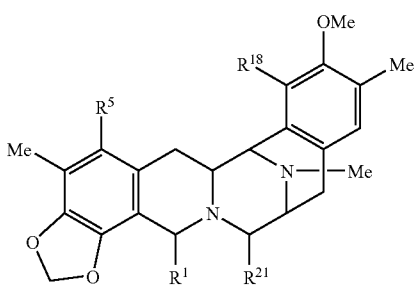

wherein:
$R^1$ is —CH$_2$—OR$^a$,
 where R$^a$ is selected from the group consisting of alkyl-CO—; haloalkyl-CO—; cycloalkylalkyl-CO—; haloalkyl-O—CO—; arylalkenyl-CO—; heteroaryl-CO—; alkenyl-CO—; alkenyl; and amino acid acyl;
$R^5$ is —OR", where R" is selected from the group consisting of H; alkyl-CO—; cycloalkyl-CO—; and haloalkyl-CO—;
$R^{18}$ is —OR, where R is selected from the group consisting of H, alkyl-CO—; cycloalkylalkyl-CO—; and
$R^{21}$ R is —CN;
or a pharmaceutically acceptable salt thereof;
together with a pharmaceutically acceptable carrier.

59. A composition as claimed in claim 58, wherein said compound is of the formula:

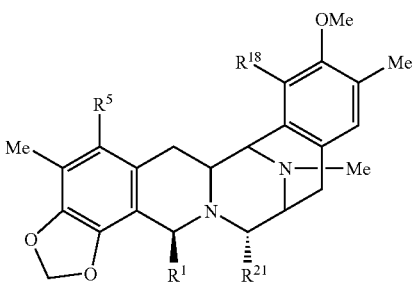

wherein $R^1$, $R^5$, $R^{18}$, and $R^{21}$ are as defined in claim 58.

60. A composition as claimed in claim 58 wherein said compound is of the formula:

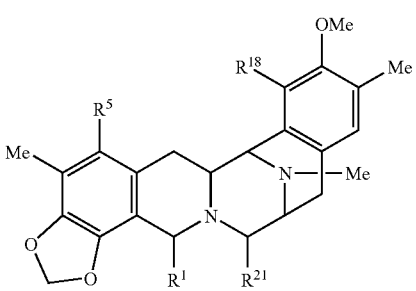

wherein $R^1$, $R^5$, $R^{18}$, and $R^{21}$ are as defined in claim 58.

61. The method as claimed in claim 23, wherein said compound is of the formula:

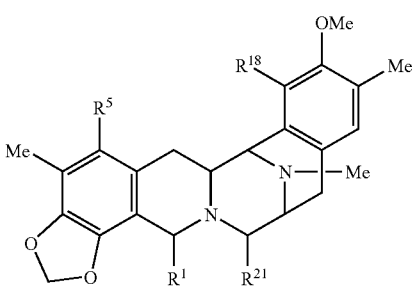

wherein $R^1$, $R^5$, and $R^{21}$ are as defined in claim 23.

62. The method of claim 61, wherein said mammal is a human.

63. The method of claim 62, wherein said compound is administered by intravenous infusion.

64. A method of treating a mammal affected by lung cancer, colon cancer, kidney cancer, prostate cancer, melanoma or leukemia which comprises administering to the affected mammal a therapeutically effective amount of a compound of the formula:

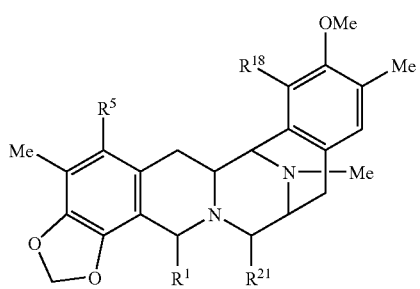

wherein:
$R^1$ is —$CH_2$—$OR^a$,
where $R^a$ is selected from the group consisting of alkyl-CO—; haloalkyl-CO—; cycloalkylalkyl-CO—; haloalkyl-O—CO—; arylalkenyl-CO—; heteroaryl-CO—; alkenyl-CO—; alkenyl; and amino acid acyl;
$R^5$ is —OR", where R" is selected from the group consisting of H; alkyl-CO—; cycloalkyl-CO—; and haloalkyl-CO—;
$R^{18}$ is —OR, where R is selected from the group consisting of H, alkyl-CO—; cycloalkylalkyl-CO—; and
$R^{21}$ is —CN;
or a pharmaceutically acceptable salt thereof.

65. The method as claimed in claim 64, wherein said compound is of the formula:

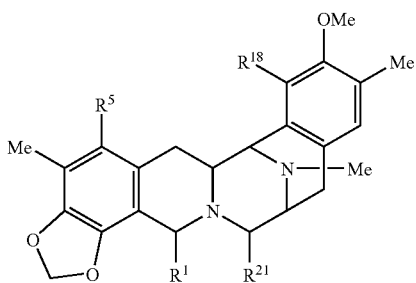

wherein $R^1$, $R^5$, $R^{18}$, and $R^{21}$ are as defined in claim 64.

66. The method as claimed in claim 64, wherein said compound is of the formula:

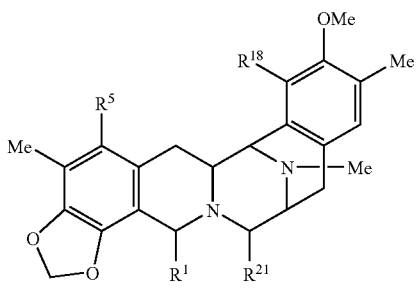

wherein $R^1$, $R^5$, $R^{18}$, and $R^{21}$ are as defined in claim 64.

* * * * *

UNITED STATES PATENT AND TRADEMARK OFFICE
CERTIFICATE OF CORRECTION

PATENT NO.        : 7,410,969 B2
APPLICATION NO.   : 11/045595
DATED             : August 12, 2008
INVENTOR(S)       : Ignacio Manzanares It is certified that error appears in the above-identified patent and that said Letters Patent is hereby corrected as shown below:

Claim 16, Column 361, line 29 (approximately), "COCH=CHArCF$_3$" in the leftmost column of the table should be changed to

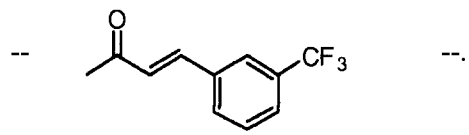

Claim 27, Column 372, lines 32-48 (approximately), the formula reading:

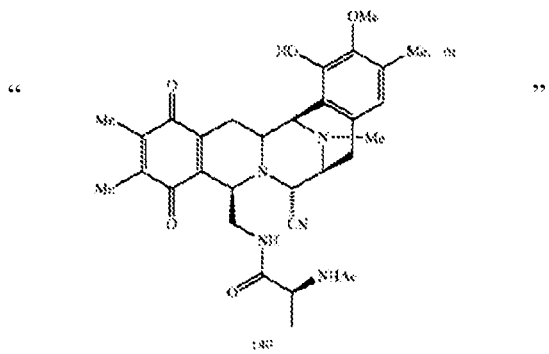

Signed and Sealed this

Nineteenth Day of October, 2010

David J. Kappos
*Director of the United States Patent and Trademark Office*

CERTIFICATE OF CORRECTION (continued)
U.S. Pat. No. 7,410,969 B2 should read:

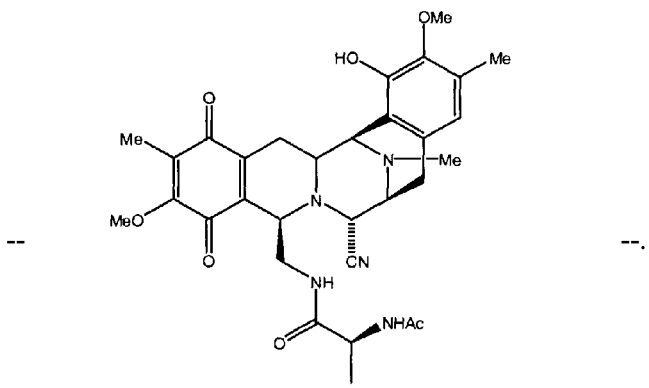

-- 140 --.

Claim 27, Column 372, lines 49-65 (approximately), the formula reading:

" 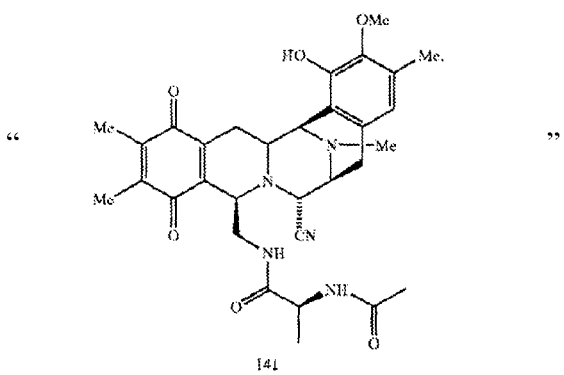 "

141 should read:
-- 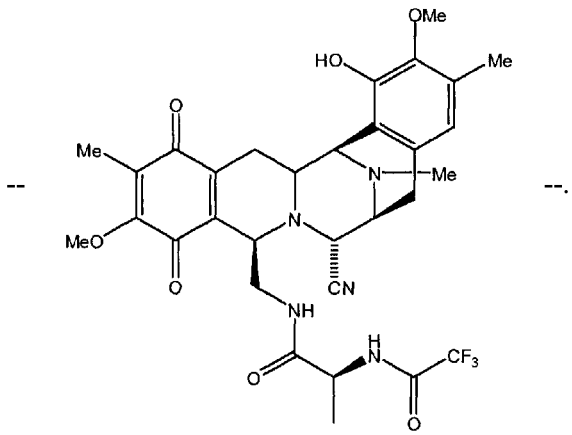 --.
141
Claim 54, Column 399, lines 5-15 (approximately), the formula reading:
" 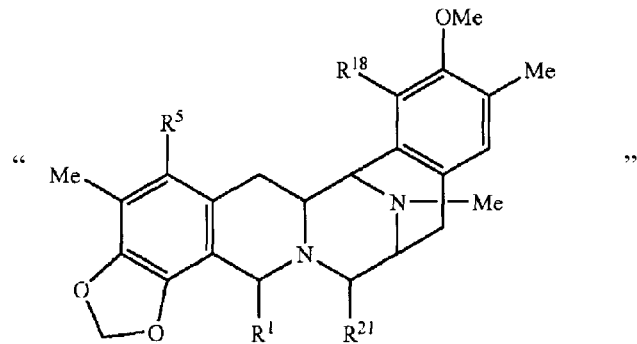 "
should read:
-- 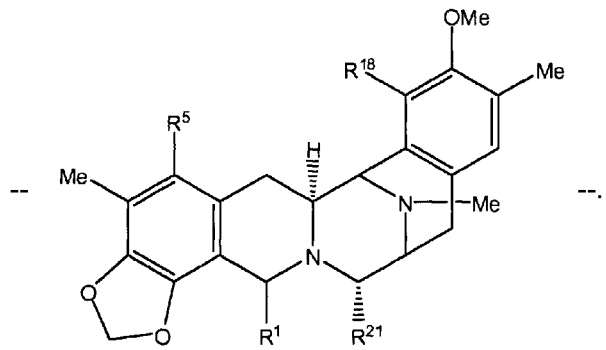 --.

Claim 57, Column 399, lines 36-49 (approximately), the formula reading:
" 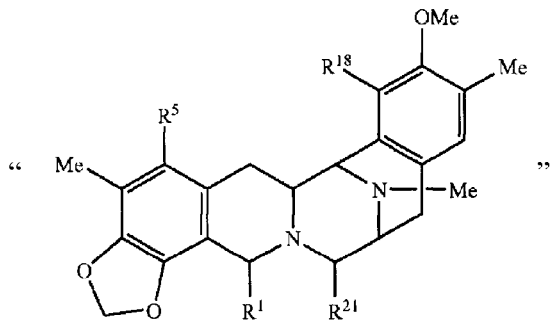 "
should read:
-- 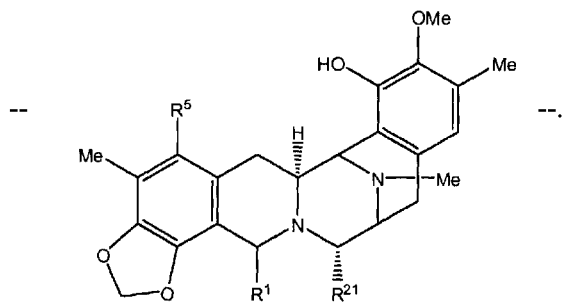 --.
Claim 60, Column 400, lines 36-49 (approximately), the formula reading:
" 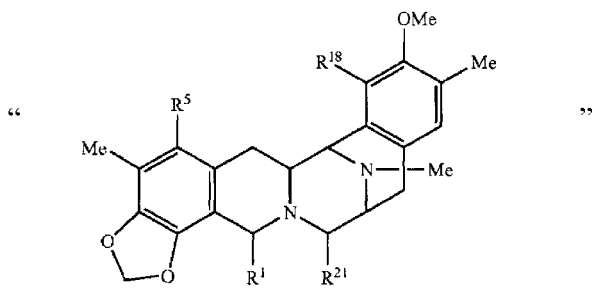 "

CERTIFICATE OF CORRECTION (continued)
U.S. Pat. No. 7,410,969 B2 should read:

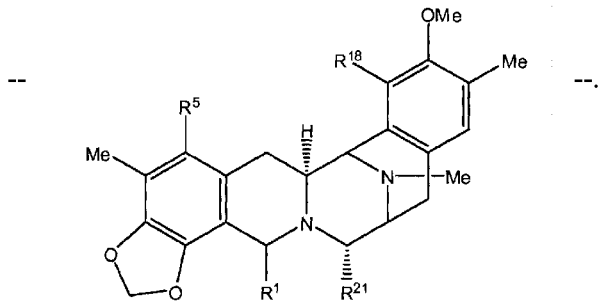

Claim 61, Column 400, lines 55-65 (approximately), the formula reading:

" 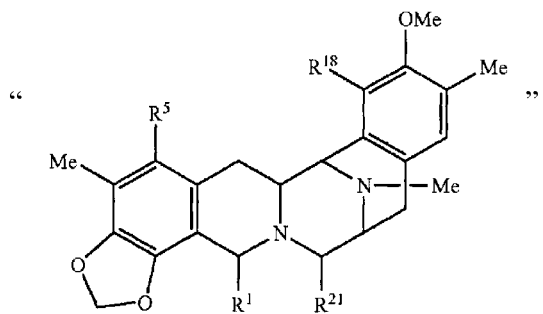 "

should read:

-- 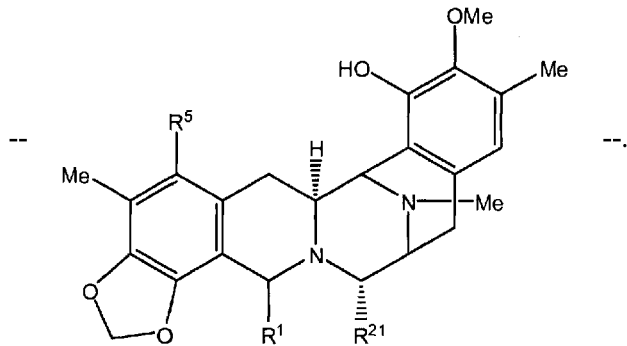 --.

CERTIFICATE OF CORRECTION (continued)
U.S. Pat. No. 7,410,969 B2

Page 6 of 6

Claim 65, Column 402, lines 5-15 (approximately), the formula reading:

" 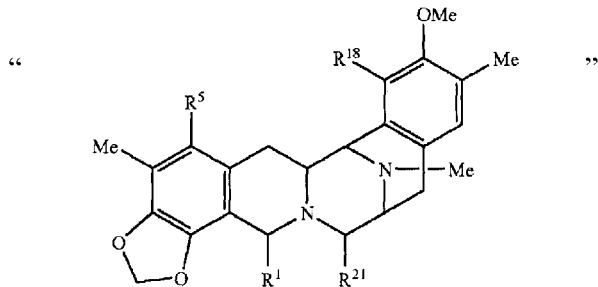 "

should read:

-- 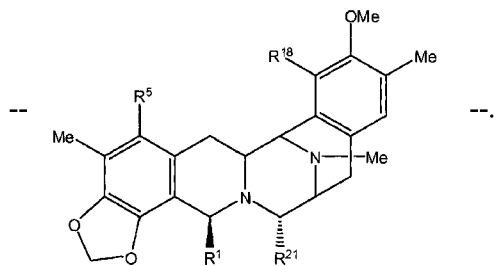 --.

Claim 66, Column 402, lines 21-31 (approximately), the formula reading:

" 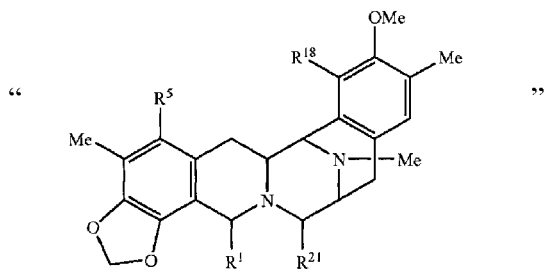 "

should read:

-- 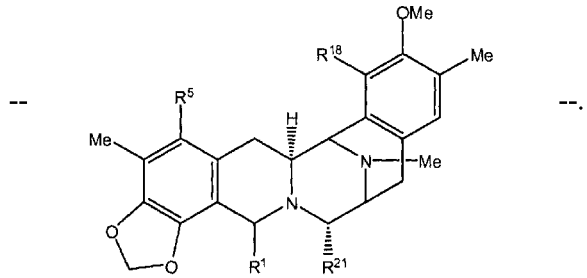 --.